US008460881B2

(12) United States Patent
Raitano et al.

(10) Patent No.: US 8,460,881 B2
(45) Date of Patent: *Jun. 11, 2013

(54) NUCLEIC ACIDS AND CORRESPONDING PROTEINS ENTITLED 254P1D6B USEFUL IN TREATMENT AND DETECTION OF CANCER

(75) Inventors: Arthur B. Raitano, Los Angeles, CA (US); Aya Jakobovits, Beverly Hills, CA (US); Pia M. Challita-Eid, Encino, CA (US); Wangmao Ge, Los Angeles, CA (US); Juan J. Perez-Villar, Santa Monica, CA (US); Steven B. Kanner, Santa Monica, CA (US)

(73) Assignee: Agensys, Inc., Santa Monica, CA (US)

( * ) Notice: Subject to any disclaimer, the term of this patent is extended or adjusted under 35 U.S.C. 154(b) by 614 days.

This patent is subject to a terminal disclaimer.

(21) Appl. No.: 12/405,166

(22) Filed: Mar. 16, 2009

(65) Prior Publication Data
US 2009/0263318 A1  Oct. 22, 2009

Related U.S. Application Data

(63) Continuation of application No. 10/764,390, filed on Jan. 23, 2004, now Pat. No. 7,638,270.

(60) Provisional application No. 60/442,526, filed on Jan. 24, 2003.

(51) Int. Cl.
G01N 33/53      (2006.01)
G01N 33/567     (2006.01)
G01N 33/574     (2006.01)

(52) U.S. Cl.
USPC ............... 435/7.1; 435/7.23; 436/63; 436/64; 436/503

(58) Field of Classification Search
None
See application file for complete search history.

(56) References Cited

U.S. PATENT DOCUMENTS

| | | | |
|---|---|---|---|
| 5,703,116 A | 12/1997 | Gaeta et al. | |
| 5,726,023 A | 3/1998 | Cheever et al. | |
| 5,869,445 A | 2/1999 | Cheever et al. | |
| 6,277,972 B1 * | 8/2001 | Afar et al. | 536/23.1 |
| 6,514,685 B1 * | 2/2003 | Moro | 435/4 |
| 2003/0175884 A1 * | 9/2003 | Umana et al. | 435/69.1 |
| 2007/0083334 A1 | 4/2007 | Mintz et al. | |

FOREIGN PATENT DOCUMENTS

| | | |
|---|---|---|
| CN | 1368510 | 9/2002 |
| EP | 1074617 * | 2/2001 |
| WO | WO-00/44899 | 8/2000 |
| WO | WO-01/64835 | 9/2001 |
| WO | WO-01/75067 | 10/2001 |
| WO | WO-02/10449 | 2/2002 |
| WO | WO-02/16439 | 2/2002 |
| WO | WO-02/068579 | 9/2002 |
| WO | WO-02/083081 | 10/2002 |
| WO | WO-03/025148 | 3/2003 |
| WO | WO-03/084467 | 10/2003 |
| WO | WO-03/087300 | 10/2003 |
| WO | WO-03/087768 | 10/2003 |
| WO | WO03087300 | * 10/2003 |
| WO | WO-2004/007711 | 1/2004 |
| WO | WO-2004/048933 | 6/2004 |
| WO | WO-2004/067716 | 8/2004 |
| WO | WO-2004/094589 | 11/2004 |

OTHER PUBLICATIONS

Charreau et al (Transgene Research, 1996, vol. 5, pp. 223-234.*
Abstract of Nancarrow et al (Methods in molecular biology, 1993, vol. 18, pp. 273-303).*
Machaty et al (Cloning Stem Cells, 202, vol. 4, pp. 21-27).*
NCBI Blast Protein, Dec. 3, 2010.*
Campbell (Monoclonal Antibody Technology (monograph), 1984, pp. 1-32).*
Yokohama (1991, 'Production of Monoclonal Antibodies', In: Current Protocols in Immunology, J.E. Coligan et al, ed.s, pp. 2.5.1-2.5.17).*
TMHMM Help Guide (downloaded from the Web Aug. 1, 2012).*
TMPred output (downloaded from the Web Aug. 1, 2012, p. 2, item 3).*
Lundegaard et al (Trends in Biotechnology, 2006, vol. 24, pp. 1-2).*
Tung et al, Bioinformatics, 2007, vol. 23, pp. 942-949.*
Abbas et al., Cellular and Molecular Immunology (1991) pp. 57-58.
Algarra et al., International Journal of Clinical and Laboratory Research (1997) 27:95-102 (abstract).
Antoinia et al., International Immunology (1995) 7:715-725.
Apostolopoulos et al., Nature Medicine (1998) 4:315-320.
Bodley et al., Anticancer Research (2000) 20:2665-2676.
Campbell, Monoclonal Antibody Technology (1984) pp. 1-32.
Conklin et al., Briefings in Bioinformatics (2000) 1:93-99.
Cripps et al., Clinical Cancer Research (2002) 8:2188-2192.
Database EMBL (Jul. 1997), EBI database accession No. AB002317.
Eck et al., "Gene-Based Therapy" in The Pharmacological Basis of Therapeutics, Goodman and Gilman, eds., (1996) pp. 77-101.
Holmes, Exp. Opin. Invest. Drugs (2001) 10:511-519.
International Search Report for PCT/US94/01965, mailed on Aug. 4 2006, 3 pages.
Jager et al., PNAS USA (2000) 97:12198-12203.
Johnson and Tracey, "Peptide and Protein Drug Delivery" in Encyclopedia of Controlled Drug Delivery (1999) 2:816-833.
Jones et al., Advanced Drug Delivery Reviews (1998) pp. 153-170.
Marshall et al., Clinical Colorectal Cancer (2004) 4:268-274.

(Continued)

Primary Examiner — Karen Canella
(74) Attorney, Agent, or Firm — Morrison & Foerster LLP

(57) ABSTRACT

A novel gene 254P1D6B and its encoded protein, and variants thereof, are described wherein 254P1D6B exhibits tissue specific expression in normal adult tissue, and is aberrantly expressed in the cancers listed in Table I. Consequently, 254P1D6B provides a diagnostic, prognostic, prophylactic and/or therapeutic target for cancer. The 254P1D6B gene or fragment thereof, or its encoded protein, or variants thereof, or a fragment thereof, can be used to elicit a humoral or cellular immune response; antibodies or T cells reactive with 254P1D6B can be used in active or passive immunization.

2 Claims, 38 Drawing Sheets

OTHER PUBLICATIONS

Matsushita et al., FEBS Letters (1999) 443:348-352.
Nagase et al., DNA Research (1997) 4:141-150.
Ohlen et al., Journal of Immunology (2001) 166:2863-2870.
Orkin et al., "Report and Recommendation of the Panel to Assess the NIH Investment in Research on Gene Therapy" NIH (1995).
Oza et al., Gynecological Oncology (2003) 89:129-133.
Paul, Fundamental Immunology (1993) pp. 249-250, 1157-1170.
Reiger et al., eds., Glossary of Genetics and Cytogenetics (1976) p. 17, lines 1-6 of the definition for allele.
Roit et al., Immunology, $5^{th}$ ed., (1998) pp. 110-111.
Sahin et al., PNAS USA (1995) 92:11810-11813.
Sarma et al., Journal of Experimental Medicine (1999) 189:811-820.
Scanlan et al., Int. Journal of Cancer (1998) 76:652-658.
Schlom, "Monoclonal Antibodies: They're More and Less Than You Think" in Molecular Basis of Clinical Oncology, Broder et al., eds., (1991).
Schultze et al., Trends in Immunology (2004) 25:659-664.
Semino et al., Journal of Biological Regulators and Homeostatic Agents (1993) 7:99-105 (abstract).
Singh et al., Glycobiology (2001) 11:587-592.
Supplementary European Search Report for EP 04704968.9, mailed May 16, 2008, 3 pages.
Tanaka et al., PNAS USA (1985) 82:3400-3404.
Tolcher et al., Clinical Cancer Research (2002) 8:2530-2535.
Verma et al., Nature (1997) 389:239-242.
Zwhalen et al., International Journal of Cancer (2000) 88:66-70.

* cited by examiner

Figure 1: 254P1D6B SSH sequence of 186 nucleotides (SEQ ID NO: 1).

```
  1 GATCCACAGA TAGGACACAA TTCTTTGGTC ATCAGTAGAC CTTGAACCAT CCAAAGTAAT
 61 GGAATTATTG GGAAGCACAA GAACATGTCT GCCACCAGCC CGGGCTCTGG GAGGACTATT
121 ATTTTCCTTC TTCACAGCCA CAGTGAGGGT GGACGTGCTG CTCAGTCCCT GCTGGTCTTT
181 TACTGTCAAA CGGAAGTGGT AGGTCCCCAC CTGGAGACCA GTCACAGTGG CTATTGCTTT
241 GTCAATATTT TCCATCTCCA CTGCACTGGG GCCTCTGACG TGCT
```

Figure 2:

Figure 2A. The cDNA (SEQ ID NO.: 2) and amino acid sequence (SEQ ID NO.: 3) of 254P1D6B v.1 clone LCP-3. The start methionine is underlined. The open reading frame extends from nucleic acid 512-3730 including the stop codon.

```
   1 gctgccgcgggcggtgggcggggatccccgggggtgcaaccttgctccacctgtgctgc
  61 cctcggcgggcctggctggccccgcgcagagcggcggcggcgctcgctgtcactgccgga
 121 ggtgagagcgcagcagtagcttcagcctgtcttgggcttggtccagattcgctcctctgg
 181 ggctacgtcccggggaagaggaagcgaggattttgctggggtggggctgtacctcttaac
 241 agcaggtgcgcgcgcgagggtgtgaacgtgtgtgtgtgtgtgtstgtgtgtgtgtgtgtg
 301 taagacctgcgatgacgacgaggaggaacaagtgggacggcgagtgatgctcagggccag
 361 cagcaacgcatggggcgagcttcagtgtcgccagcagtgaccacagttcttgaggccaaa
 421 tctggctcctaaaaaacatcaaaggaagcttgcaccaaactctcttcagggccgcctcag
   1                                                    M  A  P  P  T  G  V  L  S  S
 481 aagcctgccatcacccactgtgtggtgcacaATGGCGCCCCCCACAGGTGTGCTCTCTTC
  11  L  L  L  L  V  T  I  A  G  C  A  R  K  Q  C  S  E  G  R  T
 541 ATTGCTGCTGCTGGTGACAATTGCAGGTTGTGCCCGTAAGCAGTGCAGCGAGGGGAGGAC
  31  Y  S  N  A  V  I  S  P  N  L  E  T  T  R  I  M  R  V  S  H
 601 ATATTCCAATGCAGTCATTTCACCTAACTTGGAAACCACCAGAATCATGCGGGTGTCTCA
  51  T  F  P  V  V  D  C  T  A  A  C  D  L  S  S  C  D  L  A
 661 CACCTTCCCTGTCGTAGACTGCACGGCCGCTTGCTGTGACCTGTCCAGCTGTGACCTGGC
  71  W  W  F  E  G  R  C  Y  L  V  S  C  P  H  K  E  N  C  E  P
 721 CTGGTGGTTCGAGGGCCGCTGCTACCTGGTGAGCTGCCCCCACAAAGAGAACTGTGAGCC
  91  K  K  M  G  P  I  R  S  Y  L  T  F  V  L  R  P  V  Q  R  P
 781 CAAGAAGATGGGCCCCATCAGGTCTTATCTCACTTTTGTGCTCCGGCCTGTTCAGAGGCC
 111  A  Q  L  L  D  Y  G  D  M  M  L  N  R  G  S  P  S  G  I  W
 841 TGCACAGCTGCTGGACTATGGGGACATGATGCTGAACAGGGGCTCCCCCTCGGGGATCTG
 131  G  D  S  P  E  D  I  R  K  D  L  P  F  L  G  K  D  W  G  L
 901 GGGGGACTCACCTGAGGATATCAGAAAGGACTTGMCCTTTCTAGGCAAAGATTGGGGCCT
 151  E  E  M  S  E  Y  S  D  D  Y  R  E  L  E  K  D  L  L  Q  P
 961 AGAGGAGATGTCTGAGTACKAGATGACTACCGGGAGCTGGAGAAGGACCTCTTGCAACC
 171  S  G  K  Q  E  P  R  G  S  A  E  Y  T  D  W  G  L  L  P  G
1021 CAGTGGCAAGCAGGAGCCCAGAGGGAGTGCCGAGTACACGGACTGGGGCCTACTGCCGGG
 191  S  E  G  A  F  N  S  S  V  G  D  S  P  A  V  P  A  E  T  Q
1081 CAGCGAGGGGGCCTTCAACTCCTCTGTTGGAGACAGTCCTGCGGTGCCAGCGGAGACGCA
 211  Q  D  P  E  L  H  Y  L  N  E  S  A  S  T  P  A  P  K  L  P
1141 GCAGGACCCTGAGCTCCATTACCTGAATGAGTCGGCTTCAACCCCTGCCCCAAAACTCCC
 231  E  R  S  V  L  L  P  L  P  T  T  P  S  S  G  E  V  L  E  K
1201 TGAGAGAAGTGTGTTGCTTCCCTTGCCGACTACTCCATCTTCAGGAGAGGTGTTGGAGAA
 251  E  K  A  S  Q  L  E  Q  S  S  N  S  S  G  K  E  V  L  M
1261 AGAAAAGGCTTCTCAGCTCCAGGAACAATCCAGCAACAGCTCTGGAAAAGAGGTTCTAAT
 271  P  S  H  S  L  P  P  A  S  L  E  L  S  S  V  T  V  E  K  S
```

Figure 2A-2

```
1321 GCCTTCCCATAGTCTTCCTCCGGCAAGCCTGGAGCTCAGCTCAGTCACCGTGGAGAAAAG
 291  P  V  L  T  V  T  P  G  S  T  E  H  S  I  P  T  P  P  T  S
1381 CCCAGTGCTCACAGTCACCCCGGGGAGTACAGAGCACAGCATCCCAACACCTCCCACTAG
 311  A  A  P  S  E  S  T  P  S  E  L  P  I  S  P  T  T  A  P  R
1441 CGCAGCCCCCTCTGAGTCCACCCCATCTGAGCTACCCATATCTCCTACCACTGCTCCCAG
 331  T  V  K  E  L  T  V  S  A  G  D  N  L  I  I  T  L  P  D  N
1501 GACAGTGAAAGAACTTACGGTATCGGCTGGAGATAACCTAATTATAACTTTACCCGACAA
 351  E  V  L  K  A  F  V  A  P  A  P  P  V  E  T  T  Y  N  Y
1561 TGAAGTTGAACTGAAGGCCTTTGTTGCGCCAGCGCCACCTGTAGAAACAACCTACAACTA
 371  E  W  N  L  I  S  H  P  T  D  Y  Q  G  E  I  K  Q  G  H  K
1621 TGAATGGAATTTAATAAGCCACCCCACAGACTACCAAGGTGAAATAAAACAAGGACACAA
 391  Q  T  L  N  L  S  Q  L  S  V  G  L  Y  V  F  K  V  T  V  S
1681 GCAAACTCTTAACCTCTCTCAATTGTCCGTCGGACTTTATGTCTTCAAAGTCACTGTTTC
 411  S  E  N  A  F  G  E  G  F  V  N  V  T  V  K  P  A  R  R  V
1741 TAGTGAAAACGCCTTTGGAGAAGGATTTGTCAATGTCACTGTTAAGCCTGCCAGAAGAGT
 431  N  L  P  P  V  A  V  V  S  P  Q  L  Q  E  L  T  L  P  L  T
1801 CAACCTGCCACCTGTAGCAGTTGTTTCTCCCCAACTGCAAGAGCTCACTTTGCCTTTGAC
 451  S  A  L  I  D  G  S  Q  S  T  D  D  T  E  I  V  S  Y  H  W
1861 GTCAGCCCTCATTGATGGCAGCCAAAGTACAGATGATACTGAAATAGTGAGTTATCATTG
 471  E  E  I  N  G  P  F  I  E  E  K  T  S  V  D  S  P  V  L  R
1921 GGAAGAAATAAACGGGCCCTTCATAGAAGAGAAGACTTCAGTTGACTCTCCCGTCTTACG
 491  L  S  N  L  D  P  G  N  Y  S  F  R  L  T  V  T  D  S  D  G
1981 CTTGTCTAACCTTGATCCTGGTAACTATAGTTTCAGGTTGACTGTTACAGACTCGGACGG
 511  A  T  N  S  T  A  A  L  I  V  N  N  A  V  D  Y  P  P  V
2041 AGCCACTAACTCTACAACTGCAGCCCTAATAGTGAACAATGCTGTGGACTACCCACCAGT
 531  A  N  A  G  P  N  H  T  I  T  L  P  Q  N  S  I  T  L  N  G
2101 TGCTAATGCAGGACCAAATCACACCATAACTTTGCCCCAAAACTCCATCACTTTGAATGG
 551  N  Q  S  S  D  D  H  Q  I  V  L  Y  E  W  S  L  G  P  G  S
2161 AAACCAGAGCAGTGACGATCACCAGATTGTCCTCTATGAGTGGTCCCTGGGTCCTGGGAG
 571  E  G  K  H  V  V  M  Q  G  V  Q  T  P  Y  L  H  L  S  A  M
2221 TGAGGGCAAACATGTGGTCATGCAGGGAGTACAGACGCCATACCTTCATTTATCTGCAAT
 591  Q  E  G  D  Y  T  F  Q  L  K  V  T  D  S  S  R  Q  Q  S  T
2281 GCAGGAAGGAGATTATACATTTCAGCTGAAGGTGACAGATTCTTCAAGGCAACAGTCTAC
 611  A  V  V  T  V  I  V  Q  P  E  N  N  R  P  P  V  A  V  A  G
2341 TGCTGTRGTGACTGTGATTGTCCAGCCTGAAAACAATAGACCTCCAGTGGCTGTGGCCGG
 631  P  D  K  E  L  I  F  P  V  E  S  A  T  L  D  G  S  S  S  S
2401 CCCTGATAAAGAGCTGATCTTCCCAGTGGAAAGTGCTACCCTGGATGGGAGCAGCAGCAG
 651  D  D  H  G  I  V  F  Y  H  W  E  H  V  R  G  P  S  A  V  E
2461 CGATGACCACGGCATTGTCTTCTACCACTGGGAGCACGTCAGAGGCCCCAGTGCAGTGGA
 671  M  E  N  I  D  K  A  I  A  T  V  T  G  L  Q  V  G  T  Y  H
2521 GATGGAAAATATTGACAAAGCAATAGCCACTGTGACTGGTCTCCAGGTGGGGACCTACCA
```

Figure 2A-3

```
 691 F  R  L  T  V  K  D  Q  Q  G  L  S  S  T  S  T  L  T  V  A
2581 CTTCCGTTTGACAGTGAAAGACCAGCAGGGACTGAGCAGCACGTCCACCCTCACTGTGGC
 711 V  K  K  E  N  N  S  P  P  R  A  R  A  G  G  R  H  V  L  V
2641 TGTGAAGAAGGAAAATAATAGTCCTCCCAGAGCCCGGGCTGGTGGCAGACATGTTCTTGT
 731 L  P  N  N  S  I  T  L  D  G  S  R  S  T  D  D  Q  R  I  V
2701 GCTTCCCAATAATTCCATTACTTTGGATGGTTCAAGGTCTACTGATGACCAAAGAATTGT
 751 S  Y  L  W  I  R  D  G  Q  S  P  A  A  G  D  V  I  D  G  S
2761 GTCCTATCTGTGGATCCGGGATGGCCAGAGTCCAGCAGCTGGAGATGTCATCGATGGCTC
 771 D  H  S  V  A  L  Q  L  T  N  L  V  E  G  V  Y  T  F  H  L
2821 TGACCACAGTGTGGCTCTGCAGCTTACGAATCTGGTGGAGGGGTGTACACTTTCCACTT
 791 R  V  T  D  S  Q  G  A  S  D  T  D  T  A  T  V  E  V  Q  P
2881 GCGAGTCACCGACAGTCAGGGGCCTCGGACACAGACACTGCCACTGTGGAAGTGCAGCC
 811 D  P  R  K  S  G  L  V  E  L  T  L  Q  V  G  V  G  Q  L  T
2941 AGACCCTAGGAAGAGTGGCCTGGTGGAGCTGACCCTGCAGGTTGGTGTTGGGCAGCTGAC
 831 E  Q  R  K  D  T  L  V  R  Q  L  A  V  L  L  N  V  L  D  S
3001 AGAGCAGCGGAAGGACACCCTTGTGAGGCAGCTGGCTGTGCTGCTGAACGTGCTGGACTC
 851 D  I  K  V  Q  K  I  R  A  H  S  D  L  S  T  V  I  V  F  Y
3061 GGACATTAAGGTCCAGAAGATTCGGGCCCACTCGGATCTCAGCACCGTGATTGTGTTTTA
 871 V  Q  S  R  P  P  F  K  V  L  K  A  A  E  V  A  R  N  L  H
3121 TGTACAGAGCAGGCCGCCTTTCAAGGTTCTCAAAGCTGCTGAAGTGGCCCGAAATCTGCA
 891 M  R  L  S  K  E  K  A  D  F  L  L  F  K  V  L  R  V  D  T
3181 CATGCGGCTCTCAAAGGAGAAGGCTGACTTCTTGCTTTTCAAGGTCTTGAGGGTTGATAC
 911 A  G  C  L  L  K  C  S  G  H  G  H  C  D  P  L  T  K  R  C
3241 AGCAGGTTGCCTTCTGAAGTGTTCTGGCCATGGTCACTGCGACCCCCTCACAAAGCGCTG
 931 I  C  S  H  L  W  M  E  N  L  I  Q  R  Y  I  W  D  G  E  S
3301 CATTTGCTCTCACTTATGGATGGAGAACCTTATACAGCGTTATATCTGGGATGGAGAGAG
 951 N  C  E  W  S  I  F  Y  V  T  V  L  A  F  T  L  I  V  L  T
3361 CAACTGTGAGTGGAGTATATTCTATGTGACAGTGTTGGCTTTTACTCTTATTGTGCTAAC
 971 G  G  F  T  W  L  C  I  C  C  C  K  R  Q  K  R  T  K  I  R
3421 AGGAGGTTTCACTTGGCTTTGCATCTGCTGCTGCAAAAGACAAAAAAGGACTAAAATCAG
 991 K  K  T  K  Y  T  I  L  D  N  M  D  E  Q  E  R  M  E  L  R
3481 GAAAAAAACAAAGTACACCATCCTGGATAACATGGATGAACAGGAAAGAATGGAACTGAG
1011 P  K  Y  G  I  K  H  R  S  T  E  H  N  S  S  L  M  V  S  E
3541 GCCCAAATATGGTATCAAGCACCGAAGCACAGAGCACAACTCCAGCCTGATGGTATCCGA
1031 S  E  F  D  S  Q  D  T  I  F  S  R  E  K  M  E  R  G  N
3601 GTCTGAGTTTGACAGTGACCAGGACACAATCTTCAGCCGAGAAAAGATGGAGAGAGGGAA
1051 P  K  V  S  M  N  G  S  I  R  N  G  A  S  F  S  Y  C  S  K
3661 TCCAAAGGTTTCCATGAATGGTTCCATCAGAAATGGAGCTTCCTTCAGTTATTGCTCAAA
1071 D  R  *
3721 GGACAGATAAtggcgcagttcattgtaaagtggaaggacccyttgaatccargaccagtc
3781 agtgggagttacagcacaaaacccactcttttagaatagttcattgaccttcttccccag
```

Figure 2A-4

```
3841 tgggttagatgtgtatccccacgtactaaaagaccggttttt gaaggcacaaaacaaaaa
3901 ctttgctcttttaactgagatgcttgttaatagaaataaaggctgggtaaaactytaagg
3961 tatatacttaaaagagttttgagttttt gtagctggcacaatctcatattaaagatgaac
4021 aacgatttctatctgtagaaccttagagaaggtgaatgaaacaaggttttaaaaagggat
4081 gatttctgtcttagcygctgtgattgcctctaaggaacagcattctaaacacggtttctc
4141 ttgtaggacctgcagtcagatggctgtgtatgttaaaatagcttgtctaagaggcacggg
4201 ccatctgtggaggtacggagtcttgcatgtagcaagctttctgtgctgacggcaacactc
4261 gcacagtgccaagccctcctggttttt aattctgtgctatgtcaatggcagttttcatct
4321 ctctcaagaaagcagctgttggccattcaagagctaaggaagaatcgtattctaaggact
4381 gaggcaatagaaaggggaggaggagcttaatgccrtgcaggttgaaggtagcattgtaac
4441 attatcttttctttctctaagaaaaactacactgactcctctcggtgttgtttagcagta
4501 tagttctctaatgtaaacrgatccccagtttacattaartgcaatagaagtgattaattc
4561 attaagcatttattatgttctgtaggctgtgcgtttggactgccatagataggkataacg
4621 actcagcaattgtgtatatattccaaaactctgaaatacagtcagtcttaacttggatgg
4681 cgtggttatgatactctggtccccacaggtactttccaaaataacttgacatagatgta
4741 ttcacttcatatgtttaaaaatacatttaagttttt ctaccgaataaatcttatttcaaa
4801 catgaaagacaattaaaacattcccacccacaaagcagtactcccgagcaattaactgga
4861 gttaattgtagcctgctacgttgactggttcagggtagttccccatccacccttggtcct
4921 gaggctggtggccttggtggtgccttggcattttttgtgggaagattagaatgagagat
4981 agaaccagtgttgtggtaccaagtgtgagcacacctaaacaatatcctgttgcacaatgc
5041 tttttt aacacatgggaaaactaggaatgcattgctgatgaagaagcaaggtatttaaac
5101 accagggcaggagtgccagagaaaatgtttccccatggggttcttaaaaaaaattcagctt
5161 ttaggtgcttttgtcatctcccgsagtattcatcctcatgggaccatcttatttttactt
5221 attgtaatttactggggaaaggcagaactaaaaagtgtgtcattttatttttaaaataat
5281 tgctttgcttatgcctacactttctgtataactagccaattcaatactgtctatagtgtt
5341 agaaggaaaatgtgatttttttttttaaccagtattgagcttcataagcctagaatctg
5401 ccttatcaggtgaccagggttatggttgtttgcatgcaaatgtgaatttctggcataggg
5461 gacagcagcccaaatgtaaagtcatcgggcgtaatgaggaagaagggagtgaacatttac
5521 cgctttakgtacataacatatgcagtttacatactcatttgatccttataatcaaccttg
5581 aagaggagatactatcattcttatgttgcagatagccctctgaaggcccagagaggttaa
5641 rtaacttcccagaggtcatggccaagaagtagtggctccaagaactgaatgcaaatttt
5701 taaactgtagagttctgctttccactaaacaaagaactcctgccttgatggatggagggc
5761 aaattctggtggaacttttgggccacctgaaagttctattcccaggactaagaggaattt
5821 cttttaatggatccagagagccaaggtcagagggagagatggcctgcatagtctcctgtg
5881 gatcacacccgggccaccctccctctaggtttacagtggacttcttctgcccctcctcc
5941 ttttctgtccttggccatctcagcctggcctctctgatccttccatcacagaaggatctt
6001 gaatctctgggaaatcaaacatcacagtagtgatcagaaagtgagtcctgtcttgtcacc
6061 ccatttctcatcagaacaaagcacgagatggaatgaccaaccagcattcttcatggtgga
6121 ctgcttatcattgaggatctttgggagataaagcacgctaagagctctggacagagaaaa
6181 acaggccctagaatatgggagtgggtgtttgtagggctcayargctaacaagcactttag
6241 ttgctggtttacattcaatgaaggaggattcatacccatggcattacaaggctaagcatg
```

Figure 2A-5

```
6301 tgtatgactaaggaactatctgaaaaacatgcagcaaggtaagaaaatgtaccactcaac
6361 aagccagtgatgccaccttttgtgcgcggggaggagagtgactaccattgttttttgtgt
6421 gacaaagctatcatggactattttaatcttggttttattgcttaaaatatattattttc
6481 cctatgtgttgacaaggtatttctaatatcacactattaaatatatgcactaatctaaat
6541 aaaggtgtctgtatttctgtaatgcttattttagggggaaatttgttttctttatgct
6601 tcagggtagagggattcccttgagtataggtcagcaaactctggcctgcagcctgtgtgt
6661 gcacgccccatgagccgaaaagtgggtcttatgttttcaaatggttaaaaataaataaaa
6721 aaatttgaaacatgtgaactatatgacattcagatttgtgttcataaataaagttttatt
6781 ggaacatatcc
```

Figure 2B. The cDNA (SEQ ID NO.: 4) and amino acid sequence (SEQ ID NO.: 5) of 254P1D6B v.2.
The start methionine is underlined. The open reading frame extends from nucleic acid 512-3730 including the stop codon.

```
   1 gctgccgcgggcggtgggcggggatccccgggggtgcaaccttgctccacctgtgctgc
  61 cctcggcgggcctggctggccccgcgcagagcggcggcggcgctcgctgtcactgccgga
 121 ggtgagagcgcagcagtagcttcagcctgtcttgggcttggtccagattcgctcctctgg
 181 ggctacgtcccggggaagaggaagcgaggattttgctggggtggggctgtacctcttaac
 241 agcaggtgcgcgcgcgagggtgtgaacgtgtgtgtgtgtgtgtctgtgtgtgtgtg
 301 taagacctgcgatgacgacgaggaggaacaagtgggacggcgagtgatgctcagggccag
 361 cagcaacgcatggggcgagcttcagtgtcgccagcagtgaccacagttcttgaggccaaa
 421 tctggctcctaaaaaacatcaaaggaagcttgcaccaaactctcttcagggccgcctcag
   1                                        M  A  P  P  T  G  V  L  S  S
 481 aagcctgccatcacccactgtgtggtgcacaATGGCGCCCCCACAGGTGTGCTCTCTTC
  11  L  L  L  V  T  I  A  G  C  A  R  K  Q  C  S  E  G  R  T
 541 ATTGCTGCTGCTGGTGACAATTGCAGGTTGTGCCCGTAAGCAGTGCAGCGAGGGGAGGAC
  31  Y  S  N  A  V  I  S  P  N  L  E  T  T  R  I  M  R  V  S  H
 601 ATATTCCAATGCAGTCATTTCACCTAACTTGGAAACCACCAGAATCATGCGGGTGTCTCA
  51  T  F  P  V  V  D  C  T  A  A  C  C  D  L  S  S  C  D  L  A
 661 CACCTTCCCTGTCGTAGACTGCACGGCCGCTTGCTGTGACCTGTCCAGCTGTGACCTGGC
  71  W  W  F  E  G  R  C  Y  L  V  S  C  P  H  K  E  N  C  E  P
 721 CTGGTGGTTCGAGGGCCGCTGCTACCTGGTGAGCTGCCCCCACAAAGAGAACTGTGAGCC
  91  K  K  M  G  P  I  R  S  Y  L  T  F  V  L  R  P  V  Q  R  P
 781 CAAGAAGATGGGCCCCATCAGGTCTTATCTCACTTTTGTGCTCCGGCCTGTTCAGAGGCC
 111  A  Q  L  L  D  Y  G  D  M  M  L  N  R  G  S  P  S  G  I  W
 841 TGCACAGCTGCTGGACTATGGGGACATGATGCTGAACAGGGGCTCCCCCTCGGGGATCTG
 131  G  D  S  P  E  D  I  R  K  D  L  P  F  L  G  K  D  W  G  L
 901 GGGGGACTCACCTGAGGATATCAGAAAGGACTTGCCCTTTCTAGGCAAAGATTGGGGCCT
 151  E  E  M  S  E  Y  A  D  D  Y  R  E  L  E  K  D  L  L  Q  P
 961 AGAGGAGATGTCTGAGTACGCAGATGACTACCGGGAGCTGGAGAAGGACCTCTTGCAACC
 171  S  G  K  Q  E  P  R  G  S  A  E  Y  T  D  W  G  L  L  P  G
1021 CAGTGGCAAGCAGGAGCCCAGAGGGAGTGCCGAGTACACGGACTGGGGCCTACTGCCGGG
```

Figure 2B-2

```
 191  S  E  G  A  F  N  S  S  V  G  D  S  P  A  V  P  A  E  T  Q
1081  CAGCGAGGGGGCCTTCAACTCCTCTGTTGGAGACAGTCCTGCGGTGCCAGCGGAGACGCA
 211  Q  D  P  E  L  H  Y  L  N  E  S  A  S  T  P  A  P  K  L  P
1141  GCAGGACCCTGAGCTCCATTACCTGAATGAGTCGGCTTCAACCCCTGCCCCAAAACTCCC
 231  E  R  S  V  L  L  P  L  P  T  T  P  S  S  G  E  V  L  E  K
1201  TGAGAGAAGTGTGTTGCTTCCCTTGCCGACTACTCCATCTTCAGGAGAGGTGTTGGAGAA
 251  E  K  A  S  Q  L  Q  E  Q  S  S  N  S  S  G  K  E  V  L  M
1261  AGAAAAGGCTTCTCAGCTCCAGGAACAATCCAGCAACAGCTCTGGAAAAGAGGTTCTAAT
 271  P  S  H  S  L  P  P  A  S  L  E  L  S  S  V  T  V  E  K  S
1321  GCCTTCCCATAGTCTTCCTCCGGCAAGCCTGGAGCTCAGCTCAGTCACCGTGGAGAAAAG
 291  P  V  L  T  V  T  P  G  S  T  E  H  S  I  P  T  P  P  T  S
1381  CCCAGTGCTCACAGTCACCCCGGGGAGTACAGAGCACAGCATCCCAACACCTCCCACTAG
 311  A  A  P  S  E  S  T  P  S  E  L  P  I  S  P  T  T  A  P  R
1441  CGCAGCCCCCTCTGAGTCCACCCCATCTGAGCTACCCATATCTCCTACCACTGCTCCCAG
 331  T  V  K  E  L  T  V  S  A  G  D  N  L  I  I  T  L  P  D  N
1501  GACAGTGAAAGAACTTACGGTATCGGCTGGAGATAACCTAATTATAACTTTACCCGACAA
 351  E  V  E  L  K  A  F  V  A  P  A  P  P  V  E  T  T  Y  N  Y
1561  TGAAGTTGAACTGAAGGCCTTTGTTGCGCCAGCGCCACCTGTAGAAACAACCTACAACTA
 371  E  W  N  L  I  S  H  P  T  D  Y  Q  G  E  I  K  Q  G  H  K
1621  TGAATGGAATTTAATAAGCCACCCCACAGACTACCAAGGTGAAATAAAACAAGGACACAA
 391  Q  T  L  N  L  S  Q  L  S  V  G  L  Y  V  F  K  V  T  V  S
1681  GCAAACTCTTAACCTCTCTCAATTGTCCGTCGGACTTTATGTCTTCAAAGTCACTGTTTC
 411  S  E  N  A  F  G  E  G  F  V  N  V  T  V  K  P  A  R  R  V
1741  TAGTGAAAACGCCTTTGGAGAAGGATTTGTCAATGTCACTGTTAAGCCTGCCAGAAGAGT
 431  N  L  P  P  V  A  V  V  S  P  Q  L  Q  E  L  T  L  P  L  T
1801  CAACCTGCCACCTGTAGCAGTTGTTTCTCCCCAACTGCAAGAGCTCACTTTGCCTTTGAC
 451  S  A  L  I  D  G  S  Q  S  T  D  D  T  E  I  V  S  Y  H  W
1861  GTCAGCCCTCATTGATGGCAGCCAAAGTACAGATGATACTGAAATAGTGAGTTATCATTG
 471  E  E  I  N  G  P  F  I  E  E  K  T  S  V  D  S  P  V  L  R
1921  GGAAGAAATAAACGGGCCCTTCATAGAAGAGAAGACTTCAGTTGACTCTCCCGTCTTACG
 491  L  S  N  L  D  P  G  N  Y  S  F  R  L  T  V  T  D  S  D  G
1981  CTTGTCTAACCTTGATCCTGGTAACTATAGTTTCAGGTTGACTGTTACAGACTCGGACGG
 511  A  T  N  S  T  A  A  L  I  V  N  N  A  V  D  Y  P  P  V
2041  AGCCACTAACTCTACAACTGCAGCCCTAATAGTGAACAATGCTGTGGACTACCCACCAGT
 531  A  N  A  G  P  N  H  T  I  T  L  P  Q  N  S  I  T  L  N  G
2101  TGCTAATGCAGGACCAAATCACACCATAACTTTGCCCCAAAACTCCATCACTTTGAATGG
 551  N  Q  S  S  D  D  H  Q  I  V  L  Y  E  W  S  L  G  P  G  S
2161  AAACCAGAGCAGTGACGATCACCAGATTGTCCTCTATGAGTGGTCCCTGGGTCCTGGGAG
 571  E  G  K  H  V  V  M  Q  G  V  Q  T  P  Y  L  H  L  S  A  M
2221  TGAGGGCAAACATGTGGTCATGCAGGGAGTACAGACGCCATACCTTCATTTATCTGCAAT
 591  Q  E  G  D  Y  T  F  Q  L  K  V  T  D  S  S  R  Q  Q  S  T
```

Figure 2B-3

```
2281 GCAGGAAGGAGATTATACATTTCAGCTGAAGGTGACAGATTCTTCAAGGCAACAGTCTAC
 611  A  V  V  T  V  I  V  Q  P  E  N  N  R  P  P  V  A  V  A  G
2341 TGCTGTAGTGACTGTGATTGTCCAGCCTGAAAACAATAGACCTCCAGTGGCTGTGGCCGG
 631  P  D  K  E  L  I  F  P  V  E  S  A  T  L  D  G  S  S  S  S
2401 CCCTGATAAAGAGCTGATCTTCCCAGTGGAAAGTGCTACCCTGGATGGGAGCAGCAGCAG
 651  D  D  H  G  I  V  F  Y  H  W  E  H  V  R  G  P  S  A  V  E
2461 CGATGACCACGGCATTGTCTTCTACCACTGGGAGCACGTCAGAGGCCCCAGTGCAGTGGA
 671  M  E  N  I  D  K  A  I  A  T  V  T  G  L  Q  V  G  T  Y  H
2521 GATGGAAAATATTGACAAAGCAATAGCCACTGTGACTGGTCTCCAGGTGGGGACCTACCA
 691  F  R  L  T  V  K  D  Q  Q  G  L  S  S  T  S  T  L  T  V  A
2581 CTTCCGTTTGACAGTGAAAGACCAGCAGGGACTGAGCAGCACGTCCACCCTCACTGTGGC
 711  V  K  K  E  N  N  S  P  P  R  A  R  A  G  G  R  H  V  L  V
2641 TGTGAAGAAGGAAAATAATAGTCCTCCCAGAGCCCGGGCTGGTGGCAGACATGTTCTTGT
 731  L  P  N  N  S  I  T  L  D  G  S  R  S  T  D  D  Q  R  I  V
2701 GCTTCCCAATAATTCCATTACTTTGGATGGTTCAAGGTCTACTGATGACCAAAGAATTGT
 751  S  Y  L  W  I  R  D  G  Q  S  P  A  A  G  D  V  I  D  G  S
2761 GTCCTATCTGTGGATCCGGGATGGCCAGAGTCCAGCAGCTGGAGATGTCATCGATGGCTC
 771  D  H  S  V  A  L  Q  L  T  N  L  V  E  G  V  Y  T  F  H  L
2821 TGACCACAGTGTGGCTCTGCAGCTTACGAATCTGGTGGAGGGGGTGTACACTTTCCACTT
 791  R  V  T  D  S  Q  G  A  S  D  T  D  T  A  T  V  E  V  Q  P
2881 GCGAGTCACCGACAGTCAGGGGGCCTCGGACACAGACACTGCCACTGTGGAAGTGCAGCC
 811  D  P  R  K  S  G  L  V  E  L  T  L  Q  V  G  V  G  Q  L  T
2941 AGACCCTAGGAAGAGTGGCCTGGTGGAGCTGACCCTGCAGGTTGGTGTTGGGCAGCTGAC
 831  E  Q  R  K  D  T  L  V  R  Q  L  A  V  L  L  N  V  L  D  S
3001 AGAGCAGCGGAAGGACACCCTTGTGAGGCAGCTGGCTGTGCTGCTGAACGTGCTGGACTC
 851  D  I  K  V  Q  K  I  R  A  H  S  D  L  S  T  V  I  V  F  Y
3061 GGACATTAAGGTCCAGAAGATTCGGGCCCACTCGGATCTCAGCACCGTGATTGTGTTTTA
 871  V  Q  S  R  P  P  F  K  V  L  K  A  A  E  V  A  R  N  L  H
3121 TGTACAGAGCAGGCCGCCTTTCAAGGTTCTCAAAGCTGCTGAAGTGGCCCGAAATCTGCA
 891  M  R  L  S  K  E  A  D  F  L  L  F  K  V  L  R  V  D  T
3181 CATGCGGCTCTCAAAGGAGAAGGCTGACTTCTTGCTTTTCAAGGTCTTGAGGGTTGATAC
 911  A  G  C  L  L  K  C  S  G  H  G  H  C  D  P  L  T  K  R  C
3241 AGCAGGTTGCCTTCTGAAGTGTTCTGGCCATGGTCACTGCGACCCCCTCACAAAGCGCTG
 931  I  C  S  H  L  W  M  E  N  L  I  Q  R  Y  I  W  D  G  E  S
3301 CATTTGCTCTCACTTATGGATGGAGAACCTTATACAGCGTTATATCTGGGATGGAGAGAG
 951  N  C  E  W  S  I  F  Y  V  T  V  L  A  F  T  L  I  V  L  T
3361 CAACTGTGAGTGGAGTATATTCTATGTGACAGTGTTGGCTTTTACTCTTATTGTGCTAAC
 971  G  G  F  T  W  L  C  I  C  C  K  R  Q  K  R  T  K  I  R
3421 AGGAGGTTTCACTTGGCTTTGCATCTGCTGCTGCAAAAGACAAAAAAGGACTAAAATCAG
 991  K  K  T  K  Y  T  I  L  D  N  M  D  E  Q  E  R  M  E  L  R
3481 GAAAAAAACAAAGTACACCATCCTGGATAACATGGATGAACAGGAAAGAATGGAACTGAG
```

Figure 2B-4

```
1011 P  K  Y  G  I  K  H  R  S  T  E  H  N  S  S  L  M  V  S  E
3541 GCCCAAATATGGTATCAAGCACCGAAGCACAGAGCACAACTCCAGCCTGATGGTATCCGA
1031 S  E  F  D  S  D  Q  D  T  I  F  S  R  E  K  M  E  R  G  N
3601 GTCTGAGTTTGACAGTGACCAGGACACAATCTTCAGCCGAGAAAAGATGGAGAGAGGGAA
1051 P  K  V  S  M  N  G  S  I  R  N  G  A  S  F  S  Y  C  S  K
3661 TCCAAAGGTTTCCATGAATGGTTCCATCAGAAATGGAGCTTCCTTCAGTTATTGCTCAAA
1071 D  R  *
3721 GGACAGATAAtggcgcagttcattgtaaagtggaaggaccccttgaatccaagaccagtc
3781 agtgggagttacagcacaaaacccactcttttagaatagttcattgaccttcttccccag
3841 tgggttagatgtgtatccccacgtactaaaagaccggttttgaaggcacaaaacaaaaa
3901 ctttgctcttttaactgagatgcttgttaatagaaataaaggctgggtaaaactctaagg
3961 tatatacttaaaagagttttgagtttttgtagctggcacaatctcatattaaagatgaac
4021 aacgatttctatctgtagaaccttagagaaggtgaatgaaacaaggttttaaaaagggat
4081 gatttctgtcttagccgctgtgattgcctctaaggaacagcattctaaacacggtttctc
4141 ttgtaggacctgcagtcagatggctgtgtatgttaaaatagcttgtctaagaggcacggg
4201 ccatctgtggaggtacggagtcttgcatgtagcaagctttctgtgctgacggcaacactc
4261 gcacagtgccaagccctcctggttttttaattctgtgctatgtcaatggcagttttcatct
4321 ctctcaagaaagcagctgttggccattcaagagctaaggaagaatcgtattctaaggact
4381 gaggcaatagaaaggggaggaggagcttaatgccgtgcaggttgaaggtagcattgtaac
4441 attatcttttctttctctaagaaaaactacactgactcctctcggtgttgtttagcagta
4501 tagttctctaatgtaaacggatccccagtttacattaaatgcaatagaagtgattaattc
4561 attaagcatttattatgttctgtaggctgtgcgtttggactgccatagatagggataacg
4621 actcagcaattgtgtatatattccaaaactctgaaatacagtcagtcttaacttggatgg
4681 cgtggttatgatactctggtccccgacaggtactttccaaaataacttgacatagatgta
4741 ttcacttcatatgtttaaaaatacatttaagttttctaccgaataaatcttatttcaaa
4801 catgaaagacaattaaaacattcccacccacaaagcagtactcccgagcaattaactgga
4861 gttaattgtagcctgctacgttgactggttcagggtagttccccatccacccttggtcct
4921 gaggctggtggccttggtggtgcccttggcattttttgtgggaagattagaatgagagat
4981 agaaccagtgttgtggtaccaagtgtgagcacacctaaacaatatcctgttgcacaatgc
5041 tttttaacacatgggaaaactaggaatgcattgctgatgaagaagcaaggtatttaaac
5101 accagggcaggagtgccagagaaaatgtttccccatgggttcttaaaaaaaattcagctt
5161 ttaggtgcttttgtcatctcccggagtattcatcctcatgggaccatcttatttttactt
5221 attgtaatttactggggaaaggcagaactaaaaagtgtgtcatttatttttaaaataat
5281 tgctttgcttatgcctacactttctgtataactagccaattcaatactgtctatagtgtt
5341 agaaggaaaatgtgatttttttttttaaccagtattgagcttcataagcctagaatctg
5401 ccttatcaggtgaccagggttatggttgtttgcatgcaaatgtgaatttctggcataggg
5461 gacagcagcccaaatgtaaagtcatcgggcgtaatgaggaagaagggagtgaacatttac
5521 cgctttatgtacataacatatgcagtttacatactcatttgatccttataatcaaccttg
5581 aagaggagatactatcattcttatgttgcagatagccctctgaaggcccagagaggttaa
5641 gtaacttcccagaggtcatggccaagaagtagtggctccaagaactgaatgcaaattttt
5701 taaactgtagagttctgctttccactaaacaaagaactcctgccttgatggatggagggc
```

Figure 2B-5

```
5761 aaattctggtggaacttttgggccacctgaaagttctattcccaggactaagaggaattt
5821 cttttaatggatccagagagccaaggtcagagggagagatggcctgcatagtctcctgtg
5881 gatcacacccggccacccctccctctaggtttacagtggacttcttctgccctcctcc
5941 ttttctgtccttggccatctcagcctggcctctctgatccttccatcacagaaggatctt
6001 gaatctctgggaaatcaaacatcacagtagtgatcagaaagtgagtcctgtcttgtcacc
6061 ccatttctcatcagaacaaagcacgagatggaatgaccaaccagcattcttcatggtgga
6121 ctgcttatcattgaggatctttgggagataaagcacgctaagagctctggacagagaaaa
6181 acaggccctagaatatgggagtgggtgtttgtagggctcataggctaacaagcactttag
6241 ttgctggtttacattcaatgaaggaggattcatacccatggcattacaaggctaagcatg
6301 tgtatgactaaggaactatctgaaaaacatgcagcaaggtaagaaaatgtaccactcaac
6361 aagccagtgatgccacctttgtgcgcggggaggagagtgactaccattgttttttgtgt
6421 gacaaagctatcatggactattttaatcttggttttattgcttaaaatatattatttttc
6481 cctatgtgttgacaaggtatttctaatatcacactattaaatatatgcactaatctaaat
6541 aaaggtgtctgtatttctgtaatgcttattttaggggggaaatttgttttctttatgct
6601 tcagggtagagggattcccttgagtataggtcagcaaactctggcctgcagcctgtgtgt
6661 gcacgccccatgagccgaaaagtgggtcttatgttttcaaatggttaaaaataaataaaa
6721 aaatttgaaacatgtgaactatatgacattcagatttgtgttcataaataaagttttatt
6781 ggaacatatcc
```

Figure 2C. The cDNA (SEQ ID NO.: 6) and amino acid sequence (SEQ ID NO.: 7) of 254P1D6B v.3.
The start methionine is underlined. The open reading frame extends from nucleic acid 739-3930 including the stop codon.

```
  1 gctgccgcgggcggtgggcggggatccccgggggtgcaaccttgctccacctgtgctgc
 61 cctcggcgggcctggctggccccgcgcagagcggcggcggcgctcgctgtcactgccgga
121 ggtgagagcgcagcagtagcttcagcctgtcttgggcttggtccagattcgctcctctgg
181 ggctacgtcccggggaagaggaagcgaggattttgctggggtggggctgtacctcttaac
241 agcaggtgcgcgcgcgagggtgtgaacgtgtgtgtgtgtgtgtctgtgtgtgtgtgt
301 taagacctgcgatgacgacgaggaggaacaagtgggacggcgagtgatgctcagggccag
361 cagcaacgcatggggcgagcttcagtgtcgccagcagtgaccacaggtacggtatctact
421 tcccagagcgcctggccgagaaataggaaagagggcagccagtaggcaggccaatacccca
481 acaaaagtagaatcgagacgccctgagttcagaagttcttgaggccaaatctggctccta
541 aaaaacatcaaaggaagcttgcaccaaactctcttcagggccgcctcagaagcctgccat
601 cacccactgtgtggtgcacaatggcgccccccacaggtgtgctctcttcattgctgctgc
661 tggtgacaattgcagtttgcttatggtggatgcactcatggcaaaaaaatcactggtgag
  1                          M  T  R  L  G  W  P  S  P  C  C  A  R  K
721 catcatttaagaagacccATGACTAGACTGGGCTGGCCGAGCCCATGTTGTGCCCGTAAG
 15 Q  C  S  E  G  R  T  Y  S  N  A  V  I  S  P  N  L  E  T  T
781 CAGTGCAGCGAGGGGAGGACATATTCCAATGCAGTCATTTCACCTAACTTGGAAACCACC
 35 R  I  M  R  V  S  H  T  F  P  V  V  D  C  T  A  A  C  D
841 AGAATCATGCGGGTGTCTCACACCTTCCCTGTCGTAGACTGCACGGCCGCTTGCTGTGAC
 55 L  S  S  C  D  L  A  W  F  E  G  R  C  Y  L  V  S  C  P
```

Figure 2C-2

```
 901 CTGTCCAGCTGTGACCTGGCCTGGTGGTTCGAGGGCCGCTGCTACCTGGTGAGCTGCCCC
  75 H   K   E   N   C   E   P   K   K   M   G   P   I   R   S   Y   L   T   F   V
 961 CACAAAGAGAACTGTGAGCCCAAGAAGATGGGCCCCATCAGGTCTTATCTCACTTTTGTG
  95 L   R   P   V   Q   R   P   A   Q   L   L   D   Y   G   D   M   M   L   N   R
1021 CTCCGGCCTGTTCAGAGGCCTGCACAGCTGCTGGACTATGGGGACATGATGCTGAACAGG
 115 G   S   P   S   G   I   W   G   D   S   P   E   D   I   R   K   D   L   P   F
1081 GGCTCCCCCTCGGGGATCTGGGGGGACTCACCTGAGGATATCAGAAAGGACTTGCCCTTT
 135 L   G   K   D   W   G   L   E   E   M   S   E   Y   S   D   D   Y   R   E   L
1141 CTAGGCAAAGATTGGGGCCTAGAGGAGATGTCTGAGTACTCAGATGACTACCGGGAGCTG
 155 E   K   D   L   L   Q   P   S   G   K   Q   E   P   R   G   S   A   E   Y   T
1201 GAGAAGGACCTCTTGCAACCCAGTGGCAAGCAGGAGCCCAGAGGGAGTGCCGAGTACACG
 175 D   W   G   L   L   P   G   S   E   G   A   F   N   S   S   V   G   D   S   P
1261 GACTGGGGCCTACTGCCGGGCAGCGAGGGGGCCTTCAACTCCTCTGTTGGAGACAGTCCT
 195 A   V   P   A   E   T   Q   Q   D   P   E   L   H   Y   L   N   E   S   A   S
1321 GCGGTGCCAGCGGAGACGCAGCAGGACCCTGAGCTCCATTACCTGAATGAGTCGGCTTCA
 215 T   P   A   P   K   L   P   E   R   S   V   L   L   P   L   P   T   T   P   S
1381 ACCCCTGCCCCAAAACTCCCTGAGAGAAGTGTGTTGCTTCCCTTGCCGACTACTCCATCT
 235 S   G   E   V   L   E   K   E   K   A   S   Q   L   Q   E   Q   S   S   N   S
1441 TCAGGAGAGGTGTTGGAGAAAGAAAAGGCTTCTCAGCTCCAGGAACAATCCAGCAACAGC
 255 S   G   K   E   V   L   M   P   S   H   S   L   P   P   A   S   L   E   L   S
1501 TCTGGAAAAGAGGTTCTAATGCCTTCCCATAGTCTTCCTCCGGCAAGCCTGGAGCTCAGC
 275 S   V   T   V   E   K   S   P   V   L   T   V   T   P   G   S   T   E   H   S
1561 TCAGTCACCGTGGAGAAAAGCCCAGTGCTCACAGTCACCCCGGGGAGTACAGAGCACAGC
 295 I   P   T   P   P   T   S   A   A   P   S   E   S   T   P   S   E   L   P   I
1621 ATCCCAACACCTCCCACTAGCGCAGCCCCTCTGAGTCCACCCCATCTGAGCTACCCATA
 315 S   P   T   T   A   P   R   T   V   K   E   L   T   V   S   A   G   D   N   L
1681 TCTCCTACCACTGCTCCCAGGACAGTGAAAGAACTTACGGTATCGGCTGGAGATAACCTA
 335 I   I   T   L   P   D   N   E   V   E   L   K   A   F   V   A   P   A   P   P
1741 ATTATAACTTTACCCGACAATGAAGTTGAACTGAAGGCCTTTGTTGCGCCAGCGCCACCT
 355 V   E   T   T   Y   N   Y   E   W   N   L   I   S   H   P   T   D   Y   Q   G
1801 GTAGAAACAACCTACAACTATGAATGGAATTTAATAAGCCACCCCACAGACTACCAAGGT
 375 E   I   K   Q   G   H   K   Q   T   L   N   L   S   Q   L   S   V   G   L   Y
1861 GAAATAAAACAAGGACACAAGCAAACTCTTAACCTCTCTCAATTGTCCGTCGGACTTTAT
 395 V   F   K   V   T   V   S   S   E   N   A   F   G   E   G   F   V   N   V   T
1921 GTCTTCAAAGTCACTGTTTCTAGTGAAAACGCCTTTGGAGAAGGATTTGTCAATGTCACT
 415 V   K   P   A   R   R   V   N   L   P   P   V   A   V   V   S   P   Q   L   Q
1981 GTTAAGCCTGCCAGAAGAGTCAACCTGCCACCTGTAGCAGTTGTTTCTCCCCAACTGCAA
 435 E   L   T   L   P   L   T   S   A   L   I   D   G   S   Q   S   T   D   D   T
2041 GAGCTCACTTTGCCTTTGACGTCAGCCCTCATTGATGGCAGCCAAAGTACAGATGATACT
 455 E   I   V   S   Y   H   W   E   E   I   N   G   P   F   I   E   E   K   T   S
2101 GAAATAGTGAGTTATCATTGGGAAGAAATAAACGGGCCCTTCATAGAAGAGAAGACTTCA
```

Figure 2C-3

```
 475 V  D  S  P  V  L  R  L  S  N  L  D  P  G  N  Y  S  F  R  L
2161 GTTGACTCTCCCGTCTTACGCTTGTCTAACCTTGATCCTGGTAACTATAGTTTCAGGTTG
 495 T  V  T  D  S  D  G  A  T  N  S  T  T  A  A  L  I  V  N  N
2221 ACTGTTACAGACTCGGACGGAGCCACTAACTCTACAACTGCAGCCCTAATAGTGAACAAT
 515 A  V  D  Y  P  P  V  A  N  A  G  P  N  H  T  I  T  L  P  Q
2281 GCTGTGGACTACCCACCAGTTGCTAATGCAGGACCAAATCACACCATAACTTTGCCCCAA
 535 N  S  I  T  L  N  G  N  Q  S  S  D  D  H  Q  I  V  L  Y  E
2341 AACTCCATCACTTTGAATGGAAACCAGAGCAGTGACGATCACCAGATTGTCCTCTATGAG
 555 W  S  L  G  P  G  S  E  G  K  H  V  V  M  Q  G  V  Q  T  P
2401 TGGTCCCTGGGTCCTGGGAGTGAGGGCAAACATGTGGTCATGCAGGGAGTACAGACGCCA
 575 Y  L  H  L  S  A  M  Q  E  G  D  Y  T  F  Q  L  K  V  T  D
2461 TACCTTCATTTATCTGCAATGCAGGAAGGAGATTATACATTTCAGCTGAAGGTGACAGAT
 595 S  S  R  Q  Q  S  T  A  V  V  T  V  I  V  Q  P  E  N  N  R
2521 TCTTCAAGGCAACAGTCTACTGCTGTGGTGACTGTGATTGTCCAGCCTGAAAACAATAGA
 615 P  P  V  A  V  A  G  P  D  K  E  L  I  F  P  V  E  S  A  T
2581 CCTCCAGTGGCTGTGGCCGGCCCTGATAAAGAGCTGATCTTCCCAGTGGAAAGTGCTACC
 635 L  D  G  S  S  S  D  D  H  G  I  V  F  Y  H  W  E  H  V
2641 CTGGATGGGAGCAGCAGCAGCGATGACCACGGCATTGTCTTCTACCACTGGGAGCACGTC
 655 R  G  P  S  A  V  E  M  E  N  I  D  K  A  I  A  T  V  T  G
2701 AGAGGCCCCAGTGCAGTGGAGATGGAAAATATTGACAAAGCAATAGCCACTGTGACTGGT
 675 L  Q  V  G  T  Y  H  F  R  L  T  V  K  D  Q  Q  G  L  S  S
2761 CTCCAGGTGGGGACCTACCACTTCCGTTTGACAGTGAAAGACCAGCAGGGACTGAGCAGC
 695 T  S  T  L  T  V  A  V  K  K  E  N  N  S  P  P  R  A  R  A
2821 ACGTCCACCCTCACTGTGGCTGTGAAGAAGGAAAATAATAGTCCTCCCAGAGCCCGGGCT
 715 G  G  R  H  V  L  V  L  P  N  N  S  I  T  L  D  G  S  R  S
2881 GGTGGCAGACATGTTCTTGTGCTTCCCAATAATTCCATTACTTTGGATGGTTCAAGGTCT
 735 T  D  D  Q  R  I  V  S  Y  L  W  I  R  D  G  Q  S  P  A  A
2941 ACTGATGACCAAAGAATTGTGTCCTATCTGTGGATCCGGGATGGCCAGAGTCCAGCAGCT
 755 G  D  V  I  D  G  S  D  H  S  V  A  L  Q  L  T  N  L  V  E
3001 GGAGATGTCATCGATGGCTCTGACCACAGTGTGGCTCTGCAGCTTACGAATCTGGTGGAG
 775 G  V  Y  T  F  H  L  R  V  T  D  S  Q  G  A  S  D  T  D  T
3061 GGGGTGTACACTTTCCACTTGCGAGTCACCGACAGTCAGGGGGCCTCGGACACAGACACT
 795 A  T  V  E  V  Q  P  D  P  R  K  S  G  L  V  E  L  T  L  Q
3121 GCCACTGTGGAAGTGCAGCCAGACCCTAGGAAGAGTGGCCTGGTGGAGCTGACCCTGCAG
 815 V  G  V  G  Q  L  T  E  Q  R  K  D  T  L  V  R  Q  L  A  V
3181 GTTGGTGTTGGGCAGCTGACAGAGCAGCGGAAGGACACCCTTGTGAGGCAGCTGGCTGTG
 835 L  L  N  V  L  D  S  D  I  K  V  Q  K  I  R  A  H  S  D  L
3241 CTGCTGAACGTGCTGGACTCGGACATTAAGGTCCAGAAGATTCGGGCCCACTCGGATCTC
 855 S  T  V  I  V  F  Y  V  Q  S  R  P  P  F  K  V  L  K  A  A
3301 AGCACCGTGATTGTGTTTTATGTACAGAGCAGGCCGCCTTTCAAGGTTCTCAAAGCTGCT
 875 E  V  A  R  N  L  H  M  R  L  S  K  E  K  A  D  F  L  L  F
```

Figure 2C-4

```
3361 GAAGTGGCCCGAAATCTGCACATGCGGCTCTCAAAGGAGAAGGCTGACTTCTTGCTTTTC
 895 K  V  L  R  V  D  T  A  G  C  L  L  K  C  S  G  H  G  H  C
3421 AAGGTCTTGAGGGTTGATACAGCAGGTTGCCTTCTGAAGTGTTCTGGCCATGGTCACTGC
 915 D  P  L  T  K  R  C  I  C  S  H  L  W  M  E  N  L  I  Q  R
3481 GACCCCCTCACAAAGCGCTGCATTTGCTCTCACTTATGGATGGAGAACCTTATACAGCGT
 935 Y  I  W  D  G  E  S  N  C  E  W  S  I  F  Y  V  T  V  L  A
3541 TATATCTGGGATGGAGAGAGCAACTGTGAGTGGAGTATATTCTATGTGACAGTGTTGGCT
 955 F  T  L  I  V  L  T  G  G  F  T  W  L  C  I  C  C  C  K  R
3601 TTTACTCTTATTGTGCTAACAGGAGGTTTCACTTGGCTTTGCATCTGCTGCTGCAAAAGA
 975 Q  K  R  T  K  I  R  K  K  T  K  Y  T  I  L  D  N  M  D  E
3661 CAAAAAAGGACTAAAATCAGGAAAAAAACAAAGTACACCATCCTGGATAACATGGATGAA
 995 Q  E  R  M  E  L  R  P  K  Y  G  I  K  H  R  S  T  E  H  N
3721 CAGGAAAGAATGGAACTGAGGCCCAAATATGGTATCAAGCACCGAAGCACAGAGCACAAC
1015 S  S  L  M  V  S  E  S  E  F  D  S  D  Q  D  T  I  F  S  R
3781 TCCAGCCTGATGGTATCCGAGTCTGAGTTTGACAGTGACCAGGACACAATCTTCAGCCGA
1035 E  K  M  E  R  G  N  P  K  V  S  M  N  G  S  I  R  N  G  A
3841 GAAAAGATGGAGAGAGGGAATCCAAAGGTTTCCATGAATGGTTCCATCAGAAATGGAGCT
1055 S  F  S  Y  C  S  K  D  R  *
3901 TCCTTCAGTTATTGCTCAAAGGACAGATAAtggcgcagttcattgtaaagtggaaggacc
3961 ccttgaatccaagaccagtcagtgggagttacagcacaaaacccactcttttagaatagt
4021 tcattgaccttcttccccagtgggttagatgtgtatccccacgtactaaaagaccggttt
4081 ttgaaggcacaaaacaaaaactttgctcttttaactgagatgcttgttaatagaaataaa
4141 ggctgggtaaaactctaaggtatatacttaaaagagttttgagttttttgtagctggcaca
4201 atctcatattaaagatgaacaacgatttctatctgtagaaccttagagaaggtgaatgaa
4261 acaaggttttaaaaagggatgatttctgtcttagccgctgtgattgcctctaaggaacag
4321 cattctaaacacggtttctcttgtaggacctgcagtcagatggctgtgtatgttaaaata
4381 gcttgtctaagaggcacgggccatctgtggaggtacggagtcttgcatgtagcaagcttt
4441 ctgtgctgacggcaacactcgcacagtgccaagccctcctggttttttaattctgtgctat
4501 gtcaatggcagttttcatctctctcaagaaagcagctgttggccattcaagagctaagga
4561 agaatcgtattctaaggactgaggcaatagaaaggggaggaggagcttaatgccgtgcag
4621 gttgaaggtagcattgtaacattatcttttctttctctaagaaaaactacactgactcct
4681 ctcggtgttgtttagcagtatagttctctaatgtaaacggatccccagtttacattaaat
4741 gcaatagaagtgattaattcattaagcatttattatgttctgtaggctgtgcgtttggac
4801 tgccatagatagggataacgactcagcaattgtgtatatattccaaaactctgaaataca
4861 gtcagtcttaacttggatggcgtggttatgatactctggtccccgacaggtactttccaa
4921 aataacttgacatagatgtattcacttcatatgtttaaaaatacatttaagttttttctac
4981 cgaataaatcttatttcaaacatgaaagacaattaaaacattcccacccacaaagcagta
5041 ctcccgagcaattaactggagttaattgtagcctgctacgttgactggttcagggtagtt
5101 ccccatccaccttggtcctgaggctggtggccttggtggtgcccttggcatttttttgtg
5161 ggaagattagaatgagagatagaaccagtgttgtggtaccaagtgtgagcacacctaaac
5221 aatatcctgttgcacaatgctttttttaacacatgggaaaactaggaatgcattgctgatg
```

Figure 2C-5

```
5281 aagaagcaaggtatttaaacaccagggcaggagtgccagagaaaatgtttccccatgggt
5341 tcttaaaaaaaattcagcttttaggtgcttttgtcatctcccggagtattcatcctcatg
5401 ggaccatcttattttacttattgtaatttactggggaaaggcagaactaaaaagtgtgt
5461 catttttatttttaaataattgctttgcttatgcctacactttctgtataactagccaat
5521 tcaatactgtctatagtgttagaaggaaaatgtgattttttttttttaaccagtattgag
5581 cttcataagcctagaatctgccttatcaggtgaccagggttatggttgtttgcatgcaaa
5641 tgtgaatttctggcataggggacagcagcccaaatgtaaagtcatcgggcgtaatgagga
5701 agaagggagtgaacatttaccgctttatgtacataacatatgcagtttacatactcattt
5761 gatccttataatcaaccttgaagaggagatactatcattcttatgttgcagatagccctc
5821 tgaaggcccagagaggttaagtaacttcccagaggtcatggccaagaagtagtggctcca
5881 agaactgaatgcaaatttttaaactgtagagttctgctttccactaaacaaagaactcc
5941 tgccttgatggatggagggcaaattctggtggaacttttgggccacctgaaagttctatt
6001 cccaggactaagaggaatttcttttaatggatccagagagccaaggtcagagggagagat
6061 ggcctgcatagtctcctgtggatcacacccgggccacccctccctctaggtttacagtgg
6121 acttcttctgccctcctccttttctgtccttggccatctcagcctggcctctctgatcc
6181 ttccatcacagaaggatcttgaatctctgggaaatcaaacatcacagtagtgatcagaaa
6241 gtgagtcctgtcttgtcaccccatttctcatcagaacaaagcacgagatggaatgaccaa
6301 ccagcattcttcatggtggactgcttatcattgaggatctttgggagataaagcacgcta
6361 agagctctggacagagaaaaacaggccctagaatatgggagtgggtgtttgtagggctca
6421 taggctaacaagcactttagttgctggtttacattcaatgaaggaggattcatacccatg
6481 gcattacaaggctaagcatgtgtatgactaaggaactatctgaaaaacatgcagcaaggt
6541 aagaaaatgtaccactcaacaagccagtgatgccacctttgtgcgcggggaggagagtg
6601 actaccattgttttttgtgtgacaaagctatcatggactattttaatcttggttttattg
6661 cttaaaatatattatttttccctatgtgttgacaaggtatttctaatatcacactattaa
6721 atatatgcactaatctaaataaaggtgtctgtattttctgtaatgcttattttaggggg
6781 aaatttgttttctttatgcttcagggtagagggattcccttgagtataggtcagcaaact
6841 ctggcctgcagcctgtgtgtgcacgccccatgagccgaaaagtgggtcttatgttttcaa
6901 atggttaaaaataaataaaaaaatttgaaacatgtgaactatatgacattcagatttgtg
6961 ttcataaataaagttttattggaacatatcc
```

Figure 2D. 254P1D6B v.4 through v.20, SNP variants of 254P1D6B v.1. The 254P1D6B v.4 through v.20 proteins have 1072 amino acids. Variants 254P1D6B v.4 through v.20 are variants with single nucleotide difference from 254P1D6B v.1. 254P1D6B v.5 and v.6 proteins differ from 254P1D6B v.1 by one amino acid. 254P1D6B v.4 and v.7 through v.20 proteins code for the same protein as v.1. Though these SNP variants are shown separately, they can also occur in any combinations and in any of the transcript variants listed above in Figures 2A, Figure 2B and Figure 2C.

| Variant | Nucleic acid position | Nucleic Acid Variation | Amino Acid Position | Amino Acid Variation |
|---|---|---|---|---|
| 254P1D6B v.4 | 286 | C/G | Silent variant | |
| 254P1D6B v.5 | 935 | C/A | 142 | P=>T |
| 254P1D6B v.6 (Identical AA as v.2) | 980 | T/G | 157 | S=>A |
| 254P1D6B v.7 | 2347 | G/A | Silent variant | |
| 254P1D6B v.8 | 3762 | C/T | Silent variant | |
| 254P1D6B v.9 | 3772 | A/G | Silent variant | |
| 254P1D6B v.10 | 3955 | C/T | Silent variant | |
| 254P1D6B v.11 | 4096 | C/T | Silent variant | |
| 254P1D6B v.12 | 4415 | G/A | Silent variant | |
| 254P1D6B v.13 | 4519 | G/A | Silent variant | |
| 254P1D6B v.14 | 4539 | A/G | Silent variant | |
| 254P1D6B v.15 | 4614 | G/T | Silent variant | |
| 254P1D6B v.16 | 5184 | G/C | Silent variant | |
| 254P1D6B v.17 | 5528 | T/G | Silent variant | |
| 254P1D6B v.18 | 5641 | G/A | Silent variant | |
| 254P1D6B v.19 | 6221 | T/C | Silent variant | |
| 254P1D6B v.20 | 6223 | G/A | Silent variant | |

Figure 3:

Figure 3A. Amino acid sequence 254P1D6B v.1 clone LCP-3 (SEQ ID NO.: 8). The 254P1D6B v.1 clone LCP-3 protein has 1072 amino acids.

```
   1 MAPPTGVLSS LLLLVTIAGC ARKQCSEGRT YSNAVISPNL ETTRIMRVSH TFPVVDCTAA
  61 CCDLSSCDLA WWFEGRCYLV SCPHKENCEP KKMGPIRSYL TFVLRPVQRP AQLLDYGDMM
 121 LNRGSPSGIW GDSPEDIRKD LPFLGKDWGL EEMSEYSDDY RELEKDLLQP SGKQEPRGSA
 181 EYTDWGLLPG SEGAFNSSVG DSPAVPAETQ QDPELHYLNE SASTPAPKLP ERSVLLPLPT
 241 TPSSGEVLEK EKASQLQEQS SNSSGKEVLM PSHSLPPASL ELSSVTVEKS PVLTVTPGST
 301 EHSIPTPPTS AAPSESTPSE LPISPTTAPR TVKELTVSAG DNLIITLPDN EVELKAFVAP
 361 APPVETTYNY EWNLISHPTD YQGEIKQGHK QTLNLSQLSV GLYVFKVTVS SENAFGEGFV
 421 NVTVKPARRV NLPPVAVVSP QLQELTLPLT SALIDGSQST DDTEIVSYHW EEINGPFIEE
 481 KTSVDSPVLR LSNLDPGNYS FRLTVTDSDG ATNSTTAALI VNNAVDYPPV ANAGPNHTIT
 541 LPQNSITLNG NQSSDDHQIV LYEWSLGPGS EGKHVVMQGV QTPYLHLSAM QEGDYTFQLK
 601 VTDSSRQQST AVVTVIVQPE NNRPPVAVAG PDKELIFPVE SATLDGSSSS DDHGIVFYHW
 661 EHVRGPSAVE MENIDKAIAT VTGLQVGTYH FRLTVKDQQG LSSTSTLTVA VKKENNSPPR
 721 ARAGGRHVLV LPNNSITLDG SRSTDDQRIV SYLWIRDGQS PAAGDVIDGS DHSVALQLTN
 781 LVEGVYTFHL RVTDSQGASD TDTATVEVQP DPRKSGLVEL TLQVGVGQLT EQRKDTLVRQ
 841 LAVLLNVLDS DIKVQKIRAH SDLSTVIVFY VQSRPPFKVL KAAEVARNLH MRLSKEKADF
 901 LLFKVLRVDT AGCLLKCSGH GHCDPLTKRC ICSHLWMENL IQRYIWDGES NCEWSIFYVT
 961 VLAFTLIVLT GGFTWLCICC CKRQKRTKIR KKTKYTILDN MDEQERMELR PKYGIKHRST
1021 EHNSSLMVSE SEFDSDQDTI FSREKMERGN PKVSMNGSIR NGASFSYCSK DR
```

Figure 3B. Amino acid sequence 254P1D6B v.2 (SEQ ID NO.: 9). The 254P1D6B v.2 protein has 1072 amino acids.

```
   1 MAPPTGVLSS LLLLVTIAGC ARKQCSEGRT YSNAVISPNL ETTRIMRVSH TFPVVDCTAA
  61 CCDLSSCDLA WWFEGRCYLV SCPHKENCEP KKMGPIRSYL TFVLRPVQRP AQLLDYGDMM
 121 LNRGSPSGIW GDSPEDIRKD LPFLGKDWGL EEMSEYADDY RELEKDLLQP SGKQEPRGSA
 181 EYTDWGLLPG SEGAFNSSVG DSPAVPAETQ QDPELHYLNE SASTPAPKLP ERSVLLPLPT
 241 TPSSGEVLEK EKASQLQEQS SNSSGKEVLM PSHSLPPASL ELSSVTVEKS PVLTVTPGST
 301 EHSIPTPPTS AAPSESTPSE LPISPTTAPR TVKELTVSAG DNLIITLPDN EVELKAFVAP
 361 APPVETTYNY EWNLISHPTD YQGEIKQGHK QTLNLSQLSV GLYVFKVTVS SENAFGEGFV
 421 NVTVKPARRV NLPPVAVVSP QLQELTLPLT SALIDGSQST DDTEIVSYHW EEINGPFIEE
 481 KTSVDSPVLR LSNLDPGNYS FRLTVTDSDG ATNSTTAALI VNNAVDYPPV ANAGPNHTIT
 541 LPQNSITLNG NQSSDDHQIV LYEWSLGPGS EGKHVVMQGV QTPYLHLSAM QEGDYTFQLK
 601 VTDSSRQQST AVVTVIVQPE NNRPPVAVAG PDKELIFPVE SATLDGSSSS DDHGIVFYHW
 661 EHVRGPSAVE MENIDKAIAT VTGLQVGTYH FRLTVKDQQG LSSTSTLTVA VKKENNSPPR
 721 ARAGGRHVLV LPNNSITLDG SRSTDDQRIV SYLWIRDGQS PAAGDVIDGS DHSVALQLTN
 781 LVEGVYTFHL RVTDSQGASD TDTATVEVQP DPRKSGLVEL TLQVGVGQLT EQRKDTLVRQ
 841 LAVLLNVLDS DIKVQKIRAH SDLSTVIVFY VQSRPPFKVL KAAEVARNLH MRLSKEKADF
 901 LLFKVLRVDT AGCLLKCSGH GHCDPLTKRC ICSHLWMENL IQRYIWDGES NCEWSIFYVT
```

Figure 3B-2

```
 961 VLAFTLIVLT GGFTWLCICC CKRQKRTKIR KKTKYTILDN MDEQERMELR PKYGIKHRST
1021 EHNSSLMVSE SEFDSDQDTI FSREKMERGN PKVSMNGSIR NGASFSYCSK DR
```

Figure 3C. Amino acid sequence 254P1D6B v.3 (SEQ ID NO: 10). The 254P1D6B v.3 protein has 1063 amino acids.

```
   1 MTRLGWPSPC CARKQCSEGR TYSNAVISPN LETTRIMRVS HTFPVVDCTA ACCDLSSCDL
  61 AWWFEGRCYL VSCPHKENCE PKKMGPIRSY LTFVLRPVQR PAQLLDYGDM MLNRGSPSGI
 121 WGDSPEDIRK DLPFLGKDWG LEEMSEYSDD YRELEKDLLQ PSGKQEPRGS AEYTDWGLLP
 181 GSEGAFNSSV GDSPAVPAET QQDPELHYLN ESASTPAPKL PERSVLLPLP TTPSSGEVLE
 241 KEKASQLQEQ SSNSSGKEVL MPSHSLPPAS LELSSVTVEK SPVLTVTPGS TEHSIPTPPT
 301 SAAPSESTPS ELPISPTTAP RTVKELTVSA GDNLIITLPD NEVELKAFVA PAPPVETTYN
 361 YEWNLISHPT DYQGEIKQGH KQTLNLSQLS VGLYVFKVTV SSENAFGEGF VNVTVKPARR
 421 VNLPPVAVVS PQLQELTLPL TSALIDGSQS TDDTEIVSYH WEEINGPFIE EKTSVDSPVL
 481 RLSNLDPGNY SFRLTVTDSD GATNSTTAAL IVNNAVDYPP VANAGPNHTI TLPQNSITLN
 541 GNQSSDDHQI VLYEWSLGPG SEGKHVVMQG VQTPYLHLSA MQEGDYTFQL KVTDSSRQQS
 601 TAVVTVIVQP ENNRPPVAVA GPDKELIFPV ESATLDGSSS SDDHGIVFYH WEHVRGPSAV
 661 EMENIDKAIA TVTGLQVGTY HFRLTVKDQQ GLSSTSTLTV AVKKENNSPP RARAGGRHVL
 721 VLPNNSITLD GSRSTDDQRI VSYLWIRDGQ SPAAGDVIDG SDHSVALQLT NLVEGVYTFH
 781 LRVTDSQGAS DTDTATVEVQ PDPRKSGLVE LTLQVGVGQL TEQRKDTLVR QLAVLLNVLD
 841 SDIKVQKIRA HSDLSTVIVF YVQSRPPFKV LKAAEVARNL HMRLSKEKAD FLLFKVLRVD
 901 TAGCLLKCSG HGHCDPLTKR CICSHLWMEN LIQRYIWDGE SNCEWSIFYV TVLAFTLIVL
 961 TGGFTWLCIC CKRQKRTKI RKKTKYTILD NMDEQERMEL RPKYGIKHRS TEHNSSLMVS
1021 ESEFDSDQDT IFSREKMERG NPKVSMNGSI RNGASFSYCS KDR
```

Figure 3D. Amino acid sequence 254P1D6B v.5 (SEQ ID NO: 11). The 254P1D6B v.5 protein has 1072 amino acids.

```
   1 MAPPTGVLSS LLLLVTIAGC ARKQCSEGRT YSNAVISPNL ETTRIMRVSH TFPVVDCTAA
  61 CCDLSSCDLA WWFEGRCYLV SCPHKENCEP KKMGPIRSYL TFVLRPVQRP AQLLDYGDMM
 121 LNRGSPSGIW GDSPEDIRKD LTFLGKDWGL EEMSEYSDDY RELEKDLLQP SGKQEPRGSA
 181 EYTDWGLLPG SEGAFNSSVG DSPAVPAETQ QDPELHYLNE SASTPAPKLP ERSVLLPLPT
 241 TPSSGEVLEK EKASQLQEQS SNSSGKEVLM PSHSLPPASL ELSSVTVEKS PVLTVTPGST
 301 EHSIPTPPTS AAPSESTPSE LPISPTTAPR TVKELTVSAG DNLIITLPDN EVELKAFVAP
 361 APPVETTYNY EWNLISHPTD YQGEIKQGHK QTLNLSQLSV GLYVFKVTVS SENAFGEGFV
 421 NVTVKPARRV NLPPVAVVSP QLQELTLPLT SALIDGSQST DDTEIVSYHW EEINGPFIEE
 481 KTSVDSPVLR LSNLDPGNYS FRLTVTDSDG ATNSTTAALI VNNAVDYPPV ANAGPNHTIT
 541 LPQNSITLNG NQSSDDHQIV LYEWSLGPGS EGKHVVMQGV QTPYLHLSAM QEGDYTFQLK
 601 VTDSSRQQST AVVTVIVQPE NNRPPVAVAG PDKELIFPVE SATLDGSSSS DDHGIVFYHW
 661 EHVRGPSAVE MENIDKAIAT VTGLQVGTYH FRLTVKDQQG LSSTSTLTVA VKKENNSPPR
 721 ARAGGRHVLV LPNNSITLDG SRSTDDQRIV SYLWIRDGQS PAAGDVIDGS DHSVALQLTN
 781 LVEGVYTFHL RVTDSQGASD TDTATVEVQP DPRKSGLVEL TLQVGVGQLT EQRKDTLVRQ
 841 LAVLLNVLDS DIKVQKIRAH SDLSTVIVFY VQSRPPFKVL KAAEVARNLH MRLSKEKADF
```

Figure 3D-2

```
 901 LLFKVLRVDT AGCLLKCSGH GHCDPLTKRC ICSHLWMENL IQRYIWDGES NCEWSIFYVT
 961 VLAFTLIVLT GGFTWLCICC CKRQKRTKIR KKTKYTILDN MDEQERMELR PKYGIKHRST
1021 EHNSSLMVSE SEFDSDQDTI FSREKMERGN PKVSMNGSIR NGASFSYCSK DR
```

Figure 3E. Amino acid sequence 254P1D6B v.6 (SEQ ID NO: 12). The 254P1D6B v.6 protein has 1072 amino acids.

```
   1 MAPPTGVLSS LLLLVTIAGC ARKQCSEGRT YSNAVISPNL ETTRIMRVSH TFPVVDCTAA
  61 CCDLSSCDLA WWFEGRCYLV SCPHKENCEP KKMGPIRSYL TFVLRPVQRP AQLLDYGDMM
 121 LNRGSPSGIW GDSPEDIRKD LPFLGKDWGL EEMSEYADDY RELEKDLLQP SGKQEPRGSA
 181 EYTDWGLLPG SEGAFNSSVG DSPAVPAETQ QDPELHYLNE SASTPAPKLP ERSVLLPLPT
 241 TPSSGEVLEK EKASQLQEQS SNSSGKEVLM PSHSLPPASL ELSSVTVEKS PVLTVTPGST
 301 EHSIPTPPTS AAPSESTPSE LPISPTTAPR TVKELTVSAG DNLIITLPDN EVELKAFVAP
 361 APPVETTYNY EWNLISHPTD YQGEIKQGHK QTLNLSQLSV GLYVFKVTVS SENAFGEGFV
 421 NVTVKPARRV NLPPVAVVSP QLQELTLPLT SALIDGSQST DDTEIVSYHW EEINGPFIEE
 481 KTSVDSPVLR LSNLDPGNYS FRLTVTDSDG ATNSTTAALI VNNAVDYPPV ANAGPNHTIT
 541 LPQNSITLNG NQSSDDHQIV LYEWSLGPGS EGKHVVMQGV QTPYLHLSAM QEGDYTFQLK
 601 VTDSSRQQST AVVTVIVQPE NNRPPVAVAG PDKELIFPVE SATLDGSSSS DDHGIVFYHW
 661 EHVRGPSAVE MENIDKAIAT VTGLQVGTYH FRLTVKDQQG LSSTSTLTVA VKKENNSPPR
 721 ARAGGRHVLV LPNNSITLDG SRSTDDQRIV SYLWIRDGQS PAAGDVIDGS DHSVALQLTN
 781 LVEGVYTFHL RVTDSQGASD TDTATVEVQP DPRKSGLVEL TLQVGVGQLT EQRKDTLVRQ
 841 LAVLLNVLDS DIKVQKIRAH SDLSTVIVFY VQSRPPFKVL KAAEVARNLH MRLSKEKADF
 901 LLFKVLRVDT AGCLLKCSGH GHCDPLTKRC ICSHLWMENL IQRYIWDGES NCEWSIFYVT
 961 VLAFTLIVLT GGFTWLCICC CKRQKRTKIR KKTKYTILDN MDEQERMELR PKYGIKHRST
1021 EHNSSLMVSE SEFDSDQDTI FSREKMERGN PKVSMNGSIR NGASFSYCSK DR
```

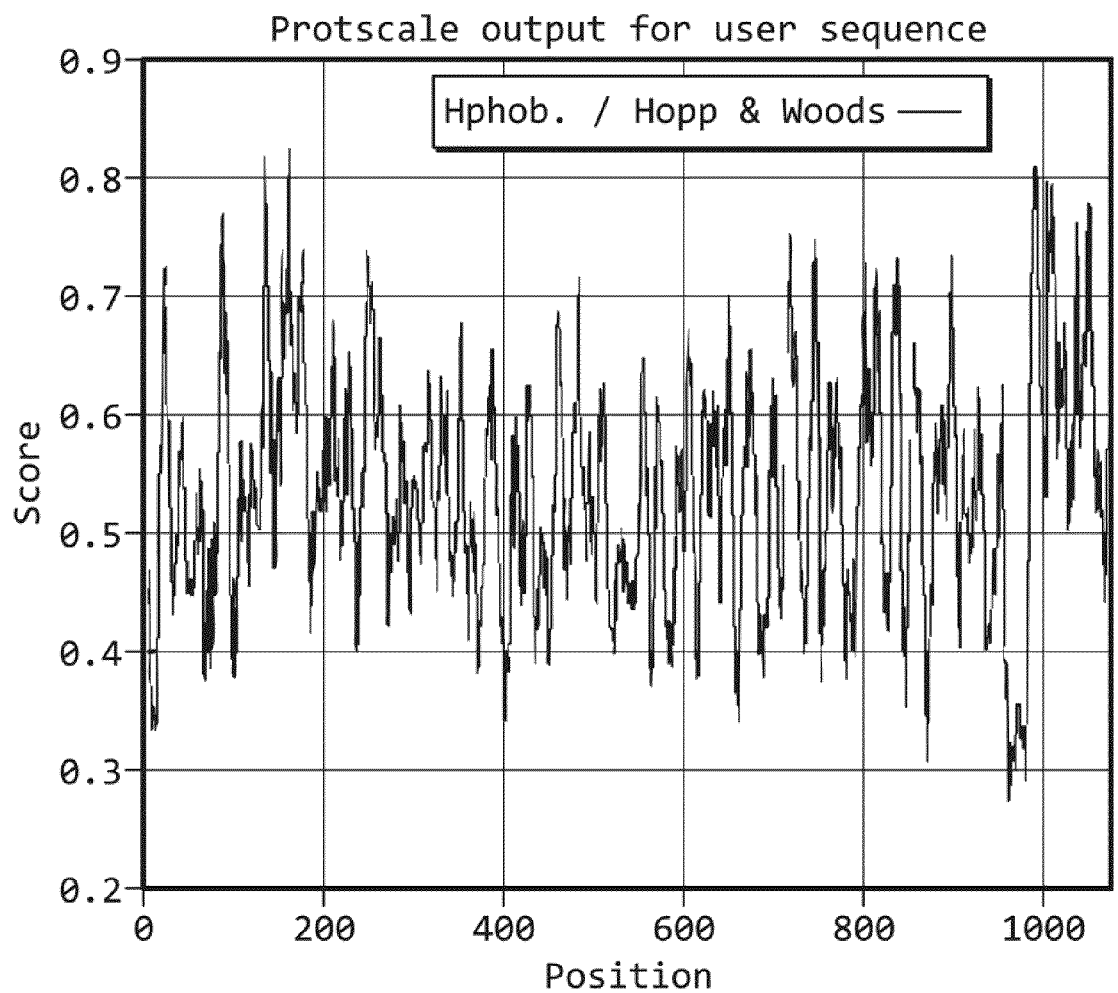

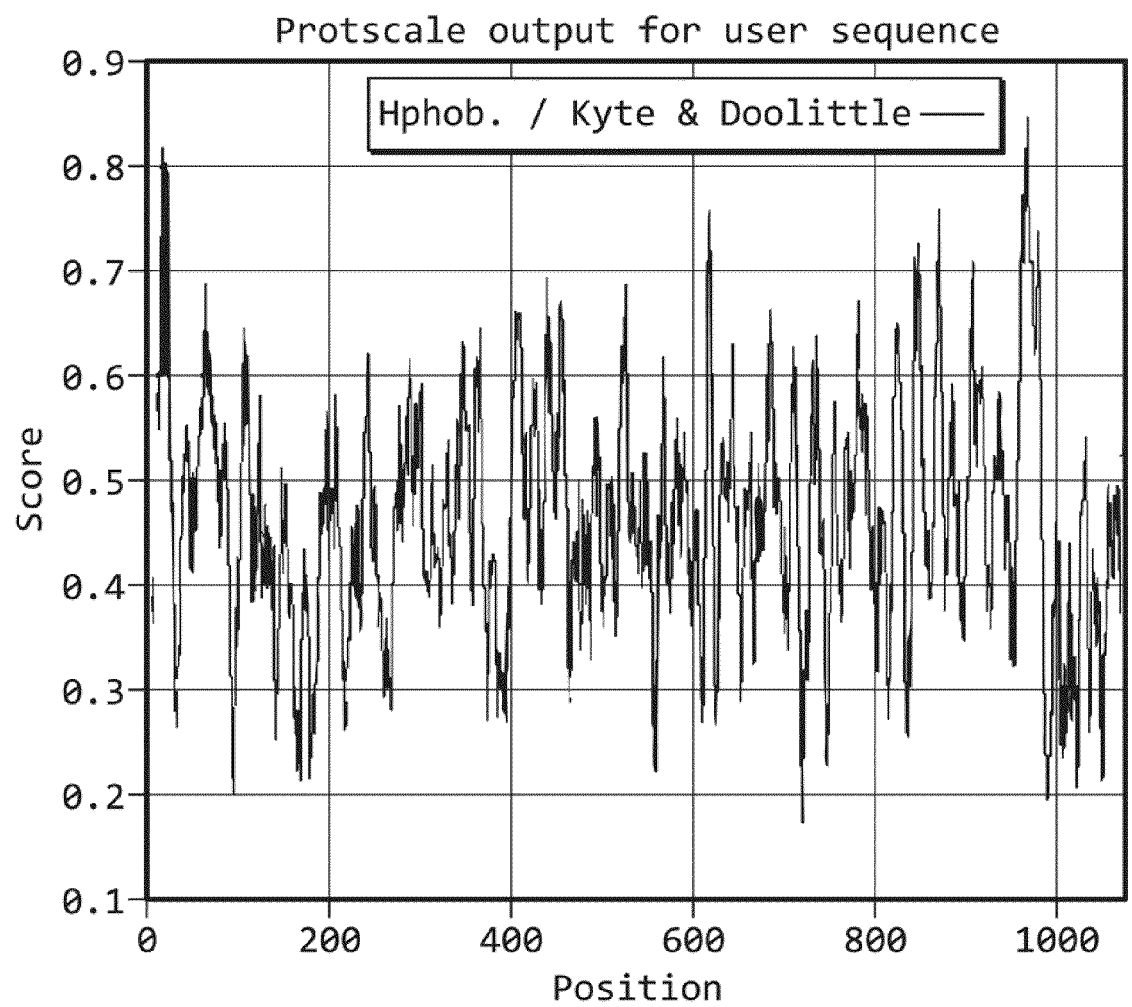
Figure 6: 254P1D6B variant 1 Hydrophilicity Profile
(Kyte J., Doolittle R.F., 1982. J. Mol. Biol. 157:105-132)

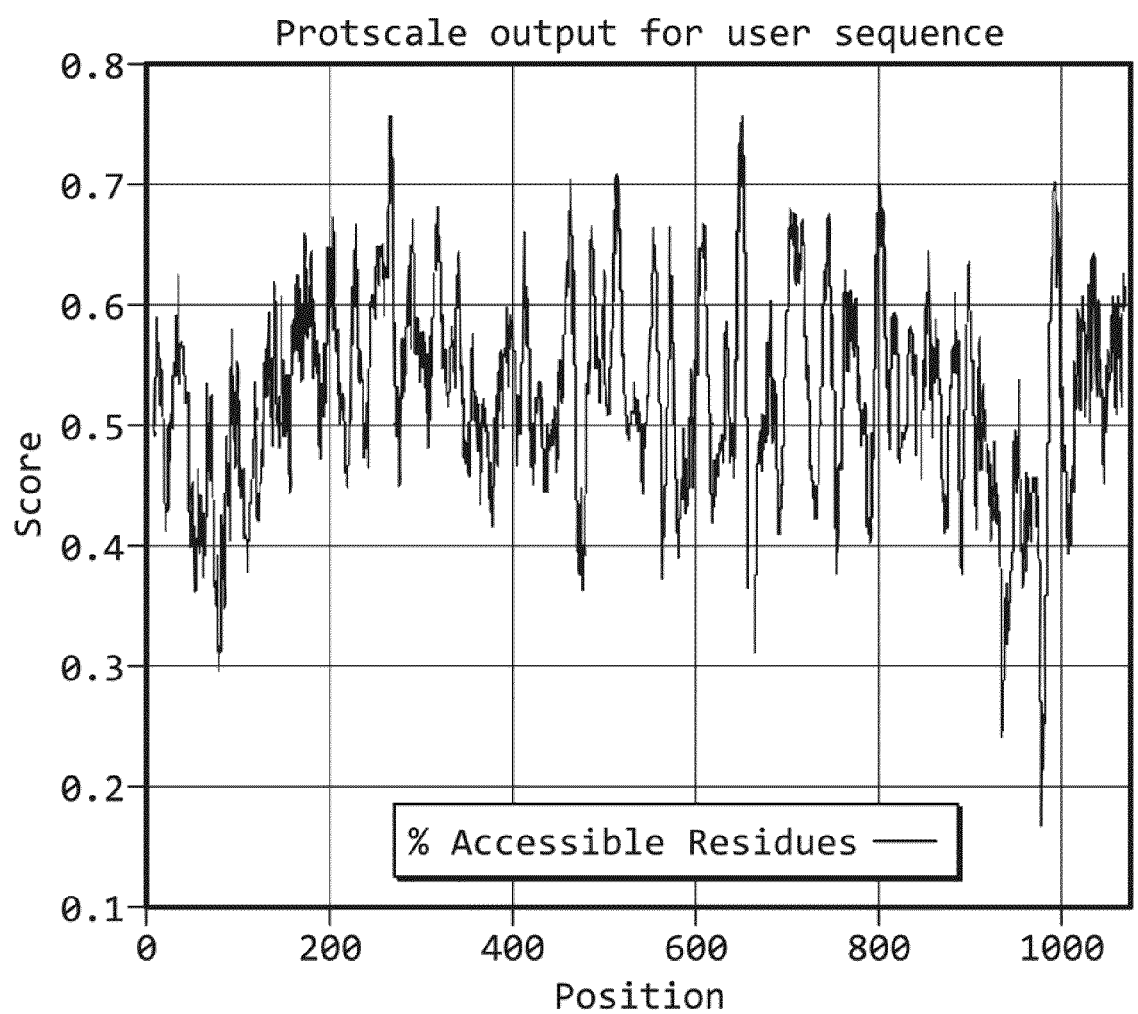
Figure 7: 254P1D6B variant 1
% Accessible Residues Profile
(Janin J., 1979. Nature 277:491-492)

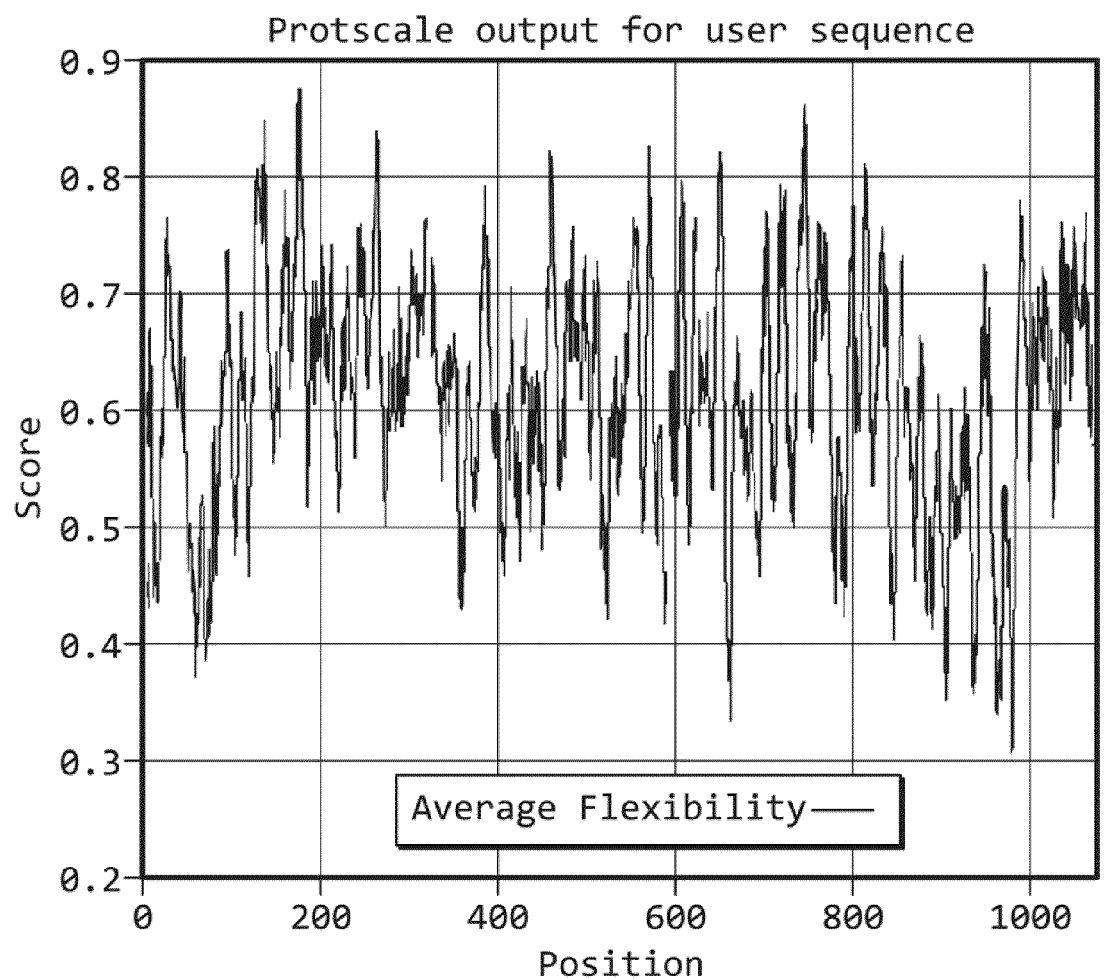
Figure 8: 254P1D6B variant 1 Average Flexibility Profile
(Bhaskaran R., Ponnuswamy P.K., 1988. Int. J. Pept. Protein Res. 32:242-255)

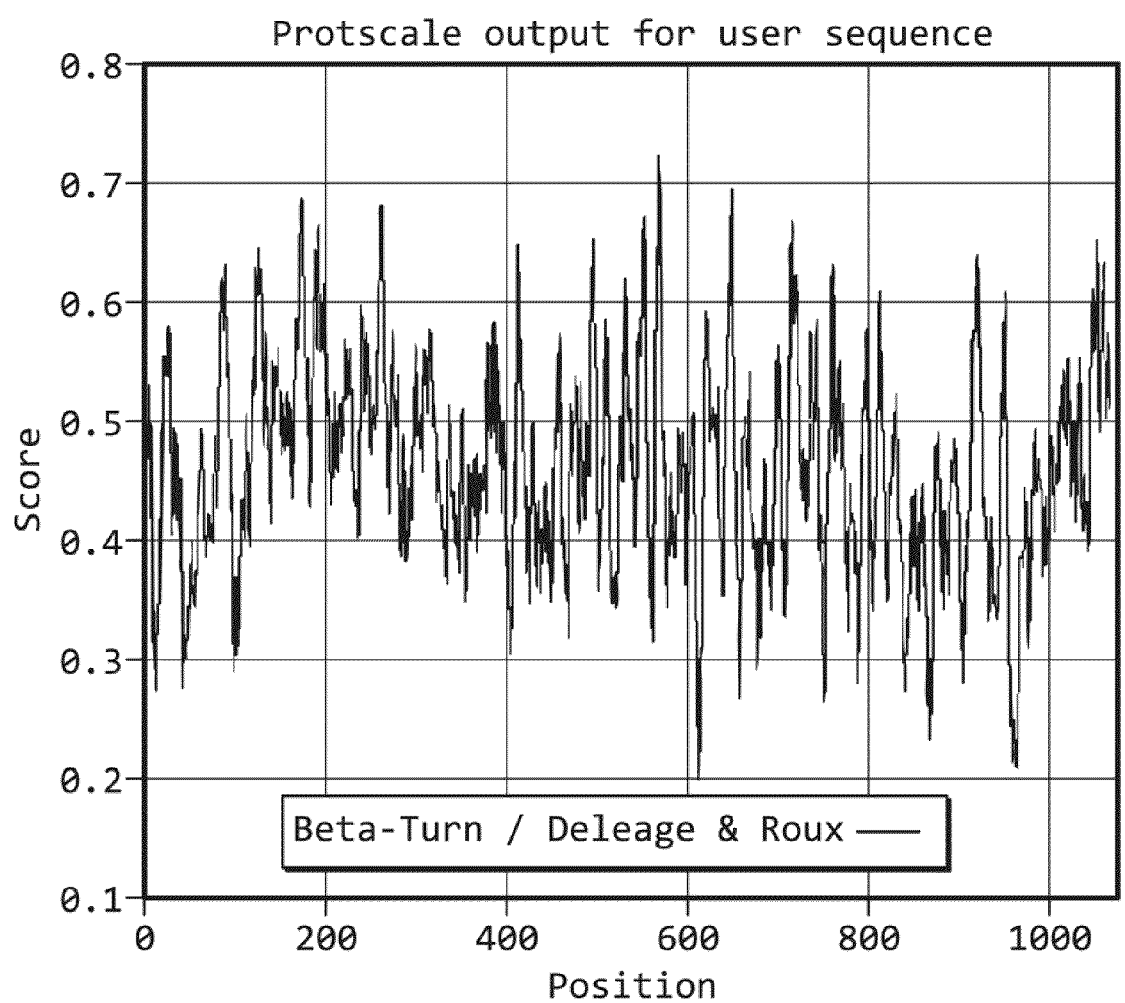

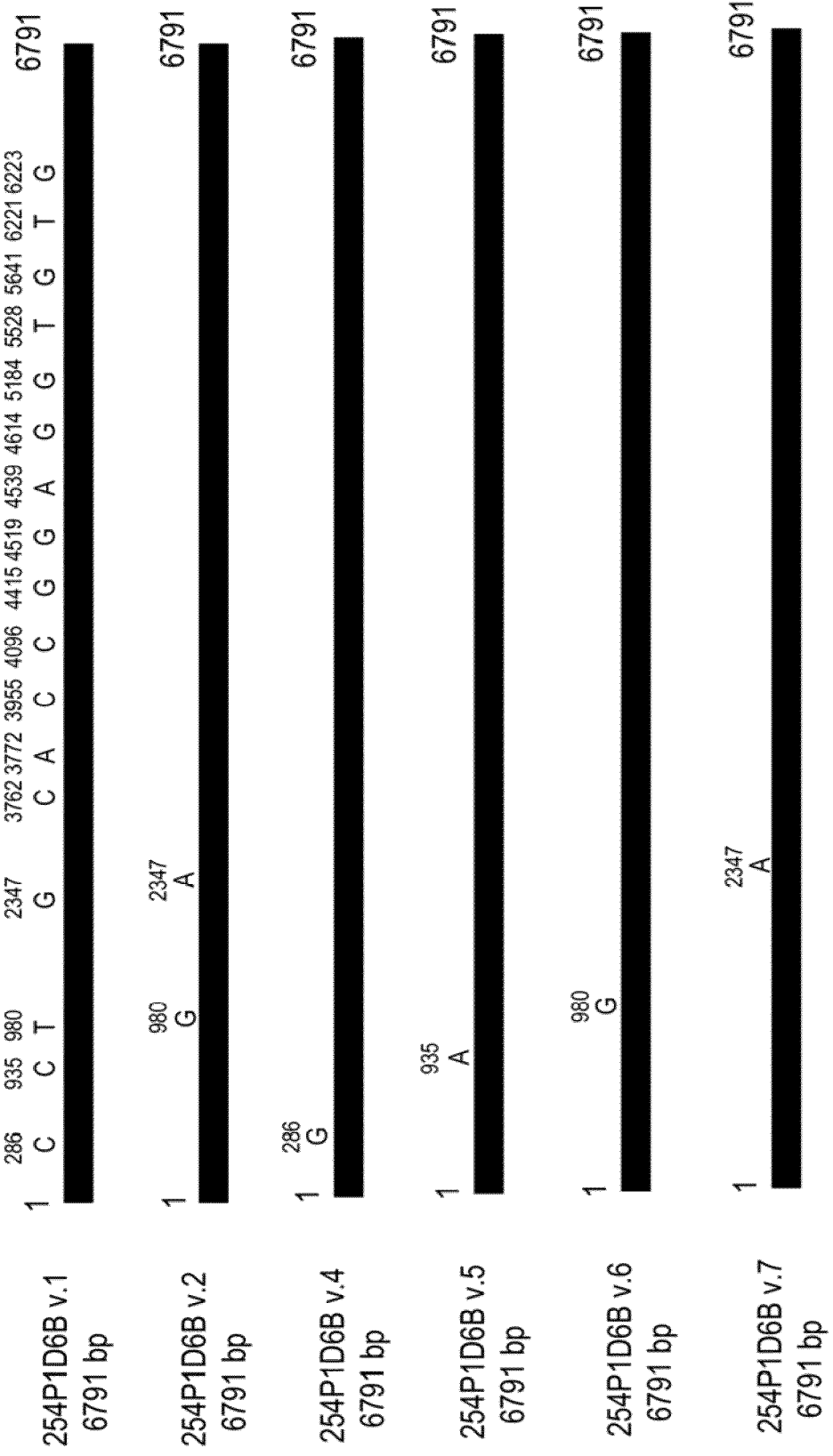

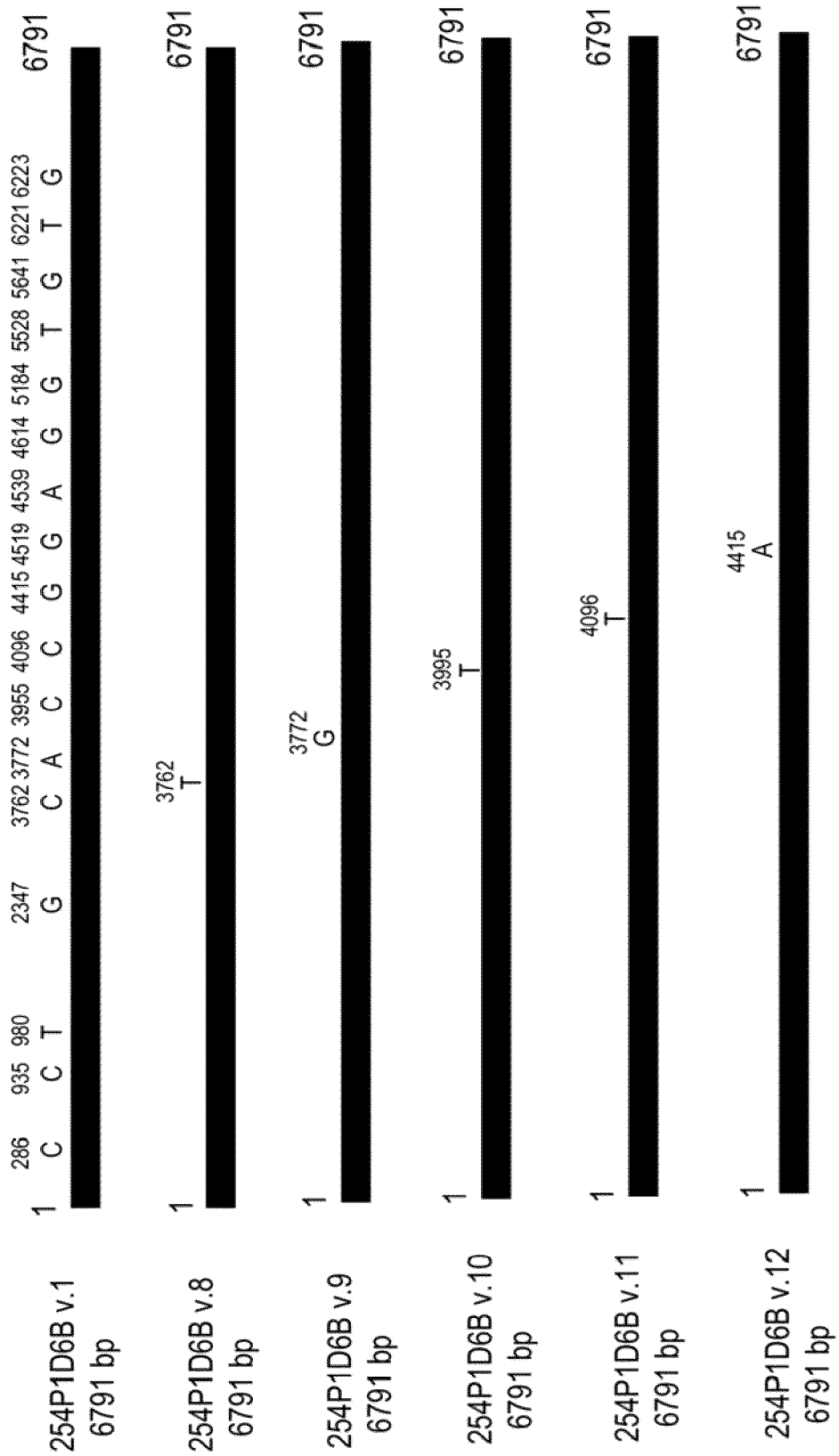

Figure 13A: Secondary structure prediction of 254P1D6B variant 1

```
         10        20        30        40        50        60        70        80
         |         |         |         |         |         |         |         |
MAPPTGVLSSLLLLVTIAGCARKQCSEGRTYSNAVISPNLETTRIMRVSHTFPVVDCTAACCDLSSCDLAWWFEGRCYLV
ccccccchhhhhhhhhhchccccccccccccceeeecccccccccceeeeeeecccceeeccccccceeeeeecccceeee
SCPHKENCEPKKMGPIRSYLTFVLRPVQRPAQLLDYGDMMLNRGSPSGIWGDSPEDIRKDLPFLGKDWGLEEMSEYSDDY
ecccccccccccceheeecccchhcccchhccchhcccccccccccchccccccccccccccccccccchhhhcchhh
RELEKDLLQPSGKQEPRGSAEYTDWGLLPGSEGAFNSSVGDSPAVPAETQQDPELHYILNESASTPAPKLPERSVLLPT
hhhhhhcccccccccccccccccccccccccccccccccccccccceecccccccccccccccccceeeccccc
TPSSGEVLEKEKASQLQEQSSNSSGKEVLMPSHSLPPASLELSSVTVEKSPVLTVTPGSTEHSIPTPPTSAAPSESTPSE
ccccchhhhhhhhhchhccccccceeeeeeccccccccccceeeeccccccccceeecccccccccccccccc
LPISPTTAPRTVKELTVSAGDNLIITLPDNEVELKAFVAPAPPVETTYNYEWNLISHPTDYQGEIKQGHKQTLNLSQLSV
cccccccccccceeeeccccccceeeeccccccccccccceeeecccccccccccccchhchhheeheeec
GLYVFKVTVSSENAFGEGFVNVTVKPARRVNLPPVAVVSPQLQELTLPLTSALIDGSQSTDDTEIVSYHWEEINGPFIEE
ceeeeeeccccccccccceeeecccccccccccccccceeecccchhcccccccceeeeehhccccceec
KTSVDSPVLRLSNLDPGNYSFRLTVTDSDGATNSTTAALIVNNAVDYPPVANAGPNHTITLPQNSITLNGNQSSDDHQIV
cccccccceeeccccccccceeeeccccccccccccccchhhhccccccccceeecccccccccceeeee Alpha helix (h): 18.19%
Extended strand (e): 24.81%
Random coil (c): 57.00%
```

Figure 13A-2

```
           570         580         590         600         610         620         630         640
            |           |           |           |           |           |           |           |
LYEWSLGPGSEGKHVVMQGVQTPYLIHLSAMQEGDYTFQLKVTDSSRQQSTAVVTVIVQPENNRPPVAVAGPDKELIFPVE
eeeecccccccccccccccceeeehcccccccceeeccccccccccccccceeeeeeeeeccccccccccceeeeeeeec
SATLDGSSSSDDHGIVFYHWEHVRGPSAVEMENIDKAIATVTGLQVGTYHFRLTVKDQQGLSSTSTLTVAVKKENNSPPR
ccccccccccccceeeeeeeeccccccccccccchhhhhhhhcccccccceeceeeeeeeccccccccceeeeecccccc
ARAGGRHVLVLPNSITLDGSRSTDDQRIVSYLWIRDGQSPAAGDVIDGSDHSVALQLTNLVEGVYTFHLRVTDSQGASD
ccccceeeeeeeecccccccccceeeecccccccccceeeeccccccccccceeehhhhhhchceeeeeeeeccccccc
TDTATVEVQPDPRKSGLVELTLQVGVGQLTEQRKDTLVRQLAVLLNVLDSDIKVQKIRAHSDLSTVIVFYVQSRPPFKVL
cccceeeeccccccccceeeeeeeeeccccccchhhhhhhhhhhhcccchhhehccccccceeeeeeeeeccccccchhh
KAAEVARNLHMRLSKEKADFLLEFKVLRVDTAGCLLKCSGHGHCDPLTKRCICSHLWMENLIQRYIWDGESNCEWSIFYVT
hhhhhhhhhhhhhhhhhhhhhhhhhheheeeecceeecccccccccccchhhhhhhhhheccccccchhhhhhhh
VLAFTLIVLTGGFTWLCICCCKRQKRTKIRKKTKYTILDNMDEQERMELRPKYGIKHRSTEHNSSLMVSESEFDSDQDTI
hheeeeeecccccccccccceeeeeeeeeeechhccccccccccceeecccchhhhhcccccceeeccccccccchhh
FSREKMERGNPKVSMNGSIRNGASFSYCSKDR
ehhhhhcccccccccccceeeccccccccccc Alpha helix(h) :   18.19%
Extended strand (e) :   24.81%
Random coil(c) :   57.00%
```

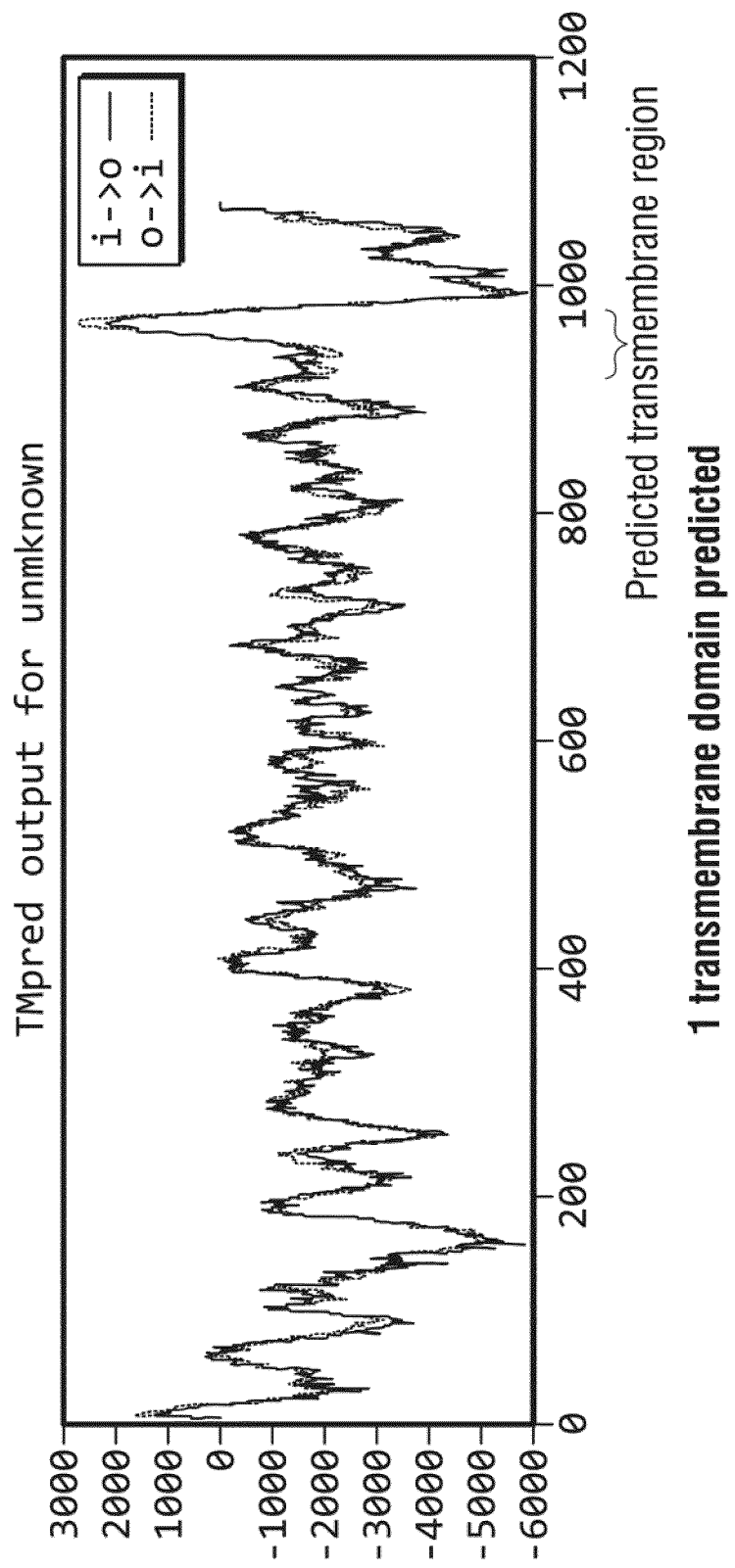
Figure 13B: Transmembrane prediction for 254P1D6B variant 1

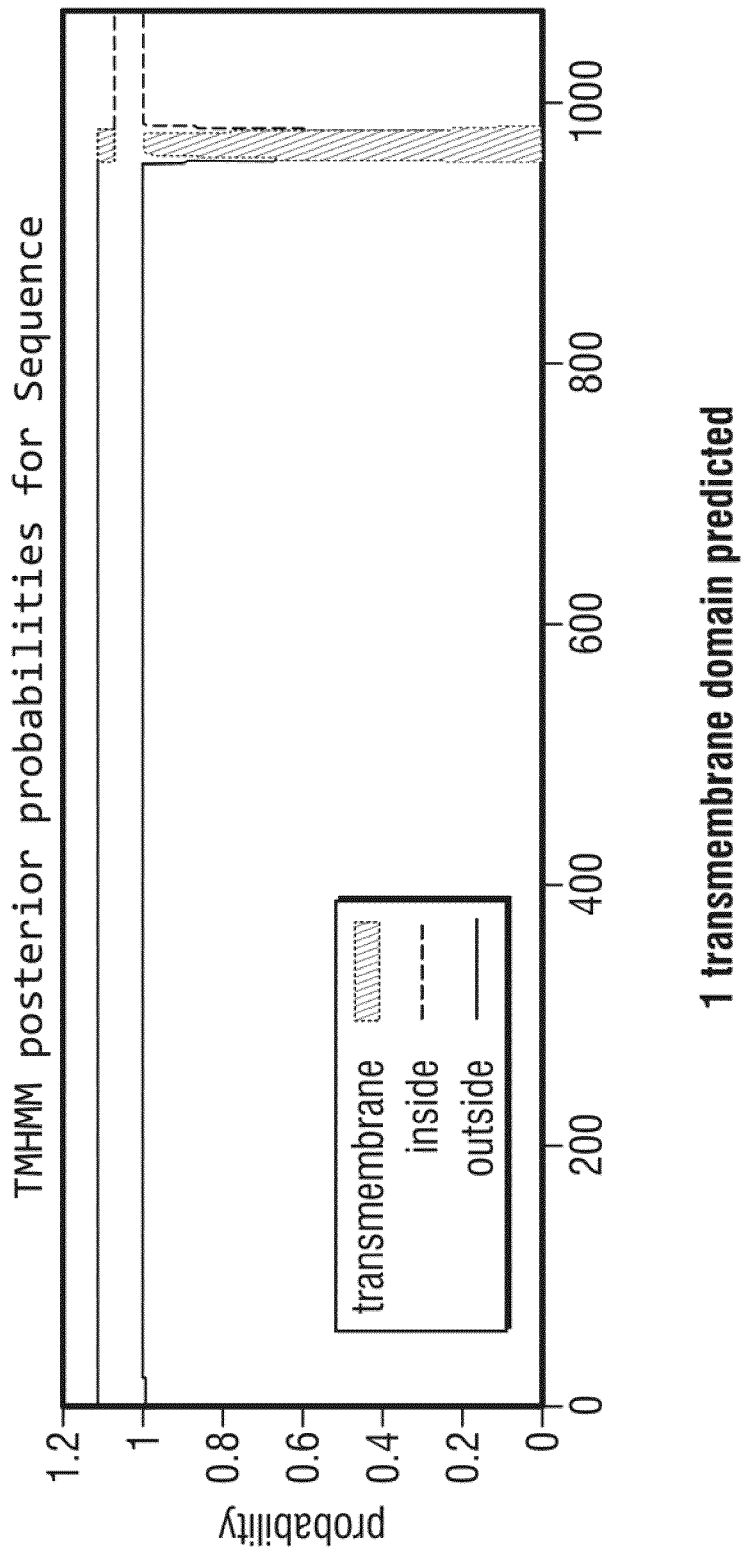
Figure 13C: Transmembrane prediction for 254P1D6B variant 1

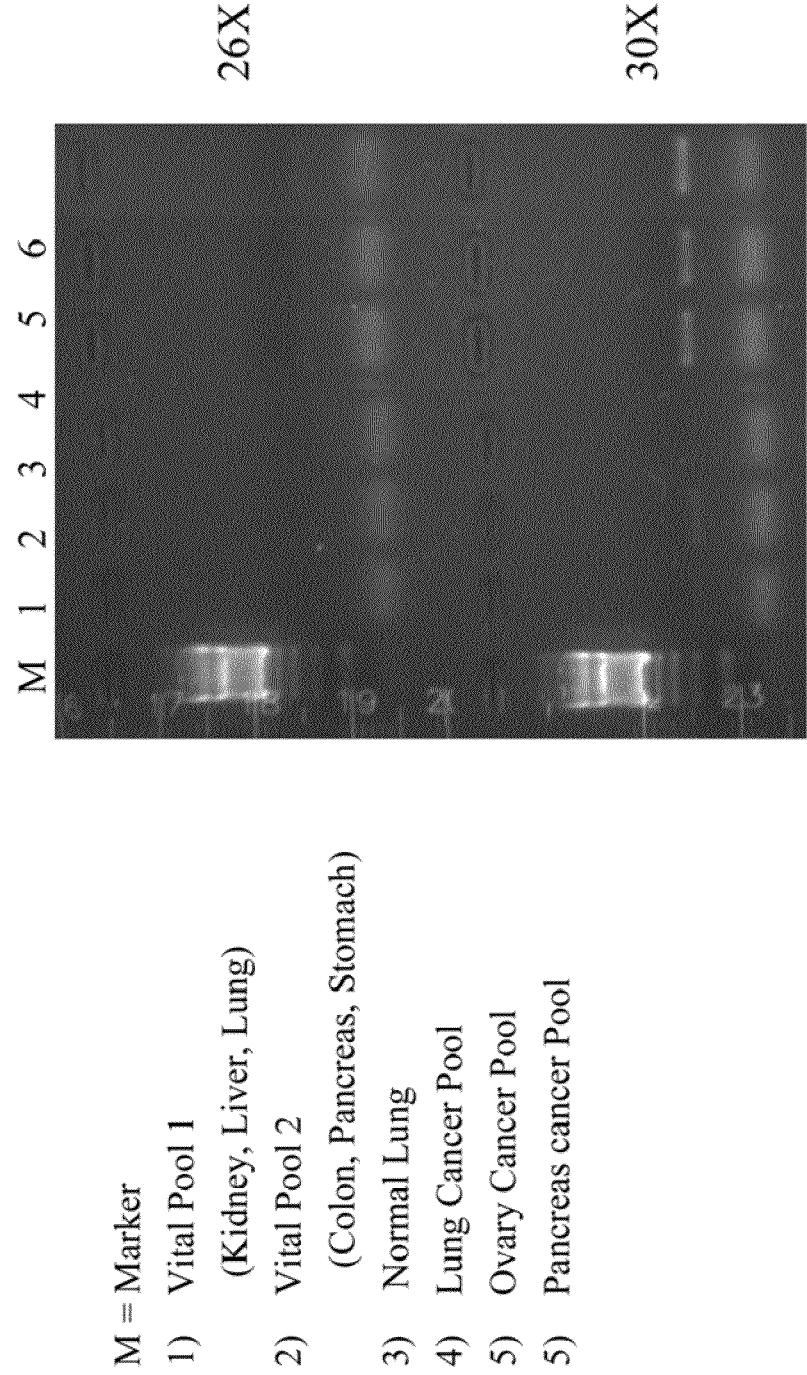
Figure 14A: 254P1D6B Expression by RT-PCR
M = Marker
1) Vital Pool 1
   (Kidney, Liver, Lung)
2) Vital Pool 2
   (Colon, Pancreas, Stomach)
3) Normal Lung
4) Lung Cancer Pool
5) Ovary Cancer Pool
5) Pancreas cancer Pool

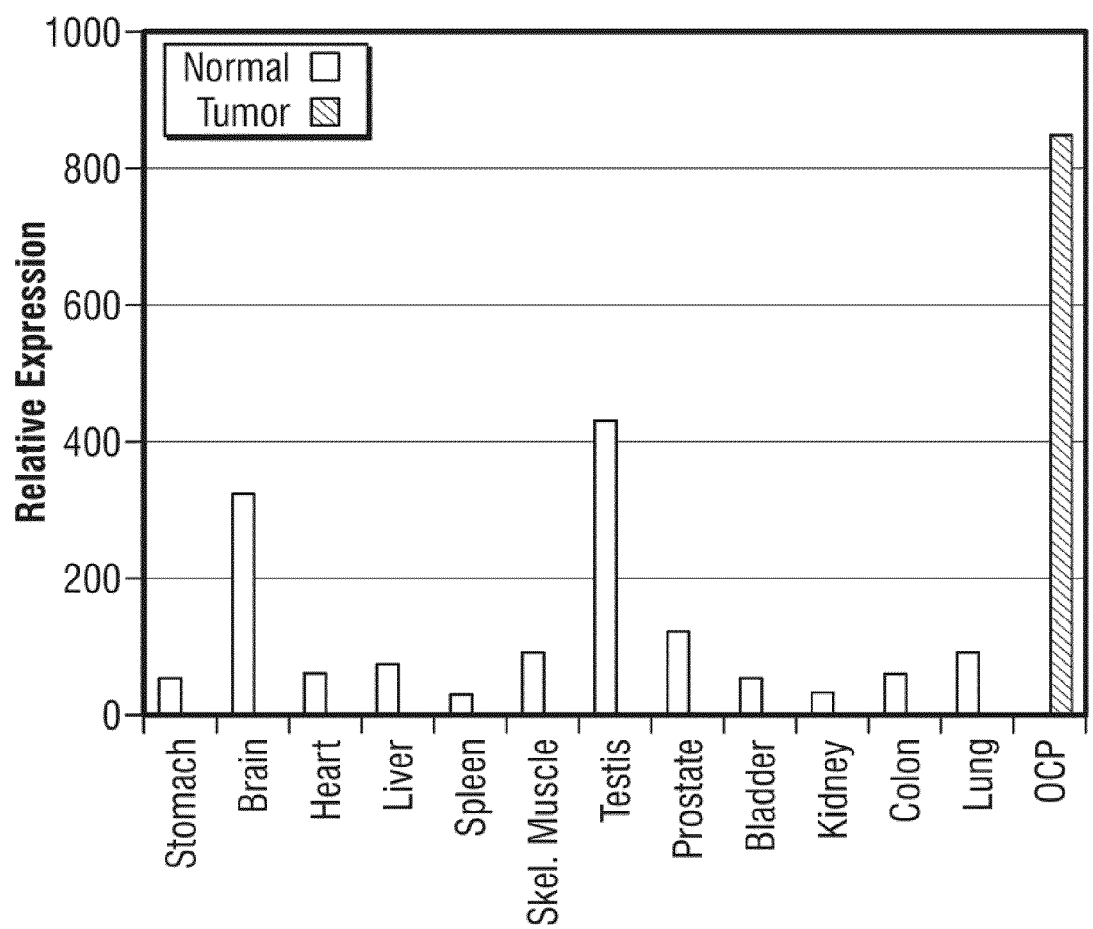
Figure 14B: Expression of 254P1D6B in Normal Human Tissues and Ovarian Patient Specimens

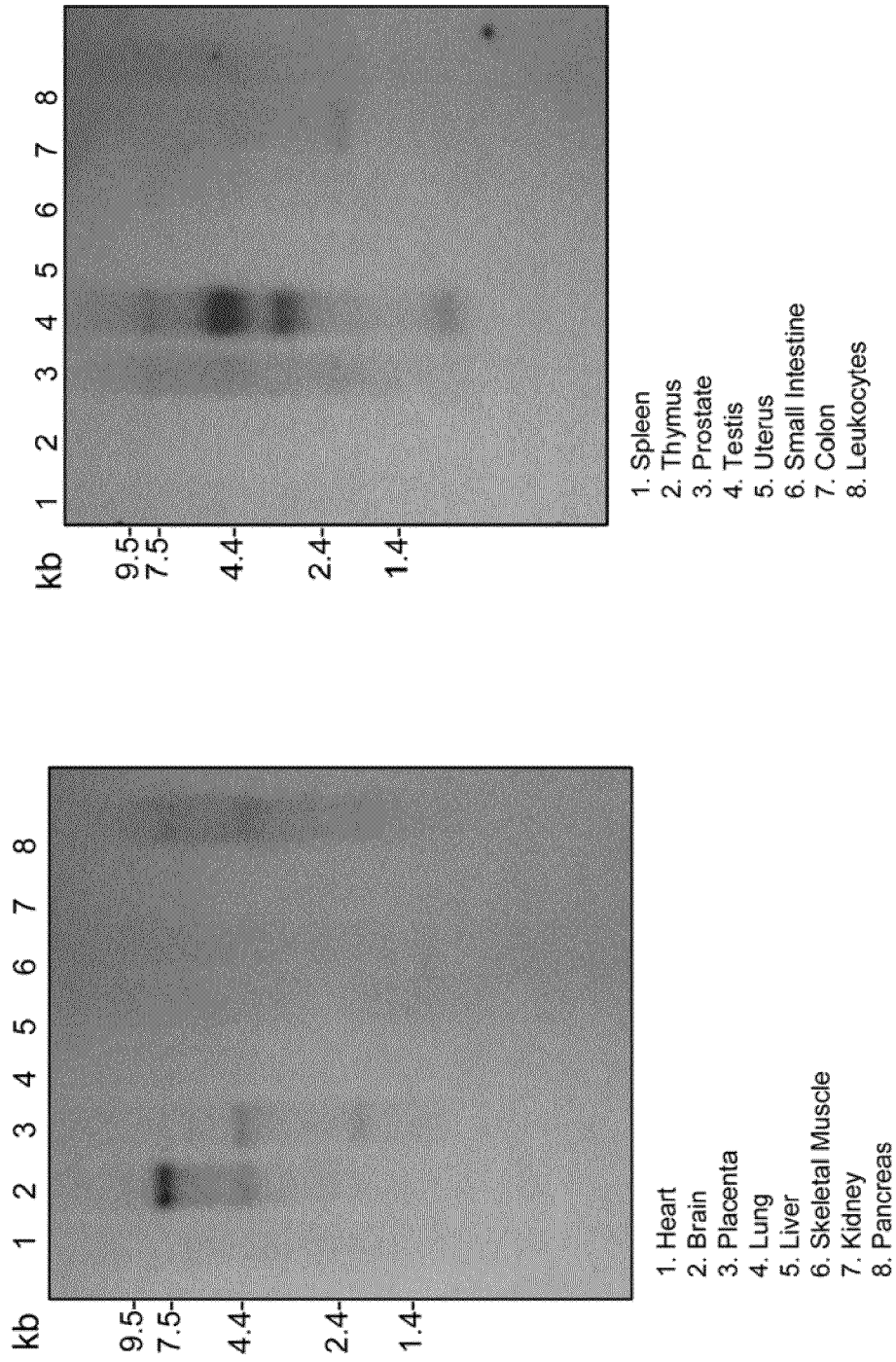
Figure 15: Expression of 254P1D6B in Normal Tissues

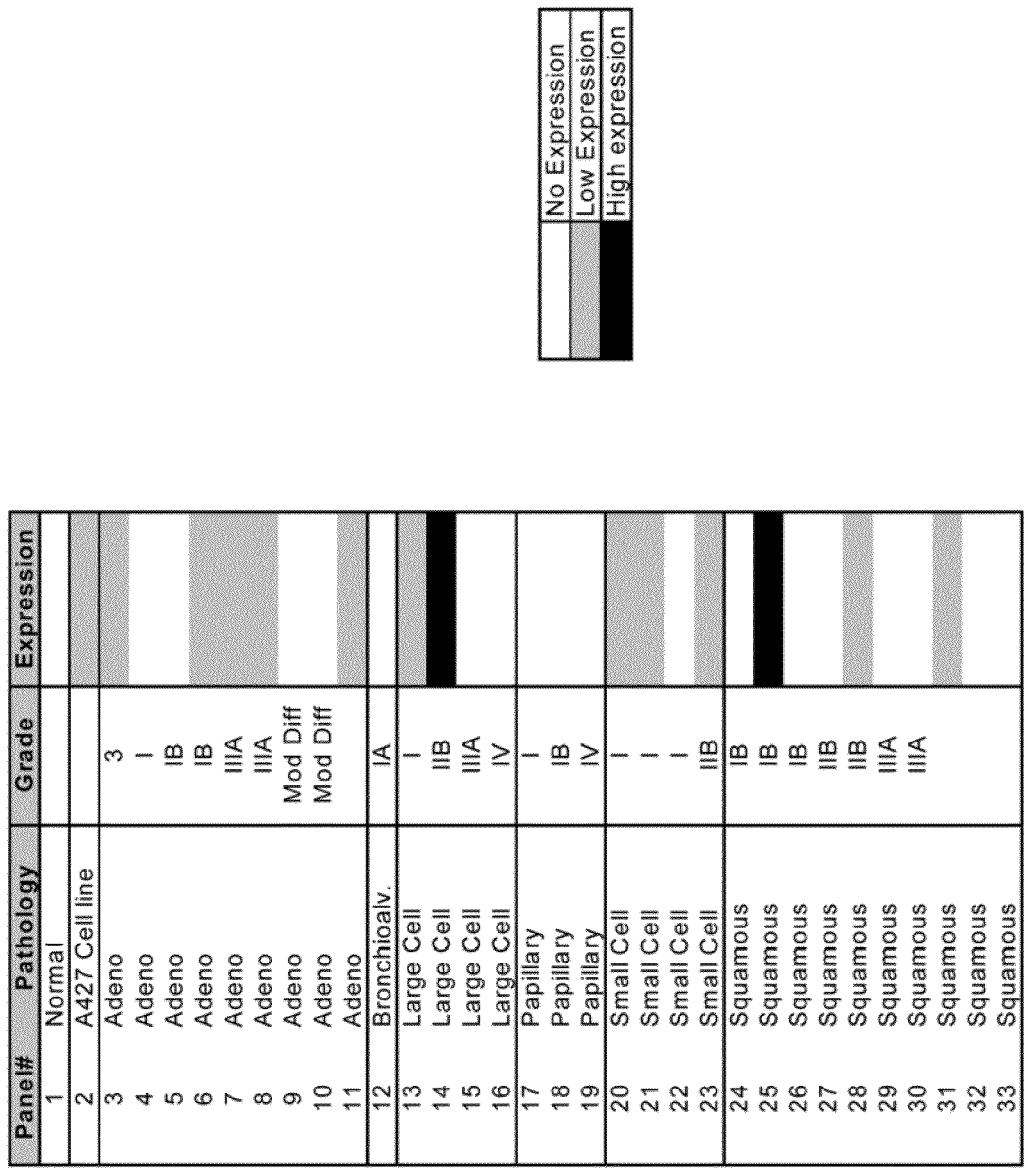
Figure 16: Expression of 254P1D6B in Lung Cancer Patient Specimens

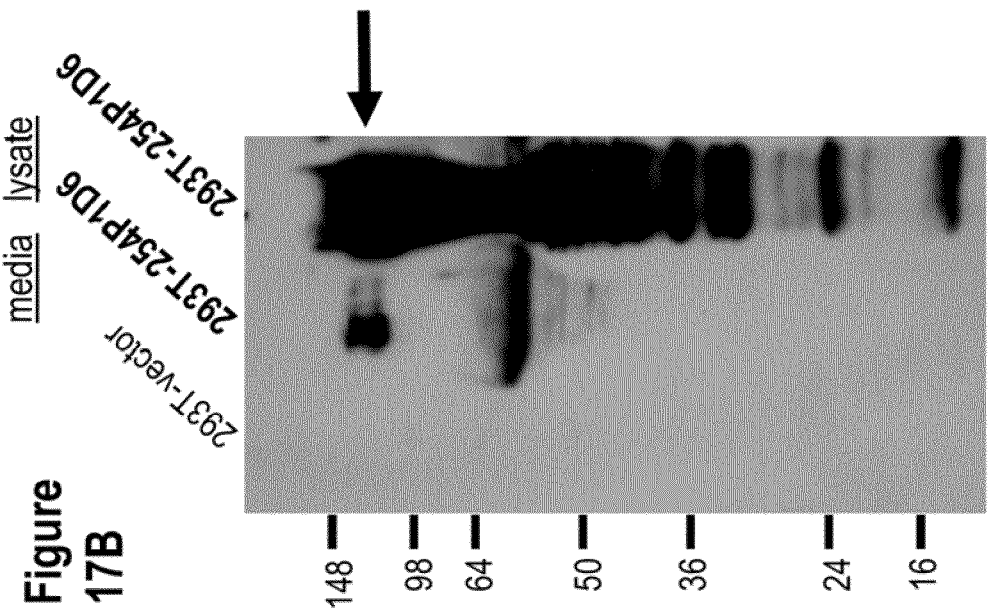
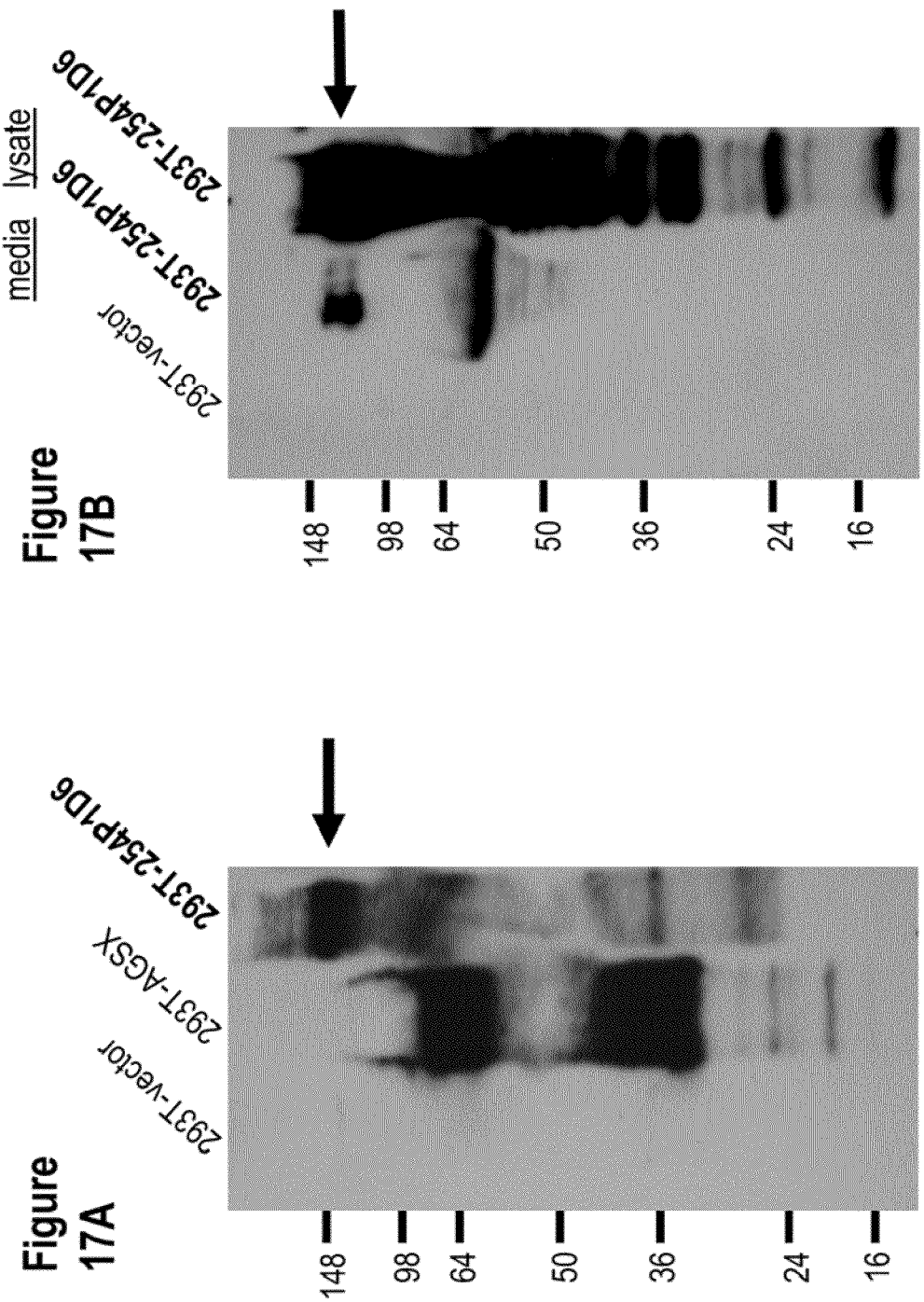
Figure 17: Expression of 254P1D6b in 293T cells

NUCLEIC ACIDS AND CORRESPONDING PROTEINS ENTITLED 254P1D6B USEFUL IN TREATMENT AND DETECTION OF CANCER

CROSS-REFERENCE TO RELATED APPLICATIONS

This application is a non-provisional utility patent application that is a continuation of U.S. non-provisional utility application U.S. Ser. No. 10/764,390, filed 23 Jan. 2004 now U.S. Pat. No. 7,638,270, now allowed; and this application claims priority from U.S. provisional patent application U.S. Ser. No. 60/442,526, filed 24 Jan. 2003. The contents of the applications listed in this paragraph are fully incorporated by reference herein.

FIELD OF THE INVENTION

The invention described herein relates to genes and their encoded proteins, termed 254P1D6B and variants thereof, expressed in certain cancers, and to diagnostic and therapeutic methods and compositions useful in the management of cancers that express 254P1D6B.

BACKGROUND OF THE INVENTION

Cancer is the second leading cause of human death next to coronary disease. Worldwide, millions of people die from cancer every year. In the United States alone, as reported by the American Cancer Society, cancer causes the death of well over a half-million people annually, with over 1.2 million new cases diagnosed per year. While deaths from heart disease have been declining significantly, those resulting from cancer generally are on the rise. In the early part of the next century, cancer is predicted to become the leading cause of death.

Worldwide, several cancers stand out as the leading killers. In particular, carcinomas of the lung, prostate, breast, colon, pancreas, and ovary represent the primary causes of cancer death. These and virtually all other carcinomas share a common lethal feature. With very few exceptions, metastatic disease from a carcinoma is fatal. Moreover, even for those cancer patients who initially survive their primary cancers, common experience has shown that their lives are dramatically altered. Many cancer patients experience strong anxieties driven by the awareness of the potential for recurrence or treatment failure. Many cancer patients experience physical debilitations following treatment. Furthermore, many cancer patients experience a recurrence.

Worldwide, prostate cancer is the fourth most prevalent cancer in men. In North America and Northern Europe, it is by far the most common cancer in males and is the second leading cause of cancer death in men. In the United States alone, well over 30,000 men die annually of this disease—second only to lung cancer. Despite the magnitude of these figures, there is still no effective treatment for metastatic prostate cancer. Surgical prostatectomy, radiation therapy, hormone ablation therapy, surgical castration and chemotherapy continue to be the main treatment modalities. Unfortunately, these treatments are ineffective for many and are often associated with undesirable consequences.

On the diagnostic front, the lack of a prostate tumor marker that can accurately detect early-stage, localized tumors remains a significant limitation in the diagnosis and management of this disease. Although the serum prostate specific antigen (PSA) assay has been a very useful tool, however its specificity and general utility is widely regarded as lacking in several important respects.

Progress in identifying additional specific markers for prostate cancer has been improved by the generation of prostate cancer xenografts that can recapitulate different stages of the disease in mice. The LAPC (Los Angeles Prostate Cancer) xenografts are prostate cancer xenografts that have survived passage in severe combined immune deficient (SCID) mice and have exhibited the capacity to mimic the transition from androgen dependence to androgen independence (Klein et al., 1997, Nat. Med. 3:402). More recently identified prostate cancer markers include PCTA-1 (Su et al., 1996, Proc. Natl. Acad. Sci. USA 93: 7252), prostate-specific membrane (PSM) antigen (Pinto et al., Clin Cancer Res 1996 Sep. 2 (9): 1445-51), STEAP (Hubert, et al., Proc Natl Acad Sci USA. 1999 Dec. 7; 96(25): 14523-8) and prostate stem cell antigen (PSCA) (Reiter et al., 1998, Proc. Natl. Acad. Sci. USA 95: 1735).

While previously identified markers such as PSA, PSM, PCTA and PSCA have facilitated efforts to diagnose and treat prostate cancer, there is need for the identification of additional markers and therapeutic targets for prostate and related cancers in order to further improve diagnosis and therapy.

Renal cell carcinoma (RCC) accounts for approximately 3 percent of adult malignancies. Once adenomas reach a diameter of 2 to 3 cm, malignant potential exists. In the adult, the two principal malignant renal tumors are renal cell adenocarcinoma and transitional cell carcinoma of the renal pelvis or ureter. The incidence of renal cell adenocarcinoma is estimated at more than 29,000 cases in the United States, and more than 11,600 patients died of this disease in 1998. Transitional cell carcinoma is less frequent, with an incidence of approximately 500 cases per year in the United States.

Surgery has been the primary therapy for renal cell adenocarcinoma for many decades. Until recently, metastatic disease has been refractory to any systemic therapy. With recent developments in systemic therapies, particularly immunotherapies, metastatic renal cell carcinoma may be approached aggressively in appropriate patients with a possibility of durable responses. Nevertheless, there is a remaining need for effective therapies for these patients.

Of all new cases of cancer in the United States, bladder cancer represents approximately 5 percent in men (fifth most common neoplasm) and 3 percent in women (eighth most common neoplasm). The incidence is increasing slowly, concurrent with an increasing older population. In 1998, there was an estimated 54,500 cases, including 39,500 in men and 15,000 in women. The age-adjusted incidence in the United States is 32 per 100,000 for men and eight per 100,000 in women. The historic male/female ratio of 3:1 may be decreasing related to smoking patterns in women. There were an estimated 11,000 deaths from bladder cancer in 1998 (7,800 in men and 3,900 in women). Bladder cancer incidence and mortality strongly increase with age and will be an increasing problem as the population becomes more elderly.

Most bladder cancers recur in the bladder. Bladder cancer is managed with a combination of transurethral resection of the bladder (TUR) and intravesical chemotherapy or immunotherapy. The multifocal and recurrent nature of bladder cancer points out the limitations of TUR. Most muscle-invasive cancers are not cured by TUR alone. Radical cystectomy and urinary diversion is the most effective means to eliminate the cancer but carry an undeniable impact on urinary and sexual function. There continues to be a significant need for treatment modalities that are beneficial for bladder cancer patients.

An estimated 130,200 cases of colorectal cancer occurred in 2000 in the United States, including 93,800 cases of colon cancer and 36,400 of rectal cancer. Colorectal cancers are the third most common cancers in men and women. Incidence rates declined significantly during 1992-1996 (−2.1% per year). Research suggests that these declines have been due to increased screening and polyp removal, preventing progression of polyps to invasive cancers. There were an estimated 56,300 deaths (47,700 from colon cancer, 8,600 from rectal cancer) in 2000, accounting for about 11% of all U.S. cancer deaths.

At present, surgery is the most common form of therapy for colorectal cancer, and for cancers that have not spread, it is frequently curative. Chemotherapy, or chemotherapy plus radiation, is given before or after surgery to most patients whose cancer has deeply perforated the bowel wall or has spread to the lymph nodes. A permanent colostomy (creation of an abdominal opening for elimination of body wastes) is occasionally needed for colon cancer and is infrequently required for rectal cancer. There continues to be a need for effective diagnostic and treatment modalities for colorectal cancer.

There were an estimated 164,100 new cases of lung and bronchial cancer in 2000, accounting for 14% of all U.S. cancer diagnoses. The incidence rate of lung and bronchial cancer is declining significantly in men, from a high of 86.5 per 100,000 in 1984 to 70.0 in 1996. In the 1990s, the rate of increase among women began to slow. In 1996, the incidence rate in women was 42.3 per 100,000.

Lung and bronchial cancer caused an estimated 156,900 deaths in 2000, accounting for 28% of all cancer deaths. During 1992-1996, mortality from lung cancer declined significantly among men (−1.7% per year) while rates for women were still significantly increasing (0.9% per year). Since 1987, more women have died each year of lung cancer than breast cancer, which, for over 40 years, was the major cause of cancer death in women. Decreasing lung cancer incidence and mortality rates most likely resulted from decreased smoking rates over the previous 30 years; however, decreasing smoking patterns among women lag behind those of men. Of concern, although the declines in adult tobacco use have slowed, tobacco use in youth is increasing again.

Treatment options for lung and bronchial cancer are determined by the type and stage of the cancer and include surgery, radiation therapy, and chemotherapy. For many localized cancers, surgery is usually the treatment of choice. Because the disease has usually spread by the time it is discovered, radiation therapy and chemotherapy are often needed in combination with surgery. Chemotherapy alone or combined with radiation is the treatment of choice for small cell lung cancer; on this regimen, a large percentage of patients experience remission, which in some cases is long lasting. There is however, an ongoing need for effective treatment and diagnostic approaches for lung and bronchial cancers.

An estimated 182,800 new invasive cases of breast cancer were expected to occur among women in the United States during 2000. Additionally, about 1,400 new cases of breast cancer were expected to be diagnosed in men in 2000. After increasing about 4% per year in the 1980s, breast cancer incidence rates in women have leveled off in the 1990s to about 110.6 cases per 100,000.

In the U.S. alone, there were an estimated 41,200 deaths (40,800 women, 400 men) in 2000 due to breast cancer. Breast cancer ranks second among cancer deaths in women. According to the most recent data, mortality rates declined significantly during 1992-1996 with the largest decreases in younger women, both white and black. These decreases were probably the result of earlier detection and improved treatment.

Taking into account the medical circumstances and the patient's preferences, treatment of breast cancer may involve lumpectomy (local removal of the tumor) and removal of the lymph nodes under the arm; mastectomy (surgical removal of the breast) and removal of the lymph nodes under the arm; radiation therapy; chemotherapy; or hormone therapy. Often, two or more methods are used in combination. Numerous studies have shown that, for early stage disease, long-term survival rates after lumpectomy plus radiotherapy are similar to survival rates after modified radical mastectomy. Significant advances in reconstruction techniques provide several options for breast reconstruction after mastectomy. Recently, such reconstruction has been done at the same time as the mastectomy.

Local excision of ductal carcinoma in situ (DCIS) with adequate amounts of surrounding normal breast tissue may prevent the local recurrence of the DCIS. Radiation to the breast and/or tamoxifen may reduce the chance of DCIS occurring in the remaining breast tissue. This is important because DCIS, if left untreated, may develop into invasive breast cancer. Nevertheless, there are serious side effects or sequalae to these treatments. There is, therefore, a need for efficacious breast cancer treatments.

There were an estimated 23,100 new cases of ovarian cancer in the United States in 2000. It accounts for 4% of all cancers among women and ranks second among gynecologic cancers. During 1992-1996, ovarian cancer incidence rates were significantly declining. Consequent to ovarian cancer, there were an estimated 14,000 deaths in 2000. Ovarian cancer causes more deaths than any other cancer of the female reproductive system.

Surgery, radiation therapy, and chemotherapy are treatment options for ovarian cancer. Surgery usually includes the removal of one or both ovaries, the fallopian tubes (salpingo-oophorectomy), and the uterus (hysterectomy). In some very early tumors, only the involved ovary will be removed, especially in young women who wish to have children. In advanced disease, an attempt is made to remove all intra-abdominal disease to enhance the effect of chemotherapy. There continues to be an important need for effective treatment options for ovarian cancer.

There were an estimated 28,300 new cases of pancreatic cancer in the United States in 2000. Over the past 20 years, rates of pancreatic cancer have declined in men. Rates among women have remained approximately constant but may be beginning to decline. Pancreatic cancer caused an estimated 28,200 deaths in 2000 in the United States. Over the past 20 years, there has been a slight but significant decrease in mortality rates among men (about −0.9% per year) while rates have increased slightly among women.

Surgery, radiation therapy, and chemotherapy are treatment options for pancreatic cancer. These treatment options can extend survival and/or relieve symptoms in many patients but are not likely to produce a cure for most. There is a significant need for additional therapeutic and diagnostic options for pancreatic cancer.

SUMMARY OF THE INVENTION

The present invention relates to a gene, designated 254P1D6B, that has now been found to be over-expressed in the cancer(s) listed in Table I. Northern blot expression analysis of 254P1D6B gene expression in normal tissues shows a restricted expression pattern in adult tissues. The nucleotide (FIG. 2) and amino acid (FIG. 2, and FIG. 3) sequences of 254P1D6B are provided. The tissue-related profile of 254P1D6B in normal adult tissues, combined with the overexpression observed in the tissues listed in Table I, shows that 254P1D6B is aberrantly over-expressed in at least some cancers, and thus serves as a useful diagnostic, prophylactic, prognostic, and/or therapeutic target for cancers of the tissue(s) such as those listed in Table I.

The invention provides polynucleotides corresponding or complementary to all or part of the 254P1D6B genes, mRNAs, and/or coding sequences, preferably in isolated form, including polynucleotides encoding 254P1D6B-related proteins and fragments of 4, 5, 6, 7, 8, 9, 10, 11, 12, 13, 14, 15, 16, 17, 18, 19, 20, 21, 22, 23, 24, 25, or more than 25 contiguous amino acids; at least 30, 35, 40, 45, 50, 55, 60, 65, 70, 80, 85, 90, 95, 100 or more than 100 contiguous amino acids of a 254P1D6B-related protein, as well as the peptides/proteins themselves; DNA, RNA, DNA/RNA hybrids, and related molecules, polynucleotides or oligonucleotides complementary or having at least a 90% homology to the 254P1D6B genes or mRNA sequences or parts thereof, and polynucleotides or oligonucleotides that hybridize to the 254P1D6B genes, mRNAs, or to 254P1D6B-encoding polynucleotides. Also provided are means for isolating cDNAs and the genes encoding 254P1D6B. Recombinant DNA molecules containing 254P1D6B polynucleotides, cells transformed or transduced with such molecules, and host-vector systems for the expression of 254P1D6B gene products are also provided. The invention further provides antibodies that bind to 254P1D6B proteins and polypeptide fragments thereof, including polyclonal and monoclonal antibodies, murine and other mammalian antibodies, chimeric antibodies, humanized and fully human antibodies, and antibodies labeled with a detectable marker or therapeutic agent. In certain embodiments, there is a proviso that the entire nucleic acid sequence of FIG. 2 is not encoded and/or the entire amino acid sequence of FIG. 2 is not prepared. In certain embodiments, the entire nucleic acid sequence of FIG. 2 is encoded and/or the entire amino acid sequence of FIG. 2 is prepared, either of which are in respective human unit dose forms.

The invention further provides methods for detecting the presence and status of 254P1D6B polynucleotides and proteins in various biological samples, as well as methods for identifying cells that express 254P1D6B. A typical embodiment of this invention provides methods for monitoring 254P1D6B gene products in a tissue or hematology sample having or suspected of having some form of growth dysregulation such as cancer.

The invention further provides various immunogenic or therapeutic compositions and strategies for treating cancers that express 254P1D6B such as cancers of tissues listed in Table I, including therapies aimed at inhibiting the transcription, translation, processing or function of 254P1D6B as well as cancer vaccines. In one aspect, the invention provides compositions, and methods comprising them, for treating a cancer that expresses 254P1D6B in a human subject wherein the composition comprises a carrier suitable for human use and a human unit dose of one or more than one agent that inhibits the production or function of 254P1D6B. Preferably, the carrier is a uniquely human carrier. In another aspect of the invention, the agent is a moiety that is immunoreactive with 254P1D6B protein. Non-limiting examples of such moieties include, but are not limited to, antibodies (such as single chain, monoclonal, polyclonal, humanized, chimeric, or human antibodies), functional equivalents thereof (whether naturally occurring or synthetic), and combinations thereof. The antibodies can be conjugated to a diagnostic or therapeutic moiety. In another aspect, the agent is a small molecule as defined herein.

In another aspect, the agent comprises one or more than one peptide which comprises a cytotoxic T lymphocyte (CTL) epitope that binds an HLA class I molecule in a human to elicit a CTL response to 254P1D6B and/or one or more than one peptide which comprises a helper T lymphocyte (HTL) epitope which binds an HLA class II molecule in a human to elicit an HTL response. The peptides of the invention may be on the same or on one or more separate polypeptide molecules. In a further aspect of the invention, the agent comprises one or more than one nucleic acid molecule that expresses one or more than one of the CTL or HTL response stimulating peptides as described above. In yet another aspect of the invention, the one or more than one nucleic acid molecule may express a moiety that is immunologically reactive with 254P1D6B as described above. The one or more than one nucleic acid molecule may also be, or encodes, a molecule that inhibits production of 254P1D6B. Non-limiting examples of such molecules include, but are not limited to, those complementary to a nucleotide sequence essential for production of 254P1D6B (e.g. antisense sequences or molecules that form a triple helix with a nucleotide double helix essential for 254P1D6B production) or a ribozyme effective to lyse 254P1D6B mRNA.

Note that to determine the starting position of any peptide set forth in Tables VIII-XXI and XXII to XLIX (collectively HLA Peptide Tables) respective to its parental protein, e.g., variant 1, variant 2, etc., reference is made to three factors: the particular variant, the length of the peptide in an HLA Peptide Table, and the Search Peptides in Table VII. Generally, a unique Search Peptide is used to obtain HLA peptides of a particular for a particular variant. The position of each Search Peptide relative to its respective parent molecule is listed in Table VII. Accordingly, if a Search Peptide begins at position "X", one must add the value "X-1" to each position in Tables VIII-XXI and XXII to XLIX to obtain the actual position of the HLA peptides in their parental molecule. For example, if a particular Search Peptide begins at position 150 of its parental molecule, one must add 150-1, i.e., 149 to each HLA peptide amino acid position to calculate the position of that amino acid in the parent molecule.

One embodiment of the invention comprises an HLA peptide, that occurs at least twice in Tables VIII-XXI and XXII to XLIX collectively, or an oligonucleotide that encodes the HLA peptide. Another embodiment of the invention comprises an HLA peptide that occurs at least once in Tables VIII-XXI and at least once in tables XXII to XLIX, or an oligonucleotide that encodes the HLA peptide.

Another embodiment of the invention is antibody epitopes, which comprise a peptide regions, or an oligonucleotide encoding the peptide region, that has one two, three, four, or five of the following characteristics:

i) a peptide region of at least 5 amino acids of a particular peptide of FIG. 3, in any whole number increment up to the full length of that protein in FIG. 3, that includes an amino acid position having a value equal to or greater than 0.5, 0.6, 0.7, 0.8, 0.9, or having a value equal to 1.0, in the Hydrophilicity profile of FIG. 5;

ii) a peptide region of at least 5 amino acids of a particular peptide of FIG. 3, in any whole number increment up to the full length of that protein in FIG. 3, that includes an amino acid position having a value equal to or less than 0.5, 0.4, 0.3, 0.2, 0.1, or having a value equal to 0.0, in the Hydropathicity profile of FIG. 6;

iii) a peptide region of at least 5 amino acids of a particular peptide of FIG. 3, in any whole number increment up to the full length of that protein in FIG. 3, that includes an amino acid position having a value equal to or greater than 0.5, 0.6, 0.7, 0.8, 0.9, or having a value equal to 1.0, in the Percent Accessible Residues profile of FIG. 7;

iv) a peptide region of at least 5 amino acids of a particular peptide of FIG. 3, in any whole number increment up to the full length of that protein in FIG. 3, that includes an amino acid position having a value equal to or greater than 0.5, 0.6, 0.7, 0.8, 0.9, or having a value equal to 1.0, in the Average Flexibility profile of FIG. 8; or v) a peptide region of at least 5 amino acids of a particular peptide of FIG. 3, in any whole number increment up to the full length of that protein in FIG. 3, that includes an amino acid position having a value equal to or greater than 0.5, 0.6, 0.7, 0.8, 0.9, or having a value equal to 1.0, in the Beta-turn profile of FIG. 9.

BRIEF DESCRIPTION OF THE FIGURES

FIG. 1. The 254P1D6B SSH sequence of 284 nucleotides.

FIG. 2. A) The cDNA and amino acid sequence of 254P1D6B variant 1 (also called "254P1D6B v.1" or "254P1D6B variant 1") is shown in FIG. 2A. The start methionine is underlined. The open reading frame extends from nucleic acid 512-3730 including the stop codon.

B) The cDNA and amino acid sequence of 254P1D6B variant 2 (also called "254P1D6B v.2") is shown in FIG. 2B. The codon for the start methionine is underlined. The open reading frame extends from nucleic acid 512-3730 including the stop codon.

C) The cDNA and amino acid sequence of 254P1D6B variant 3 (also called "254P1D6B v.3") is shown in FIG. 2C. The codon for the start methionine is underlined. The open reading frame extends from nucleic acid 739-3930 including the stop codon.

D) 254P1D6B v.4 through v.20, SNP variants of 254P1D6B v.1. The 254P1D6B v.4 through v.20 (also called "254P1D6B variant 4 through variant 20") proteins have 1072 amino acids. Variants 254P1D6B v.4 through v.20 are variants with single nucleotide difference from 254P1D6B v.1. 254P1D6B v.5 and v.6 proteins differ from 254P1D6B v.1 by one amino acid. 254P1D6B v.4 and v.7 through v.20 proteins code for the same protein as v.1. Though these SNP variants are shown separately, they can also occur in any combinations and in any of the transcript variants listed above in FIG. 2A, FIG. 2B, and FIG. 2C.

Figures 3, 12:
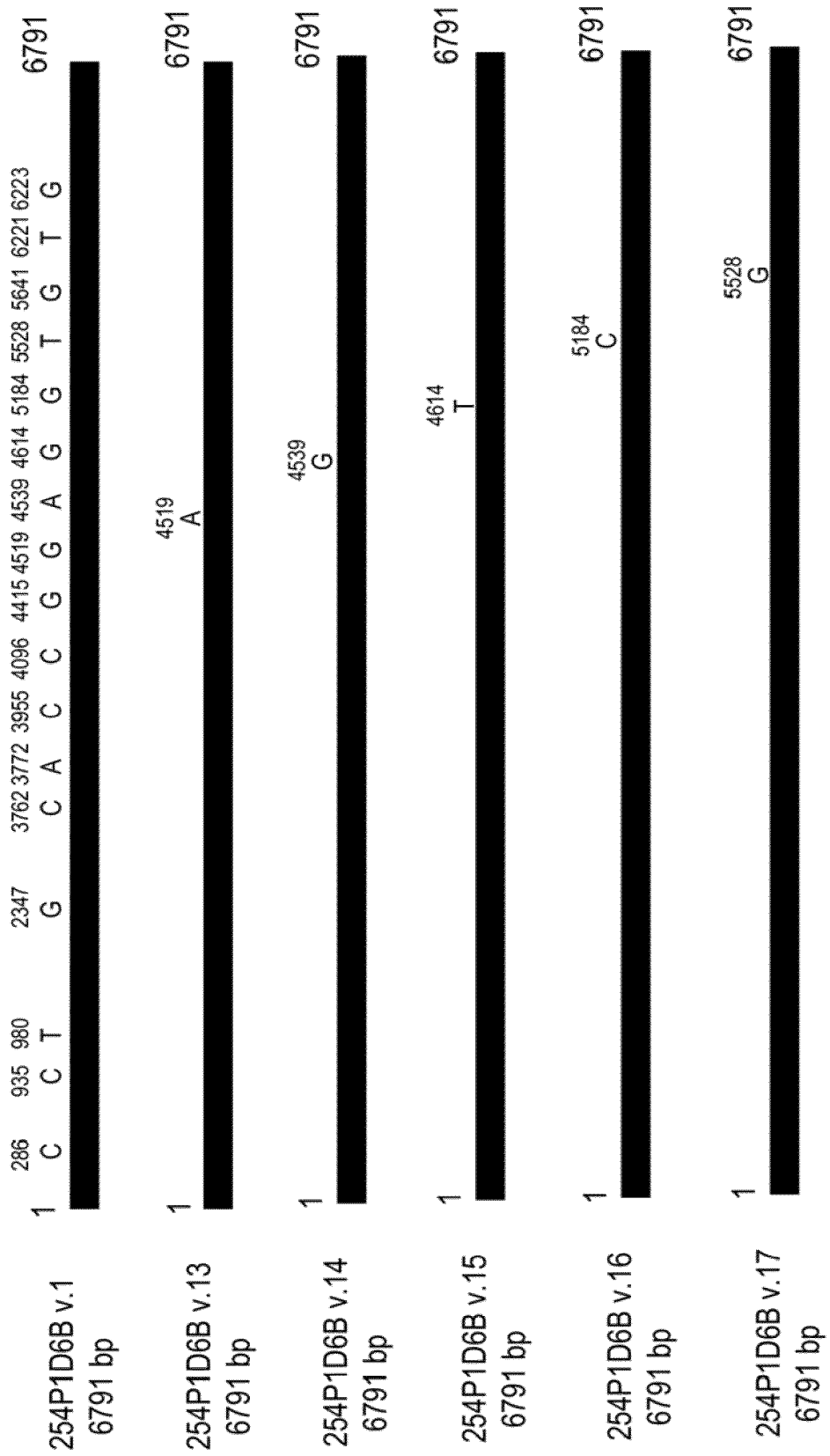

FIG. 3. A) The amino acid sequence of 254P1D6B v.1 clone LCP-3 is shown in FIG. 3A; it has 1072 amino acids.

B) The amino acid sequence of 254P1D6B v.2 is shown in FIG. 3B; it has 1072 amino acids.

C) The amino acid sequence of 254P1D6B v.3 is shown in FIG. 3C; it has 1063 amino acids.

D) The amino acid sequence of 254P1D6B v.5 is shown in FIG. 3D; it has 1072 amino acids.

E) The amino acid sequence of 254P1D6B v.6 is shown in FIG. 3E; it has 1072 amino acids.

As used herein, a reference to 254P1D6B includes all variants thereof, including those shown in FIGS. 2, 3, 10, 11, and 12 unless the context clearly indicates otherwise.

Figures 4, 12:
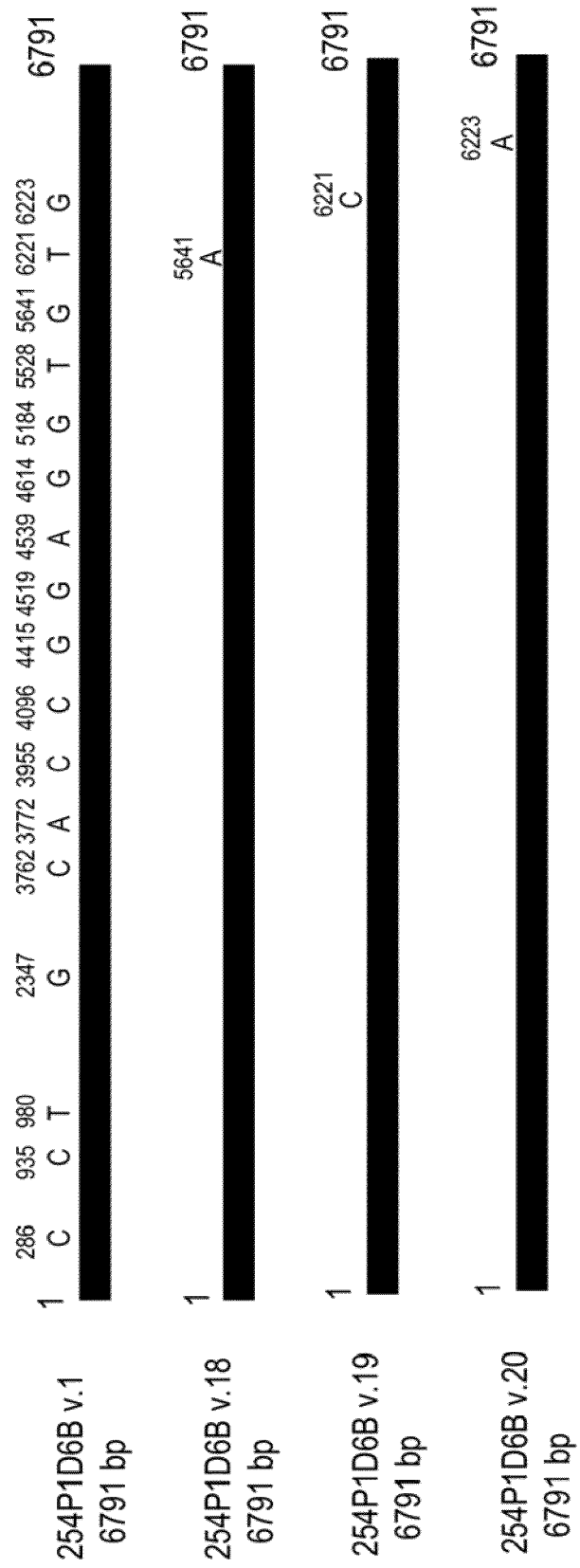

FIG. 4. Intentionally Omitted.

FIG. 5. Hydrophilicity amino acid profile of 254P1D6B v.1 determined by computer algorithm sequence analysis using the method of Hopp and Woods (Hopp T. P., Woods K. R., 1981. Proc. Natl. Acad. Sci. U.S.A. 78:3824-3828) accessed on the Protscale website located on the World Wide Web at (expasy.ch/cgi-bin/protscale.pl) through the ExPasy molecular biology server.

FIG. 6. Hydropathicity amino acid profile of 254P1D6B v.1 determined by computer algorithm sequence analysis using the method of Kyte and Doolittle (Kyte J., Doolittle R. F., 1982. J. Mol. Biol. 157:105-132) accessed on the ProtScale website located on the World Wide Web at (.expasy.ch/cgi-bin/protscale.pl) through the ExPasy molecular biology server.

FIG. 7. Percent accessible residues amino acid profile of 254P1D6B v.1 determined by computer algorithm sequence analysis using the method of Janin (Janin J., 1979 Nature 277:491-492) accessed on the ProtScale website located on the World Wide Web at (.expasy.ch/cgi-bin/protscale.pl) through the ExPasy molecular biology server.

FIG. 8. Average flexibility amino acid profile of 254P1D6B v.1 determined by computer algorithm sequence analysis using the method of Bhaskaran and Ponnuswamy (Bhaskaran R., and Ponnuswamy P. K., 1988. Int. J. Pept. Protein Res. 32:242-255) accessed on the ProtScale website located on the World Wide Web at (.expasy.ch/cgi-bin/protscale.pl) through the ExPasy molecular biology server.

FIG. 9. Beta-turn amino acid profile of 254P1D6B v.1 determined by computer algorithm sequence analysis using the method of Deleage and Roux (Deleage, G., Roux B. 1987 Protein Engineering 1:289-294) accessed on the ProtScale website located on the World Wide Web at (.expasy.ch/cgi-bin/protscale.pl) through the ExPasy molecular biology server.

Figure 10:
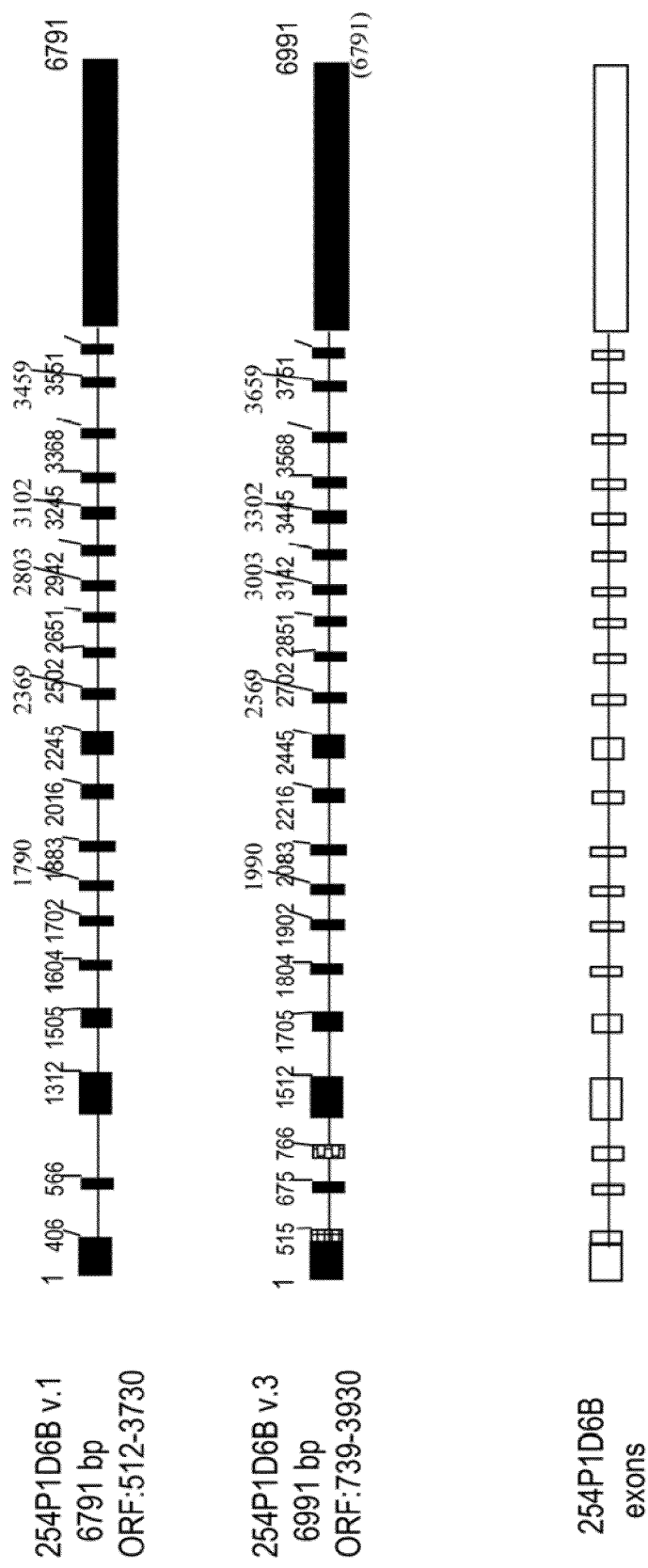

FIG. 10. Structures of transcript variants of 254P1D6B. Variant 254P1D6B v.3 was identified as a transcript variant of 254P1D6B v.1. Variant 254P1D6B v.3 extended exon 1 by 109 bp as compared to v.1 and added an exon in between exons 2 and 3 of variant v.1. Poly A tails and SNP are not shown here. Numbers in "( )" underneath the boxes correspond to those of 254P1D6B v.1. Lengths of introns and exons are not proportional.

Figure 11:
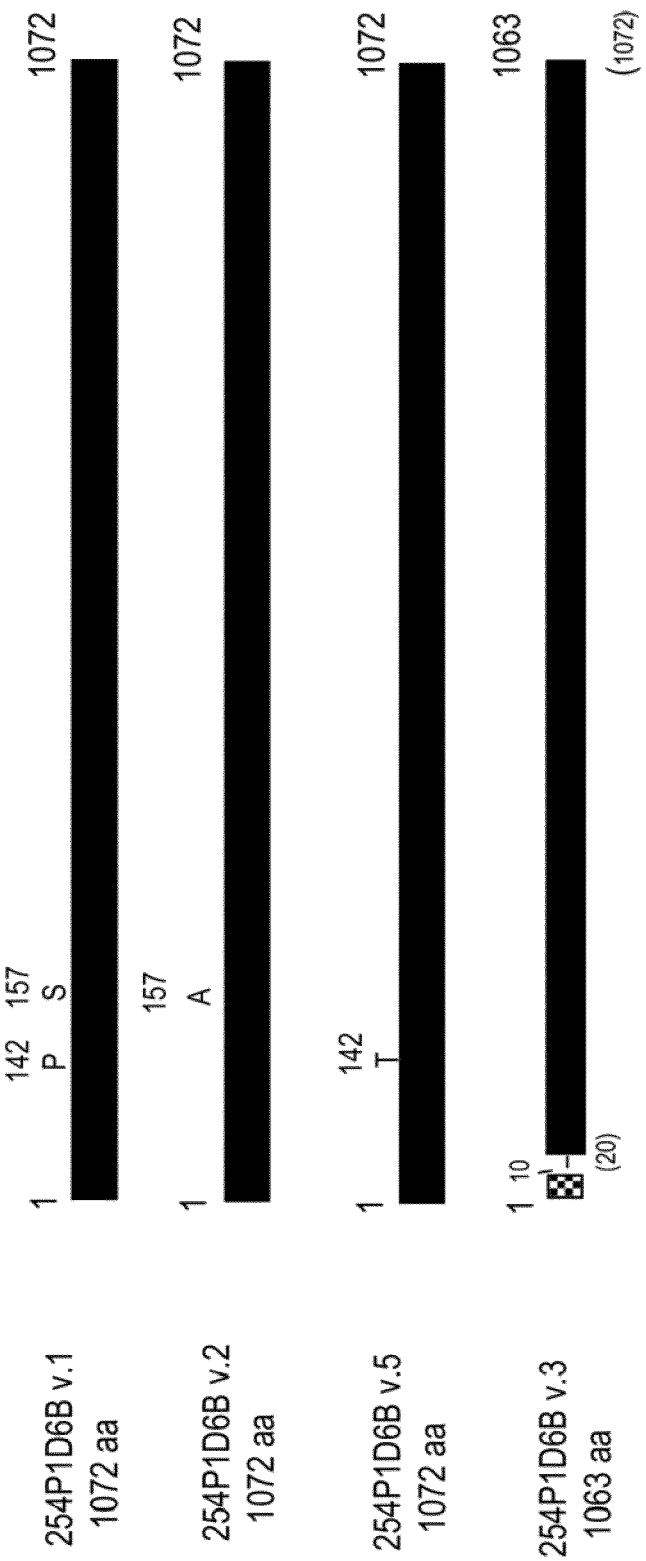

FIG. 11. Schematic alignment of protein variants of 254P1D6B. Protein variants correspond to nucleotide variants. Nucleotide variants 254P1D6B v.4 and v.7 through v.20 coded for the same protein as v.1. Variant v.2 coded the same protein as variant v.6. 254P1D6Bv.5 coded for a protein that differed by one amino acid from v.1. Nucleotide variant 254P1D6B v.3 was a transcript variant of v.1, as shown in FIG. 10, and coded a protein that differed from v.1 in the N-terminal. SNP in v.1 could also appear in v.3. Single amino acid differences were indicated above the boxes. Black boxes represent the same sequence as 254P1D6B v.1. Numbers underneath the box correspond to 254P1D6B.

FIG. 12. Schematic alignment of SNP variants of 254P1D6B. Variants 254P1D6B v.4 through v.20 were variants with single nucleotide differences as compared to variant v.1 (ORF: 512-3730). Though these SNP variants were shown separately, they could also occur in any combinations, (e.g., occur with 254P1D6Bv.2, and in any transcript variants that contained the base pairs, such as v.3 shown in FIG. 10. Numbers correspond to those of 254P1D6B v.1. Black box shows the same sequence as 254P1D6B v.1. SNPs are indicated above the box.

FIG. 13. Secondary structure and transmembrane domains prediction for 254P1D6b protein variant 1.

FIG. 13A: The secondary structures of 254P1D6b protein variant was predicted using the HNN—Hierarchical Neural Network method (NPS@: Network Protein Sequence Analysis TIBS 2000 March Vol. 25, No 3 [291]:147-150 Combet C., Blanchet C., Geourjon C. and Deléage G., on the World Wide Web at pbil.ibcp.fr/cgi-bin/npsa_automat.pl?page=npsa_nn.html), accessed from the ExPasy molecular biology server located on the World Wide Web at .expasy.ch/tools/. This method predicts the presence and location of alpha helices, extended strands, and random coils from the primary protein sequence. The percent of the protein variant in a given secondary structure is also listed. FIG. 13B: Schematic representation of the probability of existence of transmembrane regions of 254P1D6b variant 1 based on the TMpred algorithm of Hofmann and Stoffel which utilizes TMBASE (K. Hofmann, W. Stoffel. TMBASE-A database of membrane spanning protein segments Biol. Chem. Hoppe-Seyler 374:166, 1993). FIG. 13C: Schematic representation of the probability of the existence of transmembrane regions of 254P1D6b variant 1 based on the TMHMM algorithm of Sonnhammer, von Heijne, and Krogh (Erik L. L. Sonnhammer, Gunnar von Heijne, and Anders Krogh: A hidden Markov model for predicting transmembrane helices in protein sequences. In Proc. of Sixth Int. Conf. on Intelligent Systems for Molecular Biology, p 175-182 Ed J. Glasgow, T. Littlejohn, F. Major, R. Lathrop, D. Sankoff, and C. Sensen Menlo Park, Calif.: AAAI Press, 1998). The TMpred and TMHMM algorithms are accessed from the ExPasy molecular biology server located on the World Wide Web at .expasy.ch/tools/.

FIG. 14. Expression of 254P1D6B by RT-PCR. First strand cDNA was prepared from vital pool 1 (liver, lung and kidney), vital pool 2 (pancreas, colon and stomach), normal lung, ovary cancer pool, lung cancer pool (FIG. 14A), as well as from normal stomach, brain, heart, liver, spleen, skeletal muscle, testis, prostate, bladder, kidney, colon, lung and ovary cancer pool (FIG. 14B). Normalization was performed by PCR using primers to actin and GAPDH. Semi-quantitative PCR, using primers to 254P1D6B, was performed at 26 and 30 cycles of amplification. Results show strong expression of 254P1D6B in lung cancer pool and ovary cancer pool but not in normal lung nor in vital pool 1. Low expression was detected in vital pool 2.

FIG. 15. Expression of 254P1D6B in normal tissues. Two multiple tissue northern blots (Clontech) both with 2 ug of mRNA/lane were probed with the 254P1D6B sequence. Size standards in kilobases (kb) are indicated on the side. Results show expression of two 254P1D6B transcript, 4.4 kb and 7.5 kb primarily in brain and testis, and only the 4.4 kb transcript in placenta, but not in any other normal tissue tested.

FIG. 16. Expression of 254P1D6B in lung cancer patient specimens. First strand cDNA was prepared from normal lung lung cancer cell line A427 and a panel of lung cancer patient specimens. Normalization was performed by PCR using primers to actin and GAPDH. Semi-quantitative PCR, using primers to 254P1D6B, was performed at 26 and 30 cycles of amplification. Results show expression of 254P1D6B in 13 out of 30 tumor specimens tested but not in normal lung. Expression was also detected in the A427 cell line.

FIG. 17. Expression of 254P1D6b in 293T cells. FIG. 17A. 293T cells were transfected with either an empty pcDNA 3.1 vector plasmid or pcDNA 3.1 plasmid encoding the full length cDNA of 254P1D6b. 2 days post-transfection, lysates were prepared from the transfected cells and separated by SDS-PAGE, transferred to nitrocellulose and subjected to Western blotting using an anti-His pAb (Santa Cruz Biotechnology, Santa Cruz, Calif.) to detect the C-terminal epitope tag on the protein. An arrow indicates the band corresponding to the full length 254P1D6b protein product. An additional verified lysate containing an epitope tagged AGSX protein served as a positive control. FIG. 17B. 293T cells were transfected with either an empty vector or the Tag5 expression vector encoding the extracellular domain (ECD) of 254P1D6 (amino acids 26-953) and subjected to SDS-PAGE and Western blotting as described above. An arrow indicates the band corresponding to the 254P1D6b ECD present in the lysates and the media from transfected cells.

DETAILED DESCRIPTION OF THE INVENTION

Outline of Sections
I.) Definitions
II.) 254P1D6B Polynucleotides
II.A.) Uses of 254P1D6B Polynucleotides
   II.A.1.) Monitoring of Genetic Abnormalities
   II.A.2.) Antisense Embodiments
   II.A.3.) Primers and Primer Pairs
   II.A.4.) Isolation of 254P1D6B-Encoding Nucleic Acid Molecules
   II.A.5.) Recombinant Nucleic Acid Molecules and Host-Vector Systems
III.) 254P1D6B-related Proteins
III.A.) Motif-bearing Protein Embodiments
III.B.) Expression of 254P1D6B-related Proteins
III.C.) Modifications of 254P1D6B-related Proteins
III.D.) Uses of 254P1D6B-related Proteins
IV.) 254P1D6B Antibodies
V.) 254P1D6B Cellular Immune Responses
VI.) 254P1D6B Transgenic Animals
VII.) Methods for the Detection of 254P1D6B
VIII.) Methods for Monitoring the Status of 254P1D6B-related Genes and Their Products
IX.) Identification of Molecules That Interact With 254P1D6B
X.) Therapeutic Methods and Compositions
X.A.) Anti-Cancer Vaccines
X.B.) 254P1D6B as a Target for Antibody-Based Therapy
X.C.) 254P1D6B as a Target for Cellular Immune Responses
   X.C.1. Minigene Vaccines
   X.C.2. Combinations of CTL Peptides with Helper Peptides
   X.C.3. Combinations of CTL Peptides with T Cell Priming Agents
   X.C.4. Vaccine Compositions Comprising DC Pulsed with CTL and/or HTL Peptides
X.D.) Adoptive Immunotherapy
X.E.) Administration of Vaccines for Therapeutic or Prophylactic Purposes
XI.) Diagnostic and Prognostic Embodiments of 254P1D6B.
XII.) Inhibition of 254P1D6B Protein Function
XII.A.) Inhibition of 254P1D6B With Intracellular Antibodies
XII.B.) Inhibition of 254P1D6B with Recombinant Proteins
XII.C.) Inhibition of 254P1D6B Transcription or Translation
XII.D.) General Considerations for Therapeutic Strategies
XIII.) Identification, Characterization and Use of Modulators of 254P1D6B
XIV.) RNAi and Therapeutic use of small interfering RNA
XV.) KITS/Articles of Manufacture
I.) Definitions:

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art, such as, for example, the widely utilized molecular cloning methodologies described in Sambrook et al., Molecular Cloning: A Laboratory Manual 2nd. edition (1989) Cold Spring Harbor Laboratory Press, Cold Spring Harbor, N.Y. As appropriate, procedures involving the use of commercially available kits and reagents are generally carried out in accordance with manufacturer defined protocols and/or parameters unless otherwise noted.

The terms "advanced prostate cancer", "locally advanced prostate cancer", "advanced disease" and "locally advanced disease" mean prostate cancers that have extended through the prostate capsule, and are meant to include stage C disease under the American Urological Association (AUA) system, stage C1-C2 disease under the Whitmore-Jewett system, and stage T3-T4 and N+ disease under the TNM (tumor, node, metastasis) system. In general, surgery is not recommended for patients with locally advanced disease, and these patients have substantially less favorable outcomes compared to patients having clinically localized (organ-confined) prostate cancer. Locally advanced disease is clinically identified by palpable evidence of induration beyond the lateral border of the prostate, or asymmetry or induration above the prostate base. Locally advanced prostate cancer is presently diagnosed pathologically following radical prostatectomy if the tumor invades or penetrates the prostatic capsule, extends into the surgical margin, or invades the seminal vesicles.

"Altering the native glycosylation pattern" is intended for purposes herein to mean deleting one or more carbohydrate moieties found in native sequence 254P1D6B (either by removing the underlying glycosylation site or by deleting the glycosylation by chemical and/or enzymatic means), and/or adding one or more glycosylation sites that are not present in the native sequence 254P1D6B. In addition, the phrase includes qualitative changes in the glycosylation of the native proteins, involving a change in the nature and proportions of the various carbohydrate moieties present.

The term "analog" refers to a molecule which is structurally similar or shares similar or corresponding attributes with another molecule (e.g. a 254P1D6B-related protein). For example, an analog of a 254P1D6B protein can be specifically bound by an antibody or T cell that specifically binds to 254P1D6B.

The term "antibody" is used in the broadest sense. Therefore, an "antibody" can be naturally occurring or man-made such as monoclonal antibodies produced by conventional hybridoma technology. Anti-254P1D6B antibodies comprise monoclonal and polyclonal antibodies as well as fragments containing the antigen-binding domain and/or one or more complementarity determining regions of these antibodies.

An "antibody fragment" is defined as at least a portion of the variable region of the immunoglobulin molecule that binds to its target, i.e., the antigen-binding region. In one embodiment it specifically covers single anti-254P1D6B antibodies and clones thereof (including agonist, antagonist and neutralizing antibodies) and anti-254P1D6B antibody compositions with polyepitopic specificity.

The term "codon optimized sequences" refers to nucleotide sequences that have been optimized for a particular host species by replacing any codons having a usage frequency of less than about 20%. Nucleotide sequences that have been optimized for expression in a given host species by elimination of spurious polyadenylation sequences, elimination of exon/intron splicing signals, elimination of transposon-like repeats and/or optimization of GC content in addition to codon optimization are referred to herein as an "expression enhanced sequences."

A "combinatorial library" is a collection of diverse chemical compounds generated by either chemical synthesis or biological synthesis by combining a number of chemical "building blocks" such as reagents. For example, a linear combinatorial chemical library, such as a polypeptide (e.g., mutein) library, is formed by combining a set of chemical building blocks called amino acids in every possible way for a given compound length (i.e., the number of amino acids in a polypeptide compound). Numerous chemical compounds are synthesized through such combinatorial mixing of chemical building blocks (Gallop et al., J. Med. Chem. 37(9): 1233-1251 (1994)).

Preparation and screening of combinatorial libraries is well known to those of skill in the art. Such combinatorial chemical libraries include, but are not limited to, peptide libraries (see, e.g., U.S. Pat. No. 5,010,175, Furka, Pept. Prot. Res. 37:487-493 (1991), Houghton et al., Nature, 354:84-88 (1991)), peptoids (PCT Publication No WO 91/19735), encoded peptides (PCT Publication WO 93/20242), random bio-oligomers (PCT Publication WO 92/00091), benzodiazepines (U.S. Pat. No. 5,288,514), diversomers such as hydantoins, benzodiazepines and dipeptides (Hobbs et al., Proc. Nat. Acad. Sci. USA 90:6909-6913 (1993)), vinylogous polypeptides (Hagihara et al., J. Amer. Chem. Soc. 114:6568 (1992)), nonpeptidal peptidomimetics with a Beta-D-Glucose scaffolding (Hirschmann et al., J. Amer. Chem. Soc. 114:9217-9218 (1992)), analogous organic syntheses of small compound libraries (Chen et al., J. Amer. Chem. Soc. 116:2661 (1994)), oligocarbamates (Cho, et al., Science 261: 1303 (1993)), and/or peptidyl phosphonates (Campbell et al., J. Org. Chem. 59:658 (1994)). See, generally, Gordon et al., J. Med. Chem. 37:1385 (1994), nucleic acid libraries (see, e.g., Stratagene, Corp.), peptide nucleic acid libraries (see, e.g., U.S. Pat. No. 5,539,083), antibody libraries (see, e.g., Vaughn et al., Nature Biotechnology 14(3): 309-314 (1996), and PCT/US96/10287), carbohydrate libraries (see, e.g., Liang et al., Science 274:1520-1522 (1996), and U.S. Pat. No. 5,593,853), and small organic molecule libraries (see, e.g., benzodiazepines, Baum, C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288, 514; and the like).

Devices for the preparation of combinatorial libraries are commercially available (see, e.g., 357 NIPS, 390 NIPS, Advanced Chem Tech, Louisville Ky.; Symphony, Rainin, Woburn, Mass.; 433A, Applied Biosystems, Foster City, Calif.; 9050, Plus, Millipore, Bedford, NIA). A number of well-known robotic systems have also been developed for solution phase chemistries. These systems include automated workstations such as the automated synthesis apparatus developed by Takeda Chemical Industries, LTD. (Osaka, Japan) and many robotic systems utilizing robotic arms (Zymate H, Zymark Corporation, Hopkinton, Mass.; Orca, Hewlett-Packard, Palo Alto, Calif.), which mimic the manual synthetic operations performed by a chemist. Any of the above devices are suitable for use with the present invention. The nature and implementation of modifications to these devices (if any) so that they can operate as discussed herein will be apparent to persons skilled in the relevant art. In addition, numerous combinatorial libraries are themselves commercially available (see, e.g., ComGenex, Princeton, N.J.; Asinex, Moscow, RU; Tripos, Inc., St. Louis, Mo.;

ChemStar, Ltd, Moscow, RU; 3D Pharmaceuticals, Exton, Pa.; Martek Biosciences, Columbia, Md.; etc.).

The term "cytotoxic agent" refers to a substance that inhibits or prevents the expression activity of cells, function of cells and/or causes destruction of cells. The term is intended to include radioactive isotopes chemotherapeutic agents, and toxins such as small molecule toxins or enzymatically active toxins of bacterial, fungal, plant or animal origin, including fragments and/or variants thereof. Examples of cytotoxic agents include, but are not limited to auristatins, auromycins, maytansinoids, yttrium, bismuth, ricin, ricin A-chain, combrestatin, duocarmycins, dolostatins, doxorubicin, daunorubicin, taxol, cisplatin, cc1065, ethidium bromide, mitomycin, etoposide, tenoposide, vincristine, vinblastine, colchicine, dihydroxy anthracin dione, actinomycin, diphtheria toxin, *Pseudomonas* exotoxin (PE) A, PE40, abrin, abrin A chain, modeccin A chain, alpha-sarcin, gelonin, mitogellin, restrictocin, phenomycin, enomycin, curicin, crotin, calicheamicin, Sapaonaria officinalis inhibitor, and glucocorticoid and other chemotherapeutic agents, as well as radioisotopes such as $At^{211}$, $I^{131}$, $I^{125}$, $Y^{90}$ $Re^{186}$, $Re^{188}$, $Sm^{153}$, $Bi^{212\ or\ 213}$, $P^{32}$ and radioactive isotopes of Lu including $Lu^{177}$. Antibodies may also be conjugated to an anti-cancer pro-drug activating enzyme capable of converting the pro-drug to its active form.

The "gene product" is sometimes referred to herein as a protein or mRNA. For example, a "gene product of the invention" is sometimes referred to herein as a "cancer amino acid sequence", "cancer protein", "protein of a cancer listed in Table I", a "cancer mRNA", "mRNA of a cancer listed in Table I", etc. In one embodiment, the cancer protein is encoded by a nucleic acid of FIG. 2. The cancer protein can be a fragment, or alternatively, be the full-length protein to the fragment encoded by the nucleic acids of FIG. 2. In one embodiment, a cancer amino acid sequence is used to determine sequence identity or similarity. In another embodiment, the sequences are naturally occurring allelic variants of a protein encoded by a nucleic acid of FIG. 2. In another embodiment, the sequences are sequence variants as further described herein.

"High throughput screening" assays for the presence, absence, quantification, or other properties of particular nucleic acids or protein products are well known to those of skill in the art. Similarly, binding assays and reporter gene assays are similarly well known. Thus, e.g., U.S. Pat. No. 5,559,410 discloses high throughput screening methods for proteins; U.S. Pat. No. 5,585,639 discloses high throughput screening methods for nucleic acid binding (i.e., in arrays); while U.S. Pat. Nos. 5,576,220 and 5,541,061 disclose high throughput methods of screening for ligand/antibody binding.

In addition, high throughput screening systems are commercially available (see, e.g., Amersham Biosciences, Piscataway, N.J.; Zymark Corp., Hopkinton, Mass.; Air Technical Industries, Mentor, Ohio; Beckman Instruments, Inc. Fullerton, Calif.; Precision Systems, Inc., Natick, Mass.; etc.). These systems typically automate entire procedures, including all sample and reagent pipetting, liquid dispensing, timed incubations, and final readings of the microplate in detector (s) appropriate for the assay. These configurable systems provide high throughput and rapid start up as well as a high degree of flexibility and customization. The manufacturers of such systems provide detailed protocols for various high throughput systems. Thus, e.g., Zymark Corp. provides technical bulletins describing screening systems for detecting the modulation of gene transcription, ligand binding, and the like.

The term "homolog" refers to a molecule which exhibits homology to another molecule, by for example, having sequences of chemical residues that are the same or similar at corresponding positions.

"Human Leukocyte Antigen" or "HLA" is a human class I or class II Major Histocompatibility Complex (MHC) protein (see, e.g., Stites, et al., IMMUNOLOGY, $8^{TH}$ ED., Lange Publishing, Los Altos, Calif. (1994).

The terms "hybridize", "hybridizing", "hybridizes" and the like, used in the context of polynucleotides, are meant to refer to conventional hybridization conditions, preferably such as hybridization in 50% formamide/6×SSC/0.1% SDS/100 μg/ml ssDNA, in which temperatures for hybridization are above 37 degrees C. and temperatures for washing in 01XSSC/0.1% SDS are above 55 degrees C.

The phrases "isolated" or "biologically pure" refer to material which is substantially or essentially free from components which normally accompany the material as it is found in its native state. Thus, isolated peptides in accordance with the invention preferably do not contain materials normally associated with the peptides in their in situ environment. For example, a polynucleotide is said to be "isolated" when it is substantially separated from contaminant polynucleotides that correspond or are complementary to genes other than the 254P1D6B genes or that encode polypeptides other than 254P1D6B gene product or fragments thereof. A skilled artisan can readily employ nucleic acid isolation procedures to obtain an isolated 254P1D6B polynucleotide. A protein is said to be "isolated," for example, when physical, mechanical or chemical methods are employed to remove the 254P1D6B proteins from cellular constituents that are normally associated with the protein. A skilled artisan can readily employ standard purification methods to obtain an isolated 254P1D6B protein. Alternatively, an isolated protein can be prepared by chemical means.

The term "mammal" refers to any organism classified as a mammal, including mice, rats, rabbits, dogs, cats, cows, horses and humans. In one embodiment of the invention, the mammal is a mouse. In another embodiment of the invention, the mammal is a human.

The terms "metastatic prostate cancer" and "metastatic disease" mean prostate cancers that have spread to regional lymph nodes or to distant sites, and are meant to include stage D disease under the AUA system and stage TxNxM+ under the TNM system. As is the case with locally advanced prostate cancer, surgery is generally not indicated for patients with metastatic disease, and hormonal (androgen ablation) therapy is a preferred treatment modality. Patients with metastatic prostate cancer eventually develop an androgen-refractory state within 12 to 18 months of treatment initiation. Approximately half of these androgen-refractory patients die within 6 months after developing that status. The most common site for prostate cancer metastasis is bone. Prostate cancer bone metastases are often osteoblastic rather than osteolytic (i.e., resulting in net bone formation). Bone metastases are found most frequently in the spine, followed by the femur, pelvis, rib cage, skull and humerus. Other common sites for metastasis include lymph nodes, lung, liver and brain. Metastatic prostate cancer is typically diagnosed by open or laparoscopic pelvic lymphadenectomy, whole body radionuclide scans, skeletal radiography, and/or bone lesion biopsy.

The term "modulator" or "test compound" or "drug candidate" or grammatical equivalents as used herein describe any molecule, e.g., protein, oligopeptide, small organic molecule, polysaccharide, polynucleotide, etc., to be tested for the capacity to directly or indirectly alter the cancer phenotype or the expression of a cancer sequence, e.g., a nucleic acid or protein sequences, or effects of cancer sequences (e.g., signaling, gene expression, protein interaction, etc.) In one aspect, a modulator will neutralize the effect of a cancer protein of the invention. By "neutralize" is meant that an activity of a protein is inhibited or blocked, along with the consequent effect on the cell. In another aspect, a modulator will neutralize the effect of a gene, and its corresponding protein, of the invention by normalizing levels of said protein. In preferred embodiments, modulators alter expression profiles, or expression profile nucleic acids or proteins provided herein, or downstream effector pathways. In one embodiment, the modulator suppresses a cancer phenotype, e.g. to a normal tissue fingerprint. In another embodiment, a modulator induced a cancer phenotype. Generally, a plurality of assay mixtures is run in parallel with different agent concentrations to obtain a differential response to the various concentrations. Typically, one of these concentrations serves as a negative control, i.e., at zero concentration or below the level of detection.

Modulators, drug candidates or test compounds encompass numerous chemical classes, though typically they are organic molecules, preferably small organic compounds having a molecular weight of more than 100 and less than about 2,500 Daltons. Preferred small molecules are less than 2000, or less than 1500 or less than 1000 or less than 500 D. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Modulators also comprise biomolecules such as peptides, saccharides, fatty acids, steroids, purines, pyrimidines, derivatives, structural analogs or combinations thereof. Particularly preferred are peptides. One class of modulators are peptides, for example of from about five to about 35 amino acids, with from about five to about 20 amino acids being preferred, and from about 7 to about 15 being particularly preferred. Preferably, the cancer modulatory protein is soluble, includes a non-transmembrane region, and/or, has an N-terminal Cys to aid in solubility. In one embodiment, the C-terminus of the fragment is kept as a free acid and the N-terminus is a free amine to aid in coupling, i.e., to cysteine. In one embodiment, a cancer protein of the invention is conjugated to an immunogenic agent as discussed herein. In one embodiment, the cancer protein is conjugated to BSA. The peptides of the invention, e.g., of preferred lengths, can be linked to each other or to other amino acids to create a longer peptide/protein. The modulatory peptides can be digests of naturally occurring proteins as is outlined above, random peptides, or "biased" random peptides. In a preferred embodiment, peptide/protein-based modulators are antibodies, and fragments thereof, as defined herein.

Modulators of cancer can also be nucleic acids. Nucleic acid modulating agents can be naturally occurring nucleic acids, random nucleic acids, or "biased" random nucleic acids. For example, digests of prokaryotic or eukaryotic genomes can be used in an approach analogous to that outlined above for proteins.

The term "monoclonal antibody" refers to an antibody obtained from a population of substantially homogeneous antibodies, i.e., the antibodies comprising the population are identical except for possible naturally occurring mutations that are present in minor amounts.

A "motif", as in biological motif of a 254P1D6B-related protein, refers to any pattern of amino acids forming part of the primary sequence of a protein, that is associated with a particular function (e.g. protein-protein interaction, protein-DNA interaction, etc) or modification (e.g. that is phosphorylated, glycosylated or amidated), or localization (e.g. secretory sequence, nuclear localization sequence, etc.) or a sequence that is correlated with being immunogenic, either humorally or cellularly. A motif can be either contiguous or capable of being aligned to certain positions that are generally correlated with a certain function or property. In the context of HLA motifs, "motif" refers to the pattern of residues in a peptide of defined length, usually a peptide of from about 8 to about 13 amino acids for a class I HLA motif and from about 6 to about 25 amino acids for a class II HLA motif, which is recognized by a particular HLA molecule. Peptide motifs for HLA binding are typically different for each protein encoded by each human HLA allele and differ in the pattern of the primary and secondary anchor residues.

A "pharmaceutical excipient" comprises a material such as an adjuvant, a carrier, pH-adjusting and buffering agents, tonicity adjusting agents, wetting agents, preservative, and the like.

"Pharmaceutically acceptable" refers to a non-toxic, inert, and/or composition that is physiologically compatible with humans or other mammals.

The term "polynucleotide" means a polymeric form of nucleotides of at least 10 bases or base pairs in length, either ribonucleotides or deoxynucleotides or a modified form of either type of nucleotide, and is meant to include single and double stranded forms of DNA and/or RNA. In the art, this term if often used interchangeably with "oligonucleotide". A polynucleotide can comprise a nucleotide sequence disclosed herein wherein thymidine (T), as shown for example in FIG. 2, can also be uracil (U); this definition pertains to the differences between the chemical structures of DNA and RNA, in particular the observation that one of the four major bases in RNA is uracil (U) instead of thymidine (T).

The term "polypeptide" means a polymer of at least about 4, 5, 6, 7, or 8 amino acids. Throughout the specification, standard three letter or single letter designations for amino acids are used. In the art, this term is often used interchangeably with "peptide" or "protein".

An HLA "primary anchor residue" is an amino acid at a specific position along a peptide sequence which is understood to provide a contact point between the immunogenic peptide and the HLA molecule. One to three, usually two, primary anchor residues within a peptide of defined length generally defines a "motif" for an immunogenic peptide. These residues are understood to fit in close contact with peptide binding groove of an HLA molecule, with their side chains buried in specific pockets of the binding groove. In one embodiment, for example, the primary anchor residues for an HLA class I molecule are located at position 2 (from the amino terminal position) and at the carboxyl terminal position of a 8, 9, 10, 11, or 12 residue peptide epitope in accordance with the invention. Alternatively, in another embodiment, the primary anchor residues of a peptide binds an HLA class II molecule are spaced relative to each other, rather than to the termini of a peptide, where the peptide is generally of at least 9 amino acids in length. The primary anchor positions for each motif and supermotif are set forth in Table IV. For example, analog peptides can be created by altering the presence or absence of particular residues in the primary and/or secondary anchor positions shown in Table IV. Such analogs are used to modulate the binding affinity and/or population coverage of a peptide comprising a particular HLA motif or supermotif.

"Radioisotopes" include, but are not limited to the following (non-limiting exemplary uses are also set forth):

Examples of Medical Isotopes:

| Isotope | Description of use |
|---|---|
| Actinium-225 (AC-225) | See Thorium-229 (Th-229) |
| Actinium-227 (AC-227) | Parent of Radium-223 (Ra-223) which is an alpha emitter used to treat metastases in the skeleton resulting from cancer (i.e., breast and prostate cancers), and cancer radioimmunotherapy |
| Bismuth-212 (Bi-212) | See Thorium-228 (Th-228) |
| Bismuth-213 (Bi-213) | See Thorium-229 (Th-229) |
| Cadmium-109 (Cd-109) | Cancer detection |
| Cobalt-60 (Co-60) | Radiation source for radiotherapy of cancer, for food irradiators, and for sterilization of medical supplies |
| Copper-64 (Cu-64) | A positron emitter used for cancer therapy and SPECT imaging |
| Copper-67 (Cu-67) | Beta/gamma emitter used in cancer radioimmunotherapy and diagnostic studies (i.e., breast and colon cancers, and lymphoma) |
| Dysprosium-166 (Dy-166) | Cancer radioimmunotherapy |
| Erbium-169 (Er-169) | Rheumatoid arthritis treatment, particularly for the small joints associated with fingers and toes |
| Europium-152 (Eu-152) | Radiation source for food irradiation and for sterilization of medical supplies |
| Europium-154 (Eu-154) | Radiation source for food irradiation and for sterilization of medical supplies |
| Gadolinium-153 (Gd-153) | Osteoporosis detection and nuclear medical quality assurance devices |
| Gold-198 (Au-198) | Implant and intracavity therapy of ovarian, prostate, and brain cancers |
| Holmium-166 (Ho-166) | Multiple myeloma treatment in targeted skeletal therapy, cancer radioimmunotherapy, bone marrow ablation, and rheumatoid arthritis treatment |
| Iodine-125 (I-125) | Osteoporosis detection, diagnostic imaging, tracer drugs, brain cancer treatment, radiolabeling, tumor imaging, mapping of receptors in the brain, interstitial radiation therapy, brachytherapy for treatment of prostate cancer, determination of glomerular filtration rate (GFR), determination of plasma volume, detection of deep vein thrombosis of the legs |
| Iodine-131 (I-131) | Thyroid function evaluation, thyroid disease detection, treatment of thyroid cancer as well as other non-malignant thyroid diseases (i.e., Graves disease, goiters, and hyperthyroidism), treatment of leukemia, lymphoma, and other forms of cancer (e.g., breast cancer) using radioimmunotherapy |
| Iridium-192 (Ir-192) | Brachytherapy, brain and spinal cord tumor treatment, treatment of blocked arteries (i.e., arteriosclerosis and restenosis), and implants for breast and prostate tumors |
| Lutetium-177 (Lu-177) | Cancer radioimmunotherapy and treatment of blocked arteries (i.e., arteriosclerosis and restenosis) |
| Molybdenum-99 (Mo-99) | Parent of Technetium-99m (Tc-99m) which is used for imaging the brain, liver, lungs, heart, and other organs. Currently, Tc-99m is the most widely used radioisotope used for diagnostic imaging of various cancers and diseases involving the brain, heart, liver, lungs; also used in detection of deep vein thrombosis of the legs |
| Osmium-194 (Os-194) | Cancer radioimmunotherapy |
| Palladium-103 (Pd-103) | Prostate cancer treatment |
| Platinum-195m (Pt-195m) | Studies on biodistribution and metabolism of cisplatin, a chemotherapeutic drug |
| Phosphorus-32 (P-32) | Polycythemia rubra vera (blood cell disease) and leukemia treatment, bone cancer diagnosis/treatment; colon, pancreatic, and liver cancer treatment; radiolabeling nucleic acids for in vitro research, diagnosis of superficial tumors, treatment of blocked arteries (i.e., arteriosclerosis and restenosis), and intracavity therapy |
| Phosphorus-33 (P-33) | Leukemia treatment, bone disease diagnosis/treatment, radiolabeling, and treatment of blocked arteries (i.e., arteriosclerosis and restenosis) |
| Radium-223 (Ra-223) | See Actinium-227 (Ac-227) |
| Rhenium-186 (Re-186) | Bone cancer pain relief, rheumatoid arthritis treatment, and diagnosis and treatment of lymphoma and bone, breast, colon, and liver cancers using radioimmunotherapy |
| Rhenium-188 (Re-188) | Cancer diagnosis and treatment using radioimmunotherapy, bone cancer pain relief, treatment of rheumatoid arthritis, and treatment of prostate cancer |
| Rhodium-105 (Rh-105) | Cancer radioimmunotherapy |

Examples of Medical Isotopes:

| Isotope | Description of use |
| --- | --- |
| Samarium-145 (Sm-145) | Ocular cancer treatment |
| Samarium-153 (Sm-153) | Cancer radioimmunotherapy and bone cancer pain relief |
| Scandium-47 (Sc-47) | Cancer radioimmunotherapy and bone cancer pain relief |
| Selenium-75 (Se-75) | Radiotracer used in brain studies, imaging of adrenal cortex by gamma-scintigraphy, lateral locations of steroid secreting tumors, pancreatic scanning, detection of hyperactive parathyroid glands, measure rate of bile acid loss from the endogenous pool |
| Strontium-85 (Sr-85) | Bone cancer detection and brain scans |
| Strontium-89 (Sr-89) | Bone cancer pain relief, multiple myeloma treatment, and osteoblastic therapy |
| Technetium-99m (Tc-99m) | See Molybdenum-99 (Mo-99) |
| Thorium-228 (Th-228) | Parent of Bismuth-212 (Bi-212) which is an alpha emitter used in cancer radioimmunotherapy |
| Thorium-229 (Th-229) | Parent of Actinium-225 (Ac-225) and grandparent of Bismuth-213 (Bi-213) which are alpha emitters used in cancer radioimmunotherapy |
| Thulium-170 (Tm-170) | Gamma source for blood irradiators, energy source for implanted medical devices |
| Tin-117m (Sn-117m) | Cancer immunotherapy and bone cancer pain relief |
| Tungsten-188 (W-188) | Parent for Rhenium-188 (Re-188) which is used for cancer diagnostics/treatment, bone cancer pain relief, rheumatoid arthritis treatment, and treatment of blocked arteries (i.e., arteriosclerosis and restenosis) |
| Xenon-127 (Xe-127) | Neuroimaging of brain disorders, high resolution SPECT studies, pulmonary function tests, and carebral blood flow studies |
| Ytterbium-175 (Yb-175) | Cancer radioimmunotherapy |
| Yttrium-90 (Y-90) | Microseeds obtained from irradiating Yttrium-89 (Y-89) for liver cancer treatment |
| Yttrium-91 (Y-91) | A gamma-emitting label for Yttrium-90 (Y-90) which is used for cancer radioimmunotherapy (i.e., lymphoma, breast, colon, kidney, lung, ovarian, prostate, pancreatic, and inoperable liver cancers) |

By "randomized" or grammatical equivalents as herein applied to nucleic acids and proteins is meant that each nucleic acid and peptide consists of essentially random nucleotides and amino acids, respectively. These random peptides (or nucleic acids, discussed herein) can incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents.

In one embodiment, a library is "fully randomized," with no sequence preferences or constants at any position. In another embodiment, the library is a "biased random" library. That is, some positions within the sequence either are held constant, or are selected from a limited number of possibilities. For example, the nucleotides or amino acid residues are randomized within a defined class, e.g., of hydrophobic amino acids, hydrophilic residues, sterically biased (either small or large) residues, towards the creation of nucleic acid binding domains, the creation of cysteines, for cross-linking, prolines for SH-3 domains, serines, threonines, tyrosines or histidines for phosphorylation sites, etc., or to purines, etc.

A "recombinant" DNA or RNA molecule is a DNA or RNA molecule that has been subjected to molecular manipulation in vitro.

Non-limiting examples of small molecules include compounds that bind or interact with 254P1D6B, ligands including hormones, neuropeptides, chemokines, odorants, phospholipids, and functional equivalents thereof that bind and preferably inhibit 254P1D6B protein function. Such non-limiting small molecules preferably have a molecular weight of less than about 10 kDa, more preferably below about 9, about 8, about 7, about 6, about 5 or about 4 kDa. In certain embodiments, small molecules physically associate with, or bind, 254P1D6B protein; are not found in naturally occurring metabolic pathways; and/or are more soluble in aqueous than non-aqueous solutions "Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured nucleic acid sequences to reanneal when complementary strands are present in an environment below their melting temperature. The higher the degree of desired homology between the probe and hybridizable sequence, the higher the relative temperature that can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995).

"Stringent conditions" or "high stringency conditions", as defined herein, are identified by, but not limited to, those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium. citrate) and 50% formamide at 55° C., followed by a high-stringency wash consisting of 0.1×SSC containing EDTA at 55° C. "Moderately stringent conditions" are described by, but not limited to, those in Sambrook et al., Molecular Cloning: A Laboratory Manual, New York: Cold Spring Harbor Press, 1989, and include the use of washing solution and hybridization conditions (e.g., temperature, ionic strength and % SDS) less stringent than those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/mL denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

An HLA "supermotif" is a peptide binding specificity shared by HLA molecules encoded by two or more HLA alleles. Overall phenotypic frequencies of HLA-supertypes in different ethnic populations are set forth in Table IV (F). The non-limiting constituents of various supertypes are as follows:

A2: A*0201, A*0202, A*0203, A*0204, A*0205, A*0206, A*6802, A*6901, A*0207
A3 A3, A11, A31, A*3301, A*6801, A*0301, A*1101, A*3101
B7: B7, B*3501-03, B*51, B*5301, B*5401, B*5501, B*5502, B*5601, B*6701, B*7801, B*0702, B*5101, B*5602
B44: B*3701, B*4402, B*4403, B*60 (B*4001), B61 (B*4006)
A1: A*0102, A*2604, A*3601, A*4301, A*8001
A24: A*24, A*30, A*2403, A*2404, A*3002, A*3003
B27: B*1401-02, B*1503, B*1509, B*1510, B*1518, B*3801-02, B*3901, B*3902,
B*3903-04, B*4801-02, B*7301, B*2701-08
B58: B*1516, B*1517, B*5701, B*5702, B58
B62: B*4601, B52, B*1501 (B62), B*1502 (B75), B*1513 (B77)

Calculated population coverage afforded by different HLA-supertype combinations are set forth in Table IV (G).

As used herein "to treat" or "therapeutic" and grammatically related terms, refer to any improvement of any consequence of disease, such as prolonged survival, less morbidity, and/or a lessening of side effects which are the byproducts of an alternative therapeutic modality; full eradication of disease is not required.

A "transgenic animal" (e.g., a mouse or rat) is an animal having cells that contain a transgene, which transgene was introduced into the animal or an ancestor of the animal at a prenatal, e.g., an embryonic stage. A "transgene" is a DNA that is integrated into the genome of a cell from which a transgenic animal develops.

As used herein, an HLA or cellular immune response "vaccine" is a composition that contains or encodes one or more peptides of the invention. There are numerous embodiments of such vaccines, such as a cocktail of one or more individual peptides; one or more peptides of the invention comprised by a polyepitopic peptide; or nucleic acids that encode such individual peptides or polypeptides, e.g., a minigene that encodes a polyepitopic peptide. The "one or more peptides" can include any whole unit integer from 1-150 or more, e.g., at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 105, 110, 115, 120, 125, 130, 135, 140, 145, or 150 or more peptides of the invention. The peptides or polypeptides can optionally be modified, such as by lipidation, addition of targeting or other sequences. HLA class I peptides of the invention can be admixed with, or linked to, HLA class II peptides, to facilitate activation of both cytotoxic T lymphocytes and helper T lymphocytes. HLA vaccines can also comprise peptide-pulsed antigen presenting cells, e.g., dendritic cells.

The term "variant" refers to a molecule that exhibits a variation from a described type or norm, such as a protein that has one or more different amino acid residues in the corresponding position(s) of a specifically described protein (e.g. the 254P1D6B protein shown in FIG. 2 or FIG. 3. An analog is an example of a variant protein. Splice isoforms and single nucleotides polymorphisms (SNPs) are further examples of variants.

The "254P1D6B-related proteins" of the invention include those specifically identified herein, as well as allelic variants, conservative substitution variants, analogs and homologs that can be isolated/generated and characterized without undue experimentation following the methods outlined herein or readily available in the art. Fusion proteins that combine parts of different 254P1D6B proteins or fragments thereof, as well as fusion proteins of a 254P1D6B protein and a heterologous polypeptide are also included. Such 254P1D6B proteins are collectively referred to as the 254P1D6B-related proteins, the proteins of the invention, or 254P1D6B. The term "254P1D6B-related protein" refers to a polypeptide fragment or a 254P1D6B protein sequence of 4, 5, 6, 7, 8, 9, 10, 11, 12, 13, 14, 15, 16, 17, 18, 19, 20, 21, 22, 23, 24, 25, or more than 25 amino acids; or, at least 30, 35, 40, 45, 50, 55, 60, 65, 70, 80, 85, 90, 95, 100, 105, 110, 115, 120, 125, 130, 135, 140, 145, 150, 155, 160, 165, 170, 175, 180, 185, 190, 195, 200, 225, 250, 275, 300, 325, 350, 375, 400, 425, 450, 475, 500, 525, 550, 575, or 576 or more amino acids.

II.) 254P1D6B Polynucleotides

One aspect of the invention provides polynucleotides corresponding or complementary to all or part of a 254P1D6B gene, mRNA, and/or coding sequence, preferably in isolated form, including polynucleotides encoding a 254P1D6B-related protein and fragments thereof, DNA, RNA, DNA/RNA hybrid, and related molecules, polynucleotides or oligonucleotides complementary to a 254P1D6B gene or mRNA sequence or a part thereof, and polynucleotides or oligonucleotides that hybridize to a 254P1D6B gene, mRNA, or to a 254P1D6B encoding polynucleotide (collectively, "254P1D6B polynucleotides"). In all instances when referred to in this section, T can also be U in FIG. 2.

Embodiments of a 254P1D6B polynucleotide include: a 254P1D6B polynucleotide having the sequence shown in FIG. 2, the nucleotide sequence of 254P1D6B as shown in FIG. 2 wherein T is U; at least 10 contiguous nucleotides of a polynucleotide having the sequence as shown in FIG. 2; or, at least 10 contiguous nucleotides of a polynucleotide having the sequence as shown in FIG. 2 where T is U. For example, embodiments of 254P1D6B nucleotides comprise, without limitation:

(I) a polynucleotide comprising, consisting essentially of, or consisting of a sequence as shown in FIG. 2, wherein T can also be U;

(II) a polynucleotide comprising, consisting essentially of, or consisting of the sequence as shown in FIG. 2A, from nucleotide residue number 512 through nucleotide residue number 3730, including the stop codon, wherein T can also be U;

(III) a polynucleotide comprising, consisting essentially of, or consisting of the sequence as shown in FIG. 2B, from nucleotide residue number 512 through nucleotide residue number 3730, including the stop codon, wherein T can also be U;

(IV) a polynucleotide comprising, consisting essentially of, or consisting of the sequence as shown in FIG. 2C, from nucleotide residue number 739 through nucleotide residue number 3930, including the a stop codon, wherein T can also be U;

(V) a polynucleotide comprising, consisting essentially of, or consisting of the sequence as shown in FIG. 2D, from nucleotide residue number 512 through nucleotide residue number 3730, including the stop codon, wherein T can also be U;

(VI) a polynucleotide that encodes a 254P1D6B-related protein that is at least 90, 91, 92, 93, 94, 95, 96, 97, 98, 99 or 100% homologous to an entire amino acid sequence shown in FIG. 2A-D;

(VII) a polynucleotide that encodes a 254P1D6B-related protein that is at least 90, 91, 92, 93, 94, 95, 96, 97, 98, 99 or 100% identical to an entire amino acid sequence shown in FIG. 2A-D;

(VIII) a polynucleotide that encodes at least one peptide set forth in Tables VIII-XXI and XXII-XLIX;

(IX) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIGS. 3A, 3B, 3D, and 3E in any whole number increment up to 1072 that includes at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Hydrophilicity profile of FIG. 5;

(X) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIGS. 3A, 3B, 3D, and 3E in any whole number increment up to 1072 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value less than 0.5 in the Hydropathicity profile of FIG. 6;

(XI) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIGS. 3A, 3B, 3D, and 3E in any whole number increment up to 1072 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Percent Accessible Residues profile of FIG. 7;

(XII) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIGS. 3A, 3B, 3D, and 3E in any whole number increment up to 1072 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Average Flexibility profile of FIG. 8;

(XIII) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIGS. 3A, 3B, 3D, and 3E in any whole number increment up to 1072 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Beta-turn profile of FIG. 9;

(XIV) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3C in any whole number increment up to 1063 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Hydrophilicity profile of FIG. 5;

(XV) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3C in any whole number increment up to 1063 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value less than 0.5 in the Hydropathicity profile of FIG. 6;

(XVI) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3C in any whole number increment up to 1063 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Percent Accessible Residues profile of FIG. 7;

(XVII) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3C in any whole number increment up to 1063 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Average Flexibility profile of FIG. 8;

(XVIII) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3C in any whole number increment up to 1063 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Beta-turn profile of FIG. 9;

(XIX) a polynucleotide that is fully complementary to a polynucleotide of any one of (I)-(XVIII);

(XX) a polynucleotide that is fully complementary to a polynucleotide of any one of (I)-(XIX);

(XXI) a peptide that is encoded by any of (I) to (XX); and;

(XXII) a composition comprising a polynucleotide of any of (I)-(XX) or peptide of (XXI) together with a pharmaceutical excipient and/or in a human unit dose form;

(XXIII) a method of using a polynucleotide of any (I)-(XX) or peptide of (XXI) or a composition of (XXII) in a method to modulate a cell expressing 254P1D6B;

(XXIV) a method of using a polynucleotide of any (I)-(XX) or peptide of (XXI) or a composition of (XXII) in a method to diagnose, prophylaxis, prognose, or treat an individual who bears a cell expressing 254P1D6B;

(XXV) a method of using a polynucleotide of any (I)-(XX) or peptide of (XXI) or a composition of (XXII) in a method to diagnose, prophylax, prognose, or treat an individual who bears a cell expressing 254P1D6B, said cell from a cancer of a tissue listed in Table I;

(XXVI) a method of using a polynucleotide of any (I)-(XX) or peptide of (XXI) or a composition of (XXII) in a method to diagnose, prophylax, prognose, or treat a a cancer;

(XXVII) a method of using a polynucleotide of any (I)-(XX) or peptide of (XXI) or a composition of (XXII) in a method to diagnose, prophylax, prognose, or treat a a cancer of a tissue listed in Table I; and;

(XXVIII) a method of using a polynucleotide of any (I)-(XX) or peptide of (XXI) or a composition of (XXII) in a method to identify or characterize a modulator of a cell expressing 254P1D6B.

As used herein, a range is understood to disclose specifically all whole unit positions thereof.

Typical embodiments of the invention disclosed herein include 254P1D6B polynucleotides that encode specific portions of 254P1D6B mRNA sequences (and those which are complementary to such sequences) such as those that encode the proteins and/or fragments thereof, for example:

(a)4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1025, 1050, 1060. 1065, 1070, and 1072 or more contiguous amino acids of 254P1D6B variant 1; the maximal lengths relevant for other variants are: variant 2, 1072 amino acids; variant 3, 1063 amino acids, variant 5, 1072 amino acids, variant 6, 1072 amino acids, and variants 4, 7-20, 1072 amoni acids.

For example, representative embodiments of the invention disclosed herein include: polynucleotides and their encoded peptides themselves encoding about amino acid 1 to about amino acid 10 of the 254P1D6B protein shown in FIG. 2 or FIG. 3, polynucleotides encoding about amino acid 10 to about amino acid 20 of the 254P1D6B protein shown in FIG. 2 or FIG. 3, polynucleotides encoding about amino acid 20 to about amino acid 30 of the 254P1D6B protein shown in FIG. 2 or FIG. 3, polynucleotides encoding about amino acid 30 to about amino acid 40 of the 254P1D6B protein shown in FIG. 2 or FIG. 3, polynucleotides encoding about amino acid 40 to about amino acid 50 of the 254P1D6B protein shown in FIG. 2 or FIG. 3, polynucleotides encoding about amino acid 50 to about amino acid 60 of the 254P1D6B protein shown in FIG. 2 or FIG. 3, polynucleotides encoding about amino acid 60 to about amino acid 70 of the 254P1D6B protein shown in FIG. 2 or FIG. 3, polynucleotides encoding about amino acid 70 to about amino acid 80 of the 254P1D6B protein shown in FIG. 2 or FIG. 3, polynucleotides encoding about amino acid 80 to about amino acid 90 of the 254P1D6B protein shown in FIG. 2 or FIG. 3, polynucleotides encoding about amino acid 90 to about amino acid 100 of the 254P1D6B protein shown in FIG. 2 or FIG. 3, in increments of about 10 amino acids, ending at the carboxyl terminal amino acid set forth in FIG. 2 or FIG. 3. Accordingly, polynucleotides encoding portions of the amino acid sequence (of about 10 amino acids), of amino acids, 100 through the carboxyl terminal amino acid of the 254P1D6B protein are embodiments of the invention. Wherein it is understood that each particular amino acid position discloses that position plus or minus five amino acid residues.

Polynucleotides encoding relatively long portions of a 254P1D6B protein are also within the scope of the invention. For example, polynucleotides encoding from about amino acid 1 (or 20 or 30 or 40 etc.) to about amino acid 20, (or 30, or 40 or 50 etc.) of the 254P1D6B protein "or variant" shown in FIG. 2 or FIG. 3 can be generated by a variety of techniques well known in the art. These polynucleotide fragments can include any portion of the 254P1D6B sequence as shown in FIG. 2.

Additional illustrative embodiments of the invention disclosed herein include 254P1D6B polynucleotide fragments encoding one or more of the biological motifs contained within a 254P1D6B protein "or variant" sequence, including one or more of the motif-bearing subsequences of a 254P1D6B protein "or variant" set forth in Tables VIII-XXI and XXII-XLIX. In another embodiment, typical polynucleotide fragments of the invention encode one or more of the regions of 254P1D6B protein or variant that exhibit homology to a known molecule. In another embodiment of the invention, typical polynucleotide fragments can encode one or more of the 254P1D6B protein or variant N-glycosylation sites, cAMP and cGMP-dependent protein kinase phosphorylation sites, casein kinase II phosphorylation sites or N-myristoylation site and amidation sites.

Note that to determine the starting position of any peptide set forth in Tables VIII-XXI and Tables XXII to XLIX (collectively HLA Peptide Tables) respective to its parental protein, e.g., variant 1, variant 2, etc., reference is made to three factors: the particular variant, the length of the peptide in an HLA Peptide Table, and the Search Peptides listed in Table VII. Generally, a unique Search Peptide is used to obtain HLA peptides for a particular variant. The position of each Search Peptide relative to its respective parent molecule is listed in Table VII. Accordingly, if a Search Peptide begins at position "X", one must add the value "X minus 1" to each position in Tables VIII-XXI and Tables XXII-IL to obtain the actual position of the HLA peptides in their parental molecule. For example if a particular Search Peptide begins at position 150 of its parental molecule, one must add 150-1, i.e., 149 to each HLA peptide amino acid position to calculate the position of that amino acid in the parent molecule.

II.A.) Uses of 254P1D6B Polynucleotides

II.A.1.) Monitoring of Genetic Abnormalities

The polynucleotides of the preceding paragraphs have a number of different specific uses. The human 254P1D6B gene maps to the chromosomal location set forth in the Example entitled "Chromosomal Mapping of 254P1D6B." For example, because the 254P1D6B gene maps to this chromosome, polynucleotides that encode different regions of the 254P1D6B proteins are used to characterize cytogenetic abnormalities of this chromosomal locale, such as abnormalities that are identified as being associated with various cancers. In certain genes, a variety of chromosomal abnormalities including rearrangements have been identified as frequent cytogenetic abnormalities in a number of different cancers (see e.g. Krajinovic et al., Mutat. Res. 382(3-4): 81-83 (1998); Johansson et al., Blood 86(10): 3905-3914 (1995) and Finger et al., P.N.A.S. 85(23): 9158-9162 (1988)). Thus, polynucleotides encoding specific regions of the 254P1D6B proteins provide new tools that can be used to delineate, with greater precision than previously possible, cytogenetic abnormalities in the chromosomal region that encodes 254P1D6B that may contribute to the malignant phenotype. In this context, these polynucleotides satisfy a need in the art for expanding the sensitivity of chromosomal screening in order to identify more subtle and less common chromosomal abnormalities (see e.g. Evans et al., Am. J. Obstet. Gynecol 171(4): 1055-1057 (1994)).

Furthermore, as 254P1D6B was shown to be highly expressed in prostate and other cancers, 254P1D6B polynucleotides are used in methods assessing the status of 254P1D6B gene products in normal versus cancerous tissues. Typically, polynucleotides that encode specific regions of the 254P1D6B proteins are used to assess the presence of perturbations (such as deletions, insertions, point mutations, or alterations resulting in a loss of an antigen etc.) in specific regions of the 254P1D6B gene, such as regions containing one or more motifs. Exemplary assays include both RT-PCR assays as well as single-strand conformation polymorphism (SSCP) analysis (see, e.g., Marrogi et al., J. Cutan. Pathol. 26(8): 369-378 (1999), both of which utilize polynucleotides encoding specific regions of a protein to examine these regions within the protein.

II.A.2.) Antisense Embodiments

Other specifically contemplated nucleic acid related embodiments of the invention disclosed herein are genomic DNA, cDNAs, ribozymes, and antisense molecules, as well as nucleic acid molecules based on an alternative backbone, or including alternative bases, whether derived from natural sources or synthesized, and include molecules capable of inhibiting the RNA or protein expression of 254P1D6B. For example, antisense molecules can be RNAs or other molecules, including peptide nucleic acids (PNAs) or non-nucleic acid molecules such as phosphorothioate derivatives that specifically bind DNA or RNA in a base pair-dependent manner. A skilled artisan can readily obtain these classes of nucleic acid molecules using the 254P1D6B polynucleotides and polynucleotide sequences disclosed herein.

Antisense technology entails the administration of exogenous oligonucleotides that bind to a target polynucleotide located within the cells. The term "antisense" refers to the fact that such oligonucleotides are complementary to their intracellular targets, e.g., 254P1D6B. See for example, Jack Cohen, Oligodeoxynucleotides, Antisense Inhibitors of Gene Expression, CRC Press, 1989; and Synthesis 1:1-5 (1988). The 254P1D6B antisense oligonucleotides of the present invention include derivatives such as S-oligonucleotides (phosphorothioate derivatives or S-oligos, see, Jack Cohen, supra), which exhibit enhanced cancer cell growth inhibitory action. S-oligos (nucleoside phosphorothioates) are isoelectronic analogs of an oligonucleotide (O-oligo) in which a nonbridging oxygen atom of the phosphate group is replaced by a sulfur atom. The S-oligos of the present invention can be prepared by treatment of the corresponding O-oligos with 3H-1,2-benzodithiol-3-one-1,1-dioxide, which is a sulfur transfer reagent. See, e.g., Iyer, R. P. et al., J. Org. Chem. 55:4693-4698 (1990); and Tyer, R. P. et al., J. Am. Chem. Soc. 112:1253-1254 (1990). Additional 254P1D6B antisense oligonucleotides of the present invention include morpholino antisense oligonucleotides known in the art (see, e.g., Partridge et al. 1996, Antisense & Nucleic Acid Drug Development 6: 169-175).

The 254P1D6B antisense oligonucleotides of the present invention typically can be RNA or DNA that is complementary to and stably hybridizes with the first 100 5' codons or last 100 3' codons of a 254P1D6B genomic sequence or the corresponding mRNA. Absolute complementarity is not required, although high degrees of complementarity are preferred. Use of an oligonucleotide complementary to this region allows for the selective hybridization to 254P1D6B mRNA and not to mRNA specifying other regulatory subunits of protein kinase. In one embodiment, 254P1D6B antisense oligonucleotides of the present invention are 15 to 30-mer fragments of the antisense DNA molecule that have a sequence that hybridizes to 254P1D6B mRNA. Optionally, 254P1D6B antisense oligonucleotide is a 30-mer oligonucleotide that is complementary to a region in the first 10 5' codons or last 10 3' codons of 254P1D6B. Alternatively, the antisense molecules are modified to employ ribozymes in the inhibition of 254P1D6B expression, see, e.g., L. A. Couture & D. T. Stinchcomb; Trends Genet 12: 510-515 (1996).

II.A.3.) Primers and Primer Pairs

Further specific embodiments of these nucleotides of the invention include primers and primer pairs, which allow the specific amplification of polynucleotides of the invention or of any specific parts thereof, and probes that selectively or specifically hybridize to nucleic acid molecules of the invention or to any part thereof. Probes can be labeled with a detectable marker, such as, for example, a radioisotope, fluorescent compound, bioluminescent compound, a chemiluminescent compound, metal chelator or enzyme. Such probes and primers are used to detect the presence of a 254P1D6B polynucleotide in a sample and as a means for detecting a cell expressing a 254P1D6B protein.

Examples of such probes include polypeptides comprising all or part of the human 254P1D6B cDNA sequence shown in FIG. 2. Examples of primer pairs capable of specifically amplifying 254P1D6B mRNAs are also described in the Examples. As will be understood by the skilled artisan, a great many different primers and probes can be prepared based on the sequences provided herein and used effectively to amplify and/or detect a 254P1D6B mRNA.

The 254P1D6B polynucleotides of the invention are useful for a variety of purposes, including but not limited to their use as probes and primers for the amplification and/or detection of the 254P1D6B gene(s), mRNA(s), or fragments thereof, as reagents for the diagnosis and/or prognosis of prostate cancer and other cancers; as coding sequences capable of directing the expression of 254P1D6B polypeptides; as tools for modulating or inhibiting the expression of the 254P1D6B gene(s) and/or translation of the 254P1D6B transcript(s); and as therapeutic agents.

The present invention includes the use of any probe as described herein to identify and isolate a 254P1D6B or 254P1D6B related nucleic acid sequence from a naturally occurring source, such as humans or other mammals, as well as the isolated nucleic acid sequence per se, which would comprise all or most of the sequences found in the probe used.

II.A.4.) Isolation of 254P1D6B-Encoding Nucleic Acid Molecules

The 254P1D6B cDNA sequences described herein enable the isolation of other polynucleotides encoding 254P1D6B gene product(s), as well as the isolation of polynucleotides encoding 254P1D6B gene product homologs, alternatively spliced isoforms, allelic variants, and mutant forms of a 254P1D6B gene product as well as polynucleotides that encode analogs of 254P1D6B-related proteins. Various molecular cloning methods that can be employed to isolate full length cDNAs encoding a 254P1D6B gene are well known (see, for example, Sambrook, J. et al., Molecular Cloning: A Laboratory Manual, 2d edition, Cold Spring Harbor Press, New York, 1989; Current Protocols in Molecular Biology. Ausubel et al., Eds., Wiley and Sons, 1995). For example, lambda phage cloning methodologies can be conveniently employed, using commercially available cloning systems (e.g., Lambda ZAP Express, Stratagene). Phage clones containing 254P1D6B gene cDNAs can be identified by probing with a labeled 254P1D6B cDNA or a fragment thereof. For example, in one embodiment, a 254P1D6B cDNA (e.g., FIG. 2) or a portion thereof can be synthesized and used as a probe to retrieve overlapping and full-length cDNAs corresponding to a 254P1D6B gene. A 254P1D6B gene itself can be isolated by screening genomic DNA libraries, bacterial artificial chromosome libraries (BACs), yeast artificial chromosome libraries (YACs), and the like, with 254P1D6B DNA probes or primers.

II.A.5.) Recombinant Nucleic Acid Molecules and Host-Vector Systems

The invention also provides recombinant DNA or RNA molecules containing a 254P1D6B polynucleotide, a fragment, analog or homologue thereof, including but not limited to phages, plasmids, phagemids, cosmids, YACs, BACs, as well as various viral and non-viral vectors well known in the art, and cells transformed or transfected with such recombinant DNA or RNA molecules. Methods for generating such molecules are well known (see, for example, Sambrook et al., 1989, supra).

The invention further provides a host-vector system comprising a recombinant DNA molecule containing a 254P1D6B polynucleotide, fragment, analog or homologue thereof within a suitable prokaryotic or eukaryotic host cell. Examples of suitable eukaryotic host cells include a yeast cell, a plant cell, or an animal cell, such as a mammalian cell or an insect cell (e.g., a baculovirus-infectible cell such as an Sf9 or HighFive cell). Examples of suitable mammalian cells include various prostate cancer cell lines such as DU145 and TsuPr1, other transfectable or transducible prostate cancer cell lines, primary cells (PrEC), as well as a number of mammalian cells routinely used for the expression of recombinant proteins (e.g., COS, CHO, 293, 293T cells). More particularly, a polynucleotide comprising the coding sequence of 254P1D6B or a fragment, analog or homolog thereof can be used to generate 254P1D6B proteins or fragments thereof using any number of host-vector systems routinely used and widely known in the art.

A wide range of host-vector systems suitable for the expression of 254P1D6B proteins or fragments thereof are available, see for example, Sambrook et al., 1989, supra; Current Protocols in Molecular Biology, 1995, supra). Preferred vectors for mammalian expression include but are not limited to pcDNA 3.1 myc-His-tag (Invitrogen) and the retroviral vector pSRαtkneo (Muller et al., 1991, MCB 11:1785). Using these expression vectors, 254P6D6B can be expressed in several prostate cancer and non-prostate cell lines, including for example 293, 293T, rat-1, NIH 3T3 and TsuPr1. The host-vector systems of the invention are useful for the production of a 254P1D6B protein or fragment thereof. Such host-vector systems can be employed to study the functional properties of 254P1D6B and 254P1D6B mutations or analogs.

Recombinant human 254P1D6B protein or an analog or homolog or fragment thereof can be produced by mammalian cells transfected with a construct encoding a 254P1D6B-related nucleotide. For example, 293T cells can be transfected with an expression plasmid encoding 254P1D6B or fragment, analog or homolog thereof, a 254P1D6B-related protein is expressed in the 293T cells, and the recombinant 254P1D6B protein is isolated using standard purification methods (e.g., affinity purification using anti-254P1D6B antibodies). In another embodiment, a 254P1D6B coding sequence is subcloned into the retroviral vector pSRαMSVtkneo and used to infect various mammalian cell lines, such as NIH 3T3, TsuPr1, 293 and rat-1 in order to establish 254P1D6B expressing cell lines. Various other expression systems well known in the art can also be employed. Expression constructs encoding a leader peptide joined in frame to a 254P1D6B coding sequence can be used for the generation of a secreted form of recombinant 254P1D6B protein.

As discussed herein, redundancy in the genetic code permits variation in 254P1D6B gene sequences. In particular, it is known in the art that specific host species often have specific codon preferences, and thus one can adapt the disclosed sequence as preferred for a desired host. For example, preferred analog codon sequences typically have rare codons (i.e., codons having a usage frequency of less than about 20% in known sequences of the desired host) replaced with higher frequency codons. Codon preferences for a specific species are calculated, for example, by utilizing codon usage tables available on the INTERNET such as at URL dna.affrc.gojp/~nakamura/codon.html.

Additional sequence modifications are known to enhance protein expression in a cellular host. These include elimination of sequences encoding spurious polyadenylation signals, exon/intron splice site signals, transposon-like repeats, and/or other such well-characterized sequences that are deleterious to gene expression. The GC content of the sequence is adjusted to levels average for a given cellular host, as calculated by reference to known genes expressed in the host cell. Where possible, the sequence is modified to avoid predicted hairpin secondary mRNA structures. Other useful modifications include the addition of a translational initiation consensus sequence at the start of the open reading frame, as described in Kozak, *Mol. Cell Biol.*, 9:5073-5080 (1989). Skilled artisans understand that the general rule that eukaryotic ribosomes initiate translation exclusively at the 5' proximal AUG codon is abrogated only under rare conditions (see, e.g., Kozak PNAS 92(7): 2662-2666, (1995) and Kozak NAR 15(20): 8125-8148 (1987)).

III.) 254P1D6B-related Proteins

Another aspect of the present invention provides 254P1D6B-related proteins. Specific embodiments of 254P1D6B proteins comprise a polypeptide having all or part of the amino acid sequence of human 254P1D6B as shown in FIG. 2 or FIG. 3. Alternatively, embodiments of 254P1D6B proteins comprise variant, homolog or analog polypeptides that have alterations in the amino acid sequence of 254P1D6B shown in FIG. 2 or FIG. 3.

Embodiments of a 254P1D6B polypeptide include: a 254P1D6B polypeptide having a sequence shown in FIG. 2, a peptide sequence of a 254P1D6B as shown in FIG. 2 wherein T is U; at least 10 contiguous nucleotides of a polypeptide having the sequence as shown in FIG. 2; or, at least 10 contiguous peptides of a polypeptide having the sequence as shown in FIG. 2 where T is U. For example, embodiments of 254P1D6B peptides comprise, without limitation:

(I) a protein comprising, consisting essentially of, or consisting of an amino acid sequence as shown in FIG. 2A-D or FIGS. 3A-E;

(II) a 254P1D6B-related protein that is at least 90, 91, 92, 93, 94, 95, 96, 97, 98, 99 or 100% homologous to an entire amino acid sequence shown in FIG. 2A-D or 3A-E;

(III) a 254P1D6B-related protein that is at least 90, 91, 92, 93, 94, 95, 96, 97, 98, 99 or 100% identical to an entire amino acid sequence shown in FIG. 2A-D or 3A-E;

(IV) a protein that comprises at least one peptide set forth in Tables VIII to XLIX, optionally with a proviso that it is not an entire protein of FIG. 2;

(V) a protein that comprises at least one peptide set forth in Tables VIII-XXI, collectively, which peptide is also set forth in Tables XXII to XLIX, collectively, optionally with a proviso that it is not an entire protein of FIG. 2;

(VI) a protein that comprises at least two peptides selected from the peptides set forth in Tables VIII-XLIX, optionally with a proviso that it is not an entire protein of FIG. 2;

(VII) a protein that comprises at least two peptides selected from the peptides set forth in Tables VIII to XLIX collectively, with a proviso that the protein is not a contiguous sequence from an amino acid sequence of FIG. 2;

(VIII) a protein that comprises at least one peptide selected from the peptides set forth in Tables VIII-XXI; and at least one peptide selected from the peptides set forth in Tables XXII to XLIX, with a proviso that the protein is not a contiguous sequence from an amino acid sequence of FIG. 2;

(IX) a polypeptide comprising at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a protein of FIGS. 3A, 3B, 3D, and 3E in any whole number increment up to 1072 respectively that includes at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Hydrophilicity profile of FIG. 5;

(X) a polypeptide comprising at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a protein of FIGS. 3A, 3B, 3D, and 3E, in any whole number increment up to 1072 respectively that includes at least at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value less than 0.5 in the Hydropathicity profile of FIG. 6;

(XI) a polypeptide comprising at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a protein of FIGS. 3A, 3B, 3D, and 3E, in any whole number increment up to 1072 respectively that includes at least at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Percent Accessible Residues profile of FIG. 7;

(XII) a polypeptide comprising at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a protein of FIGS. 3A, 3B, 3D, and 3E, in any whole number increment up to 1072 respectively that includes at least at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Average Flexibility profile of FIG. 8;

(XIII) a polypeptide comprising at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, amino acids of a protein of FIGS. 3A, 3B, 3D, and 3E in any whole number increment up to 1072 respectively that includes at least at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Beta-turn profile of FIG. 9;

(XIV) a polypeptide comprising at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a protein of FIG. 3C, in any whole number increment up to 1063 respectively that includes at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Hydrophilicity profile of FIG. 5;

(XV) a polypeptide comprising at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a protein of FIG. 3C, in any whole number increment up to 1063 respectively that includes at least at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value less than 0.5 in the Hydropathicity profile of FIG. 6;

(XVI) a polypeptide comprising at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a protein of FIG. 3C, in any whole number increment up to 1063 respectively that includes at least at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Percent Accessible Residues profile of FIG. 7;

(XVII) a polypeptide comprising at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a protein of FIG. 3C, in any whole number increment up to 1063 respectively that includes at least at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Average Flexibility profile of FIG. 8;

(XVIII) a polypeptide comprising at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, amino acids of a protein of FIG. 3C in any whole number increment up to 1063 respectively that includes at least at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Beta-turn profile of FIG. 9;

(XIX) a peptide that occurs at least twice in Tables VIII-XXI and XXII to XLIX, collectively;

(XX) a peptide that occurs at least three times in Tables VIII-XXI and XXII to XLIX, collectively;

(XXI) a peptide that occurs at least four times in Tables VIII-XXI and XXII to XLIX, collectively;

(XXII) a peptide that occurs at least five times in Tables VIII-XXI and XXII to XLIX, collectively;

(XXIII) a peptide that occurs at least once in Tables VIII-XXI, and at least once in tables XXII to XLIX;

(XXIV) a peptide that occurs at least once in Tables VIII-XXI, and at least twice in tables XXII to XLIX;

(XXV) a peptide that occurs at least twice in Tables VIII-XXI, and at least once in tables XXII to XLIX;

(XXVI) a peptide that occurs at least twice in Tables VIII-XXI, and at least twice in tables XXII to XLIX;

(XXVII) a peptide which comprises one two, three, four, or five of the following characteristics, or an oligonucleotide encoding such peptide:

i) a region of at least 5 amino acids of a particular peptide of FIG. 3, in any whole number increment up to the full length of that protein in FIG. 3, that includes an amino acid position having a value equal to or greater than 0.5, 0.6, 0.7, 0.8, 0.9, or having a value equal to 1.0, in the Hydrophilicity profile of FIG. 5;

ii) a region of at least 5 amino acids of a particular peptide of FIG. 3, in any whole number increment up to the full length of that protein in FIG. 3, that includes an amino acid position having a value equal to or less than 0.5, 0.4, 0.3, 0.2, 0.1, or having a value equal to 0.0, in the Hydropathicity profile of FIG. 6;

iii) a region of at least 5 amino acids of a particular peptide of FIG. 3, in any whole number increment up to the full length of that protein in FIG. 3, that includes an amino acid position having a value equal to or greater than 0.5, 0.6, 0.7, 0.8, 0.9, or having a value equal to 1.0, in the Percent Accessible Residues profile of FIG. 7;

iv) a region of at least 5 amino acids of a particular peptide of FIG. 3, in any whole number increment up to the full length of that protein in FIG. 3, that includes an amino acid position having a value equal to or greater than 0.5, 0.6, 0.7, 0.8, 0.9, or having a value equal to 1.0, in the Average Flexibility profile of FIG. 8; or, v) a region of at least 5 amino acids of a particular peptide of FIG. 3, in any whole number increment up to the full length of that protein in FIG. 3, that includes an amino acid position having a value equal to or greater than 0.5, 0.6, 0.7, 0.8, 0.9, or having a value equal to 1.0, in the Beta-turn profile of FIG. 9;

(XXVIII) a composition comprising a peptide of (I)-(XXVII) or an antibody or binding region thereof together with a pharmaceutical excipient and/or in a human unit dose form.

(XXIX) a method of using a peptide of (I)-(XXVII), or an antibody or binding region thereof or a composition of (XXVIII) in a method to modulate a cell expressing 254P1D6B;

(XXX) a method of using a peptide of (I)-(XXVII) or an antibody or binding region thereof or a composition of (XXVIII) in a method to diagnose, prophylax, prognose, or treat an individual who bears a cell expressing 254P1D6B;

(XXXI) a method of using a peptide of (I)-(XXVII) or an antibody or binding region thereof or a composition (XXVIII) in a method to diagnose, prophylax, prognose, or treat an individual who bears a cell expressing 254P1D6B, said cell from a cancer of a tissue listed in Table I;

(XXXII) a method of using a peptide of (I)-(XXVII) or an antibody or binding region thereof or a composition of (XXVIII) in a method to diagnose, prophylax, prognose, or treat a a cancer;

(XXXIII) a method of using a peptide of (I)-(XXVII) or an antibody or binding region thereof or a composition of (XXVIII) in a method to diagnose, prophylax, prognose, or treat a a cancer of a tissue listed in Table I; and;

(XXXIV) a method of using a a peptide of (I)-(XXVII) or an antibody or binding region thereof or a composition (XXVIII) in a method to identify or characterize a modulator of a cell expressing 254P1D6B As used herein, a range is understood to specifically disclose all whole unit positions thereof.

Typical embodiments of the invention disclosed herein include 254P1D6B polynucleotides that encode specific portions of 254P1D6B mRNA sequences (and those which are complementary to such sequences) such as those that encode the proteins and/or fragments thereof, for example:

(a) 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1025, 1050, 1060, 1070 and 1072 or more contiguous amino acids of 254P1D6B variant 1; the maximal lengths relevant for other variants are: variant 2, 1072 amino acids; variant 3, 1063 amino acids, variant 5, 1072 amino acids, variant 6, 1072 amino acids, and variants 4, 7-20, 1072 amino acids.

In general, naturally occurring allelic variants of human 254P1D6B share a high degree of structural identity and homology (e.g., 90% or more homology). Typically, allelic variants of a 254P1D6B protein contain conservative amino acid substitutions within the 254P1D6B sequences described herein or contain a substitution of an amino acid from a corresponding position in a homologue of 254P1D6B. One class of 254P1D6B allelic variants are proteins that share a high degree of homology with at least a small region of a particular 254P1D6B amino acid sequence, but further contain a radical departure from the sequence, such as a non-conservative substitution, truncation, insertion or frame shift. In comparisons of protein sequences, the terms, similarity, identity, and homology each have a distinct meaning as appreciated in the field of genetics. Moreover, orthology and paralogy can be important concepts describing the relationship of members of a given protein family in one organism to the members of the same family in other organisms.

Amino acid abbreviations are provided in Table II. Conservative amino acid substitutions can frequently be made in a protein without altering either the conformation or the function of the protein. Proteins of the invention can comprise 1, 2, 3, 4, 5, 6, 7, 8, 9, 10, 11, 12, 13, 14, 15 conservative substitutions. Such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently be interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments (see, e.g. Table III herein; pages 13-15 "Biochemistry" $2^{nd}$ ED. Lubert Stryer ed (Stanford University); Henikoff et al., PNAS1992 Vol 89 10915-10919; Lei et al., J Biol Chem 1995 May 19; 270(20):11882-6).

Embodiments of the invention disclosed herein include a wide variety of art-accepted variants or analogs of 254P1D6B proteins such as polypeptides having amino acid insertions, deletions and substitutions. 254P1D6B variants can be made using methods known in the art such as site-directed mutagenesis, alanine scanning, and PCR mutagenesis. Site-directed mutagenesis (Carter et al., *Nucl. Acids Res.*, 13:4331 (1986); Zoller et al., *Nucl. Acids Res.*, 10:6487 (1987)), cassette mutagenesis (Wells et al., Gene, 34:315 (1985)), restriction selection mutagenesis (Wells et al., *Philos. Trans. R. Soc. London SerA*, 317:415 (1986)) or other known techniques can be performed on the cloned DNA to produce the 254P1D6B variant DNA.

Scanning amino acid analysis can also be employed to identify one or more amino acids along a contiguous sequence that is involved in a specific biological activity such as a protein-protein interaction. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant. Alanine is also typically preferred because it is the most common amino acid. Further, it is frequently found in both buried and exposed positions (Creighton, The Proteins, (W.H. Freeman & Co., N.Y.); Chothia, J. Mol. Biol., 150:1 (1976)). If alanine substitution does not yield adequate amounts of variant, an isosteric amino acid can be used.

As defined herein, 254P1D6B variants, analogs or homologs, have the distinguishing attribute of having at least one epitope that is "cross reactive" with a 254P1D6B protein having an amino acid sequence of FIG. 3. As used in this sentence, "cross reactive" means that an antibody or T cell that specifically binds to a 254P1D6B variant also specifically binds to a 254P1D6B protein having an amino acid sequence set forth in FIG. 3. A polypeptide ceases to be a variant of a protein shown in FIG. 3, when it no longer contains any epitope capable of being recognized by an antibody or T cell that specifically binds to the starting 254P1D6B protein. Those skilled in the art understand that antibodies that recognize proteins bind to epitopes of varying size, and a grouping of the order of about four or five amino acids, contiguous or not, is regarded as a typical number of amino acids in a minimal epitope. See, e.g., Nair et al., J. Immunol 2000 165 (12): 6949-6955; Hebbes et al., Mol Immunol (1989) 26(9): 865-73; Schwartz et al., J Immunol (1985) 135(4):2598-608.

Other classes of 254P1D6B-related protein variants share 70%, 75%, 80%, 85% or 90% or more similarity with an amino acid sequence of FIG. 3, or a fragment thereof. Another specific class of 254P1D6B protein variants or analogs comprises one or more of the 254P1D6B biological motifs described herein or presently known in the art. Thus, encompassed by the present invention are analogs of 254P1D6B fragments (nucleic or amino acid) that have altered functional (e.g. immunogenic) properties relative to the starting fragment. It is to be appreciated that motifs now or which become part of the art are to be applied to the nucleic or amino acid sequences of FIG. 2 or FIG. 3.

As discussed herein, embodiments of the claimed invention include polypeptides containing less than the full amino acid sequence of a 254P1D6B protein shown in FIG. 2 or FIG. 3. For example, representative embodiments of the invention comprise peptides/proteins having any 4, 5, 6, 7, 8, 9, 10, 11, 12, 13, 14, 15 or more contiguous amino acids of a 254P1D6B protein shown in FIG. 2 or FIG. 3.

Moreover, representative embodiments of the invention disclosed herein include polypeptides consisting of about amino acid 1 to about amino acid 10 of a 254P1D6B protein shown in FIG. 2 or FIG. 3, polypeptides consisting of about amino acid 10 to about amino acid 20 of a 254P1D6B protein shown in FIG. 2 or FIG. 3, polypeptides consisting of about amino acid 20 to about amino acid 30 of a 254P1D6B protein shown in FIG. 2 or FIG. 3, polypeptides consisting of about amino acid 30 to about amino acid 40 of a 254P1D6B protein shown in FIG. 2 or FIG. 3, polypeptides consisting of about amino acid 40 to about amino acid 50 of a 254P1D6B protein shown in FIG. 2 or FIG. 3, polypeptides consisting of about amino acid 50 to about amino acid 60 of a 254P1D6B protein shown in FIG. 2 or FIG. 3, polypeptides consisting of about amino acid 60 to about amino acid 70 of a 254P1D6B protein shown in FIG. 2 or FIG. 3, polypeptides consisting of about amino acid 70 to about amino acid 80 of a 254P1D6B protein shown in FIG. 2 or FIG. 3, polypeptides consisting of about amino acid 80 to about amino acid 90 of a 254P1D6B protein shown in FIG. 2 or FIG. 3, polypeptides consisting of about amino acid 90 to about amino acid 100 of a 254P1D6B protein shown in FIG. 2 or FIG. 3, etc. throughout the entirety of a 254P1D6B amino acid sequence. Moreover, polypeptides consisting of about amino acid 1 (or 20 or 30 or 40 etc.) to about amino acid 20, (or 130, or 140 or 150 etc.) of a 254P1D6B protein shown in FIG. 2 or FIG. 3 are embodiments of the invention. It is to be appreciated that the starting and stopping positions in this paragraph refer to the specified position as well as that position plus or minus 5 residues.

254P1D6B-related proteins are generated using standard peptide synthesis technology or using chemical cleavage methods well known in the art. Alternatively, recombinant methods can be used to generate nucleic acid molecules that encode a 254P1D6B-related protein. In one embodiment, nucleic acid molecules provide a means to generate defined fragments of a 254P1D6B protein (or variants, homologs or analogs thereof).

III.A.) Motif-Bearing Protein Embodiments

Additional illustrative embodiments of the invention disclosed herein include 254P1D6B polypeptides comprising the amino acid residues of one or more of the biological motifs contained within a 254P1D6B polypeptide sequence set forth in FIG. 2 or FIG. 3. Various motifs are known in the art, and a protein can be evaluated for the presence of such motifs by a number of publicly available Internet sites (see, e.g., URL addresses: pfam.wustl.edu/; searchlauncher.bcm.tmc.edu/seq-search/struc-predict.html; psort.ims.u-tokyo.acjp/; cbs.dtu.dk/; ebi.ac.uk/interpro/scan.html; expasy.ch/tools/scnpsit1.html; Epimatrix™ and Epimer™, Brown University, brown.edu/Research/TB-HIV_Lab/epimatrix/epimatrix.html; and BIMAS, bimas.dcrt.nih.gov/.).

Motif bearing subsequences of all 254P1D6B variant proteins are set forth and identified in Tables VIII-XXI and XXII-XLIX.

Table V sets forth several frequently occurring motifs based on pfam searches (see URL address pfam.wustl.edu/). The columns of Table V list (1) motif name abbreviation, (2) percent identity found amongst the different member of the motif family, (3) motif name or description and (4) most common function; location information is included if the motif is relevant for location.

Polypeptides comprising one or more of the 254P1D6B motifs discussed above are useful in elucidating the specific characteristics of a malignant phenotype in view of the observation that the 254P1D6B motifs discussed above are associated with growth dysregulation and because 254P1D6B is overexpressed in certain cancers (See, e.g., Table I). Casein kinase II, cAMP and camp-dependent protein kinase, and Protein Kinase C, for example, are enzymes known to be associated with the development of the malignant phenotype (see e.g. Chen et al., Lab Invest., 78(2): 165-174 (1998); Gaiddon et al., Endocrinology 136(10): 4331-4338 (1995); Hall et al., Nucleic Acids Research 24(6): 1119-1126 (1996); Peterziel et al., Oncogene 18(46): 6322-6329 (1999) and O'Brian, Oncol. Rep. 5(2): 305-309 (1998)). Moreover, both glycosylation and myristoylation are protein modifications also associated with cancer and cancer progression (see e.g. Dennis et al., Biochem. Biophys. Acta 1473(1):21-34 (1999); Raju et al., Exp. Cell Res. 235(1): 145-154 (1997)). Amidation is another protein modification also associated with cancer and cancer progression (see e.g. Treston et al., J. Natl. Cancer Inst. Monogr. (13): 169-175 (1992)).

In another embodiment, proteins of the invention comprise one or more of the immunoreactive epitopes identified in accordance with art-accepted methods, such as the peptides set forth in Tables VIII-XXI and XXII-XLIX. CTL epitopes can be determined using specific algorithms to identify peptides within a 254P1D6B protein that are capable of optimally binding to specified HLA alleles (e.g., Table IV; Epimatrix™ and Epimer™, Brown University, URL brown.edu/Research/TB-HIV_Lab/epimatrix/epimatrix.html; and BIMAS, URL bimas.dcrt.nih.gov/.) Moreover, processes for identifying peptides that have sufficient binding affinity for HLA molecules and which are correlated with being immunogenic epitopes, are well known in the art, and are carried out without undue experimentation. In addition, processes for identifying peptides that are immunogenic epitopes, are well known in the art, and are carried out without undue experimentation either in vitro or in vivo.

Also known in the art are principles for creating analogs of such epitopes in order to modulate immunogenicity. For example, one begins with an epitope that bears a CTL or HTL motif (see, e.g., the HLA Class I and HLA Class II motifs/supermotifs of Table IV). The epitope is analoged by substituting out an amino acid at one of the specified positions, and replacing it with another amino acid specified for that position. For example, on the basis of residues defined in Table IV, one can substitute out a deleterious residue in favor of any other residue, such as a preferred residue; substitute a less-preferred residue with a preferred residue; or substitute an originally-occurring preferred residue with another preferred residue. Substitutions can occur at primary anchor positions or at other positions in a peptide; see, e.g., Table IV.

A variety of references reflect the art regarding the identification and generation of epitopes in a protein of interest as well as analogs thereof. See, for example, WO 97/33602 to Chesnut et al.; Sette, Immunogenetics 1999 50(3-4): 201-212; Sette et al., J. Immunol. 2001 166(2): 1389-1397; Sidney et al., Hum. Immunol. 1997 58(1): 12-20; Kondo et al., Immunogenetics 1997 45(4): 249-258; Sidney et al., J. Immunol. 1996 157(8): 3480-90; and Falk et al., Nature 351: 290-6 (1991); Hunt et al., Science 255:1261-3 (1992); Parker et al., J. Immunol. 149:3580-7 (1992); Parker et al., J. Immunol. 152:163-75 (1994)); Kast et al., 1994 152(8): 3904-12; Borras-Cuesta et al., Hum. Immunol. 2000 61(3): 266-278; Alexander et al., J. Immunol. 2000 164(3); 164(3): 1625-1633; Alexander et al., PMID: 7895164, UI: 95202582; O'Sullivan et al., J. Immunol. 1991 147(8): 2663-2669; Alexander et al., Immunity 1994 1(9): 751-761 and Alexander et al., Immunol. Res. 1998 18(2): 79-92.

Related embodiments of the invention include polypeptides comprising combinations of the different motifs set forth in Table VI, and/or, one or more of the predicted CTL epitopes of Tables VIII-XXI and XXII-XLIX, and/or, one or more of the predicted HTL epitopes of Tables XLVI-XLIX, and/or, one or more of the T cell binding motifs known in the art. Preferred embodiments contain no insertions, deletions or substitutions either within the motifs or within the intervening sequences of the polypeptides. In addition, embodiments which include a number of either N-terminal and/or C-terminal amino acid residues on either side of these motifs may be desirable (to, for example, include a greater portion of the polypeptide architecture in which the motif is located). Typically, the number of N-terminal and/or C-terminal amino acid residues on either side of a motif is between about 1 to about 100 amino acid residues, preferably 5 to about 50 amino acid residues.

254P1D6B-related proteins are embodied in many forms, preferably in isolated form. A purified 254P1D6B protein molecule will be substantially free of other proteins or molecules that impair the binding of 254P1D6B to antibody, T cell or other ligand. The nature and degree of isolation and purification will depend on the intended use. Embodiments of a 254P1D6B-related proteins include purified 254P1D6B-related proteins and functional, soluble 254P1D6B-related proteins. In one embodiment, a functional, soluble 254P1D6B protein or fragment thereof retains the ability to be bound by antibody, T cell or other ligand.

The invention also provides 254P1D6B proteins comprising biologically active fragments of a 254P1D6B amino acid sequence shown in FIG. 2 or FIG. 3. Such proteins exhibit properties of the starting 254P1D6B protein, such as the ability to elicit the generation of antibodies that specifically bind an epitope associated with the starting 254P1D6B protein; to be bound by such antibodies; to elicit the activation of HTL or CTL; and/or, to be recognized by HTL or CTL that also specifically bind to the starting protein.

254P1D6B-related polypeptides that contain particularly interesting structures can be predicted and/or identified using various analytical techniques well known in the art, including, for example, the methods of Chou-Fasman, Garnier-Robson, Kyte-Doolittle, Eisenberg, Karplus-Schultz or Jameson-Wolf analysis, or based on immunogenicity. Fragments that contain such structures are particularly useful in generating subunit-specific anti-254P1D6B antibodies or T cells or in identifying cellular factors that bind to 254P1D6B. For example, hydrophilicity profiles can be generated, and immunogenic peptide fragments identified, using the method of Hopp, T. P. and Woods, K. R., 1981, Proc. Natl. Acad. Sci. U.S.A. 78:3824-3828. Hydropathicity profiles can be generated, and immunogenic peptide fragments identified, using the method of Kyte, J. and Doolittle, R. F., 1982, J. Mol. Biol. 157:105-132. Percent (%) Accessible Residues profiles can be generated, and immunogenic peptide fragments identified, using the method of Janin J., 1979, Nature 277:491-492. Average Flexibility profiles can be generated, and immunogenic peptide fragments identified, using the method of Bhaskaran R., Ponnuswamy P. K., 1988, Int. J. Pept. Protein Res. 32:242-255. Beta-turn profiles can be generated, and immunogenic peptide fragments identified, using the method of Deleage, G., Roux B., 1987, Protein Engineering 1:289-294.

CTL epitopes can be determined using specific algorithms to identify peptides within a 254P1D6B protein that are capable of optimally binding to specified HLA alleles (e.g., by using the SYFPEITHI site at World Wide Web URL syfpeithi.bmi-heidelberg.com/; the listings in Table IV(A)-(E); Epimatrix™ and Epimer™, Brown University, URL (brown.edu/Research/TB-HIV_Lab/epimatrix/epimatrix.html); and BIMAS, URL bimas.dcrt.nih.gov/). Illustrating this, peptide epitopes from 254P1D6B that are presented in the context of human MHC Class I molecules, e.g., HLA-A1, A2, A3, A11, A24, B7 and B35 were predicted (see, e.g., Tables VIII-XXI, XXII-XLIX). Specifically, the complete amino acid sequence of the 254P1D6B protein and relevant portions of other variants, i.e., for HLA Class I predictions 9 flanking residues on either side of a point mutation or exon junction, and for HLA Class II predictions 14 flanking residues on either side of a point mutation or exon junction corresponding to that variant, were entered into the HLA Peptide Motif Search algorithm found in the Bioinformatics and Molecular Analysis Section (BIMAS) web site listed above; in addition to the site SYFPEITHI, at URL syfpeithi.bmi-heidelberg.com/.

The HLA peptide motif search algorithm was developed by Dr. Ken Parker based on binding of specific peptide sequences in the groove of HLA Class 1 molecules, in particular HLA-A2 (see, e.g., Falk et al., Nature 351: 290-6 (1991); Hunt et al., Science 255:1261-3 (1992); Parker et al., J. Immunol. 149:3580-7 (1992); Parker et al., J. Immunol.

152:163-75 (1994)). This algorithm allows location and ranking of 8-mer, 9-mer, and 10-mer peptides from a complete protein sequence for predicted binding to HLA-A2 as well as numerous other HLA Class I molecules. Many HLA class I binding peptides are 8-, 9-, 10 or 11-mers. For example, for Class I HLA-A2, the epitopes preferably contain a leucine (L) or methionine (M) at position 2 and a valine (V) or leucine (L) at the C-terminus (see, e.g., Parker et al., J. Immunol. 149: 3580-7 (1992)). Selected results of 254P1D6B predicted binding peptides are shown in Tables VIII-XXI and XXII-XLIX herein. In Tables VIII-XXI and XXII-XLVII, selected candidates, 9-mers and 10-mers, for each family member are shown along with their location, the amino acid sequence of each specific peptide, and an estimated binding score. In Tables XLVI-XLIX, selected candidates, 15-mers, for each family member are shown along with their location, the amino acid sequence of each specific peptide, and an estimated binding score. The binding score corresponds to the estimated half time of dissociation of complexes containing the peptide at 37° C. at pH 6.5. Peptides with the highest binding score are predicted to be the most tightly bound to HLA Class I on the cell surface for the greatest period of time and thus represent the best immunogenic targets for T-cell recognition.

Actual binding of peptides to an HLA allele can be evaluated by stabilization of HLA expression on the antigen-processing defective cell line T2 (see, e.g., Xue et al., Prostate 30:73-8 (1997) and Peshwa et al. Prostate 36:129-38 (1998)). Immunogenicity of specific peptides can be evaluated in vitro by stimulation of CD8+ cytotoxic T lymphocytes (CTL) in the presence of antigen presenting cells such as dendritic cells.

It is to be appreciated that every epitope predicted by the BIMAS site, Epimer™ and Epimatrix™ sites, or specified by the HLA class I or class II motifs available in the art or which become part of the art such as set forth in Table IV (or determined using World Wide Web site URL syfpeithi.bmi-heidelberg.com/, or BIMAS, bimas.dcrt.nih.gov/) are to be "applied" to a 254P1D6B protein in accordance with the invention. As used in this context "applied" means that a 254P1D6B protein is evaluated, e.g., visually or by computer-based patterns finding methods, as appreciated by those of skill in the relevant art. Every subsequence of a 254P1D6B protein of 8, 9, 10, or 11 amino acid residues that bears an HLA Class I motif, or a subsequence of 9 or more amino acid residues that bear an HLA Class II motif are within the scope of the invention.

III.B.) Expression of 254P1D6B-Related Proteins

In an embodiment described in the examples that follow, 254P1D6B can be conveniently expressed in cells (such as 293T cells) transfected with a commercially available expression vector such as a CMV-driven expression vector encoding 254P1D6B with a C-terminal 6×His and MYC tag (pcDNA3.1/mycHIS, Invitrogen or Tag5, GenHunter Corporation, Nashville Tenn.). The Tag5 vector provides an IgGK secretion signal that can be used to facilitate the production of a secreted 254P1D6B protein in transfected cells. The secreted HIS-tagged 254P1D6B in the culture media can be purified, e.g., using a nickel column using standard techniques.

III.C.) Modifications of 254P1D6B-Related Proteins

Modifications of 254P1D6B-related proteins such as covalent modifications are included within the scope of this invention. One type of covalent modification includes reacting targeted amino acid residues of a 254P1D6B polypeptide with an organic derivatizing agent that is capable of reacting with selected side chains or the N- or C-terminal residues of a 254P1D6B protein. Another type of covalent modification of a 254P1D6B polypeptide included within the scope of this invention comprises altering the native glycosylation pattern of a protein of the invention. Another type of covalent modification of 254P1D6B comprises linking a 254P1D6B polypeptide to one of a variety of nonproteinaceous polymers, e.g., polyethylene glycol (PEG), polypropylene glycol, or polyoxyalkylenes, in the manner set forth in U.S. Pat. No. 4,640,835; 4,496,689; 4,301,144; 4,670,417; 4,791,192 or 4,179,337.

The 254P1D6B-related proteins of the present invention can also be modified to form a chimeric molecule comprising 254P1D6B fused to another, heterologous polypeptide or amino acid sequence. Such a chimeric molecule can be synthesized chemically or recombinantly. A chimeric molecule can have a protein of the invention fused to another tumor-associated antigen or fragment thereof. Alternatively, a protein in accordance with the invention can comprise a fusion of fragments of a 254P1D6B sequence (amino or nucleic acid) such that a molecule is created that is not, through its length, directly homologous to the amino or nucleic acid sequences shown in FIG. 2 or FIG. 3. Such a chimeric molecule can comprise multiples of the same subsequence of 254P1D6B. A chimeric molecule can comprise a fusion of a 254P1D6B-related protein with a polyhistidine epitope tag, which provides an epitope to which immobilized nickel can selectively bind, with cytokines or with growth factors. The epitope tag is generally placed at the amino- or carboxyl-terminus of a 254P1D6B protein. In an alternative embodiment, the chimeric molecule can comprise a fusion of a 254P1D6B-related protein with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of a 254P1D6B polypeptide in place of at least one variable region within an Ig molecule. In a preferred embodiment, the immunoglobulin fusion includes the hinge, CH2 and CH3, or the hinge, CH1, CH2 and CH3 regions of an IgGI molecule. For the production of immunoglobulin fusions see, e.g., U.S. Pat. No. 5,428,130 issued Jun. 27, 1995.

III.D.) Uses of 254P1D6B-Related Proteins

The proteins of the invention have a number of different specific uses. As 254P1D6B is highly expressed in prostate and other cancers, 254P1D6B-related proteins are used in methods that assess the status of 254P1D6B gene products in normal versus cancerous tissues, thereby elucidating the malignant phenotype. Typically, polypeptides from specific regions of a 254P1D6B protein are used to assess the presence of perturbations (such as deletions, insertions, point mutations etc.) in those regions (such as regions containing one or more motifs). Exemplary assays utilize antibodies or T cells targeting 254P1D6B-related proteins comprising the amino acid residues of one or more of the biological motifs contained within a 254P1D6B polypeptide sequence in order to evaluate the characteristics of this region in normal versus cancerous tissues or to elicit an immune response to the epitope. Alternatively, 254P1D6B-related proteins that contain the amino acid residues of one or more of the biological motifs in a 254P1D6B protein are used to screen for factors that interact with that region of 254P1D6B.

254P1D6B protein fragments/subsequences are particularly useful in generating and characterizing domain-specific antibodies (e.g., antibodies recognizing an extracellular or intracellular epitope of a 254P1D6B protein), for identifying agents or cellular factors that bind to 254P1D6B or a particular structural domain thereof, and in various therapeutic and diagnostic contexts, including but not limited to diagnostic assays, cancer vaccines and methods of preparing such vaccines.

Proteins encoded by the 254P1D6B genes, or by analogs, homologs or fragments thereof, have a variety of uses, including but not limited to generating antibodies and in methods for identifying ligands and other agents and cellular constituents that bind to a 254P1D6B gene product. Antibodies raised against a 254P1D6B protein or fragment thereof are useful in diagnostic and prognostic assays, and imaging methodologies in the management of human cancers characterized by expression of 254P1D6B protein, such as those listed in Table I. Such antibodies can be expressed intracellularly and used in methods of treating patients with such cancers. 254P1D6B-related nucleic acids or proteins are also used in generating HTL or CTL responses.

Various immunological assays useful for the detection of 254P1D6B proteins are used, including but not limited to various types of radioimmunoassays, enzyme-linked immunosorbent assays (ELISA), enzyme-linked immunofluorescent assays (ELIFA), immunocytochemical methods, and the like. Antibodies can be labeled and used as immunological imaging reagents capable of detecting 254P1D6B-expressing cells (e.g., in radioscintigraphic imaging methods). 254P1D6B proteins are also particularly useful in generating cancer vaccines, as further described herein.

IV.) 254P1D6B Antibodies

Another aspect of the invention provides antibodies that bind to 254P1D6B-related proteins. Preferred antibodies specifically bind to a 254P1D6B-related protein and do not bind (or bind weakly) to peptides or proteins that are not 254P1D6B-related proteins under physiological conditions. In this context, examples of physiological conditions include: 1) phosphate buffered saline; 2) Tris-buffered saline containing 25 mM Tris and 150 mM NaCl; or normal saline (0.9% NaCl); 4) animal serum such as human serum; or, 5) a combination of any of 1) through 4); these reactions preferably taking place at pH 7.5, alternatively in a range of pH 7.0 to 8.0, or alternatively in a range of pH 6.5 to 8.5; also, these reactions taking place at a temperature between 4° C. to 37° C. For example, antibodies that bind 254P1D6B can bind 254P1D6B-related proteins such as the homologs or analogs thereof.

254P1D6B antibodies of the invention are particularly useful in cancer (see, e.g., Table I) diagnostic and prognostic assays, and imaging methodologies. Similarly, such antibodies are useful in the treatment, diagnosis, and/or prognosis of other cancers, to the extent 254P1D6B is also expressed or overexpressed in these other cancers. Moreover, intracellularly expressed antibodies (e.g., single chain antibodies) are therapeutically useful in treating cancers in which the expression of 254P1D6B is involved, such as advanced or metastatic prostate cancers.

The invention also provides various immunological assays useful for the detection and quantification of 254P1D6B and mutant 254P1D6B-related proteins. Such assays can comprise one or more 254P1D6B antibodies capable of recognizing and binding a 254P1D6B-related protein, as appropriate. These assays are performed within various immunological assay formats well known in the art, including but not limited to various types of radioimmunoassays, enzyme-linked immunosorbent assays (ELISA), enzyme-linked immunofluorescent assays (ELIFA), and the like.

Immunological non-antibody assays of the invention also comprise T cell immunogenicity assays (inhibitory or stimulatory) as well as major histocompatibility complex (MHC) binding assays.

In addition, immunological imaging methods capable of detecting prostate cancer and other cancers expressing 254P1D6B are also provided by the invention, including but not limited to radioscintigraphic imaging methods using labeled 254P1D6B antibodies. Such assays are clinically useful in the detection, monitoring, and prognosis of 254P1D6B expressing cancers such as prostate cancer.

254P1D6B antibodies are also used in methods for purifying a 254P1D6B-related protein and for isolating 254P1D6B homologues and related molecules. For example, a method of purifying a 254P1D6B-related protein comprises incubating a 254P1D6B antibody, which has been coupled to a solid matrix, with a lysate or other solution containing a 254P1D6B-related protein under conditions that permit the 254P1D6B antibody to bind to the 254P1D6B-related protein; washing the solid matrix to eliminate impurities; and eluting the 254P1D6B-related protein from the coupled antibody. Other uses of 254P1D6B antibodies in accordance with the invention include generating anti-idiotypic antibodies that mimic a 254P1D6B protein.

Various methods for the preparation of antibodies are well known in the art. For example, antibodies can be prepared by immunizing a suitable mammalian host using a 254P1D6B-related protein, peptide, or fragment, in isolated or immunoconjugated form (Antibodies: A Laboratory Manual, CSH Press, Eds., Harlow, and Lane (1988); Harlow, Antibodies, Cold Spring Harbor Press, NY (1989)). In addition, fusion proteins of 254P1D6B can also be used, such as a 254P1D6B GST-fusion protein. In a particular embodiment, a GST fusion protein comprising all or most of the amino acid sequence of FIG. 2 or FIG. 3 is produced, then used as an immunogen to generate appropriate antibodies. In another embodiment, a 254P1D6B-related protein is synthesized and used as an immunogen.

In addition, naked DNA immunization techniques known in the art are used (with or without purified 254P1D6B-related protein or 254P1D6B expressing cells) to generate an immune response to the encoded immunogen (for review, see Donnelly et al. 1997, Ann. Rev. Immunol. 15: 617-648).

The amino acid sequence of a 254P1D6B protein as shown in FIG. 2 or FIG. 3 can be analyzed to select specific regions of the 254P1D6B protein for generating antibodies. For example, hydrophobicity and hydrophilicity analyses of a 254P1D6B amino acid sequence are used to identify hydrophilic regions in the 254P1D6B structure. Regions of a 254P1D6B protein that show immunogenic structure, as well as other regions and domains, can readily be identified using various other methods known in the art, such as Chou-Fasman, Garnier-Robson, Kyte-Doolittle, Eisenberg, Karplus-Schultz or Jameson-Wolf analysis. Hydrophilicity profiles can be generated using the method of Hopp, T. P. and Woods, K. R., 1981, Proc. Natl. Acad. Sci. U.S.A. 78:3824-3828. Hydropathicity profiles can be generated using the method of Kyte, J. and Doolittle, R. F., 1982, J. Mol. Biol. 157:105-132. Percent (%) Accessible Residues profiles can be generated using the method of Janin J., 1979, Nature 277:491-492. Average Flexibility profiles can be generated using the method of Bhaskaran R., Ponnuswamy P. K., 1988, Int. J. Pept. Protein Res. 32:242-255. Beta-turn profiles can be generated using the method of Deleage, G., Roux B., 1987, Protein Engineering 1:289-294. Thus, each region identified by any of these programs or methods is within the scope of the present invention. Methods for the generation of 254P1D6B antibodies are further illustrated by way of the examples provided herein. Methods for preparing a protein or polypeptide for use as an immunogen are well known in the art. Also well known in the art are methods for preparing immunogenic conjugates of a protein with a carrier, such as BSA, KLH or other carrier protein. In some circumstances, direct conjugation using, for example, carbodiimide reagents are used; in other instances linking reagents such as those supplied by Pierce Chemical Co., Rockford, Ill., are effective. Administration of a 254P1D6B immunogen is often conducted by injection over a suitable time period and with use of a suitable adjuvant, as is understood in the art. During the immunization schedule, titers of antibodies can be taken to determine adequacy of antibody formation.

254P1D6B monoclonal antibodies can be produced by various means well known in the art. For example, immortalized cell lines that secrete a desired monoclonal antibody are prepared using the standard hybridoma technology of Kohler and Milstein or modifications that immortalize antibody-producing B cells, as is generally known. Immortalized cell lines that secrete the desired antibodies are screened by immunoassay in which the antigen is a 254P1D6B-related protein. When the appropriate immortalized cell culture is identified, the cells can be expanded and antibodies produced either from in vitro cultures or from ascites fluid.

The antibodies or fragments of the invention can also be produced, by recombinant means. Regions that bind specifically to the desired regions of a 254P1D6B protein can also be produced in the context of chimeric or complementarity-determining region (CDR) grafted antibodies of multiple species origin. Humanized or human 254P1D6B antibodies can also be produced, and are preferred for use in therapeutic contexts. Methods for humanizing murine and other non-human antibodies, by substituting one or more of the non-human antibody CDRs for corresponding human antibody sequences, are well known (see for example, Jones et al., 1986, Nature 321: 522-525; Riechmann et al., 1988, Nature 332: 323-327; Verhoeyen et al., 1988, Science 239: 1534-1536). See also, Carter et al., 1993, Proc. Natl. Acad. Sci. USA 89: 4285 and Sims et al., 1993, J. Immunol. 151: 2296.

Methods for producing fully human monoclonal antibodies include phage display and transgenic methods (for review, see Vaughan et al., 1998, Nature Biotechnology 16: 535-539). Fully human 254P1D6B monoclonal antibodies can be generated using cloning technologies employing large human Ig gene combinatorial libraries (i.e., phage display) (Griffiths and Hoogenboom, Building an in vitro immune system: human antibodies from phage display libraries. In: Protein Engineering of Antibody Molecules for Prophylactic and Therapeutic Applications in Man, Clark, M. (Ed.), Nottingham Academic, pp 45-64 (1993); Burton and Barbas, Human Antibodies from combinatorial libraries. Id., pp 65-82). Fully human 254P1D6B monoclonal antibodies can also be produced using transgenic mice engineered to contain human immunoglobulin gene loci as described in PCT Patent Application WO98/24893, Kucherlapati and Jakobovits et al., published Dec. 3, 1997 (see also, Jakobovits, 1998, Exp. Opin. Invest. Drugs 7(4): 607-614; U.S. Pat. Nos. 6,162,963 issued 19 Dec. 2000; 6,150,584 issued 12 Nov. 2000; and, 6,114,598 issued 5 Sep. 2000). This method avoids the in vitro manipulation required with phage display technology and efficiently produces high affinity authentic human antibodies.

Reactivity of 254P1D6B antibodies with a 254P1D6B-related protein can be established by a number of well known means, including Western blot, immunoprecipitation, ELISA, and FACS analyses using, as appropriate, 254P1D6B-related proteins, 254P1D6B-expressing cells or extracts thereof. A 254P1D6B antibody or fragment thereof can be labeled with a detectable marker or conjugated to a second molecule. Suitable detectable markers include, but are not limited to, a radioisotope, a fluorescent compound, a bioluminescent compound, chemiluminescent compound, a metal chelator or an enzyme. Further, bi-specific antibodies specific for two or more 254P1D6B epitopes are generated using methods generally known in the art. Homodimeric antibodies can also be generated by cross-linking techniques known in the art (e.g., Wolff et al., Cancer Res. 53: 2560-2565).

V.) 254P1D6B Cellular Immune Responses

The mechanism by which T cells recognize antigens has been delineated. Efficacious peptide epitope vaccine compositions of the invention induce a therapeutic or prophylactic immune responses in very broad segments of the world-wide population. For an understanding of the value and efficacy of compositions of the invention that induce cellular immune responses, a brief review of immunology-related technology is provided.

A complex of an HLA molecule and a peptidic antigen acts as the ligand recognized by HLA-restricted T cells (Buus, S. et al. Cell 47:1071, 1986; Babbitt, B. P. et al., Nature 317:359, 1985; Townsend, A. and Bodmer, H., Annu. Rev. Immunol. 7:601, 1989; Germain, R. N., Annu. Rev. Immunol. 11:403, 1993). Through the study of single amino acid substituted antigen analogs and the sequencing of endogenously bound, naturally processed peptides, critical residues that correspond to motifs required for specific binding to HLA antigen molecules have been identified and are set forth in Table IV (see also, e.g., Southwood, et al., J. Immunol. 160:3363, 1998; Rammensee, et al., Immunogenetics 41:178, 1995; Rammensee et al., SYFPEITHI, access via World Wide Web at URL (134.2.96.221/scripts.hlaserver.dll/home.htm); Sette, A. and Sidney, J. Curr. Opin. Immunol. 10:478, 1998; Engelhard, V. H., Curr. Opin. Immunol. 6:13, 1994; Sette, A. and Grey, H. M., Curr. Opin. Immunol. 4:79, 1992; Sinigaglia, F. and Hammer, J. Curr. Biol. 6:52, 1994; Ruppert et al., Cell 74:929-937, 1993; Kondo et al., J. Immunol. 155:4307-4312, 1995; Sidney et al., J. Immunol. 157:3480-3490, 1996; Sidney et al., Human Immunol. 45:79-93, 1996; Sette, A. and Sidney, J. Immunogenetics 1999 November; 50(3-4):201-12, Review).

Furthermore, x-ray crystallographic analyses of HLA-peptide complexes have revealed pockets within the peptide binding cleft/groove of HLA molecules which accommodate, in an allele-specific mode, residues borne by peptide ligands; these residues in turn determine the HLA binding capacity of the peptides in which they are present. (See, e.g., Madden, D. R. Annu. Rev. Immunol. 13:587, 1995; Smith, et al. Immunity 4:203, 1996; Fremont et al., Immunity 8:305, 1998; Stern et al., Structure 2:245, 1994; Jones, E. Y. Curr. Opin. Immunol. 9:75, 1997; Brown, J. H. et al., Nature 364:33, 1993; Guo, H. C. et al., Proc. Natl. Acad. Sci. USA 90:8053, 1993; Guo, H. C. et al., Nature 360:364, 1992; Silver, M. L. et al., Nature 360:367, 1992; Matsumura, M. et al., Science 257:927, 1992; Madden et al., Cell 70:1035, 1992; Fremont, D. H. et al., Science 257:919, 1992; Saper, M. A., Bjorkman, P. J. and Wiley, D.C., J. Mol. Biol. 219:277, 1991.)

Accordingly, the definition of class I and class II allele-specific HLA binding motifs, or class I or class II supermotifs allows identification of regions within a protein that are correlated with binding to particular HLA antigen(s).

Thus, by a process of HLA motif identification, candidates for epitope-based vaccines have been identified; such candidates can be further evaluated by HLA-peptide binding assays to determine binding affinity and/or the time period of association of the epitope and its corresponding HLA molecule. Additional confirmatory work can be performed to select, amongst these vaccine candidates, epitopes with preferred characteristics in terms of population coverage, and/or immunogenicity.

Various strategies can be utilized to evaluate cellular immunogenicity, including:

1) Evaluation of primary T cell cultures from normal individuals (see, e.g., Wentworth, P. A. et al., *Mol. Immunol.* 32:603, 1995; Celis, E. et al., *Proc. Natl. Acad. Sci. USA* 91:2105, 1994; Tsai, V. et al., *J. Immunol.* 158:1796, 1997; Kawashima, I. et al., *Human Immunol.* 59:1, 1998). This procedure involves the stimulation of peripheral blood lymphocytes (PBL) from normal subjects with a test peptide in the presence of antigen presenting cells in vitro over a period of several weeks. T cells specific for the peptide become activated during this time and are detected using, e.g., a lymphokine- or $^{51}$Cr-release assay involving peptide sensitized target cells.

2) Immunization of HLA transgenic mice (see, e.g., Wentworth, P. A. et al., *J. Immunol.* 26:97, 1996; Wentworth, P. A. et al., *Int. Immunol.* 8:651, 1996; Alexander, J. et al., *J. Immunol.* 159:4753, 1997). For example, in such methods peptides in incomplete Freund's adjuvant are administered subcutaneously to HLA transgenic mice. Several weeks following immunization, splenocytes are removed and cultured in vitro in the presence of test peptide for approximately one week. Peptide-specific T cells are detected using, e.g., a $^{51}$Cr-release assay involving peptide sensitized target cells and target cells expressing endogenously generated antigen.

3) Demonstration of recall T cell responses from immune individuals who have been either effectively vaccinated and/or from chronically ill patients (see, e.g., Rehermann, B. et al., *J. Exp. Med.* 181:1047, 1995; Doolan, D. L. et al., *Immunity* 7:97, 1997; Bertoni, R. et al., *J. Clin. Invest.* 100:503, 1997; Threlkeld, S. C. et al., *J. Immunol.* 159:1648, 1997; Diepolder, H. M. et al., *J. Virol.* 71:6011, 1997). Accordingly, recall responses are detected by culturing PBL from subjects that have been exposed to the antigen due to disease and thus have generated an immune response "naturally", or from patients who were vaccinated against the antigen. PBL from subjects are cultured in vitro for 1-2 weeks in the presence of test peptide plus antigen presenting cells (APC) to allow activation of "memory" T cells, as compared to "naive" T cells. At the end of the culture period, T cell activity is detected using assays including $^{51}$Cr release involving peptide-sensitized targets, T cell proliferation, or lymphokine release.

VI.) 254P1D6B Transgenic Animals

Nucleic acids that encode a 254P1D6B-related protein can also be used to generate either transgenic animals or "knock out" animals that, in turn, are useful in the development and screening of therapeutically useful reagents. In accordance with established techniques, cDNA encoding 254P1D6B can be used to clone genomic DNA that encodes 254P1D6B. The cloned genomic sequences can then be used to generate transgenic animals containing cells that express DNA that encode 254P1D6B. Methods for generating transgenic animals, particularly animals such as mice or rats, have become conventional in the art and are described, for example, in U.S. Pat. Nos. 4,736,866 issued 12 Apr. 1988, and 4,870,009 issued 26 Sep. 1989. Typically, particular cells would be targeted for 254P1D6B transgene incorporation with tissue-specific enhancers.

Transgenic animals that include a copy of a transgene encoding 254P1D6B can be used to examine the effect of increased expression of DNA that encodes 254P1D6B. Such animals can be used as tester animals for reagents thought to confer protection from, for example, pathological conditions associated with its overexpression. In accordance with this aspect of the invention, an animal is treated with a reagent and a reduced incidence of a pathological condition, compared to untreated animals that bear the transgene, would indicate a potential therapeutic intervention for the pathological condition.

Alternatively, non-human homologues of 254P1D6B can be used to construct a 254P1D6B "knock out" animal that has a defective or altered gene encoding 254P1D6B as a result of homologous recombination between the endogenous gene encoding 254P1D6B and altered genomic DNA encoding 254P1D6B introduced into an embryonic cell of the animal. For example, cDNA that encodes 254P1D6B can be used to clone genomic DNA encoding 254P1D6B in accordance with established techniques. A portion of the genomic DNA encoding 254P1D6B can be deleted or replaced with another gene, such as a gene encoding a selectable marker that can be used to monitor integration. Typically, several kilobases of unaltered flanking DNA (both at the 5' and 3' ends) are included in the vector (see, e.g., Thomas and Capecchi, *Cell*, 51:503 (1987) for a description of homologous recombination vectors). The vector is introduced into an embryonic stem cell line (e.g., by electroporation) and cells in which the introduced DNA has homologously recombined with the endogenous DNA are selected (see, e.g., Li et al., *Cell*, 69:915 (1992)). The selected cells are then injected into a blastocyst of an animal (e.g., a mouse or rat) to form aggregation chimeras (see, e.g., Bradley, in *Teratocarcinomas and Embryonic Stem Cells: A Practical Approach*, E. J. Robertson, ed. (IRL, Oxford, 1987), pp. 113-152). A chimeric embryo can then be implanted into a suitable pseudopregnant female foster animal, and the embryo brought to term to create a "knock out" animal. Progeny harboring the homologously recombined DNA in their germ cells can be identified by standard techniques and used to breed animals in which all cells of the animal contain the homologously recombined DNA. Knock out animals can be characterized, for example, for their ability to defend against certain pathological conditions or for their development of pathological conditions due to absence of a 254P1D6B polypeptide.

VII.) Methods for the Detection of 254P1D6B

Another aspect of the present invention relates to methods for detecting 254P1D6B polynucleotides and 254P1D6B-related proteins, as well as methods for identifying a cell that expresses 254P1D6B. The expression profile of 254P1D6B makes it a diagnostic marker for metastasized disease. Accordingly, the status of 254P1D6B gene products provides information useful for predicting a variety of factors including susceptibility to advanced stage disease, rate of progression, and/or tumor aggressiveness. As discussed in detail herein, the status of 254P1D6B gene products in patient samples can be analyzed by a variety protocols that are well known in the art including immunohistochemical analysis, the variety of Northern blotting techniques including in situ hybridization, RT-PCR analysis (for example on laser capture micro-dissected samples), Western blot analysis and tissue array analysis.

More particularly, the invention provides assays for the detection of 254P1D6B polynucleotides in a biological sample, such as serum, bone, prostate, and other tissues, urine, semen, cell preparations, and the like. Detectable 254P1D6B polynucleotides include, for example, a 254P1D6B gene or fragment thereof, 254P1D6B mRNA, alternative splice variant 254P1D6B mRNAs, and recombinant DNA or RNA molecules that contain a 254P1D6B polynucleotide. A number of methods for amplifying and/or detecting the presence of 254P1D6B polynucleotides are well known in the art and can be employed in the practice of this aspect of the invention.

In one embodiment, a method for detecting a 254P1D6B mRNA in a biological sample comprises producing cDNA from the sample by reverse transcription using at least one primer; amplifying the cDNA so produced using a 254P1D6B polynucleotides as sense and antisense primers to amplify 254P1D6B cDNAs therein; and detecting the presence of the amplified 254P1D6B cDNA. Optionally, the sequence of the amplified 254P1D6B cDNA can be determined.

In another embodiment, a method of detecting a 254P1D6B gene in a biological sample comprises first isolating genomic DNA from the sample; amplifying the isolated genomic DNA using 254P1D6B polynucleotides as sense and antisense primers; and detecting the presence of the amplified 254P1D6B gene. Any number of appropriate sense and antisense probe combinations can be designed from a 254P1D6B nucleotide sequence (see, e.g., FIG. 2) and used for this purpose.

The invention also provides assays for detecting the presence of a 254P1D6B protein in a tissue or other biological sample such as serum, semen, bone, prostate, urine, cell preparations, and the like. Methods for detecting a 254P1D6B-related protein are also well known and include, for example, immunoprecipitation, immunohistochemical analysis, Western blot analysis, molecular binding assays, ELISA, ELIFA and the like. For example, a method of detecting the presence of a 254P1D6B-related protein in a biological sample comprises first contacting the sample with a 254P1D6B antibody, a 254P1D6B-reactive fragment thereof, or a recombinant protein containing an antigen-binding region of a 254P1D6B antibody; and then detecting the binding of 254P1D6B-related protein in the sample.

Methods for identifying a cell that expresses 254P1D6B are also within the scope of the invention. In one embodiment, an assay for identifying a cell that expresses a 254P1D6B gene comprises detecting the presence of 254P1D6B mRNA in the cell. Methods for the detection of particular mRNAs in cells are well known and include, for example, hybridization assays using complementary DNA probes (such as in situ hybridization using labeled 254P1D6B riboprobes, Northern blot and related techniques) and various nucleic acid amplification assays (such as RT-PCR using complementary primers specific for 254P1D6B, and other amplification type detection methods, such as, for example, branched DNA, SISBA, TMA and the like). Alternatively, an assay for identifying a cell that expresses a 254P1D6B gene comprises detecting the presence of 254P1D6B-related protein in the cell or secreted by the cell. Various methods for the detection of proteins are well known in the art and are employed for the detection of 254P1D6B-related proteins and cells that express 254P1D6B-related proteins.

254P1D6B expression analysis is also useful as a tool for identifying and evaluating agents that modulate 254P1D6B gene expression. For example, 254P1D6B expression is significantly upregulated in prostate cancer, and is expressed in cancers of the tissues listed in Table I. Identification of a molecule or biological agent that inhibits 254P1D6B expression or over-expression in cancer cells is of therapeutic value. For example, such an agent can be identified by using a screen that quantifies 254P1D6B expression by RT-PCR, nucleic acid hybridization or antibody binding.

VIII.) Methods for Monitoring the Status of 254P1D6B-related Genes and Their Products Oncogenesis is known to be a multistep process where cellular growth becomes progressively dysregulated and cells progress from a normal physiological state to precancerous and then cancerous states (see, e.g., Alers et al., Lab Invest. 77(5): 437-438 (1997) and Isaacs et al., Cancer Surv. 23: 19-32 (1995)). In this context, examining a biological sample for evidence of dysregulated cell growth (such as aberrant 254P1D6B expression in cancers) allows for early detection of such aberrant physiology, before a pathologic state such as cancer has progressed to a stage that therapeutic options are more limited and or the prognosis is worse. In such examinations, the status of 254P1D6B in a biological sample of interest can be compared, for example, to the status of 254P1D6B in a corresponding normal sample (e.g. a sample from that individual or alternatively another individual that is not affected by a pathology). An alteration in the status of 254P1D6B in the biological sample (as compared to the normal sample) provides evidence of dysregulated cellular growth. In addition to using a biological sample that is not affected by a pathology as a normal sample, one can also use a predetermined normative value such as a predetermined normal level of mRNA expression (see, e.g., Grever et al., J. Comp. Neurol. 1996 Dec. 9; 376(2): 306-14 and U.S. Pat. No. 5,837,501) to compare 254P1D6B status in a sample.

The term "status" in this context is used according to its art accepted meaning and refers to the condition or state of a gene and its products. Typically, skilled artisans use a number of parameters to evaluate the condition or state of a gene and its products. These include, but are not limited to the location of expressed gene products (including the location of 254P1D6B expressing cells) as well as the level, and biological activity of expressed gene products (such as 254P1D6B mRNA, polynucleotides and polypeptides). Typically, an alteration in the status of 254P1D6B comprises a change in the location of 254P1D6B and/or 254P1D6B expressing cells and/or an increase in 254P1D6B mRNA and/or protein expression.

254P1D6B status in a sample can be analyzed by a number of means well known in the art, including without limitation, immunohistochemical analysis, in situ hybridization, RT-PCR analysis on laser capture micro-dissected samples, Western blot analysis, and tissue array analysis. Typical protocols for evaluating the status of a 254P1D6B gene and gene products are found, for example in Ausubel et al. eds., 1995, Current Protocols In Molecular Biology, Units 2 (Northern Blotting), 4 (Southern Blotting), 15 (Immunoblotting) and 18 (PCR Analysis). Thus, the status of 254P1D6B in a biological sample is evaluated by various methods utilized by skilled artisans including, but not limited to genomic Southern analysis (to examine, for example perturbations in a 254P1D6B gene), Northern analysis and/or PCR analysis of 254P1D6B mRNA (to examine, for example alterations in the polynucleotide sequences or expression levels of 254P1D6B mRNAs), and, Western and/or immunohistochemical analysis (to examine, for example alterations in polypeptide sequences, alterations in polypeptide localization within a sample, alterations in expression levels of 254P1D6B proteins and/or associations of 254P1D6B proteins with polypeptide binding partners). Detectable 254P1D6B polynucleotides include, for example, a 254P1D6B gene or fragment thereof, 254P1D6B mRNA, alternative splice variants, 254P1D6B mRNAs, and recombinant DNA or RNA molecules containing a 254P1D6B polynucleotide.

The expression profile of 254P1D6B makes it a diagnostic marker for local and/or metastasized disease, and provides information on the growth or oncogenic potential of a biological sample. In particular, the status of 254P1D6B provides information useful for predicting susceptibility to particular disease stages, progression, and/or tumor aggressiveness. The invention provides methods and assays for determining 254P1D6B status and diagnosing cancers that express 254P1D6B, such as cancers of the tissues listed in Table I. For example, because 254P1D6B mRNA is so highly expressed in prostate and other cancers relative to normal prostate tissue, assays that evaluate the levels of 254P1D6B mRNA transcripts or proteins in a biological sample can be used to diagnose a disease associated with 254P1D6B dysregulation, and can provide prognostic information useful in defining appropriate therapeutic options.

The expression status of 254P1D6B provides information including the presence, stage and location of dysplastic, precancerous and cancerous cells, predicting susceptibility to various stages of disease, and/or for gauging tumor aggressiveness. Moreover, the expression profile makes it useful as an imaging reagent for metastasized disease. Consequently, an aspect of the invention is directed to the various molecular prognostic and diagnostic methods for examining the status of 254P1D6B in biological samples such as those from individuals suffering from, or suspected of suffering from a pathology characterized by dysregulated cellular growth, such as cancer.

As described above, the status of 254P1D6B in a biological sample can be examined by a number of well-known procedures in the art. For example, the status of 254P1D6B in a biological sample taken from a specific location in the body can be examined by evaluating the sample for the presence or absence of 254P1D6B expressing cells (e.g. those that express 254P1D6B mRNAs or proteins). This examination can provide evidence of dysregulated cellular growth, for example, when 254P1D6B expressing cells are found in a biological sample that does not normally contain such cells (such as a lymph node), because such alterations in the status of 254P1D6B in a biological sample are often associated with dysregulated cellular growth. Specifically, one indicator of dysregulated cellular growth is the metastases of cancer cells from an organ of origin (such as the prostate) to a different area of the body (such as a lymph node). In this context, evidence of dysregulated cellular growth is important for example because occult lymph node metastases can be detected in a substantial proportion of patients with prostate cancer, and such metastases are associated with known predictors of disease progression (see, e.g., Murphy et al., Prostate 42(4): 315-317 (2000);Su et al., Semin. Surg. Oncol. 18(1): 17-28 (2000) and Freeman et al., J Urol 1995 August 154(2 Pt 1):474-8).

In one aspect, the invention provides methods for monitoring 254P1D6B gene products by determining the status of 254P1D6B gene products expressed by cells from an individual suspected of having a disease associated with dysregulated cell growth (such as hyperplasia or cancer) and then comparing the status so determined to the status of 254P1D6B gene products in a corresponding normal sample. The presence of aberrant 254P1D6B gene products in the test sample relative to the normal sample provides an indication of the presence of dysregulated cell growth within the cells of the individual.

In another aspect, the invention provides assays useful in determining the presence of cancer in an individual, comprising detecting a significant increase in 254P1D6B mRNA or protein expression in a test cell or tissue sample relative to expression levels in the corresponding normal cell or tissue. The presence of 254P1D6B mRNA can, for example, be evaluated in tissues including but not limited to those listed in Table I. The presence of significant 254P1D6B expression in any of these tissues is useful to indicate the emergence, presence and/or severity of a cancer, since the corresponding normal tissues do not express 254P1D6B mRNA or express it at lower levels.

In a related embodiment, 254P1D6B status is determined at the protein level rather than at the nucleic acid level. For example, such a method comprises determining the level of 254P1D6B protein expressed by cells in a test tissue sample and comparing the level so determined to the level of 254P1D6B expressed in a corresponding normal sample. In one embodiment, the presence of 254P1D6B protein is evaluated, for example, using immunohistochemical methods. 254P1D6B antibodies or binding partners capable of detecting 254P1D6B protein expression are used in a variety of assay formats well known in the art for this purpose.

In a further embodiment, one can evaluate the status of 254P1D6B nucleotide and amino acid sequences in a biological sample in order to identify perturbations in the structure of these molecules. These perturbations can include insertions, deletions, substitutions and the like. Such evaluations are useful because perturbations in the nucleotide and amino acid sequences are observed in a large number of proteins associated with a growth dysregulated phenotype (see, e.g., Marrogi et al., 1999, J. Cutan. Pathol. 26(8):369-378). For example, a mutation in the sequence of 254P1D6B may be indicative of the presence or promotion of a tumor. Such assays therefore have diagnostic and predictive value where a mutation in 254P1D6B indicates a potential loss of function or increase in tumor growth.

A wide variety of assays for observing perturbations in nucleotide and amino acid sequences are well known in the art. For example, the size and structure of nucleic acid or amino acid sequences of 254P1D6B gene products are observed by the Northern, Southern, Western, PCR and DNA sequencing protocols discussed herein. In addition, other methods for observing perturbations in nucleotide and amino acid sequences such as single strand conformation polymorphism analysis are well known in the art (see, e.g., U.S. Pat. Nos. 5,382,510 issued 7 Sep. 1999, and 5,952,170 issued 17 Jan. 1995).

Additionally, one can examine the methylation status of a 254P1D6B gene in a biological sample. Aberrant demethylation and/or hypermethylation of CpG islands in gene 5' regulatory regions frequently occurs in immortalized and transformed cells, and can result in altered expression of various genes. For example, promoter hypermethylation of the pi-class glutathione S-transferase (a protein expressed in normal prostate but not expressed in >90% of prostate carcinomas) appears to permanently silence transcription of this gene and is the most frequently detected genomic alteration in prostate carcinomas (De Marzo et al., Am. J. Pathol. 155(6): 1985-1992 (1999)). In addition, this alteration is present in at least 70% of cases of high-grade prostatic intraepithelial neoplasia (PIN) (Brooks et al., Cancer Epidemiol. Biomarkers Prev., 1998, 7:531-536). In another example, expression of the LAGE-I tumor specific gene (which is not expressed in normal prostate but is expressed in 25-50% of prostate cancers) is induced by deoxy-azacytidine in lymphoblastoid cells, suggesting that tumoral expression is due to demethylation (Lethe et al., Int. J. Cancer 76(6): 903-908 (1998)). A variety of assays for examining methylation status of a gene are well known in the art. For example, one can utilize, in Southern hybridization approaches, methylation-sensitive restriction enzymes that cannot cleave sequences that contain methylated CpG sites to assess the methylation status of CpG islands. In addition, MSP (methylation specific PCR) can rapidly profile the methylation status of all the CpG sites present in a CpG island of a given gene. This procedure involves initial modification of DNA by sodium bisulfite (which will convert all unmethylated cytosines to uracil) followed by amplification using primers specific for methylated versus unmethylated DNA. Protocols involving methylation interference can also be found for example in Current Protocols In Molecular Biology, Unit 12, Frederick M. Ausubel et al. eds., 1995.

Gene amplification is an additional method for assessing the status of 254P1D6B. Gene amplification is measured in a sample directly, for example, by conventional Southern blotting or Northern blotting to quantitate the transcription of mRNA (Thomas, 1980, Proc. Natl. Acad. Sci. USA, 77:5201-5205), dot blotting (DNA analysis), or in situ hybridization, using an appropriately labeled probe, based on the sequences provided herein. Alternatively, antibodies are employed that recognize specific duplexes, including DNA duplexes, RNA duplexes, and DNA-RNA hybrid duplexes or DNA-protein duplexes. The antibodies in turn are labeled and the assay carried out where the duplex is bound to a surface, so that upon the formation of duplex on the surface, the presence of antibody bound to the duplex can be detected.

Biopsied tissue or peripheral blood can be conveniently assayed for the presence of cancer cells using for example, Northern, dot blot or RT-PCR analysis to detect 254P1D6B expression. The presence of RT-PCR amplifiable 254P1D6B mRNA provides an indication of the presence of cancer. RT-PCR assays are well known in the art. RT-PCR detection assays for tumor cells in peripheral blood are currently being evaluated for use in the diagnosis and management of a number of human solid tumors. In the prostate cancer field, these include RT-PCR assays for the detection of cells expressing PSA and PSM (Verkaik et al., 1997, Urol. Res. 25:373-384; Ghossein et al., 1995, J. Clin. Oncol. 13:1195-2000; Heston et al., 1995, Clin. Chem. 41:1687-1688).

A further aspect of the invention is an assessment of the susceptibility that an individual has for developing cancer. In one embodiment, a method for predicting susceptibility to cancer comprises detecting 254P1D6B mRNA or 254P1D6B protein in a tissue sample, its presence indicating susceptibility to cancer, wherein the degree of 254P1D6B mRNA expression correlates to the degree of susceptibility. In a specific embodiment, the presence of 254P1D6B in prostate or other tissue is examined, with the presence of 254P1D6B in the sample providing an indication of prostate cancer susceptibility (or the emergence or existence of a prostate tumor). Similarly, one can evaluate the integrity 254P1D6B nucleotide and amino acid sequences in a biological sample, in order to identify perturbations in the structure of these molecules such as insertions, deletions, substitutions and the like. The presence of one or more perturbations in 254P1D6B gene products in the sample is an indication of cancer susceptibility (or the emergence or existence of a tumor).

The invention also comprises methods for gauging tumor aggressiveness. In one embodiment, a method for gauging aggressiveness of a tumor comprises determining the level of 254P1D6B mRNA or 254P1D6B protein expressed by tumor cells, comparing the level so determined to the level of 254P1D6B mRNA or 254P1D6B protein expressed in a corresponding normal tissue taken from the same individual or a normal tissue reference sample, wherein the degree of 254P1D6B mRNA or 254P1D6B protein expression in the tumor sample relative to the normal sample indicates the degree of aggressiveness. In a specific embodiment, aggressiveness of a tumor is evaluated by determining the extent to which 254P1D6B is expressed in the tumor cells, with higher expression levels indicating more aggressive tumors. Another embodiment is the evaluation of the integrity of 254P1D6B nucleotide and amino acid sequences in a biological sample, in order to identify perturbations in the structure of these molecules such as insertions, deletions, substitutions and the like. The presence of one or more perturbations indicates more aggressive tumors.

Another embodiment of the invention is directed to methods for observing the progression of a malignancy in an individual over time. In one embodiment, methods for observing the progression of a malignancy in an individual over time comprise determining the level of 254P1D6B mRNA or 254P1D6B protein expressed by cells in a sample of the tumor, comparing the level so determined to the level of 254P1D6B mRNA or 254P1D6B protein expressed in an equivalent tissue sample taken from the same individual at a different time, wherein the degree of 254P1D6B mRNA or 254P1D6B protein expression in the tumor sample over time provides information on the progression of the cancer. In a specific embodiment, the progression of a cancer is evaluated by determining 254P1D6B expression in the tumor cells over time, where increased expression over time indicates a progression of the cancer. Also, one can evaluate the integrity 254P1D6B nucleotide and amino acid sequences in a biological sample in order to identify perturbations in the structure of these molecules such as insertions, deletions, substitutions and the like, where the presence of one or more perturbations indicates a progression of the cancer.

The above diagnostic approaches can be combined with any one of a wide variety of prognostic and diagnostic protocols known in the art. For example, another embodiment of the invention is directed to methods for observing a coincidence between the expression of 254P1D6B gene and 254P1D6B gene products (or perturbations in 254P1D6B gene and 254P1D6B gene products) and a factor that is associated with malignancy, as a means for diagnosing and prognosticating the status of a tissue sample. A wide variety of factors associated with malignancy can be utilized, such as the expression of genes associated with malignancy (e.g. PSA, PSCA and PSM expression for prostate cancer etc.) as well as gross cytological observations (see, e.g., Bocking et al., 1984, Anal. Quant. Cytol. 6(2):74-88; Epstein, 1995, Hum. Pathol. 26(2):223-9; Thorson et al., 1998, Mod. Pathol. 11(6):543-51; Baisden et al., 1999, Am. J. Surg. Pathol. 23(8):918-24). Methods for observing a coincidence between the expression of 254P1D6B gene and 254P1D6B gene products (or perturbations in 254P1D6B gene and 254P1D6B gene products) and another factor that is associated with malignancy are useful, for example, because the presence of a set of specific factors that coincide with disease provides information crucial for diagnosing and prognosticating the status of a tissue sample.

In one embodiment, methods for observing a coincidence between the expression of 254P1D6B gene and 254P1D6B gene products (or perturbations in 254P1D6B gene and 254P1D6B gene products) and another factor associated with malignancy entails detecting the overexpression of 254P1D6B mRNA or protein in a tissue sample, detecting the overexpression of PSA mRNA or protein in a tissue sample (or PSCA or PSM expression), and observing a coincidence of 254P1D6B mRNA or protein and PSA mRNA or protein overexpression (or PSCA or PSM expression). In a specific embodiment, the expression of 254P1D6B and PSA mRNA in prostate tissue is examined, where the coincidence of 254P1D6B and PSA mRNA overexpression in the sample indicates the existence of prostate cancer, prostate cancer susceptibility or the emergence or status of a prostate tumor.

Methods for detecting and quantifying the expression of 254P1D6B mRNA or protein are described herein, and standard nucleic acid and protein detection and quantification technologies are well known in the art. Standard methods for the detection and quantification of 254P1D6B mRNA include in situ hybridization using labeled 254P1D6B riboprobes, Northern blot and related techniques using 254P1D6B polynucleotide probes, RT-PCR analysis using primers specific for 254P1D6B, and other amplification type detection methods, such as, for example, branched DNA, SISBA, TMA and the like. In a specific embodiment, semi-quantitative RT-PCR is used to detect and quantify 254P1D6B mRNA expression. Any number of primers capable of amplifying 254P1D6B can be used for this purpose, including but not limited to the various primer sets specifically described herein. In a specific embodiment, polyclonal or monoclonal antibodies specifically reactive with the wild-type 254P1D6B protein can be used in an immunohistochemical assay of biopsied tissue.

IX.) Identification of Molecules that Interact with 254P1D6B

The 254P1D6B protein and nucleic acid sequences disclosed herein allow a skilled artisan to identify proteins, small molecules and other agents that interact with 254P1D6B, as well as pathways activated by 254P1D6B via any one of a variety of art accepted protocols. For example, one can utilize one of the so-called interaction trap systems (also referred to as the "two-hybrid assay"). In such systems, molecules interact and reconstitute a transcription factor which directs expression of a reporter gene, whereupon the expression of the reporter gene is assayed. Other systems identify protein-protein interactions in vivo through reconstitution of a eukaryotic transcriptional activator, see, e.g., U.S. Pat. Nos. 5,955,280 issued 21 Sep. 1999, 5,925,523 issued 20 Jul. 1999, 5,846,722 issued 8 Dec. 1998 and 6,004,746 issued 21 Dec. 1999. Algorithms are also available in the art for genome-based predictions of protein function (see, e.g., Marcotte, et al., Nature 402: 4 Nov. 1999, 83-86).

Alternatively one can screen peptide libraries to identify molecules that interact with 254P1D6B protein sequences. In such methods, peptides that bind to 254P1D6B are identified by screening libraries that encode a random or controlled collection of amino acids. Peptides encoded by the libraries are expressed as fusion proteins of bacteriophage coat proteins, the bacteriophage particles are then screened against the 254P1D6B protein(s).

Accordingly, peptides having a wide variety of uses, such as therapeutic, prognostic or diagnostic reagents, are thus identified without any prior information on the structure of the expected ligand or receptor molecule. Typical peptide libraries and screening methods that can be used to identify molecules that interact with 254P1D6B protein sequences are disclosed for example in U.S. Pat. Nos. 5,723,286 issued 3 Mar. 1998 and 5,733,731 issued 31 Mar. 1998.

Alternatively, cell lines that express 254P1D6B are used to identify protein-protein interactions mediated by 254P1D6B. Such interactions can be examined using immunoprecipitation techniques (see, e.g., Hamilton B. J., et al. Biochem. Biophys. Res. Commun. 1999, 261:646-51). 254P1D6B protein can be immunoprecipitated from 254P1D6B-expressing cell lines using anti-254P1D6B antibodies. Alternatively, antibodies against His-tag can be used in a cell line engineered to express fusions of 254P1D6B and a His-tag (vectors mentioned above). The immunoprecipitated complex can be examined for protein association by procedures such as Western blotting, $^{35}$S-methionine labeling of proteins, protein microsequencing, silver staining and two-dimensional gel electrophoresis.

Small molecules and ligands that interact with 254P1D6B can be identified through related embodiments of such screening assays. For example, small molecules can be identified that interfere with protein function, including molecules that interfere with 254P1D6B's ability to mediate phosphorylation and de-phosphorylation, interaction with DNA or RNA molecules as an indication of regulation of cell cycles, second messenger signaling or tumorigenesis. Similarly, small molecules that modulate 254P1D6B-related ion channel, protein pump, or cell communication functions are identified and used to treat patients that have a cancer that expresses 254P1D6B (see, e.g., Hille, B., Ionic Channels of Excitable Membranes $2^{nd}$ Ed., Sinauer Assoc., Sunderland, Mass., 1992). Moreover, ligands that regulate 254P1D6B function can be identified based on their ability to bind 254P1D6B and activate a reporter construct. Typical methods are discussed for example in U.S. Pat. No. 5,928,868 issued 27 Jul. 1999, and include methods for forming hybrid ligands in which at least one ligand is a small molecule. In an illustrative embodiment, cells engineered to express a fusion protein of 254P1D6B and a DNA-binding protein are used to co-express a fusion protein of a hybrid ligand/small molecule and a cDNA library transcriptional activator protein. The cells further contain a reporter gene, the expression of which is conditioned on the proximity of the first and second fusion proteins to each other, an event that occurs only if the hybrid ligand binds to target sites on both hybrid proteins. Those cells that express the reporter gene are selected and the unknown small molecule or the unknown ligand is identified. This method provides a means of identifying modulators, which activate or inhibit 254P1D6B.

An embodiment of this invention comprises a method of screening for a molecule that interacts with a 254P1D6B amino acid sequence shown in FIG. 2 or FIG. 3, comprising the steps of contacting a population of molecules with a 254P1D6B amino acid sequence, allowing the population of molecules and the 254P1D6B amino acid sequence to interact under conditions that facilitate an interaction, determining the presence of a molecule that interacts with the 254P1D6B amino acid sequence, and then separating molecules that do not interact with the 254P1D6B amino acid sequence from molecules that do. In a specific embodiment, the method further comprises purifying, characterizing and identifying a molecule that interacts with the 254P1D6B amino acid sequence. The identified molecule can be used to modulate a function performed by 254P1D6B. In a preferred embodiment, the 254P1D6B amino acid sequence is contacted with a library of peptides.

X) Therapeutic Methods and Compositions

The identification of 254P1D6B as a protein that is normally expressed in a restricted set of tissues, but which is also expressed in cancers such as those listed in Table I, opens a number of therapeutic approaches to the treatment of such cancers.

Of note, targeted antitumor therapies have been useful even when the targeted protein is expressed on normal tissues, even vital normal organ tissues. A vital organ is one that is necessary to sustain life, such as the heart or colon. A non-vital organ is one that can be removed whereupon the individual is still able to survive. Examples of non-vital organs are ovary, breast, and prostate.

For example, Herceptin® is an FDA approved pharmaceutical that has as its active ingredient an antibody which is immunoreactive with the protein variously known as HER2, HER2/neu, and erb-b-2. It is marketed by Genentech and has been a commercially successful antitumor agent. Herceptin sales reached almost $400 million in 2002. Herceptin is a treatment for HER2 positive metastatic breast cancer. However, the expression of HER2 is not limited to such tumors. The same protein is expressed in a number of normal tissues.

In particular, it is known that HER2/neu is present in normal kidney and heart, thus these tissues are present in all human recipients of Herceptin. The presence of HER2/neu in normal kidney is also confirmed by Latif, Z., et al., *B.J.U. International* (2002) 89:5-9. As shown in this article (which evaluated whether renal cell carcinoma should be a preferred indication for anti-HER2 antibodies such as Herceptin) both protein and mRNA are produced in benign renal tissues. Notably, HER2/neu protein was strongly overexpressed in benign renal tissue.

Despite the fact that HER2/neu is expressed in such vital tissues as heart and kidney, Herceptin is a very useful, FDA approved, and commercially successful drug. The effect of Herceptin on cardiac tissue, i.e., "cardiotoxicity," has merely been a side effect to treatment. When patients were treated with Herceptin alone, significant cardiotoxicity occurred in a very low percentage of patients.

Of particular note, although kidney tissue is indicated to exhibit normal expression, possibly even higher expression than cardiac tissue, kidney has no appreciable Herceptin side effect whatsoever. Moreover, of the diverse array of normal tissues in which HER2 is expressed, there is very little occurrence of any side effect. Only cardiac tissue has manifested any appreciable side effect at all. A tissue such as kidney, where HER2/neu expression is especially notable, has not been the basis for any side effect.

Furthermore, favorable therapeutic effects have been found for antitumor therapies that target epidermal growth factor receptor (EGFR). EGFR is also expressed in numerous normal tissues. There have been very limited side effects in normal tissues following use of anti-EGFR therapeutics.

Thus, expression of a target protein in normal tissue, even vital normal tissue, does not defeat the utility of a targeting agent for the protein as a therapeutic for certain tumors in which the protein is also overexpressed.

Accordingly, therapeutic approaches that inhibit the activity of a 254P1D6B protein are useful for patients suffering from a cancer that expresses 254P1D6B. These therapeutic approaches generally fall into two classes. One class comprises various methods for inhibiting the binding or association of a 254P1D6B protein with its binding partner or with other proteins. Another class comprises a variety of methods for inhibiting the transcription of a 254P1D6B gene or translation of 254P1D6B mRNA.

X.A.) Anti-Cancer Vaccines

The invention provides cancer vaccines comprising a 254P1D6B-related protein or 254P1D6B-related nucleic acid. In view of the expression of 254P1D6B, cancer vaccines prevent and/or treat 254P1D6B-expressing cancers with minimal or no effects on non-target tissues. The use of a tumor antigen in a vaccine that generates humoral and/or cell-mediated immune responses as anti-cancer therapy is well known in the art and has been employed in prostate cancer using human PSMA and rodent PAP immunogens (Hodge et al., 1995, Int. J. Cancer 63:231-237; Fong et al., 1997, J. Immunol. 159:3113-3117).

Such methods can be readily practiced by employing a 254P1D6B-related protein, or a 254P1D6B-encoding nucleic acid molecule and recombinant vectors capable of expressing and presenting the 254P1D6B immunogen (which typically comprises a number of antibody or T cell epitopes). Skilled artisans understand that a wide variety of vaccine systems for delivery of immunoreactive epitopes are known in the art (see, e.g., Heryln et al., Ann Med 1999 February 31(1):66-78; Maruyama et al., Cancer Immunol Immunother 2000 June 49(3):123-32) Briefly, such methods of generating an immune response (e.g. humoral and/or cell-mediated) in a mammal, comprise the steps of: exposing the mammal's immune system to an immunoreactive epitope (e.g. an epitope present in a 254P1D6B protein shown in FIG. 3 or analog or homolog thereof) so that the mammal generates an immune response that is specific for that epitope (e.g. generates antibodies that specifically recognize that epitope). In a preferred method, a 254P1D6B immunogen contains a biological motif, see e.g., Tables VIII-XXI and XXII-XLIX, or a peptide of a size range from 254P1D6B indicated in FIG. 5, FIG. 6, FIG. 7, FIG. 8, and FIG. 9.

The entire 254P1D6B protein, immunogenic regions or epitopes thereof can be combined and delivered by various means. Such vaccine compositions can include, for example, lipopeptides (e.g., Vitiello, A. et al., *J. Clin. Invest.* 95:341, 1995), peptide compositions encapsulated in poly(DL-lactide-co-glycolide) ("PLG") microspheres (see, e.g., Eldridge, et al., *Molec. Immunol.* 28:287-294, 1991: Alonso et al., *Vaccine* 12:299-306, 1994; Jones et al., *Vaccine* 13:675-681, 1995), peptide compositions contained in immune stimulating complexes (ISCOMS) (see, e.g., Takahashi et al., *Nature* 344:873-875, 1990; Hu et al., *Clin Exp Immunol.* 113:235-243, 1998), multiple antigen peptide systems (MAPs) (see e.g., Tam, J. P., *Proc. Natl. Acad. Sci. U.S.A.* 85:5409-5413, 1988; Tam, J. P., *J. Immunol. Methods* 196:17-32, 1996), peptides formulated as multivalent peptides; peptides for use in ballistic delivery systems, typically crystallized peptides, viral delivery vectors (Perkus, M. E. et al., In: *Concepts in vaccine development*, Kaufmann, S. H. E., ed., p. 379, 1996; Chakrabarti, S. et al., *Nature* 320:535, 1986; Hu, S. L. et al., *Nature* 320:537, 1986; Kieny, M.-P. et al., *AIDS Bio/Technology* 4:790, 1986; Top, F. H. et al., *J. Infect. Dis.* 124:148, 1971; Chanda, P. K. et al., *Virology* 175:535, 1990), particles of viral or synthetic origin (e.g., Kofler, N. et al., *J. Immunol. Methods.* 192:25, 1996; Eldridge, J. H. et al., *Sem. Hematol.* 30:16, 1993; Falo, L. D., Jr. et al., *Nature Med.* 7:649, 1995), adjuvants (Warren, H. S., Vogel, F. R., and Chedid, L. A. *Annu. Rev. Immunol.* 4:369, 1986; Gupta, R. K. et al., *Vaccine* 11:293, 1993), liposomes (Reddy, R. et al., *J. Immunol.* 148:1585, 1992; Rock, K. L., *Immunol. Today* 17:131, 1996), or, naked or particle absorbed cDNA (Ulmer, J. B. et al., *Science* 259:1745, 1993; Robinson, H. L., Hunt, L. A., and Webster, R. G., *Vaccine* 11:957, 1993; Shiver, J. W. et al., In: *Concepts in vaccine development*, Kaufmann, S. H. E., ed., p. 423, 1996; Cease, K. B., and Berzofsky, J. A., *Annu. Rev. Immunol.* 12:923, 1994 and Eldridge, J. H. et al., *Sem. Hematol.* 30:16, 1993). Toxin-targeted delivery technologies, also known as receptor mediated targeting, such as those of Avant Immunotherapeutics, Inc. (Needham, Mass.) may also be used.

In patients with 254P1D6B-associated cancer, the vaccine compositions of the invention can also be used in conjunction with other treatments used for cancer, e.g., surgery, chemotherapy, drug therapies, radiation therapies, etc. including use in combination with immune adjuvants such as IL-2, IL-12, GM-CSF, and the like.

Cellular Vaccines:

CTL epitopes can be determined using specific algorithms to identify peptides within 254P1D6B protein that bind corresponding HLA alleles (see e.g., Table IV; Epimer™ and Epimatrix™, Brown University (URL brown.edu/Research/TB-HIV_Lab/epimatrix/epimatrix.html); and, BIMAS, (URL bimas.dcrt.nih.gov/; SYFPEITHI at URL syfpeithi.bmi-heidelberg.com/). In a preferred embodiment, a 254P1D6B immunogen contains one or more amino acid sequences identified using techniques well known in the art, such as the sequences shown in Tables VIII-XXI and XXII-XLIX or a peptide of 8, 9, 10 or 11 amino acids specified by an HLA Class I motif/supermotif (e.g., Table IV (A), Table IV (D), or Table IV (E)) and/or a peptide of at least 9 amino acids that comprises an HLA Class II motif/supermotif (e.g., Table IV (B) or Table IV (C)). As is appreciated in the art, the HLA Class I binding groove is essentially closed ended so that peptides of only a particular size range can fit into the groove and be bound, generally HLA Class I epitopes are 8, 9, 10, or 11 amino acids long. In contrast, the HLA Class II binding groove is essentially open ended; therefore a peptide of about 9 or more amino acids can be bound by an HLA Class II molecule. Due to the binding groove differences between HLA Class I and II, HLA Class I motifs are length specific, i.e., position two of a Class I motif is the second amino acid in an amino to carboxyl direction of the peptide. The amino acid positions in a Class II motif are relative only to each other, not the overall peptide, i.e., additional amino acids can be attached to the amino and/or carboxyl termini of a motif-bearing sequence. HLA Class II epitopes are often 9, 10, 11, 12, 13, 14, 15, 16, 17, 18, 19, 20, 21, 22, 23, 24, or 25 amino acids long, or longer than 25 amino acids.

Antibody-Based Vaccines

A wide variety of methods for generating an immune response in a mammal are known in the art (for example as the first step in the generation of hybridomas). Methods of generating an immune response in a mammal comprise exposing the mammal's immune system to an immunogenic epitope on a protein (e.g. a 254P1D6B protein) so that an immune response is generated. A typical embodiment consists of a method for generating an immune response to 254P1D6B in a host, by contacting the host with a sufficient amount of at least one 254P1D6B B cell or cytotoxic T-cell epitope or analog thereof; and at least one periodic interval thereafter re-contacting the host with the 254P1D6B B cell or cytotoxic T-cell epitope or analog thereof. A specific embodiment consists of a method of generating an immune response against a 254P1D6B-related protein or a man-made multiepitopic peptide comprising: administering 254P1D6B immunogen (e.g. a 254P1D6B protein or a peptide fragment thereof, a 254P1D6B fusion protein or analog etc.) in a vaccine preparation to a human or another mammal. Typically, such vaccine preparations further contain a suitable adjuvant (see, e.g., U.S. Pat. No. 6,146,635) or a universal helper epitope such as a PADRE™ peptide (Epimmune Inc., San Diego, Calif.; see, e.g., Alexander et al., J. Immunol. 2000 164(3); 164(3): 1625-1633; Alexander et al., Immunity 1994 1(9): 751-761 and Alexander et al., Immunol. Res. 1998 18(2): 79-92). An alternative method comprises generating an immune response in an individual against a 254P1D6B immunogen by: administering in vivo to muscle or skin of the individual's body a DNA molecule that comprises a DNA sequence that encodes a 254P1D6B immunogen, the DNA sequence operatively linked to regulatory sequences which control the expression of the DNA sequence; wherein the DNA molecule is taken up by cells, the DNA sequence is expressed in the cells and an immune response is generated against the immunogen (see, e.g., U.S. Pat. No. 5,962,428). Optionally a genetic vaccine facilitator such as anionic lipids; saponins; lectins; estrogenic compounds; hydroxylated lower alkyls; dimethyl sulfoxide; and urea is also administered. In addition, an antiidiotypic antibody can be administered that mimics 254P1D6B, in order to generate a response to the target antigen.

Nucleic Acid Vaccines:

Vaccine compositions of the invention include nucleic acid-mediated modalities. DNA or RNA that encode protein(s) of the invention can be administered to a patient. Genetic immunization methods can be employed to generate prophylactic or therapeutic humoral and cellular immune responses directed against cancer cells expressing 254P1D6B. Constructs comprising DNA encoding a 254P1D6B-related protein/immunogen and appropriate regulatory sequences can be injected directly into muscle or skin of an individual, such that the cells of the muscle or skin take-up the construct and express the encoded 254P1D6B protein/immunogen. Alternatively, a vaccine comprises a 254P1D6B-related protein. Expression of the 254P1D6B-related protein immunogen results in the generation of prophylactic or therapeutic humoral and cellular immunity against cells that bear a 254P1D6B protein. Various prophylactic and therapeutic genetic immunization techniques known in the art can be used (for review, see information and references published at Internet address genweb.com). Nucleic acid-based delivery is described, for instance, in Wolff et. al., Science 247:1465 (1990) as well as U.S. Pat. Nos. 5,580,859; 5,589,466; 5,804,566; 5,739,118; 5,736,524; 5,679,647; WO 98/04720. Examples of DNA-based delivery technologies include "naked DNA", facilitated (bupivacaine, polymers, peptide-mediated) delivery, cationic lipid complexes, and particle-mediated ("gene gun") or pressure-mediated delivery (see, e.g., U.S. Pat. No. 5,922,687).

For therapeutic or prophylactic immunization purposes, proteins of the invention can be expressed via viral or bacterial vectors. Various viral gene delivery systems that can be used in the practice of the invention include, but are not limited to, vaccinia, fowlpox, canarypox, adenovirus, influenza, poliovirus, adeno-associated virus, lentivirus, and sindbis virus (see, e.g., Restifo, 1996, Curr. Opin. Immunol. 8:658-663; Tsang et al. J. Natl. Cancer Inst. 87:982-990 (1995)). Non-viral delivery systems can also be employed by introducing naked DNA encoding a 254P1D6B-related protein into the patient (e.g., intramuscularly or intradermally) to induce an anti-tumor response.

Vaccinia virus is used, for example, as a vector to express nucleotide sequences that encode the peptides of the invention. Upon introduction into a host, the recombinant vaccinia virus expresses the protein immunogenic peptide, and thereby elicits a host immune response. Vaccinia vectors and methods useful in immunization protocols are described in, e.g., U.S. Pat. No. 4,722,848. Another vector is BCG (Bacille Calmette Guerin). BCG vectors are described in Stover et al., Nature 351:456-460 (1991). A wide variety of other vectors useful for therapeutic administration or immunization of the peptides of the invention, e.g. adeno and adeno-associated virus vectors, retroviral vectors, *Salmonella typhi* vectors, detoxified anthrax toxin vectors, and the like, will be apparent to those skilled in the art from the description herein.

Thus, gene delivery systems are used to deliver a 254P1D6B-related nucleic acid molecule. In one embodiment, the full-length human 254P1D6B cDNA is employed. In another embodiment, 254P1D6B nucleic acid molecules encoding specific cytotoxic T lymphocyte (CTL) and/or antibody epitopes are employed.

Ex Vivo Vaccines

Various ex vivo strategies can also be employed to generate an immune response. One approach involves the use of antigen presenting cells (APCs) such as dendritic cells (DC) to present 254P1D6B antigen to a patient's immune system. Dendritic cells express MHC class I and II molecules, B7 co-stimulator, and IL-12, and are thus highly specialized antigen presenting cells. In prostate cancer, autologous dendritic cells pulsed with peptides of the prostate-specific membrane antigen (PSMA) are being used in a Phase I clinical trial to stimulate prostate cancer patients' immune systems (Tjoa et al., 1996, Prostate 28:65-69; Murphy et al., 1996, Prostate 29:371-380). Thus, dendritic cells can be used to present 254P1D6B peptides to T cells in the context of MHC class I or II molecules. In one embodiment, autologous dendritic cells are pulsed with 254P1D6B peptides capable of binding to MHC class I and/or class II molecules. In another embodiment, dendritic cells are pulsed with the complete 254P1D6B protein. Yet another embodiment involves engineering the overexpression of a 254P1D6B gene in dendritic cells using various implementing vectors known in the art, such as adenovirus (Arthur et al., 1997, Cancer Gene Ther. 4:17-25), retrovirus (Henderson et al., 1996, Cancer Res. 56:3763-3770), lentivirus, adeno-associated virus, DNA transfection (Ribas et al., 1997, Cancer Res. 57:2865-2869), or tumor-derived RNA transfection (Ashley et al., 1997, J. Exp. Med. 186: 1177-1182). Cells that express 254P1D6B can also be engineered to express immune modulators, such as GM-CSF, and used as immunizing agents.

X.B.) 254P1D6B as a Target for Antibody-Based Therapy

254P1D6B is an attractive target for antibody-based therapeutic strategies. A number of antibody strategies are known in the art for targeting both extracellular and intracellular molecules (see, e.g., complement and ADCC mediated killing as well as the use of intrabodies). Because 254P1D6B is expressed by cancer cells of various lineages relative to corresponding normal cells, systemic administration of 254P1D6B-immunoreactive compositions are prepared that exhibit excellent sensitivity without toxic, non-specific and/or non-target effects caused by binding of the immunoreactive composition to non-target organs and tissues. Antibodies specifically reactive with domains of 254P1D6B are useful to treat 254P1D6B-expressing cancers systemically, either as conjugates with a toxin or therapeutic agent, or as naked antibodies capable of inhibiting cell proliferation or function.

254P1D6B antibodies can be introduced into a patient such that the antibody binds to 254P1D6B and modulates a function, such as an interaction with a binding partner, and consequently mediates destruction of the tumor cells and/or inhibits the growth of the tumor cells. Mechanisms by which such antibodies exert a therapeutic effect can include complement-mediated cytolysis, antibody-dependent cellular cytotoxicity, modulation of the physiological function of 254P1D6B, inhibition of ligand binding or signal transduction pathways, modulation of tumor cell differentiation, alteration of tumor angiogenesis factor profiles, and/or apoptosis.

Those skilled in the art understand that antibodies can be used to specifically target and bind immunogenic molecules such as an immunogenic region of a 254P1D6B sequence shown in FIG. 2 or FIG. 3. In addition, skilled artisans understand that it is routine to conjugate antibodies to cytotoxic agents (see, e.g., Slevers et al. Blood 93:11 3678-3684 (Jun. 1, 1999)). When cytotoxic and/or therapeutic agents are delivered directly to cells, such as by conjugating them to antibodies specific for a molecule expressed by that cell (e.g. 254P1D6B), the cytotoxic agent will exert its known biological effect (i.e. cytotoxicity) on those cells.

A wide variety of compositions and methods for using antibody-cytotoxic agent conjugates to kill cells are known in the art. In the context of cancers, typical methods entail administering to an animal having a tumor a biologically effective amount of a conjugate comprising a selected cytotoxic and/or therapeutic agent linked to a targeting agent (e.g. an anti-254P1D6B antibody) that binds to a marker (e.g. 254P1D6B) expressed, accessible to binding or localized on the cell surfaces. A typical embodiment is a method of delivering a cytotoxic and/or therapeutic agent to a cell expressing 254P1D6B, comprising conjugating the cytotoxic agent to an antibody that immunospecifically binds to a 254P1D6B epitope, and, exposing the cell to the antibody-agent conjugate. Another illustrative embodiment is a method of treating an individual suspected of suffering from metastasized cancer, comprising a step of administering parenterally to said individual a pharmaceutical composition comprising a therapeutically effective amount of an antibody conjugated to a cytotoxic and/or therapeutic agent.

Cancer immunotherapy using anti-254P1D6B antibodies can be done in accordance with various approaches that have been successfully employed in the treatment of other types of cancer, including but not limited to colon cancer (Arlen et al., 1998, Crit. Rev. Immunol. 18:133-138), multiple myeloma (Ozaki et al., 1997, Blood 90:3179-3186, Tsunenari et al., 1997, Blood 90:2437-2444), gastric cancer (Kasprzyk et al., 1992, Cancer Res. 52:2771-2776), B-cell lymphoma (Funakoshi et al., 1996, J. Immunother. Emphasis Tumor Immunol. 19:93-101), leukemia (Zhong et al., 1996, Leuk. Res. 20:581-589), colorectal cancer (Moun et al., 1994, Cancer Res. 54:6160-6166; Velders et al., 1995, Cancer Res. 55:4398-4403), and breast cancer (Shepard et al., 1991, J. Clin. Immunol. 11: 117-127). Some therapeutic approaches involve conjugation of naked antibody to a toxin or radioisotope, such as the conjugation of $Y^{91}$ or $I^{131}$ to anti-CD20 antibodies (e.g., Zevalin™, IDEC Pharmaceuticals Corp. or Bexxar™, Coulter Pharmaceuticals), while others involve co-administration of antibodies and other therapeutic agents, such as Herceptin™ (trastuzumab) with paclitaxel (Genentech, Inc.). The antibodies can be conjugated to a therapeutic agent. To treat prostate cancer, for example, 254P1D6B antibodies can be administered in conjunction with radiation, chemotherapy or hormone ablation. Also, antibodies can be conjugated to a toxin such as calicheamicin (e.g., Mylotarg™, Wyeth-Ayerst, Madison, N.J., a recombinant humanized $IgG_4$ kappa antibody conjugated to antitumor antibiotic calicheamicin) or a maytansinoid (e.g., taxane-based Tumor-Activated Prodrug, TAP, platform, ImmunoGen, Cambridge, Mass., also see e.g., U.S. Pat. No. 5,416,064).

Although 254P1D6B antibody therapy is useful for all stages of cancer, antibody therapy can be particularly appropriate in advanced or metastatic cancers. Treatment with the antibody therapy of the invention is indicated for patients who have received one or more rounds of chemotherapy. Alternatively, antibody therapy of the invention is combined with a chemotherapeutic or radiation regimen for patients who have not received chemotherapeutic treatment. Additionally, antibody therapy can enable the use of reduced dosages of concomitant chemotherapy, particularly for patients who do not tolerate the toxicity of the chemotherapeutic agent very well. Fan et al. (Cancer Res. 53:4637-4642, 1993), Prewett et al. (International J. of Onco. 9:217-224, 1996), and Hancock et al. (Cancer Res. 51:4575-4580, 1991) describe the use of various antibodies together with chemotherapeutic agents.

Although 254P1D6B antibody therapy is useful for all stages of cancer, antibody therapy can be particularly appropriate in advanced or metastatic cancers. Treatment with the antibody therapy of the invention is indicated for patients who have received one or more rounds of chemotherapy. Alternatively, antibody therapy of the invention is combined with a chemotherapeutic or radiation regimen for patients who have not received chemotherapeutic treatment. Additionally, antibody therapy can enable the use of reduced dosages of concomitant chemotherapy, particularly for patients who do not tolerate the toxicity of the chemotherapeutic agent very well.

Cancer patients can be evaluated for the presence and level of 254P1D6B expression, preferably using immunohistochemical assessments of tumor tissue, quantitative 254P1D6B imaging, or other techniques that reliably indicate the presence and degree of 254P1D6B expression. Immunohistochemical analysis of tumor biopsies or surgical specimens is preferred for this purpose. Methods for immunohistochemical analysis of tumor tissues are well known in the art.

Anti-254P1D6B monoclonal antibodies that treat prostate and other cancers include those that initiate a potent immune response against the tumor or those that are directly cytotoxic. In this regard, anti-254P1D6B monoclonal antibodies (mAbs) can elicit tumor cell lysis by either complement-mediated or antibody-dependent cell cytotoxicity (ADCC) mechanisms, both of which require an intact Fc portion of the immunoglobulin molecule for interaction with effector cell Fc receptor sites on complement proteins. In addition, anti-254P1D6B mAbs that exert a direct biological effect on tumor growth are useful to treat cancers that express 254P1D6B. Mechanisms by which directly cytotoxic mAbs act include: inhibition of cell growth, modulation of cellular differentiation, modulation of tumor angiogenesis factor profiles, and the induction of apoptosis. The mechanism(s) by which a particular anti-254P1D6B mAb exerts an anti-tumor effect is evaluated using any number of in vitro assays that evaluate cell death such as ADCC, ADMMC, complement-mediated cell lysis, and so forth, as is generally known in the art.

In some patients, the use of murine or other non-human monoclonal antibodies, or human/mouse chimeric mAbs can induce moderate to strong immune responses against the non-human antibody. This can result in clearance of the antibody from circulation and reduced efficacy. In the most severe cases, such an immune response can lead to the extensive formation of immune complexes which, potentially, can cause renal failure. Accordingly, preferred monoclonal antibodies used in the therapeutic methods of the invention are those that are either fully human or humanized and that bind specifically to the target 254P1D6B antigen with high affinity but exhibit low or no antigenicity in the patient.

Therapeutic methods of the invention contemplate the administration of single anti-254P1D6B mAbs as well as combinations, or cocktails, of different mAbs. Such mAb cocktails can have certain advantages inasmuch as they contain mAbs that target different epitopes, exploit different effector mechanisms or combine directly cytotoxic mAbs with mAbs that rely on immune effector functionality. Such mAbs in combination can exhibit synergistic therapeutic effects. In addition, anti-254P1D6B mAbs can be administered concomitantly with other therapeutic modalities, including but not limited to various chemotherapeutic agents, androgen-blockers, immune modulators (e.g., IL-2, GM-CSF), surgery or radiation. The anti-254P1D6B mAbs are administered in their "naked" or unconjugated form, or can have a therapeutic agent(s) conjugated to them.

Anti-254P1D6B antibody formulations are administered via any route capable of delivering the antibodies to a tumor cell. Routes of administration include, but are not limited to, intravenous, intraperitoneal, intramuscular, intratumor, intradermal, and the like. Treatment generally involves repeated administration of the anti-254P1D6B antibody preparation, via an acceptable route of administration such as intravenous injection (IV), typically at a dose in the range of about 0.1, 0.2, 0.3, 0.4, 0.5, 0.6, 0.7, 0.8, 0.9., 1, 2, 3, 4, 5, 6, 7, 8, 9, 10, 15, 20, or 25 mg/kg body weight. In general, doses in the range of 10-1000 mg mAb per week are effective and well tolerated.

Based on clinical experience with the Herceptin™ mAb in the treatment of metastatic breast cancer, an initial loading dose of approximately 4 mg/kg patient body weight IV, followed by weekly doses of about 2 mg/kg IV of the anti-254P1D6B mAb preparation represents an acceptable dosing regimen. Preferably, the initial loading dose is administered as a 90-minute or longer infusion. The periodic maintenance dose is administered as a 30 minute or longer infusion, provided the initial dose was well tolerated. As appreciated by those of skill in the art, various factors can influence the ideal dose regimen in a particular case. Such factors include, for example, the binding affinity and half life of the Ab or mAbs used, the degree of 254P1D6B expression in the patient, the extent of circulating shed 254P1D6B antigen, the desired steady-state antibody concentration level, frequency of treatment, and the influence of chemotherapeutic or other agents used in combination with the treatment method of the invention, as well as the health status of a particular patient.

Optionally, patients should be evaluated for the levels of 254P1D6B in a given sample (e.g. the levels of circulating 254P1D6B antigen and/or 254P1D6B expressing cells) in order to assist in the determination of the most effective dosing regimen, etc. Such evaluations are also used for monitoring purposes throughout therapy, and are useful to gauge therapeutic success in combination with the evaluation of other parameters (for example, urine cytology and/or ImmunoCyt levels in bladder cancer therapy, or by analogy, serum PSA levels in prostate cancer therapy).

Anti-idiotypic anti-254P1D6B antibodies can also be used in anti-cancer therapy as a vaccine for inducing an immune response to cells expressing a 254P1D6B-related protein. In particular, the generation of anti-idiotypic antibodies is well known in the art; this methodology can readily be adapted to generate anti-idiotypic anti-254P1D6B antibodies that mimic an epitope on a 254P1D6B-related protein (see, for example, Wagner et al., 1997, Hybridoma 16: 33-40; Foon et al., 1995, J. Clin. Invest. 96:334-342; Herlyn et al., 1996, Cancer Immunol. Immunother. 43:65-76). Such an anti-idiotypic antibody can be used in cancer vaccine strategies.

X.C.) 254P1D6B as a Target for Cellular Immune Responses

Vaccines and methods of preparing vaccines that contain an immunogenically effective amount of one or more HLA-binding peptides as described herein are further embodiments of the invention. Furthermore, vaccines in accordance with the invention encompass compositions of one or more of the claimed peptides. A peptide can be present in a vaccine individually. Alternatively, the peptide can exist as a homopolymer comprising multiple copies of the same peptide, or as a heteropolymer of various peptides. Polymers have the advantage of increased immunological reaction and, where different peptide epitopes are used to make up the polymer, the additional ability to induce antibodies and/or CTLs that react with different antigenic determinants of the pathogenic organism or tumor-related peptide targeted for an immune response. The composition can be a naturally occurring region of an antigen or can be prepared, e.g., recombinantly or by chemical synthesis.

Carriers that can be used with vaccines of the invention are well known in the art, and include, e.g., thyroglobulin, albumins such as human serum albumin, tetanus toxoid, polyamino acids such as poly L-lysine, poly L-glutamic acid, influenza, hepatitis B virus core protein, and the like. The vaccines can contain a physiologically tolerable (i.e., acceptable) diluent such as water, or saline, preferably phosphate buffered saline. The vaccines also typically include an adjuvant. Adjuvants such as incomplete Freund's adjuvant, aluminum phosphate, aluminum hydroxide, or alum are examples of materials well known in the art. Additionally, as disclosed herein, CTL responses can be primed by conjugating peptides of the invention to lipids, such as tripalmitoyl-S-glycerylcysteinlyseryl-serine ($P_3CSS$). Moreover, an adjuvant such as a synthetic cytosine-phosphorothioatedguanine-containing (CpG) oligonucleotides has been found to increase CTL responses 10- to 100-fold. (see, e.g. Davila and Celis, J. Immunol. 165:539-547 (2000))

Upon immunization with a peptide composition in accordance with the invention, via injection, aerosol, oral, transdermal, transmucosal, intrapleural, intrathecal, or other suitable routes, the immune system of the host responds to the vaccine by producing large amounts of CTLs and/or HTLs specific for the desired antigen. Consequently, the host becomes at least partially immune to later development of cells that express or overexpress 254P1D6B antigen, or derives at least some therapeutic benefit when the antigen was tumor-associated.

In some embodiments, it may be desirable to combine the class I peptide components with components that induce or facilitate neutralizing antibody and or helper T cell responses directed to the target antigen. A preferred embodiment of such a composition comprises class I and class II epitopes in accordance with the invention. An alternative embodiment of such a composition comprises a class I and/or class II epitope in accordance with the invention, along with a cross reactive HTL epitope such as PADRE™ (Epimmune, San Diego, Calif.) molecule (described e.g., in U.S. Pat. No. 5,736,142).

A vaccine of the invention can also include antigen-presenting cells (APC), such as dendritic cells (DC), as a vehicle to present peptides of the invention. Vaccine compositions can be created in vitro, following dendritic cell mobilization and harvesting, whereby loading of dendritic cells occurs in vitro. For example, dendritic cells are transfected, e.g., with a minigene in accordance with the invention, or are pulsed with peptides. The dendritic cell can then be administered to a patient to elicit immune responses in vivo. Vaccine compositions, either DNA- or peptide-based, can also be administered in vivo in combination with dendritic cell mobilization whereby loading of dendritic cells occurs in vivo.

Preferably, the following principles are utilized when selecting an array of epitopes for inclusion in a polyepitopic composition for use in a vaccine, or for selecting discrete epitopes to be included in a vaccine and/or to be encoded by nucleic acids such as a minigene. It is preferred that each of the following principles be balanced in order to make the selection. The multiple epitopes to be incorporated in a given vaccine composition may be, but need not be, contiguous in sequence in the native antigen from which the epitopes are derived.

1.) Epitopes are selected which, upon administration, mimic immune responses that have been observed to be correlated with tumor clearance. For HLA Class I this includes 3-4 epitopes that come from at least one tumor associated antigen (TAA). For HLA Class II a similar rationale is employed; again 3-4 epitopes are selected from at least one TAA (see, e.g., Rosenberg et al., *Science* 278:1447-1450). Epitopes from one TAA may be used in combination with epitopes from one or more additional TAAs to produce a vaccine that targets tumors with varying expression patterns of frequently-expressed TAAs.

2.) Epitopes are selected that have the requisite binding affinity established to be correlated with immunogenicity: for HLA Class I an $IC_{50}$ of 500 nM or less, often 200 nM or less; and for Class II an $IC_{50}$ of 1000 nM or less.

3.) Sufficient supermotif bearing-peptides, or a sufficient array of allele-specific motif-bearing peptides, are selected to give broad population coverage. For example, it is preferable to have at least 80% population coverage. A Monte Carlo analysis, a statistical evaluation known in the art, can be employed to assess the breadth, or redundancy of, population coverage.

4.) When selecting epitopes from cancer-related antigens it is often useful to select analogs because the patient may have developed tolerance to the native epitope.

5.) Of particular relevance are epitopes referred to as "nested epitopes." Nested epitopes occur where at least two epitopes overlap in a given peptide sequence. A nested peptide sequence can comprise B cell, HLA class I and/or HLA class II epitopes. When providing nested epitopes, a general objective is to provide the greatest number of epitopes per sequence. Thus, an aspect is to avoid providing a peptide that is any longer than the amino terminus of the amino terminal epitope and the carboxyl terminus of the carboxyl terminal epitope in the peptide. When providing a multi-epitopic sequence, such as a sequence comprising nested epitopes, it is generally important to screen the sequence in order to insure that it does not have pathological or other deleterious biological properties.

6.) If a polyepitopic protein is created, or when creating a minigene, an objective is to generate the smallest peptide that encompasses the epitopes of interest. This principle is similar, if not the same as that employed when selecting a peptide comprising nested epitopes. However, with an artificial polyepitopic peptide, the size minimization objective is balanced against the need to integrate any spacer sequences between epitopes in the polyepitopic protein. Spacer amino acid residues can, for example, be introduced to avoid junctional epitopes (an epitope recognized by the immune system, not present in the target antigen, and only created by the man-made juxtaposition of epitopes), or to facilitate cleavage between epitopes and thereby enhance epitope presentation. Junctional epitopes are generally to be avoided because the recipient may generate an immune response to that non-native epitope. Of particular concern is a junctional epitope that is a "dominant epitope." A dominant epitope may lead to such a zealous response that immune responses to other epitopes are diminished or suppressed.

7.) Where the sequences of multiple variants of the same target protein are present, potential peptide epitopes can also be selected on the basis of their conservancy. For example, a criterion for conservancy may define that the entire sequence of an HLA class I binding peptide or the entire 9-mer core of a class II binding peptide be conserved in a designated percentage of the sequences evaluated for a specific protein antigen.

X.C.1. Minigene Vaccines

A number of different approaches are available which allow simultaneous delivery of multiple epitopes. Nucleic acids encoding the peptides of the invention are a particularly useful embodiment of the invention. Epitopes for inclusion in a minigene are preferably selected according to the guidelines set forth in the previous section. A preferred means of administering nucleic acids encoding the peptides of the invention uses minigene constructs encoding a peptide comprising one or multiple epitopes of the invention.

The use of multi-epitope minigenes is described below and in, Ishioka et al., *J. Immunol.* 162:3915-3925, 1999; An, L. and Whitton, J. L., *J. Virol.* 71:2292, 1997; Thomson, S. A. et al., *J. Immunol.* 157:822, 1996; Whitton, J. L. et al., *J. Virol.* 67:348, 1993; Hanke, R. et al., *Vaccine* 16:426, 1998. For example, a multi-epitope DNA plasmid encoding supermotif- and/or motif-bearing epitopes derived 254P1D6B, the PADRE® universal helper T cell epitope or multiple HTL epitopes from 254P1D6B (see e.g., Tables VIII-XXI and XXII to XLIX), and an endoplasmic reticulum-translocating signal sequence can be engineered. A vaccine may also comprise epitopes that are derived from other TAAs.

The immunogenicity of a multi-epitopic minigene can be confirmed in transgenic mice to evaluate the magnitude of CTL induction responses against the epitopes tested. Further, the immunogenicity of DNA-encoded epitopes in vivo can be correlated with the in vitro responses of specific CTL lines against target cells transfected with the DNA plasmid. Thus, these experiments can show that the minigene serves to both: 1.) generate a CTL response and 2.) that the induced CTLs recognized cells expressing the encoded epitopes.

For example, to create a DNA sequence encoding the selected epitopes (minigene) for expression in human cells, the amino acid sequences of the epitopes may be reverse translated. A human codon usage table can be used to guide the codon choice for each amino acid. These epitope-encoding DNA sequences may be directly adjoined, so that when translated, a continuous polypeptide sequence is created. To optimize expression and/or immunogenicity, additional elements can be incorporated into the minigene design. Examples of amino acid sequences that can be reverse translated and included in the minigene sequence include: HLA class I epitopes, HLA class II epitopes, antibody epitopes, a ubiquitination signal sequence, and/or an endoplasmic reticulum targeting signal. In addition, HLA presentation of CTL and HTL epitopes may be improved by including synthetic (e.g. poly-alanine) or naturally-occurring flanking sequences adjacent to the CTL or HTL epitopes; these larger peptides comprising the epitope(s) are within the scope of the invention.

The minigene sequence may be converted to DNA by assembling oligonucleotides that encode the plus and minus strands of the minigene. Overlapping oligonucleotides (30-100 bases long) may be synthesized, phosphorylated, purified and annealed under appropriate conditions using well known techniques. The ends of the oligonucleotides can be joined, for example, using T4 DNA ligase. This synthetic minigene, encoding the epitope polypeptide, can then be cloned into a desired expression vector.

Standard regulatory sequences well known to those of skill in the art are preferably included in the vector to ensure expression in the target cells. Several vector elements are desirable: a promoter with a down-stream cloning site for minigene insertion; a polyadenylation signal for efficient transcription termination; an *E. coli* origin of replication; and an *E. coli* selectable marker (e.g. ampicillin or kanamycin resistance). Numerous promoters can be used for this purpose, e.g., the human cytomegalovirus (hCMV) promoter. See, e.g., U.S. Pat. Nos. 5,580,859 and 5,589,466 for other suitable promoter sequences.

Additional vector modifications may be desired to optimize minigene expression and immunogenicity. In some cases, introns are required for efficient gene expression, and one or more synthetic or naturally-occurring introns could be incorporated into the transcribed region of the minigene. The inclusion of mRNA stabilization sequences and sequences for replication in mammalian cells may also be considered for increasing minigene expression.

Once an expression vector is selected, the minigene is cloned into the polylinker region downstream of the promoter. This plasmid is transformed into an appropriate *E. coli* strain, and DNA is prepared using standard techniques. The orientation and DNA sequence of the minigene, as well as all other elements included in the vector, are confirmed using restriction mapping and DNA sequence analysis. Bacterial cells harboring the correct plasmid can be stored as a master cell bank and a working cell bank.

In addition, immunostimulatory sequences (ISSs or CpGs) appear to play a role in the immunogenicity of DNA vaccines. These sequences may be included in the vector, outside the minigene coding sequence, if desired to enhance immunogenicity.

In some embodiments, a bi-cistronic expression vector which allows production of both the minigene-encoded epitopes and a second protein (included to enhance or decrease immunogenicity) can be used. Examples of proteins or polypeptides that could beneficially enhance the immune response if co-expressed include cytokines (e.g., IL-2, IL-12, GM-CSF), cytokine-inducing molecules (e.g., LeIF), costimulatory molecules, or for HTL responses, pan-DR binding proteins (PADRE™, Epimmune, San Diego, Calif.). Helper (HTL) epitopes can be joined to intracellular targeting signals and expressed separately from expressed CTL epitopes; this allows direction of the HTL epitopes to a cell compartment different than that of the CTL epitopes. If required, this could facilitate more efficient entry of HTL epitopes into the HLA class II pathway, thereby improving HTL induction. In contrast to HTL or CTL induction, specifically decreasing the immune response by co-expression of immunosuppressive molecules (e.g. TGF-β) may be beneficial in certain diseases.

Therapeutic quantities of plasmid DNA can be produced for example, by fermentation in *E. coli*, followed by purification. Aliquots from the working cell bank are used to inoculate growth medium, and grown to saturation in shaker flasks or a bioreactor according to well-known techniques. Plasmid DNA can be purified using standard bioseparation technologies such as solid phase anion-exchange resins supplied by QIAGEN, Inc. (Valencia, Calif.). If required, supercoiled DNA can be isolated from the open circular and linear forms using gel electrophoresis or other methods.

Purified plasmid DNA can be prepared for injection using a variety of formulations. The simplest of these is reconstitution of lyophilized DNA in sterile phosphate-buffer saline (PBS). This approach, known as "naked DNA," is currently being used for intramuscular (IM) administration in clinical trials. To maximize the immunotherapeutic effects of minigene DNA vaccines, an alternative method for formulating purified plasmid DNA may be desirable. A variety of methods have been described, and new techniques may become available. Cationic lipids, glycolipids, and fusogenic liposomes can also be used in the formulation (see, e.g., as described by WO 93/24640; Mannino & Gould-Fogerite, *BioTechniques* 6(7): 682 (1988); U.S. Pat. No. 5,279,833; WO 91/06309; and Felgner, et al., *Proc. Nat'l Acad. Sci. USA* 84:7413 (1987). In addition, peptides and compounds referred to collectively as protective, interactive, non-condensing compounds (PINC) could also be complexed to purified plasmid DNA to influence variables such as stability, intramuscular dispersion, or trafficking to specific organs or cell types.

Target cell sensitization can be used as a functional assay for expression and HLA class I presentation of minigene-encoded CTL epitopes. For example, the plasmid DNA is introduced into a mammalian cell line that is suitable as a target for standard CTL chromium release assays. The transfection method used will be dependent on the final formulation. Electroporation can be used for "naked" DNA, whereas cationic lipids allow direct in vitro transfection. A plasmid expressing green fluorescent protein (GFP) can be co-transfected to allow enrichment of transfected cells using fluorescence activated cell sorting (FACS). These cells are then chromium-51 ($^{51}Cr$) labeled and used as target cells for epitope-specific CTL lines; cytolysis, detected by $^{51}Cr$ release, indicates both production of, and HLA presentation of, minigene-encoded CTL epitopes. Expression of HTL epitopes may be evaluated in an analogous manner using assays to assess HTL activity.

In vivo immunogenicity is a second approach for functional testing of minigene DNA formulations. Transgenic mice expressing appropriate human HLA proteins are immunized with the DNA product. The dose and route of administration are formulation dependent (e.g., IM for DNA in PBS, intraperitoneal (i.p.) for lipid-complexed DNA). Twenty-one days after immunization, splenocytes are harvested and restimulated for one week in the presence of peptides encoding each epitope being tested. Thereafter, for CTL effector cells, assays are conducted for cytolysis of peptide-loaded, $^{51}$Cr-labeled target cells using standard techniques. Lysis of target cells that were sensitized by HLA loaded with peptide epitopes, corresponding to minigene-encoded epitopes, demonstrates DNA vaccine function for in vivo induction of CTLs. Immunogenicity of HTL epitopes is confirmed in transgenic mice in an analogous manner.

Alternatively, the nucleic acids can be administered using ballistic delivery as described, for instance, in U.S. Pat. No. 5,204,253. Using this technique, particles comprised solely of DNA are administered. In a further alternative embodiment, DNA can be adhered to particles, such as gold particles.

Minigenes can also be delivered using other bacterial or viral delivery systems well known in the art, e.g., an expression construct encoding epitopes of the invention can be incorporated into a viral vector such as vaccinia.

X.C.2. Combinations of CTL Peptides with Helper Peptides

Vaccine compositions comprising CTL peptides of the invention can be modified, e.g., analoged, to provide desired attributes, such as improved serum half life, broadened population coverage or enhanced immunogenicity.

For instance, the ability of a peptide to induce CTL activity can be enhanced by linking the peptide to a sequence which contains at least one epitope that is capable of inducing a T helper cell response. Although a CTL peptide can be directly linked to a T helper peptide, often CTL epitope/HTL epitope conjugates are linked by a spacer molecule. The spacer is typically comprised of relatively small, neutral molecules, such as amino acids or amino acid mimetics, which are substantially uncharged under physiological conditions. The spacers are typically selected from, e.g., Ala, Gly, or other neutral spacers of nonpolar amino acids or neutral polar amino acids. It will be understood that the optionally present spacer need not be comprised of the same residues and thus may be a hetero- or homo-oligomer. When present, the spacer will usually be at least one or two residues, more usually three to six residues and sometimes 10 or more residues. The CTL peptide epitope can be linked to the T helper peptide epitope either directly or via a spacer either at the amino or carboxy terminus of the CTL peptide. The amino terminus of either the immunogenic peptide or the T helper peptide may be acylated.

In certain embodiments, the T helper peptide is one that is recognized by T helper cells present in a majority of a genetically diverse population. This can be accomplished by selecting peptides that bind to many, most, or all of the HLA class II molecules. Examples of such amino acid bind many HLA Class II molecules include sequences from antigens such as tetanus toxoid at positions 830-843 QYIKANSKFIGITE; (SEQ ID NO:13), *Plasmodium falciparum* circumsporozoite (CS) protein at positions 378-398 DIEKKIAKMEKASSVFNVVNS; (SEQ ID NO:14), and *Streptococcus* 18 kD protein at positions 116-131 GAVDSILGGVATYGAA; (SEQ ID NO:15). Other examples include peptides bearing a DR 1-4-7 supermotif, or either of the DR3 motifs.

Alternatively, it is possible to prepare synthetic peptides capable of stimulating T helper lymphocytes, in a loosely HLA-restricted fashion, using amino acid sequences not found in nature (see, e.g., PCT publication WO 95/07707). These synthetic compounds called Pan-DR-binding epitopes (e.g., PADRE™, Epimmune, Inc., San Diego, Calif.) are designed, most preferably, to bind most HLA-DR (human HLA class II) molecules. For instance, a pan-DR-binding epitope peptide having the formula: xKXVAAWTLKAAx (SEQ ID NO:16), where "X" is either cyclohexylalanine, phenylalanine, or tyrosine, and a is either D-alanine or L-alanine, has been found to bind to most HLA-DR alleles, and to stimulate the response of T helper lymphocytes from most individuals, regardless of their HLA type. An alternative of a pan-DR binding epitope comprises all "L" natural amino acids and can be provided in the form of nucleic acids that encode the epitope.

HTL peptide epitopes can also be modified to alter their biological properties. For example, they can be modified to include D-amino acids to increase their resistance to proteases and thus extend their serum half life, or they can be conjugated to other molecules such as lipids, proteins, carbohydrates, and the like to increase their biological activity. For example, a T helper peptide can be conjugated to one or more palmitic acid chains at either the amino or carboxyl termini.

X.C.3. Combinations of CTL Peptides with T Cell Priming Agents

In some embodiments it may be desirable to include in the pharmaceutical compositions of the invention at least one component which primes B lymphocytes or T lymphocytes. Lipids have been identified as agents capable of priming CTL in vivo. For example, palmitic acid residues can be attached to the ε- and α-amino groups of a lysine residue and then linked, e.g., via one or more linking residues such as Gly, Gly-Gly-, Ser, Ser-Ser, or the like, to an immunogenic peptide. The lipidated peptide can then be administered either directly in a micelle or particle, incorporated into a liposome, or emulsified in an adjuvant, e.g., incomplete Freund's adjuvant. In a preferred embodiment, a particularly effective immunogenic composition comprises palmitic acid attached to ε- and α-amino groups of Lys, which is attached via linkage, e.g., Ser-Ser, to the amino terminus of the immunogenic peptide.

As another example of lipid priming of CTL responses, *E. coli* lipoproteins, such as tripalmitoyl-S-glycerylcysteinylseryl-serine ($P_3CSS$) can be used to prime virus specific CTL when covalently attached to an appropriate peptide (see, e.g., Deres, et al., *Nature* 342:561, 1989). Peptides of the invention can be coupled to $P_3CSS$, for example, and the lipopeptide administered to an individual to prime specifically an immune response to the target antigen. Moreover, because the induction of neutralizing antibodies can also be primed with $P_3CSS$-conjugated epitopes, two such compositions can be combined to more effectively elicit both humoral and cell-mediated responses.

X.C.4. Vaccine Compositions Comprising DC Pulsed with CTL and/or HTL Peptides

An embodiment of a vaccine composition in accordance with the invention comprises ex vivo administration of a cocktail of epitope-bearing peptides to PBMC, or isolated DC therefrom, from the patient's blood. A pharmaceutical to facilitate harvesting of DC can be used, such as Progenipoietin™ (Pharmacia-Monsanto, St. Louis, Mo.) or GM-CSF/IL-4. After pulsing the DC with peptides and prior to reinfusion into patients, the DC are washed to remove unbound peptides. In this embodiment, a vaccine comprises peptide-pulsed DCs which present the pulsed peptide epitopes complexed with HLA molecules on their surfaces.

The DC can be pulsed ex vivo with a cocktail of peptides, some of which stimulate CTL responses to 254P1D6B. Optionally, a helper T cell (HTL) peptide, such as a natural or artificial loosely restricted HLA Class II peptide, can be included to facilitate the CTL response. Thus, a vaccine in accordance with the invention is used to treat a cancer which expresses or overexpresses 254P1D6B.

X.D. Adoptive Immunotherapy

Antigenic 254P1D6B-related peptides are used to elicit a CTL and/or HTL response ex vivo, as well. The resulting CTL or HTL cells, can be used to treat tumors in patients that do not respond to other conventional forms of therapy, or will not respond to a therapeutic vaccine peptide or nucleic acid in accordance with the invention. Ex vivo CTL or HTL responses to a particular antigen are induced by incubating in tissue culture the patient's, or genetically compatible, CTL or HTL precursor cells together with a source of antigen-presenting cells (APC), such as dendritic cells, and the appropriate immunogenic peptide. After an appropriate incubation time (typically about 7-28 days), in which the precursor cells are activated and expanded into effector cells, the cells are infused back into the patient, where they will destroy (CTL) or facilitate destruction (HTL) of their specific target cell (e.g., a tumor cell). Transfected dendritic cells may also be used as antigen presenting cells.

X.E. Administration of Vaccines for Therapeutic or Prophylactic Purposes

Pharmaceutical and vaccine compositions of the invention are typically used to treat and/or prevent a cancer that expresses or overexpresses 254P1D6B. In therapeutic applications, peptide and/or nucleic acid compositions are administered to a patient in an amount sufficient to elicit an effective B cell, CTL and/or HTL response to the antigen and to cure or at least partially arrest or slow symptoms and/or complications. An amount adequate to accomplish this is defined as "therapeutically effective dose." Amounts effective for this use will depend on, e.g., the particular composition administered, the manner of administration, the stage and severity of the disease being treated, the weight and general state of health of the patient, and the judgment of the prescribing physician.

For pharmaceutical compositions, the immunogenic peptides of the invention, or DNA encoding them, are generally administered to an individual already bearing a tumor that expresses 254P1D6B. The peptides or DNA encoding them can be administered individually or as fusions of one or more peptide sequences. Patients can be treated with the immunogenic peptides separately or in conjunction with other treatments, such as surgery, as appropriate.

For therapeutic use, administration should generally begin at the first diagnosis of 254P1D6B-associated cancer. This is followed by boosting doses until at least symptoms are substantially abated and for a period thereafter. The embodiment of the vaccine composition (i.e., including, but not limited to embodiments such as peptide cocktails, polyepitopic polypeptides, minigenes, or TAA-specific CTLs or pulsed dendritic cells) delivered to the patient may vary according to the stage of the disease or the patient's health status. For example, in a patient with a tumor that expresses 254P1D6B, a vaccine comprising 254P1D6B-specific CTL may be more efficacious in killing tumor cells in patient with advanced disease than alternative embodiments.

It is generally important to provide an amount of the peptide epitope delivered by a mode of administration sufficient to stimulate effectively a cytotoxic T cell response; compositions which stimulate helper T cell responses can also be given in accordance with this embodiment of the invention.

The dosage for an initial therapeutic immunization generally occurs in a unit dosage range where the lower value is about 1, 5, 50, 500, or 1,000 µg and the higher value is about 10,000; 20,000; 30,000; or 50,000 µg. Dosage values for a human typically range from about 500 µg to about 50,000 µg per 70 kilogram patient. Boosting dosages of between about 1.0 µg to about 50,000 µg of peptide pursuant to a boosting regimen over weeks to months may be administered depending upon the patient's response and condition as determined by measuring the specific activity of CTL and HTL obtained from the patient's blood. Administration should continue until at least clinical symptoms or laboratory tests indicate that the neoplasia, has been eliminated or reduced and for a period thereafter. The dosages, routes of administration, and dose schedules are adjusted in accordance with methodologies known in the art.

In certain embodiments, the peptides and compositions of the present invention are employed in serious disease states, that is, life-threatening or potentially life threatening situations. In such cases, as a result of the minimal amounts of extraneous substances and the relative nontoxic nature of the peptides in preferred compositions of the invention, it is possible and may be felt desirable by the treating physician to administer substantial excesses of these peptide compositions relative to these stated dosage amounts.

The vaccine compositions of the invention can also be used purely as prophylactic agents. Generally the dosage for an initial prophylactic immunization generally occurs in a unit dosage range where the lower value is about 1, 5, 50, 500, or 1000 µg and the higher value is about 10,000; 20,000; 30,000; or 50,000 µg. Dosage values for a human typically range from about 500 µg to about 50,000 µg per 70 kilogram patient. This is followed by boosting dosages of between about 1.0 µg to about 50,000 µg of peptide administered at defined intervals from about four weeks to six months after the initial administration of vaccine. The immunogenicity of the vaccine can be assessed by measuring the specific activity of CTL and HTL obtained from a sample of the patient's blood.

The pharmaceutical compositions for therapeutic treatment are intended for parenteral, topical, oral, nasal, intrathecal, or local (e.g. as a cream or topical ointment) administration. Preferably, the pharmaceutical compositions are administered parentally, e.g., intravenously, subcutaneously, intradermally, or intramuscularly. Thus, the invention provides compositions for parenteral administration which comprise a solution of the immunogenic peptides dissolved or suspended in an acceptable carrier, preferably an aqueous carrier.

A variety of aqueous carriers may be used, e.g., water, buffered water, 0.8% saline, 0.3% glycine, hyaluronic acid and the like. These compositions may be sterilized by conventional, well-known sterilization techniques, or may be sterile filtered. The resulting aqueous solutions may be packaged for use as is, or lyophilized, the lyophilized preparation being combined with a sterile solution prior to administration.

The compositions may contain pharmaceutically acceptable auxiliary substances as required to approximate physiological conditions, such as pH-adjusting and buffering agents, tonicity adjusting agents, wetting agents, preservatives, and the like, for example, sodium acetate, sodium lactate, sodium chloride, potassium chloride, calcium chloride, sorbitan monolaurate, triethanolamine oleate, etc.

The concentration of peptides of the invention in the pharmaceutical formulations can vary widely, i.e., from less than about 0.1%, usually at or at least about 2% to as much as 20% to 50% or more by weight, and will be selected primarily by fluid volumes, viscosities, etc., in accordance with the particular mode of administration selected.

A human unit dose form of a composition is typically included in a pharmaceutical composition that comprises a human unit dose of an acceptable carrier, in one embodiment an aqueous carrier, and is administered in a volume/quantity that is known by those of skill in the art to be used for administration of such compositions to humans (see, e.g., Remington's Pharmaceutical Sciences, 17$^{th}$ Edition, A. Gennaro, Editor, Mack Publishing Co., Easton, Pa., 1985). For example a peptide dose for initial immunization can be from about 1 to about 50,000 µg, generally 100-5,000 µg, for a 70 kg patient. For example, for nucleic acids an initial immunization may be performed using an expression vector in the form of naked nucleic acid administered IM (or SC or ID) in the amounts of 0.5-5 mg at multiple sites. The nucleic acid (0.1 to 1000 µg) can also be administered using a gene gun. Following an incubation period of 3-4 weeks, a booster dose is then administered. The booster can be recombinant fowlpox virus administered at a dose of 5-107 to 5×10$^9$ pfu.

For antibodies, a treatment generally involves repeated administration of the anti-254P1D6B antibody preparation, via an acceptable route of administration such as intravenous injection (IV), typically at a dose in the range of about 0.1 to about 10 mg/kg body weight. In general, doses in the range of 10-500 mg mAb per week are effective and well tolerated. Moreover, an initial loading dose of approximately 4 mg/kg patient body weight IV, followed by weekly doses of about 2 mg/kg IV of the anti-254P1D6B mAb preparation represents an acceptable dosing regimen. As appreciated by those of skill in the art, various factors can influence the ideal dose in a particular case. Such factors include, for example, half life of a composition, the binding affinity of an Ab, the immunogenicity of a substance, the degree of 254P1D6B expression in the patient, the extent of circulating shed 254P1D6B antigen, the desired steady-state concentration level, frequency of treatment, and the influence of chemotherapeutic or other agents used in combination with the treatment method of the invention, as well as the health status of a particular patient. Non-limiting preferred human unit doses are, for example, 500 µg-1 mg, 1 mg-50 mg, 50 mg-100 mg, 100 mg-200 mg, 200 mg-300 mg, 400 mg-500 mg, 500 mg-600 mg, 600 mg-700 mg, 700 mg-800 mg, 800 mg-900 mg, 900 mg-1 g, or 1 mg-700 mg. In certain embodiments, the dose is in a range of 2-5 mg/kg body weight, e.g., with follow on weekly doses of 1-3 mg/kg; 0.5 mg, 1, 2, 3, 4, 5, 6, 7, 8, 9, 10 mg/kg body weight followed, e.g., in two, three or four weeks by weekly doses; 0.5-10 mg/kg body weight, e.g., followed in two, three or four weeks by weekly doses; 225, 250, 275, 300, 325, 350, 375, 400 mg m$^2$ of body area weekly; 1-600 mg m$^2$ of body area weekly; 225-400 mg m$^2$ of body area weekly; these does can be followed by weekly doses for 2, 3, 4, 5, 6, 7, 8, 9, 19, 11, 12 or more weeks.

In one embodiment, human unit dose forms of polynucleotides comprise a suitable dosage range or effective amount that provides any therapeutic effect. As appreciated by one of ordinary skill in the art a therapeutic effect depends on a number of factors, including the sequence of the polynucleotide, molecular weight of the polynucleotide and route of administration. Dosages are generally selected by the physician or other health care professional in accordance with a variety of parameters known in the art, such as severity of symptoms, history of the patient and the like. Generally, for a polynucleotide of about 20 bases, a dosage range may be selected from, for example, an independently selected lower limit such as about 0.1, 0.25, 0.5, 1, 2, 5, 10, 20, 30, 40, 50, 60, 70, 80, 90, 100, 200, 300, 400 or 500 mg/kg up to an independently selected upper limit, greater than the lower limit, of about 60, 80, 100, 200, 300, 400, 500, 750, 1000, 1500, 2000, 3000, 4000, 5000, 6000, 7000, 8000, 9000 or 10,000 mg/kg. For example, a dose may be about any of the following: 0.1 to 100 mg/kg, 0.1 to 50 mg/kg, 0.1 to 25 mg/kg, 0.1 to 10 mg/kg, 1 to 500 mg/kg, 100 to 400 mg/kg, 200 to 300 mg/kg, 1 to 100 mg/kg, 100 to 200 mg/kg, 300 to 400 mg/kg, 400 to 500 mg/kg, 500 to 1000 mg/kg, 500 to 5000 mg/kg, or 500 to 10,000 mg/kg. Generally, parenteral routes of administration may require higher doses of polynucleotide compared to more direct application to the nucleotide to diseased tissue, as do polynucleotides of increasing length.

In one embodiment, human unit dose forms of T-cells comprise a suitable dosage range or effective amount that provides any therapeutic effect. As appreciated by one of ordinary skill in the art, a therapeutic effect depends on a number of factors. Dosages are generally selected by the physician or other health care professional in accordance with a variety of parameters known in the art, such as severity of symptoms, history of the patient and the like. A dose may be about 10$^4$ cells to about 10$^6$ cells, about 10$^6$ cells to about 10$^8$ cells, about 10$^8$ to about 10$^{11}$ cells, or about 10$^8$ to about 5×10$^{10}$ cells. A dose may also about 10$^6$ cells/m$^2$ to about 10$^{10}$ cells/m$^2$, or about 10$^6$ cells/m$^2$ to about 10$^8$ cells/m$^2$.

Proteins(s) of the invention, and/or nucleic acids encoding the protein(s), can also be administered via liposomes, which may also serve to: 1) target the proteins(s) to a particular tissue, such as lymphoid tissue; 2) to target selectively to diseases cells; or, 3) to increase the half-life of the peptide composition. Liposomes include emulsions, foams, micelles, insoluble monolayers, liquid crystals, phospholipid dispersions, lamellar layers and the like. In these preparations, the peptide to be delivered is incorporated as part of a liposome, alone or in conjunction with a molecule which binds to a receptor prevalent among lymphoid cells, such as monoclonal antibodies which bind to the CD45 antigen, or with other therapeutic or immunogenic compositions. Thus, liposomes either filled or decorated with a desired peptide of the invention can be directed to the site of lymphoid cells, where the liposomes then deliver the peptide compositions. Liposomes for use in accordance with the invention are formed from standard vesicle-forming lipids, which generally include neutral and negatively charged phospholipids and a sterol, such as cholesterol. The selection of lipids is generally guided by consideration of, e.g., liposome size, acid liability and stability of the liposomes in the blood stream. A variety of methods are available for preparing liposomes, as described in, e.g., Szoka, et al., *Ann. Rev. Biophys. Bioeng.* 9:467 (1980), and U.S. Pat. Nos. 4,235,871, 4,501,728, 4,837,028, and 5,019,369.

For targeting cells of the immune system, a ligand to be incorporated into the liposome can include, e.g., antibodies or fragments thereof specific for cell surface determinants of the desired immune system cells. A liposome suspension containing a peptide may be administered intravenously, locally, topically, etc. in a dose which varies according to, inter alia, the manner of administration, the peptide being delivered, and the stage of the disease being treated.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient, that is, one or more peptides of the invention, and more preferably at a concentration of 25%-75%.

For aerosol administration, immunogenic peptides are preferably supplied in finely divided form along with a surfactant and propellant. Typical percentages of peptides are about 0.01%-20% by weight, preferably about 1%-10%. The surfactant must, of course, be nontoxic, and preferably soluble in the propellant. Representative of such agents are the esters or partial esters of fatty acids containing from about 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute about 0.1%-20% by weight of the composition, preferably about 0.25-5%. The balance of the composition is ordinarily propellant. A carrier can also be included, as desired, as with, e.g., lecithin for intranasal delivery.

XI.) Diagnostic and Prognostic Embodiments of 254P1D6B.

As disclosed herein, 254P1D6B polynucleotides, polypeptides, reactive cytotoxic T cells (CTL), reactive helper T cells (HTL) and anti-polypeptide antibodies are used in well known diagnostic, prognostic and therapeutic assays that examine conditions associated with dysregulated cell growth such as cancer, in particular the cancers listed in Table I (see, e.g., both its specific pattern of tissue expression as well as its overexpression in certain cancers as described for example in the Example entitled "Expression analysis of 254P1D6B in normal tissues, and patient specimens").

254P1D6B can be analogized to a prostate associated antigen PSA, the archetypal marker that has been used by medical practitioners for years to identify and monitor the presence of prostate cancer (see, e.g., Merrill et al., J. Urol. 163(2): 503-5120 (2000); Polascik et al., J. Urol. August; 162(2):293-306 (1999) and Fortier et al., J. Nat. Cancer Inst. 91(19): 1635-1640 (1999)). A variety of other diagnostic markers are also used in similar contexts including p53 and K-ras (see, e.g., Tulchinsky et al., Int J Mol Med 1999 July 4(1):99-102 and Minimoto et al., Cancer Detect Prev 2000; 24(1):1-12). Therefore, this disclosure of 254P1D6B polynucleotides and polypeptides (as well as 254P1D6B polynucleotide probes and anti-254P1D6B antibodies used to identify the presence of these molecules) and their properties allows skilled artisans to utilize these molecules in methods that are analogous to those used, for example, in a variety of diagnostic assays directed to examining conditions associated with cancer.

Typical embodiments of diagnostic methods which utilize the 254P1D6B polynucleotides, polypeptides, reactive T cells and antibodies are analogous to those methods from well-established diagnostic assays, which employ, e.g., PSA polynucleotides, polypeptides, reactive T cells and antibodies. For example, just as PSA polynucleotides are used as probes (for example in Northern analysis, see, e.g., Sharief et al., Biochem. Mol. Biol. Int. 33(3):567-74 (1994)) and primers (for example in PCR analysis, see, e.g., Okegawa et al., J. Urol. 163(4): 1189-1190 (2000)) to observe the presence and/or the level of PSA mRNAs in methods of monitoring PSA overexpression or the metastasis of prostate cancers, the 254P1D6B polynucleotides described herein can be utilized in the same way to detect 254P1D6B overexpression or the metastasis of prostate and other cancers expressing this gene. Alternatively, just as PSA polypeptides are used to generate antibodies specific for PSA which can then be used to observe the presence and/or the level of PSA proteins in methods to monitor PSA protein overexpression (see, e.g., Stephan et al., Urology 55(4):560-3 (2000)) or the metastasis of prostate cells (see, e.g., Alanen et al., Pathol. Res. Pract. 192(3):233-7 (1996)), the 254P1D6B polypeptides described herein can be utilized to generate antibodies for use in detecting 254P1D6B overexpression or the metastasis of prostate cells and cells of other cancers expressing this gene.

Specifically, because metastases involves the movement of cancer cells from an organ of origin (such as the lung or prostate gland etc.) to a different area of the body (such as a lymph node), assays which examine a biological sample for the presence of cells expressing 254P1D6B polynucleotides and/or polypeptides can be used to provide evidence of metastasis. For example, when a biological sample from tissue that does not normally contain 254P1D6B-expressing cells (lymph node) is found to contain 254P1D6B-expressing cells such as the 254P1D6B expression seen in LAPC4 and LAPC9, xenografts isolated from lymph node and bone metastasis, respectively, this finding is indicative of metastasis.

Alternatively 254P1D6B polynucleotides and/or polypeptides can be used to provide evidence of cancer, for example, when cells in a biological sample that do not normally express 254P1D6B or express 254P1D6B at a different level are found to express 254P1D6B or have an increased expression of 254P1D6B (see, e.g., the 254P1D6B expression in the cancers listed in Table I and in patient samples etc. shown in the accompanying Figures). In such assays, artisans may further wish to generate supplementary evidence of metastasis by testing the biological sample for the presence of a second tissue restricted marker (in addition to 254P1D6B) such as PSA, PSCA etc. (see, e.g., Alanen et al., Pathol. Res. Pract. 192(3): 233-237 (1996)).

The use of immunohistochemistry to identify the presence of a 254P1D6B polypeptide within a tissue section can indicate an altered state of certain cells within that tissue. It is well understood in the art that the ability of an antibody to localize to a polypeptide that is expressed in cancer cells is a way of diagnosing presence of disease, disease stage, progression and/or tumor aggressiveness. Such an antibody can also detect an altered distribution of the polypeptide within the cancer cells, as compared to corresponding non-malignant tissue.

The 254P1D6B polypeptide and immunogenic compositions are also useful in view of the phenomena of altered subcellular protein localization in disease states. Alteration of cells from normal to diseased state causes changes in cellular morphology and is often associated with changes in subcellular protein localization/distribution. For example, cell membrane proteins that are expressed in a polarized manner in normal cells can be altered in disease, resulting in distribution of the protein in a non-polar manner over the whole cell surface.

The phenomenon of altered subcellular protein localization in a disease state has been demonstrated with MUC1 and Her2 protein expression by use of immunohistochemical means. Normal epithelial cells have a typical apical distribution of MUC1, in addition to some supranuclear localization of the glycoprotein, whereas malignant lesions often demonstrate an apolar staining pattern (Diaz et al., The Breast Journal, 7; 40-45 (2001); Zhang et al., Clinical Cancer Research, 4; 2669-2676 (1998): Cao, et al., The Journal of Histochemistry and Cytochemistry, 45: 1547-1557 (1997)). In addition, normal breast epithelium is either negative for Her2 protein or exhibits only a basolateral distribution whereas malignant cells can express the protein over the whole cell surface (De Potter, et al., International Journal of Cancer, 44; 969-974 (1989): McCormick, et al., 117; 935-943 (2002)). Alternatively, distribution of the protein may be altered from a surface only localization to include diffuse cytoplasmic expression in the diseased state. Such an example can be seen with MUC1 (Diaz, et al., The Breast Journal, 7: 40-45 (2001)).

Alteration in the localization/distribution of a protein in the cell, as detected by immunohistochemical methods, can also provide valuable information concerning the favorability of certain treatment modalities. This last point is illustrated by a situation where a protein may be intracellular in normal tissue, but cell surface in malignant cells; the cell surface location makes the cells favorably amenable to antibody-based diagnostic and treatment regimens. When such an alteration of protein localization occurs for 254P1D6B, the 254P1D6B protein and immune responses related thereto are very useful. Accordingly, the ability to determine whether alteration of subcellular protein localization occurred for 24P4C12 make the 254P1D6B protein and immune responses related thereto very useful. Use of the 254P1D6B compositions allows those skilled in the art to make important diagnostic and therapeutic decisions.

Immunohistochemical reagents specific to 254P1D6B are also useful to detect metastases of tumors expressing 254P1D6B when the polypeptide appears in tissues where 254P1D6B is not normally produced.

Thus, 254P1D6B polypeptides and antibodies resulting from immune responses thereto are useful in a variety of important contexts such as diagnostic, prognostic, preventative and/or therapeutic purposes known to those skilled in the art.

Just as PSA polynucleotide fragments and polynucleotide variants are employed by skilled artisans for use in methods of monitoring PSA, 254P1D6B polynucleotide fragments and polynucleotide variants are used in an analogous manner. In particular, typical PSA polynucleotides used in methods of monitoring PSA are probes or primers which consist of fragments of the PSA cDNA sequence. Illustrating this, primers used to PCR amplify a PSA polynucleotide must include less than the whole PSA sequence to function in the polymerase chain reaction. In the context of such PCR reactions, skilled artisans generally create a variety of different polynucleotide fragments that can be used as primers in order to amplify different portions of a polynucleotide of interest or to optimize amplification reactions (see, e.g., Caetano-Anolles, G. Biotechniques 25(3): 472-476, 478-480 (1998); Robertson et al., Methods Mol. Biol. 98:121-154 (1998)). An additional illustration of the use of such fragments is provided in the Example entitled "Expression analysis of 254P1D6B in normal tissues, and patient specimens," where a 254P1D6B polynucleotide fragment is used as a probe to show the expression of 254P1D6B RNAs in cancer cells. In addition, variant polynucleotide sequences are typically used as primers and probes for the corresponding mRNAs in PCR and Northern analyses (see, e.g., Sawai et al., Fetal Diagn. Ther. 1996 November-December 11(6):407-13 and Current Protocols In Molecular Biology, Volume 2, Unit 2, Frederick M. Ausubel et al. eds., 1995)). Polynucleotide fragments and variants are useful in this context where they are capable of binding to a target polynucleotide sequence (e.g., a 254P1D6B polynucleotide shown in FIG. 2 or variant thereof) under conditions of high stringency.

Furthermore, PSA polypeptides which contain an epitope that can be recognized by an antibody or T cell that specifically binds to that epitope are used in methods of monitoring PSA. 254P1D6B polypeptide fragments and polypeptide analogs or variants can also be used in an analogous manner. This practice of using polypeptide fragments or polypeptide variants to generate antibodies (such as anti-PSA antibodies or T cells) is typical in the art with a wide variety of systems such as fusion proteins being used by practitioners (see, e.g., Current Protocols In Molecular Biology, Volume 2, Unit 16, Frederick M. Ausubel et al. eds., 1995). In this context, each epitope(s) functions to provide the architecture with which an antibody or T cell is reactive. Typically, skilled artisans create a variety of different polypeptide fragments that can be used in order to generate immune responses specific for different portions of a polypeptide of interest (see, e.g., U.S. Pat. No. 5,840,501 and U.S. Pat. No. 5,939,533). For example it may be preferable to utilize a polypeptide comprising one of the 254P1D6B biological motifs discussed herein or a motif-bearing subsequence which is readily identified by one of skill in the art based on motifs available in the art. Polypeptide fragments, variants or analogs are typically useful in this context as long as they comprise an epitope capable of generating an antibody or T cell specific for a target polypeptide sequence (e.g. a 254P1D6B polypeptide shown in FIG. 3).

As shown herein, the 254P1D6B polynucleotides and polypeptides (as well as the 254P1D6B polynucleotide probes and anti-254P1D6B antibodies or T cells used to identify the presence of these molecules) exhibit specific properties that make them useful in diagnosing cancers such as those listed in Table I. Diagnostic assays that measure the presence of 254P1D6B gene products, in order to evaluate the presence or onset of a disease condition described herein, such as prostate cancer, are used to identify patients for preventive measures or further monitoring, as has been done so successfully with PSA. Moreover, these materials satisfy a need in the art for molecules having similar or complementary characteristics to PSA in situations where, for example, a definite diagnosis of metastasis of prostatic origin cannot be made on the basis of a test for PSA alone (see, e.g., Alanen et al., Pathol. Res. Pract. 192(3): 233-237 (1996)), and consequently, materials such as 254P1D6B polynucleotides and polypeptides (as well as the 254P1D6B polynucleotide probes and anti-254P1D6B antibodies used to identify the presence of these molecules) need to be employed to confirm a metastases of prostatic origin.

Finally, in addition to their use in diagnostic assays, the 254P1D6B polynucleotides disclosed herein have a number of other utilities such as their use in the identification of ontogenetic associated chromosomal abnormalities in the chromosomal region to which the 254P1D6B gene maps (see the Example entitled "Chromosomal Mapping of 254P1D6B" below). Moreover, in addition to their use in diagnostic assays, the 254P1D6B-related proteins and polynucleotides disclosed herein have other utilities such as their use in the forensic analysis of tissues of unknown origin (see, e.g., Takahama K Forensic Sci Int 1996 Jun. 28; 80(1-2): 63-9).

Additionally, 254P1D6B-related proteins or polynucleotides of the invention can be used to treat a pathologic condition characterized by the over-expression of 254P1D6B. For example, the amino acid or nucleic acid sequence of FIG. 2 or FIG. 3, or fragments of either, can be used to generate an immune response to a 254P1D6B antigen. Antibodies or other molecules that react with 254P1D6B can be used to modulate the function of this molecule, and thereby provide a therapeutic benefit.

XII.) Inhibition of 254P1D6B Protein Function

The invention includes various methods and compositions for inhibiting the binding of 254P1D6B to its binding partner or its association with other protein(s) as well as methods for inhibiting 254P1D6B function.

XII.A.) Inhibition of 254P1D6B with Intracellular Antibodies

In one approach, a recombinant vector that encodes single chain antibodies that specifically bind to 254P1D6B are introduced into 254P1D6B expressing cells via gene transfer technologies. Accordingly, the encoded single chain anti-254P1D6B antibody is expressed intracellularly, binds to 254P1D6B protein, and thereby inhibits its function. Methods for engineering such intracellular single chain antibodies are well known. Such intracellular antibodies, also known as "intrabodies", are specifically targeted to a particular compartment within the cell, providing control over where the inhibitory activity of the treatment is focused. This technology has been successfully applied in the art (for review, see Richardson and Marasco, 1995, TIBTECH vol. 13). Intrabodies have been shown to virtually eliminate the expression of otherwise abundant cell surface receptors (see, e.g., Richardson et al., 1995, Proc. Natl. Acad. Sci. USA 92: 3137-3141; Beerli et al., 1994, J. Biol. Chem. 289: 23931-23936; Deshane et al., 1994, Gene Ther. 1: 332-337).

Single chain antibodies comprise the variable domains of the heavy and light chain joined by a flexible linker polypeptide, and are expressed as a single polypeptide. Optionally, single chain antibodies are expressed as a single chain variable region fragment joined to the light chain constant region. Well-known intracellular trafficking signals are engineered into recombinant polynucleotide vectors encoding such single chain antibodies in order to target precisely the intrabody to the desired intracellular compartment. For example, intrabodies targeted to the endoplasmic reticulum (ER) are engineered to incorporate a leader peptide and, optionally, a C-terminal ER retention signal, such as the KDEL amino acid motif. Intrabodies intended to exert activity in the nucleus are engineered to include a nuclear localization signal. Lipid moieties are joined to intrabodies in order to tether the intrabody to the cytosolic side of the plasma membrane. Intrabodies can also be targeted to exert function in the cytosol. For example, cytosolic intrabodies are used to sequester factors within the cytosol, thereby preventing them from being transported to their natural cellular destination.

In one embodiment, intrabodies are used to capture 254P1D6B in the nucleus, thereby preventing its activity within the nucleus. Nuclear targeting signals are engineered into such 254P1D6B intrabodies in order to achieve the desired targeting. Such 254P1D6B intrabodies are designed to bind specifically to a particular 254P1D6B domain. In another embodiment, cytosolic intrabodies that specifically bind to a 254P1D6B protein are used to prevent 254P1D6B from gaining access to the nucleus, thereby preventing it from exerting any biological activity within the nucleus (e.g., preventing 254P1D6B from forming transcription complexes with other factors).

In order to specifically direct the expression of such intrabodies to particular cells, the transcription of the intrabody is placed under the regulatory control of an appropriate tumor-specific promoter and/or enhancer. In order to target intrabody expression specifically to prostate, for example, the PSA promoter and/or promoter/enhancer can be utilized (See, for example, U.S. Pat. No. 5,919,652 issued 6 Jul. 1999).

XII.B.) Inhibition of 254P1D6B with Recombinant Proteins

In another approach, recombinant molecules bind to 254P1D6B and thereby inhibit 254P1D6B function. For example, these recombinant molecules prevent or inhibit 254P1D6B from accessing/binding to its binding partner(s) or associating with other protein(s). Such recombinant molecules can, for example, contain the reactive part(s) of a 254P1D6B specific antibody molecule. In a particular embodiment, the 254P1D6B binding domain of a 254P1D6B binding partner is engineered into a dimeric fusion protein, whereby the fusion protein comprises two 254P1D6B ligand binding domains linked to the Fc portion of a human IgG, such as human IgG1. Such IgG portion can contain, for example, the $C_H2$ and $C_H3$ domains and the hinge region, but not the $C_H1$ domain. Such dimeric fusion proteins are administered in soluble form to patients suffering from a cancer associated with the expression of 254P1D6B, whereby the dimeric fusion protein specifically binds to 254P1D6B and blocks 254P1D6B interaction with a binding partner. Such dimeric fusion proteins are further combined into multimeric proteins using known antibody linking technologies.

XII.C.) Inhibition of 254P1D6B Transcription or Translation

The present invention also comprises various methods and compositions for inhibiting the transcription of the 254P1D6B gene. Similarly, the invention also provides methods and compositions for inhibiting the translation of 254P1D6B mRNA into protein.

In one approach, a method of inhibiting the transcription of the 254P1D6B gene comprises contacting the 254P1D6B gene with a 254P1D6B antisense polynucleotide. In another approach, a method of inhibiting 254P1D6B mRNA translation comprises contacting a 254P1D6B mRNA with an antisense polynucleotide. In another approach, a 254P1D6B specific ribozyme is used to cleave a 254P1D6B message, thereby inhibiting translation. Such antisense and ribozyme based methods can also be directed to the regulatory regions of the 254P1D6B gene, such as 254P1D6B promoter and/or enhancer elements. Similarly, proteins capable of inhibiting a 254P1D6B gene transcription factor are used to inhibit 254P1D6B mRNA transcription. The various polynucleotides and compositions useful in the aforementioned methods have been described above. The use of antisense and ribozyme molecules to inhibit transcription and translation is well known in the art.

Other factors that inhibit the transcription of 254P1D6B by interfering with 254P1D6B transcriptional activation are also useful to treat cancers expressing 254P1D6B. Similarly, factors that interfere with 254P1D6B processing are useful to treat cancers that express 254P1D6B. Cancer treatment methods utilizing such factors are also within the scope of the invention.

XII.D.) General Considerations for Therapeutic Strategies

Gene transfer and gene therapy technologies can be used to deliver therapeutic polynucleotide molecules to tumor cells synthesizing 254P1D6B (i.e., antisense, ribozyme, polynucleotides encoding intrabodies and other 254P1D6B inhibitory molecules). A number of gene therapy approaches are known in the art. Recombinant vectors encoding 254P1D6B antisense polynucleotides, ribozymes, factors capable of interfering with 254P1D6B transcription, and so forth, can be delivered to target tumor cells using such gene therapy approaches.

The above therapeutic approaches can be combined with any one of a wide variety of surgical, chemotherapy or radiation therapy regimens. The therapeutic approaches of the invention can enable the use of reduced dosages of chemotherapy (or other therapies) and/or less frequent administration, an advantage for all patients and particularly for those that do not tolerate the toxicity of the chemotherapeutic agent well.

The anti-tumor activity of a particular composition (e.g., antisense, ribozyme, intrabody), or a combination of such compositions, can be evaluated using various in vitro and in vivo assay systems. In vitro assays that evaluate therapeutic activity include cell growth assays, soft agar assays and other assays indicative of tumor promoting activity, binding assays capable of determining the extent to which a therapeutic composition will inhibit the binding of 254P1D6B to a binding partner, etc.

In vivo, the effect of a 254P1D6B therapeutic composition can be evaluated in a suitable animal model. For example, xenogeneic prostate cancer models can be used, wherein human prostate cancer explants or passaged xenograft tissues are introduced into immune compromised animals, such as nude or SCID mice (Klein et al., 1997, Nature Medicine 3: 402-408). For example, PCT Patent Application WO98/16628 and U.S. Pat. No. 6,107,540 describe various xenograft models of human prostate cancer capable of recapitulating the development of primary tumors, micrometastasis, and the formation of osteoblastic metastases characteristic of late stage disease. Efficacy can be predicted using assays that measure inhibition of tumor formation, tumor regression or metastasis, and the like.

In vivo assays that evaluate the promotion of apoptosis are useful in evaluating therapeutic compositions. In one embodiment, xenografts from tumor bearing mice treated with the therapeutic composition can be examined for the presence of apoptotic foci and compared to untreated control xenograft-bearing mice. The extent to which apoptotic foci are found in the tumors of the treated mice provides an indication of the therapeutic efficacy of the composition.

The therapeutic compositions used in the practice of the foregoing methods can be formulated into pharmaceutical compositions comprising a carrier suitable for the desired delivery method. Suitable carriers include any material that when combined with the therapeutic composition retains the anti-tumor function of the therapeutic composition and is generally non-reactive with the patient's immune system. Examples include, but are not limited to, any of a number of standard pharmaceutical carriers such as sterile phosphate buffered saline solutions, bacteriostatic water, and the like (see, generally, Remington's Pharmaceutical Sciences $16^{th}$ Edition, A. Osal., Ed., 1980).

Therapeutic formulations can be solubilized and administered via any route capable of delivering the therapeutic composition to the tumor site. Potentially effective routes of administration include, but are not limited to, intravenous, parenteral, intraperitoneal, intramuscular, intratumor, intradermal, intraorgan, orthotopic, and the like. A preferred formulation for intravenous injection comprises the therapeutic composition in a solution of preserved bacteriostatic water, sterile unpreserved water, and/or diluted in polyvinylchloride or polyethylene bags containing 0.9% sterile Sodium Chloride for Injection, USP. Therapeutic protein preparations can be lyophilized and stored as sterile powders, preferably under vacuum, and then reconstituted in bacteriostatic water (containing for example, benzyl alcohol preservative) or in sterile water prior to injection.

Dosages and administration protocols for the treatment of cancers using the foregoing methods will vary with the method and the target cancer, and will generally depend on a number of other factors appreciated in the art.

XIII.) Identification, Characterization and Use of Modulators of 254P1D6B

Methods to Identify and Use Modulators

In one embodiment, screening is performed to identify modulators that induce or suppress a particular expression profile, suppress or induce specific pathways, preferably generating the associated phenotype thereby. In another embodiment, having identified differentially expressed genes important in a particular state; screens are performed to identify modulators that alter expression of individual genes, either increase or decrease. In another embodiment, screening is performed to identify modulators that alter a biological function of the expression product of a differentially expressed gene. Again, having identified the importance of a gene in a particular state, screens are performed to identify agents that bind and/or modulate the biological activity of the gene product.

In addition, screens are done for genes that are induced in response to a candidate agent. After identifying a modulator (one that suppresses a cancer expression pattern leading to a normal expression pattern, or a modulator of a cancer gene that leads to expression of the gene as in normal tissue) a screen is performed to identify genes that are specifically modulated in response to the agent. Comparing expression profiles between normal tissue and agent-treated cancer tissue reveals genes that are not expressed in normal tissue or cancer tissue, but are expressed in agent treated tissue, and vice versa. These agent-specific sequences are identified and used by methods described herein for cancer genes or proteins. In particular these sequences and the proteins they encode are used in marking or identifying agent-treated cells. In addition, antibodies are raised against the agent-induced proteins and used to target novel therapeutics to the treated cancer tissue sample.

Modulator-Related Identification and Screening Assays: Gene Expression-Related Assays Proteins, nucleic acids, and antibodies of the invention are used in screening assays. The cancer-associated proteins, antibodies, nucleic acids, modified proteins and cells containing these sequences are used in screening assays, such as evaluating the effect of drug candidates on a "gene expression profile," expression profile of polypeptides or alteration of biological function. In one embodiment, the expression profiles are used, preferably in conjunction with high throughput screening techniques to allow monitoring for expression profile genes after treatment with a candidate agent (e.g., Davis, G F, et al., J Biol Screen 7:69 (2002); Zlokarnik, et al., Science 279:84-8 (1998); Heid, Genome Res 6:986-94, 1996).

The cancer proteins, antibodies, nucleic acids, modified proteins and cells containing the native or modified cancer proteins or genes are used in screening assays. That is, the present invention comprises methods for screening for compositions which modulate the cancer phenotype or a physiological function of a cancer protein of the invention. This is done on a gene itself or by evaluating the effect of drug candidates on a "gene expression profile" or biological function. In one embodiment, expression profiles are used, preferably in conjunction with high throughput screening techniques to allow monitoring after treatment with a candidate agent, see Zlokarnik, supra.

A variety of assays are executed directed to the genes and proteins of the invention. Assays are run on an individual nucleic acid or protein level. That is, having identified a particular gene as up regulated in cancer, test compounds are screened for the ability to modulate gene expression or for binding to the cancer protein of the invention. "Modulation" in this context includes an increase or a decrease in gene expression. The preferred amount of modulation will depend on the original change of the gene expression in normal versus tissue undergoing cancer, with changes of at least 10%, preferably 50%, more preferably 100-300%, and in some embodiments 300-1000% or greater. Thus, if a gene exhibits a 4-fold increase in cancer tissue compared to normal tissue, a decrease of about four-fold is often desired; similarly, a 10-fold decrease in cancer tissue compared to normal tissue a target value of a 10-fold increase in expression by the test compound is often desired. Modulators that exacerbate the type of gene expression seen in cancer are also useful, e.g., as an upregulated target in further analyses.

The amount of gene expression is monitored using nucleic acid probes and the quantification of gene expression levels, or, alternatively, a gene product itself is monitored, e.g., through the use of antibodies to the cancer protein and standard immunoassays. Proteomics and separation techniques also allow for quantification of expression.

Expression Monitoring to Identify Compounds that Modify Gene Expression

In one embodiment, gene expression monitoring, i.e., an expression profile, is monitored simultaneously for a number of entities. Such profiles will typically involve one or more of the genes of FIG. 2. In this embodiment, e.g., cancer nucleic acid probes are attached to biochips to detect and quantify cancer sequences in a particular cell. Alternatively, PCR can be used. Thus, a series, e.g., wells of a microtiter plate, can be used with dispensed primers in desired wells. A PCR reaction can then be performed and analyzed for each well.

Expression monitoring is performed to identify compounds that modify the expression of one or more cancer-associated sequences, e.g., a polynucleotide sequence set out in FIG. 2. Generally, a test modulator is added to the cells prior to analysis. Moreover, screens are also provided to identify agents that modulate cancer, modulate cancer proteins of the invention, bind to a cancer protein of the invention, or interfere with the binding of a cancer protein of the invention and an antibody or other binding partner.

In one embodiment, high throughput screening methods involve providing a library containing a large number of potential therapeutic compounds (candidate compounds). Such "combinatorial chemical libraries" are then screened in one or more assays to identify those library members (particular chemical species or subclasses) that display a desired characteristic activity. The compounds thus identified can serve as conventional "lead compounds," as compounds for screening, or as therapeutics.

In certain embodiments, combinatorial libraries of potential modulators are screened for an ability to bind to a cancer polypeptide or to modulate activity. Conventionally, new chemical entities with useful properties are generated by identifying a chemical compound (called a "lead compound") with some desirable property or activity, e.g., inhibiting activity, creating variants of the lead compound, and evaluating the property and activity of those variant compounds. Often, high throughput screening (HTS) methods are employed for such an analysis.

As noted above, gene expression monitoring is conveniently used to test candidate modulators (e.g., protein, nucleic acid or small molecule). After the candidate agent has been added and the cells allowed to incubate for a period, the sample containing a target sequence to be analyzed is, e.g., added to a biochip.

If required, the target sequence is prepared using known techniques. For example, a sample is treated to lyse the cells, using known lysis buffers, electroporation, etc., with purification and/or amplification such as PCR performed as appropriate. For example, an in vitro transcription with labels covalently attached to the nucleotides is performed. Generally, the nucleic acids are labeled with biotin-FITC or PE, or with cy3 or cy5.

The target sequence can be labeled with, e.g. a fluorescent, a chemiluminescent, a chemical, or a radioactive signal, to provide a means of detecting the target sequence's specific binding to a probe. The label also can be an enzyme, such as alkaline phosphatase or horseradish peroxidase, which when provided with an appropriate substrate produces a product that is detected. Alternatively, the label is a labeled compound or small molecule, such as an enzyme inhibitor, that binds but is not catalyzed or altered by the enzyme. The label also can be a moiety or compound, such as, an epitope tag or biotin which specifically binds to streptavidin. For the example of biotin, the streptavidin is labeled as described above, thereby, providing a detectable signal for the bound target sequence. Unbound labeled streptavidin is typically removed prior to analysis.

As will be appreciated by those in the art, these assays can be direct hybridization assays or can comprise "sandwich assays", which include the use of multiple probes, as is generally outlined in U.S. Pat. Nos. 5,681,702; 5,597,909; 5,545, 730; 5,594,117; 5,591,584; 5,571,670; 5,580,731; 5,571,670; 5,591,584; 5,624,802; 5,635,352; 5,594,118; 5,359,100; 5,124,246; and 5,681,697. In this embodiment, in general, the target nucleic acid is prepared as outlined above, and then added to the biochip comprising a plurality of nucleic acid probes, under conditions that allow the formation of a hybridization complex.

A variety of hybridization conditions are used in the present invention, including high, moderate and low stringency conditions as outlined above. The assays are generally run under stringency conditions which allow formation of the label probe hybridization complex only in the presence of target. Stringency can be controlled by altering a step parameter that is a thermodynamic variable, including, but not limited to, temperature, formamide concentration, salt concentration, chaotropic salt concentration pH, organic solvent concentration, etc. These parameters may also be used to control non-specific binding, as is generally outlined in U.S. Pat. No. 5,681,697. Thus, it can be desirable to perform certain steps at higher stringency conditions to reduce non-specific binding.

The reactions outlined herein can be accomplished in a variety of ways. Components of the reaction can be added simultaneously, or sequentially, in different orders, with preferred embodiments outlined below. In addition, the reaction may include a variety of other reagents. These include salts, buffers, neutral proteins, e.g. albumin, detergents, etc. which can be used to facilitate optimal hybridization and detection, and/or reduce nonspecific or background interactions. Reagents that otherwise improve the efficiency of the assay, such as protease inhibitors, nuclease inhibitors, anti-microbial agents, etc., may also be used as appropriate, depending on the sample preparation methods and purity of the target. The assay data are analyzed to determine the expression levels of individual genes, and changes in expression levels as between states, forming a gene expression profile.

Biological Activity-Related Assays

The invention provides methods identify or screen for a compound that modulates the activity of a cancer-related gene or protein of the invention. The methods comprise adding a test compound, as defined above, to a cell comprising a cancer protein of the invention. The cells contain a recombinant nucleic acid that encodes a cancer protein of the invention. In another embodiment, a library of candidate agents is tested on a plurality of cells.

In one aspect, the assays are evaluated in the presence or absence or previous or subsequent exposure of physiological signals, e.g. hormones, antibodies, peptides, antigens, cytokines, growth factors, action potentials, pharmacological agents including chemotherapeutics, radiation, carcinogenics, or other cells (i.e., cell-cell contacts). In another example, the determinations are made at different stages of the cell cycle process. In this way, compounds that modulate genes or proteins of the invention are identified. Compounds with pharmacological activity are able to enhance or interfere with the activity of the cancer protein of the invention. Once identified, similar structures are evaluated to identify critical structural features of the compound.

In one embodiment, a method of modulating (e.g., inhibiting) cancer cell division is provided; the method comprises administration of a cancer modulator. In another embodiment, a method of modulating (e.g., inhibiting) cancer is provided; the method comprises administration of a cancer modulator. In a further embodiment, methods of treating cells or individuals with cancer are provided; the method comprises administration of a cancer modulator.

In one embodiment, a method for modulating the status of a cell that expresses a gene of the invention is provided. As used herein status comprises such art-accepted parameters such as growth, proliferation, survival, function, apoptosis, senescence, location, enzymatic activity, signal transduction, etc. of a cell. In one embodiment, a cancer inhibitor is an antibody as discussed above. In another embodiment, the cancer inhibitor is an antisense molecule. A variety of cell growth, proliferation, and metastasis assays are known to those of skill in the art, as described herein.

High Throughput Screening to Identify Modulators

The assays to identify suitable modulators are amenable to high throughput screening. Preferred assays thus detect enhancement or inhibition of cancer gene transcription, inhibition or enhancement of polypeptide expression, and inhibition or enhancement of polypeptide activity.

In one embodiment, modulators evaluated in high throughput screening methods are proteins, often naturally occurring proteins or fragments of naturally occurring proteins. Thus, e.g., cellular extracts containing proteins, or random or directed digests of proteinaceous cellular extracts, are used. In this way, libraries of proteins are made for screening in the methods of the invention. Particularly preferred in this embodiment are libraries of bacterial, fungal, viral, and mammalian proteins, with the latter being preferred, and human proteins being especially preferred. Particularly useful test compound will be directed to the class of proteins to which the target belongs, e.g., substrates for enzymes, or ligands and receptors.

Use of Soft Agar Growth and Colony Formation to Identify and Characterize Modulators Normal cells require a solid substrate to attach and grow. When cells are transformed, they lose this phenotype and grow detached from the substrate. For example, transformed cells can grow in stirred suspension culture or suspended in semi-solid media, such as semi-solid or soft agar. The transformed cells, when transfected with tumor suppressor genes, can regenerate normal phenotype and once again require a solid substrate to attach to and grow. Soft agar growth or colony formation in assays are used to identify modulators of cancer sequences, which when expressed in host cells, inhibit abnormal cellular proliferation and transformation. A modulator reduces or eliminates the host cells' ability to grow suspended in solid or semisolid media, such as agar.

Techniques for soft agar growth or colony formation in suspension assays are described in Freshney, Culture of Animal Cells a Manual of Basic Technique (3rd ed., 1994). See also, the methods section of Garkavtsev et al. (1996), supra.

Evaluation of Contact Inhibition and Growth Density Limitation to Identify and Characterize Modulators Normal cells typically grow in a flat and organized pattern in cell culture until they touch other cells. When the cells touch one another, they are contact inhibited and stop growing. Transformed cells, however, are not contact inhibited and continue to grow to high densities in disorganized foci. Thus, transformed cells grow to a higher saturation density than corresponding normal cells. This is detected morphologically by the formation of a disoriented monolayer of cells or cells in foci. Alternatively, labeling index with (3H)-thymidine at saturation density is used to measure density limitation of growth, similarly an MTT or Alamar blue assay will reveal proliferation capacity of cells and the ability of modulators to affect same. See Freshney (1994), supra. Transformed cells, when transfected with tumor suppressor genes, can regenerate a normal phenotype and become contact inhibited and would grow to a lower density.

In this assay, labeling index with $^3$H-thymidine at saturation density is a preferred method of measuring density limitation of growth. Transformed host cells are transfected with a cancer-associated sequence and are grown for 24 hours at saturation density in non-limiting medium conditions. The percentage of cells labeling with (3H)-thymidine is determined by incorporated cpm.

Contact independent growth is used to identify modulators of cancer sequences, which had led to abnormal cellular proliferation and transformation. A modulator reduces or eliminates contact independent growth, and returns the cells to a normal phenotype.

Evaluation of Growth Factor or Serum Dependence to Identify and Characterize Modulators Transformed cells have lower serum dependence than their normal counterparts (see, e.g., Temin, J. Natl. Cancer Inst. 37:167-175 (1966); Eagle et al., J. Exp. Med. 131:836-879 (1970)); Freshney, supra. This is in part due to release of various growth factors by the transformed cells. The degree of growth factor or serum dependence of transformed host cells can be compared with that of control. For example, growth factor or serum dependence of a cell is monitored in methods to identify and characterize compounds that modulate cancer-associated sequences of the invention.

Use of Tumor-Specific Marker Levels to Identify and Characterize Modulators

Tumor cells release an increased amount of certain factors (hereinafter "tumor specific markers") than their normal counterparts. For example, plasminogen activator (PA) is released from human glioma at a higher level than from normal brain cells (see, e.g., Gullino, Angiogenesis, Tumor Vascularization, and Potential Interference with Tumor Growth, in Biological Responses in Cancer, pp. 178-184 (Mihich (ed.) 1985)). Similarly, Tumor Angiogenesis Factor (TAF) is released at a higher level in tumor cells than their normal counterparts. See, e.g., Folkman, Angiogenesis and Cancer, Sem Cancer Biol. (1992)), while bFGF is released from endothelial tumors (Ensoli, B et al).

Various techniques which measure the release of these factors are described in Freshney (1994), supra. Also, see, Unkless et al., J. Biol. Chem. 249:4295-4305 (1974); Strickland & Beers, J. Biol. Chem. 251:5694-5702 (1976); Whur et al., Br. J. Cancer 42:305 312 (1980); Gullino, Angiogenesis, Tumor Vascularization, and Potential Interference with Tumor Growth, in Biological Responses in Cancer, pp. 178-184 (Mihich (ed.) 1985); Freshney, Anticancer Res. 5:111-130 (1985). For example, tumor specific marker levels are monitored in methods to identify and characterize compounds that modulate cancer-associated sequences of the invention.

Invasiveness into Matrigel to Identify and Characterize Modulators

The degree of invasiveness into Matrigel or an extracellular matrix constituent can be used as an assay to identify and characterize compounds that modulate cancer associated sequences. Tumor cells exhibit a positive correlation between malignancy and invasiveness of cells into Matrigel or some other extracellular matrix constituent. In this assay, tumorigenic cells are typically used as host cells. Expression of a tumor suppressor gene in these host cells would decrease invasiveness of the host cells. Techniques described in Cancer Res. 1999; 59:6010; Freshney (1994), supra, can be used. Briefly, the level of invasion of host cells is measured by using filters coated with Matrigel or some other extracellular matrix constituent. Penetration into the gel, or through to the distal side of the filter, is rated as invasiveness, and rated histologically by number of cells and distance moved, or by prelabeling the cells with $^{125}$I and counting the radioactivity on the distal side of the filter or bottom of the dish. See, e.g., Freshney (1984), supra.

Evaluation of Tumor Growth In Vivo to Identify and Characterize Modulators

Effects of cancer-associated sequences on cell growth are tested in transgenic or immune-suppressed organisms. Transgenic organisms are prepared in a variety of art-accepted ways. For example, knock-out transgenic organisms, e.g., mammals such as mice, are made, in which a cancer gene is disrupted or in which a cancer gene is inserted. Knock-out transgenic mice are made by insertion of a marker gene or other heterologous gene into the endogenous cancer gene site in the mouse genome via homologous recombination. Such mice can also be made by substituting the endogenous cancer gene with a mutated version of the cancer gene, or by mutating the endogenous cancer gene, e.g., by exposure to carcinogens.

To prepare transgenic chimeric animals, e.g., mice, a DNA construct is introduced into the nuclei of embryonic stem cells. Cells containing the newly engineered genetic lesion are injected into a host mouse embryo, which is re-implanted into a recipient female. Some of these embryos develop into chimeric mice that possess germ cells some of which are derived from the mutant cell line. Therefore, by breeding the chimeric mice it is possible to obtain a new line of mice containing the introduced genetic lesion (see, e.g., Capecchi et al., Science 244:1288 (1989)). Chimeric mice can be derived according to U.S. Pat. No. 6,365,797, issued 2 Apr. 2002; U.S. Pat. No. 6,107,540 issued 22 Aug. 2000; Hogan et al., Manipulating the Mouse Embryo: A laboratory Manual., Cold Spring Harbor Laboratory (1988) and Teratocarcinomas and Embryonic Stem Cells: A Practical Approach, Robertson, ed., IRL Press, Washington, D.C., (1987).

Alternatively, various immune-suppressed or immune-deficient host animals can be used. For example, a genetically athymic "nude" mouse (see, e.g., Giovanella et al., J. Natl. Cancer Inst. 52:921 (1974)), a SCID mouse, a thymectornized mouse, or an irradiated mouse (see, e.g., Bradley et al., Br. J. Cancer 38:263 (1978); Selby et al., Br. J. Cancer 41:52 (1980)) can be used as a host. Transplantable tumor cells (typically about $10^6$ cells) injected into isogenic hosts produce invasive tumors in a high proportion of cases, while normal cells of similar origin will not. In hosts which developed invasive tumors, cells expressing cancer-associated sequences are injected subcutaneously or orthotopically. Mice are then separated into groups, including control groups and treated experimental groups) e.g. treated with a modulator). After a suitable length of time, preferably 4-8 weeks, tumor growth is measured (e.g., by volume or by its two largest dimensions, or weight) and compared to the control. Tumors that have statistically significant reduction (using, e.g., Student's T test) are said to have inhibited growth.

In Vitro Assays to Identify and Characterize Modulators

Assays to identify compounds with modulating activity can be performed in vitro. For example, a cancer polypeptide is first contacted with a potential modulator and incubated for a suitable amount of time, e.g., from 0.5 to 48 hours. In one embodiment, the cancer polypeptide levels are determined in vitro by measuring the level of protein or mRNA. The level of protein is measured using immunoassays such as Western blotting, ELISA and the like with an antibody that selectively binds to the cancer polypeptide or a fragment thereof. For measurement of mRNA, amplification, e.g., using PCR, LCR, or hybridization assays, e.g., Northern hybridization, RNAse protection, dot blotting, are preferred. The level of protein or mRNA is detected using directly or indirectly labeled detection agents, e.g., fluorescently or radioactively labeled nucleic acids, radioactively or enzymatically labeled antibodies, and the like, as described herein.

Alternatively, a reporter gene system can be devised using a cancer protein promoter operably linked to a reporter gene such as luciferase, green fluorescent protein, CAT, or P-gal. The reporter construct is typically transfected into a cell. After treatment with a potential modulator, the amount of reporter gene transcription, translation, or activity is measured according to standard techniques known to those of skill in the art (Davis G F, supra; Gonzalez, J. & Negulescu, P. Curr. Opin. Biotechnol. 1998: 9:624).

As outlined above, in vitro screens are done on individual genes and gene products. That is, having identified a particular differentially expressed gene as important in a particular state, screening of modulators of the expression of the gene or the gene product itself is performed.

In one embodiment, screening for modulators of expression of specific gene(s) is performed. Typically, the expression of only one or a few genes is evaluated. In another embodiment, screens are designed to first find compounds that bind to differentially expressed proteins. These compounds are then evaluated for the ability to modulate differentially expressed activity. Moreover, once initial candidate compounds are identified, variants can be further screened to better evaluate structure activity relationships.

Binding Assays to Identify and Characterize Modulators

In binding assays in accordance with the invention, a purified or isolated gene product of the invention is generally used. For example, antibodies are generated to a protein of the invention, and immunoassays are run to determine the amount and/or location of protein. Alternatively, cells comprising the cancer proteins are used in the assays.

Thus, the methods comprise combining a cancer protein of the invention and a candidate compound such as a ligand, and determining the binding of the compound to the cancer protein of the invention. Preferred embodiments utilize the human cancer protein; animal models of human disease of can also be developed and used. Also, other analogous mammalian proteins also can be used as appreciated by those of skill in the art. Moreover, in some embodiments variant or derivative cancer proteins are used.

Generally, the cancer protein of the invention, or the ligand, is non-diffusibly bound to an insoluble support. The support can, e.g., be one having isolated sample receiving areas (a microtiter plate, an array, etc.). The insoluble supports can be made of any composition to which the compositions can be bound, is readily separated from soluble material, and is otherwise compatible with the overall method of screening. The surface of such supports can be solid or porous and of any convenient shape.

Examples of suitable insoluble supports include microtiter plates, arrays, membranes and beads. These are typically made of glass, plastic (e.g., polystyrene), polysaccharide, nylon, nitrocellulose, or Teflon™, etc. Microtiter plates and arrays are especially convenient because a large number of assays can be carried out simultaneously, using small amounts of reagents and samples. The particular manner of binding of the composition to the support is not crucial so long as it is compatible with the reagents and overall methods of the invention, maintains the activity of the composition and is nondiffusable. Preferred methods of binding include the use of antibodies which do not sterically block either the ligand binding site or activation sequence when attaching the protein to the support, direct binding to "sticky" or ionic supports, chemical crosslinking, the synthesis of the protein or agent on the surface, etc. Following binding of the protein or ligand/binding agent to the support, excess unbound material is removed by washing. The sample receiving areas may then be blocked through incubation with bovine serum albumin (BSA), casein or other innocuous protein or other moiety.

Once a cancer protein of the invention is bound to the support, and a test compound is added to the assay. Alternatively, the candidate binding agent is bound to the support and the cancer protein of the invention is then added. Binding agents include specific antibodies, non-natural binding agents identified in screens of chemical libraries, peptide analogs, etc.

Of particular interest are assays to identify agents that have a low toxicity for human cells. A wide variety of assays can be used for this purpose, including proliferation assays, cAMP assays, labeled in vitro protein-protein binding assays, electrophoretic mobility shift assays, immunoassays for protein binding, functional assays (phosphorylation assays, etc.) and the like.

A determination of binding of the test compound (ligand, binding agent, modulator, etc.) to a cancer protein of the invention can be done in a number of ways. The test compound can be labeled, and binding determined directly, e.g., by attaching all or a portion of the cancer protein of the invention to a solid support, adding a labeled candidate compound (e.g., a fluorescent label), washing off excess reagent, and determining whether the label is present on the solid support. Various blocking and washing steps can be utilized as appropriate.

In certain embodiments, only one of the components is labeled, e.g., a protein of the invention or ligands labeled. Alternatively, more than one component is labeled with different labels, e.g., $I^{125}$, for the proteins and a fluorophore for the compound. Proximity reagents, e.g., quenching or energy transfer reagents are also useful.

Competitive Binding to Identify and Characterize Modulators

In one embodiment, the binding of the "test compound" is determined by competitive binding assay with a "competitor." The competitor is a binding moiety that binds to the target molecule (e.g., a cancer protein of the invention). Competitors include compounds such as antibodies, peptides, binding partners, ligands, etc. Under certain circumstances, the competitive binding between the test compound and the competitor displaces the test compound. In one embodiment, the test compound is labeled. Either the test compound, the competitor, or both, is added to the protein for a time sufficient to allow binding. Incubations are performed at a temperature that facilitates optimal activity, typically between four and 40° C. Incubation periods are typically optimized, e.g., to facilitate rapid high throughput screening; typically between zero and one hour will be sufficient. Excess reagent is generally removed or washed away. The second component is then added, and the presence or absence of the labeled component is followed, to indicate binding.

In one embodiment, the competitor is added first, followed by the test compound. Displacement of the competitor is an indication that the test compound is binding to the cancer protein and thus is capable of binding to, and potentially modulating, the activity of the cancer protein. In this embodiment, either component can be labeled. Thus, e.g., if the competitor is labeled, the presence of label in the post-test compound wash solution indicates displacement by the test compound. Alternatively, if the test compound is labeled, the presence of the label on the support indicates displacement.

In an alternative embodiment, the test compound is added first, with incubation and washing, followed by the competitor. The absence of binding by the competitor indicates that the test compound binds to the cancer protein with higher affinity than the competitor. Thus, if the test compound is labeled, the presence of the label on the support, coupled with a lack of competitor binding, indicates that the test compound binds to and thus potentially modulates the cancer protein of the invention.

Accordingly, the competitive binding methods comprise differential screening to identity agents that are capable of modulating the activity of the cancer proteins of the invention. In this embodiment, the methods comprise combining a cancer protein and a competitor in a first sample. A second sample comprises a test compound, the cancer protein, and a competitor. The binding of the competitor is determined for both samples, and a change, or difference in binding between the two samples indicates the presence of an agent capable of binding to the cancer protein and potentially modulating its activity. That is, if the binding of the competitor is different in the second sample relative to the first sample, the agent is capable of binding to the cancer protein.

Alternatively, differential screening is used to identify drug candidates that bind to the native cancer protein, but cannot bind to modified cancer proteins. For example the structure of the cancer protein is modeled and used in rational drug design to synthesize agents that interact with that site, agents which generally do not bind to site-modified proteins. Moreover, such drug candidates that affect the activity of a native cancer protein are also identified by screening drugs for the ability to either enhance or reduce the activity of such proteins.

Positive controls and negative controls can be used in the assays. Preferably control and test samples are performed in at least triplicate to obtain statistically significant results. Incubation of all samples occurs for a time sufficient to allow for the binding of the agent to the protein. Following incubation, samples are washed free of non-specifically bound material and the amount of bound, generally labeled agent determined. For example, where a radiolabel is employed, the samples can be counted in a scintillation counter to determine the amount of bound compound.

A variety of other reagents can be included in the screening assays. These include reagents like salts, neutral proteins, e.g. albumin, detergents, etc. which are used to facilitate optimal protein-protein binding and/or reduce non-specific or background interactions. Also reagents that otherwise improve the efficiency of the assay, such as protease inhibitors, nuclease inhibitors, anti-microbial agents, etc., can be used. The mixture of components is added in an order that provides for the requisite binding.

Use of Polynucleotides to Down-Regulate or Inhibit a Protein of the Invention.

Polynucleotide modulators of cancer can be introduced into a cell containing the target nucleotide sequence by formation of a conjugate with a ligand-binding molecule, as described in WO 91/04753. Suitable ligand-binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell. Alternatively, a polynucleotide modulator of cancer can be introduced into a cell containing the target nucleic acid sequence, e.g., by formation of a polynucleotide-lipid complex, as described in WO 90/10448. It is understood that the use of antisense molecules or knock out and knock in models may also be used in screening assays as discussed above, in addition to methods of treatment.

Inhibitory and Antisense Nucleotides

In certain embodiments, the activity of a cancer-associated protein is down-regulated, or entirely inhibited, by the use of antisense polynucleotide or inhibitory small nuclear RNA (snRNA), i.e., a nucleic acid complementary to, and which can preferably hybridize specifically to, a coding mRNA nucleic acid sequence, e.g., a cancer protein of the invention, mRNA, or a subsequence thereof. Binding of the antisense polynucleotide to the mRNA reduces the translation and/or stability of the mRNA.

In the context of this invention, antisense polynucleotides can comprise naturally occurring nucleotides, or synthetic species formed from naturally occurring subunits or their close homologs. Antisense polynucleotides may also have altered sugar moieties or inter-sugar linkages. Exemplary among these are the phosphorothioate and other sulfur containing species which are known for use in the art. Analogs are comprised by this invention so long as they function effectively to hybridize with nucleotides of the invention. See, e.g., Isis Pharmaceuticals, Carlsbad, Calif.; Sequitor, Inc., Natick, Mass.

Such antisense polynucleotides can readily be synthesized using recombinant means, or can be synthesized in vitro. Equipment for such synthesis is sold by several vendors, including Applied Biosystems. The preparation of other oligonucleotides such as phosphorothioates and alkylated derivatives is also well known to those of skill in the art.

Antisense molecules as used herein include antisense or sense oligonucleotides. Sense oligonucleotides can, e.g., be employed to block transcription by binding to the anti-sense strand. The antisense and sense oligonucleotide comprise a single stranded nucleic acid sequence (either RNA or DNA) capable of binding to target mRNA (sense) or DNA (antisense) sequences for cancer molecules. Antisense or sense oligonucleotides, according to the present invention, comprise a fragment generally at least about 12 nucleotides, preferably from about 12 to 30 nucleotides. The ability to derive an antisense or a sense oligonucleotide, based upon a cDNA sequence encoding a given protein is described in, e.g., Stein & Cohen (Cancer Res. 48:2659 (1988 and van der Krol et al. (BioTechniques 6:958 (1988)).

Ribozymes

In addition to antisense polynucleotides, ribozymes can be used to target and inhibit transcription of cancer-associated nucleotide sequences. A ribozyme is an RNA molecule that catalytically cleaves other RNA molecules. Different kinds of ribozymes have been described, including group I ribozymes, hammerhead ribozymes, hairpin ribozymes, RNase P, and axhead ribozymes (see, e.g., Castanotto et al., Adv. in Pharmacology 25: 289-317 (1994) for a general review of the properties of different ribozymes).

The general features of hairpin ribozymes are described, e.g., in Hampel et al., Nucl. Acids Res. 18:299-304 (1990); European Patent Publication No. 0360257; U.S. Pat. No. 5,254,678. Methods of preparing are well known to those of skill in the art (see, e.g., WO 94/26877; Ojwang et al., Proc. Natl. Acad. Sci. USA 90:6340-6344 (1993); Yamada et al., Human Gene Therapy 1:39-45 (1994); Leavitt et al., Proc. Natl. Acad. Sci. USA 92:699-703 (1995); Leavitt et al., Human Gene Therapy 5: 1151-120 (1994); and Yamada et al., Virology 205: 121-126 (1994)).

Use of Modulators in Phenotypic Screening

In one embodiment, a test compound is administered to a population of cancer cells, which have an associated cancer expression profile. By "administration" or "contacting" herein is meant that the modulator is added to the cells in such a manner as to allow the modulator to act upon the cell, whether by uptake and intracellular action, or by action at the cell surface. In some embodiments, a nucleic acid encoding a proteinaceous agent (i.e., a peptide) is put into a viral construct such as an adenoviral or retroviral construct, and added to the cell, such that expression of the peptide agent is accomplished, e.g., PCT US97/01019. Regulatable gene therapy systems can also be used. Once the modulator has been administered to the cells, the cells are washed if desired and are allowed to incubate under preferably physiological conditions for some period. The cells are then harvested and a new gene expression profile is generated. Thus, e.g., cancer tissue is screened for agents that modulate, e.g., induce or suppress, the cancer phenotype. A change in at least one gene, preferably many, of the expression profile indicates that the agent has an effect on cancer activity. Similarly, altering a biological function or a signaling pathway is indicative of modulator activity. By defining such a signature for the cancer phenotype, screens for new drugs that alter the phenotype are devised. With this approach, the drug target need not be known and need not be represented in the original gene/protein expression screening platform, nor does the level of transcript for the target protein need to change. The modulator inhibiting function will serve as a surrogate marker As outlined above, screens are done to assess genes or gene products. That is, having identified a particular differentially expressed gene as important in a particular state, screening of modulators of either the expression of the gene or the gene product itself is performed.

Use of Modulators to Affect Peptides of the Invention

Measurements of cancer polypeptide activity, or of the cancer phenotype are performed using a variety of assays. For example, the effects of modulators upon the function of a cancer polypeptide(s) are measured by examining parameters described above. A physiological change that affects activity is used to assess the influence of a test compound on the polypeptides of this invention. When the functional outcomes are determined using intact cells or animals, a variety of effects can be assesses such as, in the case of a cancer associated with solid tumors, tumor growth, tumor metastasis, neovascularization, hormone release, transcriptional changes to both known and uncharacterized genetic markers (e.g., by Northern blots), changes in cell metabolism such as cell growth or pH changes, and changes in intracellular second messengers such as cGNIP.

Methods of Identifying Characterizing Cancer-Associated Sequences

Expression of various gene sequences is correlated with cancer. Accordingly, disorders based on mutant or variant cancer genes are determined. In one embodiment, the invention provides methods for identifying cells containing variant cancer genes, e.g., determining the presence of, all or part, the sequence of at least one endogenous cancer gene in a cell. This is accomplished using any number of sequencing techniques. The invention comprises methods of identifying the cancer genotype of an individual, e.g., determining all or part of the sequence of at least one gene of the invention in the individual. This is generally done in at least one tissue of the individual, e.g., a tissue set forth in Table I, and may include the evaluation of a number of tissues or different samples of the same tissue. The method may include comparing the sequence of the sequenced gene to a known cancer gene, i.e., a wild-type gene to determine the presence of family members, homologies, mutations or variants. The sequence of all or part of the gene can then be compared to the sequence of a known cancer gene to determine if any differences exist. This is done using any number of known homology programs, such as BLAST, Bestfit, etc. The presence of a difference in the sequence between the cancer gene of the patient and the known cancer gene correlates with a disease state or a propensity for a disease state, as outlined herein.

In a preferred embodiment, the cancer genes are used as probes to determine the number of copies of the cancer gene in the genome. The cancer genes are used as probes to determine the chromosomal localization of the cancer genes. Information such as chromosomal localization finds use in providing a diagnosis or prognosis in particular when chromosomal abnormalities such as translocations, and the like are identified in the cancer gene locus.

XIV.) RNAi and Therapeutic Use of Small Interfering RNA (siRNAs)

The present invention is also directed towards siRNA oligonucleotides, particularly double stranded RNAs encompassing at least a fragment of the 254P1D6B coding region or 5" UTR regions, or complement, or any antisense oligonucleotide specific to the 254P1D6B sequence. In one embodiment such oligonucleotides are used to elucidate a function of 254P1D6B, or are used to screen for or evaluate modulators of 254P1D6B function or expression. In another embodiment, gene expression of 254P1D6B is reduced by using siRNA transfection and results in significantly diminished proliferative capacity of transformed cancer cells that endogenously express the antigen; cells treated with specific 254P1D6B siRNAs show reduced survival as measured, e.g., by a metabolic readout of cell viability, correlating to the reduced proliferative capacity. Thus, 254P1D6B siRNA compositions comprise siRNA (double stranded RNA) that correspond to the nucleic acid ORF sequence of the 254P1D6B protein or subsequences thereof, these subsequences are generally 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or more than 35 contiguous RNA nucleotides in length and contain sequences that are complementary and non-complementary to at least a portion of the mRNA coding sequence In a preferred embodiment, the subsequences are 19-25 nucleotides in length, most preferably 21-23 nucleotides in length.

RNA interference is a novel approach to silencing genes in vitro and in vivo, thus small double stranded RNAs (siRNAs) are valuable therapeutic agents. The power of siRNAs to silence specific gene activities has now been brought to animal models of disease and is used in humans as well. For example, hydrodynamic infusion of a solution of siRNA into a mouse with a siRNA against a particular target has been proven to be therapeutically effective.

The pioneering work by Song et al. indicates that one type of entirely natural nucleic acid, small interfering RNAs (siRNAs), served as therapeutic agents even without further chemical modification (Song, E., et al. "RNA interference targeting Fas protects mice from fulminant hepatitis" Nat. Med. 9(3): 347-51 (2003)). This work provided the first in vivo evidence that infusion of siRNAs into an animal could alleviate disease. In that case, the authors gave mice injections of siRNA designed to silence the FAS protein (a cell death receptor that when over-activated during inflammatory response induces hepatocytes and other cells to die). The next day, the animals were given an antibody specific to Fas. Control mice died of acute liver failure within a few days, while over 80% of the siRNA-treated mice remained free from serious disease and survived. About 80% to 90% of their liver cells incorporated the naked siRNA oligonucleotides. Furthermore, the RNA molecules functioned for 10 days before losing effect after 3 weeks.

For use in human therapy, siRNA is delivered by efficient systems that induce long-lasting RNAi activity. A major caveat for clinical use is delivering siRNAs to the appropriate cells. Hepatocytes seem to be particularly receptive to exogenous RNA. Today, targets located in the liver are attractive because liver is an organ that can be readily targeted by nucleic acid molecules and viral vectors. However, other tissue and organs targets are preferred as well.

Formulations of siRNAs with compounds that promote transit across cell membranes are used to improve administration of siRNAs in therapy. Chemically modified synthetic siRNA, that are resistant to nucleases and have serum stability have concomitant enhanced duration of RNAi effects, are an additional embodiment.

Thus, siRNA technology is a therapeutic for human malignancy by delivery of siRNA molecules directed to 254P1D6B to individuals with the cancers, such as those listed in Table I. Such administration of siRNAs leads to reduced growth of cancer cells expressing 254P1D6B, and provides an anti-tumor therapy, lessening the morbidity and/or mortality associated with malignancy.

The effectiveness of this modality of gene product knockdown is significant when measured in vitro or in vivo. Effectiveness in vitro is readily demonstrable through application of siRNAs to cells in culture (as described above) or to aliquots of cancer patient biopsies when in vitro methods are used to detect the reduced expression of 254P1D6B protein.

XV.) Kits/Articles of Manufacture

For use in the laboratory, prognostic, prophylactic, diagnostic and therapeutic applications described herein, kits are within the scope of the invention. Such kits can comprise a carrier, package, or container that is compartmentalized to receive one or more containers such as vials, tubes, and the like, each of the container(s) comprising one of the separate elements to be used in the method, along with a label or insert comprising instructions for use, such as a use described herein. For example, the container(s) can comprise a probe that is or can be detectably labeled. Such probe can be an antibody or polynucleotide specific for a protein or a gene or message of the invention, respectively. Where the method utilizes nucleic acid hybridization to detect the target nucleic acid, the kit can also have containers containing nucleotide(s) for amplification of the target nucleic acid sequence. Kits can comprise a container comprising a reporter, such as a biotin-binding protein, such as avidin or streptavidin, bound to a reporter molecule, such as an enzymatic, fluorescent, or radioisotope label; such a reporter can be used with, e.g., a nucleic acid or antibody. The kit can include all or part of the amino acid sequences in FIG. 2 or FIG. 3 or analogs thereof, or a nucleic acid molecule that encodes such amino acid sequences.

The kit of the invention will typically comprise the container described above and one or more other containers associated therewith that comprise materials desirable from a commercial and user standpoint, including buffers, diluents, filters, needles, syringes; carrier, package, container, vial and/or tube labels listing contents and/or instructions for use, and package inserts with instructions for use.

A label can be present on or with the container to indicate that the composition is used for a specific therapy or non-therapeutic application, such as a prognostic, prophylactic, diagnostic or laboratory application, and can also indicate directions for either in vivo or in vitro use, such as those described herein. Directions and or other information can also be included on an insert(s) or label(s) which is included with or on the kit. The label can be on or associated with the container. A label a can be on a container when letters, numbers or other characters forming the label are molded or etched into the container itself, a label can be associated with a container when it is present within a receptacle or carrier that also holds the container, e.g., as a package insert. The label can indicate that the composition is used for diagnosing, treating, prophylaxing or prognosing a condition, such as a neoplasia of a tissue set forth in Table I.

The terms "kit" and "article of manufacture" can be used as synonyms.

In another embodiment of the invention, an article(s) of manufacture containing compositions, such as amino acid sequence(s), small molecule(s), nucleic acid sequence(s), and/or antibody(s), e.g., materials useful for the diagnosis, prognosis, prophylaxis and/or treatment of neoplasias of tissues such as those set forth in Table I is provided. The article of manufacture typically comprises at least one container and at least one label. Suitable containers include, for example, bottles, vials, syringes, and test tubes. The containers can be formed from a variety of materials such as glass, metal or plastic. The container can hold amino acid sequence(s), small molecule(s), nucleic acid sequence(s), cell population(s) and/or antibody(s). In one embodiment, the container holds a polynucleotide for use in examining the mRNA expression profile of a cell, together with reagents used for this purpose. In another embodiment a container comprises an antibody, binding fragment thereof or specific binding protein for use in evaluating protein expression of 254P1D6B in cells and tissues, or for relevant laboratory, prognostic, diagnostic, prophylactic and therapeutic purposes; indications and/or directions for such uses can be included on or with such container, as can reagents and other compositions or tools used for these purposes. In another embodiment, a container comprises materials for eliciting a cellular or humoral immune response, together with associated indications and/or directions. In another embodiment, a container comprises materials for adoptive immunotherapy, such as cytotoxic T cells (CTL) or helper T cells (HTL), together with associated indications and/or directions; reagents and other compositions or tools used for such purpose can also be included.

The container can alternatively hold a composition that is effective for treating, diagnosis, prognosing or prophylaxing a condition and can have a sterile access port (for example the container can be an intravenous solution bag or a vial having a stopper pierceable by a hypodermic injection needle). The active agents in the composition can be an antibody capable of specifically binding 254P1D6B and modulating the function of 254P1D6B.

The article of manufacture can further comprise a second container comprising a pharmaceutically-acceptable buffer, such as phosphate-buffered saline, Ringer's solution and/or dextrose solution. It can further include other materials desirable from a commercial and user standpoint, including other buffers, diluents, filters, stirrers, needles, syringes, and/or package inserts with indications and/or instructions for use.

EXAMPLES

Various aspects of the invention are further described and illustrated by way of the several examples that follow, none of which is intended to limit the scope of the invention.

Example 1

SSH-Generated Isolation of cDNA Fragment of the 254P1D6B Gene

To isolate genes that are over-expressed in prostate cancer we used the Suppression Subtractive Hybridization (SSH) procedure using cDNA derived from prostate cancer xenograft tissues. LAPC-9AD xenograft was obtained from Dr. Charles Sawyers (UCLA) and was generated as described (Klein et al., 1997, Nature Med. 3:402-408; Craft et al., 1999, Cancer Res. 59:5030-5036). LAPC-9AD$^2$ was generated from LAPC-9AD xenograft by growing LAPC-9AD xenograft tissues within a piece of human bone implanted in SCID mice. Tumors were then harvested and subsequently passaged subcutaneously into other SCID animals to generate LAPC-9AD$^2$.

The 254P1D6B SSH cDNA of 284 bp is listed in FIG. 1. The full length 254P1D6B variant 1 and variants 2-20, cDNAs and ORFs are described in FIG. 2 with the protein sequences listed in FIG. 3.

Materials and Methods

RNA Isolation:

Tumor tissues were homogenized in Trizol reagent (Life Technologies, Gibco BRL) using 10 ml/g tissue or 10 ml/10$^8$ cells to isolate total RNA. Poly A RNA was purified from total RNA using Qiagen's Oligotex mRNA Mini and Midi kits. Total and mRNA were quantified by spectrophotometric analysis (O.D. 260/280 nm) and analyzed by gel electrophoresis.

Oligonucleotides:

The following HPLC purified oligonucleotides were used.

```
DPNCDN (cDNA synthesis primer):
                                           (SEQ ID NO: 17)
5'TTTTGATCAAGCTT₃₀3'

Adaptor 1:
                                           (SEQ ID NO: 18)
5'CTAATACGACTCACTATAGGGCTCGAGCGGCCGCCCGGGCAG3'

(SEQ ID NO: 19)
3'GGCCCGTCCTAG5'

Adaptor 2:
                                           (SEQ ID NO: 20)
5'GTAATACGACTCACTATAGGGCAGCGTGGTCGCGGCCGAG3'

(SEQ ID NO: 21)
3'CGGCTCCTAG5'

PCR primer 1:
                                           (SEQ ID NO: 22)
5'CTAATACGACTCACTATAGGGC3'
```

```
Nested primer (NP)1:
                                                  (SEQ ID NO: 23)
5'TCGAGCGGCCGCCCGGGCAGGA3'

Nested primer (NP)2:
                                                  (SEQ ID NO: 24)
5'AGCGTGGTCGCGGCCGAGGA3'
```

Suppression Subtractive Hybridization:

Suppression Subtractive Hybridization (SSH) was used to identify cDNAs corresponding to genes that may be differentially expressed in prostate cancer. The SSH reaction utilized cDNA from prostate cancer xenograft LAPC-9AD$^2$. The gene 254P1D6B was derived from a prostate cancer xenograft LAPC-9AD minus prostate cancer xenograft LAPC-9AD tissues. The SSH DNA sequence (FIG. 1) was identified.

The cDNA derived from prostate cancer xenograft LAPC-9AD tissue was used as the source of the "driver" cDNA, while the cDNA from prostate cancer xenograft LAPC-9AD$^2$ was used as the source of the "tester" cDNA. Double stranded cDNAs corresponding to tester and driver cDNAs were synthesized from 2 µg of poly(A)$^+$ RNA isolated from the relevant tissue, as described above, using CLONTECH's PCR-Select cDNA Subtraction Kit and 1 ng of oligonucleotide DPNCDN as primer. First- and second-strand synthesis were carried out as described in the Kit's user manual protocol (CLONTECH Protocol No. PT1117-1, Catalog No. K1804-1). The resulting cDNA was digested with Dpn II for 3 hrs at 37° C. Digested cDNA was extracted with phenol/chloroform (1:1) and ethanol precipitated.

Tester cDNA was generated by diluting 1 µl of Dpn II digested cDNA from the relevant tissue source (see above) (400 ng) in 5 µl of water. The diluted cDNA (2 µl, 160 ng) was then ligated to 2 µl of Adaptor 1 and Adaptor 2 (10 µM), in separate ligation reactions, in a total volume of 10 µl at 16° C. overnight, using 400 u of T4 DNA ligase (CLONTECH). Ligation was terminated with 1 µl of 0.2 M EDTA and heating at 72° C. for 5 min.

The first hybridization was performed by adding 1.5 µl (600 ng) of driver cDNA to each of two tubes containing 1.5 µl (20 ng) Adaptor 1- and Adaptor 2-ligated tester cDNA. In a final volume of 4 µl, the samples were overlaid with mineral oil, denatured in an MJ Research thermal cycler at 98° C. for 1.5 minutes, and then were allowed to hybridize for 8 hrs at 68° C. The two hybridizations were then mixed together with an additional 1 µl of fresh denatured driver cDNA and were allowed to hybridize overnight at 68° C. The second hybridization was then diluted in 200 µl of 20 mM Hepes, pH 8.3, 50 mM NaCl, 0.2 mM EDTA, heated at 70° C. for 7 min. and stored at −20° C.

PCR Amplification, Cloning and Sequencing of Gene Fragments Generated from SSH:

To amplify gene fragments resulting from SSH reactions, two PCR amplifications were performed. In the primary PCR reaction 1 µl of the diluted final hybridization mix was added to 1 µl of PCR primer 1 (10 µM), 0.5 µl dNTP mix (10 µM), 2.5 µl 10× reaction buffer (CLONTECH) and 0.5 µl 50× Advantage cDNA polymerase Mix (CLONTECH) in a final volume of 25 µl. PCR 1 was conducted using the following conditions: 75° C. for 5 min., 94° C. for 25 sec., then 27 cycles of 94° C. for 10 sec, 66° C. for 30 sec, 72° C. for 1.5 min. Five separate primary PCR reactions were performed for each experiment. The products were pooled and diluted 1:10 with water. For the secondary PCR reaction, 1 µl from the pooled and diluted primary PCR reaction was added to the same reaction mix as used for PCR 1, except that primers NP1 and NP2 (10 µM) were used instead of PCR primer 1. PCR 2 was performed using 10-12 cycles of 94° C. for 10 sec, 68° C. for 30 sec, and 72° C. for 1.5 minutes. The PCR products were analyzed using 2% agarose gel electrophoresis.

The PCR products were inserted into pCR2.1 using the T/A vector cloning kit (Invitrogen). Transformed E. coli were subjected to blue/white and ampicillin selection. White colonies were picked and arrayed into 96 well plates and were grown in liquid culture overnight. To identify inserts, PCR amplification was performed on 1 ml of bacterial culture using the conditions of PCR1 and NP1 and NP2 as primers. PCR products were analyzed using 2% agarose gel electrophoresis.

Bacterial clones were stored in 20% glycerol in a 96 well format. Plasmid DNA was prepared, sequenced, and subjected to nucleic acid homology searches of the GenBank, dBest, and NCI-CGAP databases.

RT-PCR Expression Analysis:

First strand cDNAs can be generated from 1 µg of mRNA with oligo (dT) 12-18 priming using the Gibco-BRL Super-script Preamplification system. The manufacturer's protocol was used which included an incubation for 50 min at 42° C. with reverse transcriptase followed by RNAse H treatment at 37° C. for 20 min. After completing the reaction, the volume can be increased to 200 µl with water prior to normalization. First strand cDNAs from 16 different normal human tissues can be obtained from Clontech.

Normalization of the first strand cDNAs from multiple tissues was performed by using the primers 5'atatcgc-cgcgctcgtcgtcgacaa3' (SEQ ID NO:25) and 5'agccacacg-cagctcattgtagaagg 3' (SEQ ID NO:26) to amplify β-actin. First strand cDNA (5 µl) were amplified in a total volume of 50 µl containing 0.4 µM primers, 0.2 µM each dNTPs, 1×PCR buffer (Clontech, 10 mM Tris-HCL, 1.5 mM MgCl$_2$, 50 mM KCl, pH8.3) and 1× Klentaq DNA polymerase (Clontech). Five µl of the PCR reaction can be removed at 18, 20, and 22 cycles and used for agarose gel electrophoresis. PCR was performed using an MJ Research thermal cycler under the following conditions: Initial denaturation can be at 94° C. for 15 sec, followed by a 18, 20, and 22 cycles of 94° C. for 15, 65° C. for 2 min, 72° C. for 5 sec. A final extension at 72° C. was carried out for 2 min. After agarose gel electrophoresis, the band intensities of the 283 bp β-actin bands from multiple tissues were compared by visual inspection. Dilution factors for the first strand cDNAs were calculated to result in equal β-actin band intensities in all tissues after 22 cycles of PCR. Three rounds of normalization can be required to achieve equal band intensities in all tissues after 22 cycles of PCR.

To determine expression levels of the 254P1D6B gene, 5 µl of normalized first strand cDNA were analyzed by PCR using 26, and 30 cycles of amplification. Semi-quantitative expression analysis can be achieved by comparing the PCR products at cycle numbers that give light band intensities.

A typical RT-PCR expression analysis is shown in FIGS. 14(a) and 14(b). First strand cDNA was prepared from vital pool 1 (liver, lung and kidney), vital pool 2 (pancreas, colon and stomach), normal lung ovary cancer pool, lung cancer pool (FIG. 14A), as well as from normal stomach, brain, heart, liver, spleen, skeletal muscle, testis, prostate, bladder, kidney, colon, lung and ovary cancer pool (FIG. 14B). Normalization was performed by PCR using primers to actin and GAPDH. Semi-quantitative PCR, using primers to 254P1D6B, was performed at 26 and 30 cycles of amplification. Results show strong expression of 254P1D6B in lung cancer pool and ovary cancer pool but not in normal lung nor in vital pool 1. Low expression was detected in vital pool 2.

Example 2

Isolation of Full Length 254P1D6B Encoding DNA

To isolate genes that are involved in prostate cancer, an experiment was conducted using the prostate cancer xenograft LAPC-9AD$^2$. The gene 254P1D6B was derived from a subtraction consisting of a prostate cancer xenograft LAPC-9AD$^2$ minus prostate cancer xenograft LAPC-9AD. The SSH DNA sequence (FIG. 1) was designated 254P1D6B. Variants of 254P1D6B were identified (FIGS. 2 and 3).

Example 3

Chromosomal Mapping of 254P1D6B

Chromosomal localization can implicate genes in disease pathogenesis. Several chromosome mapping approaches are available including fluorescent in situ hybridization (FISH), human/hamster radiation hybrid (RH) panels (Walter et al., 1994; Nature Genetics 7:22; Research Genetics, Huntsville Ala.), human-rodent somatic cell hybrid panels such as is available from the Cornell Institute (Camden, N.J.), and genomic viewers utilizing BLAST homologies to sequenced and mapped genomic clones (NCBI, Bethesda, Md.).

254P1D6B maps to chromosome 6p22 using 254P1D6B sequence and the NCBI BLAST tool: located on the world wide web at: (ncbi.nlm.nih.gov/genome/seq/page.cgi?F=HsBlast.html&&ORG=Hs).

Example 4

Expression Analysis of 254P1D6B in Normal Tissues and Patient Specimens

FIGS. 14(a) and 14(b) shows expression of 254P1D6B by RT-PCR. First strand cDNA was prepared from vital pool 1 (liver, lung and kidney), vital pool 2 (pancreas, colon and stomach), normal lung ovary cancer pool, lung cancer pool (FIG. 14A), as well as from normal stomach, brain, heart, liver, spleen, skeletal muscle, testis, prostate, bladder, kidney, colon, lung and ovary cancer pool (FIG. 14B). Normalization was performed by PCR using primers to actin and GAPDH. Semi-quantitative PCR, using primers to 254P1D6B, was performed at 26 and 30 cycles of amplification. Results show strong expression of 254P1D6B in lung cancer pool and ovary cancer pool but not in normal lung nor in vital pool 1. Low expression was detected in vital pool 2.

FIG. 15 shows expression of 254P1D6B in normal tissues. Two multiple tissue northern blots (Clontech) both with 2 µg of mRNA/lane were probed with the 254P1D6B sequence. Size standards in kilobases (kb) are indicated on the side. Results show expression of two 254P1D6B transcript, 4.4 kb and 7.5 kb primarily in brain and testis, and only the 4.4 kb transcript in placenta, but not in any other normal tissue tested.

FIG. 16 shows expression of 254P1D6B in lung cancer patient specimens. First strand cDNA was prepared from normal lung cancer cell line A427 and a panel of lung cancer patient specimens. Normalization was performed by PCR using primers to actin and GAPDH. Semi-quantitative PCR, using primers to 254P1D6B, was performed at 26 and 30 cycles of amplification. Results show expression of 254P1D6B in 13 out of 30 tumor specimens tested but not in normal lung. Expression was also detected in the A427 cell line.

Example 5

Splice Variants of 254P1D6B

As used herein, the term variant or comprises Transcript variants and Single Nucleotide Polymorphisms (SNPs). Transcript variants are variants of mature mRNA from the same gene which arise by alternative transcription or alternative splicing. Alternative transcripts are transcripts from the same gene but start transcription at different points. Splice variants are mRNA variants spliced differently from the same transcript. In eukaryotes, when a multi-exon gene is transcribed from genomic DNA, the initial RNA is spliced to produce functional mRNA, which has only exons and is used for translation into an amino acid sequence. Accordingly, a given gene can have zero to many alternative transcripts and each transcript can have zero to many splice variants. Each transcript variant has a unique exon makeup, and can have different coding and/or non-coding (5' or 3' end) portions, from the original transcript. Transcript variants can code for the same, similar or different proteins with the same or a similar function or can encode proteins with different functions, and can be expressed in the same tissue at the same time, or in different tissues at the same time, or in the same tissue at different times, or in different tissues at different times. Proteins encoded by transcript variants can have similar or different subcellular or extracellular localizations, e.g., secreted versus intracellular.

Transcript variants are identified by a variety of art-accepted methods. For example, alternative transcripts and splice variants are identified by full-length cloning experiments, or by use of full-length transcript and EST sequences. First, all human ESTs were grouped into clusters which show direct or indirect identity with each other. Second, ESTs in the same cluster were further grouped into sub-clusters and assembled into a consensus sequence. The original gene sequence is compared to the consensus sequence(s) or other full-length sequences. Each consensus sequence is a potential splice variant for that gene. Even when a variant is identified that is not yet a full-length clone, that portion of the variant is very useful as a research tool, e.g., for antigen generation and for further cloning of the full-length splice variant, using techniques known to those skilled in the art.

Moreover, computer programs are available to those skilled in the art that identify transcript variants based on genomic sequences. Genomic-based transcript variant identification programs include FgenesH (A. Salamov and V. Solovyev, "Ab initio gene finding in *Drosophila* genomic DNA," Genome Research. 2000 April; 10(4):516-22); Grail (URL compbio.ornl.gov/Grail-bin/EmptyGrailForm) and GenScan (URL genes.mit.edu/GENSCAN.html). For a general discussion of splice variant identification protocols see., e.g., Southan, C., A genomic perspective on human proteases, FEBS Lett. 2001 June 8; 498(2-3):214-8; de Souza, S. J., et al., Identification of human chromosome 22 transcribed sequences with ORF expressed sequence tags, Proc. Natl. Acad. Sci. USA. 2000 Nov. 7; 97(23):12690-3.

To further confirm the parameters of a transcript variant, a variety of techniques are available in the art, such as full-length cloning, proteomic validation, PCR-based validation, and 5' RACE validation, etc. (see e.g., Proteomic Validation: Brennan, S. O., et al., Albumin banks peninsula: a new termination variant characterized by electrospray mass spectrometry, Biochem Biophys Acta. 1999 Aug. 17; 1433(1-2): 321-6; Ferranti P, et al., Differential splicing of pre-messenger RNA produces multiple forms of mature caprine alpha(s1)-casein, Eur J Biochem. 1997 Oct. 1; 249(1):1-7. For PCR-based Validation: Wellmann S, et al., Specific reverse transcription-PCR quantification of vascular endothelial growth factor (VEGF) splice variants by LightCycler technology, Clin Chem. 2001 April; 47(4):654-60; Jia, H. P., et al., Discovery of new human beta-defensins using a genomics-based approach, Gene. 2001 Jan. 24; 263(1-2): 211-8. For PCR-based and 5' RACE Validation: Brigle, K. E., et al., Organization of the murine reduced folate carrier gene and identification of variant splice forms, Biochem Biophys Acta. 1997 Aug. 7; 1353(2): 191-8).

It is known in the art that genomic regions are modulated in cancers. When the genomic region to which a gene maps is modulated in a particular cancer, the alternative transcripts or splice variants of the gene are modulated as well. Disclosed herein is that 254P1D6B has a particular expression profile related to cancer (See, e.g., Table I). Alternative transcripts and splice variants of 254P1D6B are also be involved in cancers in the same or different tissues, thus serving as tumor-associated markers/antigens.

Using the full-length gene and EST sequences, one additional transcript variant was identified, designated as 254P1D6B v.3. The boundaries of exons in the original transcript, 254P1D6B v.1 are shown in Table LI. The structures of the transcript variants are shown in FIG. 10. Variant 254P1D6B v.3 extended exon 1 of v.1 by 109 base pairs and added an exon in between exons 2 and 3 of v.1.

Table LII shows nucleotide sequence of the transcript variant. Table LIII shows the alignment of the transcript variant with nucleic acid sequence of 254P1D6B v.1. Table LIV lays out amino acid translation of the transcript variant for the identified reading frame orientation. Table LV displays alignments of the amino acid sequence encoded by the splice variant with that of 254P1D6B v.1.

Example 6

Single Nucleotide Polymorphisms of 254P1D6B

A Single Nucleotide Polymorphism (SNP) is a single base pair variation in a nucleotide sequence at a specific location. At any given point of the genome, there are four possible nucleotide base pairs: A/T, C/G, G/C and T/A. Genotype refers to the specific base pair sequence of one or more locations in the genome of an individual. Haplotype refers to the base pair sequence of more than one location on the same DNA molecule (or the same chromosome in higher organisms), often in the context of one gene or in the context of several tightly linked genes. SNPs that occur on a cDNA are called cSNPs. These cSNPs may change amino acids of the protein encoded by the gene and thus change the functions of the protein. Some SNPs cause inherited diseases; others contribute to quantitative variations in phenotype and reactions to environmental factors including diet and drugs among individuals. Therefore, SNPs and/or combinations of alleles (called haplotypes) have many applications, including diagnosis of inherited diseases, determination of drug reactions and dosage, identification of genes responsible for diseases, and analysis of the genetic relationship between individuals (P. Nowotny, J. M. Kwon and A. M. Goate, "SNP analysis to dissect human traits," Curr. Opin. Neurobiol. 2001 October; 11(5):637-641; M. Pirmohamed and B. K. Park, "Genetic susceptibility to adverse drug reactions," Trends Pharmacol. Sci. 2001 June; 22(6):298-305; J. H. Riley, C. J. Allan, E. Lai and A. Roses, "The use of single nucleotide polymorphisms in the isolation of common disease genes," Pharmacogenomics. 2000 February; 1(1):39-47; R. Judson, J. C. Stephens and A. Windemuth, "The predictive power of haplotypes in clinical response," Pharmacogenomics. 2000 February; 1(1):15-26).

SNPs are identified by a variety of art-accepted methods (P. Bean, "The promising voyage of SNP target discovery," Am. Clin. Lab. 2001 October-November; 20(9):18-20; K. M. Weiss, "In search of human variation," Genome Res. 1998 July; 8(7):691-697; M. M. She, "Enabling large-scale pharmacogenetic studies by high-throughput mutation detection and genotyping technologies," Clin. Chem. 2001 February; 47(2):164-172). For example, SNPs are identified by sequencing DNA fragments that show polymorphism by gel-based methods such as restriction fragment length polymorphism (RFLP) and denaturing gradient gel electrophoresis (DGGE). They can also be discovered by direct sequencing of DNA samples pooled from different individuals or by comparing sequences from different DNA samples. With the rapid accumulation of sequence data in public and private databases, one can discover SNPs by comparing sequences using computer programs (Z. Gu, L. Hillier and P. Y. Kwok, "Single nucleotide polymorphism hunting in cyberspace," Hum. Mutat. 1998; 12(4):221-225). SNPs can be verified and genotype or haplotype of an individual can be determined by a variety of methods including direct sequencing and high throughput microarrays (P. Y. Kwok, "Methods for genotyping single nucleotide polymorphisms," Annu. Rev. Genomics Hum. Genet. 2001; 2:235-258; M. Kokoris, K. Dix, K. Moynihan, J. Mathis, B. Erwin, P. Grass, B. Hines and A. Duesterhoeft, "High-throughput SNP genotyping with the Masscode system," Mol. Diagn. 2000 December; 5(4):329-340).

Using the methods described above, seventeen SNPs were identified in the original transcript, 254P1D6B v.1, at positions 286 (C/G), 935 (C/A), 980 (T/G), 2347 (G/A), 3762 (C/T), 3772 (A/G), 3955 (C/T), 4096 (C/T), 4415 (G/A), 4519 (G/A), 4539 (A/G), 4614 (G/T), 5184 (G/C), 5528 (T/G), 5641 (G/A), 6221 (T/C) and 6223 (G/A). The transcripts or proteins with alternative alleles were designated as variants 254P1D6B v.4 through v.20, respectively. FIG. 12 shows the schematic alignment of the SNP variants. FIG. 11 shows the schematic alignment of protein variants, corresponding to nucleotide variants. Nucleotide variants that code for the same amino acid sequence as variant 1 are not shown in FIG. 11. These alleles of the SNPs, though shown separately here, can occur in different combinations (haplotypes, such as v.2) and in any one of the transcript variants (such as 254P1D6B v.3) that contains the sequence context of the SNPs.

Example 7

Production of Recombinant 254P1D6B in Prokaryotic Systems

To express recombinant 254P1D6b and 254P1D6b variants in prokaryotic cells, the full or partial length 254P1D6B and 254P1D6B variant cDNA sequences are cloned into any one of a variety of expression vectors known in the art. One or more of the following regions of 254P1D6B variants are expressed: the full length sequence presented in FIGS. 2 and 3, or any 8, 9, 10, 11, 12, 13, 14, 15, 16, 17, 18, 19, 20, 21, 22, 23, 24, 25, 26, 27, 28, 29, 30 or more contiguous amino acids from 254P1D6B, variants, or analogs thereof.

A. In Vitro Transcription and Translation Constructs:

pCRII: To generate 254P1D6B sense and anti-sense RNA probes for RNA in situ investigations, pCRII constructs (Invitrogen, Carlsbad Calif.) are generated encoding either all or fragments of the 254P1D6B cDNA. The pCRII vector has Sp6 and T7 promoters flanking the insert to drive the transcription of 254P1D6B RNA for use as probes in RNA in situ hybridization experiments. These probes are used to analyze the cell and tissue expression of 254P1D6B at the RNA level. Transcribed 254P1D6B RNA representing the cDNA amino acid coding region of the 254P1D6B gene is used in in vitro translation systems such as the TnT™ Coupled Reticulolysate System (Promega, Corp., Madison, Wis.) to synthesize 254P1D6B protein.

B. Bacterial Constructs:

pGEX Constructs: To generate recombinant 254P1D6B proteins in bacteria that are fused to the Glutathione S-transferase (GST) protein, all or parts of the 254P1D6B cDNA protein coding sequence are cloned into the pGEX family of GST-fusion vectors (Amersham Pharmacia Biotech, Piscataway, N.J.). These constructs allow controlled expression of recombinant 254P1D6B protein sequences with GST fused at the amino-terminus and a six histidine epitope (6xHis) at the carboxyl-terminus. The GST and 6xHis tags permit purification of the recombinant fusion protein from induced bacteria with the appropriate affinity matrix and allow recognition of the fusion protein with anti-GST and anti-His antibodies. The 6xHis tag is generated by adding 6 histidine codons to the cloning primer at the 3' end, e.g., of the open reading frame (ORF). A proteolytic cleavage site, such as the PreScission™ recognition site in pGEX-6P-1, may be employed such that it permits cleavage of the GST tag from 254P1D6B-related protein. The ampicillin resistance gene and pBR322 origin permits selection and maintenance of the pGEX plasmids in E. coli.

pMAL Constructs:

To generate, in bacteria, recombinant 254P1D6B proteins that are fused to maltose-binding protein (MBP), all or parts of the 254P1D6B cDNA protein coding sequence are fused to the MBP gene by cloning into the pMAL-c2X and pMAL-p2X vectors (New England Biolabs, Beverly, Mass.). These constructs allow controlled expression of recombinant 254P1D6B protein sequences with MBP fused at the amino-terminus and a 6xHis epitope tag at the carboxyl-terminus. The MBP and 6xHis tags permit purification of the recombinant protein from induced bacteria with the appropriate affinity matrix and allow recognition of the fusion protein with anti-MBP and anti-His antibodies. The 6xHis epitope tag is generated by adding 6 histidine codons to the 3' cloning primer. A Factor Xa recognition site permits cleavage of the pMAL tag from 254P1D6B. The pMAL-c2X and pMAL-p2X vectors are optimized to express the recombinant protein in the cytoplasm or periplasm respectively. Periplasm expression enhances folding of proteins with disulfide bonds.

pET Constructs:

To express 254P1D6B in bacterial cells, all or parts of the 254P1D6B cDNA protein coding sequence are cloned into the pET family of vectors (Novagen, Madison, Wis.). These vectors allow tightly controlled expression of recombinant 254P1D6B protein in bacteria with and without fusion to proteins that enhance solubility, such as NusA and thioredoxin (Trx), and epitope tags, such as 6xHis and S-Tag™ that aid purification and detection of the recombinant protein. For example, constructs are made utilizing pET NusA fusion system 43.1 such that regions of the 254P1D6B protein are expressed as amino-terminal fusions to NusA.

C. Yeast Constructs:

pESC Constructs:

To express 254P1D6B in the yeast species Saccharomyces cerevisiae for generation of recombinant protein and functional studies, all or parts of the 254P1D6B cDNA protein coding sequence are cloned into the pESC family of vectors each of which contain 1 of 4 selectable markers, HIS3, TRP1, LEU2, and URA3 (Stratagene, La Jolla, Calif.). These vectors allow controlled expression from the same plasmid of up to 2 different genes or cloned sequences containing either Flag™ or Myc epitope tags in the same yeast cell. This system is useful to confirm protein-protein interactions of 254P1D6B. In addition, expression in yeast yields similar post-translational modifications, such as glycosylations and phosphorylations that are found when expressed in eukaryotic cells.

pESP Constructs:

To express 254P1D6B in the yeast species Saccharomyces pombe, all or parts of the 254P1D6B cDNA protein coding sequence are cloned into the pESP family of vectors. These vectors allow controlled high level of expression of a 254P1D6B protein sequence that is fused at either the amino terminus or at the carboxyl terminus to GST which aids purification of the recombinant protein. A Flag™ epitope tag allows detection of the recombinant protein with anti-Flag™ antibody.

Example 8

Production of Recombinant 254P1D6B in Higher Eukaryotic Systems

A. Mammalian Constructs:

To express recombinant 254P1D6B in eukaryotic cells, the full or partial length 254P1D6B cDNA sequences were cloned into any one of a variety of expression vectors known in the art. One or more of the following regions of 254P1D6B were expressed in these constructs, amino acids 1 to 1072, or any 8, 9, 10, 11, 12, 13, 14, 15, 16, 17, 18, 19, 20, 21, 22, 23, 24, 25, 26, 27, 28, 29, 30 or more contiguous amino acids from 254P1D6B v.1, v.2, v.5, and v.6; amino acids 1 to 1063 of v.3; or any 8, 9, 10, 11, 12, 13, 14, 15, 16, 17, 18, 19, 20, 21, 22, 23, 24, 25, 26, 27, 28, 29, 30 or more contiguous amino acids from 254P1D6B variants, or analogs thereof.

The constructs can be transfected into any one of a wide variety of mammalian cells such as 293T cells. Transfected 293T cell lysates can be probed with the anti-254P1D6B polyclonal serum, described herein.

pcDNA4/HisMax Constructs:

To express 254P1D6B in mammalian cells, a 254P1D6B ORF, or portions thereof, of 254P1D6B are cloned into pcDNA4/HisMax Version A (Invitrogen, Carlsbad, Calif.). Protein expression is driven from the cytomegalovirus (CMV) promoter and the SP16 translational enhancer. The recombinant protein has Xpress™ and six histidine (6xHis) epitopes fused to the amino-terminus. The pcDNA4/HisMax vector also contains the bovine growth hormone (BGH) polyadenylation signal and transcription termination sequence to enhance mRNA stability along with the SV40 origin for episomal replication and simple vector rescue in cell lines expressing the large T antigen. The Zeocin resistance gene allows for selection of mammalian cells expressing the protein and the ampicillin resistance gene and ColE1 origin permits selection and maintenance of the plasmid in E. coli.

pcDNA3.1/MycHis Constructs:

To express 254P1D6B in mammalian cells, a 254P1D6B ORF, or portions thereof, of 254P1D6B with a consensus Kozak translation initiation site was cloned into pcDNA3.1/ MycHis Version A (Invitrogen, Carlsbad, Calif.). Protein expression was driven from the cytomegalovirus (CMV) promoter. The recombinant proteins have the myc epitope and 6×His epitope fused to the carboxyl-terminus. The pcDNA3.1/MycHis vector also contains the bovine growth hormone (BGH) polyadenylation signal and transcription termination sequence to enhance mRNA stability, along with the SV40 origin for episomal replication and simple vector rescue in cell lines expressing the large T antigen. The Neomycin resistance gene can be used, as it allows for selection of mammalian cells expressing the protein and the ampicillin resistance gene and ColE1 origin permits selection and maintenance of the plasmid in *E. coli.*

The complete ORF of 254P1D6B v.2 was cloned into the pcDNA3.1/MycHis construct to generate 254P1D6B.pcDNA3.1/MycHis. FIG. 17A shows expression of 254P1D6B.pcDNA3.1/MycHis following transfection into 293T cells. 293T cells were transfected with either 254P1D6B.pcDNA3.1/MycHis or pcDNA3.1/MycHis vector control. Forty hours later, cell lysates were collected. Samples were run on an SDS-PAGE acrylamide gel, blotted and stained with anti-his antibody. The blot was developed using the ECL chemiluminescence kit and visualized by autoradiography. Results show expression of 254P1D6B from the 254P1D6B.pcDNA3.1MycHis construct in the lysates of transfected cells.

pcDNA3.1/CT-GFP-TOPO Construct:

To express 254P1D6B in mammalian cells and to allow detection of the recombinant proteins using fluorescence, a 254P1D6B ORF, or portions thereof, with a consensus Kozak translation initiation site are cloned into pcDNA3.1/CT-GFP-TOPO (Invitrogen, Calif.). Protein expression is driven from the cytomegalovirus (CMV) promoter. The recombinant proteins have the Green Fluorescent Protein (GFP) fused to the carboxyl-terminus facilitating non-invasive, in vivo detection and cell biology studies. The pcDNA3.1 CT-GFP-TOPO vector also contains the bovine growth hormone (BGH) polyadenylation signal and transcription termination sequence to enhance mRNA stability along with the SV40 origin for episomal replication and simple vector rescue in cell lines expressing the large T antigen. The Neomycin resistance gene allows for selection of mammalian cells that express the protein and the ampicillin resistance gene and ColE1 origin permits selection and maintenance of the plasmid in *E. coli.* Additional constructs with an amino-terminal GFP fusion are made in pcDNA3.1/NT-GFP-TOPO spanning the entire length of a 254P1D6B protein.

PAPtag:

A 254P1D6B ORF, or portions thereof, is cloned into pAPtag-5 (GenHunter Corp. Nashville, Tenn.). This construct generates an alkaline phosphatase fusion at the carboxyl-terminus of a 254P1D6B protein while fusing the IgGK signal sequence to the amino-terminus. Constructs are also generated in which alkaline phosphatase with an amino-terminal IgGK signal sequence is fused to the amino-terminus of a 254P1D6B protein. The resulting recombinant 254P1D6B proteins are optimized for secretion into the media of transfected mammalian cells and can be used to identify proteins such as ligands or receptors that interact with 254P1D6B proteins. Protein expression is driven from the CMV promoter and the recombinant proteins also contain myc and 6×His epitopes fused at the carboxyl-terminus that facilitates detection and purification. The Zeocin resistance gene present in the vector allows for selection of mammalian cells expressing the recombinant protein and the ampicillin resistance gene permits selection of the plasmid in *E. coli.* pTag5:

A 254P1D6B ORF, or portions thereof, were cloned into pTag-5. This vector is similar to pAPtag but without the alkaline phosphatase fusion. This construct generates 254P1D6B protein with an amino-terminal IgGK signal sequence and myc and 6×His epitope tags at the carboxyl-terminus that facilitate detection and affinity purification. The resulting recombinant 254P1D6B protein is optimized for secretion into the media of transfected mammalian cells, and is used as immunogen or ligand to identify proteins such as ligands or receptors that interact with the 254P1D6B proteins. Protein expression is driven from the CMV promoter. The Zeocin resistance gene present in the vector allows for selection of mammalian cells expressing the protein, and the ampicillin resistance gene permits selection of the plasmid in *E. coli.*

The extracellular domain, amino acids 26-953, of 254P1D6B v.1 was cloned into the pTag5 construct to generate 254P1D6B.pTag5. FIG. 17B shows expression and secretion of the extracellular domain of 254P1D6B following 254P1D6B.pTag5 vector transfection into 293T cells. 293T cells were transfected with 254P1D6B.pTag5 construct. Forty hours later, supernatant as well as cell lysates were collected. Samples were run on an SDS-PAGE acrylamide gel, blotted and stained with anti-his antibody. The blot was developed using the ECL chemiluminescence kit and visualized by autoradiography. Results show expression and secretion of 254P1D6B from the 254P1D6B.pTag5 transfected cells.

PsecFc:

A 254P1D6B ORF, or portions thereof, is also cloned into psecFc. The psecFc vector was assembled by cloning the human immunoglobulin G1 (IgG) Fc (hinge, CH2, CH3 regions) into pSecTag2 (Invitrogen, California). This construct generates an IgG1 Fc fusion at the carboxyl-terminus of the 254P1D6B proteins, while fusing the IgGK signal sequence to N-terminus. 254P1D6B fusions utilizing the murine IgG1 Fc region are also used. The resulting recombinant 254P1D6B proteins are optimized for secretion into the media of transfected mammalian cells, and can be used as immunogens or to identify proteins such as ligands or receptors that interact with 254P1D6B protein. Protein expression is driven from the CMV promoter. The hygromycin resistance gene present in the vector allows for selection of mammalian cells that express the recombinant protein, and the ampicillin resistance gene permits selection of the plasmid in *E. coli.* pSRα Constructs:

To generate mammalian cell lines that express 254P1D6B constitutively, 254P1D6B ORF, or portions thereof, of 254P1D6B were cloned into pSRα constructs. Amphotropic and ecotropic retroviruses were generated by transfection of pSRα constructs into the 293T-10A1 packaging line or co-transfection of pSRα and a helper plasmid (containing deleted packaging sequences) into the 293 cells, respectively. The retrovirus is used to infect a variety of mammalian cell lines, resulting in the integration of the cloned gene, 254P1D6B, into the host cell-lines. Protein expression is driven from a long terminal repeat (LTR). The Neomycin resistance gene present in the vector allows for selection of mammalian cells that express the protein, and the ampicillin resistance gene and ColE1 origin permit selection and maintenance of the plasmid in *E. coli.* The retroviral vectors can thereafter be used for infection and generation of various cell lines using, for example, PC3, NIH 3T3, TsuPr1, 293 or rat-1 cells.

Additional pSRα constructs are made that fuse an epitope tag such as the FLAG™ tag to the carboxyl-terminus of 254P1D6B sequences to allow detection using anti-Flag™ antibodies. For example, the FLAG™ sequence 5' gattacaaggat gacgacgataag 3' (SEQ ID NO:27) is added to cloning primer at the 3' end of the ORF. Additional pSRα constructs are made to produce both amino-terminal and carboxyl-terminal GFP and myc/6xHis fusion proteins of the full-length 254P1D6B proteins.

Additional Viral Vectors:

Additional constructs are made for viral-mediated delivery and expression of 254P1D6B. High virus titer leading to high level expression of 254P1D6B is achieved in viral delivery systems such as adenoviral vectors and herpes amplicon vectors. A 254P1D6B coding sequences or fragments thereof are amplified by PCR and subcloned into the AdEasy shuttle vector (Stratagene). Recombination and virus packaging are performed according to the manufacturer's instructions to generate adenoviral vectors. Alternatively, 254P1D6B coding sequences or fragments thereof are cloned into the HSV-1 vector (Imgenex) to generate herpes viral vectors. The viral vectors are thereafter used for infection of various cell lines such as PC3, NIH 3T3, 293 or rat-1 cells.

Regulated Expression Systems:

To control expression of 254P1D6B in mammalian cells, coding sequences of 254P1D6B, or portions thereof, are cloned into regulated mammalian expression systems such as the T-Rex System (Invitrogen), the GeneSwitch System (Invitrogen) and the tightly-regulated Ecdysone System (Stratagene). These systems allow the study of the temporal and concentration dependent effects of recombinant 254P1D6B. These vectors are thereafter used to control expression of 254P1D6B in various cell lines such as PC3, NIH 3T3, 293 or rat-1 cells.

B. Baculovirus Expression Systems

To generate recombinant 254P1D6B proteins in a baculovirus expression system, 254P1D6B ORF, or portions thereof, are cloned into the baculovirus transfer vector pBlueBac 4.5 (Invitrogen), which provides a His-tag at the N-terminus. Specifically, pBlueBac-254P1D6B is co-transfected with helper plasmid pBac-N-Blue (Invitrogen) into SF9 (*Spodoptera frugiperda*) insect cells to generate recombinant baculovirus (see Invitrogen instruction manual for details). Baculovirus is then collected from cell supernatant and purified by plaque assay.

Recombinant 254P1D6B protein is then generated by infection of HighFive insect cells (Invitrogen) with purified baculovirus. Recombinant 254P1D6B protein can be detected using anti-254P1D6B or anti-His-tag antibody. 254P1D6B protein can be purified and used in various cell-based assays or as immunogen to generate polyclonal and monoclonal antibodies specific for 254P1D6B.

Example 9

Antigenicity Profiles and Secondary Structure

FIG. 5, FIG. 6, FIG. 7, FIG. 8, and FIG. 9 depict graphically five amino acid profiles of 254P1D6B variant 1, each assessment available by accessing the ProtScale website located on the World Wide Web at (.expasy.ch/cgi-bin/protscale.pl) on the ExPasy molecular biology server.

These profiles: FIG. 5, Hydrophilicity, (Hopp T. P., Woods K. R., 1981. Proc. Natl. Acad. Sci. U.S.A. 78:3824-3828); FIG. 6, Hydropathicity, (Kyte J., Doolittle R. F., 1982. J. Mol. Biol. 157:105-132); FIG. 7, Percentage Accessible Residues (Janin J., 1979 Nature 277:491-492); FIG. 8, Average Flexibility, (Bhaskaran R., and Ponnuswamy P. K., 1988. Int. J. Pept. Protein Res. 32:242-255); FIG. 9, Beta-turn (Deleage, G., Roux B. 1987 Protein Engineering 1:289-294); and optionally others available in the art, such as on the ProtScale website, were used to identify antigenic regions of each of the 254P1D6B variant proteins. Each of the above amino acid profiles of 254P1D6B variants were generated using the following ProtScale parameters for analysis: 1) A window size of 9; 2) 100% weight of the window edges compared to the window center; and, 3) amino acid profile values normalized to lie between 0 and 1.

Hydrophilicity (FIG. 5), Hydropathicity (FIG. 6) and Percentage Accessible Residues (FIG. 7) profiles were used to determine stretches of hydrophilic amino acids (i.e., values greater than 0.5 on the Hydrophilicity and Percentage Accessible Residues profile, and values less than 0.5 on the Hydropathicity profile). Such regions are likely to be exposed to the aqueous environment, be present on the surface of the protein, and thus available for immune recognition, such as by antibodies.

Average Flexibility (FIG. 8) and Beta-turn (FIG. 9) profiles determine stretches of amino acids (i.e., values greater than 0.5 on the Beta-turn profile and the Average Flexibility profile) that are not constrained in secondary structures such as beta sheets and alpha helices. Such regions are also more likely to be exposed on the protein and thus accessible to immune recognition, such as by antibodies.

Antigenic sequences of the 254P1D6B variant proteins indicated, e.g., by the profiles set forth in FIG. 5, FIG. 6, FIG. 7, FIG. 8, and/or FIG. 9 are used to prepare immunogens, either peptides or nucleic acids that encode them, to generate therapeutic and diagnostic anti-254P1D6B antibodies. The immunogen can be any 5, 6, 7, 8, 9, 10, 11, 12, 13, 14, 15, 16, 17, 18, 19, 20, 21, 22, 23, 24, 25, 30, 35, 40, 45, 50 or more than 50 contiguous amino acids, or the corresponding nucleic acids that encode them, from the 254P1D6B protein variants listed in FIGS. 2 and 3. In particular, peptide immunogens of the invention can comprise, a peptide region of at least 5 amino acids of FIGS. 2 and 3 in any whole number increment that includes an amino acid position having a value greater than 0.5 in the Hydrophilicity profiles of FIG. 5; a peptide region of at least 5 amino acids of FIGS. 2 and 3 in any whole number increment that includes an amino acid position having a value less than 0.5 in the Hydropathicity profile of FIG. 6; a peptide region of at least 5 amino acids of FIGS. 2 and 3 in any whole number increment that includes an amino acid position having a value greater than 0.5 in the Percent Accessible Residues profiles of FIG. 7; a peptide region of at least 5 amino acids of FIGS. 2 and 3 in any whole number increment that includes an amino acid position having a value greater than 0.5 in the Average Flexibility profiles on FIG. 8; and, a peptide region of at least 5 amino acids of FIGS. 2 and 3 in any whole number increment that includes an amino acid position having a value greater than 0.5 in the Beta-turn profile of FIG. 9. Peptide immunogens of the invention can also comprise nucleic acids that encode any of the forgoing.

All immunogens of the invention, peptide or nucleic acid, can be embodied in human unit dose form, or comprised by a composition that includes a pharmaceutical excipient compatible with human physiology.

The secondary structure of 254P1D6B protein variant 1, namely the predicted presence and location of alpha helices, extended strands, and random coils, are predicted from the primary amino acid sequence using the HNN—Hierarchical Neural Network method (NPS@: Network Protein Sequence Analysis TIBS 2000 March Vol. 25, No 3 [291]:147-150 Combet C., Blanchet C., Geourjon C. and Deleage G., on the World Wide Web at pbil.ibcp.fr/cgi-bin/npsa_automat.pl?page=npsa_nn.html), accessed from the ExPasy molecular biology server located on the World Wide Web at (.expasy.ch/tools/). The analysis indicates that 254P1D6B variant 1 is composed of 18.19% alpha helix, 24.81% extended strand, and 57.00% random coil (FIG. 13A).

Analysis for the potential presence of transmembrane domains in the 254P1D6B variant protein 1 was carried out using a variety of transmembrane prediction algorithms accessed from the ExPasy molecular biology server located on the World Wide Web at (.expasy.ch/tools/). Shown graphically in FIG. 13B is the result of analysis of variant 1 using the TMpred program and in FIG. 13C results using the TMHMM program. Both the TMpred program and the TMHMM program predict the presence of 1 transmembrane domain. Analyses of the variants using other structural prediction programs are summarized in Table VI.

Example 10

Generation of 254P1D6B Polyclonal Antibodies

Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. In addition to immunizing with a full length 254P1D6B protein variant, computer algorithms are employed in design of immunogens that, based on amino acid sequence analysis contain characteristics of being antigenic and available for recognition by the immune system of the immunized host (see the Example entitled "Antigenicity Profiles and Secondary Structures"). Such regions would be predicted to be hydrophilic, flexible, in beta-turn conformations, and be exposed on the surface of the protein (see, e.g., FIG. 5, FIG. 6, FIG. 7, FIG. 8, or FIG. 9 for amino acid profiles that indicate such regions of 254P1D6B protein variant 1).

For example, recombinant bacterial fusion proteins or peptides containing hydrophilic, flexible, beta-turn regions of 254P1D6B protein variants are used as antigens to generate polyclonal antibodies in New Zealand White rabbits or monoclonal antibodies as described in the Example entitled "Generation of 254P1D6B Monoclonal Antibodies (mAbs)". For example, in 254P1D6B variant 1, such regions include, but are not limited to, amino acids 21-32, amino acids 82-96, amino acids 147-182, amino acids 242-270, amino acids 618-638, amino acids 791-818, and amino acids 980-1072. It is useful to conjugate the immunizing agent to a protein known to be immunogenic in the mammal being immunized. Examples of such immunogenic proteins include, but are not limited to, keyhole limpet hemocyanin (KLH), serum albumin, bovine thyroglobulin, and soybean trypsin inhibitor. In one embodiment, a peptide encoding amino acids 147-182 of 254P1D6B variant 1 was conjugated to KLH and used to immunize a rabbit. Alternatively the immunizing agent may include all or portions of the 254P1D6B variant proteins, analogs or fusion proteins thereof. For example, the 254P1D6B variant 1 amino acid sequence can be fused using recombinant DNA techniques to any one of a variety of fusion protein partners that are well known in the art, such as glutathione-S-transferase (GST) and HIS tagged fusion proteins. In another embodiment, amino acids 980-1072 of 254P1D6B variant 1 is fused to GST using recombinant techniques and the pGEX expression vector, expressed, purified and used to immunize a rabbit. Such fusion proteins are purified from induced bacteria using the appropriate affinity matrix.

Other recombinant bacterial fusion proteins that may be employed include maltose binding protein, LacZ, thioredoxin, NusA, or an immunoglobulin constant region (see the section entitled "Production of 254P1D6B in Prokaryotic Systems" and Current Protocols In Molecular Biology, Volume 2, Unit 16, Frederick M. Ausubul et al. eds., 1995; Linsley, P.S., Brady, W., Umes, M., Grosmaire, L., Damle, N., and Ledbetter, L. (1991) J. Exp. Med. 174, 561-566).

In addition to bacterial derived fusion proteins, mammalian expressed protein antigens are also used. These antigens are expressed from mammalian expression vectors such as the Tag5 and Fc-fusion vectors (see the section entitled "Production of Recombinant 254P1D6B in Eukaryotic Systems"), and retains post-translational modifications such as glycosylations found in native protein. In one embodiment, amino acids 26-953 of 254P1D6B variant 1 was cloned into the Tag5 mammalian secretion vector, and expressed in 293T cells (FIG. 17). The recombinant protein is purified by metal chelate chromatography from tissue culture supernatants of 293T cells stably expressing the recombinant vector. The purified Tag5 254P1D6B protein is then used as immunogen.

During the immunization protocol, it is useful to mix or emulsify the antigen in adjuvants that enhance the immune response of the host animal. Examples of adjuvants include, but are not limited to, complete Freund's adjuvant (CFA) and MPL-TDM adjuvant (monophosphoryl Lipid A, synthetic trehalose dicorynomycolate).

In a typical protocol, rabbits are initially immunized subcutaneously with up to 200 µg, typically 100-200 µg, of fusion protein or peptide conjugated to KLH mixed in complete Freund's adjuvant (CFA). Rabbits are then injected subcutaneously every two weeks with up to 200 µg, typically 100-200 µg, of the immunogen in incomplete Freund's adjuvant (IFA). Test bleeds are taken approximately 7-10 days following each immunization and used to monitor the titer of the antiserum by ELISA.

To test reactivity and specificity of immune serum, such as the rabbit serum derived from immunization with the GST-fusion of 254P1D6B variant 1 protein, the full-length 254P1D6B variant 1 cDNA is cloned into pcDNA 3.1 myc-his expression vector (Invitrogen, see the Example entitled "Production of Recombinant 254P1D6B in Eukaryotic Systems"). After transfection of the constructs into 293T cells, cell lysates are probed with the anti-254P1D6B serum and with anti-His antibody (Santa Cruz Biotechnologies, Santa Cruz, Calif.) to determine specific reactivity to denatured 254P1D6B protein using the Western blot technique (FIG. 17). In addition, the immune serum is tested by fluorescence microscopy, flow cytometry and immunoprecipitation against 293T and other recombinant 254P1D6B-expressing cells to determine specific recognition of native protein. Western blot, immunoprecipitation, fluorescent microscopy, and flow cytometric techniques using cells that endogenously express 254P1D6B are also carried out to test reactivity and specificity.

Anti-serum from rabbits immunized with 254P1D6B variant fusion proteins, such as GST and MBP fusion proteins, are purified by depletion of antibodies reactive to the fusion partner sequence by passage over an affinity column containing the fusion partner either alone or in the context of an irrelevant fusion protein. For example, antiserum derived from a GST-254P1D6B variant 1 fusion protein is first purified by passage over a column of GST protein covalently coupled to AffiGel matrix (BioRad, Hercules, Calif.). The antiserum is then affinity purified by passage over a column composed of a MBP-254P1D6B fusion protein covalently coupled to Affigel matrix. The serum is then further purified by protein G affinity chromatography to isolate the IgG fraction. Sera from other His-tagged antigens and peptide immunized rabbits as well as fusion partner depleted sera are affinity purified by passage over a column matrix composed of the original protein immunogen or free peptide.

Example 11

Generation of 254P1D6B Monoclonal Antibodies (mAbs)

In one embodiment, therapeutic mAbs to 254P1D6B variants comprise those that react with epitopes specific for each variant protein or specific to sequences in common between the variants that would disrupt or modulate the biological function of the 254P1D6B variants, for example those that would disrupt the interaction with ligands and binding partners. Immunogens for generation of such mAbs include those designed to encode or contain the entire 254P1D6B protein variant sequence, regions predicted to contain functional motifs, and regions of the 254P1D6B protein variants predicted to be antigenic from computer analysis of the amino acid sequence (see, e.g., FIG. 5, FIG. 6, FIG. 7, FIG. 8, or FIG. 9, and the Example entitled "Antigenicity Profiles and Secondary Structures"). Immunogens include peptides, recombinant bacterial proteins, and mammalian expressed Tag 5 proteins and human and murine IgG FC fusion proteins. In addition, cells engineered to express high levels of a respective 254P1D6B variant, such as 293T-254P1D6B variant 1 or 300.19-254P1D6B variant 1 murine Pre-B cells, are used to immunize mice.

To generate mAbs to a 254P1D6B variant, mice are first immunized intraperitoneally (IP) with, typically, 10-50 µg of protein immunogen or $10^7$ 254P1D6B-expressing cells mixed in complete Freund's adjuvant. Mice are then subsequently immunized IP every 2-4 weeks with, typically, 10-50 µg of protein immunogen or $10^7$ cells mixed in incomplete Freund's adjuvant. Alternatively, MPL-TDM adjuvant is used in immunizations. In addition to the above protein and cell-based immunization strategies, a DNA-based immunization protocol is employed in which a mammalian expression vector encoding a 254P1D6B variant sequence is used to immunize mice by direct injection of the plasmid DNA. For example, amino acids 26-953 of 254P1D6B of variant 1 is cloned into the Tag5 mammalian secretion vector and the recombinant vector will then be used as immunogen. In another example the same amino acids are cloned into an Fc-fusion secretion vector in which the 254P1D6B variant 1 sequence is fused at the amino-terminus to an IgK leader sequence and at the carboxyl-terminus to the coding sequence of the human or murine IgG Fc region. This recombinant vector is then used as immunogen. The plasmid immunization protocols are used in combination with purified proteins expressed from the same vector and with cells expressing the respective 254P1D6B variant.

Alternatively, mice may be immunized directly into their footpads. In this case, 10-50 µg of protein immunogen or $10^7$ 254P1D6B-expressing cells are injected sub-cutaneously into the footpad of each hind leg. The first immunization is given with Titermax (Sigma™) as an adjuvant and subsequent injections are given with Alum-gel in conjunction with CpG oligonucleotide sequences with the exception of the final injection which is given with PBS. Injections are given twice weekly (every three to four days) for a period of 4 weeks and mice are sacrificed 3-4 days after the final injection, at which point lymph nodes immediately draining from the footpad are harvested and the B-cells are collected for use as antibody producing fusion partners.

During the immunization protocol, test bleeds are taken 7-10 days following an injection to monitor titer and specificity of the immune response. Once appropriate reactivity and specificity is obtained as determined by ELISA, Western blotting, immunoprecipitation, fluorescence microscopy, and flow cytometric analyses, fusion and hybridoma generation is then carried out with established procedures well known in the art (see, e.g., Harlow and Lane, 1988).

In one embodiment for generating 254P1D6B monoclonal antibodies, a GST-fusion of variant 1 antigen encoding amino acids 21-182 is expressed and purified from bacteria. Balb C mice are initially immunized intraperitoneally with 25 µg of the GST-254P1D6B variant 1 protein mixed in complete Freund's adjuvant. Mice are subsequently immunized every two weeks with 25 µg of the antigen mixed in incomplete Freund's adjuvant for a total of three immunizations. ELISA using the GST-fusion antigen and a cleavage product from which the GST portion is removed determines the titer of serum from immunized mice. Reactivity and specificity of serum to full length 254P1D6B variant 1 protein is monitored by Western blotting, immunoprecipitation and flow cytometry using 293T cells transfected with an expression vector encoding the 254P1D6B variant 1 cDNA (see e.g., the Example entitled "Production of Recombinant 254P1D6B in Eukaryotic Systems" and FIG. 17). Other recombinant 254P1D6B variant 1-expressing cells or cells endogenously expressing 254P1D6B variant 1 are also used. Mice showing the strongest reactivity are rested and given a final injection of antigen in PBS and then sacrificed four days later. The spleens of the sacrificed mice are harvested and fused to SPO/2 myeloma cells using standard procedures (Harlow and Lane, 1988). Supernatants from HAT selected growth wells are screened by ELISA, Western blot, immunoprecipitation, fluorescent microscopy, and flow cytometry to identify 254P1D6B specific antibody-producing clones.

The binding affinity of 254P1D6B variant specific monoclonal antibodies is determined using standard technologies. Affinity measurements quantify the strength of antibody to epitope binding and are used to help define which 254P1D6B variant monoclonal antibodies preferred for diagnostic or therapeutic use, as appreciated by one of skill in the art. The BIAcore system (Uppsala, Sweden) is a preferred method for determining binding affinity. The BIAcore system uses surface plasmon resonance (SPR, Welford K. 1991, Opt. Quant. Elect. 23:1; Morton and Myszka, 1998, Methods in Enzymology 295: 268) to monitor biomolecular interactions in real time. BIAcore analysis conveniently generates association rate constants, dissociation rate constants, equilibrium dissociation constants, and affinity constants.

Example 12

HLA Class I and Class II Binding Assays

HLA class I and class II binding assays using purified HLA molecules are performed in accordance with disclosed protocols (e.g., PCT publications WO 94/20127 and WO 94/03205; Sidney et al., *Current Protocols in Immunology* 18.3.1 (1998); Sidney, et al., *J. Immunol.* 154:247 (1995); Sette, et al., *Mol. Immunol.* 31:813 (1994)). Briefly, purified MHC molecules (5 to 500 nM) are incubated with various unlabeled peptide inhibitors and 1-10 nM $^{125}$I-radiolabeled probe peptides as described. Following incubation, MHC-peptide complexes are separated from free peptide by gel filtration and the fraction of peptide bound is determined.

Typically, in preliminary experiments, each MHC preparation is titered in the presence of fixed amounts of radiolabeled peptides to determine the concentration of HLA molecules necessary to bind 10-20% of the total radioactivity. All subsequent inhibition and direct binding assays are performed using these HLA concentrations.

Since under these conditions [label]<[HLA] and $IC_{50} \geqq$ [HLA], the measured $IC_{50}$ values are reasonable approximations of the true $K_D$ values. Peptide inhibitors are typically tested at concentrations ranging from 120 µg/ml to 1.2 ng/ml, and are tested in two to four completely independent experiments. To allow comparison of the data obtained in different experiments, a relative binding Figure is calculated for each peptide by dividing the $IC_{50}$ of a positive control for inhibition by the $IC_{50}$ for each tested peptide (typically unlabeled versions of the radiolabeled probe peptide). For database purposes, and inter-experiment comparisons, relative binding values are compiled. These values can subsequently be converted back into $IC_{50}$ nM values by dividing the $IC_{50}$ nM of the positive controls for inhibition by the relative binding of the peptide of interest. This method of data compilation is accurate and consistent for comparing peptides that have been tested on different days, or with different lots of purified MHC.

Binding assays as outlined above may be used to analyze HLA supermotif and/or HLA motif-bearing peptides (see Table IV).

Example 13

Identification of HLA Supermotif- and Motif-Bearing CTL Candidate Epitopes

HLA vaccine compositions of the invention can include multiple epitopes. The multiple epitopes can comprise multiple HLA supermotifs or motifs to achieve broad population coverage. This example illustrates the identification and confirmation of supermotif- and motif-bearing epitopes for the inclusion in such a vaccine composition. Calculation of population coverage is performed using the strategy described below.

Computer Searches and Algorithms for Identification of Supermotif and/or Motif-Bearing Epitopes The searches performed to identify the motif-bearing peptide sequences in the Example entitled "Antigenicity Profiles" and Tables VIII-XXI and XXII-XLIX employ the protein sequence data from the gene product of 254P1D6B set forth in FIGS. 2 and 3, the specific search peptides used to generate the tables are listed in Table VII.

Computer searches for epitopes bearing HLA Class I or Class II supermotifs or motifs are performed as follows. All translated 254P1D6B protein sequences are analyzed using a text string search software program to identify potential peptide sequences containing appropriate HLA binding motifs; such programs are readily produced in accordance with information in the art in view of known motif/supermotif disclosures. Furthermore, such calculations can be made mentally.

Identified A2-, A3-, and DR-supermotif sequences are scored using polynomial algorithms to predict their capacity to bind to specific HLA-Class I or Class II molecules. These polynomial algorithms account for the impact of different amino acids at different positions, and are essentially based on the premise that the overall affinity (or AG) of peptide-HLA molecule interactions can be approximated as a linear polynomial function of the type:

$$\text{``}\Delta G\text{''} = a_{1i} \times a_{2i} \times a_{3i} \ldots \times a_{ni}$$

where $a_{ji}$ is a coefficient which represents the effect of the presence of a given amino acid (j) at a given position (i) along the sequence of a peptide of n amino acids. The crucial assumption of this method is that the effects at each position are essentially independent of each other (i.e., independent binding of individual side-chains). When residue j occurs at position i in the peptide, it is assumed to contribute a constant amount $j_i$ to the free energy of binding of the peptide irrespective of the sequence of the rest of the peptide.

The method of derivation of specific algorithm coefficients has been described in Gulukota et al., *J. Mol. Biol.* 267:1258-126, 1997; (see also Sidney et al., *Human Immunol.* 45:79-93, 1996; and Southwood et al., *J. Immunol.* 160:3363-3373, 1998). Briefly, for all i positions, anchor and non-anchor alike, the geometric mean of the average relative binding (ARB) of all peptides carrying j is calculated relative to the remainder of the group, and used as the estimate of $j_i$. For Class II peptides, if multiple alignments are possible, only the highest scoring alignment is utilized, following an iterative procedure. To calculate an algorithm score of a given peptide in a test set, the ARB values corresponding to the sequence of the peptide are multiplied. If this product exceeds a chosen threshold, the peptide is predicted to bind. Appropriate thresholds are chosen as a function of the degree of stringency of prediction desired.

Selection of HLA-A2 Supertype Cross-Reactive Peptides

Protein sequences from 254P1D6B are scanned utilizing motif identification software, to identify 8-, 9-10- and 11-mer sequences containing the HLA-A2-supermotif main anchor specificity. Typically, these sequences are then scored using the protocol described above and the peptides corresponding to the positive-scoring sequences are synthesized and tested for their capacity to bind purified HLA-A*0201 molecules in vitro (HLA-A*0201 is considered a prototype A2 supertype molecule).

These peptides are then tested for the capacity to bind to additional A2-supertype molecules (A*0202, A*0203, A*0206, and A*6802). Peptides that bind to at least three of the five A2-supertype alleles tested are typically deemed A2-supertype cross-reactive binders. Preferred peptides bind at an affinity equal to or less than 500 nM to three or more HLA-A2 supertype molecules.

Selection of HLA-A3 Supermotif-Bearing Epitopes

The 254P1D6B protein sequence(s) scanned above is also examined for the presence of peptides with the HLA-A3-supermotif primary anchors. Peptides corresponding to the HLA A3 supermotif-bearing sequences are then synthesized and tested for binding to HLA-A*0301 and HLA-A*1101 molecules, the molecules encoded by the two most prevalent A3-supertype alleles. The peptides that bind at least one of the two alleles with binding affinities of $\leqq 500$ nM, often $\leqq 200$ nM, are then tested for binding cross-reactivity to the other common A3-supertype alleles (e.g., A*3101, A*3301, and A*6801) to identify those that can bind at least three of the five HLA-A3-supertype molecules tested.

Selection of HLA-B7 Supermotif Bearing Epitopes

The 254P1D6B protein(s) scanned above is also analyzed for the presence of 8-, 9-10-, or 1-mer peptides with the HLA-B7-supermotif. Corresponding peptides are synthesized and tested for binding to HLA-B*0702, the molecule encoded by the most common B7-supertype allele (i.e., the prototype B7 supertype allele). Peptides binding B*0702 with $IC_{50}$ of $\leqq 500$ nM are identified using standard methods. These peptides are then tested for binding to other common B7-supertype molecules (e.g., B*3501, B*5101, B*5301, and B*5401). Peptides capable of binding to three or more of the five B7-supertype alleles tested are thereby identified.

Selection of A1 and A24 Motif-Bearing Epitopes

To further increase population coverage, HLA-A1 and -A24 epitopes can also be incorporated into vaccine compositions. An analysis of the 254P1D6B protein can also be performed to identify HLA-A1- and A24-motif-containing sequences.

High affinity and/or cross-reactive binding epitopes that bear other motif and/or supermotifs are identified using analogous methodology.

Example 14

Confirmation of Immunogenicity

Cross-reactive candidate CTL A2-supermotif-bearing peptides that are identified as described herein are selected to confirm in vitro immunogenicity. Confirmation is performed using the following methodology:

Target Cell Lines for Cellular Screening:

The 0.221A2.1 cell line, produced by transferring the HLA-A2.1 gene into the HLA-A, -B, —C null mutant human B-lymphoblastoid cell line 721.221, is used as the peptide-loaded target to measure activity of HLA-A2.1-restricted CTL. This cell line is grown in RPMI-1640 medium supplemented with antibiotics, sodium pyruvate, nonessential amino acids and 10% (v/v) heat inactivated FCS. Cells that express an antigen of interest, or transfectants comprising the gene encoding the antigen of interest, can be used as target cells to confirm the ability of peptide-specific CTLs to recognize endogenous antigen.

Primary CTL Induction Cultures:

Generation of Dendritic Cells (DC):

PBMCs are thawed in RPMI with 30 g/ml DNAse, washed twice and resuspended in complete medium (RPMI-1640 plus 5% AB human serum, non-essential amino acids, sodium pyruvate, L-glutamine and penicillin/streptomycin). The monocytes are purified by plating $10 \times 10^6$ PBMC/well in a 6-well plate. After 2 hours at 37° C., the non-adherent cells are removed by gently shaking the plates and aspirating the supernatants. The wells are washed a total of three times with 3 ml RPMI to remove most of the non-adherent and loosely adherent cells. Three ml of complete medium containing 50 ng/ml of GM-CSF and 1,000 U/ml of IL-4 are then added to each well. TNFα is added to the DCs on day 6 at 75 ng/ml and the cells are used for CTL induction cultures on day 7.

Induction of CTL with DC and Peptide:

CD8+ T-cells are isolated by positive selection with Dynal immunomagnetic beads (Dynabeads® M-450) and the Detacha-Bead™ reagent. Typically about $200-250 \times 10^6$ PBMC are processed to obtain $24 \times 10^6$ CD8' T-cells (enough for a 48-well plate culture). Briefly, the PBMCs are thawed in RPMI with 30 μg/ml DNAse, washed once with PBS containing 1% human AB serum and resuspended in PBS/1% AB serum at a concentration of $20 \times 10^6$ cells/ml. The magnetic beads are washed 3 times with PBS/AB serum, added to the cells (140 μl beads/$20 \times 10^6$ cells) and incubated for 1 hour at 4° C. with continuous mixing. The beads and cells are washed 4× with PBS/AB serum to remove the nonadherent cells and resuspended at $100 \times 10^6$ cells/ml (based on the original cell number) in PBS/AB serum containing 100 μl/ml Detacha-Bead® reagent and 30 μg/ml DNAse. The mixture is incubated for 1 hour at room temperature with continuous mixing. The beads are washed again with PBS/AB/DNAse to collect the CD8+ T-cells. The DC are collected and centrifuged at 1300 rpm for 5-7 minutes, washed once with PBS with 1% BSA, counted and pulsed with 40 μg/ml of peptide at a cell concentration of $1-2 \times 10^6$/ml in the presence of 3 μg/ml 82-microglobulin for 4 hours at 20° C. The DC are then irradiated (4,200 rads), washed 1 time with medium and counted again.

Setting Up Induction Cultures:

0.25 ml cytokine-generated DC (at $1 \times 10^5$ cells/ml) are co-cultured with 0.25 ml of CD8+ T-cells (at $2 \times 10^6$ cell/ml) in each well of a 48-well plate in the presence of 10 ng/ml of IL-7. Recombinant human IL-10 is added the next day at a final concentration of 10 ng/ml and rhuman IL-2 is added 48 hours later at 10 IU/ml.

Restimulation of the Induction Cultures with Peptide-Pulsed Adherent Cells:

Seven and fourteen days after the primary induction, the cells are restimulated with peptide-pulsed adherent cells. The PBMCs are thawed and washed twice with RPMI and DNAse. The cells are resuspended at $5 \times 10^6$ cells/ml and irradiated at 4200 rads. The PBMCs are plated at $2 \times 10^6$ in 0.5 ml complete medium per well and incubated for 2 hours at 37° C. The plates are washed twice with RPMI by tapping the plate gently to remove the nonadherent cells and the adherent cells pulsed with 10 μg/ml of peptide in the presence of 3 μg/ml 82 microglobulin in 0.25 ml RPMI/5% AB per well for 2 hours at 37° C. Peptide solution from each well is aspirated and the wells are washed once with RPMI. Most of the media is aspirated from the induction cultures (CD8+ cells) and brought to 0.5 ml with fresh media. The cells are then transferred to the wells containing the peptide-pulsed adherent cells. Twenty four hours later recombinant human IL-10 is added at a final concentration of 10 ng/ml and recombinant human IL2 is added the next day and again 2-3 days later at 501 U/ml (Tsai et al., *Critical Reviews in Immunology* 18(1-2):65-75, 1998). Seven days later, the cultures are assayed for CTL activity in a $^{51}$Cr release assay. In some experiments the cultures are assayed for peptide-specific recognition in the in situ IFNγ ELISA at the time of the second restimulation followed by assay of endogenous recognition 7 days later. After expansion, activity is measured in both assays for a side-by-side comparison.

Measurement of CTL Lytic Activity by $^{51}$Cr Release.

Seven days after the second restimulation, cytotoxicity is determined in a standard (5 hr) $^{51}$Cr release assay by assaying individual wells at a single E:T. Peptide-pulsed targets are prepared by incubating the cells with 10 μg/ml peptide overnight at 37° C.

Adherent target cells are removed from culture flasks with trypsin-EDTA. Target cells are labeled with 200 μCi of $^{51}$Cr sodium chromate (Dupont, Wilmington, Del.) for 1 hour at 37° C. Labeled target cells are resuspended at $10^6$ per ml and diluted 1:10 with K562 cells at a concentration of $3.3 \times 10^6$/ml (an NK-sensitive erythroblastoma cell line used to reduce non-specific lysis). Target cells (100 μl) and effectors (100 μl) are plated in 96 well round-bottom plates and incubated for 5 hours at 37° C. At that time, 100 μl of supernatant are collected from each well and percent lysis is determined according to the formula:

[(cpm of the test sample-cpm of the spontaneous $^{51}$Cr release sample)/(cpm of the maximal $^{51}$Cr release sample-cpm of the spontaneous $^{51}$Cr release sample)]×100.

Maximum and spontaneous release are determined by incubating the labeled targets with 1% Triton X-100 and media alone, respectively. A positive culture is defined as one in which the specific lysis (sample-background) is 10% or higher in the case of individual wells and is 15% or more at the two highest E:T ratios when expanded cultures are assayed.

In Situ Measurement of Human IFNγ Production as an Indicator of Peptide-Specific and Endogenous Recognition Immulon 2 plates are coated with mouse anti-human IFNγ monoclonal antibody (4 µg/ml 0.1M NaHCO$_3$, pH8.2) overnight at 4° C. The plates are washed with Ca$^{2+}$, Mg$^{2+}$-free PBS/0.05% Tween 20 and blocked with PBS/10% FCS for two hours, after which the CTLs (100 µl/well) and targets (100 µl/well) are added to each well, leaving empty wells for the standards and blanks (which received media only). The target cells, either peptide-pulsed or endogenous targets, are used at a concentration of 1×10$^6$ cells/ml. The plates are incubated for 48 hours at 37° C. with 5% CO$_2$.

Recombinant human IFN-gamma is added to the standard wells starting at 400 pg or 1200 pg/100 microliter/well and the plate incubated for two hours at 37° C. The plates are washed and 100 µl of biotinylated mouse anti-human IFN-gamma monoclonal antibody (2 microgram/ml in PBS/3% FCS/0.05% Tween 20) are added and incubated for 2 hours at room temperature. After washing again, 100 microliter HRP-streptavidin (1:4000) are added and the plates incubated for one hour at room temperature. The plates are then washed 6× with wash buffer, 100 microliter/well developing solution (TMB 1:1) are added, and the plates allowed to develop for 5-15 minutes. The reaction is stopped with 50 microliter/well 1M H$_3$PO$_4$ and read at OD450. A culture is considered positive if it measured at least 50 pg of IFN-gamma/well above background and is twice the background level of expression.

CTL Expansion.

Those cultures that demonstrate specific lytic activity against peptide-pulsed targets and/or tumor targets are expanded over a two week period with anti-CD3. Briefly, 5×10$^4$ CD8+ cells are added to a T25 flask containing the following: 1×10$^6$ irradiated (4,200 rad) PBMC (autologous or allogeneic) per ml, 2×10$^5$ irradiated (8,000 rad) EBV-transformed cells per ml, and OKT3 (anti-CD3) at 30 ng per ml in RPMI-1640 containing 10% (v/v) human AB serum, non-essential amino acids, sodium pyruvate, 25 µM 2-mercaptoethanol, L-glutamine and penicillin/streptomycin. Recombinant human IL2 is added 24 hours later at a final concentration of 2001 U/ml and every three days thereafter with fresh media at 501 U/ml. The cells are split if the cell concentration exceeds 1×10$^6$/ml and the cultures are assayed between days 13 and 15 at E:T ratios of 30, 10, 3 and 1:1 in the $^{51}$Cr release assay or at 1×10$^6$/ml in the in situ IFNγ assay using the same targets as before the expansion.

Cultures are expanded in the absence of anti-CD3$^+$ as follows. Those cultures that demonstrate specific lytic activity against peptide and endogenous targets are selected and 5×10$^4$ CD8$^+$ cells are added to a T25 flask containing the following: 1×10$^6$ autologous PBMC per ml which have been peptide-pulsed with 10 µg/ml peptide for two hours at 37° C. and irradiated (4,200 rad); 2×10$^5$ irradiated (8,000 rad) EBV-transformed cells per ml RPMI-1640 containing 10% (v/v) human AB serum, non-essential AA, sodium pyruvate, 25 mM 2-ME, L-glutamine and gentamicin.

Immunogenicity of A2 Supermotif-Bearing Peptides

A2-supermotif cross-reactive binding peptides are tested in the cellular assay for the ability to induce peptide-specific CTL in normal individuals. In this analysis, a peptide is typically considered to be an epitope if it induces peptide-specific CTLs in at least individuals, and preferably, also recognizes the endogenously expressed peptide.

Immunogenicity can also be confirmed using PBMCs isolated from patients bearing a tumor that expresses 254P1D6B. Briefly, PBMCs are isolated from patients, re-stimulated with peptide-pulsed monocytes and assayed for the ability to recognize peptide-pulsed target cells as well as transfected cells endogenously expressing the antigen.

Evaluation of A*03/A11 Immunogenicity

HLA-A3 supermotif-bearing cross-reactive binding peptides are also evaluated for immunogenicity using methodology analogous for that used to evaluate the immunogenicity of the HLA-A2 supermotif peptides.

Evaluation of B7 Immunogenicity

Immunogenicity screening of the B7-supertype cross-reactive binding peptides identified as set forth herein are confirmed in a manner analogous to the confirmation of A2- and A3-supermotif-bearing peptides.

Peptides bearing other supermotifs/motifs, e.g., HLA-A1, HLA-A24 etc. are also confirmed using similar methodology Example 15

Implementation of the Extended Supermotif to Improve the Binding Capacity of Native Epitopes by Creating Analogs HLA motifs and supermotifs (comprising primary and/or secondary residues) are useful in the identification and preparation of highly cross-reactive native peptides, as demonstrated herein. Moreover, the definition of HLA motifs and supermotifs also allows one to engineer highly cross-reactive epitopes by identifying residues within a native peptide sequence which can be analoged to confer upon the peptide certain characteristics, e.g. greater cross-reactivity within the group of HLA molecules that comprise a supertype, and/or greater binding affinity for some or all of those HLA molecules. Examples of analoging peptides to exhibit modulated binding affinity are set forth in this example.

Analoging at Primary Anchor Residues

Peptide engineering strategies are implemented to further increase the cross-reactivity of the epitopes. For example, the main anchors of A2-supermotif-bearing peptides are altered, for example, to introduce a preferred L, I, V, or M at position 2, and I or V at the C-terminus.

To analyze the cross-reactivity of the analog peptides, each engineered analog is initially tested for binding to the prototype A2 supertype allele A*0201, then, if A*0201 binding capacity is maintained, for A2-supertype cross-reactivity.

Alternatively, a peptide is confirmed as binding one or all supertype members and then analoged to modulate binding affinity to any one (or more) of the supertype members to add population coverage.

The selection of analogs for immunogenicity in a cellular screening analysis is typically further restricted by the capacity of the parent wild type (WT) peptide to bind at least weakly, i.e., bind at an IC$_{50}$ of 500 nM or less, to three of more A2 supertype alleles. The rationale for this requirement is that the WT peptides must be present endogenously in sufficient quantity to be biologically relevant. Analoged peptides have been shown to have increased immunogenicity and cross-reactivity by T cells specific for the parent epitope (see, e.g., Parkhurst et al., J. Immunol. 157:2539, 1996; and Pogue et al., Proc. Natl. Acad. Sci. USA 92:8166, 1995).

In the cellular screening of these peptide analogs, it is important to confirm that analog-specific CTLs are also able to recognize the wild-type peptide and, when possible, target cells that endogenously express the epitope.

Analoging of HLA-A3 and B7-Supermotif-Bearing Peptides

Analogs of HLA-A3 supermotif-bearing epitopes are generated using strategies similar to those employed in analoging HLA-A2 supermotif-bearing peptides. For example, peptides binding to ⅗ of the A3-supertype molecules are engineered at primary anchor residues to possess a preferred residue (V, S, M, or A) at position 2.

The analog peptides are then tested for the ability to bind A*03 and A*11 (prototype A3 supertype alleles). Those peptides that demonstrate ≦500 nM binding capacity are then confirmed as having A3-supertype cross-reactivity.

Similarly to the A2- and A3-motif bearing peptides, peptides binding 3 or more B7-supertype alleles can be improved, where possible, to achieve increased cross-reactive binding or greater binding affinity or binding half life. B7 supermotif-bearing peptides are, for example, engineered to possess a preferred residue (V, I, L, or F) at the C-terminal primary anchor position, as demonstrated by Sidney et al. (*J. Immunol.* 157:3480-3490, 1996).

Analoging at primary anchor residues of other motif and/or supermotif-bearing epitopes is performed in a like manner.

The analog peptides are then be confirmed for immunogenicity, typically in a cellular screening assay. Again, it is generally important to demonstrate that analog-specific CTLs are also able to recognize the wild-type peptide and, when possible, targets that endogenously express the epitope.

Analoging at Secondary Anchor Residues

Moreover, HLA supermotifs are of value in engineering highly cross-reactive peptides and/or peptides that bind HLA molecules with increased affinity by identifying particular residues at secondary anchor positions that are associated with such properties. For example, the binding capacity of a B7 supermotif-bearing peptide with an F residue at position 1 is analyzed. The peptide is then analoged to, for example, substitute L for F at position 1. The analoged peptide is evaluated for increased binding affinity, binding half life and/or increased cross-reactivity. Such a procedure identifies analoged peptides with enhanced properties.

Engineered analogs with sufficiently improved binding capacity or cross-reactivity can also be tested for immunogenicity in HLA-B7-transgenic mice, following for example, IFA immunization or lipopeptide immunization. Analoged peptides are additionally tested for the ability to stimulate a recall response using PBMC from patients with 254P1D6B-expressing tumors.

Other Analoging Strategies

Another form of peptide analoging, unrelated to anchor positions, involves the substitution of a cysteine with α-amino butyric acid. Due to its chemical nature, cysteine has the propensity to form disulfide bridges and sufficiently alter the peptide structurally so as to reduce binding capacity. Substitution of α-amino butyric acid for cysteine not only alleviates this problem, but has been shown to improve binding and crossbinding capabilities in some instances (see, e.g., the review by Sette et al., In: Persistent Viral Infections, Eds. R. Ahmed and I. Chen, John Wiley & Sons, England, 1999).

Thus, by the use of single amino acid substitutions, the binding properties and/or cross-reactivity of peptide ligands for HLA supertype molecules can be modulated.

Example 16

Identification and Confirmation of 254P1D6B-Derived Sequences with HLA-DR Binding Motifs Peptide epitopes bearing an HLA class II supermotif or motif are identified and confirmed as outlined below using methodology similar to that described for HLA Class I peptides.

Selection of HLA-DR-Supermotif-Bearing Epitopes.

To identify 254P1D6B-derived, HLA class II HTL epitopes, a 254P1D6B antigen is analyzed for the presence of sequences bearing an HLA-DR-motif or supermotif. Specifically, 15-mer sequences are selected comprising a DR-supermotif, comprising a 9-mer core, and three-residue N- and C-terminal flanking regions (15 amino acids total).

Protocols for predicting peptide binding to DR molecules have been developed (Southwood et al., *J. Immunol.* 160: 3363-3373, 1998). These protocols, specific for individual DR molecules, allow the scoring, and ranking, of 9-mer core regions. Each protocol not only scores peptide sequences for the presence of DR-supermotif primary anchors (i.e., at position 1 and position 6) within a 9-mer core, but additionally evaluates sequences for the presence of secondary anchors. Using allele-specific selection tables (see, e.g., Southwood et al., ibid.), it has been found that these protocols efficiently select peptide sequences with a high probability of binding a particular DR molecule. Additionally, it has been found that performing these protocols in tandem, specifically those for DR1, DR4w4, and DR7, can efficiently select DR cross-reactive peptides.

The 254P1D6B-derived peptides identified above are tested for their binding capacity for various common HLA-DR molecules. All peptides are initially tested for binding to the DR molecules in the primary panel: DR1, DR4w4, and DR7. Peptides binding at least two of these three DR molecules are then tested for binding to DR2w2 β1, DR2w2 β2, DR6w19, and DR9 molecules in secondary assays. Finally, peptides binding at least two of the four secondary panel DR molecules, and thus cumulatively at least four of seven different DR molecules, are screened for binding to DR4w15, DR5w11, and DR8w2 molecules in tertiary assays. Peptides binding at least seven of the ten DR molecules comprising the primary, secondary, and tertiary screening assays are considered cross-reactive DR binders. 254P1D6B-derived peptides found to bind common HLA-DR alleles are of particular interest.

Selection of DR3 Motif Peptides

Because HLA-DR3 is an allele that is prevalent in Caucasian, Black, and Hispanic populations, DR3 binding capacity is a relevant criterion in the selection of HTL epitopes. Thus, peptides shown to be candidates may also be assayed for their DR3 binding capacity. However, in view of the binding specificity of the DR3 motif, peptides binding only to DR3 can also be considered as candidates for inclusion in a vaccine formulation.

To efficiently identify peptides that bind DR3, target 254P1D6B antigens are analyzed for sequences carrying one of the two DR3-specific binding motifs reported by Geluk et al. (*J. Immunol.* 152:5742-5748, 1994). The corresponding peptides are then synthesized and confirmed as having the ability to bind DR3 with an affinity of 1 μM or better, i.e., less than 1 μM. Peptides are found that meet this binding criterion and qualify as HLA class II high affinity binders.

DR3 binding epitopes identified in this manner are included in vaccine compositions with DR supermotif-bearing peptide epitopes.

Similarly to the case of HLA class I motif-bearing peptides, the class II motif-bearing peptides are analoged to improve affinity or cross-reactivity. For example, aspartic acid at position 4 of the 9-mer core sequence is an optimal residue for DR3 binding, and substitution for that residue often improves DR 3 binding.

Example 17

Immunogenicity of 254P1D6B-Derived HTL Epitopes

This example determines immunogenic DR supermotif- and DR3 motif-bearing epitopes among those identified using the methodology set forth herein.

Immunogenicity of HTL epitopes are confirmed in a manner analogous to the determination of immunogenicity of CTL epitopes, by assessing the ability to stimulate HTL responses and/or by using appropriate transgenic mouse models. Immunogenicity is determined by screening for: 1.) in vitro primary induction using normal PBMC or 2.) recall responses from patients who have 254P1D6B-expressing tumors.

Example 18

Calculation of Phenotypic Frequencies of HLA-Supertypes in Various Ethnic Backgrounds to Determine Breadth of Population Coverage This example illustrates the assessment of the breadth of population coverage of a vaccine composition comprised of multiple epitopes comprising multiple supermotifs and/or motifs.

In order to analyze population coverage, gene frequencies of HLA alleles are determined. Gene frequencies for each HLA allele are calculated from antigen or allele frequencies utilizing the binomial distribution formulae gf=1-(SQRT(1-af)) (see, e.g., Sidney et al., *Human Immunol.* 45:79-93, 1996). To obtain overall phenotypic frequencies, cumulative gene frequencies are calculated, and the cumulative antigen frequencies derived by the use of the inverse formula [af=1-(1-Cgf)$^2$].

Where frequency data is not available at the level of DNA typing, correspondence to the serologically defined antigen frequencies is assumed. To obtain total potential supertype population coverage no linkage disequilibrium is assumed, and only alleles confirmed to belong to each of the supertypes are included (minimal estimates). Estimates of total potential coverage achieved by inter-loci combinations are made by adding to the A coverage the proportion of the non-A covered population that could be expected to be covered by the B alleles considered (e.g., total=A+B*(1-A)). Confirmed members of the A3-like supertype are A3, A11, A31, A*3301, and A*6801. Although the A3-like supertype may also include A34, A66, and A*7401, these alleles were not included in overall frequency calculations. Likewise, confirmed members of the A2-like supertype family are A*0201, A*0202, A*0203, A*0204, A*0205, A*0206, A*0207, A*6802, and A*6901. Finally, the B7-like supertype-confirmed alleles are: B7, B*3501-03, B51, B*5301, B*5401, B*5501-2, B*5601, B*6701, and B*7801 (potentially also B*1401, B*3504-06, B*4201, and B*5602).

Population coverage achieved by combining the A2-, A3- and B7-supertypes is approximately 86% in five major ethnic groups. Coverage may be extended by including peptides bearing the A1 and A24 motifs. On average, A1 is present in 12% and A24 in 29% of the population across five different major ethnic groups (Caucasian, North American Black, Chinese, Japanese, and Hispanic). Together, these alleles are represented with an average frequency of 39% in these same ethnic populations. The total coverage across the major ethnicities when A1 and A24 are combined with the coverage of the A2-, A3- and B7-supertype alleles is >95%, see, e.g., Table IV (G). An analogous approach can be used to estimate population coverage achieved with combinations of class II motif-bearing epitopes.

Immunogenicity studies in humans (e.g., Bertoni et al., *J. Clin. Invest.* 100:503, 1997; Doolan et al., *Immunity* 7:97, 1997; and Threlkeld et al., *J. Immunol.* 159:1648, 1997) have shown that highly cross-reactive binding peptides are almost always recognized as epitopes. The use of highly cross-reactive binding peptides is an important selection criterion in identifying candidate epitopes for inclusion in a vaccine that is immunogenic in a diverse population.

With a sufficient number of epitopes (as disclosed herein and from the art), an average population coverage is predicted to be greater than 95% in each of five major ethnic populations. The game theory Monte Carlo simulation analysis, which is known in the art (see e.g., Osborne, M. J. and Rubinstein, A. "A course in game theory" MIT Press, 1994), can be used to estimate what percentage of the individuals in a population comprised of the Caucasian, North American Black, Japanese, Chinese, and Hispanic ethnic groups would recognize the vaccine epitopes described herein. A preferred percentage is 90%. A more preferred percentage is 95%.

Example 19

CTL Recognition of Endogenously Processed Antigens after Priming

This example confirms that CTL induced by native or analoged peptide epitopes identified and selected as described herein recognize endogenously synthesized, i.e., native antigens.

Effector cells isolated from transgenic mice that are immunized with peptide epitopes, for example HLA-A2 supermotif-bearing epitopes, are re-stimulated in vitro using peptide-coated stimulator cells. Six days later, effector cells are assayed for cytotoxicity and the cell lines that contain peptide-specific cytotoxic activity are further re-stimulated. An additional six days later, these cell lines are tested for cytotoxic activity on $^{51}$Cr labeled Jurkat-A2.1/K$^b$ target cells in the absence or presence of peptide, and also tested on $^{51}$Cr labeled target cells bearing the endogenously synthesized antigen, i.e. cells that are stably transfected with 254P1D6B expression vectors.

The results demonstrate that CTL lines obtained from animals primed with peptide epitope recognize endogenously synthesized 254P1D6B antigen. The choice of transgenic mouse model to be used for such an analysis depends upon the epitope(s) that are being evaluated. In addition to HLA-A*0201/Kb transgenic mice, several other transgenic mouse models including mice with human A11, which may also be used to evaluate A3 epitopes, and B7 alleles have been characterized and others (e.g., transgenic mice for HLA-A1 and A24) are being developed. HLA-DR1 and HLA-DR3 mouse models have also been developed, which may be used to evaluate HTL epitopes.

Example 20

Activity of CTL-HTL Conjugated Epitopes in Transgenic Mice

This example illustrates the induction of CTLs and HTLs in transgenic mice, by use of a 254P1D6B-derived CTL and HTL peptide vaccine compositions. The vaccine composition used herein comprise peptides to be administered to a patient with a 254P1D6B-expressing tumor. The peptide composition can comprise multiple CTL and/or HTL epitopes. The epitopes are identified using methodology as described herein. This example also illustrates that enhanced immunogenicity can be achieved by inclusion of one or more HTL epitopes in a CTL vaccine composition; such a peptide composition can comprise an HTL epitope conjugated to a CTL epitope. The CTL epitope can be one that binds to multiple HLA family members at an affinity of 500 nM or less, or analogs of that epitope. The peptides may be lipidated, if desired.

Immunization Procedures:

Immunization of transgenic mice is performed as described (Alexander et al., *J. Immunol.* 159:4753-4761, 1997). For example, A2/Kb mice, which are transgenic for the human HLA A2.1 allele and are used to confirm the immunogenicity of HLA-A*0201 motif- or HLA-A2 supermotif-bearing epitopes, and are primed subcutaneously (base of the tail) with a 0.1 ml of peptide in Incomplete Freund's Adjuvant, or if the peptide composition is a lipidated CTL/HTL conjugate, in DMSO/saline, or if the peptide composition is a polypeptide, in PBS or Incomplete Freund's Adjuvant. Seven days after priming, splenocytes obtained from these animals are restimulated with syngeneic irradiated LPS-activated lymphoblasts coated with peptide.

Cell Lines:

Target cells for peptide-specific cytotoxicity assays are Jurkat cells transfected with the HLA-A2.1/$K^b$ chimeric gene (e.g., Vitiello et al., *J. Exp. Med.* 173:1007, 1991)

In Vitro CTL Activation:

One week after priming, spleen cells ($30 \times 10^6$ cells/flask) are co-cultured at 37° C. with syngeneic, irradiated (3000 rads), peptide coated lymphoblasts ($1 \times 10^6$ cells/flask) in 10 ml of culture medium/T25 flask. After six days, effector cells are harvested and assayed for cytotoxic activity.

Assay for Cytotoxic Activity:

Target cells (1.0 to $1.5 \times 10^6$) are incubated at 37° C. in the presence of 200 µl of $^{51}$Cr. After 60 minutes, cells are washed three times and resuspended in R10 medium. Peptide is added where required at a concentration of 1 µg/ml. For the assay, $10^{4}$ $^{51}$Cr-labeled target cells are added to different concentrations of effector cells (final volume of 200 µl) in U-bottom 96-well plates. After a six hour incubation period at 37° C., a 0.1 ml aliquot of supernatant is removed from each well and radioactivity is determined in a Micromedic automatic gamma counter. The percent specific lysis is determined by the formula: percent specific release=100× (experimental release−spontaneous release)/(maximum release−spontaneous release). To facilitate comparison between separate CTL assays run under the same conditions, % $^{51}$Cr release data is expressed as lytic units/$10^6$ cells. One lytic unit is arbitrarily defined as the number of effector cells required to achieve 30% lysis of 10,000 target cells in a six hour $^{51}$Cr release assay. To obtain specific lytic units/106, the lytic units/$10^6$ obtained in the absence of peptide is subtracted from the lytic units/106 obtained in the presence of peptide. For example, if 30% $^{51}$Cr release is obtained at the effector (E): target (T) ratio of 50:1 (i.e., $5 \times 10^5$ effector cells for 10,000 targets) in the absence of peptide and 5:1 (i.e., $5 \times 10^4$ effector cells for 10,000 targets) in the presence of peptide, the specific lytic units would be: $[(1/50,000)-(1/500,000)] \times 10^{6=18}$ LU.

The results are analyzed to assess the magnitude of the CTL responses of animals injected with the immunogenic CTL/HTL conjugate vaccine preparation and are compared to the magnitude of the CTL response achieved using, for example, CTL epitopes as outlined above in the Example entitled "Confirmation of Immunogenicity." Analyses similar to this may be performed to confirm the immunogenicity of peptide conjugates containing multiple CTL epitopes and/or multiple HTL epitopes. In accordance with these procedures, it is found that a CTL response is induced, and concomitantly that an HTL response is induced upon administration of such compositions.

Example 21

Selection of CTL and HTL epitopes for inclusion in a 254P1D6B-Specific Vaccine

This example illustrates a procedure for selecting peptide epitopes for vaccine compositions of the invention. The peptides in the composition can be in the form of a nucleic acid sequence, either single or one or more sequences (i.e., minigene) that encodes peptide(s), or can be single and/or polyepitopic peptides.

The following principles are utilized when selecting a plurality of epitopes for inclusion in a vaccine composition. Each of the following principles is balanced in order to make the selection.

Epitopes are selected which, upon administration, mimic immune responses that are correlated with 254P1D6B clearance. The number of epitopes used depends on observations of patients who spontaneously clear 254P1D6B. For example, if it has been observed that patients who spontaneously clear 254P1D6B-expressing cells generate an immune response to at least three (3) epitopes from 254P1D6B antigen, then at least three epitopes should be included for HLA class I. A similar rationale is used to determine HLA class II epitopes.

Epitopes are often selected that have a binding affinity of an $IC_{50}$ of 500 nM or less for an HLA class I molecule, or for class II, an $IC_{50}$ of 1000 nM or less; or HLA Class I peptides with high binding scores from the BIMAS web site, at URL bimas.dcrt.nih.gov/.

In order to achieve broad coverage of the vaccine through out a diverse population, sufficient supermotif bearing peptides, or a sufficient array of allele-specific motif bearing peptides, are selected to give broad population coverage. In one embodiment, epitopes are selected to provide at least 80% population coverage. A Monte Carlo analysis, a statistical evaluation known in the art, can be employed to assess breadth, or redundancy, of population coverage.

When creating polyepitopic compositions, or a minigene that encodes same, it is typically desirable to generate the smallest peptide possible that encompasses the epitopes of interest. The principles employed are similar, if not the same, as those employed when selecting a peptide comprising nested epitopes. For example, a protein sequence for the vaccine composition is selected because it has maximal number of epitopes contained within the sequence, i.e., it has a high concentration of epitopes. Epitopes may be nested or overlapping (i.e., frame shifted relative to one another). For example, with overlapping epitopes, two 9-mer epitopes and one 10-mer epitope can be present in a 10 amino acid peptide. Each epitope can be exposed and bound by an HLA molecule upon administration of such a peptide. A multi-epitopic, peptide can be generated synthetically, recombinantly, or via cleavage from the native source. Alternatively, an analog can be made of this native sequence, whereby one or more of the epitopes comprise substitutions that alter the cross-reactivity and/or binding affinity properties of the polyepitopic peptide. Such a vaccine composition is administered for therapeutic or prophylactic purposes. This embodiment provides for the possibility that an as yet undiscovered aspect of immune system processing will apply to the native nested sequence and thereby facilitate the production of therapeutic or prophylactic immune response-inducing vaccine compositions. Additionally such an embodiment provides for the possibility of motif-bearing epitopes for an HLA makeup that is presently unknown. Furthermore, this embodiment (absent the creating of any analogs) directs the immune response to multiple peptide sequences that are actually present in 254P1D6B, thus avoiding the need to evaluate any junctional epitopes. Lastly, the embodiment provides an economy of scale when producing nucleic acid vaccine compositions. Related to this embodiment, computer programs can be derived in accordance with principles in the art, which identify in a target sequence, the greatest number of epitopes per sequence length.

A vaccine composition comprised of selected peptides, when administered, is safe, efficacious, and elicits an immune response similar in magnitude to an immune response that controls or clears cells that bear or overexpress 254P1D6B.

Example 22

Construction of "Minigene" Multi-Epitope DNA Plasmids

This example discusses the construction of a minigene expression plasmid. Minigene plasmids may, of course, contain various configurations of B cell, CTL and/or HTL epitopes or epitope analogs as described herein.

A minigene expression plasmid typically includes multiple CTL and HTL peptide epitopes. In the present example, HLA-A2, -A3, -B7 supermotif-bearing peptide epitopes and HLA-A1 and -A24 motif-bearing peptide epitopes are used in conjunction with DR supermotif-bearing epitopes and/or DR3 epitopes. HLA class I supermotif or motif-bearing peptide epitopes derived 254P1D6B, are selected such that multiple supermotifs/motifs are represented to ensure broad population coverage. Similarly, HLA class II epitopes are selected from 254P1D6B to provide broad population coverage, i.e. both HLA DR-1-4-7 supermotif-bearing epitopes and HLA DR-3 motif-bearing epitopes are selected for inclusion in the minigene construct. The selected CTL and HTL epitopes are then incorporated into a minigene for expression in an expression vector.

Such a construct may additionally include sequences that direct the HTL epitopes to the endoplasmic reticulum. For example, the Ii protein may be fused to one or more HTL epitopes as described in the art, wherein the CLIP sequence of the Ii protein is removed and replaced with an HLA class II epitope sequence so that HLA class II epitope is directed to the endoplasmic reticulum, where the epitope binds to an HLA class II molecules.

This example illustrates the methods to be used for construction of a minigene-bearing expression plasmid. Other expression vectors that may be used for minigene compositions are available and known to those of skill in the art.

The minigene DNA plasmid of this example contains a consensus Kozak sequence and a consensus murine kappa Ig-light chain signal sequence followed by CTL and/or HTL epitopes selected in accordance with principles disclosed herein. The sequence encodes an open reading frame fused to the Myc and His antibody epitope tag coded for by the pcDNA 3.1 Myc-His vector.

Overlapping oligonucleotides that can, for example, average about 70 nucleotides in length with 15 nucleotide overlaps, are synthesized and HPLC-purified. The oligonucleotides encode the selected peptide epitopes as well as appropriate linker nucleotides, Kozak sequence, and signal sequence. The final multiepitope minigene is assembled by extending the overlapping oligonucleotides in three sets of reactions using PCR. A Perkin/Elmer 9600 PCR machine is used and a total of 30 cycles are performed using the following conditions: 95° C. for 15 sec, annealing temperature (5° below the lowest calculated Tm of each primer pair) for 30 sec, and 72° C. for 1 min.

For example, a minigene is prepared as follows. For a first PCR reaction, 5 μg of each of two oligonucleotides are annealed and extended: In an example using eight oligonucleotides, i.e., four pairs of primers, oligonucleotides 1+2, 3+4, 5+6, and 7+8 are combined in 100 μl reactions containing Pfu polymerase buffer (1×=10 mM KCL, 10 mM $(NH4)_2SO_4$, 20 mM Tris-chloride, pH 8.75, 2 mM $MgSO_4$, 0.1% Triton X-100, 100 μg/ml BSA), 0.25 mM each dNTP, and 2.5 U of Pfu polymerase. The full-length dimer products are gel-purified, and two reactions containing the product of 1+2 and 3+4, and the product of 5+6 and 7+8 are mixed, annealed, and extended for 10 cycles. Half of the two reactions are then mixed, and 5 cycles of annealing and extension carried out before flanking primers are added to amplify the full length product. The full-length product is gel-purified and cloned into pCR-blunt (Invitrogen) and individual clones are screened by sequencing.

Example 23

The Plasmid Construct and the Degree to which it Induces Immunogenicity

The degree to which a plasmid construct, for example a plasmid constructed in accordance with the previous Example, is able to induce immunogenicity is confirmed in vitro by determining epitope presentation by APC following transduction or transfection of the APC with an epitope-expressing nucleic acid construct. Such a study determines "antigenicity" and allows the use of human APC. The assay determines the ability of the epitope to be presented by the APC in a context that is recognized by a T cell by quantifying the density of epitope-HLA class I complexes on the cell surface. Quantitation can be performed by directly measuring the amount of peptide eluted from the APC (see, e.g., Sijts et al., *J. Immunol.* 156:683-692, 1996; Demotz et al., *Nature* 342:682-684, 1989); or the number of peptide-HLA class I complexes can be estimated by measuring the amount of lysis or lymphokine release induced by diseased or transfected target cells, and then determining the concentration of peptide necessary to obtain equivalent levels of lysis or lymphokine release (see, e.g., Kageyama et al., *J. Immunol.* 154:567-576, 1995).

Alternatively, immunogenicity is confirmed through in vivo injections into mice and subsequent in vitro assessment of CTL and HTL activity, which are analyzed using cytotoxicity and proliferation assays, respectively, as detailed e.g., in Alexander et al., *Immunity* 1:751-761, 1994.

For example, to confirm the capacity of a DNA minigene construct containing at least one HLA-A2 supermotif peptide to induce CTLs in vivo, HLA-A2.1/K transgenic mice, for example, are immunized intramuscularly with 100 μg of naked cDNA. As a means of comparing the level of CTLs induced by cDNA immunization, a control group of animals is also immunized with an actual peptide composition that comprises multiple epitopes synthesized as a single polypeptide as they would be encoded by the minigene.

Splenocytes from immunized animals are stimulated twice with each of the respective compositions (peptide epitopes encoded in the minigene or the polyepitopic peptide), then assayed for peptide-specific cytotoxic activity in a $^{51}$Cr release assay. The results indicate the magnitude of the CTL response directed against the A2-restricted epitope, thus indicating the in vivo immunogenicity of the minigene vaccine and polyepitopic vaccine.

It is, therefore, found that the minigene elicits immune responses directed toward the HLA-A2 supermotif peptide epitopes as does the polyepitopic peptide vaccine. A similar analysis is also performed using other HLA-A3 and HLA-B7 transgenic mouse models to assess CTL induction by HLA-A3 and HLA-B7 motif or supermotif epitopes, whereby it is also found that the minigene elicits appropriate immune responses directed toward the provided epitopes.

To confirm the capacity of a class II epitope-encoding minigene to induce HTLs in vivo, DR transgenic mice, or for those epitopes that cross react with the appropriate mouse MHC molecule, I-A$^b$-restricted mice, for example, are immunized intramuscularly with 100 µg of plasmid DNA. As a means of comparing the level of HTLs induced by DNA immunization, a group of control animals is also immunized with an actual peptide composition emulsified in complete Freund's adjuvant. CD4+ T cells, i.e. HTLs, are purified from splenocytes of immunized animals and stimulated with each of the respective compositions (peptides encoded in the minigene). The HTL response is measured using a $^3$H-thymidine incorporation proliferation assay, (see, e.g., Alexander et al. Immunity 1:751-761, 1994). The results indicate the magnitude of the HTL response, thus demonstrating the in vivo immunogenicity of the minigene.

DNA minigenes, constructed as described in the previous Example, can also be confirmed as a vaccine in combination with a boosting agent using a prime boost protocol. The boosting agent can consist of recombinant protein (e.g., Barnett et al., *Aids Res. and Human Retroviruses* 14, Supplement 3:S299-S309, 1998) or recombinant vaccinia, for example, expressing a minigene or DNA encoding the complete protein of interest (see, e.g., Hanke et al., *Vaccine* 16:439-445, 1998; Sedegah et al., *Proc. Natl. Acad. Sci. USA* 95:7648-53, 1998; Hanke and McMichael, *Immunol. Letters* 66:177-181, 1999; and Robinson et al., *Nature Med.* 5:526-34, 1999).

For example, the efficacy of the DNA minigene used in a prime boost protocol is initially evaluated in transgenic mice. In this example, A2.1/K$^b$ transgenic mice are immunized IM with 100 µg of a DNA minigene encoding the immunogenic peptides including at least one HLA-A2 supermotif-bearing peptide. After an incubation period (ranging from 3-9 weeks), the mice are boosted IP with 10$^7$ pfu/mouse of a recombinant vaccinia virus expressing the same sequence encoded by the DNA minigene. Control mice are immunized with 100 µg of DNA or recombinant vaccinia without the minigene sequence, or with DNA encoding the minigene, but without the vaccinia boost. After an additional incubation period of two weeks, splenocytes from the mice are immediately assayed for peptide-specific activity in an ELISPOT assay. Additionally, splenocytes are stimulated in vitro with the A2-restricted peptide epitopes encoded in the minigene and recombinant vaccinia, then assayed for peptide-specific activity in an alpha, beta and/or gamma IFN ELISA.

It is found that the minigene utilized in a prime-boost protocol elicits greater immune responses toward the HLA-A2 supermotif peptides than with DNA alone. Such an analysis can also be performed using HLA-A11 or HLA-B7 transgenic mouse models to assess CTL induction by HLA-A3 or HLA-B7 motif or supermotif epitopes. The use of prime boost protocols in humans is described below in the Example entitled "Induction of CTL Responses Using a Prime Boost Protocol."

Example 24

Peptide Compositions for Prophylactic Uses

Vaccine compositions of the present invention can be used to prevent 254P1D6B expression in persons who are at risk for tumors that bear this antigen. For example, a polyepitopic peptide epitope composition (or a nucleic acid comprising the same) containing multiple CTL and HTL epitopes such as those selected in the above Examples, which are also selected to target greater than 80% of the population, is administered to individuals at risk for a 254P1D6B-associated tumor.

For example, a peptide-based composition is provided as a single polypeptide that encompasses multiple epitopes. The vaccine is typically administered in a physiological solution that comprises an adjuvant, such as Incomplete Freunds Adjuvant. The dose of peptide for the initial immunization is from about 1 to about 50,000 µg, generally 100-5,000 µg, for a 70 kg patient. The initial administration of vaccine is followed by booster dosages at 4 weeks followed by evaluation of the magnitude of the immune response in the patient, by techniques that determine the presence of epitope-specific CTL populations in a PBMC sample. Additional booster doses are administered as required. The composition is found to be both safe and efficacious as a prophylaxis against 254P1D6B-associated disease.

Alternatively, a composition typically comprising transfecting agents is used for the administration of a nucleic acid-based vaccine in accordance with methodologies known in the art and disclosed herein.

Example 25

Polyepitopic Vaccine Compositions Derived from Native 254P1D6B Sequences

A native 254P1D6B polyprotein sequence is analyzed, preferably using computer algorithms defined for each class I and/or class II supermotif or motif, to identify "relatively short" regions of the polyprotein that comprise multiple epitopes. The "relatively short" regions are preferably less in length than an entire native antigen. This relatively short sequence that contains multiple distinct or overlapping, "nested" epitopes can be used to generate a minigene construct. The construct is engineered to express the peptide, which corresponds to the native protein sequence. The "relatively short" peptide is generally less than 250 amino acids in length, often less than 100 amino acids in length, preferably less than 75 amino acids in length, and more preferably less than 50 amino acids in length. The protein sequence of the vaccine composition is selected because it has maximal number of epitopes contained within the sequence, i.e., it has a high concentration of epitopes. As noted herein, epitope motifs may be nested or overlapping (i.e., frame shifted relative to one another). For example, with overlapping epitopes, two 9-mer epitopes and one 10-mer epitope can be present in a 10 amino acid peptide. Such a vaccine composition is administered for therapeutic or prophylactic purposes.

The vaccine composition will include, for example, multiple CTL epitopes from 254P1D6B antigen and at least one HTL epitope. This polyepitopic native sequence is administered either as a peptide or as a nucleic acid sequence which encodes the peptide. Alternatively, an analog can be made of this native sequence, whereby one or more of the epitopes comprise substitutions that alter the cross-reactivity and/or binding affinity properties of the polyepitopic peptide.

The embodiment of this example provides for the possibility that an as yet undiscovered aspect of immune system processing will apply to the native nested sequence and thereby facilitate the production of therapeutic or prophylactic immune response-inducing vaccine compositions. Additionally, such an embodiment provides for the possibility of motif-bearing epitopes for an HLA makeup(s) that is presently unknown. Furthermore, this embodiment (excluding an analoged embodiment) directs the immune response to multiple peptide sequences that are actually present in native 254P1D6B, thus avoiding the need to evaluate any junctional epitopes. Lastly, the embodiment provides an economy of scale when producing peptide or nucleic acid vaccine compositions.

Related to this embodiment, computer programs are available in the art which can be used to identify in a target sequence, the greatest number of epitopes per sequence length.

Example 26

Polyepitopic Vaccine Compositions from Multiple Antigens

The 254P1D6B peptide epitopes of the present invention are used in conjunction with epitopes from other target tumor-associated antigens, to create a vaccine composition that is useful for the prevention or treatment of cancer that expresses 254P1D6B and such other antigens. For example, a vaccine composition can be provided as a single polypeptide that incorporates multiple epitopes from 254P1D6B as well as tumor-associated antigens that are often expressed with a target cancer associated with 254P1D6B expression, or can be administered as a composition comprising a cocktail of one or more discrete epitopes. Alternatively, the vaccine can be administered as a minigene construct or as dendritic cells which have been loaded with the peptide epitopes in vitro.

Example 27

Use of Peptides to Evaluate an Immune Response

Peptides of the invention may be used to analyze an immune response for the presence of specific antibodies, CTL or HTL directed to 254P1D6B. Such an analysis can be performed in a manner described by Ogg et al., Science 279: 2103-2106, 1998. In this Example, peptides in accordance with the invention are used as a reagent for diagnostic or prognostic purposes, not as an immunogen.

In this example highly sensitive human leukocyte antigen tetrameric complexes ("tetramers") are used for a cross-sectional analysis of, for example, 254P1D6B HLA-A*0201-specific CTL frequencies from HLA A*0201-positive individuals at different stages of disease or following immunization comprising a 254P1D6B peptide containing an A*0201 motif. Tetrameric complexes are synthesized as described (Musey et al., N. Engl. J. Med. 337:1267, 1997). Briefly, purified HLA heavy chain (A*0201 in this example) and β2-microglobulin are synthesized by means of a prokaryotic expression system. The heavy chain is modified by deletion of the transmembrane-cytosolic tail and COOH-terminal addition of a sequence containing a BirA enzymatic biotinylation site. The heavy chain, β2-microglobulin, and peptide are refolded by dilution. The 45-kD refolded product is isolated by fast protein liquid chromatography and then biotinylated by BirA in the presence of biotin (Sigma, St. Louis, Mo.), adenosine 5' triphosphate and magnesium. Streptavidin-phycoerythrin conjugate is added in a 1:4 molar ratio, and the tetrameric product is concentrated to 1 mg/ml. The resulting product is referred to as tetramer-phycoerythrin.

For the analysis of patient blood samples, approximately one million PBMCs are centrifuged at 300 g for 5 minutes and resuspended in 50 µl of cold phosphate-buffered saline. Tricolor analysis is performed with the tetramer-phycoerythrin, along with anti-CD8-Tricolor, and anti-CD38. The PBMCs are incubated with tetramer and antibodies on ice for 30 to 60 min and then washed twice before formaldehyde fixation. Gates are applied to contain >99.98% of control samples. Controls for the tetramers include both A*0201-negative individuals and A*0201-positive non-diseased donors. The percentage of cells stained with the tetramer is then determined by flow cytometry. The results indicate the number of cells in the PBMC sample that contain epitope-restricted CTLs, thereby readily indicating the extent of immune response to the 254P1D6B epitope, and thus the status of exposure to 254P1D6B, or exposure to a vaccine that elicits a protective or therapeutic response.

Example 28

Use of Peptide Epitopes to Evaluate Recall Responses

The peptide epitopes of the invention are used as reagents to evaluate T cell responses, such as acute or recall responses, in patients. Such an analysis may be performed on patients who have recovered from 254P1D6B-associated disease or who have been vaccinated with a 254P1D6B vaccine.

For example, the class I restricted CTL response of persons who have been vaccinated may be analyzed. The vaccine may be any 254P1D6B vaccine. PBMC are collected from vaccinated individuals and HLA typed. Appropriate peptide epitopes of the invention that, optimally, bear supermotifs to provide cross-reactivity with multiple HLA supertype family members, are then used for analysis of samples derived from individuals who bear that HLA type.

PBMC from vaccinated individuals are separated on Ficoll-Histopaque density gradients (Sigma Chemical Co., St. Louis, Mo.), washed three times in HBSS (GIBCO Laboratories), resuspended in RPMI-1640 (GIBCO Laboratories) supplemented with L-glutamine (2 mM), penicillin (50 U/ml), streptomycin (50 µg/ml), and Hepes (10 mM) containing 10% heat-inactivated human AB serum (complete RPMI) and plated using microculture formats. A synthetic peptide comprising an epitope of the invention is added at 10 µg/ml to each well and HBV core 128-140 epitope is added at 1 µg/ml to each well as a source of T cell help during the first week of stimulation.

In the microculture format, $4 \times 10^5$ PBMC are stimulated with peptide in 8 replicate cultures in 96-well round bottom plate in 100 µl/well of complete RPMI. On days 3 and 10, 100 µl of complete RPMI and 20 U/ml final concentration of rIL-2 are added to each well. On day 7 the cultures are transferred into a 96-well flat-bottom plate and restimulated with peptide, rIL-2 and 105 irradiated (3,000 rad) autologous feeder cells. The cultures are tested for cytotoxic activity on day 14. A positive CTL response requires two or more of the eight replicate cultures to display greater than 10% specific $^{51}$Cr release, based on comparison with non-diseased control subjects as previously described (Rehermann, et al., Nature Med. 2:1104,1108, 1996; Rehermann et al., J. Clin. Invest. 97:1655-1665, 1996; and Rehermann et al. J. Clin. Invest. 98:1432-1440, 1996).

Target cell lines are autologous and allogeneic EBV-transformed B-LCL that are either purchased from the American Society for Histocompatibility and Immunogenetics (ASHI, Boston, Mass.) or established from the pool of patients as described (Guilhot, et al. J. Virol. 66:2670-2678, 1992).

Cytotoxicity assays are performed in the following manner. Target cells consist of either allogeneic HLA-matched or autologous EBV-transformed B lymphoblastoid cell line that are incubated overnight with the synthetic peptide epitope of the invention at 10 µM, and labeled with 100 µCi of $^{51}$Cr (Amersham Corp., Arlington Heights, Ill.) for 1 hour after which they are washed four times with HBSS.

Cytolytic activity is determined in a standard 4-h, split well $^{51}$Cr release assay using U-bottomed 96 well plates containing 3,000 targets/well. Stimulated PBMC are tested at effector/target (E/T) ratios of 20-50:1 on day 14. Percent cytotoxicity is determined from the formula: 100×[(experimental release-spontaneous release)/maximum release-spontaneous release)]. Maximum release is determined by lysis of targets by detergent (2% Triton X-100; Sigma Chemical Co., St. Louis, Mo.). Spontaneous release is <25% of maximum release for all experiments.

The results of such an analysis indicate the extent to which HLA-restricted CTL populations have been stimulated by previous exposure to 254P1D6B or a 254P1D6B vaccine.

Similarly, Class II restricted HTL responses may also be analyzed. Purified PBMC are cultured in a 96-well flat bottom plate at a density of $1.5 \times 10^5$ cells/well and are stimulated with 10 µg/ml synthetic peptide of the invention, whole 254P1D6B antigen, or PHA. Cells are routinely plated in replicates of 4-6 wells for each condition. After seven days of culture, the medium is removed and replaced with fresh medium containing 10 U/ml IL-2. Two days later, 1 µCi $^3$H-thymidine is added to each well and incubation is continued for an additional 18 hours. Cellular DNA is then harvested on glass fiber mats and analyzed for $^3$H-thymidine incorporation. Antigen-specific T cell proliferation is calculated as the ratio of $^3$H-thymidine incorporation in the presence of antigen divided by the $^3$H-thymidine incorporation in the absence of antigen.

Example 29

Induction of Specific CTL Response in Humans

A human clinical trial for an immunogenic composition comprising CTL and HTL epitopes of the invention is set up as an IND Phase I, dose escalation study and carried out as a randomized, double-blind, placebo-controlled trial. Such a trial is designed, for example, as follows:

A total of about 27 individuals are enrolled and divided into 3 groups:

Group I: 3 subjects are injected with placebo and 6 subjects are injected with 5 µg of peptide composition;

Group II: 3 subjects are injected with placebo and 6 subjects are injected with 50 µg peptide composition;

Group III: 3 subjects are injected with placebo and 6 subjects are injected with 500 µg of peptide composition.

After 4 weeks following the first injection, all subjects receive a booster inoculation at the same dosage.

The endpoints measured in this study relate to the safety and tolerability of the peptide composition as well as its immunogenicity. Cellular immune responses to the peptide composition are an index of the intrinsic activity of this the peptide composition, and can therefore be viewed as a measure of biological efficacy. The following summarize the clinical and laboratory data that relate to safety and efficacy endpoints.

Safety: The incidence of adverse events is monitored in the placebo and drug treatment group and assessed in terms of degree and reversibility.

Evaluation of Vaccine Efficacy: For evaluation of vaccine efficacy, subjects are bled before and after injection. Peripheral blood mononuclear cells are isolated from fresh heparinized blood by Ficoll-Hypaque density gradient centrifugation, aliquoted in freezing media and stored frozen. Samples are assayed for CTL and HTL activity.

The vaccine is found to be both safe and efficacious.

Example 30

Phase II Trials in Patients Expressing 254P1D6B

Phase II trials are performed to study the effect of administering the CTL-HTL peptide compositions to patients having cancer that expresses 254P1D6B. The main objectives of the trial are to determine an effective dose and regimen for inducing CTLs in cancer patients that express 254P1D6B, to establish the safety of inducing a CTL and HTL response in these patients, and to see to what extent activation of CTLs improves the clinical picture of these patients, as manifested, e.g., by the reduction and/or shrinking of lesions. Such a study is designed, for example, as follows:

The studies are performed in multiple centers. The trial design is an open-label, uncontrolled, dose escalation protocol wherein the peptide composition is administered as a single dose followed six weeks later by a single booster shot of the same dose. The dosages are 50, 500 and 5,000 micrograms per injection. Drug-associated adverse effects (severity and reversibility) are recorded.

There are three patient groupings. The first group is injected with 50 micrograms of the peptide composition and the second and third groups with 500 and 5,000 micrograms of peptide composition, respectively. The patients within each group range in age from 21-65 and represent diverse ethnic backgrounds. All of them have a tumor that expresses 254P1D6B.

Clinical manifestations or antigen-specific T-cell responses are monitored to assess the effects of administering the peptide compositions. The vaccine composition is found to be both safe and efficacious in the treatment of 254P1D6B-associated disease.

Example 31

Induction of CTL Responses Using a Prime Boost Protocol

A prime boost protocol similar in its underlying principle to that used to confirm the efficacy of a DNA vaccine in transgenic mice, such as described above in the Example entitled "The Plasmid Construct and the Degree to Which It Induces Immunogenicity," can also be used for the administration of the vaccine to humans. Such a vaccine regimen can include an initial administration of, for example, naked DNA followed by a boost using recombinant virus encoding the vaccine, or recombinant protein/polypeptide or a peptide mixture administered in an adjuvant.

For example, the initial immunization may be performed using an expression vector, such as that constructed in the Example entitled "Construction of "Minigene" Multi-Epitope DNA Plasmids" in the form of naked nucleic acid administered IM (or SC or ID) in the amounts of 0.5-5 mg at multiple sites. The nucleic acid (0.1 to 1000 µg) can also be administered using a gene gun. Following an incubation period of 3-4 weeks, a booster dose is then administered. The booster can be recombinant fowlpox virus administered at a dose of $5\text{-}10^7$ to $5\times10^9$ pfu. An alternative recombinant virus, such as an MVA, canarypox, adenovirus, or adeno-associated virus, can also be used for the booster, or the polyepitopic protein or a mixture of the peptides can be administered. For evaluation of vaccine efficacy, patient blood samples are obtained before immunization as well as at intervals following administration of the initial vaccine and booster doses of the vaccine. Peripheral blood mononuclear cells are isolated from fresh heparinized blood by Ficoll-Hypaque density gradient centrifugation, aliquoted in freezing media and stored frozen. Samples are assayed for CTL and HTL activity.

Analysis of the results indicates that a magnitude of response sufficient to achieve a therapeutic or protective immunity against 254P1D6B is generated.

Example 32

Administration of Vaccine Compositions Using Dendritic Cells (DC)

Vaccines comprising peptide epitopes of the invention can be administered using APCs, or "professional" APCs such as DC. In this example, peptide-pulsed DC are administered to a patient to stimulate a CTL response in vivo. In this method, dendritic cells are isolated, expanded, and pulsed with a vaccine comprising peptide CTL and HTL epitopes of the invention. The dendritic cells are infused back into the patient to elicit CTL and HTL responses in vivo. The induced CTL and HTL then destroy or facilitate destruction, respectively, of the target cells that bear the 254P1D6B protein from which the epitopes in the vaccine are derived.

For example, a cocktail of epitope-comprising peptides is administered ex vivo to PBMC, or isolated DC therefrom. A pharmaceutical to facilitate harvesting of DC can be used, such as Progenipoietin™ (Monsanto, St. Louis, Mo.) or GM-CSF/IL-4. After pulsing the DC with peptides, and prior to reinfusion into patients, the DC are washed to remove unbound peptides.

As appreciated clinically, and readily determined by one of skill based on clinical outcomes, the number of DC reinfused into the patient can vary (see, e.g., Nature Med. 4:328, 1998; Nature Med. 2:52, 1996 and Prostate 32:272, 1997). Although $2\text{-}50\times10^6$ DC per patient are typically administered, larger number of DC, such as 107 or 108 can also be provided. Such cell populations typically contain between 50-90% DC.

In some embodiments, peptide-loaded PBMC are injected into patients without purification of the DC. For example, PBMC generated after treatment with an agent such as Progenipoietin™ are injected into patients without purification of the DC. The total number of PBMC that are administered often ranges from 108 to 1010. Generally, the cell doses injected into patients is based on the percentage of DC in the blood of each patient, as determined, for example, by immunofluorescence analysis with specific anti-DC antibodies. Thus, for example, if Progenipoietin™ mobilizes 2% DC in the peripheral blood of a given patient, and that patient is to receive $5\times10^6$ DC, then the patient will be injected with a total of $2.5\times10^8$ peptide-loaded PBMC. The percent DC mobilized by an agent such as Progenipoietin™ is typically estimated to be between 2-10%, but can vary as appreciated by one of skill in the art.

Ex Vivo Activation of CTL/HTL Responses

Alternatively, ex vivo CTL or HTL responses to 254P1D6B antigens can be induced by incubating, in tissue culture, the patient's, or genetically compatible, CTL or HTL precursor cells together with a source of APC, such as DC, and immunogenic peptides. After an appropriate incubation time (typically about 7-28 days), in which the precursor cells are activated and expanded into effector cells, the cells are infused into the patient, where they will destroy (CTL) or facilitate destruction (HTL) of their specific target cells, i.e., tumor cells.

Example 33

An Alternative Method of Identifying and Confirming Motif-Bearing Peptides

Another method of identifying and confirming motif-bearing peptides is to elute them from cells bearing defined MHC molecules. For example, EBV transformed B cell lines used for tissue typing have been extensively characterized to determine which HLA molecules they express. In certain cases these cells express only a single type of HLA molecule. These cells can be transfected with nucleic acids that express the antigen of interest, e.g. 254P1D6B. Peptides produced by endogenous antigen processing of peptides produced as a result of transfection will then bind to HLA molecules within the cell and be transported and displayed on the cell's surface. Peptides are then eluted from the HLA molecules by exposure to mild acid conditions and their amino acid sequence determined, e.g., by mass spectral analysis (e.g., Kubo et al., J. Immunol. 152:3913, 1994). Because the majority of peptides that bind a particular HLA molecule are motif-bearing, this is an alternative modality for obtaining the motif-bearing peptides correlated with the particular HLA molecule expressed on the cell.

Alternatively, cell lines that do not express endogenous HLA molecules can be transfected with an expression construct encoding a single HLA allele. These cells can then be used as described, i.e., they can then be transfected with nucleic acids that encode 254P1D6B to isolate peptides corresponding to 254P1D6B that have been presented on the cell surface. Peptides obtained from such an analysis will bear motif(s) that correspond to binding to the single HLA allele that is expressed in the cell.

As appreciated by one in the art, one can perform a similar analysis on a cell bearing more than one HLA allele and subsequently determine peptides specific for each HLA allele expressed. Moreover, one of skill would also recognize that means other than transfection, such as loading with a protein antigen, can be used to provide a source of antigen to the cell.

Example 34

Complementary Polynucleotides

Sequences complementary to the 254P1D6B-encoding sequences, or any parts thereof, are used to detect, decrease, or inhibit expression of naturally occurring 254P1D6B. Although use of oligonucleotides comprising from about 15 to 30 base pairs is described, essentially the same procedure is used with smaller or with larger sequence fragments. Appropriate oligonucleotides are designed using, e.g., OLIGO 4.06 software (National Biosciences) and the coding sequence of 254P1D6B. To inhibit transcription, a complementary oligonucleotide is designed from the most unique 5' sequence and used to prevent promoter binding to the coding sequence. To inhibit translation, a complementary oligonucleotide is designed to prevent ribosomal binding to a 254P1D6B-encoding transcript.

Example 35

Purification of Naturally-Occurring or Recombinant 254P1D6B Using 254P1D6B-Specific Antibodies Naturally occurring or recombinant 254P1D6B is substantially purified by immunoaffinity chromatography using antibodies specific for 254P1D6B. An immunoaffinity column is constructed by covalently coupling anti-254P1D6B antibody to an activated chromatographic resin, such as CNBr-activated SEPHAROSE (Amersham Pharmacia Biotech). After the coupling, the resin is blocked and washed according to the manufacturer's instructions.

Media containing 254P1D6B are passed over the immunoaffinity column, and the column is washed under conditions that allow the preferential absorbance of 254P1D6B (e.g., high ionic strength buffers in the presence of detergent). The column is eluted under conditions that disrupt antibody/254P1D6B binding (e.g., a buffer of pH 2 to pH 3, or a high concentration of a chaotrope, such as urea or thiocyanate ion), and GCR.P is collected.

Example 36

Identification of Molecules which Interact with 254P1D6B

254P1D6B, or biologically active fragments thereof, are labeled with 1211 Bolton-Hunter reagent. (See, e.g., Bolton et al. (1973) Biochem. J. 133:529.) Candidate molecules previously arrayed in the wells of a multi-well plate are incubated with the labeled 254P1D6B, washed, and any wells with labeled 254P1D6B complex are assayed. Data obtained using different concentrations of 254P1D6B are used to calculate values for the number, affinity, and association of 254P1D6B with the candidate molecules.

Example 37

In Vivo Assay for 254P1D6B Tumor Growth Promotion

The effect of a 254P1D6B protein on tumor cell growth can be confirmed in vivo by gene overexpression in a variety of cancer cells such as those in Table I. For example, as appropriate, SCID mice can be injected SQ on each flank with $1 \times 10^6$ prostate, kidney, colon or bladder cancer cells (such as PC3, LNCaP, SCaBER, UM-UC-3, HT1376, SK-CO, Caco, RT4, T24, Caki, A-498 and SW839 cells) containing tkNeo empty vector or 254P1D6B.

At least two strategies can be used:

(1) Constitutive 254P1D6B expression under regulation of a promoter such as a constitutive promoter obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), or from heterologous mammalian promoters, e.g., the actin promoter or an immunoglobulin promoter, provided such promoters are compatible with the host cell systems.

(2) Regulated expression under control of an inducible vector system, such as ecdysone, tet, etc., can be used provided such promoters are compatible with the host cell systems. Tumor volume is then monitored at the appearance of palpable tumors or by following serum markers such as PSA. Tumor development is followed over time to validate that 254P1D6B-expressing cells grow at a faster rate and/or that tumors produced by 254P1D6B-expressing cells demonstrate characteristics of altered aggressiveness (e.g., enhanced metastasis, vascularization, reduced responsiveness to chemotherapeutic drugs). Tumor volume is evaluated by caliper measurements. Additionally, mice can be implanted with the same cells orthotopically in the prostate, bladder, colon or kidney to determine if 254P1D6B has an effect on local growth, e.g., in the prostate, bladder, colon or kidney or on the ability of the cells to metastasize, specifically to lungs or lymph nodes (Saffran et al., Proc Natl Acad Sci USA. 2001, 98: 2658; Fu, X., et al., Int. J. Cancer, 1991. 49: 938-939; Chang, S., et al., Anticancer Res., 1997, 17: 3239-3242; Peralta, E. A., et al., J. Urol., 1999. 162: 1806-1811). For instance, the orthotopic growth of PC3 and PC3-254P1D6B can be compared in the prostate of SCID mice. Such experiments reveal the effect of 254P1D6B on orthotopic tumor growth, metastasis and/or angiogenic potential.

Furthermore, this assay is useful to confirm the inhibitory effect of candidate therapeutic compositions, such as 254P1D6B antibodies or intrabodies, and 254P1D6B antisense molecules or ribozymes, or 254P1D6B directed small molecules, on cells that express a 254P1D6B protein.

Example 38

254P1D6B Monoclonal Antibody-Mediated Inhibition of Tumors In Vivo

The significant expression of 254P1D6B, in cancer tissues, together with its restricted expression in normal tissues makes 254P1D6B an excellent target for antibody therapy. Similarly, 254P1D6B is a target for T cell-based immunotherapy. Thus, the therapeutic efficacy of anti-254P1D6B mAbs is evaluated, e.g., in human prostate cancer xenograft mouse models using androgen-independent LAPC-4 and LAPC-9 xenografts (Craft, N., et al. Cancer Res, 1999. 59(19): p. 5030-5036), kidney cancer xenografts (AGS-K3, AGS-K6), kidney cancer metastases to lymph node (AGS-K6 met) xenografts, and kidney cancer cell lines transfected with 254P1D6B, such as 769P-254P1D6B, A498-254P1D6B.

Antibody efficacy on tumor growth and metastasis formation is studied, e.g., in mouse orthotopic prostate cancer xenograft models and mouse kidney xenograft models. The antibodies can be unconjugated, as discussed in this example, or can be conjugated to a therapeutic modality, as appreciated in the art. Anti-254P1D6B mAbs inhibit formation of both the androgen-dependent LAPC-9 and androgen-independent PC3-254P1D6B tumor xenografts. Anti-254P1D6B mAbs also retard the growth of established orthotopic tumors and prolonged survival of tumor-bearing mice. These results indicate the utility of anti-254P1D6B mAbs in the treatment of local and advanced stages of, e.g., prostate cancer. (See, e.g., Saffran, D., et al., PNAS10: 1073-1078 or located on the World Wide Web at (.pnas.org/cgi/doi/10.1073/pnas.051624698). Similarly, anti-254P1D6B mAbs inhibit formation of AGS-K3 and AGS-K6 tumors in SCID mice, and prevent or retard the growth A498-254P1D6B tumor xenografts. These results indicate the use of anti-254P1D6B mAbs in the treatment of prostate and/or kidney cancer.

Administration of the anti-254P1D6B mAbs leads to retardation of established orthotopic tumor growth and inhibition of metastasis to distant sites, resulting in a significant prolongation in the survival of tumor-bearing mice. These studies indicate that 254P1D6B is an attractive target for immunotherapy and demonstrate the therapeutic use of anti-254P1D6B mAbs for the treatment of local and metastatic cancer. This example demonstrates that unconjugated 254P1D6B monoclonal antibodies are effective to inhibit the growth of human prostate tumor xenografts and human kidney xenografts grown in SCID mice.

Tumor Inhibition Using Multiple Unconjugated 254P1D6B Mabs Materials and Methods 254P1D6B Monoclonal Antibodies:

Monoclonal antibodies are obtained against 254P1D6B, as described in Example 11 entitled: *Generation of 254P1D6B Monoclonal Antibodies (mAbs)*, or may be obtained commercially. The antibodies are characterized by ELISA, Western blot, FACS, and immunoprecipitation for their capacity to bind 254P1D6B. Epitope mapping data for the anti-254P1D6B mAbs, as determined by ELISA and Western analysis, recognize epitopes on a 254P1D6B protein. Immunohistochemical analysis of cancer tissues and cells is performed with these antibodies.

The monoclonal antibodies are purified from ascites or hybridoma tissue culture supernatants by Protein-G Sepharose chromatography, dialyzed against PBS, filter sterilized, and stored at −20° C. Protein determinations are performed by a Bradford assay (Bio-Rad, Hercules, Calif.). A therapeutic monoclonal antibody or a cocktail comprising a mixture of individual monoclonal antibodies is prepared and used for the treatment of mice receiving subcutaneous or orthotopic injections of, e.g., LAPC-9 prostate tumor xenografts.

Cancer Xenografts and Cell Lines

The LAPC-9 xenograft, which expresses a wild-type androgen receptor and produces prostate-specific antigen (PSA), is passaged in 6- to 8-week-old male ICR-severe combined immunodeficient (SCID) mice (Taconic Farms) by subcutaneous (s.c.) trocar implant (Craft, N., et al., 1999, Cancer Res. 59:5030-5036). The AGS-K3 and AGS-K6 kidney xenografts are also passaged by subcutaneous implants in 6- to 8-week old SCID mice. Single-cell suspensions of tumor cells are prepared as described in Craft, et al. The prostate carcinoma cell line PC3 (American Type Culture Collection) is maintained in RPMI supplemented with L-glutamine and 10% FBS, and the kidney carcinoma line A498 (American Type Culture Collection) is maintained in DMEM supplemented with L-glutamine and 10% FBS.

PC3-254P1D6B and A498-254P1D6B cell populations are generated by retroviral gene transfer as described in Hubert, R. S., et al., STEAP: A Prostate-specific Cell-surface Antigen Highly Expressed in Human Prostate Tumors, Proc Natl. Acad. Sci. USA, 1999. 96(25): p. 14523-14528. Anti-254P1D6B staining is detected by using, e.g., an FITC-conjugated goat anti-mouse antibody (Southern Biotechnology Associates) followed by analysis on a Coulter Epics-XL flow cytometer.

Xenograft Mouse Models.

Subcutaneous (s.c.) tumors are generated by injection of $1 \times 10^6$ LAPC-9, AGS-K3, AGS-K6, PC3, PC3-254P1D6B, A498 or A498-254P1D6B cells mixed at a 1:1 dilution with Matrigel (Collaborative Research) in the right flank of male SCID mice. To test antibody efficacy on tumor formation, i.p. antibody injections are started on the same day as tumor-cell injections. As a control, mice are injected with either purified mouse IgG (ICN) or PBS; or a purified monoclonal antibody that recognizes an irrelevant antigen not expressed in human cells. In preliminary studies, no difference is found between mouse IgG or PBS on tumor growth. Tumor sizes are determined by vernier caliper measurements, and the tumor volume is calculated as length×width×height. Mice with s.c. tumors greater than 1.5 cm in diameter are sacrificed. PSA levels are determined by using a PSA ELISA kit (Anogen, Mississauga, Ontario). Circulating levels of anti-254P1D6B mAbs are determined by a capture ELISA kit (Bethyl Laboratories, Montgomery, Tex.). (See, e.g., (Saffran, D., et al., PNAS10:1073-1078 or on the world wide web as pnas.org/cgi/doi/10.1073/pnas.051624698)

Orthotopic prostate injections are performed under anesthesia by using ketamine/xylazine. For prostate orthotopic studies, an incision is made through the abdominal muscles to expose the bladder and seminal vesicles, which then are delivered through the incision to expose the dorsal prostate. LAPC-9 cells ($5 \times 10^5$) mixed with Matrigel are injected into each dorsal lobe in a 10 µl volume. To monitor tumor growth, mice are bled on a weekly basis for determination of PSA levels. For kidney orthotopic models, an incision is made through the abdominal muscles to expose the kidney. AGS-K3 or AGS-K6 cells mixed with Matrigel are injected under the kidney capsule. The mice are segregated into groups for appropriate treatments, with anti-254P1D6B or control mAbs being injected i.p.

Anti-254P1D6B mAbs Inhibit Growth of 254P1D6B-Expressing Xenograft-Cancer Tumors The effect of anti-254P1D6B mAbs on tumor formation is tested by using, e.g., LAPC-9 and/or AGS-K3 orthotopic models. As compared with the s.c. tumor model, the orthotopic model, which requires injection of tumor cells directly in the mouse prostate or kidney, respectively, results in a local tumor growth, development of metastasis in distal sites, deterioration of mouse health, and subsequent death (Saffran, D., et al., PNAS supra; Fu, X., et al., Int J Cancer, 1992. 52(6): p. 987-90; Kubota, T., J Cell Biochem, 1994. 56(1): p. 4-8). The features make the orthotopic model more representative of human disease progression and allow for tracking of the therapeutic effect of mAbs on clinically relevant end points.

Accordingly, tumor cells are injected into the mouse prostate or kidney, and the mice are segregated into two groups and treated with either: a) 200-500 µg, of anti-254P1D6B Ab, or b) PBS for two to five weeks.

As noted, a major advantage of the orthotopic prostate-cancer model is the ability to study the development of metastases. Formation of metastasis in mice bearing established orthotopic tumors is studied by IHC analysis on lung sections using an antibody against a prostate-specific cell-surface protein STEAP expressed at high levels in LAPC-9 xenografts (Hubert, R. S., et al., Proc Natl. Acad. Sci. USA, 1999. 96(25): p. 14523-14528) or anti-G250 antibody for kidney cancer models. G250 is a clinically relevant marker for renal clear cell carcinoma, which is selectively expressed on tumor but not normal kidney cells (Grabmaier K et al., Int J. Cancer. 2000, 85: 865).

Mice bearing established orthotopic LAPC-9 tumors are administered 500-1000 g injections of either anti-254P1D6B mAb or PBS over a 4-week period. Mice in both groups are allowed to establish a high tumor burden (PSA levels greater than 300 ng/ml), to ensure a high frequency of metastasis formation in mouse lungs. Mice then are killed and their prostate/kidney and lungs are analyzed for the presence of tumor cells by IHC analysis.

These studies demonstrate a broad anti-tumor efficacy of anti-254P1D6B antibodies on initiation and/or progression of prostate and kidney cancer in xenograft mouse models. Anti-254P1D6B antibodies inhibit tumor formation of both androgen-dependent and androgen-independent prostate tumors as well as retarding the growth of already established tumors and prolong the survival of treated mice. Moreover, anti-254P1D6B mAbs demonstrate a dramatic inhibitory effect on the spread of local prostate tumor to distal sites, even in the presence of a large tumor burden. Similar therapeutic effects are seen in the kidney cancer model. Thus, anti-254P1D6B mAbs are efficacious on major clinically relevant end points (tumor growth), prolongation of survival, and health.

Example 39

Therapeutic and Diagnostic Use of Anti-254P1D6B Antibodies in Humans

Anti-254P1D6B monoclonal antibodies are safely and effectively used for diagnostic, prophylactic, prognostic and/or therapeutic purposes in humans. Western blot and immunohistochemical analysis of cancer tissues and cancer xenografts with anti-254P1D6B mAb show strong extensive staining in carcinoma but significantly lower or undetectable levels in normal tissues. Detection of 254P1D6B in carcinoma and in metastatic disease demonstrates the usefulness of the mAb as a diagnostic and/or prognostic indicator. Anti-254P1D6B antibodies are therefore used in diagnostic applications such as immunohistochemistry of kidney biopsy specimens to detect cancer from suspect patients.

As determined by flow cytometry, anti-254P1D6B mAb specifically binds to carcinoma cells. Thus, anti-254P1D6B antibodies are used in diagnostic whole body imaging applications, such as radioimmunoscintigraphy and radioimmunotherapy, (see, e.g., Potamianos S., et. al. Anticancer Res 20(2A):925-948 (2000)) for the detection of localized and metastatic cancers that exhibit expression of 254P1D6B. Shedding or release of an extracellular domain of 254P1D6B into the extracellular milieu, such as that seen for alkaline phosphodiesterase B10 (Meerson, N. R., Hepatology 27:563-568 (1998)), allows diagnostic detection of 254P1D6B by anti-254P1D6B antibodies in serum and/or urine samples from suspect patients.

Anti-254P1D6B antibodies that specifically bind 254P1D6B are used in therapeutic applications for the treatment of cancers that express 254P1D6B. Anti-254P1D6B antibodies are used as an unconjugated modality and as conjugated form in which the antibodies are attached to one of various therapeutic or imaging modalities well known in the art, such as a prodrugs, enzymes or radioisotopes. In preclinical studies, unconjugated and conjugated anti-254P1D6B antibodies are tested for efficacy of tumor prevention and growth inhibition in the SCID mouse cancer xenograft models, e.g., kidney cancer models AGS-K3 and AGS-K6, (see, e.g., the Example entitled "254P1D6B Monoclonal Antibody-mediated Inhibition of Bladder and Lung Tumors In Vivo"). Either conjugated and unconjugated anti-254P1D6B antibodies are used as a therapeutic modality in human clinical trials either alone or in combination with other treatments as described in following Examples.

Example 40

Human Clinical Trials for the Treatment and Diagnosis of Human

Carcinomas through use of Human Anti-254P1D6B Antibodies In vivo

Antibodies are used in accordance with the present invention which recognize an epitope on 254P1D6B, and are used in the treatment of certain tumors such as those listed in Table I. Based upon a number of factors, including 254P1D6B expression levels, tumors such as those listed in Table I are presently preferred indications. In connection with each of these indications, three clinical approaches are successfully pursued.

I.) Adjunctive therapy: In adjunctive therapy, patients are treated with anti-254P1D6B antibodies in combination with a chemotherapeutic or antineoplastic agent and/or radiation therapy. Primary cancer targets, such as those listed in Table I, are treated under standard protocols by the addition anti-254P1D6B antibodies to standard first and second line therapy. Protocol designs address effectiveness as assessed by reduction in tumor mass as well as the ability to reduce usual doses of standard chemotherapy. These dosage reductions allow additional and/or prolonged therapy by reducing dose-related toxicity of the chemotherapeutic agent. Anti-254P1D6B antibodies are utilized in several adjunctive clinical trials in combination with the chemotherapeutic or antineoplastic agents adriamycin (advanced prostate carcinoma), cisplatin (advanced head and neck and lung carcinomas), taxol (breast cancer), and doxorubicin (preclinical).

II.) Monotherapy: In connection with the use of the anti-254P1D6B antibodies in monotherapy of tumors, the antibodies are administered to patients without a chemotherapeutic or antineoplastic agent. In one embodiment, monotherapy is conducted clinically in end stage cancer patients with extensive metastatic disease. Patients show some disease stabilization. Trials demonstrate an effect in refractory patients with cancerous tumors.

III.) Imaging Agent: Through binding a radionuclide (e.g., iodine or yttrium ($I^{131}$, $Y^{90}$) to anti-254P1D6B antibodies, the radiolabeled antibodies are utilized as a diagnostic and/or imaging agent. In such a role, the labeled antibodies localize to both solid tumors, as well as, metastatic lesions of cells expressing 254P1D6B. In connection with the use of the anti-254P1D6B antibodies as imaging agents, the antibodies are used as an adjunct to surgical treatment of solid tumors, as both a pre-surgical screen as well as a post-operative follow-up to determine what tumor remains and/or returns. In one embodiment, a ($^{111}$In)-254P1D6B antibody is used as an imaging agent in a Phase I human clinical trial in patients having a carcinoma that expresses 254P1D6B (by analogy see, e.g., Divgi et al. *J. Natl. Cancer Inst.* 83:97-104 (1991)). Patients are followed with standard anterior and posterior gamma camera. The results indicate that primary lesions and metastatic lesions are identified.

Dose and Route of Administration

As appreciated by those of ordinary skill in the art, dosing considerations can be determined through comparison with the analogous products that are in the clinic. Thus, anti-254P1D6B antibodies can be administered with doses in the range of 5 to 400 mg/m$^2$, with the lower doses used, e.g., in connection with safety studies. The affinity of anti-254P1D6B antibodies relative to the affinity of a known antibody for its target is one parameter used by those of skill in the art for determining analogous dose regimens. Further, anti-254P1D6B antibodies that are fully human antibodies, as compared to the chimeric antibody, have slower clearance; accordingly, dosing in patients with such fully human anti-254P1D6B antibodies can be lower, perhaps in the range of 50 to 300 mg/m$^2$, and still remain efficacious. Dosing in mg/m$^2$, as opposed to the conventional measurement of dose in mg/kg, is a measurement based on surface area and is a convenient dosing measurement that is designed to include patients of all sizes from infants to adults.

Three distinct delivery approaches are useful for delivery of anti-254P1D6B antibodies. Conventional intravenous delivery is one standard delivery technique for many tumors.

However, in connection with tumors in the peritoneal cavity, such as tumors of the ovaries, biliary duct, other ducts, and the like, intraperitoneal administration may prove favorable for obtaining high dose of antibody at the tumor and to also minimize antibody clearance. In a similar manner, certain solid tumors possess vasculature that is appropriate for regional perfusion. Regional perfusion allows for a high dose of antibody at the site of a tumor and minimizes short term clearance of the antibody.

Clinical Development Plan (CDP)

Overview: The CDP follows and develops treatments of anti-254P1D6B antibodies in connection with adjunctive therapy, monotherapy, and as an imaging agent. Trials initially demonstrate safety and thereafter confirm efficacy in repeat doses. Trails are open label comparing standard chemotherapy with standard therapy plus anti-254P1D6B antibodies. As will be appreciated, one criteria that can be utilized in connection with enrollment of patients is 254P1D6B expression levels in their tumors as determined by biopsy.

As with any protein or antibody infusion-based therapeutic, safety concerns are related primarily to (i) cytokine release syndrome, i.e., hypotension, fever, shaking, chills; (ii) the development of an immunogenic response to the material (i.e., development of human antibodies by the patient to the antibody therapeutic, or HAHA response); and, (iii) toxicity to normal cells that express 254P1D6B. Standard tests and follow-up are utilized to monitor each of these safety concerns. Anti-254P1D6B antibodies are found to be safe upon human administration.

Example 41

Human Clinical Trial Adjunctive Therapy with Human Anti-254P1D6B Antibody and Chemotherapeutic Agent A phase I human clinical trial is initiated to assess the safety of six intravenous doses of a human anti-254P1D6B antibody in connection with the treatment of a solid tumor, e.g., a cancer of a tissue listed in Table I. In the study, the safety of single doses of anti-254P1D6B antibodies when utilized as an adjunctive therapy to an antineoplastic or chemotherapeutic agent as defined herein, such as, without limitation: cisplatin, topotecan, doxorubicin, adriamycin, taxol, or the like, is assessed. The trial design includes delivery of six single doses of an anti-254P1D6B antibody with dosage of antibody escalating from approximately about 25 mg/m$^2$ to about 275 mg/m$^2$ over the course of the treatment in accordance with the following schedule:

|  | Day 0 | Day 7 | Day 14 | Day 21 | Day 28 | Day 35 |
|---|---|---|---|---|---|---|
| mAb Dose | 25 mg/m$^2$ | 75 mg/m$^2$ | 125 mg/m$^2$ | 175 mg/m$^2$ | 225 mg/m$^2$ | 275 mg/m$^2$ |
| Chemotherapy (standard dose) | + | + | + | + | + | + |

Patients are closely followed for one-week following each administration of antibody and chemotherapy. In particular, patients are assessed for the safety concerns mentioned above: (i) cytokine release syndrome, i.e., hypotension, fever, shaking, chills; (ii) the development of an immunogenic response to the material (i.e., development of human antibodies by the patient to the human antibody therapeutic, or HAHA response); and, (iii) toxicity to normal cells that express 254P1D6B. Standard tests and follow-up are utilized to monitor each of these safety concerns. Patients are also assessed for clinical outcome, and particularly reduction in tumor mass as evidenced by MRI or other imaging.

The anti-254P1D6B antibodies are demonstrated to be safe and efficacious, Phase II trials confirm the efficacy and refine optimum dosing.

Example 42

Human Clinical Trial

Monotherapy with Human Anti-254P1D6B Antibody

Anti-254P1D6B antibodies are safe in connection with the above-discussed adjunctive trial, a Phase II human clinical trial confirms the efficacy and optimum dosing for monotherapy. Such trial is accomplished, and entails the same safety and outcome analyses, to the above-described adjunctive trial with the exception being that patients do not receive chemotherapy concurrently with the receipt of doses of anti-254P1D6B antibodies.

Example 43

Human Clinical Trial

Diagnostic Imaging with Anti-254P1D6B Antibody

Once again, as the adjunctive therapy discussed above is safe within the safety criteria discussed above, a human clinical trial is conducted concerning the use of anti-254P1D6B antibodies as a diagnostic imaging agent. The protocol is designed in a substantially similar manner to those described in the art, such as in Divgi et al. *J. Natl. Cancer Inst.* 83:97-104 (1991). The antibodies are found to be both safe and efficacious when used as a diagnostic modality.

Example 44

Involvement in Tumor Progression

The 254P1D6B gene contributes to the growth of cancer cells. The role of 254P1D6B in tumor growth is confirmed in a variety of primary and transfected cell lines including prostate, colon, bladder and kidney cell lines, as well as NIH 3T3 cells engineered to stably express 254P1D6B. Parental cells lacking 254P1D6B and cells expressing 254P1D6B are evaluated for cell growth using a well-documented proliferation assay (Fraser S P, et al., Prostate 2000; 44:61, Johnson D E, Ochieng J, Evans S L. Anticancer Drugs. 1996, 7:288). The effect of 254P1D6B can also be observed on cell cycle progression. Control and 254P1D6B-expressing cells are grown in low serum overnight, and treated with 10% FBS for 48 and 72 hrs. Cells are analyzed for BrdU and propidium iodide incorporation by FACS analysis.

To confirm the role of 254P1D6B in the transformation process, its effect in colony forming assays is investigated. Parental NIH-3T3 cells lacking 254P1D6B are compared to NIH-3T3 cells expressing 254P1D6B, using a soft agar assay under stringent and more permissive conditions (Song Z. et al. Cancer Res. 2000; 60:6730).

To confirm the role of 254P1D6B in invasion and metastasis of cancer cells, a well-established assay is used. A non-limiting example is the use of an assay which provides a basement membrane or an analog thereof used to detect whether cells are invasive (e.g., a Transwell Insert System assay (Becton Dickinson) (Cancer Res. 1999; 59:6010)).

Control cells, including prostate, and bladder cell lines lacking 254P1D6B are compared to cells expressing 254P1D6B. Cells are loaded with the fluorescent dye, calcein, and plated in the top well of a support structure coated with a basement membrane analog (e.g. the Transwell insert) and used in the assay. Invasion is determined by fluorescence of cells in the lower chamber relative to the fluorescence of the entire cell population.

254P1D6B also plays a role in cell cycle and apoptosis. Parental cells and cells expressing 254P1D6B are compared for differences in cell cycle regulation using a well-established BrdU assay (Abdel-Malek Z A. J Cell Physiol. 1988, 136:247). In short, cells are grown under both optimal (full serum) and limiting (low serum) conditions are labeled with BrdU and stained with anti-BrdU Ab and propidium iodide. Cells are analyzed for entry into the G1, S, and G2M phases of the cell cycle. Alternatively, the effect of stress on apoptosis is evaluated in control parental cells and cells expressing 254P1D6B, including normal and tumor prostate, and kidney cells. Engineered and parental cells are treated with various chemotherapeutic agents, such as etoposide, flutamide, etc, and protein synthesis inhibitors, such as cycloheximide. Cells are stained with annexin V-FITC and cell death is measured by FACS analysis. The modulation of cell death by 254P1D6B can play a critical role in regulating tumor progression and tumor load.

When 254P1D6B plays a role in cell growth, transformation, invasion or apoptosis, it is used as a target for diagnostic, prognostic, preventative and/or therapeutic purposes.

Example 45

Involvement in Angiogenesis

Angiogenesis or new capillary blood vessel formation is necessary for tumor growth (Hanahan D, Folkman J. Cell. 1996, 86:353; Folkman J. Endocrinology. 1998 139:441). 254P1D6B plays a role in angiogenesis. Several assays have been developed to measure angiogenesis in vitro and in vivo, such as the tissue culture assays endothelial cell tube formation and endothelial cell proliferation. Using these assays as well as in vitro neo-vascularization, the role of 254P1D6B in angiogenesis, enhancement or inhibition, is confirmed. For example, endothelial cells engineered to express 254P1D6B are evaluated using tube formation and proliferation assays. The effect of 254P1D6B is also confirmed in animal models in vivo. For example, cells either expressing or lacking 254P1D6B are implanted subcutaneously in immunocompromised mice. Endothelial cell migration and angiogenesis are evaluated 5-15 days later using immunohistochemistry techniques. 254P1D6B affects angiogenesis, and it is used as a target for diagnostic, prognostic, preventative and/or therapeutic purposes.

Example 46

Involvement in Cell Adhesion

Cell adhesion plays a critical role in tissue colonization and metastasis. 254P1D6B participates in cellular organization, and as a consequence cell adhesion and motility. To confirm that 254P1D6B regulates cell adhesion, control cells lacking 254P1D6B are compared to cells expressing 254P1D6B, using techniques previously described (see, e.g., Haier et al, Br. J. Cancer. 1999, 80:1867; Lehr and Pienta, J. Natl. Cancer Inst. 1998, 90:118). Briefly, in one embodiment, cells labeled with a fluorescent indicator, such as calcein, are incubated on tissue culture wells coated with media alone or with matrix proteins. Adherent cells are detected by fluorimetric analysis and percent adhesion is calculated. In another embodiment, cells lacking or expressing 254P1D6B are analyzed for their ability to mediate cell-cell adhesion using similar experimental techniques as described above. Both of these experimental systems are used to identify proteins, antibodies and/or small molecules that modulate cell adhesion to extracellular matrix and cell-cell interaction. Cell adhesion plays a critical role in tumor growth, progression, and, colonization, and 254P1D6B is involved in these processes. Thus, it serves as a diagnostic, prognostic, preventative and/or therapeutic modality.

Example 47

In Vitro Biologic Target Validation

Target Activation/Inactivation RNA Interference (RNAi)

Systematic alteration of 254P1D6B gene activity in relevant cell assays or in animal models is an approach for understanding gene function. There are two complementary platforms to alter gene function: Target activation and target inactivation. 254P1D6B target gene activation induces a disease phenotype (i.e. tumurogenesis) by mimicking the differential gene activity that occurs in several tumors. Conversely, 254P1D6B target inactivation reverses a phenotype found in a particular disease and mimics the inhibition of the target with a putative lead compound/agent.

RNA interference (RNAi) technology is implemented to a variety of cell assays relevant to oncology. RNAi is a post-transcriptional gene silencing mechanism activated by double stranded RNA (dsRNA). RNAi induces specific mRNA degradation leading to changes in protein expression and subsequently in gene function. In mammalian cells, dsRNAs (>30 bp) can activate the interferon pathway which induces non-specific mRNA degradation and protein translation inhibition. When transfecting small synthetic dsRNA (21-23 nucleotides in length), the activation of the interferon pathway is no longer observed, however these dsRNAs have the correct composition to activate the RNAi pathway targeting for degradation, specifically some mRNAs. See, Elbashir S. M., et. al., *Duplexes of 21-nucleotide RNAs Mediate RNA interference in Cultured Mammalian Cells*, Nature 411(6836):494-8 (2001). Thus, RNAi technology is used successfully in mammalian cells to silence targeted genes.

Loss of cell proliferation control is a hallmark of cancerous cells; thus, assessing the role of 254P1D6B specific target genes in cell survival/proliferation assays is relevant. RNAi technology is implemented to the cell survival (cellular metabolic activity as measured by MTS) and proliferation (DNA synthesis as measured by $^3$H-thymidine uptake) assays as a first filter to assess 254P1D6B target validation (TV). Tetrazolium-based calorimetric assays (i.e. MTT and MTS) detect viable cells exclusively. Living cells are metabolically active and can reduce tetrazolium salts to colored formazan compounds. Dead cells do not reduce the salts.

An alternative method to analyze 254P1D6B cell proliferation is the measurement of DNA synthesis as a marker for proliferation. Labeled DNA precursors (i.e. $^3$H-Thymidine) are used and their incorporation to DNA is quantified. Incorporation of the labeled precursor into DNA is directly proportional to the amount of cell division occurring in the culture.

Correlating 254P1D6B cellular phenotype with gene knockdown is critical following RNAi treatments to draw valid conclusions and rule out toxicity or other non-specific effects of these reagents. Assays to measure the levels of expression of both protein and mRNA for the 254P1D6B target after RNAi treatments are important. Specific antibodies against the 254P1D6B target permit this question to be addressed by performing Western blotting with whole cell lysates.

An alternative method is the use of a tagged full length 254P1D6B target cDNA inserted in a mammalian expression vector (i.e. pcDNA3 series) providing a tag for which commercial Abs are available (Myc, His, V5 etc) is transiently co-transfected with individual siRNAs for 254P1D6B gene target, for instance in COS cells. Transgene expression permits the evaluation of which siRNA is efficiently silencing target gene expression, thus providing the necessary information to correlate gene function with protein knockdown. Both endogenous and transgene expression approaches show similar results.

A further alternative method for 254P1D6B target gene expression is measurement of mRNA levels by RT-PCR or by Taqman/Cybergreen. These methods are applied in a high throughput manner and are used in cases where neither Abs nor full length cDNAs are available. Using this method, poly-A mRNA purification and a careful design of primers/probes (should be 5' to the siRNA targeted sequence) is needed for the Taqman approach. Some considerations apply to the primer design if pursuing RT-PCR from total RNA (primers should flank the siRNA targeted sequence). However, in some instances, the correlation between mRNA/protein is not complete (i.e., protein a with long half life) and the results could be misleading.

Several siRNAs per 254P1D6B target gene are selected and tested in parallel in numerous cell lines (usually with different tissue origin) in the survival and proliferation assays. Any phenotypic effect of the siRNAs in these assays is correlated with the protein and/or mRNA knockdown levels in the same cell lines. To further correlate cell phenotype and specific gene knockdown by RNAi, serial siRNA titrations are performed and are tested in parallel cell phenotype and gene knockdown. When 254P1D6B is responsible for the phenotype, a similar $IC_{50}$ value in both assays is obtained.

Another method used to measure cell proliferation is performing clonogenic assays. In these assays, a defined number of cells are plated onto the appropriate matrix and the number of colonies formed after a period of growth following siRNA treatment is counted.

In 254P1D6B cancer target validation, complementing the cell survival/proliferation analysis with apoptosis and cell cycle profiling studies are considered. The biochemical hallmark of the apoptotic process is genomic DNA fragmentation, an irreversible event that commits the cell to die. A method to observe fragmented DNA in cells is the immunological detection of histone-complexed DNA fragments by an immunoassay (i.e. cell death detection ELISA) which measures the enrichment of histone-complexed DNA fragments (mono- and oligo-nucleosomes) in the cytoplasm of apoptotic cells. This assay does not require pre-labeling of the cells and can detect DNA degradation in cells that do not proliferate in vitro (i.e. freshly isolated tumor cells).

The most important effector molecules for triggering apoptotic cell death are caspases. Caspases are proteases that when activated cleave numerous substrates at the carboxy-terminal site of an aspartate residue mediating very early stages of apoptosis upon activation. All caspases are synthesized as pro-enzymes and activation involves cleavage at aspartate residues. In particular, caspase 3 seems to play a central role in the initiation of cellular events of apoptosis. Assays for determination of caspase 3 activation detect early events of apoptosis. Following RNAi treatments, Western blot detection of active caspase 3 presence or proteolytic cleavage of products (i.e. PARP) found in apoptotic cells further support an active induction of apoptosis. Because the cellular mechanisms that result in apoptosis are complex, each has its advantages and limitations. Consideration of other criteria/endpoints such as cellular morphology, chromatin condensation, membrane bebbling, apoptotic bodies help to further support cell death as apoptotic.

Not all the gene targets that regulate cell growth are anti-apoptotic, the DNA content of permeabilized cells is measured to obtain the profile of DNA content or cell cycle profile. Nuclei of apoptotic cells contain less DNA due to the leaking out to the cytoplasm (sub-G1 population). In addition, the use of DNA stains (i.e. propidium iodide) also differentiate between the different phases of the cell cycle in the cell population due to the presence of different quantities of DNA in G0/G1, S and G2/M. In these studies the subpopulations can be quantified.

For the 254P1D6B gene, RNAi studies facilitate the contribution of the gene product in cancer pathways. Such active RNAi molecules have use in identifying assays to screen for mAbs that are active anti-tumor therapeutics. When 254P1D6B plays a role in cell survival, cell proliferation, tumorogenesis, or apoptosis, it is used as a target for diagnostic, prognostic, preventative and/or therapeutic purposes.

Example 48

RNA Interference (RNAi)

Various protocols for achieving RNA interference are available.

Exemplary Protocol 1

RNA interference (RNAi) makes use of sequence specific double stranded RNA to prevent gene expression. Small interfering RNA (siRNA) is transfected into mammalian cells and thereby induce sequence specific mRNA degradation (Elbashir, et al., *Nature*, 2001; vol. 411: 494-498).

The sense strand of 254P1D6B is labeled at 3' with fluorescein, 6-FAM (ABS 494 nm, EMM 525 nm, green). The siRNA is dissolved in RNA-free sterile buffer (100 mM KOAc, 30 mM HEPES KOH, 2 mM MOAc, at pH 7.4) to make 20 µM stock (200-fold concentration). The siRNA is transfected into cells seeded on 6-well plates with oligofectamine reagent (GIBCO/Invitrogen, Carlsbad, Calif.). The final concentration of siRNA is determined.

254P1D6B protein expression is detected 24 hours after transfection by immunostaining followed by flow cytometry. In addition, confirmation of altered gene expression is performed by Western blotting. Expression reduction is confirmed by Western blot analysis where 254P1D6B protein is substantially reduced in 254P1D6B RNAi treated cells relative to control and untreated cells.

Exemplary Protocol 2

In one embodiment, the day before siRNA transfection, cells are plated in media (e.g., RPMI 1640 (GIBCO/Invitrogen, Carlsbad, Calif.) with 10% FBS without antibiotics) at $2 \times 10^3$ cells/well in 80 µl (96 well plate format) for the survival, proliferation and apoptosis assays. In another embodiment, the day before siRNA transfection, cells are plated in media (e.g., RPMI 1640 with 10% FBS without antibiotics) at $5 \times 10^4$ cells/well in 800 µl (12 well plate format) for the cell cycle analysis by flow cytometry, gene silencing by Western blot and/or PCR analysis. In parallel with the 254P1D6B siRNA sequences, the following sequences are included in every experiment as controls. Mock transfected cells with Lipofectamine 2000 (GIBCO/Invitrogen, Carlsbad, Calif.) and annealing buffer (no siRNA), non-specific siRNA (targeted sequence not represented in the human genome 5' AAT-TCTCCGAACGTGTCACGTTT 3'; commercial control from Xeragon/Qiagen, Valencia, Calif.) (SEQ ID NO:275); Luciferase specific siRNA (targeted sequence: 5' AAGG-GACGAAGACGAACACWUCTT 3') (SEQ ID NO:276) and Eg5 specific siRNA (targeted sequence: 5' AACTGAA-GACCTGAAGACAATAA 3') (SEQ ID NO:277). The siRNAs are used at various concentrations (ranging from 200 µM to 100 nM) and 1 µg/ml Lipofectamine 2000.

The procedure is as follows: First siRNAs are diluted in OPTIMEM (serum-free transfection media, Invitrogen) at suitable µM (10-fold concentrated) and incubated 5-10 min at room temperature (RT). Lipofectamine 2000 was diluted at 10 µg/ml (10-fold concentrated) for the total number transfections and incubated 5-10 min RT. Appropriate amounts of diluted 10-fold concentrated Lipofectamine 2000 are mixed 1:1 with diluted 10-fold concentrated siRNA and incubated at RT for 20-30 minutes (5-fold concentrated transfection solution). 20 or 200 µl of the 5-fold concentrated transfection solutions were added to the respective samples and incubated at 37° C. for 48 to 96 hours (depending upon the assay employed, such as proliferation, apoptosis, survival, cell cycle analysis, migration or Western blot).

Reduced gene expression of 254P1D6B using siRNA transfection results in significantly diminished proliferation of transformed cancer cells that endogenously express the antigen. Cells treated with specific siRNAs show reduced survival as measured, e.g., by a metabolic readout of cell viability, corresponding to the reduced proliferative capacity. Further, such cells undergo apoptosis in response to RNAi as measured, e.g., by a nucleosome-release assay (Roche Applied Science, Indianapolis, Ind.) or detection of sub-G1 populations during cell cycle analysis by propidium iodide staining and flow cytometry. These results demonstrate that siRNA treatment provides an effective therapeutic for the elimination of cancer cells that specifically express the 254P1D6B antigen.

Throughout this application, various website data content, publications, patent applications and patents are referenced. (Websites are referenced by their Uniform Resource Locator, or URL, addresses on the World Wide Web.) The disclosures of each of these references are hereby incorporated by reference herein in their entireties.

The present invention is not to be limited in scope by the embodiments disclosed herein, which are intended as single illustrations of individual aspects of the invention, and any that are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

Tables:

TABLE I

Tissues that Express 254P1D6B when malignant:

Lung

Ovary

Prostate

Pancreas

Breast

TABLE II

Amino Acid Abbreviations

| SINGLE LETTER | THREE LETTER | FULL NAME |
| --- | --- | --- |
| F | Phe | phenylalanine |
| L | Leu | leucine |
| S | Ser | serine |
| Y | Tyr | tyrosine |
| C | Cys | cysteine |
| W | Trp | tryptophan |
| P | Pro | proline |
| H | His | histidine |
| Q | Gln | glutamine |
| R | Arg | arginine |
| I | Ile | isoleucine |
| M | Met | methionine |
| T | Thr | threonine |
| N | Asn | asparagine |
| K | Lys | lysine |
| V | Val | valine |
| A | Ala | alanine |
| D | Asp | aspartic acid |
| E | Glu | glutamic acid |
| G | Gly | glycine |

TABLE III

Amino Acid Substitution Matrix
Adapted from the GCG Software 9.0 BLOSUM62 amino acid substitution matrix (block substitution matrix). The higher the value, the more likely a substitution is found in related, natural proteins. (See world wide web URL ikp.unibe.ch/manual/blosum62.html)

| A | C | D | E | F | G | H | I | K | L | M | N | P | Q | R | S | T | V | W | Y | . |
| --- | --- | --- | --- | --- | --- | --- | --- | --- | --- | --- | --- | --- | --- | --- | --- | --- | --- | --- | --- | --- |
| 4 | 0 | −2 | −1 | −2 | 0 | −2 | −1 | −1 | −1 | −1 | −2 | −1 | −1 | −1 | 1 | 0 | 0 | −3 | −2 | A |
|   | 9 | −3 | −4 | −2 | −3 | −3 | −1 | −3 | −1 | −1 | −3 | −3 | −3 | −3 | −1 | −1 | −1 | −2 | −2 | C |
|   |   | 6 | 2 | −3 | −1 | −1 | −3 | −1 | −4 | −3 | 1 | −1 | 0 | −2 | 0 | −1 | −3 | −4 | −3 | D |
|   |   |   | 5 | −3 | −2 | 0 | −3 | 1 | −3 | −2 | 0 | −1 | 2 | 0 | 0 | −1 | −2 | −3 | −2 | E |
|   |   |   |   | 6 | −3 | −1 | 0 | −3 | 0 | 0 | −3 | −4 | −3 | −3 | −2 | −2 | −1 | 1 | 3 | F |
|   |   |   |   |   | 6 | −2 | −4 | −2 | −4 | −3 | 0 | −2 | −2 | −2 | 0 | −2 | −3 | −2 | −3 | G |
|   |   |   |   |   |   | 8 | −3 | −1 | −3 | −2 | 1 | −2 | 0 | 0 | −1 | −2 | −3 | −2 | 2 | H |
|   |   |   |   |   |   |   | 4 | −3 | 2 | 1 | −3 | −3 | −3 | −3 | −2 | −1 | 3 | −3 | −1 | I |
|   |   |   |   |   |   |   |   | 5 | −2 | −1 | 0 | −1 | 1 | 2 | 0 | −1 | −2 | −3 | −2 | K |
|   |   |   |   |   |   |   |   |   | 4 | 2 | −3 | −3 | −2 | −2 | −2 | −1 | 1 | −2 | −1 | L |

TABLE III-continued

Amino Acid Substitution Matrix
Adapted from the GCG Software 9.0 BLOSUM62 amino acid substitution matrix (block substitution matrix). The higher the value, the more likely a substitution is found in related, natural proteins. (See world wide web URL ikp.unibe.ch/manual/blosum62.html)

| A | C | D | E | F | G | H | I | K | L | M | N | P | Q | R | S | T | V | W | Y |   |
|---|---|---|---|---|---|---|---|---|---|---|---|---|---|---|---|---|---|---|---|---|
|   |   |   |   |   |   |   |   |   |   | 5 | −2 | −2 | 0 | −1 | −1 | −1 | 1 | −1 | −1 | M |
|   |   |   |   |   |   |   |   |   |   |   | 6 | −2 | 0 | 0 | 1 | 0 | −3 | −4 | −2 | N |
|   |   |   |   |   |   |   |   |   |   |   |   | 7 | −1 | −2 | −1 | −1 | −2 | −4 | −3 | P |
|   |   |   |   |   |   |   |   |   |   |   |   |   | 5 | 1 | 0 | −1 | −2 | −2 | −1 | Q |
|   |   |   |   |   |   |   |   |   |   |   |   |   |   | 5 | −1 | −1 | −3 | −3 | −2 | R |
|   |   |   |   |   |   |   |   |   |   |   |   |   |   |   | 4 | 1 | −2 | −3 | −2 | S |
|   |   |   |   |   |   |   |   |   |   |   |   |   |   |   |   | 5 | 0 | −2 | −2 | T |
|   |   |   |   |   |   |   |   |   |   |   |   |   |   |   |   |   | 4 | −3 | −1 | V |
|   |   |   |   |   |   |   |   |   |   |   |   |   |   |   |   |   |   | 11 | 2 | W |
|   |   |   |   |   |   |   |   |   |   |   |   |   |   |   |   |   |   |   | 7 | Y |

Table IV

HLA Class I/II Motifs/Supermotifs

TABLE IV (A)

| | HLA Class I Supermotifs/Motifs | | |
|---|---|---|---|
| | POSITION 2 (Primary Anchor) | POSITION 3 (Primary Anchor) | POSITION C Terminus (Primary Anchor) |
| SUPERMOTIF | | | |
| A1 | T*ILVMS* | | F*WY* |
| A2 | LIVMATQ | | IVMATL |
| A3 | VSMATLI | | RK |
| A24 | YFWIVLMT | | FIYWLM |
| B7 | P | | VILFMWYA |
| B27 | RHK | | FYLWMIVA |
| B44 | ED | | FWYLIMVA |
| B58 | ATS | | FWYLIVMA |
| B62 | QLIVMP | | FWYMIVLA |
| MOTIFS | | | |
| A1 | TSM | | Y |
| A1 | | DEAS | Y |
| A2.1 | LMVQIAT | | VLIMAT |
| A3 | LMVISATFCGD | | KYRHFA |

TABLE IV (A)-continued

| | HLA Class I Supermotifs/Motifs | | |
|---|---|---|---|
| | POSITION 2 (Primary Anchor) | POSITION 3 (Primary Anchor) | POSITION C Terminus (Primary Anchor) |
| A11 | VTMLISAGNCDF | | KRYH |
| A24 | YFWM | | FLIW |
| A*3101 | MVTALIS | | RK |
| A*3301 | MVALFIST | | RK |
| A*6801 | AVTMSLI | | RK |
| B*0702 | P | | LMFWYAIV |
| B*3501 | P | | LMFWYIVA |
| B51 | P | | LIVFWYAM |
| B*5301 | P | | IMFWYALV |
| B*5401 | P | | ATIVLMFWY |

Bolded residues are preferred, italicized residues are less preferred: A peptide is considered motif-bearing if it has primary anchors at each primary anchor position for a motif or supermotif as specified in the above table.

TABLE IV (B)

| HLA Class II Supermotif | | |
|---|---|---|
| 1 | 6 | 9 |
| W, F, Y, V, I, L | A, V, I, L, P, C, S, T | A, V, I, L, C, S, T, M, Y |

TABLE IV (C)

| HLA Class II Motifs | | | | | | | | | |
|---|---|---|---|---|---|---|---|---|---|
| MOTIFS | | 1° anchor 1 | 2 | 3 | 4 | 5 | 1° anchor 6 | 7 | 8 | 9 |
| DR4 | preferred | FMY*LIVW* | M | T | | I | VST*CPALIM* | MH | | MH |
|  | deleterious | | | W | | | | R | | WDE |
| DR1 | preferred | MF*LIVWY* | | | PAMQ | | VMAT*SPLIC* | M | | AVM |
|  | deleterious | | C | CH | FD | CWD | | GDE | D | |
| DR7 | preferred | MF*LIVWY* | M | W | A | | IVMSA*CTPL* | M | | IV |
|  | deleterious | | C | | G | | | GRD | N | G |

| | MOTIFS | 1° anchor 1 | 2 | 3 | 1° anchor 4 | 5 | 1° anchor 6 |
|---|---|---|---|---|---|---|---|
| Motif a preferred | | LIVMFY | | | D | | |
| Motif b preferred | | LIVMFAY | | | DNQEST | | KRH |
| DR Supermotif | | MF*LIVWY* | | | | | VMSTA*CPLI* |

Italicized residues indicate less preferred or "tolerated" residues

TABLE IV (D)

HLA Class I Supermotifs

| SUPER-MOTIFS | | POSITION: | | | | | | | |
|---|---|---|---|---|---|---|---|---|---|
| | | 1 | 2 | 3 | 4 | 5 | 6 | 7 | 8 | C-terminus |

| SUPER-MOTIFS | | 1 | 2 | 3 | 4/5 | 6 | 7 | 8 | C-terminus |
|---|---|---|---|---|---|---|---|---|---|
| A1 | | | 1° Anchor TI*LVMS* | | | | | | 1° Anchor FWY |
| A2 | | | 1° Anchor LIVM*ATQ* | | | | | | 1° Anchor LIVMAT |
| A3 | Preferred | | 1° Anchor VSMA*TLI* | YFW (4/5) | | YFW (3/5) | YFW (4/5) | P (4/5) | 1° Anchor RK |
| | deleterious | | DE (3/5); P (5/5) | DE (4/5) | | | | | |
| A24 | | | 1° Anchor YF*WIVLMT* | | | | | | 1° Anchor FIY*WLM* |
| B7 | Preferred | FWY (5/5) LIVM (3/5) | 1° Anchor P | FWY (4/5) | | | | FWY (3/5) | 1° Anchor VILF*MWYA* |
| | deleterious | DE (3/5); P (5/5); G (4/5); A (3/5); QN (3/5) | | | | DE (3/5) | G (4/5) | QN (4/5) | DE (4/5) | |
| B27 | | | 1° Anchor RHK | | | | | | 1° Anchor FYL*WMIVA* |
| B44 | | | 1° Anchor E*D* | | | | | | 1° Anchor FWYLIMVA |
| B58 | | | 1° Anchor ATS | | | | | | 1° Anchor FWY*LIVMA* |
| B62 | | | 1° Anchor Q*LIVMP* | | | | | | 1° Anchor FWY*MIVLA* |

Italicized residues indicate less preferred or "tolerated" residues

TABLE IV (E)

HLA Class I Motifs

| | | POSITION | | | | |
|---|---|---|---|---|---|---|
| | | 1 | 2 | 3 | 4 | 5 |
| A1 9-mer | preferred | GFYW | 1° Anchor STM | DEA | YFW | |
| | deleterious | DE | | RHKLIVMP | A | G |
| A1 9-mer | preferred | GRHK | ASTCLIVM | 1° Anchor DE*AS* | GSTC | |
| | deleterious | A | RHKDEPYFW | | DE | PQN |
| A1 10-mer | preferred | YFW | 1° Anchor STM | DEAQN | A | YFWQN |
| | deleterious | GP | | RHKGLIVM | DE | RHK |
| A1 10-mer | preferred | YFW | STCLIVM | 1° Anchor DE*AS* | A | YFW |
| | deleterious | RHK | RHKDEPYFW | | | P |
| A2.1 9-mer | preferred | YFW | 1° Anchor LM*IVQAT* | YFW | STC | YFW |
| | deleterious | DEP | | DERKH | | |
| A2.1 10-mer | preferred | AYFW | 1° Anchor LM*IVQAT* | LVIM | G | |
| | deleterious | DEP | | DE | RKHA | P |
| A3 | preferred | RHK | 1° Anchor LMVISATFCGD | YFW | PRHK YFW | A |
| | deleterious | DEP | | DE | | |
| A11 | preferred | A | 1° Anchor VTLMISAGNC *DF* | YFW | YFW | A |
| | deleterious | DEP | | | | |
| A24 9-mer | preferred | YFWRHK | 1° Anchor YFW*M* | | STC | |
| | deleterious | DEG | | DE | G | QNP |
| A24 10-mer | Preferred | | 1° Anchor YFW*M* | | P | YFWP |
| | Deleterious | | | GDE | QN | RHK |
| A3101 | Preferred | RHK | 1° Anchor MVT*ALIS* | YFW | P | |
| | Deleterious | DEP | | DE | | ADE |

TABLE IV (E)-continued

| HLA Class I Motifs | | | | | | |
|---|---|---|---|---|---|---|
| A3301 | Preferred | | 1° Anchor MVAL*FIST* | YFW | | |
| | Deleterious | GP | | DE | | |
| A6801 | Preferred | YFWSTC | 1° Anchor AVT*MSLI* | | | YFWLI VM |
| | deleterious | GP | | DEG | | RHK |
| B0702 | Preferred | RHKFWY | 1° Anchor P | RHK | | RHK |
| | deleterious | DEQNP | | DEP | DE | DE |
| B3501 | Preferred | FWYLIVM | 1° Anchor P | FWY | | |
| | deleterious | AGP | | | | G |
| B51 | Preferred | LIVMFWY | 1° Anchor P | FWY | STC | FWY |
| | deleterious | AGPDERH KSTC | | | | DE |
| B5301 | preferred | LIVMFWY | 1° Anchor P | FWY | STC | FWY |
| | deleterious | AGPQN | | | | |
| B5401 | preferred | FWY | 1° Anchor P | FWYLIVM | | LIVM |
| | deleterious | GPQNDE | | GDESTC | | RHKDE |

| | | POSITION | | | | |
|---|---|---|---|---|---|---|
| | | 6 | 7 | 8 | 9 or C-terminus | C-terminus |
| A1 9-mer | preferred | P | DEQN | YFW | 1° Anchor Y | |
| | deleterious | A | | | | |
| A1 9-mer | preferred | ASTC | LIVM | DE | 1° Anchor Y | |
| | deleterious | RHK | PG | GP | | |
| A1 10-mer | preferred | | PASTC | GDE | P | 1° Anchor Y |
| | deleterious | QNA | RHKYFW | RHK | A | |
| A1 10-mer | preferred | | PG | G | YFW | 1° Anchor Y |
| | deleterious | G | | PRHK | QN | |
| A2.1 9-mer | preferred | | A | P | 1° Anchor V*LIMAT* | |
| | deleterious | RKH | DERKH | | | |
| A2.1 10-mer | preferred | G | | FYWLV IM | | 1° Anchor V*LIMAT* |
| | deleterious | | RKH | DERKH | RKH | |
| A3 | preferred | YFW | | P | 1° Anchor KYR*HFA* | |
| | deleterious | | | | | |
| A11 | preferred | YFW | YFW | P | 1° Anchor K*RYH* | |
| | deleterious | | A | G | | |
| A24 9-mer | preferred | | YFW | YFW | 1° Anchor FLIW | |
| | deleterious | DERHK | G | AQN | | |
| A24 10-mer | Preferred | | P | | | 1° Anchor FLIW |
| | Deleterious | DE | A | QN | DEA | |
| A3101 | Preferred | YFW | YFW | AP | 1° Anchor R*K* | |
| | Deleterious | DE | DE | DE | | |
| A3301 | Preferred | | AYFW | | 1° Anchor RK | |
| | Deleterious | | | | | |
| A6801 | Preferred | | YFW | P | 1° Anchor RK | |
| | deleterious | | | A | | |
| B0702 | Preferred | RHK | RHK | PA | 1° Anchor LMF*WYAIV* | |
| | deleterious | GDE | QN | DE | | |
| B3501 | Preferred | | FWY | | 1° Anchor LMFWY*IVA* | |
| | deleterious | G | | | | |
| B51 | Preferred | G | | FWY | 1° Anchor LIVF*WYAM* | |
| | deleterious | G | DEQN | GDE | | |

TABLE IV (E)-continued

| | | | HLA Class I Motifs | | |
|---|---|---|---|---|---|
| B5301 | preferred | | LIVMFWY | FWY | 1° Anchor |
| | | | | | IMFWY*ALV* |
| | deleterious | G | RHKQN | DE | |
| B5401 | preferred | | ALIVM | FWYAP | 1° Anchor |
| | | | | | ATIV*LMFWY* |
| | deleterious | DE | QNDGE | DE | |

TABLE IV (F)

Summary of HLA-supertypes
Overall phenotypic frequencies of HLA-supertypes in different ethnic populations

| | Specificity | | Phenotypic frequency | | | | | |
|---|---|---|---|---|---|---|---|---|
| Supertype | Position 2 | C-Terminus | Caucasian | N.A. Black | Japanese | Chinese | Hispanic | Average |
| B7 | P | AILMVFWY | 43.2 | 55.1 | 57.1 | 43.0 | 49.3 | 49.5 |
| A3 | AILMVST | RK | 37.5 | 42.1 | 45.8 | 52.7 | 43.1 | 44.2 |
| A2 | AILMVT | AILMVT | 45.8 | 39.0 | 42.4 | 45.9 | 43.0 | 42.2 |
| A24 | YF (WIVLMT) | FI (YWLM) | 23.9 | 38.9 | 58.6 | 40.1 | 38.3 | 40.0 |
| B44 | E (D) | FWYLIMVA | 43.0 | 21.2 | 42.9 | 39.1 | 39.0 | 37.0 |
| A1 | TI (LVMS) | FWY | 47.1 | 16.1 | 21.8 | 14.7 | 26.3 | 25.2 |
| B27 | RHK | FYL (WMI) | 28.4 | 26.1 | 13.3 | 13.9 | 35.3 | 23.4 |
| B62 | QL (IVMP) | FWY (MIV) | 12.6 | 4.8 | 36.5 | 25.4 | 11.1 | 18.1 |
| B58 | ATS | FWY (LIV) | 10.0 | 25.1 | 1.6 | 9.0 | 5.9 | 10.3 |

TABLE IV (G)

Calculated population coverage afforded by different HLA-supertype combinations

| | Phenotypic frequency | | | | | |
|---|---|---|---|---|---|---|
| HLA-supertypes | Caucasian | N.A Blacks | Japanese | Chinese | Hispanic | Average |
| A2, A3 and B7 | 83.0 | 86.1 | 87.5 | 88.4 | 86.3 | 86.2 |
| A2, A3, B7, A24, B44 and A1 | 99.5 | 98.1 | 100.0 | 99.5 | 99.4 | 99.3 |
| A2, A3, B7, A24, B44, A1, B27, B62, and B58 | 99.9 | 99.6 | 100.0 | 99.8 | 99.9 | 99.8 |

Motifs indicate the residues defining supertype specificites. The motifs incorporate residues determined on the basis of published data to be recognized by multiple alleles within the supertype. Residues within brackets are additional residues also predicted to be tolerated by multiple alleles within the supertype.

TABLE V

Frequently Occurring Motifs

| Name | avrg. % identity | Description | Potential Function |
|---|---|---|---|
| zf-C2H2 | 34% | Zinc finger, C2H2 type | Nucleic acid-binding protein functions as transcription factor, nuclear location probable |
| cytochrome_b_N | 68% | Cytochrome b(N-terminal)/b6/petB | membrane bound oxidase, generate superoxide |
| Ig | 19% | Immunoglobulin domain | domains are one hundred amino acids long and include a conserved intradomain disulfide bond. |
| WD40 | 18% | WD domain, G-beta repeat | tandem repeats of about 40 residues, each containing a Trp-Asp motif. Function in signal transduction and protein interaction |
| PDZ | 23% | PDZ domain | may function in targeting signaling molecules to sub-membranous sites |

TABLE V-continued

Frequently Occurring Motifs

| Name | avrg. % identity | Description | Potential Function |
|---|---|---|---|
| LRR | 28% | Leucine Rich Repeat | short sequence motifs involved in protein-protein interactions |
| Pkinase | 23% | Protein kinase domain | conserved catalytic core common to both serine/threonine and tyrosine protein kinases containing an ATP binding site and a catalytic site |
| PH | 16% | PH domain | pleckstrin homology involved in intracellular signaling or as constituents of the cytoskeleton |
| EGF | 34% | EGF-like domain | 30-40 amino-acid long found in the extracellular domain of membrane-bound proteins or in secreted proteins |
| Rvt | 49% | Reverse transcriptase (RNA-dependent DNA polymerase) | |
| Ank | 25% | Ank repeat | Cytoplasmic protein, associates integral membrane proteins to the cytoskeleton |
| Oxidored_q1 | 32% | NADH-Ubiquinone/plastoquinone (complex I), various chains | membrane associated. Involved in proton translocation across the membrane |
| Efhand | 24% | EF hand | calcium-binding domain, consists of a 12 residue loop flanked on both sides by a 12 residue alpha-helical domain |
| Rvp | 79% | Retroviral aspartyl protease | Aspartyl or acid proteases, centered on a catalytic aspartyl residue |
| Collagen | 42% | Collagen triple helix repeat (20 copies) | extracellular structural proteins involved in formation of connective tissue. The sequence consists of the G-X-Y and the polypeptide chains forms a triple helix. |
| Fn3 | 20% | Fibronectin type III domain | Located in the extracellular ligand-binding region of receptors and is about 200 amino acid residues long with two pairs of cysteines involved in disulfide bonds |
| 7tm_1 | 19% | 7 transmembrane receptor (rhodopsin family) | seven hydrophobic transmembrane regions, with the N-terminus located extracellularly while the C-terminus is cytoplasmic. Signal through G proteins |

TABLE VI

Post-translational modifications of 254P1D6B

N-Glycosylation site (start position indicated)

| 196 | NSSV | (SEQ ID NO: 28) |
| 219 | NESA | (SEQ ID NO: 29) |
| 262 | NSSG | (SEQ ID NO: 30) |
| 394 | NLSQ | (SEQ ID NO: 31) |
| 421 | NVTV | (SEQ ID NO: 32) |
| 498 | NYSF | (SEQ ID NO: 33) |
| 513 | NSTT | (SEQ ID NO: 34) |
| 536 | NHTI | (SEQ ID NO: 35) |
| 551 | NQSS | (SEQ ID NO: 36) |
| 715 | NNSP | (SEQ ID NO: 37) |
| 733 | NNSI | (SEQ ID NO: 38) |
| 1023 | NSSL | (SEQ ID NO: 39) |
| 1056 | NGSI | (SEQ ID NO: 40) |

Tyrosine sulfation site (Start Position indicated)

| 156 | EEMSEYSDDYRE | (SEQ ID NO: 41) |
| 160 | EYSDDYRELEK | (SEQ ID NO: 42) |
| 527 | NNAVDYPPVANAGPNH | (SEQ ID NO: 43) |

Serine predictions (Staff Position indicated)

| 9 | TGVLSSLLL | (SEQ ID NO: 44) |
| 10 | GVLSSLLLL | (SEQ ID NO: 45) |

TABLE VI-continued

Post-translational modifications of 254P1D6B

| 26 | RKQCSEGRT | (SEQ ID NO: 46) |
| 32 | GRTYSNAVI | (SEQ ID NO: 47) |
| 37 | NAVISPNLE | (SEQ ID NO: 48) |
| 49 | IMRVSHTFP | (SEQ ID NO: 49) |
| 65 | CCDLSSCDL | (SEQ ID NO: 50) |
| 66 | CDLSSCDLA | (SEQ ID NO: 51) |
| 81 | CYLVSCPHK | (SEQ ID NO: 52) |
| 98 | GPIRSYLTF | (SEQ ID NO: 53) |
| 125 | LNRGSPSGI | (SEQ ID NO: 54) |
| 127 | RGSPSGIWG | (SEQ ID NO: 55) |
| 133 | IWGDSPEDI | (SEQ ID NO: 56) |
| 154 | LEEMSEYSD | (SEQ ID NO: 57) |
| 157 | MSEYSDDYR | (SEQ ID NO: 58) |
| 171 | LLQPSGKQE | (SEQ ID NO: 59) |
| 179 | EPRGSAEYT | (SEQ ID NO: 60) |
| 191 | LLPGSEGAF | (SEQ ID NO: 61) |
| 197 | GAFNSSVGD | (SEQ ID NO: 62) |
| 198 | AFNSSVGDS | (SEQ ID NO: 63) |
| 202 | SVGDSPAVP | (SEQ ID NO: 64) |
| 221 | YLNESASTP | (SEQ ID NO: 65) |
| 223 | NESASTPAP | (SEQ ID NO: 66) |
| 233 | LPERSVLLP | (SEQ ID NO: 67) |
| 243 | PTTPSSGEV | (SEQ ID NO: 68) |
| 244 | TTPSSGEVL | (SEQ ID NO: 69) |
| 254 | KEKASQLQE | (SEQ ID NO: 70) |
| 264 | SSNSSGKEV | (SEQ ID NO: 71) |

TABLE VI-continued

Post-translational modifications of 254P1D6B

| Position | Sequence | SEQ ID NO |
|---|---|---|
| 272 | VLMPSHSLP | (SEQ ID NO: 72) |
| 274 | MPSHSLPPA | (SEQ ID NO: 73) |
| 279 | LPPASLELS | (SEQ ID NO: 74) |
| 283 | SLELSSVTV | (SEQ ID NO: 75) |
| 284 | LELSSVTVE | (SEQ ID NO: 76) |
| 290 | TVEKSPVLT | (SEQ ID NO: 77) |
| 299 | VTPGSTEHS | (SEQ ID NO: 78) |
| 303 | STEHSIPTP | (SEQ ID NO: 79) |
| 310 | TPPTSAAPS | (SEQ ID NO: 80) |
| 314 | SAAPSESTP | (SEQ ID NO: 81) |
| 316 | APSESTPSE | (SEQ ID NO: 82) |
| 319 | ESTPSELPI | (SEQ ID NO: 83) |
| 324 | ELPISPTTA | (SEQ ID NO: 84) |
| 338 | ELTVSAGDN | (SEQ ID NO: 85) |
| 376 | WNLISHPTD | (SEQ ID NO: 86) |
| 396 | TLNLSQLSV | (SEQ ID NO: 87) |
| 399 | LSQLSVGLY | (SEQ ID NO: 88) |
| 410 | KYTYSSENA | (SEQ ID NO: 89) |
| 411 | VTVSSENAF | (SEQ ID NO: 90) |
| 439 | VAVVSPQLQ | (SEQ ID NO: 91) |
| 451 | LPLTSALID | (SEQ ID NO: 92) |
| 457 | LIDGSQSTD | (SEQ ID NO: 93) |
| 459 | DGSQSTDDT | (SEQ ID NO: 94) |
| 467 | TEIVSYHWE | (SEQ ID NO: 95) |
| 483 | EEKTSVDSP | (SEQ ID NO: 96) |
| 486 | TSVDSPVLR | (SEQ ID NO: 97) |
| 492 | VLRLSNLDP | (SEQ ID NO: 98) |
| 500 | PGNYSFRLT | (SEQ ID NO: 99) |
| 508 | TVTDSDGAT | (SEQ ID NO: 100) |
| 514 | GATNSTTAA | (SEQ ID NO: 101) |
| 545 | LPQNSITLN | (SEQ ID NO: 102) |
| 553 | NGNQSSDDH | (SEQ ID NO: 103) |
| 554 | GNQSSDDHQ | (SEQ ID NO: 104) |
| 565 | LYEWSLGPG | (SEQ ID NO: 105) |
| 570 | LGPGSEGKH | (SEQ ID NO: 106) |
| 588 | YLHLSAMQE | (SEQ ID NO: 107) |
| 604 | KVTDSSRQQ | (SEQ ID NO: 108) |
| 605 | VTDSSRQQS | (SEQ ID NO: 109) |
| 609 | SRQQSTAVV | (SEQ ID NO: 110) |
| 641 | FPVESATLD | (SEQ ID NO: 111) |
| 647 | TLDGSSSSD | (SEQ ID NO: 112) |
| 648 | LDGSSSSDD | (SEQ ID NO: 113) |
| 649 | DGSSSSDDH | (SEQ ID NO: 114) |
| 650 | GSSSSDDHG | (SEQ ID NO: 115) |
| 667 | VRGPSAVEM | (SEQ ID NO: 116) |
| 702 | QQGLSSTST | (SEQ ID NO: 117) |
| 703 | QGLSSTSTL | (SEQ ID NO: 118) |
| 705 | LSSTSTLTV | (SEQ ID NO: 119) |
| 717 | KENNSPPRA | (SEQ ID NO: 120) |
| 735 | LPNNSITLD | (SEQ ID NO: 121) |
| 741 | TLDGSRSTD | (SEQ ID NO: 122) |
| 743 | DGSRSTDDQ | (SEQ ID NO: 123) |
| 751 | QRIVSYLWI | (SEQ ID NO: 124) |
| 760 | RDGQSPAAG | (SEQ ID NO: 125) |
| 770 | VIDGSDHSV | (SEQ ID NO: 126) |
| 773 | GSDHSVALQ | (SEQ ID NO: 127) |
| 795 | RVTDSQGAS | (SEQ ID NO: 128) |
| 799 | SQGASDTDT | (SEQ ID NO: 129) |
| 815 | DPRKSGLVE | (SEQ ID NO: 130) |
| 850 | NVLDSDIKV | (SEQ ID NO: 131) |
| 861 | IRAHSDLST | (SEQ ID NO: 132) |
| 864 | HSDLSTVIV | (SEQ ID NO: 133) |
| 873 | FYVQSRPPF | (SEQ ID NO: 134) |
| 894 | HMRLSKEKA | (SEQ ID NO: 135) |
| 918 | LLKCSGHGH | (SEQ ID NO: 136) |
| 933 | RCICSHLWM | (SEQ ID NO: 137) |
| 950 | WDGESNCEW | (SEQ ID NO: 138) |
| 955 | NCEWSIFYV | (SEQ ID NO: 139) |
| 1019 | IKHRSTEHN | (SEQ ID NO: 140) |
| 1024 | TEHNSSLMV | (SEQ ID NO: 141) |
| 1025 | EHNSSLMVS | (SEQ ID NO: 142) |
| 1029 | SLMVSESEF | (SEQ ID NO: 143) |
| 1031 | MVSESEFDS | (SEQ ID NO: 144) |
| 1035 | SEFDSDQDT | (SEQ ID NO: 145) |
| 1042 | DTIFSREKM | (SEQ ID NO: 146) |
| 1054 | NPKVSMNGS | (SEQ ID NO: 147) |
| 1058 | SMNGSIRNG | (SEQ ID NO: 148) |
| 1064 | RNGASFSYC | (SEQ ID NO: 149) |
| 1066 | GASFSYCSK | (SEQ ID NO: 150) |
| 1069 | FSYCSKDR | (SEQ ID NO: 151) |

Threonine predictions (Start Position indicated)

| Position | Sequence | SEQ ID NO |
|---|---|---|
| 5 | MAPPTGYLS | (SEQ ID NO: 152) |
| 16 | LLLVTIAGC | (SEQ ID NO: 153) |
| 30 | SEGRTYSNA | (SEQ ID NO: 154) |
| 42 | PNLETTRIM | (SEQ ID NO: 155) |
| 43 | NLETTRIMR | (SEQ ID NO: 156) |
| 51 | RVSHTFPVV | (SEQ ID NO: 157) |
| 58 | VVDCTAACC | (SEQ ID NO: 158) |
| 101 | RSYLTFVLR | (SEQ ID NO: 159) |
| 183 | SAEYTDWGL | (SEQ ID NO: 160) |
| 209 | VPAETQQDP | (SEQ ID NO: 161) |
| 224 | ESASTPAPK | (SEQ ID NO: 162) |
| 240 | LPLPTTPSS | (SEQ ID NO: 163) |
| 241 | PLPTTPSSG | (SEQ ID NO: 164) |
| 286 | LSSVTVEKS | (SEQ ID NO: 165) |
| 294 | SPVLTVTPG | (SEQ ID NO: 166) |
| 296 | VLTVTPGST | (SEQ ID NO: 167) |
| 300 | TPGSTEHSI | (SEQ ID NO: 168) |
| 306 | HSIPTPPTS | (SEQ ID NO: 169) |
| 309 | PTPPTSAAP | (SEQ ID NO: 170) |
| 317 | PSESTPSEL | (SEQ ID NO: 171) |
| 326 | PISPTTAPR | (SEQ ID NO: 172) |
| 327 | ISPTTAPRT | (SEQ ID NO: 173) |
| 331 | TAPRTVKEL | (SEQ ID NO: 174) |
| 336 | VKELTVSAG | (SEQ ID NO: 175) |
| 346 | NLIITLPDN | (SEQ ID NO: 176) |
| 366 | PPVETTYNY | (SEQ ID NO: 177) |
| 367 | PVETTYNYE | (SEQ ID NO: 178) |
| 379 | ISHPTDYQG | (SEQ ID NO: 179) |
| 392 | GHKQTLNLS | (SEQ ID NO: 180) |
| 408 | VFKVTVSSE | (SEQ ID NO: 181) |
| 423 | FVNVTVKPA | (SEQ ID NO: 182) |
| 446 | LQELTLPLT | (SEQ ID NO: 183) |
| 450 | TLPLTSALI | (SEQ ID NO: 184) |
| 460 | GSQSTDDTE | (SEQ ID NO: 185) |
| 463 | SIDDIEIVS | (SEQ ID NO: 186) |
| 482 | IEEKTSVDS | (SEQ ID NO: 187) |
| 506 | RLTVTDSDG | (SEQ ID NO: 188) |
| 512 | SDGATNSTT | (SEQ ID NO: 189) |
| 515 | ATNSTTAAL | (SEQ ID NO: 190) |
| 516 | TNSTTAALI | (SEQ ID NO: 191) |
| 538 | GPNHTITLP | (SEQ ID NO: 192) |
| 540 | NHTITLPQN | (SEQ ID NO: 193) |
| 547 | QNSITLNGN | (SEQ ID NO: 194) |
| 582 | QGVQTPYLH | (SEQ ID NO: 195) |
| 596 | EGDYTFQLK | (SEQ ID NO: 196) |
| 602 | QLKVTDSSR | (SEQ ID NO: 197) |
| 610 | RQQSTAVVT | (SEQ ID NO: 198) |
| 614 | TAVVTVIVQ | (SEQ ID NO: 199) |
| 643 | VESATLDGS | (SEQ ID NO: 200) |
| 680 | KAIATVTGL | (SEQ ID NO: 201) |
| 682 | IATVTGLQV | (SEQ ID NO: 202) |
| 688 | LQVGTYHFR | (SEQ ID NO: 203) |
| 694 | HFRLTVKDQ | (SEQ ID NO: 204) |
| 704 | GLSSTSTLT | (SEQ ID NO: 205) |
| 706 | SSTSTLTVA | (SEQ ID NO: 206) |
| 708 | TSTLTVAVK | (SEQ ID NO: 207) |
| 737 | NNSITLDGS | (SEQ ID NO: 208) |
| 744 | GSRSTDDQR | (SEQ ID NO: 209) |
| 779 | ALQLTNLVE | (SEQ ID NO: 210) |
| 787 | EGVYTPHLR | (SEQ ID NO: 211) |
| 793 | HLRVTDSQG | (SEQ ID NO: 212) |
| 801 | GASDTDTAT | (SEQ ID NO: 213) |
| 803 | SDTDTATVE | (SEQ ID NO: 214) |
| 805 | TDTATVEVQ | (SEQ ID NO: 215) |
| 821 | LVELTLQVG | (SEQ ID NO: 216) |
| 830 | VGQLTEQRK | (SEQ ID NO: 217) |
| 836 | QRKDTLVRQ | (SEQ ID NO: 218) |
| 865 | SDLSTVIVF | (SEQ ID NO: 219) |
| 910 | LRVDTAGCL | (SEQ ID NO: 220) |
| 927 | CDPLTKRCI | (SEQ ID NO: 221) |
| 960 | IFYVTVLAF | (SEQ ID NO: 222) |
| 965 | VLAFTLIVL | (SEQ ID NO: 223) |
| 970 | LIVLTGGFT | (SEQ ID NO: 224) |

TABLE VI-continued

Post-translational modifications of 254P1D6B

| | | |
|---|---|---|
| 974 | TGGFTWLCI | (SEQ ID NO: 225) |
| 987 | RQKRTKIRK | (SEQ ID NO: 226) |
| 993 | IRKKTKYTI | (SEQ ID NO: 227) |
| 996 | KTKYTILDN | (SEQ ID NO: 228) |
| 1020 | KHRSTEHNS | (SEQ ID NO: 229) |
| 1039 | SDQDTIFSR | (SEQ ID NO: 230) |

Tyrosine predictions (Start Position indicated)

| | | |
|---|---|---|
| 31 | EGRTYSNAV | (SEQ ID NO: 231) |
| 78 | EGRCYLVSC | (SEQ ID NO: 232) |
| 99 | PIRSYLTFV | (SEQ ID NO: 233) |
| 116 | QLLDYGDMM | (SEQ ID NO: 234) |
| 156 | EMSEYSDDY | (SEQ ID NO: 235) |
| 160 | YSDDYRELE | (SEQ ID NO: 236) |
| 182 | GSAEYTDWG | (SEQ ID NO: 237) |
| 217 | PELHYLNES | (SEQ ID NO: 238) |
| 368 | VETTYNYEW | (SEQ ID NO: 239) |
| 370 | TTYNYEWNL | (SEQ ID NO: 240) |

TABLE VI-continued

Post-translational modifications of 254P1D6B

| | | |
|---|---|---|
| 381 | HPTDYQGEI | (SEQ ID NO: 241) |
| 403 | SVGLYVFKV | (SEQ ID NO: 242) |
| 468 | EIVSYHWEE | (SEQ ID NO: 243) |
| 499 | DPGNYSFRL | (SEQ ID NO: 244) |
| 527 | NAVDYPPVA | (SEQ ID NO: 245) |
| 562 | QIVLYEWSL | (SEQ ID NO: 246) |
| 584 | VQTPYLHLS | (SEQ ID NO: 247) |
| 595 | QEGDYTFQL | (SEQ ID NO: 248) |
| 658 | GIVFYHWEH | (SEQ ID NO: 249) |
| 689 | QVGTYHFRL | (SEQ ID NO: 250) |
| 752 | RIVSYLWIR | (SEQ ID NO: 251) |
| 786 | VEGVYTFHL | (SEQ ID NO: 252) |
| 870 | VIVFYVQSR | (SEQ ID NO: 253) |
| 944 | LIQRYIWDG | (SEQ ID NO: 254) |
| 958 | WSIFYVTVL | (SEQ ID NO: 255) |
| 995 | KKTKYTILD | (SEQ ID NO: 256) |
| 1013 | LRPKYGIKH | (SEQ ID NO: 257) |
| 1067 | ASFSYCSKD | (SEQ ID NO: 258) |

TABLE VII

Search Peptides

254P1D6Bv.1

```
   1 MAPPTGVLSS LLLLVTIAGC ARKQCSEGRT YSNAVISPNL ETTRIMRVSH TFPVVDCTAA   (SEQ ID NO: 259)
  61 CCDLSSCDLA WWFEGRCYLV SCPHKENCEP KKMGPIRSYL TFVLRPVQRP AQLLDYGDMM
 121 LNRGSPSGIW GDSPEDIRKD LPFLGKDWGL EEMSEYSDDY RELEKDLLQP SGKQEPRGSA
 181 EYTDWGLLPG SEGAFNSSVG DSPAVPAETQ QDPELHYLNE SASTPAPKLP ERSVLLPLPT
 241 TPSSGEVLEK EKASQLQEQS SNSSGKEVLM PSHSLPPASL ELSSVTVEKS PVLTVTPGST
 301 EHSIPTPPTS AAPSESTPSE LPISPTTAPR TVKELTVSAG DNLIITLPDN EVELKAFVAP
 361 APEVETTYNY EWNLISHPTD YQGEIKQGHK QTLNLSQLSV GLYVFKVTVS SENAFGEGFV
 421 NVTVKPARRV NLPPVAVVSP QLQELTLPLT SALIDGSQST DDTEIVSYHW EFINGEFIEE
 481 KTSVDSPVLR LSNLDPGNYS FRLTVTDSDG ATNSTTAALI VNNAVDYPPV ANAGPNHTIT
 541 LPQNSITLNG NQSSDDHQIV LYEWSLGPGS EGKHVVMQGV QTPYLHLSAM QEGDYTFQLK
 601 VTDSSRQQST AVVTVIVQPE NNRPPVAVAG PDKELIFPVE SATLDGSSSS DDHGIVFYHW
 661 EHVRGPSAVE MENIDKAIAT VTGLQVGTYH FRLTVKDQQG LSSTSTLTVA VKKENNSPPR
 721 ARAGGRHVLV LPNNSITLDG SRSTDDQRIV SYLWIRDGQS PAAGDVIDGS DHSVALQLTN
 781 LVEGVYTFHL RVTDSQGASD TDTATVEVQP DPRKSGLVEL TLQVGVGQLT EQRKDTLVRQ
 841 LAVLLNVLDS DIKVQKIRAH SDLSTVIVFY VQSRPPFKVL KAAEVARNLH MRLSKEKADF
 901 LLFKVLRVDT AGCLLKCSGH GHCDPLTKRC ICSHLWMENL IQRYIWDGES NCEWSIFYVT
 961 VLAFTLIVLT GGFTWLCICC CKRQKRTKIR KKTKYTILDN MDEQERMELR PKYGIKHRST
1021 EHNSSLMVSE SEFDSDQDTI FSREKMERGN PKVSMNGSIR NGASFSYCSK DR
```

254P1D6Bv.2

| | | |
|---|---|---|
| 9-mers, aa 149-175 | GLEEMSEYADDYRELEK | (SEQ ID NO: 260) |
| 10-mers, aa 148-176 | WGLEEMSEYADDYRELEKD | (SEQ ID NO: 261) |
| 15-mers, aa 143-181 | FLGKDWGLEEMSEYADDYRELEKDLLQPS | (SEQ ID NO: 262) |

254P1D6BV.3

| | | |
|---|---|---|
| 9-mers, aa 1-18 | MTRLGWPSPCCARKQCSE | (SEQ ID NO: 263) |
| 10-mers, aa 1-19 | MTRLGWPSPCCARKQCSEG | (SEQ ID NO: 264) |
| 15-mers, aa 1-24 | MTRLGWPSPCCARKQCSEGRTYSN | (SEQ ID NO: 265) |

254P1D6Bv.5

| | | |
|---|---|---|
| 9-mers, aa 134-150 | PEDIRKDLTFLGKDWGL | (SEQ ID NO: 266) |
| 10-mers, aa 133-151 | SPEDIRKDLTFLGKDWGLE | (SEQ ID NO: 267) |
| 15-mers, aa 128-156 | GIWGDSPEDIRKDLTFLGKDWGLEEMSEY | (SEQ ID NO: 268) |

TABLE VIII-254P1D6B v.1

HLA A1 9-mers
Each peptide is a portion of
SEQ ID NO: 3; each start
position is specified, the length
of peptide is 9 amino acids
and the end position for each
peptide is the start position
plus eight.

| Pos | Subsequence | Score |
|---|---|---|
| 493 | NLDPGNYSF | 100.0 |
| 668 | AVEMENIDK | 90.000 |
| 39 | NLETTRIMR | 45.000 |
| 649 | SSDDHGIVF | 37.500 |
| 936 | WMENLIQRY | 22.500 |
| 153 | MSEYSDDYR | 13.500 |
| 805 | TVEVQPDPR | 9.000 |
| 743 | STDDQRIVS | 6.250 |
| 182 | YTDWGLLPG | 6.250 |
| 459 | STDDTEIVS | 6.250 |
| 922 | HCDPLTKRC | 5.000 |
| 351 | EVELKAFVA | 4.500 |
| 87 | NCEPKKMGP | 4.500 |
| 244 | SGEVLEKEK | 4.500 |
| 382 | QGEIKQGHK | 4.500 |
| 462 | DTEIVSYHW | 4.500 |
| 951 | NCEWSIFYV | 4.500 |
| 553 | SSDDHQIVL | 3.750 |
| 1034 | DSDQDTIFS | 3.750 |
| 569 | GSEGKHVVM | 2.700 |
| 25 | CSEGRTYSN | 2.700 |
| 554 | SDDHQIVLY | 2.500 |
| 650 | SDDHGIVFY | 2.500 |
| 460 | TDDTEIVSY | 2.500 |
| 138 | RKDLPFLGK | 2.500 |
| 157 | SDDYRELEK | 2.500 |
| 897 | KADFLLFKV | 2.500 |
| 378 | PTDYQGEIK | 2.500 |
| 800 | DTDTATVEV | 2.500 |
| 483 | SVDSPVLRL | 2.500 |
| 113 | LLDYGDMML | 2.500 |
| 347 | LPDNEVELK | 2.500 |
| 505 | VTDSDGATN | 2.500 |
| 744 | TDDQRIVSY | 2.500 |
| 592 | EGDYTFQLK | 2.500 |

TABLE VIII-254P1D6B v.1-continued

HLA A1 9-mers
Each peptide is a portion of
SEQ ID NO: 3; each start
position is specified, the length
of peptide is 9 amino acids
and the end position for each
peptide is the start position
plus eight.

| Pos | Subsequence | Score |
|---|---|---|
| 349 | DNEVELKAF | 2.250 |
| 829 | LTEQRKDTL | 2.250 |
| 1019 | STEHNSSLM | 2.250 |
| 565 | SLGPGSEGK | 2.000 |
| 84 | HKENCEPKK | 1.800 |
| 279 | SLELSSVTV | 1.800 |
| 860 | HSDLSTVIV | 1.500 |
| 769 | GSDHSVALQ | 1.500 |
| 798 | ASDTDTATV | 1.500 |
| 410 | SSENAFGEG | 1.350 |
| 190 | GSEGAFNSS | 1.350 |
| 778 | LTNLVEGVY | 1.250 |
| 130 | WGDSPEDIR | 1.250 |
| 809 | QPDPRKSGL | 1.250 |
| 681 | VTGLQVGTY | 1.250 |
| 601 | VTDSSRQQS | 1.250 |
| 519 | LIVNNAVDY | 1.000 |
| 705 | STLTVAVKK | 1.000 |
| 862 | DLSTVIVFY | 1.000 |
| 54 | VVDCTAACC | 1.000 |
| 15 | VTIAGCARK | 1.000 |
| 524 | AVDYPPVAN | 1.000 |
| 179 | SAEYTDWGL | 0.900 |
| 712 | KKENNSPPR | 0.900 |
| 149 | GLEEMSEYS | 0.900 |
| 781 | LVEGVYTFH | 0.900 |
| 882 | AAEVARNLH | 0.900 |
| 817 | LVELTLQVG | 0.900 |
| 210 | QQDPELHYL | 0.750 |
| 395 | LSQLSVGLY | 0.750 |
| 491 | LSNLDPGNY | 0.750 |
| 315 | ESTPSELPI | 0.750 |
| 849 | DSDIKVQKI | 0.750 |
| 507 | DSDGATNST | 0.750 |

TABLE VIII-254P1D6B v.1-continued

HLA A1 9-mers
Each peptide is a portion of SEQ ID NO: 3; each start position is specified, the length of peptide is 9 amino acids and the end position for each peptide is the start position plus eight.

| Pos | Subsequence | Score |
|---|---|---|
| 587 | LSAMQEGDY | 0.750 |
| 950 | SNCEWSIFY | 0.625 |
| 339 | AGDNLIITL | 0.625 |
| 398 | LSVGLYVFK | 0.600 |
| 220 | ESASTPAPK | 0.600 |
| 704 | TSTLTVAVK | 0.600 |
| 224 | TPAPKLPER | 0.500 |
| 131 | GDSPEDIRK | 0.500 |
| 766 | VIDGSDHSV | 0.500 |
| 473 | INGPFIEEK | 0.500 |
| 373 | NLISHPTDY | 0.500 |
| 274 | SLPPASLEL | 0.500 |
| 847 | VLDSDIKVQ | 0.500 |
| 360 | PAPPVETTY | 0.500 |
| 61 | CCDLSSCDL | 0.500 |
| 907 | RVDTAGCLL | 0.500 |
| 670 | EMENIDKAI | 0.450 |
| 618 | QPENNRPPV | 0.450 |
| 299 | STEHSIPTP | 0.450 |
| 1006 | RMEIRPKYG | 0.450 |
| 638 | PVESATLDG | 0.450 |
| 469 | HWEEINGPF | 0.450 |
| 281 | ELSSVTVEK | 0.400 |
| 870 | YVQSRPPFK | 0.400 |
| 209 | TQQDPELHY | 0.375 |
| 482 | TSVDSPVLR | 0.300 |
| 302 | HSIPTPPTS | 0.300 |
| 97 | RSYLTFVLR | 0.300 |
| 375 | ISHPTDYQG | 0.300 |
| 442 | LQELTLPLT | 0.270 |
| 576 | VMQGVQTPY | 0.250 |

TABLE VIII-V2

HLA-A1-9 mers-254P1D68
Each peptide is a portion of SEQ ID NO: 5; each start position is specified, the length of peptide is 9 amino acids, and the end position for each peptide is the start position plus eight.

| Start | Subsequence | Score |
|---|---|---|
| 5 | MSEYADDYR | 13.500 |
| 9 | ADDYRELEK | 2.500 |
| 1 | GLEEMSEYA | 0.900 |
| 4 | EMSEYADDY | 0.250 |
| 8 | YADDYRELE | 0.050 |
| 2 | LEEMSEYAD | 0.009 |
| 7 | EYADDYREL | 0.001 |
| 6 | SEYADDYRE | 0.000 |
| 3 | EEMSEYADD | 0.000 |

TABLE VIII-V3

HLA-A1-9mers-254P1D68
Each peptide is a portion of SEQ ID NO: 7; each start position is specified, the length of peptide is 9 amino acids, and the end position for each peptide is the start position plus eight.

| Start | Subsequence | Score |
|---|---|---|
| 6 | WPSPCCARK | 1.000 |
| 3 | RLGWPSPCC | 0.020 |
| 5 | GWPSPCCAR | 0.005 |
| 8 | SPCCARKQC | 0.003 |
| 4 | LGWPSPCCA | 0.003 |
| 7 | PSPCCARKQ | 0.002 |
| 9 | PCCARKQCS | 0.001 |
| 1 | MTRLGWPSP | 0.001 |
| 2 | TRLGWPSPC | 0.001 |
| 10 | CCARKQCSE | 0.000 |

TABLE VIII-V5

HLA-A1-9mers-254P1D68
Each peptide is a portion of SEQ ID NO: 11; each start position is specified, the length of peptide is 9 amino acids, and the end position for each peptide is the start position plus eight.

| Start | Subsequence | Score |
|---|---|---|
| 5 | RKDLTFLGK | 2.500 |
| 8 | LTFLGKDWG | 0.025 |

TABLE VIII-V5-continued

HLA-A1-9mers-254P1D68
Each peptide is a portion of SEQ ID NO: 11; each start position is specified, the length of peptide is 9 amino acids, and the end position for each peptide is the start position plus eight.

| Start | Subsequence | Score |
|---|---|---|
| 7 | DLTFLGKDW | 0.010 |
| 1 | PEDIRKDLT | 0.003 |
| 2 | EDIRKDLTF | 0.003 |
| 9 | TFLGKDWGL | 0.001 |
| 4 | IRKDLTFLG | 0.000 |
| 3 | DIRKDLTFL | 0.000 |
| 6 | KDLTFLGKD | 6.000 |

TABLE IX

HLA-A1--10-mers-254P1D6B
Each peptide is a portion of SEQ ID NO: 3; each start position is specified, the length of peptide is 10 amino acids, and the end position for each peptide is the start position plus nine.

| Start | Subsequence | Score |
|---|---|---|
| 173 | KQEPRGSAEY | 135.000 |
| 743 | STDDQRIVSY | 125.000 |
| 459 | STDDTEIVSY | 125.000 |
| 649 | SSDDHGIVFY | 75.000 |
| 156 | YSDDYRELEK | 75.000 |
| 553 | SSDDHQIVLY | 75.000 |
| 907 | RVDTAGCLLK | 50.000 |
| 493 | NLDPGNYSFR | 50.000 |
| 860 | HSDLSTVIVF | 37.500 |
| 1034 | DSDQDTIFSR | 37.500 |
| 805 | TVEVQPDPRK | 36.000 |
| 847 | VLDSDIKVQK | 20.000 |
| 410 | SSENAFGEGF | 13.500 |
| 130 | WGDSPEDIRK | 12.500 |
| 1019 | STEHNSSLMV | 11.250 |
| 87 | NCEFKKMGPI | 9.000 |
| 849 | DSDIKVQKIR | 7.500 |
| 208 | ETQQDPELHY | 6.250 |
| 922 | HCDPLTKRCI | 5.000 |
| 628 | VAGPDKELIF | 5.000 |
| 997 | ILDNMDEQER | 5.000 |
| 781 | LVEGVYTFHL | 4.500 |

TABLE IX-continued

HLA-A1--10-mers-254P1D6B
Each peptide is a portion of SEQ ID NO: 3; each start position is specified, the length of peptide is 10 amino acids, and the end position for each peptide is the start position plus nine.

| Start | Subsequence | Score |
|---|---|---|
| 39 | NLETTRIMRV | 4.500 |
| 882 | AAEARNLHM | 4.500 |
| 949 | ESNCEWSIFY | 3.750 |
| 769 | GSDHSVALQL | 3.750 |
| 569 | GSEGKHVVMQ | 2.700 |
| 66 | SCDLAWWFEG | 2.500 |
| 182 | YTDWGLLPGS | 2.500 |
| 113 | LLDYGDMMLN | 2.500 |
| 829 | LTEQRKDTLV | 2.250 |
| 951 | NCEWSIFYVT | 1.800 |
| 477 | FIEEKTSVDS | 1.800 |
| 817 | LVELTLQVGV | 1.800 |
| 210 | QQDPELHYLN | 1.500 |
| 1036 | DQDTIFSREK | 1.500 |
| 1028 | VSESEFDSDQ | 1.350 |
| 25 | CSEGRTYSNA | 1.350 |
| 1030 | ESEFDSDQDT | 1.350 |
| 190 | GSEGAFNSSV | 1.350 |
| 601 | VTDSSRQQST | 1.250 |
| 792 | VTDSQGASDT | 1.250 |
| 505 | VTDSDGATNS | 1.250 |
| 539 | ITLPQNSITL | 1.250 |
| 1000 | NMDEQERMEL | 1.250 |
| 359 | APAPPVETTY | 1.250 |
| 800 | DTDTATVEVQ | 1.250 |
| 809 | QPDPRKSGLV | 1.250 |
| 35 | VISPNLETTR | 1.000 |
| 524 | AVDYPPVANA | 1.000 |
| 518 | ALIVNNAVDY | 1.000 |
| 186 | GLLPGSEGAF | 1.000 |
| 667 | SAVEMENIDK | 1.000 |
| 703 | STSTLTVAVK | 1.000 |
| 670 | EMENIDKAIA | 0.900 |
| 1006 | RMELRPKYGI | 0.900 |
| 179 | SAEYTDWGLL | 0.900 |

TABLE IX-continued

HLA-A1--10-mers-254P1D6B
Each peptide is a portion of SEQ ID NO: 3; each start position is specified, the length of peptide is 10 amino acids, and the end position for each peptide is the start position plus nine.

| Start | Subsequence | Score |
|---|---|---|
| 668 | AVEMENIDRA | 0.900 |
| 648 | SSSDDHGIVF | 0.750 |
| 507 | DSDGATNSTT | 0.750 |
| 273 | HSLPPASLEL | 0.750 |
| 590 | MQEGDYTFQL | 0.675 |
| 442 | LQELTLPLTS | 0.675 |
| 592 | EGDYTFQLKV | 0.625 |
| 378 | PTDYQGEIKQ | 0.625 |
| 347 | LPDNEVELKA | 0.625 |
| 872 | QSRPPFKVLK | 0.600 |
| 704 | TSTLTVAVKK | 0.600 |
| 777 | QLTNLVEGVY | 0.500 |
| 687 | GTYHFRLTVK | 0.500 |
| 897 | KADFLLFKVL | 0.500 |
| 766 | VIDGSDHSVA | 0.500 |
| 729 | LVLPNNSITL | 0.500 |
| 394 | NLSQLSVGLY | 0.500 |
| 586 | HLSAMQEGDY | 0.500 |
| 445 | LTLPLTSALI | 0.500 |
| 61 | CCDLSSCDLA | 0.500 |
| 680 | TVTGLQVGTY | 0.500 |
| 223 | STPAPKLPER | 0.500 |
| 100 | LTFVLRPVQR | 0.500 |
| 483 | SVDSPVLRLS | 0.500 |
| 1 | MAPPTGVLSS | 0.500 |
| 575 | VVMQGVQTPY | 0.500 |
| 955 | SIFYVTVLAF | 0.500 |
| 345 | ITLPDNEVEL | 0.500 |
| 164 | EKDLLQPSGK | 0.500 |
| 1039 | TIFSREKMER | 0.500 |
| 481 | KTSVDSPVLR | 0.500 |
| 490 | RLSNLDPGNY | 0.500 |
| 532 | NAGPNHTITL | 0.500 |
| 415 | FGEGFVNVTV | 0.450 |
| 936 | WMENLIQRYI | 0.450 |
| 349 | DNEVELKAFV | 0.450 |

TABLE IX-continued

HLA-A1--10-mers-254P1D6B
Each peptide is a portion of SEQ ID NO: 3; each start position is specified, the length of peptide is 10 amino acids, and the end position for each peptide is the start position plus nine.

| Start | Subsequence | Score |
|---|---|---|
| 618 | QPENNRPPVA | 0.450 |
| 286 | TVEKSPVLTV | 0.450 |
| 1001 | MDEQERMELR | 0.450 |
| 76 | RCYLVSCPHK | 0.400 |
| 397 | QLSVGLYVFK | 0.400 |
| 14 | LVTIAGCARK | 0.400 |
| 107 | VQRPAQLLDY | 0.375 |

TABLE IX-V2

HLA-A1-10mers-254P1D68
Each peptide is a portion of SEQ ID NO: 5; each start position is specified, the length of peptide is 10 amino acids, and the end position for each peptide is the start position plus nine.

| Start | Subsequence | Score |
|---|---|---|
| 9 | YADDYRELEK | 50.000 |
| 6 | MSEYADDYRE | 0.270 |
| 2 | GLEEMSEYAD | 0.180 |
| 5 | EMSEYADDYR | 0.050 |
| 4 | EEMSEYADDY | 0.025 |
| 3 | LEEMSEYADD | 0.009 |
| 10 | ADDYRELEKD | 0.003 |
| 1 | WGLEEMSEYA | 0.003 |
| 7 | SEYADDYREL | 0.001 |
| 8 | EYADDYRELE | 0.000 |

TABLE IX-V3

HLA-A1-10mers-254P1D68
Each peptide is a portion of SEQ ID NO: 7; each start position is specified, the length of peptide is 10 amino acids, and the end position for each peptide is the start position plus nine.

| Start | Subsequence | Score |
|---|---|---|
| 4 | LGWPSPCCAR | 0.025 |
| 6 | WPSPCCARKQ | 0.025 |
| 5 | GWPSPCCARK | 0.020 |
| 3 | RLGWPSPCCA | 0.010 |
| 8 | SPCCARKQCS | 0.003 |

TABLE IX-V3-continued

HLA-A1-10mers-254P1D68
Each peptide is a portion of SEQ ID NO: 7; each start position is specified, the length of peptide is 10 amino acids, and the end position for each peptide is the start position plus nine.

| Start | Subsequence | Score |
|---|---|---|
| 1 | MTRLGWPSPC | 0.003 |
| 7 | PSPCCARKQC | 0.002 |
| 10 | CCARKQCSEG | 0.001 |
| 2 | TRLGWPSPCC | 0.001 |
| 9 | PCCARKQCSE | 0.000 |

TABLE IX-V5

HLA-A1-10mers-254P1D68
Each peptide is a portion of SEQ ID NO: 11; each start position is specified, the length of peptide is 10 amino acids, and the end position for each peptide is the start position plus nine.

| Start | Subsequence | Score |
|---|---|---|
| 1 | SPEDIRKDLT | 0.225 |
| 2 | PEDIRKDLTF | 0.125 |
| 9 | LTFLGKDWGL | 0.025 |
| 8 | DLTFLGKDWG | 0.010 |
| 5 | IRKDLTFLGK | 0.005 |
| 6 | RKDLTFLGKD | 0.003 |
| 4 | DIRKDLTFLG | 0.001 |
| 7 | KDLTFLGKDW | 0.001 |
| 10 | TFLGKDWGLE | 0.000 |
| 3 | EDIRKDLTFL | 0.000 |

TABLE X-V1

HLA-A0201-HLA-9mers-254P1D68
Each peptide is a portion of SEQ ID NO: 3; each start position is specified, the length of peptide is 9 amino acids, and the end position for each peptide is the start position plus eight.

| Start | Subsequence | Score |
|---|---|---|
| 900 | FLLFKVLRV | 2722.683 |
| 401 | GLYVFKVTV | 845.752 |
| 968 | VLTGGFTWL | 379.503 |
| 228 | KLPERSVLL | 306.550 |
| 92 | KMGPIRSYL | 296.997 |
| 816 | GLVELTLQV | 285.163 |
| 7 | VLSSLLLLV | 271.948 |

TABLE X-V1-continued

HLA-A0201-HLA-9mers-254P1D68
Each peptide is a portion of SEQ ID NO: 3; each start position is specified, the length of peptide is 9 amino acids, and the end position for each peptide is the start position plus eight.

| Start | Subsequence | Score |
|---|---|---|
| 99 | YLTFVLRPV | 147.172 |
| 396 | SQLSVGLYV | 143.504 |
| 944 | YIWDGESNC | 106.931 |
| 846 | NVLDSDIKV | 92.322 |
| 441 | QLQELTLPL | 87.586 |
| 346 | TLPDNEVEL | 87.586 |
| 399 | SVGLYVFKV | 81.185 |
| 777 | QLTNLVEGV | 78.385 |
| 784 | GVYTFHLRV | 74.003 |
| 12 | LLLVTIAGC | 71.872 |
| 392 | TLNLSQLSV | 69.552 |
| 871 | VQSRPPFKV | 69.531 |
| 839 | RQLAVLLNV | 60.011 |
| 863 | LSTVIVFYV | 56.629 |
| 958 | YVTVLAFTL | 49.871 |
| 112 | QLLDYGDMM | 36.929 |
| 730 | VLPNNSITL | 36.316 |
| 960 | TVLAFTLIV | 35.082 |
| 961 | VLAFTLIVL | 34.246 |
| 655 | IVFYHWEHV | 31.887 |
| 828 | QLTEQRKDT | 30.553 |
| 452 | ALIDGSQST | 30.553 |
| 350 | NEVELKAFV | 30.497 |
| 558 | QIVLYEWSL | 22.030 |
| 394 | NLSQLSVGL | 21.362 |
| 540 | TLPQNSITL | 21.362 |
| 274 | SLPPASLEL | 21.362 |
| 577 | MQGVQTPYL | 20.251 |
| 840 | QLAVLLNVL | 20.145 |
| 836 | TLVRQLAVL | 20.145 |
| 897 | KADFLLFKV | 18.041 |
| 844 | LLNVLDSDI | 17.736 |
| 728 | VLVLPNNSI | 17.736 |
| 390 | KQTLNLSQL | 17.436 |
| 10 | SLLLLVTIA | 17.334 |

TABLE X-V1-continued

HLA-A0201-HLA-9mers-254P1D68
Each peptide is a portion of SEQ ID NO: 3; each
start position is specified, the length of
peptide is 9 amino acids, and the end position
for each peptide is the start position plus
eight.

| Start | Subsequence | Score |
|---|---|---|
| 344 | IITLPDNEV | 16.258 |
| 607 | QQSTAVVTV | 16.219 |
| 6 | GVLSSLLLL | 15.907 |
| 113 | LLDYGDMML | 14.526 |
| 687 | GTYHFRLTV | 11.747 |
| 1045 | KMERGNPKV | 11.252 |
| 210 | QQDPELHYL | 10.960 |
| 685 | QVGTYHFRL | 10.841 |
| 446 | TLPLTSALI | 10.433 |
| 591 | QEGDYTFQL | 9.878 |
| 186 | GLLPGSEGA | 9.007 |
| 673 | NIDKAIATV | 8.798 |
| 818 | VELTLQVGV | 8.507 |
| 700 | GLSSTSTLT | 7.452 |
| 437 | VVSPQLQEL | 7.309 |
| 366 | TTYNYEWNL | 7.121 |
| 766 | VIDGSDHSV | 6.503 |
| 635 | LIFPVESAT | 6.445 |
| 821 | TLQVGVGQL | 6.387 |
| 429 | RVNLPPVAV | 6.086 |
| 284 | SVTVEKSPV | 6.086 |
| 774 | VALQLTNLV | 6.076 |
| 973 | FTWLCICCC | 6.059 |
| 233 | SVLLPLPTT | 5.549 |
| 497 | GNYSFRLTV | 5.521 |
| 40 | LETTRIMRV | 5.288 |
| 191 | SEGAFNSSV | 5.139 |
| 47 | RVSHTFPVV | 4.741 |
| 419 | FVNVTVKPA | 4.599 |
| 279 | SLELSSVTV | 4.451 |
| 773 | SVALQLTNL | 4.299 |
| 782 | VEGVYTFHL | 4.096 |
| 517 | AALIVNNAV | 3.574 |
| 969 | LTGGFTWLC | 3.343 |
| 669 | VEMENIDKA | 2.808 |
| 579 | GVQTPYLHL | 2.804 |

TABLE X-V1-continued

HLA-A0201-HLA-9mers-254P1D68
Each peptide is a portion of SEQ ID NO: 3; each
start position is specified, the length of
peptide is 9 amino acids, and the end position
for each peptide is the start position plus
eight.

| Start | Subsequence | Score |
|---|---|---|
| 430 | VNLPPVAVV | 2.693 |
| 955 | SIFYVTVLA | 2.527 |
| 676 | KAIATVTGL | 2.388 |
| 858 | RAHSDLSTV | 2.222 |
| 1031 | SEFDSDQDT | 2.198 |
| 951 | NCEWSIFYV | 2.132 |
| 35 | VISPNLETT | 1.963 |
| 627 | AVAGPDKEL | 1.869 |
| 445 | LTLPLTSAL | 1.866 |
| 483 | SVDSPVLRL | 1.720 |
| 729 | LVLPNNSIT | 1.682 |
| 292 | VLTVTPGST | 1.647 |
| 678 | IATVTGLQV | 1.642 |
| 948 | GESNCEWSI | 1.521 |
| 988 | KIRKKTKYT | 1.499 |
| 962 | LAFTLIVLT | 1.497 |
| 538 | TITLPQNSI | 1.435 |
| 830 | TEQRKDTLV | 1.352 |
| 416 | GEGFVNVTV | 1.352 |
| 1020 | TEHNSSLMV | 1.352 |
| 465 | IVSYHWEEI | 1.293 |
| 822 | LQVGVGQLT | 1.284 |

TABLE X-V2

HLA-A0201-9mers-254P1D68
Each peptide is a portion of SEQ ID NO: 5; each
start position is specified, the length of
peptide is 9 amino acids, and the end position
for each peptide is the start position plus
eight.

| Start | Subsequence | Score |
|---|---|---|
| 1 | GLEEMSEYA | 3.513 |
| 4 | EMSEYADDY | 0.008 |
| 6 | SEYADDYRE | 0.001 |
| 8 | YADDYRELE | 0.001 |
| 7 | EYADDYREL | 0.000 |
| 3 | EEMSEYADD | 0.000 |

TABLE X-V2-continued

HLA-A0201-9mers-254P1D68
Each peptide is a portion of SEQ ID NO: 5; each start position is specified, the length of peptide is 9 amino acids, and the end position for each peptide is the start position plus eight.

| Start | Subsequence | Score |
|---|---|---|
| 2 | LEEMSEYAD | 0.000 |
| 5 | MSEYADDYR | 0.000 |
| 9 | ADDYRELEK | 0.000 |

TABLE X-V3

HLA-A0201-9mers-254P1D68
Each peptide is a portion of SEQ ID NO: 7; each start position is specified, the length of peptide is 9 amino acids, and the end position for each peptide is the start position plus eight.

| Start | Subsequence | Score |
|---|---|---|
| 3 | RLGWPSPCC | 4.968 |
| 4 | LGWPSPCCA | 0.458 |
| 8 | SPCCARKQC | 0.032 |
| 2 | TRLGWPSPC | 0.003 |
| 6 | WPSPCCARK | 0.000 |
| 10 | CCARKQCSE | 0.000 |
| 1 | MTRLGWPSP | 0.000 |
| 9 | PCCARKQCS | 0.000 |
| 5 | GWPSPCCAR | 0.000 |
| 7 | PSPCCARKQ | 0.000 |

TABLE X-V5

HLA-A0201-9mers-254P1D68
Each peptide is a portion of SEQ ID NO: 11; each start position is specified, the length of peptide is 9 amino acids, and the end position for each peptide is the start position plus eight.

| Start | Subsequence | Score |
|---|---|---|
| 9 | TFLGKDWGL | 0.412 |
| 3 | DIRKDLTFL | 0.212 |
| 8 | LTFLGKDWG | 0.018 |
| 7 | DLTFLGKDW | 0.006 |
| 1 | PEDIRKDLT | 0.001 |
| 6 | KDLTFLGKD | 0.000 |
| 5 | RKDLTFLGK | 0.000 |
| 4 | IRKDLTFLG | 0.000 |
| 2 | EDIRKDLTF | 0.000 |

TABLE XI-V1

HLA-A0201--10mers-254P1D68
Each peptide is a portion of SEQ ID NO: 3; each start position is specified, the length of peptide is 10 amino acids, and the end position for each peptide is the start position plus nine.

| Start | Subsequence | Score |
|---|---|---|
| 862 | DLSTVIVFYV | 382.727 |
| 112 | QLLDYGDMML | 324.068 |
| 968 | VLTGGFTWLC | 240.700 |
| 870 | YVQSRPPFKV | 162.369 |
| 576 | VMQGVQTPYL | 144.256 |
| 950 | SNCEWSIFYV | 136.577 |
| 967 | IVLTGGFTWL | 122.864 |
| 209 | TQQDPELHYL | 112.335 |
| 217 | YLNESASTPA | 93.696 |
| 11 | LLLLVTIAGC | 71.872 |
| 441 | QLQELTLPLT | 70.272 |
| 700 | GLSSTSTLTV | 69.552 |
| 843 | VLLNVLDSDI | 65.622 |
| 952 | CEWSIFYVTV | 63.982 |
| 892 | RLSKEKADFL | 57.572 |
| 6 | GVLSSLLLLV | 51.790 |
| 776 | LQLTNLVEGV | 49.989 |
| 617 | VQPENNRPPV | 49.151 |
| 901 | LLFKVLRVDT | 46.873 |
| 828 | QLTEQRKDTL | 42.917 |
| 45 | IMRVSHTFPV | 37.642 |
| 961 | VLAFTLIVLT | 29.137 |
| 1000 | NMDEQERMEL | 25.303 |
| 692 | RLTVKDQQGL | 21.362 |
| 836 | TLVRQLAVLL | 21.362 |
| 684 | LQVGTYHFRL | 21.356 |
| 92 | KMGPIRSYLT | 18.837 |
| 635 | LIFPVESATL | 18.476 |
| 120 | MLNRGSPSGI | 17.736 |
| 343 | LIITLPDNEV | 16.258 |
| 606 | RQQSTAVVTV | 16.219 |
| 808 | VQPDPRKSGL | 15.096 |
| 269 | LMPSHSLPPA | 14.029 |
| 355 | KAFVAPAPPV | 12.510 |
| 7 | VLSSLLLLVT | 11.946 |
| 729 | LVLPNNSITL | 11.757 |

TABLE XI-V1-continued

HLA-A0201--10mers-254P1D68
Each peptide is a portion of SEQ ID NO: 3; each start position is specified, the length of peptide is 10 amino acids, and the end position for each peptide is the start position plus nine.

| Start | Subsequence | Score |
|---|---|---|
| 400 | VGLYVFKVTV | 10.852 |
| 398 | LSVGLYVFKV | 10.296 |
| 39 | NLETTRIMRV | 10.238 |
| 677 | AIATVTGLQV | 9.563 |
| 958 | YVTVLAFTLI | 7.978 |
| 654 | GIVFYHWEHV | 7.966 |
| 386 | KQGHKQTLNL | 7.581 |
| 839 | RQLAVLLNVL | 7.557 |
| 821 | TLQVGVGQLT | 7.452 |
| 278 | ASLELSSVTV | 6.887 |
| 413 | NAFGEGFVNV | 6.791 |
| 141 | LPFLGKDWGL | 6.579 |
| 960 | TVLAFTLIVL | 6.522 |
| 660 | WEHVRGPSAV | 6.221 |
| 773 | SVALQLTNLV | 6.086 |
| 128 | GIWGDSPEDI | 5.834 |
| 94 | GPIRSYLTFV | 5.743 |
| 429 | RVNLPPVAVV | 5.739 |
| 904 | KVLRVDTAGC | 5.629 |
| 370 | YEWNLISHPT | 5.532 |
| 965 | TLIVLTGGFT | 5.328 |
| 352 | VELKAFVAPA | 5.311 |
| 669 | VEMENIDKAI | 5.232 |
| 728 | VLVLPNNSIT | 5.194 |
| 436 | AVVSPQLQEL | 4.299 |
| 178 | GSAEYTDWGL | 4.288 |
| 395 | LSQLSVGLYV | 4.245 |
| 12 | LLLVTIAGCA | 4.062 |
| 797 | GASDTDTATV | 3.961 |
| 1054 | SMNGSIRNGA | 3.588 |
| 391 | QTLNLSQLSV | 3.574 |
| 357 | FVAPAPPVET | 2.999 |
| 686 | VGTYHFRLTV | 2.933 |
| 551 | NQSSDDHQIV | 2.891 |
| 871 | VQSRPPFKVL | 2.868 |
| 338 | SAGDNLIITL | 2.798 |
| 827 | GQLTEQRKDT | 2.796 |
| 959 | VTVLAFTLIV | 2.559 |
| 780 | NLVEGVYTFH | 2.521 |
| 936 | WMENLIQRYI | 2.440 |
| 502 | RLTVTDSDGA | 2.434 |
| 630 | GPDKELIFPV | 2.423 |
| 247 | VLEKEKASQL | 2.324 |
| 698 | QQGLSSTSTL | 2.166 |
| 91 | KKMGPIRSYL | 2.113 |
| 765 | DVIDGSDHSV | 1.871 |
| 539 | ITLPQNSITL | 1.866 |
| 345 | ITLPDNEVEL | 1.866 |
| 198 | SVGDSPAVPA | 1.782 |
| 815 | SGLVELTLQV | 1.680 |
| 475 | GPFIEEKTSV | 1.680 |
| 444 | ELTLPLTSAL | 1.602 |
| 1031 | SEFDSDQDTI | 1.508 |
| 102 | FVLRPVQRPA | 1.480 |
| 266 | KEVLMPSHSL | 1.454 |
| 457 | SQSTDDTEIV | 1.417 |
| 633 | KELIFPVESA | 1.410 |
| 590 | MQEGDYTFQL | 1.367 |
| 26 | SEGRTYSNAV | 1.352 |
| 482 | TSVDSPVLRL | 1.315 |
| 939 | NLIQRYIWDG | 1.285 |
| 421 | NVTVKPARRV | 1.217 |
| 781 | LVEGVYTFHL | 1.180 |
| 521 | VNNAVDYPPV | 1.158 |

TABLE XI-V2

HLA-A0201-10mers-254P1D68
Each peptide is a portion of SEQ ID NO: 5; each start position is specified, the length of peptide is 10 amino acids, and the end position for each peptide is the start position plus nine.

| Start | Subsequence | Score |
|---|---|---|
| 1 | WGLEEMSEYA | 6.099 |
| 7 | SEYADDYREL | 0.399 |
| 5 | EMSEYADDYR | 0.009 |
| 2 | GLEEMSEYAD | 0.004 |
| 9 | YADDYRELEK | 0.002 |
| 4 | EEMSEYADDY | 0.000 |
| 3 | LEEMSEYADD | 0.000 |
| 6 | MSEYADDYRE | 0.000 |
| 10 | ADDYRELEKD | 0.000 |
| 8 | EYADDYRELE | 0.000 |

TABLE XI-V3

HLA-A0201-10mers-254P1D68
Each peptide is a portion of SEQ ID NO: 7; each start position is specified, the length of peptide is 10 amino acids, and the end position for each peptide is the start position plus nine.

| Start | Subsequence | Score |
|---|---|---|
| 3 | RLGWPSPCCA | 4.968 |
| 1 | MTRLGWPSPC | 0.009 |
| 2 | TRLGWPSPCC | 0.003 |
| 4 | LGWPSPCCAR | 0.001 |
| 7 | PSPCCARKQC | 0.001 |
| 10 | CCARKQCSEG | 0.000 |
| 8 | SPCCARKQCS | 0.000 |
| 6 | WPSPCCARKQ | 0.000 |
| 9 | PCCARKQCSE | 0.000 |
| 5 | GWPSPCCARK | 0.000 |

TABLE XI-V5

HLA-A0201-10mers-254P1D68
Each peptide is a portion of SEQ ID NO: 11; each start position is specified, the length of peptide is 10 amino acids, and the end position for each peptide is the start position plus nine.

| Start | Subsequence | Score |
|---|---|---|
| 9 | LTFLGKDWGL | 13.997 |
| 3 | EDIRKDLTFL | 0.028 |
| 8 | DLTFLGKDWG | 0.015 |
| 1 | SPEDIRKDLT | 0.006 |
| 7 | KDLTFLGKDW | 0.001 |
| 4 | DIRKDLTFLG | 0.000 |
| 2 | PEDIRKDLTF | 0.000 |
| 6 | RKDLTFLGKD | 0.000 |
| 10 | TFLGKDWGLE | 0.000 |
| 5 | IRKDLTFLGK | 0.000 |

TABLE XII-V1

HLA-A3-9mers-254P1D68
Each peptide is a portion of SEQ ID NO: 3; each start position is specified, the length of peptide is 9 amino acids, and the end position for each peptide is the start position plus eight.

| Start | Subsequence | Score |
|---|---|---|
| 780 | NLVEGVYTF | 40.500 |
| 565 | SLGPGSEGK | 30.000 |
| 683 | GLQVGTYHF | 18.000 |
| 68 | DLAWWFEGR | 10.800 |
| 576 | VMQGVQTPY | 9.000 |
| 397 | QLSVGLYVF | 9.000 |
| 589 | AMQEGDYTF | 9.000 |
| 281 | ELSSVTVEK | 9.000 |
| 401 | GLYVFKVTV | 9.000 |
| 493 | NLDPGNYSF | 9.000 |
| 748 | RIVSYLWIR | 8.100 |
| 39 | NLETTRIMR | 8.000 |
| 936 | WMENLIQRY | 6.000 |
| 373 | NLISHPTDY | 6.000 |
| 866 | VIVFYVQSR | 5.400 |
| 152 | EMSEYSDDY | 5.400 |
| 92 | KMGPIRSYL | 4.050 |
| 879 | VLKAAEVAR | 4.000 |
| 668 | AVEMENIDK | 4.000 |
| 598 | QLKVTDSSR | 4.000 |
| 975 | WLCICCCKR | 4.000 |

TABLE XII-V1-continued

HLA-A3-9mers-254P1D68
Each peptide is a portion of SEQ ID NO: 3; each start position is specified, the length of peptide is 9 amino acids, and the end position for each peptide is the start position plus eight.

| Start | Subsequence | Score |
|---|---|---|
| 1025 | SLMVSESEF | 3.000 |
| 968 | VLTGGFTWL | 2.700 |
| 816 | GLVELTLQV | 2.700 |
| 228 | KLPERSVLL | 2.700 |
| 1008 | ELRPKYGIK | 2.700 |
| 862 | DLSTVIVFY | 2.700 |
| 705 | STLTVAVKK | 2.250 |
| 892 | RLSKEKADF | 2.000 |
| 870 | YVQSRPPFK | 2.000 |
| 900 | FLLFKVLRV | 1.800 |
| 441 | QLQELTLPL | 1.800 |
| 961 | VLAFTLIVL | 1.800 |
| 784 | GVYTFHLRV | 1.800 |
| 274 | SLPPASLEL | 1.800 |
| 15 | VTIAGCARK | 1.500 |
| 366 | TTYNYEWNL | 1.350 |
| 728 | VLVLPNNSI | 1.350 |
| 186 | GLLPGSEGA | 1.350 |
| 836 | TLVRQLAVL | 1.350 |
| 113 | LLDYGDMML | 1.200 |
| 825 | GVGQLTEQR | 1.200 |
| 730 | VLPNNSITL | 1.200 |
| 540 | TLPQNSITL | 1.200 |
| 1052 | KVSMNGSIR | 1.200 |
| 983 | RQKRTKIRK | 1.200 |
| 112 | QLLDYGDMM | 0.900 |
| 840 | QLAVLLNVL | 0.900 |
| 615 | VIVQPENNR | 0.900 |
| 965 | TLIVLTGGF | 0.900 |
| 10 | SLLLLVTIA | 0.900 |
| 560 | VLYEWSLGP | 0.900 |
| 187 | LLPGSEGAF | 0.900 |
| 687 | GTYHFRLTV | 0.900 |
| 558 | QIVLYEWSL | 0.810 |
| 654 | GIVFYHWEH | 0.810 |
| 6 | GVLSSLLLL | 0.810 |
| 7 | VLSSLLLLV | 0.600 |
| 519 | LIVNNAVDY | 0.600 |
| 346 | TLPDNEVEL | 0.600 |
| 446 | TLPLTSALI | 0.600 |
| 394 | NLSQLSVGL | 0.600 |
| 347 | LPDNEVELK | 0.600 |
| 1062 | GASFSYCSK | 0.600 |
| 1045 | KMERGNPKV | 0.600 |
| 844 | LLNVLDSDI | 0.600 |
| 777 | QLTNLVEGV | 0.600 |
| 579 | GVQTPYLHL | 0.540 |
| 353 | ELKAFVAPA | 0.540 |
| 685 | QVGTYHFRL | 0.540 |
| 483 | SVDSPVLRL | 0.540 |
| 821 | TLQVGVGQL | 0.540 |
| 399 | SVGLYVFKV | 0.540 |
| 986 | RTKIRKKTK | 0.500 |
| 44 | RIMRVSHTF | 0.450 |
| 12 | LLLVTIAGC | 0.450 |
| 634 | ELIFPVESA | 0.405 |
| 14 | LVTIAGCAR | 0.400 |
| 392 | TLNLSQLSV | 0.400 |
| 421 | NVTVKPARR | 0.400 |
| 805 | TVEVQPDPR | 0.400 |
| 209 | TQQDPELHY | 0.360 |
| 97 | RSYLTFVLR | 0.300 |
| 700 | GLSSTSTLT | 0.300 |
| 704 | TSTLTVAVK | 0.300 |
| 473 | INGPFIEEK | 0.270 |
| 684 | LQVGTYHFR | 0.270 |
| 398 | LSVGLYVFK | 0.225 |
| 934 | HLWMENLIQ | 0.200 |
| 890 | HMRLSKEKA | 0.200 |
| 977 | CICCCKRQK | 0.200 |
| 905 | VLRVDTAGC | 0.200 |

TABLE XII-V1-continued

HLA-A3-9mers-254P1D68
Each peptide is a portion of SEQ ID NO: 3; each start position is specified, the length of peptide is 9 amino acids, and the end position for each peptide is the start position plus eight.

| Start | Subsequence | Score |
|---|---|---|
| 625 | PVAVAGPDK | 0.200 |
| 914 | LLKCSGHGH | 0.200 |
| 279 | SLELSSVTV | 0.200 |
| 138 | RKDLPFLGK | 0.180 |
| 131 | GDSPEDIRK | 0.180 |
| 681 | VTGLQVGTY | 0.180 |
| 960 | TVLAFTLIV | 0.180 |
| 884 | EVARNLHMR | 0.180 |

TABLE XII-V2

HLA-A3-9mers-254P1D68
Each peptide is a portion of SEQ ID NO: 5; each start position is specified, the length of peptide is 9 amino acids, and the end position for each peptide is the start position plus eight.

| Start | Subsequence | Score |
|---|---|---|
| 4 | EMSEYADDY | 5.400 |
| 1 | GLEEMSEYA | 0.900 |
| 9 | ADDYRELEK | 0.040 |
| 5 | MSEYADDYR | 0.020 |
| 6 | SEYADDYRE | 0.001 |
| 8 | YADDYRELE | 0.001 |
| 2 | LEEMSEYAD | 0.000 |
| 3 | EEMSEYADD | 0.000 |
| 7 | EYADDYREL | 0.000 |

TABLE XII-V3

HLA-A3-9mers-254P1D68
Each peptide is a portion of SEQ ID NO: 7; each start position is specified, the length of peptide is 9 amino acids, and the end position for each peptide is the start position plus eight.

| Start | Subsequence | Score |
|---|---|---|
| 3 | RLGWPSPCC | 0.300 |
| 6 | WPSPCCARK | 0.300 |
| 5 | GWPSPCCAR | 0.018 |
| 4 | LGWPSPCCA | 0.002 |
| 2 | TRLGWPSPC | 0.001 |

TABLE XII-V3-continued

HLA-A3-9mers-254P1D68
Each peptide is a portion of SEQ ID NO: 7; each start position is specified, the length of peptide is 9 amino acids, and the end position for each peptide is the start position plus eight.

| Start | Subsequence | Score |
|---|---|---|
| 8 | SPCCARKQC | 0.001 |
| 1 | MTRLGWPSP | 0.001 |
| 10 | CCARKQCSE | 0.000 |
| 9 | PCCARKQCS | 0.000 |
| 7 | PSPCCARKQ | 0.000 |

TABLE XII-V5

HLA-A3-9mers-254P1D68
Each peptide is a portion of SEQ ID NO: 11; each start position is specified, the length of peptide is 9 amino acids, and the end position for each peptide is the start position plus eight.

| Start | Subsequence | Score |
|---|---|---|
| 5 | RKDLTFLGK | 0.120 |
| 7 | DLTFLGKDW | 0.030 |
| 3 | DIRKDLTFL | 0.027 |
| 8 | LTFLGKDWG | 0.005 |
| 9 | TFLGKDWGL | 0.004 |
| 2 | EDIRKDLTF | 0.002 |
| 6 | KDLTFLGKD | 0.000 |
| 4 | IRKDLTFLG | 0.000 |
| 1 | PEDIRKDLT | 0.000 |

TABLE XIII-V1

HLA-A3-10mers-254P1D68
Each peptide is a portion of SEQ ID NO: 3; each start position is specified, the length of peptide is 10 amino acids, and the end position for each peptide is the start position plus nine.

| Start | Subsequence | Score |
|---|---|---|
| 934 | HLWMENLIQR | 60.000 |
| 346 | TLPDNEVELK | 60.000 |
| 847 | VLDSDIKVQK | 30.000 |
| 687 | GTYHFRLTVK | 22.500 |
| 844 | LLNVLDSDIK | 20.000 |
| 397 | QLSVGLYVFK | 20.000 |
| 683 | GLQVGTYHFR | 12.000 |
| 888 | NLHMRLSKEK | 10.000 |

TABLE XIII-V1-continued

HLA-A3-10mers-254P1D68
Each peptide is a portion of SEQ ID NO: 3; each start position is specified, the length of peptide is 10 amino acids, and the end position for each peptide is the start position plus nine.

| Start | Subsequence | Score |
|---|---|---|
| 973 | FTWLCICCCK | 7.500 |
| 655 | IVFYHWEHVR | 6.000 |
| 955 | SIFYVTVLAF | 6.000 |
| 13 | LLVTIAGCAR | 6.000 |
| 825 | GVGQLTEQRK | 6.000 |
| 518 | ALIVNNAVDY | 6.000 |
| 493 | NLDPGNYSFR | 6.000 |
| 865 | TVIVFYVQSR | 5.400 |
| 186 | GLLPGSEGAF | 4.050 |
| 472 | EINGPFIEEK | 4.050 |
| 1039 | TIFSREKMER | 4.000 |
| 907 | RVDTAGCLLK | 4.000 |
| 997 | ILDNMDEQER | 4.000 |
| 394 | NLSQLSVGLY | 3.600 |
| 805 | TVEVQPDPRK | 3.000 |
| 703 | STSTLTVAVK | 3.000 |
| 968 | VLTGGFTWLC | 2.700 |
| 1006 | RMELRPKYGI | 2.700 |
| 14 | LVTIAGCARK | 2.000 |
| 878 | KVLKAAEVAR | 1.800 |
| 152 | EMSEYSDDYR | 1.800 |
| 112 | QLLDYGDMML | 1.800 |
| 777 | QLTNLVEGVY | 1.800 |
| 1000 | NMDEQERMEL | 1.800 |
| 401 | GLYVFKVTVS | 1.800 |
| 895 | KEKADFLLFK | 1.620 |
| 128 | GIWGDSPEDI | 1.350 |
| 92 | KMGPIRSYLT | 1.350 |
| 586 | HLSAMQEGDY | 1.200 |
| 1058 | SIRNGASFSY | 1.200 |
| 241 | TPSSGEVLEK | 1.200 |
| 490 | RLSNLDPGNY | 1.200 |
| 700 | GLSSTSTLTV | 1.200 |
| 100 | LTFVLRPVQR | 1.000 |
| 76 | RCYLVSCPHK | 1.000 |

TABLE XIII-V1-continued

HLA-A3-10mers-254P1D68
Each peptide is a portion of SEQ ID NO: 3; each start position is specified, the length of peptide is 10 amino acids, and the end position for each peptide is the start position plus nine.

| Start | Subsequence | Score |
|---|---|---|
| 836 | TLVRQLAVLL | 0.900 |
| 828 | QLTEQRKDTL | 0.900 |
| 667 | SAVEMENIDK | 0.900 |
| 575 | VVMQGVQTPY | 0.900 |
| 843 | VLLNVLDSDI | 0.900 |
| 576 | VMQGVQTPYL | 0.900 |
| 614 | TVIVQPENNR | 0.900 |
| 862 | DLSTVIVFYV | 0.810 |
| 781 | LVEGVYTFHL | 0.810 |
| 780 | NLVEGVYTFH | 0.675 |
| 892 | RLSKEKADFL | 0.600 |
| 39 | NLETTRIMRV | 0.600 |
| 35 | VISPNLETTR | 0.600 |
| 406 | KVTVSSENAF | 0.600 |
| 692 | RLTVKDQQGL | 0.600 |
| 247 | VLEKEKASQL | 0.600 |
| 120 | MLNRGSPSGI | 0.600 |
| 45 | IMRVSHTFPV | 0.600 |
| 481 | KTSVDSPVLR | 0.600 |
| 419 | FVNVTVKPAR | 0.600 |
| 416 | GEGFVNVTVK | 0.540 |
| 1008 | ELRPKYGIKH | 0.540 |
| 988 | KIRKKTKYTI | 0.540 |
| 228 | KLPERSVLLP | 0.540 |
| 173 | KQEPRGSAEY | 0.540 |
| 107 | VQRPAQLLDY | 0.540 |
| 680 | TVTGLQVGTY | 0.540 |
| 901 | LLFKVLRVDT | 0.500 |
| 635 | LIFPVESATL | 0.450 |
| 804 | ATVEVQPDPR | 0.450 |
| 872 | QSRPPFKVLK | 0.450 |
| 1054 | SMNGSIRNGA | 0.450 |
| 11 | LLLLVTIAGC | 0.450 |
| 396 | SQLSVGLYVF | 0.405 |
| 939 | NLIQRYIWDG | 0.405 |
| 977 | CICCCKRQKR | 0.400 |

TABLE XIII-V1-continued

HLA-A3-10mers-254P1D68
Each peptide is a portion of SEQ ID NO: 3; each start position is specified, the length of peptide is 10 amino acids, and the end position for each peptide is the start position plus nine.

| Start | Subsequence | Score |
|---|---|---|
| 684 | LQVGTYHFRL | 0.364 |
| 7 | VLSSLLLLVT | 0.300 |
| 459 | STDDTEIVSY | 0.300 |
| 324 | SPTTAPRTVK | 0.300 |
| 269 | LMPSHSLPPA | 0.300 |
| 217 | YLNESASTPA | 0.300 |
| 743 | STDDQRIVSY | 0.300 |
| 913 | CLLKCSGHGH | 0.300 |
| 223 | STPAPKLPER | 0.300 |
| 381 | YQGEIKQGHK | 0.270 |
| 729 | LVLPNNSITL | 0.270 |
| 960 | TVLAFTLIVL | 0.270 |
| 6 | GVLSSLLLLV | 0.270 |
| 967 | IVLTGGFTWL | 0.270 |
| 149 | GLEEMSEYSD | 0.270 |
| 557 | HQIVLYEWSL | 0.243 |
| 590 | MQEGDYTFQL | 0.243 |
| 564 | WSLGPGSEGK | 0.225 |
| 441 | QLQELTLPLT | 0.225 |
| 816 | GLVELTLQVG | 0.203 |
| 986 | RTKIRKKTKY | 0.200 |

TABLE XIII-V2

HLA-A3-10mers-254P1D68
Each peptide is a portion of SEQ ID NO: 5; each start position is specified, the length of peptide is 10 amino acids, and the end position for each peptide is the start position plus nine.

| Start | Subsequence | Score |
|---|---|---|
| 5 | EMSEYADDYR | 1.800 |
| 9 | YADDYRELEK | 0.400 |
| 2 | GLEEMSEYAD | 0.270 |
| 4 | EEMSEYADDY | 0.016 |
| 7 | SEYADDYREL | 0.001 |
| 1 | WGLEEMSEYA | 0.000 |
| 6 | MSEYADDYRE | 0.000 |

TABLE XIII-V2-continued

HLA-A3-10mers-254P1D68
Each peptide is a portion of SEQ ID NO: 5; each start position is specified, the length of peptide is 10 amino acids, and the end position for each peptide is the start position plus nine.

| Start | Subsequence | Score |
|---|---|---|
| 3 | LEEMSEYADD | 0.000 |
| 10 | ADDYRELEKD | 0.000 |
| 8 | EYADDYRELE | 0.000 |

TABLE XIII-V3

HLA-A3-10mers-254P1D68
Each peptide is a portion of SEQ ID NO: 7; each start position is specified, the length of peptide is 10 amino acids, and the end position for each peptide is the start position plus nine.

| Start | Subsequence | Score |
|---|---|---|
| 3 | RLGWPSPCCA | 0.200 |
| 5 | GWPSPCCARK | 0.060 |
| 4 | LGWPSPCCAR | 0.045 |
| 1 | MTRLGWPSPC | 0.030 |
| 2 | TRLGWPSPCC | 0.001 |
| 8 | SPCCARKQCS | 0.000 |
| 10 | CCARKQCSEG | 0.000 |
| 7 | PSPCCARKQC | 0.000 |
| 6 | WPSPCCARKQ | 0.000 |
| 9 | PCCARKQCSE | 0.000 |

TABLE XIII-V5

HLA-A3-10mers-254P1D68
Each peptide is a portion of SEQ ID NO: 11; each start position is specified, the length of peptide is 10 amino acids, and the end position for each peptide is the start position plus nine.

| Start | Subsequence | Score |
|---|---|---|
| 9 | LTFLGKDWGL | 0.450 |
| 5 | IRKDLTFLGK | 0.120 |
| 8 | DLTFLGKDWG | 0.006 |
| 4 | DIRKDLTFLG | 0.002 |
| 2 | PEDIRKDLTF | 0.001 |
| 1 | SPEDIRKDLT | 0.001 |
| 7 | KDLTFLGKDW | 0.000 |
| 3 | EDIRKDLTFL | 0.000 |

TABLE XIII-V5-continued

HLA-A3-10mers-254P1D6B
Each peptide is a portion of SEQ ID NO: 11; each start position is specified, the length of peptide is 10 amino acids, and the end position for each peptide is the start position plus nine.

| Start | Subsequence | Score |
|---|---|---|
| 6 | RKDLTFLGKD | 0.000 |
| 10 | TFLGKDWGLE | 0.000 |

TABLE XIV-V1

HLA-A1101-9mers-254P1D6B
Each peptide is a portion of SEQ ID NO: 3; each start position is specified, the length of peptide is 9 amino acids, and the end position for each peptide is the start position plus eight.

| Start | Subsequence | Score |
|---|---|---|
| 668 | AVEMENIDK | 4.000 |
| 983 | RQKRTKIRK | 3.600 |
| 870 | YVQSRPPFK | 2.000 |
| 15 | VTIAGCARK | 1.500 |
| 705 | STLTVAVKK | 1.500 |
| 986 | RTKIRKKTK | 1.500 |
| 825 | GVGQLTEQR | 1.200 |
| 1052 | KVSMNGSIR | 1.200 |
| 748 | RIVSYLWIR | 0.720 |
| 1062 | GASFSYCSK | 0.600 |
| 77 | CYLVSCPHK | 0.600 |
| 421 | NVTVKPARR | 0.400 |
| 565 | SLGPGSEGK | 0.400 |
| 688 | TYHFRLTVK | 0.400 |
| 14 | LVTIAGCAR | 0.400 |
| 805 | TVEVQPDPR | 0.400 |
| 887 | RNLHMRLSK | 0.360 |
| 784 | GVYTFHLRV | 0.240 |
| 347 | LPDNEVELK | 0.200 |
| 625 | PVAVAGPDK | 0.200 |
| 6 | GVLSSLLLL | 0.180 |
| 684 | LQVGTYHFR | 0.180 |
| 258 | EQSSNSSGK | 0.180 |
| 39 | NLETTRIMR | 0.160 |
| 131 | GDSPEDIRK | 0.120 |
| 138 | RKDLPFLGK | 0.120 |

TABLE XIV-V1-continued

HLA-A1101-9mers-254P1D6B
Each peptide is a portion of SEQ ID NO: 3; each start position is specified, the length of peptide is 9 amino acids, and the end position for each peptide is the start position plus eight.

| Start | Subsequence | Score |
|---|---|---|
| 884 | EVARNLHMR | 0.120 |
| 687 | GTYHFRLTV | 0.120 |
| 615 | VIVQPENNR | 0.120 |
| 281 | ELSSVTVEK | 0.120 |
| 1008 | ELRPKYGIK | 0.120 |
| 866 | VIVFYVQSR | 0.120 |
| 579 | GVQTPYLHL | 0.120 |
| 325 | PTTAPRTVK | 0.100 |
| 378 | PTDYQGEIK | 0.100 |
| 165 | KDLLQPSGK | 0.090 |
| 967 | IVLTGGFTW | 0.090 |
| 878 | KVLKAAEVA | 0.090 |
| 806 | VEVQPDPRK | 0.090 |
| 598 | QLKVTDSSR | 0.080 |
| 879 | VLKAAEVAR | 0.080 |
| 656 | VFYHWEHVR | 0.080 |
| 975 | WLCICCCKR | 0.080 |
| 1040 | IFSREKMER | 0.080 |
| 831 | EQRKDTLVR | 0.072 |
| 845 | LNVLDSDIK | 0.060 |
| 685 | QVGTYHFRL | 0.060 |
| 958 | YVTVLAFTL | 0.060 |
| 429 | RVNLPPVAV | 0.060 |
| 1010 | RPKYGIKHR | 0.060 |
| 907 | RVDTAGCLL | 0.060 |
| 960 | TVLAFTLIV | 0.060 |
| 47 | RVSHTFPVV | 0.060 |
| 101 | TFVLRPVQR | 0.060 |
| 399 | SVGLYVFKV | 0.060 |
| 846 | NVLDSDIKV | 0.060 |
| 406 | KVTVSSENA | 0.060 |
| 839 | RQLAVLLNV | 0.054 |
| 115 | DYGDMMLNR | 0.048 |
| 169 | QPSGKQEPR | 0.040 |
| 908 | VDTAGCLLK | 0.040 |
| 483 | SVDSPVLRL | 0.040 |

TABLE XIV-V1-continued

HLA-A1101-9mers-254P1D6B
Each peptide is a portion of SEQ ID NO: 3; each start position is specified, the length of peptide is 9 amino acids, and the end position for each peptide is the start position plus eight.

| Start | Subsequence | Score |
|---|---|---|
| 224 | TPAPKLPER | 0.040 |
| 366 | TTYNYEWNL | 0.040 |
| 920 | HGHCDPLTK | 0.040 |
| 157 | SDDYRELEK | 0.040 |
| 655 | IVFYHWEHV | 6.040 |
| 977 | CICCCKRQK | 0.040 |
| 978 | ICCCKRQKR | 0.040 |
| 473 | INGPFIEEK | 0.040 |
| 816 | GLVELTLQV | 0.036 |
| 654 | GIVFYHWEH | 0.036 |
| 974 | TWLCICCCK | 0.030 |
| 398 | LSVGLYVFK | 0.030 |
| 481 | KTSVDSPVL | 0.030 |
| 97 | RSYLTFVLR | 0.024 |
| 68 | DLAWWFEGR | 0.024 |
| 401 | GLYVFKVTV | 0.024 |
| 683 | GLQVGTYHF | 0.024 |
| 44 | RIMRVSHTF | 0.024 |
| 826 | VGQLTEQRK | 0.020 |
| 889 | LHMRLSKEK | 0.020 |
| 382 | QGEIKQGHK | 0.020 |
| 980 | CCKRQKRTK | 0.020 |
| 1064 | SFSYCSKDR | 0.020 |
| 848 | LDSDIKVQK | 0.020 |
| 773 | SVALQLTNL | 0.020 |
| 84 | HKENCEPKK | 0.020 |
| 294 | TVTPGSTEH | 0.020 |
| 465 | IVSYHWEEI | 0.020 |
| 704 | TSTLTVAVK | 0.020 |
| 336 | TVSAGDNLI | 0.020 |
| 781 | LVEGVYTFH | 0.020 |
| 837 | LVRQLAVLL | 0.020 |
| 873 | SRPPFKVLK | 0.020 |
| 581 | QTPYLHLSA | 0.020 |
| 284 | SVTVEKSPV | 0.020 |

TABLE XIV-V1-continued

HLA-A1101-9mers-254P1D6B
Each peptide is a portion of SEQ ID NO: 3; each start position is specified, the length of peptide is 9 amino acids, and the end position for each peptide is the start position plus eight.

| Start | Subsequence | Score |
|---|---|---|
| 437 | VVSPQLQEL | 0.020 |
| 331 | TVKELTVSA | 0.020 |
| 351 | EVELKAFVA | 0.018 |

TABLE XIV-V2

HLA-A1101-9mers-254P1D68
Each peptide is a portion of SEQ ID NO: 5; each start position is specified, the length of peptide is 9 amino acids, and the end position for each peptide is the start position plus eight.

| Start | Subsequence | Score |
|---|---|---|
| 9 | ADDYRELEK | 0.040 |
| 1 | GLEEMSEYA | 0.012 |
| 5 | MSEYADDYR | 0.004 |
| 4 | EMSEYADDY | 0.001 |
| 6 | SEYADDYRE | 0.000 |
| 8 | YADDYRELE | 0.000 |
| 7 | EYADDYREL | 0.000 |
| 2 | LEEMSEYAD | 0.000 |
| 3 | EEMSEYADD | 0.000 |

TABLE XIV-V3

HLA-A1101-9mers-254P1D68
Each peptide is a portion of SEQ ID NO: 7; each start position is specified, the length of peptide is 9 amino acids, and the end position for each peptide is the start position plus eight.

| Start | Subsequence | Score |
|---|---|---|
| 6 | WPSPCCARK | 0.200 |
| 5 | GWPSPCCAR | 0.012 |
| 3 | RLGWPSPCC | 0.001 |
| 1 | MTRLGWPSP | 0.001 |
| 4 | LGWPSPCCA | 0.000 |
| 10 | CCARKQCSE | 0.000 |
| 8 | SPCCARKQC | 0.000 |
| 2 | TRLGWPSPC | 0.000 |
| 9 | PCCARKQCS | 0.000 |
| 7 | PSPCCARKQ | 0.000 |

TABLE XIV-V5

HLA-A1101-9mers-254P1D68
Each peptide is a portion of SEQ ID NO: 11;
each start position is specified, the length of
peptide is 9 amino acids, and the end position
for each peptide is the start position plus
eight.

| Start | Subsequence | Score |
|---|---|---|
| 5 | RKDLTFLGK | 0.120 |
| 9 | TFLGKDWGL | 0.006 |
| 8 | LTFLGKDWG | 0.002 |
| 3 | DIRKDLTFL | 0.001 |
| 7 | DLTFLGKDW | 0.001 |
| 2 | EDIRKDLTF | 0.000 |
| 6 | KDLTFLGKD | 0.000 |
| 4 | IRKDLTFLG | 0.000 |
| 1 | PEDIRKDLT | 0.000 |

TABLE XV-V1

HLA-A1101-10mers-254P1D68
Each peptide is a portion of SEQ ID NO: 3;
each start position is specified, the length of
peptide is 10 amino acids, and the end position
for each peptide is the start position plus
nine.

| Start | Subsequence | Score |
|---|---|---|
| 907 | RVDTAGCLLK | 12.000 |
| 825 | GVGQLTEQRK | 6.000 |
| 687 | GTYHFRLTVK | 6.000 |
| 14 | LVTIAGCARK | 2.000 |
| 805 | TVEVQPDPRK | 2.000 |
| 973 | FTWLCICCCK | 2.000 |
| 878 | KVLKAAEVAR | 1.800 |
| 76 | RCYLVSCPKH | 1.200 |
| 703 | STSTLTVAVK | 1.000 |
| 655 | IVFYHWEHVR | 0.800 |
| 667 | SAVEMENIDK | 0.600 |
| 865 | TVIVFYVQSR | 0.600 |
| 614 | TVIVQPENNR | 0.600 |
| 869 | FYVQSRPPFK | 0.600 |
| 481 | KTSVDSPVLR | 0.600 |
| 381 | YQGEIKQGHK | 0.600 |
| 100 | LTFVLRPVQR | 0.400 |
| 346 | TLPDNEVELK | 0.400 |
| 847 | VLDSDIKVQK | 0.400 |
| 419 | FVNVTVKPAR | 0.400 |

TABLE XV-V1-continued

HLA-A1101-10mers-254P1D68
Each peptide is a portion of SEQ ID NO: 3;
each start position is specified, the length of
peptide is 10 amino acids, and the end position
for each peptide is the start position plus
nine.

| Start | Subsequence | Score |
|---|---|---|
| 844 | LLNVLDSDIK | 0.400 |
| 241 | TPSSGEVLEK | 0.400 |
| 397 | QLSVGLYVFK | 0.400 |
| 895 | KEKADFLLFK | 0.360 |
| 934 | HLWMENLIQR | 0.320 |
| 1039 | TIFSREKMER | 0.320 |
| 804 | ATVEVQPDPR | 0.300 |
| 683 | GLQVGTYHFR | 0.240 |
| 888 | NLHMRLSKEK | 0.200 |
| 223 | STPAPKLPER | 0.200 |
| 82 | CPHKENCEPK | 0.200 |
| 324 | SPTTAPRTVK | 0.200 |
| 377 | HPTDYQGEIK | 0.200 |
| 6 | GVLSSLLLLV | 0.180 |
| 597 | FQLKVTDSSR | 0.180 |
| 983 | RQKRTKIRKK | 0.180 |
| 416 | GEGFVNVTVK | 0.180 |
| 1043 | REKMERGNPK | 0.180 |
| 919 | GHGHCDPLTK | 0.120 |
| 982 | KRQKRTKIRK | 0.120 |
| 472 | EINGPFIEEK | 0.120 |
| 13 | LLVTIAGCAR | 0.120 |
| 168 | LQPSGKQEPR | 0.120 |
| 280 | LELSSVTVEK | 0.090 |
| 1007 | MELRPKYGIK | 0.090 |
| 977 | CICCCKRQKR | 0.080 |
| 35 | VISPNLETTR | 0.080 |
| 493 | NLDPGNYSFR | 0.080 |
| 997 | ILDNMDEQER | 0.080 |
| 321 | LPISPTTAPR | 0.060 |
| 870 | YVQSRPPFKV | 0.060 |
| 257 | QEQSSNSSGK | 0.060 |
| 406 | KVTVSSENAF | 0.060 |
| 781 | LVEGVYTFHL | 0.060 |
| 960 | TVLAFTLIVL | 0.060 |

TABLE XV-V1-continued

HLA-A1101-10mers-254P1D68
Each peptide is a portion of SEQ ID NO: 3; each start position is specified, the length of peptide is 10 amino acids, and the end position for each peptide is the start position plus nine.

| Start | Subsequence | Score |
|---|---|---|
| 429 | RVNLPPVAVV | 0.060 |
| 591 | QEGDYTFQLK | 0.060 |
| 219 | NESASTPAPK | 0.060 |
| 729 | LVLPNNSITL | 0.060 |
| 330 | RTVKELTVSA | 0.045 |
| 575 | VVMQGVQTPY | 0.040 |
| 130 | WGDSPEDIRK | 0.040 |
| 20 | CARKQCSEGR | 0.040 |
| 137 | IRKDLPFLGK | 0.040 |
| 886 | ARNLHMRLSK | 0.040 |
| 286 | TVEKSPVLTV | 0.040 |
| 717 | SPPRARAGGR | 0.040 |
| 156 | YSDDYRELEK | 0.040 |
| 336 | TVSAGDNLII | 0.040 |
| 386 | KQGHKQTLNL | 0.036 |
| 624 | PPVAVAGPDK | 0.036 |
| 976 | LCICCCKRQK | 0.030 |
| 564 | WSLGPGSEGK | 0.030 |
| 985 | KRTKIRKKTK | 0.030 |
| 992 | KTKYTILDNM | 0.030 |
| 959 | VTVLAFTLIV | 0.030 |
| 967 | IVLTGGFTWL | 0.030 |
| 986 | RTKIRKKTKY | 0.030 |
| 391 | QTLNLSQLSV | 0.030 |
| 436 | AVVSPQLQEL | 0.030 |
| 539 | ITLPQNSITL | 0.030 |
| 727 | HVLVLPNNSI | 0.030 |
| 684 | LQVGTYHFRL | 0.027 |
| 839 | RQLAVLLNVL | 0.027 |
| 1006 | RMELRPKYGI | 0.024 |
| 830 | TEQRKDTLVR | 0.024 |
| 152 | EMSEYSDDYR | 0.024 |
| 988 | KIRKKTKYTI | 0.024 |
| 700 | GLSSTSTLTV | 0.024 |
| 128 | GIWGDSPEDI | 0.024 |
| 979 | CCCKRQKRTK | 0.024 |

TABLE XV-V1-continued

HLA-A1101-10mers-254P1D68
Each peptide is a portion of SEQ ID NO: 3; each start position is specified, the length of peptide is 10 amino acids, and the end position for each peptide is the start position plus nine.

| Start | Subsequence | Score |
|---|---|---|
| 423 | TVKPARRVNL | 0.020 |
| 958 | YVTVLAFTLI | 0.020 |
| 680 | TVTGLQVGTY | 0.020 |
| 366 | TTYNYEWNLI | 0.020 |
| 1061 | NGASFSYCSK | 0.020 |
| 1019 | STEHNSSLMV | 0.020 |
| 284 | SVTVEKSPVL | 0.020 |
| 872 | QSRPPFKVLK | 0.020 |
| 524 | AVDYPPVANA | 0.020 |

TABLE XV-V2

HLA-A1101-10mers-254P1D68
Each peptide is a portion of SEQ ID NO: 5; each start position is specified, the length of peptide is 10 amino acids, and the end position for each peptide is the start position plus nine.

| Start | Subsequence | Score |
|---|---|---|
| 9 | YADDYRELEK | 0.400 |
| 5 | EMSEYADDYR | 0.024 |
| 2 | GLEEMSEYAD | 0.002 |
| 4 | EEMSEYADDY | 0.000 |
| 1 | WGLEEMSEYA | 0.000 |
| 8 | EYADDYRELE | 0.000 |
| 7 | SEYADDYREL | 0.000 |
| 3 | LEEMSEYADD | 0.000 |
| 6 | MSEYADDYRE | 0.000 |
| 10 | ADDYRELEKD | 0.000 |

TABLE XV-V3

HLA-A1101-10mers-254P1D68
Each peptide is a portion of SEQ ID NO: 7; each start position is specified, the length of peptide is 10 amino acids, and the end position for each peptide is the start position plus nine.

| Start | Subsequence | Score |
|---|---|---|
| 5 | GWPSPCCARK | 0.060 |
| 3 | RLGWPSPCCA | 0.012 |
| 4 | LGWPSPCCAR | 0.008 |

TABLE XV-V3-continued

HLA-A1101-10mers-254P1D68
Each peptide is a portion of SEQ ID NO: 7; each start position is specified, the length of peptide is 10 amino acids, and the end position for each peptide is the start position plus nine.

| Start | Subsequence | Score |
|---|---|---|
| 1 | MTRLGWPSPC | 0.001 |
| 10 | CCARKQCSEG | 0.000 |
| 8 | SPCCARKQCS | 0.000 |
| 2 | TRLGWPSPCC | 0.000 |
| 6 | WPSPCCARKQ | 0.000 |
| 9 | PCCARKQCSE | 0.000 |
| 7 | PSPCCARKQC | 0.000 |

TABLE XV-V5

HLA-A1101-10mers-254P1D68
Each peptide is a portion of SEQ ID NO: 11; each start position is specified, the length of peptide is 10 amino acids, and the end position for each peptide is the start position plus nine.

| Start | Subsequence | Score |
|---|---|---|
| 9 | LTFLGKDWGL | 0.040 |
| 5 | IRKDLTFLGK | 0.040 |
| 7 | KDLTFLGKDW | 0.000 |
| 4 | DIRKDLTFLG | 0.000 |
| 10 | TFLGKDWGLE | 0.000 |
| 1 | SPEDIRKDLT | 0.000 |
| 8 | DLTFLGKDWG | 0.000 |
| 2 | PEDIRKDLTF | 0.000 |
| 3 | EDIRKDLTFL | 0.000 |
| 6 | RKDLTFLGKD | 0.000 |

TABLE XVI-V1

HLA-A24-9mers-254P1D68
Each peptide is a portion of SEQ ID NO: 3; each start position is specified, the length of peptide is 9 amino acids, and the end position for each peptide is the start position plus eight.

| Start | Subsequence | Score |
|---|---|---|
| 159 | DYRELEKDL | 288.000 |
| 155 | EYSDDYREL | 264.000 |
| 869 | FYVQSRPPF | 150.000 |
| 367 | TYNYEWNLI | 90.000 |
| 636 | IFPVESATL | 30.000 |

TABLE XVI-V1-continued

HLA-A24-9mers-254P1D68
Each peptide is a portion of SEQ ID NO: 3; each start position is specified, the length of peptide is 9 amino acids, and the end position for each peptide is the start position plus eight.

| Start | Subsequence | Score |
|---|---|---|
| 943 | RYIWDGESN | 15.000 |
| 228 | KLPERSVLL | 14.400 |
| 92 | KMGPIRSYL | 13.440 |
| 881 | KAAEVARNL | 13.440 |
| 676 | KAIATVTGL | 12.000 |
| 105 | RPVQRPAQL | 12.000 |
| 814 | KSGLVELTL | 11.200 |
| 957 | FYVTVLAFT | 10.500 |
| 133 | SPEDIRKDL | 10.080 |
| 956 | IFYVTVLAF | 10.000 |
| 1012 | KYGIKHRST | 10.000 |
| 1018 | RSTEHNSSL | 9.600 |
| 441 | QLQELTLPL | 8.640 |
| 445 | LTLPLTSAL | 8.640 |
| 44 | RIMRVSHTF | 8.400 |
| 481 | KTSVDSPVL | 8.000 |
| 390 | KQTLNLSQL | 8.000 |
| 907 | RVDTAGCLL | 8.000 |
| 274 | SLPPASLEL | 7.920 |
| 346 | TLPDNEVEL | 7.920 |
| 216 | HYLNESAST | 7.500 |
| 402 | LYVFKVTVS | 7.500 |
| 693 | LTVKDQQGL | 7.200 |
| 285 | VTVEKSPVL | 7.200 |
| 327 | TAPRTVKEL | 6.600 |
| 437 | VVSPQLQEL | 6.336 |
| 836 | TLVRQLAVL | 6.000 |
| 439 | SPQLQELTL | 6.000 |
| 6 | GVLSSLLLL | 6.000 |
| 829 | LTEQRKDTL | 6.000 |
| 540 | TLPQNSITL | 6.000 |
| 821 | TLQVGVGQL | 6.000 |
| 730 | VLPNNSITL | 6.000 |
| 579 | GVQTPYLHL | 6.000 |
| 486 | SPVLRLSNL | 6.000 |

TABLE XVI-V1-continued

HLA-A24-9mers-254P1D68
Each peptide is a portion of SEQ ID NO: 3; each start position is specified, the length of peptide is 9 amino acids, and the end position for each peptide is the start position plus eight.

| Start | Subsequence | Score |
|---|---|---|
| 954 | WSIFYVTVL | 6.000 |
| 240 | TTPSSGEVL | 6.000 |
| 511 | ATNSTTAAL | 6.000 |
| 533 | AGPNHTITL | 6.000 |
| 179 | SAEYTDWGL | 6.000 |
| 558 | QIVLYEWSL | 6.000 |
| 267 | EVLMPSHSL | 6.000 |
| 335 | LTVSAGDNL | 6.000 |
| 699 | QGLSSTSTL | 6.000 |
| 5 | TGVLSSLLL | 6.000 |
| 840 | QLAVLLNVL | 5.760 |
| 872 | QSRPPFKVL | 5.760 |
| 32 | SNAVISPNL | 5.600 |
| 469 | HWEEINGPF | 5.040 |
| 1032 | EFDSDQDTI | 5.000 |
| 594 | DYTFQLKVT | 5.000 |
| 498 | NYSFRLTVT | 5.000 |
| 785 | VYTFHLRVT | 5.000 |
| 885 | VARNHMRL | 4.800 |
| 71 | WWFEGRCYL | 4.800 |
| 893 | LSKEKADFL | 4.800 |
| 968 | VLTGGFTWL | 4.800 |
| 553 | SSDDHQIVL | 4.800 |
| 809 | QPDPRKSGL | 4.800 |
| 837 | LVRQLAVLL | 4.800 |
| 210 | QQDPELHYL | 4.800 |
| 339 | AGDNLIITL | 4.800 |
| 394 | NLSQLSVGL | 4.800 |
| 768 | DGSDHSVAL | 4.800 |
| 958 | YVTVLAFTL | 4.800 |
| 627 | AVAGPDKEL | 4.400 |
| 221 | SASTPAPKL | 4.400 |
| 113 | LLDYGDMML | 4.000 |
| 685 | QVGTYHFRL | 4.000 |
| 261 | SNSSGKEVL | 4.000 |
| 773 | SVALQLTNL | 4.000 |

TABLE XVI-V1-continued

HLA-A24-9mers-254P1D68
Each peptide is a portion of SEQ ID NO: 3; each start position is specified, the length of peptide is 9 amino acids, and the end position for each peptide is the start position plus eight.

| Start | Subsequence | Score |
|---|---|---|
| 387 | QGHKQTLNL | 4.000 |
| 56 | DCTAACCDL | 4.000 |
| 918 | SGHGHCDPL | 4.000 |
| 577 | MQGVQTPYL | 4.000 |
| 483 | SVDSPVLRL | 4.000 |
| 366 | TTYNYEWNL | 4.000 |
| 932 | CSHLWMENL | 4.000 |
| 961 | VLAFTLIVL | 4.000 |
| 61 | CCDLSSCDL | 4.000 |
| 495 | DPGNYSFRL | 4.000 |
| 136 | DIRKDLPFL | 4.000 |
| 892 | RLSKEKADF | 4.000 |
| 723 | AGGRHVLVL | 4.000 |
| 589 | AMQEGDYTF | 3.600 |
| 629 | AGPDKELIF | 3.600 |
| 780 | NLVEGVYTF | 3.600 |
| 407 | VTVSSENAF | 3.600 |
| 965 | TLIVLTGGF | 3.600 |
| 1025 | SLMVSESEF | 3.300 |
| 142 | PFLGKDWGL | 3.000 |
| 1057 | GSIRNGASF | 3.000 |
| 683 | GLQVGTYHF | 3.000 |
| 187 | LLPGSEGAF | 3.000 |
| 349 | DNEVELKAF | 3.000 |

TABLE XVI-V2

HLA-A24-9mers-254P1D68
Each peptide is a portion of SEQ ID NO: 5; each start position is specified, the length of peptide is 9 amino acids, and the end position for each peptide is the start position plus eight.

| Start | Subsequence | Score |
|---|---|---|
| 7 | EYADDYREL | 264.000 |
| 1 | GLEEMSEYA | 0.180 |
| 4 | EMSEYADDY | 0.120 |
| 5 | MSEYADDYR | 0.015 |

TABLE XVI-V2-continued

HLA-A24-9mers-254P1D68
Each peptide is a portion of SEQ ID NO: 5; each start position is specified, the length of peptide is 9 amino acids, and the end position for each peptide is the start position plus eight.

| Start | Subsequence | Score |
|---|---|---|
| 8 | YADDYRELE | 0.012 |
| 3 | EEMSEYADD | 0.002 |
| 2 | LEEMSEYAD | 0.002 |
| 9 | ADDYRELEK | 0.001 |
| 6 | SEYADDYRE | 0.001 |

TABLE XVI-V3

HLA-A24-9mers-254P1D68
Each peptide is a portion of SEQ ID NO: 7; each start position is specified, the length of peptide is 9 amino acids, and the end position for each peptide is the start position plus eight.

| Start | Subsequence | Score |
|---|---|---|
| 3 | RLGWPSPCC | 0.200 |
| 4 | LGWPSPCCA | 0.120 |
| 8 | SPCCARKQC | 0.100 |
| 5 | GWPSPCCAR | 0.015 |
| 2 | TRLGWPSPC | 0.015 |
| 6 | WPSPCCARK | 0.012 |
| 9 | PCCARKQCS | 0.012 |
| 10 | CCARKQCSE | 0.010 |
| 1 | MTRLGWPSP | 0.010 |
| 7 | PSPCCARKQ | 0.002 |

TABLE XVI-V5

HLA-A24-9mers-254P1D68
Each peptide is a portion of SEQ ID NO: 11; each start position is specified, the length of peptide is 9 amino acids, and the end position for each peptide is the start position plus eight.

| Start | Subsequence | Score |
|---|---|---|
| 9 | TFLGKDWGL | 30.000 |
| 3 | DIRKDLTFL | 4.000 |
| 2 | EDIRKDLTF | 0.300 |
| 7 | DLTFLGKDW | 0.120 |
| 8 | LTFLGKDWG | 0.010 |
| 6 | KDLTFLGKD | 0.003 |
| 5 | RKDLTFLGK | 0.002 |

TABLE XVI-V5-continued

HLA-A24-9mers-254P1D68
Each peptide is a portion of SEQ ID NO: 11; each start position is specified, the length of peptide is 9 amino acids, and the end position for each peptide is the start position plus eight.

| Start | Subsequence | Score |
|---|---|---|
| 4 | IRKDLTFLG | 0.001 |
| 1 | PEDIRKDLT | 0.001 |

TABLE XVII-V1

HLA-A24-10mers-254P1D68
Each peptide is a portion of SEQ ID NO: 3; each start position is specified, the length of peptide is 10 amino acids, and the end position for each peptide is the start position plus nine.

| Start | Subsequence | Score |
|---|---|---|
| 957 | FYVTVLAFTL | 360.000 |
| 159 | DYRELEKDLL | 240.000 |
| 839 | RQLAVLLNVL | 17.280 |
| 943 | RYIWDGESNC | 15.000 |
| 105 | RPVQRPAQLL | 14.400 |
| 897 | KADFLLFKVL | 11.520 |
| 402 | LYVFKVTVSS | 10.500 |
| 98 | SYLTFVLRPV | 10.500 |
| 132 | DSPEDIRKDL | 10.080 |
| 868 | VFYVQSRPPF | 10.000 |
| 1032 | EFDSDQDTIF | 10.000 |
| 692 | RLTVKDQQGL | 9.600 |
| 561 | LYEWSLGPGS | 9.000 |
| 229 | LPERSVLLPL | 8.400 |
| 31 | YSNAVISPNL | 8.400 |
| 2 | APPTGVLSSL | 8.400 |
| 892 | RLSKEKADFL | 8.000 |
| 720 | RARAGGRHVL | 8.000 |
| 386 | KQGHKQTLNL | 8.000 |
| 722 | RAGGRHVLVL | 8.000 |
| 436 | AVVSPQLQEL | 7.920 |
| 273 | HSLPPASLEL | 7.920 |
| 345 | ITLPDNEVEL | 7.920 |
| 367 | TYNYEWNLIS | 7.500 |
| 751 | SYLWIRDGQS | 7.500 |
| 482 | TSVDSPVLRL | 7.200 |
| 539 | ITLPQNSITL | 7.200 |

TABLE XVII-V1-continued

HLA-A24-10mers-254P1D68
Each peptide is a portion of SEQ ID NO: 3; each start position is specified, the length of peptide is 10 amino acids, and the end position for each peptide is the start position plus nine.

| Start | Subsequence | Score |
|---|---|---|
| 209 | TQQDPELHYL | 7.200 |
| 967 | IVLTGGFTWL | 7.200 |
| 836 | TLVRQLAVLL | 7.200 |
| 393 | LNLSQLSVGL | 7.200 |
| 729 | LVLPNNSITL | 7.200 |
| 808 | VQPDPRKSGL | 7.200 |
| 112 | QLLDYGDMML | 7.200 |
| 30 | TYSNAVISPN | 7.000 |
| 626 | VAVAGPDKEL | 6.600 |
| 557 | HQIVLYEWSL | 6.000 |
| 684 | LQVGTYHFRL | 6.000 |
| 835 | DTLVRQLAVL | 6.000 |
| 590 | MQEGDYTFQL | 6.000 |
| 438 | VSPQLQELTL | 6.000 |
| 247 | VLEKEKASQL | 6.000 |
| 820 | LTLQVGVGQL | 6.000 |
| 260 | SSNSSGKEVL | 6.000 |
| 576 | VMQGVQTPYL | 6.000 |
| 179 | SAEYTDWGLL | 6.000 |
| 485 | DSPVLRLSNL | 6.000 |
| 5 | TGVLSSLLLL | 6.000 |
| 960 | TVLAFTLIVL | 6.000 |
| 781 | LVEGVYTFHL | 6.000 |
| 578 | QGVQTPYLHL | 6.000 |
| 772 | HSVALQLTNL | 6.000 |
| 338 | SAGDNLIITL | 5.760 |
| 769 | GSDHSVALQL | 5.600 |
| 926 | LTKRCICSHL | 5.600 |
| 326 | TTAPRTVKEL | 5.280 |
| 1000 | NMDEQERMEL | 5.280 |
| 312 | APSESTPSEL | 5.280 |
| 893 | LSKEKADFLL | 4.800 |
| 60 | ACCDLSSCDL | 4.800 |
| 635 | LIFPVESATL | 4.800 |
| 406 | KVTVSSENAF | 4.800 |
| 423 | TVKPARRVNL | 4.800 |
| 444 | ELTLPLTSAL | 4.800 |
| 828 | QLTEQRKDTL | 4.800 |
| 884 | EVARNLHMRL | 4.800 |
| 384 | EIKQGHKQTL | 4.800 |
| 532 | NAGPNHTITL | 4.800 |
| 552 | QSSDDHQIVL | 4.800 |
| 871 | VQSRPPFKVL | 4.800 |
| 178 | GSAEYTDWGL | 4.800 |
| 220 | ESASTPAPKL | 4.400 |
| 811 | DPRKSGTVEL | 4.400 |
| 905 | VLRVDTAGCL | 4.000 |
| 141 | LPFLGKDWGL | 4.000 |
| 284 | SVTVEKSPVL | 4.000 |
| 510 | GATNSTTAAL | 4.000 |
| 698 | QQGLSSTSTL | 4.000 |
| 334 | ELTVSAGDNL | 4.000 |
| 854 | VQKIRAHSDL | 4.000 |
| 917 | CSGHGHCDPL | 4.000 |
| 931 | ICSHLWMENL | 4.000 |
| 365 | ETTYNYEWNL | 4.000 |
| 953 | EWSIFYVTVL | 4.000 |
| 226 | APKLPERSVL | 4.000 |
| 70 | AWWFEGRCYL | 4.000 |
| 186 | GLLPGSEGAF | 3.600 |
| 964 | FTLIVLTGGF | 3.600 |
| 492 | SNLDPGNYSF | 3.600 |
| 1024 | SSLMVSESEF | 3.300 |
| 1006 | RMELRPKYGI | 3.000 |
| 779 | TNLVEGVYTF | 3.000 |
| 682 | TGLQVGTYHF | 3.000 |
| 588 | SAMQEGDYTF | 3.000 |
| 93 | MGPIRSYLTF | 3.000 |
| 410 | SSENAFGEGF | 3.000 |
| 396 | SQLSVGLYVF | 3.000 |
| 648 | SSSDDHGIVF | 2.400 |

TABLE XVII-V1-continued

HLA-A24-10mers-254P1D68
Each peptide is a portion of SEQ ID NO: 3; each start position is specified, the length of peptide is 10 amino acids, and the end position for each peptide is the start position plus nine.

| Start | Subsequence | Score |
|---|---|---|
| 64 | LSSCDLAWWF | 2.400 |
| 858 | RAHSDLSTVI | 2.400 |

TABLE XVII-V2

HLA-A24-10mers-254P1D68
Each peptide is a portion of SEQ ID NO: 5; each start position is specified, the length of peptide is 10 amino acids, and the end position for each peptide is the start position plus nine.

| Start | Subsequence | Score |
|---|---|---|
| 8 | EYADDYRELE | 0.600 |
| 7 | SEYADDYREL | 0.440 |
| 1 | WGLEEMSEYA | 0.180 |
| 2 | GLEEMSEYAD | 0.018 |
| 6 | MSEYADDYRE | 0.015 |
| 4 | EEMSEYADDY | 0.015 |
| 9 | YADDYRELEK | 0.013 |
| 5 | EMSEYADDYR | 0.012 |
| 3 | LEEMSEYADD | 0.002 |
| 10 | ADDYRELEKD | 0.001 |

TABLE XVII-V3

HLA-A24-10mers-254P1D68
Each peptide is a portion of SEQ ID NO: 7; each start position is specified, the length of peptide is 10 amino acids, and the end position for each peptide is the start position plus nine.

| Start | Subsequence | Score |
|---|---|---|
| 3 | RLGWPSPCCA | 0.200 |
| 8 | SPCCARKQCS | 0.120 |
| 1 | MTRLGWPSPC | 0.100 |
| 7 | PSPCCARKQC | 0.015 |
| 5 | GWPSPCCARK | 0.015 |
| 2 | TRLGWPSPCC | 0.015 |
| 6 | WPSPCCARKQ | 0.013 |
| 4 | LGWPSPCCAR | 0.012 |
| 10 | CCARKQCSEG | 0.011 |
| 9 | PCCARKQCSE | 0.001 |

TABLE XVII-V5

HLA-A24-10mers-254P1D68
Each peptide is a portion of SEQ ID NO: 11; each start position is specified, the length of peptide is 10 amino acids and the end position for each peptide is the start position plus nine.

| Start | Subsequence | Score |
|---|---|---|
| 9 | LTFLGKDWGL | 4.000 |
| 3 | EDIRKDLTFL | 0.600 |
| 1 | SPEDIRKDLT | 0.180 |
| 10 | TFLGKDWGLE | 0.075 |
| 7 | KDLTFLGKDW | 0.036 |
| 2 | PEDIRKDLTF | 0.020 |
| 4 | DIRKDLTFLG | 0.012 |
| 8 | DLTFLGKDWG | 0.010 |
| 6 | RKDLTFLGKD | 0.002 |
| 5 | IRKDLTFLGK | 0.001 |

TABLE XVIII-V1

HLA-B7-9mers-254P1D68
Each peptide is a portion of SEQ ID NO: 3; each start position is specified, the length of peptide is 9 amino acids, and the end position for each peptide is the start position plus eight.

| Start | Subsequence | Score |
|---|---|---|
| 837 | LVRQLAVLL | 200.000 |
| 885 | VARNLHMRL | 120.000 |
| 627 | AVAGPDKEL | 90.000 |
| 105 | RPVQRPAQL | 80.000 |
| 486 | SPVLRLSNL | 80.000 |
| 495 | DPGNYSFRL | 80.000 |
| 439 | SPQLQELTL | 80.000 |
| 872 | QSRPPFKVL | 60.000 |
| 328 | APRTVKELT | 60.000 |
| 136 | DIRKDLPFL | 40.000 |
| 133 | SPEDIRKDL | 36.000 |
| 267 | EVLMPSHSL | 30.000 |

TABLE XVIII-V1-continued

HLA-B7-9mers-254P1D68
Each peptide is a portion of SEQ ID NO: 3; each start position is specified, the length of peptide is 9 amino acids, and the end position for each peptide is the start position plus eight.

| Start | Subsequence | Score |
|---|---|---|
| 579 | GVQTPYLHL | 30.000 |
| 809 | QPDPRKSGL | 24.000 |
| 437 | VVSPQLQEL | 20.000 |
| 685 | QVGTYHFRL | 20.000 |
| 773 | SVALQLTNL | 20.000 |
| 175 | EPRGSAEYT | 20.000 |
| 6 | GVLSSLLLL | 20.000 |
| 958 | YVTVLAFTL | 20.000 |
| 582 | TPYLHLSAM | 20.000 |
| 226 | APKLPERSV | 18.000 |
| 221 | SASTPAPKL | 18.000 |
| 533 | AGPNHTITL | 12.000 |
| 327 | TAPRTVKEL | 12.000 |
| 676 | KAIATVTGL | 12.000 |
| 881 | KAAEVARNL | 12.000 |
| 723 | AGGRHVLVL | 12.000 |
| 511 | ATNSTTAAL | 12.000 |
| 359 | APAPPVETT | 9.000 |
| 483 | SVDSPVLRL | 9.000 |
| 3 | PPTGVLSSL | 8.000 |
| 296 | TPGSTEHSI | 8.000 |
| 37 | SPNLETTRI | 8.000 |
| 377 | HPTDYQGEI | 8.000 |
| 92 | KMGPIRSYL | 6.000 |
| 720 | RARAGGRHV | 6.000 |
| 907 | RVDTAGCLL | 6.000 |
| 1018 | RSTEHNSSL | 4.000 |
| 346 | TLPDNEVEL | 4.000 |
| 32 | SNAVISPNL | 4.000 |
| 954 | WSIFYVTVL | 4.000 |
| 324 | SPTTAPRTV | 4.000 |
| 821 | TLQVGVGQL | 4.000 |
| 540 | TLPQNSITL | 4.000 |
| 918 | SGHGHCDPL | 4.000 |
| 927 | TKRCICSHL | 4.000 |

TABLE XVIII-V1-continued

HLA-B7-9mers-254P1D68
Each peptide is a portion of SEQ ID NO: 3; each start position is specified, the length of peptide is 9 amino acids, and the end position for each peptide is the start position plus eight.

| Start | Subsequence | Score |
|---|---|---|
| 121 | LNRGSPSGI | 4.000 |
| 814 | KSGLVELTL | 4.000 |
| 240 | TTPSSGEVL | 4.000 |
| 699 | QGLSSTSTL | 4.000 |
| 968 | VLTGGFTWL | 4.000 |
| 56 | DCTAACCDL | 4.000 |
| 445 | LTLPLTSAL | 4.000 |
| 932 | CSHLWMENL | 4.000 |
| 558 | QIVLYEWSL | 4.000 |
| 274 | SLPPASLEL | 4.000 |
| 961 | VLAFTLIVL | 4.000 |
| 390 | KQTLNLSQL | 4.000 |
| 768 | DGSDHSVAL | 4.000 |
| 893 | LSKEKADFL | 4.000 |
| 577 | MQGVQTPYL | 4.000 |
| 730 | VLPNNSITL | 4.000 |
| 228 | KLPERSVLL | 4.000 |
| 285 | VTVEKSPVL | 4.000 |
| 366 | TTYNYEWNL | 4.000 |
| 335 | LTVSAGDNL | 4.000 |
| 693 | LTVKDQQGL | 4.000 |
| 840 | QLAVLLNVL | 4.000 |
| 159 | DYRELEKDL | 4.000 |
| 567 | GPGSEGKHV | 4.000 |
| 836 | TLVRQLAVL | 4.000 |
| 5 | TGVLSSLLL | 4.000 |
| 387 | QGHKQTLNL | 4.000 |
| 261 | SNSSGKEVL | 4.000 |
| 481 | KTSVDSPVL | 4.000 |
| 441 | QLQELTLPL | 4.000 |
| 394 | NLSQLSVGL | 4.000 |
| 179 | SAEYTDWGL | 3.600 |
| 339 | AGDNLIITL | 3.600 |
| 999 | DNMDEQERM | 3.000 |
| 106 | PVQRPAQLL | 3.000 |
| 304 | IPTPPTSAA | 3.000 |

TABLE XVIII-V1-continued

HLA-B7-9mers-254P1D68
Each peptide is a portion of SEQ ID NO: 3; each start position is specified, the length of peptide is 9 amino acids, and the end position for each peptide is the start position plus eight.

| Start | Subsequence | Score |
|---|---|---|
| 924 | DPLTKRCIC | 3.000 |
| 111 | AQLLDYGDM | 3.000 |
| 34 | AVISPNLET | 2.250 |
| 434 | PVAVVSPQL | 2.000 |
| 270 | MPSHSLPPA | 2.000 |
| 811 | DPRKSGLVE | 2.000 |
| 336 | TVSAGDNLI | 2.000 |
| 465 | IVSYHWEEI | 2.000 |
| 874 | RPPFKVLKA | 2.000 |
| 604 | SSRQQSTAV | 2.000 |
| 27 | EGRTYSNAV | 2.000 |
| 52 | FPVVDCTAA | 2.000 |
| 721 | ARAGGRHVL | 1.800 |
| 531 | ANAGPNHTI | 1.800 |
| 618 | QPENNRPPV | 1.800 |
| 517 | AALIVNNAV | 1.800 |
| 621 | NNRPPVAVA | 1.500 |

TABLE XVIII-V2

HLA-B7-9mers-254P1D68
Each peptide is a portion of SEQ ID NO: 5; each start position is specified, the length of peptide is 9 amino acids, and the end position for each peptide is the start position plus eight.

| Start | Subsequence | Score |
|---|---|---|
| 7 | EYADDYREL | 0.400 |
| 1 | GLEEMSEYA | 0.030 |
| 4 | EMSEYADDY | 0.020 |
| 8 | YADDYRELE | 0.013 |
| 3 | EEMSEYADD | 0.003 |
| 5 | MSEYADDYR | 0.003 |
| 6 | SEYADDYRE | 0.001 |
| 9 | ADDYRELEK | 0.001 |
| 2 | LEEMSEYAD | 0.000 |

TABLE XVIII-V3

HLA-B7-9mers-254P1D68
Each peptide is a portion of SEQ ID NO: 7; each start position is specified, the length of peptide is 9 amino acids, and the end position for each peptide is the start position plus eight.

| Start | Subsequence | Score |
|---|---|---|
| 8 | SPCCARKQC | 3.000 |
| 6 | WPSPCCARK | 0.200 |
| 3 | RLGWPSPCC | 0.150 |
| 1 | MTRLGWPSP | 0.100 |
| 4 | LGWPSPCCA | 0.100 |
| 10 | CCARKQCSE | 0.010 |
| 2 | TRLGWPSPC | 0.010 |
| 9 | PCCARKQCS | 0.002 |
| 5 | GWPSPCCAR | 0.002 |
| 7 | PSPCCARKQ | 0.001 |

TABLE XVIII-V5

HLA-B7-9mers-254P D68
Each peptide is a portion of SEQ ID NO: 11; each start position is specified, the length of peptide is 9 amino acids, and the end position for each peptide is the start position plus eight.

| Start | Subsequence | Score |
|---|---|---|
| 3 | DIRKDLTFL | 40.00 |
| 9 | TFLGKDWGL | 0.400 |
| 7 | DLTFLGKDW | 0.020 |
| 8 | LTFLGKDWG | 0.010 |
| 2 | EDIRKDLTF | 0.002 |
| 4 | IRKDLTFLG | 0.001 |
| 6 | KDLTFLGKD | 0.001 |
| 1 | PEDIRKDLT | 0.000 |
| 5 | RKDLTFLGK | 0.000 |

TABLE XIX-V1

HLA-B7-10mers-254P1D68
Each peptide is a portion of SEQ ID NO: 3; each start position is specified, the length of peptide is 10 amino acids, and the end position for each peptide is the start position plus nine.

| Start | Subsequence | Score |
|---|---|---|
| 811 | DPRKSGLVEL | 800.000 |
| 226 | APSESTPSEL | 360.000 |
| 312 | APPTGVLSSL | 240.000 |

TABLE XIX-V1-continued

HLA-B7-10mers-254P1D68
Each peptide is a portion of SEQ ID NO: 3; each start position is specified, the length of peptide is 10 amino acids, and the end position for each peptide is the start position plus nine.

| Start | Subsequence | Score |
|---|---|---|
| 2 | APPTGVLSSL | 240.000 |
| 720 | RARAGGRHVL | 180.000 |
| 105 | RPVQRPAQLL | 120.000 |
| 328 | APRTVKELTV | 120.000 |
| 141 | LPFLGKDWGL | 80.000 |
| 436 | AVVSPQLQEL | 60.000 |
| 662 | HVRGPSAVEM | 50.000 |
| 905 | VLRVDTAGCL | 40.000 |
| 423 | TVKPARRVNL | 30.000 |
| 229 | LPERSVLLPL | 24.000 |
| 37 | SPNLETTRIM | 20.000 |
| 284 | SVTVEKSPVL | 20.000 |
| 967 | IVLTGGFTWL | 20.000 |
| 960 | TVLAFTLIVL | 20.000 |
| 729 | LVLPNNSITL | 20.000 |
| 884 | EVARNLHMRL | 20.000 |
| 626 | VAVAGPDKEL | 18.000 |
| 338 | SAGDNLIITL | 12.000 |
| 722 | RAGGRHVLVL | 12.000 |
| 60 | ACCDLSSCDL | 12.000 |
| 510 | GATNSTTAAL | 12.000 |
| 532 | NAGPNHTITL | 12.000 |
| 665 | GPSAVEMENI | 8.000 |
| 1050 | NPKVSMNGSI | 8.000 |
| 3 | PPTGVLSSLL | 8.000 |
| 433 | PPVAVVSPQL | 8.000 |
| 781 | LVEGVYTFHL | 6.000 |
| 871 | VQSRPPFKVL | 6.000 |
| 578 | QGVQTPYLHL | 6.00 |
| 627 | AVAGPDKELI | 6.000 |
| 220 | ESASTPAPKL | 6.000 |
| 482 | TSVDSPVLRL | 6.000 |
| 132 | DSPEDIRKDL | 6.000 |
| 892 | RLSKEKADFL | 4.000 |
| 260 | SSNSSGKEVL | 4.000 |
| 828 | QLTEQRKDTL | 4.000 |

TABLE XIX-V1-continued

HLA-B7-10mers-254P1D68
Each peptide is a portion of SEQ ID NO: 3; each start position is specified, the length of peptide is 10 amino acids, and the end position for each peptide is the start position plus nine.

| Start | Subsequence | Score |
|---|---|---|
| 384 | EIKQGHKQTL | 4.000 |
| 159 | DYRELEKDLL | 4.000 |
| 917 | CSGHGHCDPL | 4.000 |
| 438 | VSPQLQELTL | 4.000 |
| 485 | DSPVLRLSNL | 4.000 |
| 893 | LSKEKADFLL | 4.000 |
| 27 | EGRTYSNAVI | 4.000 |
| 326 | TTAPRTVKEL | 4.000 |
| 698 | QQGLSSTSTL | 4.000 |
| 393 | LNLSQLSVGL | 4.000 |
| 365 | ETTYNYEWNL | 4.000 |
| 238 | LPTTPSSGEV | 4.000 |
| 386 | KQGHKQTLNL | 4.000 |
| 95 | PIRSYLTFVL | 4.00 |
| 835 | DTLVRQLAVL | 4.000 |
| 820 | LTLQVGVGQL | 4.000 |
| 31 | YSNAVISPNL | 4.000 |
| 926 | LTKRCICSHL | 4.000 |
| 539 | ITLPQNSITL | 4.000 |
| 692 | RLTVKDQQGL | 4.000 |
| 5 | TGVLSSLLLL | 4.000 |
| 635 | LIFPVESATL | 4.000 |
| 557 | HQIVLYEWSL | 4.000 |
| 854 | VQKIRAHSDL | 4.000 |
| 836 | TLVRQLAVLL | 4.000 |
| 552 | QSSDDHQIVL | 4.000 |
| 740 | GSRSTDDQRI | 4.000 |
| 475 | GPFIEEKTSV | 4.000 |
| 112 | QLLDYGDMML | 4.000 |
| 345 | ITLPDNEVEL | 4.000 |
| 334 | ELTVSAGDNL | 4.000 |
| 273 | HSLPPASLEL | 4.000 |
| 988 | KIRKKTKYTI | 4.000 |
| 746 | DQRIVSYLWI | 4.000 |
| 444 | ELTLPLTSAL | 4.00 |

TABLE XIX-V1-continued

HLA-B7-10mers-254P1D68
Each peptide is a portion of SEQ ID NO: 3; each start position is specified, the length of peptide is 10 amino acids, and the end position for each peptide is the start position plus nine.

| Start | Subsequence | Score |
|---|---|---|
| 576 | VMQGVQTPYL | 4.000 |
| 684 | LQVGTYHFRL | 4.000 |
| 772 | HSVALQLTNL | 4.000 |
| 839 | RQLAVLLNVL | 4.000 |
| 567 | GPGSEGKHVV | 4.000 |
| 931 | ICSHLWMENL | 4.000 |
| 209 | TQQDPELHYL | 4.000 |
| 178 | GSAEYTDWGL | 4.000 |
| 808 | VQPDPRKSGL | 4.000 |
| 94 | GPIRSYLTFV | 4.000 |
| 897 | KADFLLFKVL | 3.600 |
| 179 | SAEYTDWGLL | 3.600 |
| 111 | AQLLDYGDMM | 3.000 |
| 317 | TPSELPISPT | 3.000 |
| 727 | HVLVLPNNSI | 3.000 |
| 882 | AAEVARNLHM | 2.700 |
| 175 | EPRGSAEYTD | 2.000 |
| 52 | FPVVDCTAAC | 2.000 |
| 336 | TVSAGDNLII | 2.000 |
| 45 | IMRVSHTFPV | 2.000 |
| 495 | DPGNYSFRLT | 2.0 |
| 874 | RPPFKVLKAA | 2.000 |
| 958 | YVTVLAFTLI | 2.000 |
| 604 | SSRQQSTAVV | 2.000 |
| 70 | AWWFEGRCYL | 1.800 |
| 91 | KKMGPIRSYL | 1.800 |

TABLE XIX-V2

HLA-B7-10mers-254P1D68
Each peptide is a portion of SEQ ID NO: 5; each start position is specified, the length of peptide is 10 amino acids, and the end position for each peptide is the start position plus nine.

| Start | Subsequence | Score |
|---|---|---|
| 7 | SEYADDYREL | 0.400 |
| 1 | WGLEEMSEYA | 0.100 |
| 5 | EMSEYADDYR | 0.010 |

TABLE XIX-V2-continued

HLA-B7-10mers-254P1D68
Each peptide is a portion of SEQ ID NO: 5; each start position is specified, the length of peptide is 10 amino acids, and the end position for each peptide is the start position plus nine.

| Start | Subsequence | Score |
|---|---|---|
| 9 | YADDYRELEK | 0.009 |
| 4 | EEMSEYADDY | 0.006 |
| 2 | GLEEMSEYAD | 0.003 |
| 6 | MSEYADDYRE | 0.003 |
| 8 | EYADDYRELE | 0.002 |
| 10 | ADDYRELEKD | 0.001 |
| 3 | LEEMSEYADD | 0.000 |

TABLE XIX-V3

HLA-B7-10mers-254P1D68
Each peptide is a portion of SEQ ID NO: 7; each start position is specified, the length of peptide is 10 amino acids, and the end position for each peptide is the start position plus nine.

| Start | Subsequence | Score |
|---|---|---|
| 1 | MTRLGWPSPC | 1.000 |
| 8 | SPCCARKQCS | 0.400 |
| 6 | WPSPCCARKQ | 0.200 |
| 3 | RLGWPSPCCA | 0.100 |
| 7 | PSPCCARKQC | 0.015 |
| 2 | TRLGWPSPCC | 0.015 |
| 4 | LGWPSPCCAR | 0.015 |
| 10 | CCARKQCSEG | 0.010 |
| 9 | PCCARKQCSE | 0.001 |
| 5 | GWPSPCCARK | 0.001 |

TABLE XIX-V5

HLA-B7-10mers-254P1D68
Each peptide is a portion of SEQ ID NO: 11; each start position is specified, the length of peptide is 10 amino acids, and the end position for each peptide is the start position plus nine.

| Start | Subsequence | Score |
|---|---|---|
| 9 | LTFLGKDWGL | 4.000 |
| 1 | SPEDIRKDLT | 0.600 |
| 3 | EDIRKDLTFL | 0.400 |
| 4 | DIRKDLTFLG | 0.100 |
| 8 | DLTFLGKDWG | 0.01 |

TABLE XIX-V5-continued

HLA-B7-10mers-254P1D68
Each peptide is a portion of SEQ ID NO: 11;
each start position is specified, the length of
peptide is 10 amino acids, and the end position
for each peptide is the start position plus
nine.

| Start | Subsequence | Score |
|---|---|---|
| 7 | KDLTFLGKDW | 0.002 |
| 10 | TFLGKDWGLE | 0.001 |
| 5 | IRKDLTFLGK | 0.001 |
| 6 | RKDLTFLGKD | 0.000 |
| 2 | PEDIRKDLTF | 0.000 |

TABLE XX-V1

HLA-B3501-9mers-254P1D68
Each peptide is a portion of SEQ ID NO: 3; each
start position is specified, the length of
peptide is 9 amino acids, and the end position
for each peptide is the start position plus
eight.

| Start | Subsequence | Score |
|---|---|---|
| 105 | RPVQRPAQL | 40.000 |
| 582 | TPYLHLSAM | 40.000 |
| 893 | LSKEKADFL | 30.000 |
| 1018 | RSTEHNSSL | 20.000 |
| 94 | GPIRSYLTF | 20.000 |
| 495 | DPGNYSFRL | 20.000 |
| 439 | SPQLQELTL | 20.000 |
| 486 | SPVLRLSNL | 20.000 |
| 377 | HPTDYQGEI | 16.000 |
| 491 | LSNLDPGNY | 15.000 |
| 872 | QSRPPFKVL | 15.0 |
| 133 | SPEDIRKDL | 12.000 |
| 226 | APKLPERSV | 12.000 |
| 881 | KAAEVARNL | 12.000 |
| 37 | SPNLETTRI | 12.000 |
| 587 | LSAMQEGDY | 10.000 |
| 814 | KSGLVELTL | 10.000 |
| 262 | NSSGKEVLM | 10.000 |
| 65 | SSCDLAWWF | 10.000 |
| 395 | LSQLSVGLY | 10.000 |
| 885 | VARNLHMRL | 9.000 |
| 296 | TPGSTEHSI | 8.000 |
| 362 | PPVETTYNY | 8.000 |

TABLE XX-V1-continued

HLA-B3501-9mers-254P1D68
Each peptide is a portion of SEQ ID NO: 3; each
start position is specified, the length of
peptide is 9 amino acids, and the end position
for each peptide is the start position plus
eight.

| Start | Subsequence | Score |
|---|---|---|
| 949 | ESNCEWSIF | 7.500 |
| 742 | RSTDDQRIV | 6.000 |
| 999 | DNMDEQERM | 6.000 |
| 148 | WGLEEMSEY | 6.000 |
| 676 | KAIATVTGL | 6.000 |
| 23 | KQCSEGRTY | 6.000 |
| 567 | GPGSEGRTY | 6.000 |
| 175 | EPRGSAEYT | 6.000 |
| 809 | QPDPRKSGL | 6.000 |
| 1050 | NPKVSMNGS | 6.000 |
| 328 | APRTVKELT | 6.000 |
| 932 | CSHLWMENL | 5.000 |
| 1057 | GSIRNGASF | 5.000 |
| 954 | WSIFYVTVL | 5.000 |
| 136 | DIRKDLPFL | 4.500 |
| 228 | KLPERSVLL | 4.000 |
| 929 | RCICSHLWM | 4.000 |
| 874 | RPPFKVLKA | 4.000 |
| 112 | QLLDYGDMM | 4.000 |
| 950 | SNCEWSIFY | 4.000 |
| 209 | TQQDPELHY | 4.000 |
| 152 | EMSEYSDDY | 4.000 |
| 324 | SPTTAPRTV | 4.000 |
| 64 | LSSCDLAWW | 3.750 |
| 720 | RARAGGRHV | 3.600 |
| 327 | TAPRTVKEL | 3.000 |
| 649 | SSDDHGIVF | 3.000 |
| 552 | QSSDDHQIV | 3.000 |
| 221 | SASTPAPKL | 3.000 |
| 52 | FPVVDCTAA | 3.000 |
| 337 | VSAGDNLII | 3.000 |
| 604 | SSRQQSTAV | 3.000 |
| 647 | SSSSDDHGI | 3.000 |
| 475 | GPFIEEKTS | 3.000 |
| 569 | GSEGKHVVM | 3.000 |
| 361 | APPVETTYN | 3.000 |

TABLE XX-V1-continued

HLA-B3501-9mers-254P1D68
Each peptide is a portion of SEQ ID NO: 3; each start position is specified, the length of peptide is 9 amino acids, and the end position for each peptide is the start position plus eight.

| Start | Subsequence | Score |
|---|---|---|
| 188 | LPGSEGAFN | 3.000 |
| 553 | SSDDHQIVL | 3.000 |
| 648 | SSSDDHGIV | 3.000 |
| 892 | RLSKEKADF | 3.000 |
| 111 | AQLLDYGDM | 3.000 |
| 481 | KTSVDSPVL | 3.000 |
| 837 | LVRQLAVLL | 3.000 |
| 458 | QSTDDTEIV | 3.000 |
| 759 | QSPAAGDVI | 2.000 |
| 780 | NLVEGVYTF | 2.000 |
| 346 | TLPDNEVEL | 2.000 |
| 681 | VTGLQVGTY | 2.000 |
| 304 | IPTPPTSAA | 2.000 |
| 541 | LPQNSITLN | 2.000 |
| 125 | SPSGIWGDS | 2.000 |
| 275 | LPPASLELS | 2.000 |
| 862 | DLSTVIVFY | 2.000 |
| 236 | LPLPTTPSS | 2.000 |
| 373 | NLISHPTDY | 2.000 |
| 665 | GPSAVEMEN | 2.000 |
| 9 | SSLLLLVTI | 2.000 |
| 270 | MPSHSLPPA | 2.000 |
| 441 | QLQELTLPL | 2.000 |
| 589 | AMQEGDYTF | 2.000 |
| 576 | VMQGVQTPY | 2.000 |
| 519 | LIVNNAVDY | 2.000 |
| 924 | DPLTKRCIC | 2.000 |
| 629 | AGPDKELIF | 2.000 |
| 359 | APAPPVETT | 2.000 |
| 778 | LTNLVEGVY | 2.000 |
| 3 | PPTGVLSSL | 2.000 |
| 608 | QSTAVVTVI | 2.000 |
| 306 | TPPTSAAPS | 2.000 |
| 285 | VTVEKSPVL | 2.000 |
| 315 | ESTPSELPI | 2.000 |

TABLE XX-V1-continued

HLA-B3501-9mers-254P1D68
Each peptide is a portion of SEQ ID NO: 3; each start position is specified, the length of peptide is 9 amino acids, and the end position for each peptide is the start position plus eight.

| Start | Subsequence | Score |
|---|---|---|
| 44 | RIVRVSHTF | 2.000 |
| 2 | APPTGVLSS | 2.000 |
| 390 | KQTLNLSQL | 2.000 |
| 1038 | DTIFSREKM | 2.000 |
| 92 | KMGPIRSYL | 2.000 |
| 768 | DGSDHSVAL | 2.000 |

TABLE XX-V2

HLA-B3501-9mers-254P1D68
Each peptide is a portion of SEQ ID NO: 5; each start position is specified, the length of peptide is 9 amino acids, and the end position for each peptide is the start position plus eight.

| Start | Subsequence | Score |
|---|---|---|
| 4 | EMSEYADDY | 4.000 |
| 7 | EYADDYREL | 0.300 |
| 1 | GLEEMSEYA | 0.060 |
| 8 | YADDYRELE | 0.018 |
| 5 | MSEYADDYR | 0.015 |
| 6 | SEYADDYRE | 0.002 |
| 3 | EEMSEYADD | 0.002 |
| 2 | LEEMSEYAD | 0.000 |
| 9 | ADDYRELEK | 0.000 |

TABLE XX-V3

HLA-B3501-9mers-254P1D68
Each peptide is a portion of SEQ ID NO: 7; each start position is specified, the length of peptide is 9 amino acids, and the end position for each peptide is the start position plus eight.

| Start | Subsequence | Score |
|---|---|---|
| 8 | SPCCARKQC | 2.000 |
| 3 | RLGWPSPCC | 0.200 |
| 6 | WPSPCCARK | 0.200 |
| 4 | LGWPSPCCA | 0.100 |
| 1 | MTRLGWPSP | 0.030 |
| 10 | CCARKQCSE | 0.010 |
| 9 | PCCARKQCS | 0.010 |

TABLE XX-V3-continued

HLA-B3501-9mers-254P1D68
Each peptide is a portion of SEQ ID NO: 7; each start position is specified, the length of peptide is 9 amino acids, and the end position for each peptide is the start position plus eight.

| Start | Subsequence | Score |
|---|---|---|
| 2 | TRLGWPSPC | 0.010 |
| 7 | PSPCCARKQ | 0.005 |
| 5 | GWPSPCCAR | 0.001 |

TABLE XX-V5

HLA-B3501-9mers-254P1D68
Each peptide is a portion of SEQ ID NO: 11; each start position is specified, the length of peptide is 9 amino acids, and the end position for each peptide is the start position plus eight.

| Start | Subsequence | Score |
|---|---|---|
| 3 | DIRKDLTFL | 4.500 |
| 7 | DLTFLGKDW | 0.500 |
| 9 | TFLGKDWGL | 0.100 |
| 2 | EDIRKDLTF | 0.100 |
| 8 | LTFLGKDWG | 0.010 |
| 4 | IRKDLTFLG | 0.006 |
| 6 | KDLTFLGKD | 0.002 |
| 5 | RKDLTFLGK | 0.001 |
| 1 | PEDIRKDLT | 0.000 |

TABLE XXI-V1

HLA-B3501-10mers-254P1D68
Each peptide is a portion of SEQ ID NO: 3; each start position is specified, the length of peptide is 10 amino acids, and the end position for each peptide is the start position plus nine.

| Start | Subsequence | Score |
|---|---|---|
| 226 | APKLPERSVL | 90.000 |
| 811 | DPRKSGLVEL | 60.000 |
| 361 | APPVETTYNY | 40.000 |
| 312 | APSESTPSEL | 40.000 |
| 1018 | RSTEHNSSLM | 40.000 |
| 359 | APAPPVETTY | 40.000 |
| 37 | SPNLETTRIM | 40.000 |
| 105 | RPVQRPAQLL | 40.000 |
| 893 | LSKEKSDFLL | 30.000 |
| 1050 | NPKVSMNGSI | 24.000 |

TABLE XXI-V1-continued

HLA-B3501-10mers-254P1D68
Each peptide is a portion of SEQ ID NO: 3; each start position is specified, the length of peptide is 10 amino acids, and the end position for each peptide is the start position plus nine.

| Start | Subsequence | Score |
|---|---|---|
| 141 | LPFLGKDWGL | 20.000 |
| 2 | APPTGVLSSL | 20.000 |
| 720 | RARAGGRHVL | 18.00 |
| 986 | RTKIRKKTKY | 12.000 |
| 1010 | RRKYGIKHRS | 12.000 |
| 992 | KTKYTIKDNM | 12.000 |
| 144 | LGKDWGLEEM | 12.000 |
| 665 | GPSAVEMENI | 12.000 |
| 328 | APRTVKELTV | 12.000 |
| 552 | QSSDDHQIVL | 10.000 |
| 648 | SSSDDHGIVF | 10.000 |
| 132 | DSPEDIRKDL | 10.000 |
| 178 | GSAEYTDWGL | 10.000 |
| 482 | TSVDSPVLRL | 10.000 |
| 949 | ESNCEWSIFY | 10.000 |
| 69 | LAWWFEGRCY | 9.000 |
| 740 | GSRSTDDQRI | 9.000 |
| 553 | SSDDHQIVLY | 6.000 |
| 649 | SSDDHGIVFY | 6.000 |
| 475 | GPFIEEKTSV | 6.000 |
| 89 | EPKKMGPIRS | 6.000 |
| 490 | RLSNLDPGNY | 6.000 |
| 722 | RAGGRHVLVL | 6.000 |
| 1058 | SIRNGASFSY | 6.000 |
| 107 | VQRPAQLLDY | 6.000 |
| 338 | SAGDNLIITL | 6.000 |
| 229 | LPERSVLLPL | 6.000 |
| 662 | HVRGPSAVEM | 6.000 |
| 485 | DSPVLRLSNL | 5.000 |
| 260 | SSNSSGKEVL | 5.000 |
| 31 | YSNAVISPNL | 5.000 |
| 1024 | SSLMVSESEF | 5.000 |
| 64 | LSSCDLAWWF | 5.000 |
| 917 | CSGHGHCDPL | 5.000 |
| 220 | ESASTPAPKL | 5.000 |
| 772 | HSVALQLTNL | 5.000 |

TABLE XXI-V1-continued

HLA-B3501-10mers-254P1D68
Each peptide is a portion of SEQ ID NO: 3; each start position is specified, the length of peptide is 10 amino acids, and the end position for each peptide is the start position plus nine.

| Start | Subsequence | Score |
|---|---|---|
| 273 | HSLPPASLEL | 5.000 |
| 438 | VSPQLQELTL | 5.000 |
| 567 | GPGSEGKHVV | 4.000 |
| 94 | GPIRSYLTFV | 4.000 |
| 238 | LPTTPSSGEV | 4.000 |
| 317 | TPSELPISPT | 4.000 |
| 874 | RPPFKVLKAA | 4.000 |
| 646 | GSSSSDDHGI | 3.000 |
| 628 | VAGPDKELIF | 3.000 |
| 510 | GATNSTTAAL | 3.000 |
| 209 | TQQDPELHYL | 3.000 |
| 905 | VLRVDTAGCL | 3.000 |
| 456 | GSQSTDDTEI | 3.000 |
| 692 | RLTVKDQQGL | 3.000 |
| 854 | VQKIRAHSDL | 3.000 |
| 36 | ISPNLETTRI | 3.000 |
| 588 | SAMQEGDYTF | 3.000 |
| 926 | LTKRCICSHL | 3.000 |
| 423 | TVKPARRVNL | 3.000 |
| 1041 | FSREKMERGN | 3.000 |
| 604 | SSRQQSTAVV | 3.000 |
| 532 | NAGPNHTITL | 3.000 |
| 384 | EIKQGHKQTL | 3.000 |
| 626 | VAVAGPDKEL | 3.000 |
| 858 | RAHSDLSTVI | 2.400 |
| 988 | KIRKKTKYTI | 2.400 |
| 892 | RLSKEKADFL | 2.000 |
| 208 | ETQQDPELHY | 2.000 |
| 495 | DPGNYSFRLT | 2.000 |
| 188 | LPGSEGAFNS | 2.000 |
| 278 | ASLELSSVTV | 2.000 |
| 270 | MPSHSLPPAS | 2.000 |
| 372 | WNLISHPTDY | 2.000 |
| 777 | QLTNLVEGVY | 2.000 |
| 581 | QTPYLHLSAM | 2.000 |

TABLE XXI-V1-continued

HLA-B3501-10mers-254P1D68
Each peptide is a portion of SEQ ID NO: 3; each start position is specified, the length of peptide is 10 amino acids, and the end position for each peptide is the start position plus nine.

| Start | Subsequence | Score |
|---|---|---|
| 828 | QLTEQRKDTL | 2.000 |
| 808 | VQPDPRKSGL | 2.000 |
| 275 | LPPASLELSS | 2.000 |
| 3 | PPTGVLSSLL | 2.000 |
| 924 | DPLTKRCICS | 2.000 |
| 680 | TVTGLQVGTY | 2.000 |
| 575 | VVMQGVQTPY | 2.000 |
| 492 | SNLDPGNYSF | 2.000 |
| 386 | KQGHKQTLNL | 2.000 |
| 52 | FPVVDCTAAC | 2.000 |
| 112 | QLLDYGDMML | 2.000 |
| 111 | AQLLDYGDMM | 2.000 |
| 433 | PPVAVVSPQL | 2.000 |
| 290 | SPVLTVTPGS | 2.000 |
| 527 | YPPVANAGPN | 2.000 |
| 586 | HLSAMQEGDY | 2.000 |
| 742 | RSTDDQRIVS | 2.000 |
| 224 | TPAPKLPERS | 2.000 |
| 8 | LSSLLLLVTI | 2.000 |

TABLE XXI

V2-HLA-B3501-10mers-254P1D68
Each peptide is a portion of SEQ ID NO: 5; each start position is specified, the length of peptide is 10 amino acids, and the end position for each peptide is the start position plus nine.

| Start | Subsequence | Score |
|---|---|---|
| 1 | WGLEEMSEYA | 0.200 |
| 4 | EEMSEYADDY | 0.200 |
| 7 | SEYADDYREL | 0.150 |
| 6 | MSEYADDYRE | 0.023 |
| 5 | EMSEYADDYR | 0.020 |
| 9 | YADDYRELEK | 0.018 |
| 2 | GLEEMSEYAD | 0.006 |
| 8 | EYADDYRELE | 0.002 |
| 10 | ADDYRELEKD | 0.000 |
| 3 | LEEMSEYADD | 0.000 |

TABLE XXI-V3

HLA-B3501-10mers-254P1D68
Each peptide is a portion of SEQ ID NO: 7; each start position is specified, the length of peptide is 10 amino acids, and the end position for each peptide is the start position plus nine.

| Start | Subsequence | Score |
|---|---|---|
| 8 | SPCCARKQCS | 2.000 |
| 1 | MTRLGWPSPC | 0.300 |
| 6 | WPSPCCARKQ | 0.200 |
| 3 | RLGWPSPCCA | 0.200 |
| 7 | PSPCCARKQC | 0.050 |
| 10 | CCARKQCSEG | 0.010 |
| 4 | LGWPSPCCAR | 0.010 |
| 2 | TRLGWPSPCC | 0.010 |
| 9 | PCCARKQCSE | 0.001 |
| 5 | GWPSPCCARK | 0.001 |

TABLE XXI-V5

HLA-B3501-10mers-254P1D68
Each peptide is a portion of SEQ ID NO: 11; each start position is specified, the length of peptide is 10 amino acids, and the end position for each peptide is the start position plus nine.

| Start | Subsequence | Score |
|---|---|---|
| 1 | SPEDIRKDLT | 1.200 |
| 9 | LTFLGKDWGL | 1.000 |
| 3 | EDIRKDLTFL | 0.150 |
| 7 | KDLTFLGKDW | 0.100 |
| 4 | DIRKDLTFLG | 0.030 |
| 8 | DLTFLGKDWG | 0.010 |
| 5 | IRKDLTFLGK | 0.006 |
| 2 | PEDIRKDLTF | 0.003 |
| 10 | TFLGKDWGLE | 0.002 |
| 6 | RKDLTFLGKD | 0.001 |

TABLE XXII-V1

HLA-A1-1-9mers-254P1D6B
Each peptide is a portion of SEQ ID NO: 3; each start position is specified, the length of peptide is 9 amino acids, and the end position for each peptide is the start position plus eight.

| Pos | 123456789 | score |
|---|---|---|
| 554 | SDDHQIVLY | 31 |
| 650 | SDDHGIVFY | 29 |

TABLE XXII-V1-continued

HLA-A1-1-9mers-254P1D6B
Each peptide is a portion of SEQ ID NO: 3; each start position is specified, the length of peptide is 9 amino acids, and the end position for each peptide is the start position plus eight.

| Pos | 123456789 | score |
|---|---|---|
| 182 | YTDWGLLPG | 26 |
| 743 | STDDQRIVS | 26 |
| 460 | TDDTEIVSY | 25 |
| 681 | VTGLQVGTY | 25 |
| 744 | TDDQRIVSY | 25 |
| 936 | WMENLIQRY | 25 |
| 778 | LTNLVEGVY | 24 |
| 108 | QRPAQLLDY | 23 |
| 459 | STDDTEIVS | 23 |
| 209 | TQQDPELHY | 22 |
| 395 | LSQLSVGLY | 22 |
| 649 | SSDDHGIVF | 22 |
| 360 | PAPPVETTY | 21 |
| 553 | SSDDHQIVL | 21 |
| 587 | LSAMQEGDY | 21 |
| 950 | SNCEWSIFY | 21 |
| 138 | RKDLPFLGK | 20 |
| 156 | YSDDYRELE | 20 |
| 483 | SVDSPVLRL | 20 |
| 695 | VKDQQGLSS | 20 |
| 792 | VTDSQGASD | 20 |
| 1019 | STEHNSSLM | 20 |
| 229 | LPERSVLLP | 19 |
| 378 | PTDYQGEIK | 19 |
| 410 | SSENAFGEG | 19 |
| 491 | LSNLDPGNY | 19 |
| 576 | VMQGVQTPY | 19 |
| 157 | SDDYRELEK | 18 |
| 190 | GSEGAFNSS | 18 |
| 299 | STEHSIPTP | 18 |
| 462 | DTEIVSYHW | 18 |
| 493 | NLDPGNYSF | 18 |
| 505 | VTDSDGATN | 18 |
| 601 | VTDSSRQQS | 18 |
| 862 | DLSTVIVFY | 18 |
| 1005 | ERMELRPKY | 18 |

TABLE XXII-V1-continued

HLA-A1-1-9mers-254P1D6B
Each peptide is a portion of SEQ ID NO: 3; each start position is specified, the length of peptide is 9 amino acids, and the end position for each peptide is the start position plus eight.

| Pos | 123456789 | score |
|---|---|---|
| 1028 | VSESEFDSD | 18 |
| 1034 | DSDQDTIFS | 18 |
| 39 | NLETTRIMR | 17 |
| 70 | AWWFEGRCY | 17 |
| 91 | KKMGPIRSY | 17 |
| 162 | ELEKDLLQP | 17 |
| 174 | QEPRGSAEY | 17 |
| 769 | GSDHSVALQ | 17 |
| 849 | DSDIKVQKI | 17 |
| 987 | TKIRKKTKY | 17 |
| 23 | KQCSEGRTY | 16 |
| 152 | EMSEYSDDY | 16 |
| 212 | DPELHYLNE | 16 |
| 373 | NLISHPTDY | 16 |
| 569 | GSEGKHVVM | 16 |
| 638 | PVESATLDG | 16 |
| 668 | AVEMENIDK | 16 |
| 800 | DTDTATVEV | 16 |
| 829 | LTEQRKDTL | 16 |
| 1003 | EQERMELRP | 16 |
| 1059 | IRNGASFSY | 16 |
| 25 | CSEGRTYSN | 15 |
| 148 | WGLEEMSEY | 15 |
| 173 | KQEPRGSAE | 15 |
| 223 | STPAPKLPE | 15 |
| 318 | PSELPISPT | 15 |
| 339 | AGDNLIITL | 15 |
| 362 | PPVETTYNY | 15 |
| 507 | DSDGATNST | 15 |
| 519 | LIVNNAVDY | 15 |
| 592 | EGDYTFQLK | 15 |
| 798 | ASDTDTATV | 15 |
| 909 | DTAGCLLKC | 15 |
| 1045 | KMERGNPKV | 15 |

TABLE XXII-V2

HLA-A1-1-9mers-254P1D6B
Each peptide is a portion of SEQ ID NO: 5; each start position is specified, the length of peptide is 9 amino acids, and the end position for each peptide is the start position plus eight.

| Pos | 123456789 | score |
|---|---|---|
| 9 | ADDYRELEK | 17 |
| 4 | EMSEYADDY | 16 |
| 8 | YADDYRELE | 16 |
| 5 | MSEYADDYR | 14 |
| 1 | GLEEMSEYA | 11 |
| 2 | LEEMSEYAD | 10 |

TABLE XXII-V3

HLA-A1-1-9mers-254P1D6B
Each peptide is a portion of SEQ ID NO: 7; each start position is specified, the length of peptide is 9 amino acids, and the end position for each peptide is the start position plus eight.

| Pos | 123456789 | score |
|---|---|---|
| 1 | MTRLGWPSP | 8 |
| 7 | PSPCCARKQ | 6 |
| 4 | LGWPSPCCA | 4 |
| 6 | WPSPCCARK | 4 |
| 8 | SPCCARKQC | 3 |

TABALE XXII-V5

HLA-A1-9mers-254P1D6B
Each peptide is a portion of SEQ ID NO: 11; each start position is specified, the length of peptide is 9 amino acids, and the end position for each peptide is the start position plus eight.

| Pos | 123456789 | score |
|---|---|---|
| 5 | RKDLTFLGK | 19 |
| 1 | PEDIRKDLT | 12 |

TABLE XXIII-V1

HLA-A0201-9mers-254P1D6B
Each peptide is a portion of SEQ ID NO: 3; each start position is specified, the length of peptide is 9 amino acids, and the end position for each peptide is the start position plus eight.

| Pos | 123456789 | score |
|---|---|---|
| 840 | QLAVLLNVL | 28 |
| 900 | FLLFKVLRV | 28 |
| 7 | VLSSLLLLV | 27 |

TABLE XXIII-V1-continued

HLA-A0201-9mers-254P1D6B
Each peptide is a portion of SEQ ID NO: 3; each start position is specified, the length of peptide is 9 amino acids, and the end position for each peptide is the start position plus eight.

| Pos | 123456789 | score |
|---|---|---|
| 274 | SLPPASLEL | 27 |
| 401 | GLYVFKVTV | 27 |
| 816 | GLVELTLQV | 27 |
| 441 | QLQELTLPL | 26 |
| 673 | NIDKAIATV | 26 |
| 821 | TLQVGVGQL | 26 |
| 836 | TLVRQLAVL | 26 |
| 961 | VLAFTLIVL | 26 |
| 228 | KLPERSVLL | 25 |
| 279 | SLELSSVTV | 25 |
| 346 | TLPDNEVEL | 25 |
| 777 | QLTNLVEGV | 25 |
| 99 | YLTFVLRPV | 24 |
| 392 | TLNLSQLSV | 24 |
| 394 | NLSQLSVGL | 24 |
| 445 | LTLPLTSAL | 24 |
| 766 | VIDGSDHSV | 24 |
| 968 | VLTGGFTWL | 24 |
| 10 | SLLLLVTIA | 23 |
| 113 | LLDYGDMML | 23 |
| 344 | IITLPDNEV | 23 |
| 399 | SVGLYVFKV | 23 |
| 437 | VVSPQLQEL | 23 |
| 452 | ALIDGSQST | 23 |
| 728 | VLVLPNNSI | 23 |
| 730 | VLPNNSITL | 23 |
| 1045 | KMERGNPKV | 23 |
| 6 | GVLSSLLLL | 22 |
| 136 | DIRKDLPFL | 22 |
| 186 | GLLPGSEGA | 22 |
| 430 | VNLPPVAVV | 22 |
| 483 | SVDSPVLRL | 22 |
| 511 | ATNSTTAAL | 22 |
| 540 | TLPQNSITL | 22 |
| 609 | STAVVTVIV | 22 |

TABLE XXIII-V1-continued

HLA-A0201-9mers-254P1D6B
Each peptide is a portion of SEQ ID NO: 3; each start position is specified, the length of peptide is 9 amino acids, and the end position for each peptide is the start position plus eight.

| Pos | 123456789 | score |
|---|---|---|
| 627 | AVAGPDKEL | 22 |
| 676 | KAIATVTGL | 22 |
| 703 | STSTLTVAV | 22 |
| 773 | SVALQLTNL | 22 |
| 844 | LLNVLDSDI | 22 |
| 9 | SSLLLLVTI | 21 |
| 12 | LLLVTIAGC | 21 |
| 35 | VISPNLETT | 21 |
| 92 | KMGPIRSYL | 21 |
| 558 | QIVLYEWSL | 21 |
| 774 | VALQLTNLV | 21 |
| 780 | NLVEGVYTF | 21 |
| 897 | KADFLLFKV | 21 |
| 95 | PIRSYLTFV | 20 |
| 221 | SASTPAPKL | 20 |
| 233 | SVLLPLPTT | 20 |
| 446 | TLPLTSALI | 20 |
| 517 | AALIVNNAV | 20 |
| 687 | GTYHFRLTV | 20 |
| 858 | RAHSDLSTV | 20 |
| 960 | TVLAFTLIV | 20 |
| 285 | VTVEKSPVL | 19 |
| 327 | TAPRTVKEL | 19 |
| 339 | AGDNLIITL | 19 |
| 429 | RVNLPPVAV | 19 |
| 538 | TITLPQNSI | 19 |
| 634 | ELIFPVESA | 19 |
| 721 | ARAGGRHVL | 19 |
| 800 | DTDTATVEV | 19 |
| 837 | LVRQLAVLL | 19 |
| 843 | VLLNVLDSD | 19 |
| 846 | NVLDSDIKV | 19 |
| 881 | KAAEVARNL | 19 |
| 112 | QLLDYGDMM | 18 |
| 234 | VLLPLPTTP | 18 |
| 287 | VEKSPVLTV | 18 |

TABLE XXIII-V1-continued

HLA-A0201-9mers-254P1D6B
Each peptide is a portion of SEQ ID NO: 3; each
start position is specified, the length of
peptide is 9 amino acids, and the end position
for each peptide is the start position plus
eight.

| Pos | 123456789 | score |
|---|---|---|
| 414 | AFGEGFVNV | 18 |
| 531 | ANAGPNHTI | 18 |
| 607 | QQSTAVVTV | 18 |
| 635 | LIFPVESAT | 18 |
| 722 | RAGGRHVLV | 18 |
| 784 | GVYTFHLRV | 18 |
| 798 | ASDTDTATV | 18 |
| 955 | SIFYVTVLA | 18 |
| 958 | YVTVLAFTL | 18 |
| 962 | LAFTLIVLT | 18 |
| 11 | LLLLVTIAG | 17 |
| 103 | VLRPVQRPA | 17 |
| 210 | QQDPELHYL | 17 |
| 217 | YLNESASTP | 17 |
| 267 | EVLMPSHSL | 17 |
| 272 | SHSLPPASL | 17 |
| 277 | PASLELSSV | 17 |
| 303 | SIPTPPTSA | 17 |
| 342 | NLIITLPDN | 17 |
| 353 | ELKAFVAPA | 17 |
| 359 | APAPPVETT | 17 |
| 397 | QLSVGLYVF | 17 |
| 427 | ARRVNLPPV | 17 |
| 444 | ELTLPLTSA | 17 |
| 493 | NLDPGNYSF | 17 |
| 565 | SLGPGSEGK | 17 |
| 579 | GVQTPYLHL | 17 |
| 589 | AMQEGDYTF | 17 |
| 693 | LTVKDQQGL | 17 |
| 701 | LSSTSTLTV | 17 |
| 723 | AGGRHVLVL | 17 |
| 736 | ITLDGSRST | 17 |
| 818 | VELTLQVGV | 17 |
| 829 | LTEQRKDTL | 17 |
| 835 | DTLVRQLAV | 17 |

TABLE XXIII-V1-continued

HLA-A0201-9mers-254P1D6B
Each peptide is a portion of SEQ ID NO: 3; each
start position is specified, the length of
peptide is 9 amino acids, and the end position
for each peptide is the start position plus
eight.

| Pos | 123456789 | score |
|---|---|---|
| 839 | RQLAVLLNV | 17 |
| 901 | LLFKVLRVD | 17 |
| 1054 | SMNGSIRNG | 17 |
| 13 | LLVTIAGCA | 16 |
| 34 | AVISPNLET | 16 |
| 120 | MLNRGSPSG | 16 |
| 197 | SSVGDSPAV | 16 |
| 292 | VLTVTPGST | 16 |
| 331 | TVKELTVSA | 16 |
| 335 | LTVSAGDNL | 16 |
| 366 | TTYNYEWNL | 16 |
| 385 | IKQGHKQTL | 16 |
| 422 | VTVKPARRV | 16 |
| 481 | KTSVDSPVL | 16 |
| 486 | SPVLRLSNL | 16 |
| 497 | GNYSFRLTV | 16 |
| 518 | ALIVNNAVD | 16 |
| 533 | AGPNHTITL | 16 |
| 560 | VLYEWSLGP | 16 |
| 593 | GDYTFQLKV | 16 |
| 605 | SRQQSTAVV | 16 |
| 636 | IFPVESATL | 16 |
| 655 | IVFYHWEHV | 16 |
| 678 | IATVTGLQV | 16 |
| 683 | GLQVGTYHF | 16 |
| 699 | QGLSSTSTL | 16 |
| 720 | RARAGGRHV | 16 |
| 812 | PRKSGLVEL | 16 |
| 877 | FKVLKAAEV | 16 |
| 885 | VARNLHMRL | 16 |
| 888 | NLHMRLSKE | 16 |
| 905 | VLRVDTAGC | 16 |
| 954 | WSIFYVTVL | 16 |
| 965 | TLIVLTGGF | 16 |
| 32 | SNAVISPNL | 15 |
| 40 | LETTRIMRV | 15 |

TABLE XXIII-V1-continued

HLA-A0201-9mers-254P1D6B
Each peptide is a portion of SEQ ID NO: 3; each
start position is specified, the length of
peptide is 9 amino acids, and the end position
for each peptide is the start position plus
eight.

| Pos | 123456789 | score |
|---|---|---|
| 47 | RVSHTFPVV | 15 |
| 50 | HTFPVVDCT | 15 |
| 71 | WWFEGRCYL | 15 |
| 78 | YLVSCPHKE | 15 |
| 128 | GIWGDSPED | 15 |
| 179 | SAEYTDWGL | 15 |
| 187 | LLPGSEGAF | 15 |
| 191 | SEGAFNSSV | 15 |
| 235 | LLPLPTTPS | 15 |
| 284 | SVTVEKSPV | 15 |
| 336 | TVSAGDNLI | 15 |
| 338 | SAGDNLIIT | 15 |
| 350 | NEVELKAFV | 15 |
| 396 | SQLSVGLYV | 15 |
| 439 | SPQLQELTL | 15 |
| 465 | IVSYHWEEI | 15 |
| 516 | TAALIVNNA | 15 |
| 525 | VDYPPVANA | 15 |
| 547 | TLNGNQSSD | 15 |
| 628 | VAGPDKELI | 15 |
| 685 | QVGTYHFRL | 15 |
| 700 | GLSSTSTLT | 15 |
| 754 | WIRDGQSPA | 15 |
| 833 | RKDTLVRQL | 15 |
| 862 | DLSTVIVFY | 15 |
| 863 | LSTVIVFYV | 15 |
| 866 | VIVFYVQSR | 15 |
| 940 | LIQRYIWDG | 15 |
| 988 | KIRKKTKYT | 15 |
| 1025 | SLMVSESEF | 15 |
| 3 | PPTGVLSSL | 14 |
| 16 | TIAGCARKQ | 14 |
| 96 | IRSYLTFVL | 14 |
| 166 | DLLQPSGKQ | 14 |
| 207 | AETQQDPEL | 14 |

TABLE XXIII-V1-continued

HLA-A0201-9mers-254P1D6B
Each peptide is a portion of SEQ ID NO: 3; each
start position is specified, the length of
peptide is 9 amino acids, and the end position
for each peptide is the start position plus
eight.

| Pos | 123456789 | score |
|---|---|---|
| 226 | APKLPERSV | 14 |
| 239 | PTTPSSGEV | 14 |
| 240 | TTPSSGEVL | 14 |
| 247 | VLEKEKASQ | 14 |
| 248 | LEKEKASQL | 14 |
| 260 | SSNSSGKEV | 14 |
| 261 | SNSSGKEVL | 14 |
| 268 | VLMPSHSLP | 14 |
| 326 | TTAPRTVKE | 14 |
| 337 | VSAGDNLII | 14 |
| 356 | AFVAPAPPV | 14 |
| 358 | VAPAPPVET | 14 |
| 390 | KQTLNLSQL | 14 |
| 416 | GEGFVNVTV | 14 |
| 431 | NLPPVAVVS | 14 |
| 434 | PVAVVSPQL | 14 |
| 453 | LIDGSQSTD | 14 |
| 539 | ITLPQNSIT | 14 |
| 575 | VVMQGVQTP | 14 |
| 591 | QEGDYTFQL | 14 |
| 643 | TLDGSSSSD | 14 |
| 669 | VEMENIDKA | 14 |
| 677 | AIATVTGLQ | 14 |
| 706 | TLTVAVKKE | 14 |
| 729 | LVLPNNSIT | 14 |
| 737 | TLDGSRSTD | 14 |
| 782 | VEGVYTFHL | 14 |
| 814 | KSGLVELTL | 14 |
| 828 | QLTEQRKDT | 14 |
| 847 | VLDSDIKVQ | 14 |
| 849 | DSDIKVQKI | 14 |
| 860 | HSDLSTVIV | 14 |
| 871 | VQSRPPFKV | 14 |
| 890 | HMRLSKEKA | 14 |
| 893 | LSKEKADFL | 14 |
| 907 | RVDTAGCLL | 14 |

TABLE XXIII-V1-continued

HLA-A0201-9mers-254P1D6B
Each peptide is a portion of SEQ ID NO: 3; each start position is specified, the length of peptide is 9 amino acids, and the end position for each peptide is the start position plus eight.

| Pos | 123456789 | score |
|---|---|---|
| 909 | DTAGCLLKC | 14 |
| 918 | SGHGHCDPL | 14 |
| 944 | YIWDGESNC | 14 |
| 966 | LIVLTGGFT | 14 |
| 37 | SPNLETTRI | 13 |
| 121 | LNRGSPSGI | 13 |
| 142 | PFLGKDWGL | 13 |
| 145 | GKDWGLEEM | 13 |
| 167 | LLQPSGKQE | 13 |
| 180 | AEYTDWGLL | 13 |
| 182 | YTDWGLLPG | 13 |
| 214 | ELHYLNESA | 13 |
| 281 | ELSSVTVEK | 13 |
| 319 | SELPISPTT | 13 |
| 320 | ELPISPTTA | 13 |
| 324 | SPTTAPRTV | 13 |
| 343 | LIITLPDNE | 13 |
| 374 | LISHPTDYQ | 13 |
| 387 | QGHKQTLNL | 13 |
| 403 | YVFKVTVSS | 13 |
| 419 | FVNVTVKPA | 13 |
| 424 | VKPARRVNL | 13 |
| 476 | PFIEEKTSV | 13 |
| 477 | FIEEKTSVD | 13 |
| 490 | RLSNLDPGN | 13 |
| 515 | TTAALIVNN | 13 |
| 522 | NNAVDYPPV | 13 |
| 530 | VANAGPNHT | 13 |
| 553 | SSDDHQIVL | 13 |
| 577 | MQGVQTPYL | 13 |
| 604 | SSRQQSTAV | 13 |
| 621 | NNRPPVAVA | 13 |
| 631 | PDKELIFPV | 13 |
| 642 | ATLDGSSSS | 13 |
| 648 | SSSDDHGIV | 13 |

TABLE XXIII-V1-continued

HLA-A0201-9mers-254P1D6B
Each peptide is a portion of SEQ ID NO: 3; each start position is specified, the length of peptide is 9 amino acids, and the end position for each peptide is the start position plus eight.

| Pos | 123456789 | score |
|---|---|---|
| 680 | TVTGLQVGT | 13 |
| 696 | KDQQGLSST | 13 |
| 745 | DDQRIVSYL | 13 |
| 748 | RIVSYLWIR | 13 |
| 752 | YLWIRDGQS | 13 |
| 758 | GQSPAAGDV | 13 |
| 768 | DGSDHSVAL | 13 |
| 770 | SDHSVALQL | 13 |
| 775 | ALQLTNLVE | 13 |
| 809 | QPDPRKSGL | 13 |
| 842 | AVLLNVLDS | 13 |
| 879 | VLKAAEVAR | 13 |
| 898 | ADFLLFKVL | 13 |
| 906 | LRVDTAGCL | 13 |
| 914 | LLKCSGHGH | 13 |
| 933 | SHLWMENLI | 13 |
| 951 | NCEWSIFYV | 13 |
| 959 | VTVLAFTLI | 13 |
| 996 | TILDNMDEQ | 13 |
| 1007 | MELRPKYGI | 13 |
| 1018 | RSTEHNSSL | 13 |

TABLE XXIII-V2

HLA-A0201-9mers-254P1D6B
Each peptide is a portion of SEQ ID NO: 5; each start position is specified, the length of peptide is 9 amino acids, and the end position for each peptide is the start position plus eight.

| Pos | 123456789 | score |
|---|---|---|
| 1 | GLEEMSEYA | 16 |
| 7 | EYADDYREL | 12 |
| 4 | EMSEYADDY | 8 |
| 8 | YADDYRELE | 8 |

TABLE XXIII-V3

HLA-A0201-9 mers-254P1D6B
Each peptide is a portion of SEQ ID NO: 7; each start position is specified, the length of peptide is 9 amino acids, and the end position for each peptide is the start position plus eight.

| Pos | 123456789 | score |
|---|---|---|
| 3 | RLGWPSPCC | 12 |
| 1 | MTRLGWPSP | 9 |
| 4 | LGWPSPCCA | 9 |
| 10 | CCARKQCSE | 5 |

TABLE XXIII

254P1D6B v5 HLA-0201-p-mers
Each peptide is a portion of SEQ ID NO: 11; each start position is specified, the length of peptide is 9 amino acids, and the end position for each peptide is the start position plus eight.

| Pos | 123456789 | score |
|---|---|---|
| 3 | DIRKDLTFL | 21 |
| 9 | TFLGKDWGL | 16 |
| 6 | KDLTFLGKD | 10 |

TABLE XXIV-V1

HLA-A0203-9 mers-254P1D6B

NoResultsFound.

TABLE XXIV-V2

HLA-A0203-9 mers-254P1D6B

NoResultsFound.

TABLE XXIV-V3

HLA-A0203-9 mers-254P1D6B

NoResultsFound.

TABLE XXIV-V5

HLA-A0203-9 mers-254P1D6B

NoResultsFound.

TABLE XXV-V1

HLA-A0203-9 mers-254P1D6B

NoResultsFound.

TABLE XXV-V2

HLA-A0203-9 mers-254P1D6B

NoResultsFound.

TABLE XXV-V3

HLA-A3-9 mers-254P1D6B
Each peptide is a portion of SEQ ID NO: 7; each start position is specified, the length of peptide is 9 amino acids, and the end position for each peptide is the start position plus eight.

| Pos | 123456789 | score |
|---|---|---|
| 6 | WPSPCCARK | 16 |
| 3 | RLGWPSPCC | 14 |
| 1 | MTRLGWPSP | 8 |
| 2 | TRLGWPSPC | 8 |
| 10 | CCARKQCSE | 7 |

TABLE XXV-V5

HLA-A3-9 mers-254P1D6B
Each peptide is a portion of SEQ ID NO: 11; each start position is specified, the length of peptide is 9 amino acids, and the end position for each peptide is the start position plus eight.

| Pos | 1 2 3 4 5 6 7 8 9 | score |
|---|---|---|
| 2 | EDIRKDLTF | 18 |
| 5 | RKDLTFLGK | 18 |
| 7 | DLTFLGKDW | 13 |
| 3 | DIRKDLTFL | 12 |

TABLE XXVI-V1

HLA-A26-9 mers-254P1D6B
Each peptide is a portion of SEQ ID NO: 3; each start position is specified, the length of peptide is 9 amino acids, and the end position for each peptide is the start position plus eight.

| Pos | 123456789 | score |
|---|---|---|
| 267 | EVLMPSHSL | 29 |
| 884 | EVARNLHMR | 26 |
| 483 | SVDSPVLRL | 25 |
| 6 | GVLSSLLLL | 24 |
| 135 | EDIRKDLPF | 24 |
| 136 | DIRKDLPFL | 24 |
| 246 | EVLEKEKAS | 24 |
| 681 | VTGLQVGTY | 24 |
| 1005 | ERMELRPKY | 24 |

TABLE XXVI-V1-continued

HLA-A26-9 mers-254P1D6B
Each peptide is a portion of SEQ ID NO: 3; each start position is specified, the length of peptide is 9 amino acids, and the end position for each peptide is the start position plus eight.

| Pos | 123456789 | score |
|---|---|---|
| 285 | VTVEKSPVL | 23 |
| 437 | VVSPQLQEL | 23 |
| 745 | DDQRIVSYL | 23 |
| 765 | DVIDGSDHS | 23 |
| 773 | SVALQLTNL | 23 |
| 152 | EMSEYSDDY | 22 |
| 335 | LTVSAGDNL | 22 |
| 407 | VTVSSENAF | 22 |
| 807 | EVQPDPRKS | 22 |
| 862 | DLSTVIVFY | 22 |
| 909 | DTAGCLLKC | 22 |
| 41 | ETTRIMRVS | 21 |
| 349 | DNEVELKAF | 21 |
| 351 | EVELKAFVA | 21 |
| 958 | YVTVLAFTL | 21 |
| 1038 | DTIFSREKM | 21 |
| 365 | ETTYNYEWN | 20 |
| 445 | LTLPLTSAL | 20 |
| 693 | LTVKDQQGL | 20 |
| 155 | EYSDDYREL | 19 |
| 159 | DYRELEKDL | 19 |
| 240 | TTPSSGEVL | 19 |
| 417 | EGFVNVTVK | 19 |
| 434 | PVAVVSPQL | 19 |
| 464 | EIVSYHWEE | 19 |
| 519 | LIVNNAVDY | 19 |
| 579 | GVQTPYLHL | 19 |
| 611 | AVVTVIVQP | 19 |
| 634 | ELIFPVESA | 19 |
| 778 | LTNLVEGVY | 19 |
| 780 | NLVEGVYTF | 19 |
| 837 | LVRQLAVLL | 19 |
| 907 | RVDTAGCLL | 19 |
| 949 | ESNCEWSIF | 19 |
| 4 | PTGVLSSLL | 18 |
| 106 | PVQRPAQLL | 18 |

TABLE XXVI-V1-continued

HLA-A26-9 mers-254P1D6B
Each peptide is a portion of SEQ ID NO: 3; each start position is specified, the length of peptide is 9 amino acids, and the end position for each peptide is the start position plus eight.

| Pos | 123456789 | score |
|---|---|---|
| 208 | ETQQDPELH | 18 |
| 461 | DDTEIVSYH | 18 |
| 486 | SPVLRLSNL | 18 |
| 511 | ATNSTTAAL | 18 |
| 627 | AVAGPDKEL | 18 |
| 672 | ENIDKAIAT | 18 |
| 685 | QVGTYHFRL | 18 |
| 768 | DGSDHSVAL | 18 |
| 835 | DTLVRQLAV | 18 |
| 50 | HTFPVVDCT | 17 |
| 56 | DCTAACCDL | 17 |
| 366 | TTYNYEWNL | 17 |
| 436 | AVVSPQLQE | 17 |
| 558 | QIVLYEWSL | 17 |
| 612 | VVTVIVQPE | 17 |
| 802 | DTATVEVQP | 17 |
| 829 | LTEQRKDTL | 17 |
| 836 | TLVRQLAVL | 17 |
| 987 | TKIRKKTKY | 17 |
| 34 | AVISPNLET | 16 |
| 53 | PVVDCTAAC | 16 |
| 162 | ELEKDLLQP | 16 |
| 233 | SVLLPLPTT | 16 |
| 330 | RTVKELTVS | 16 |
| 362 | PPVETTYNY | 16 |
| 390 | KQTLNLSQL | 16 |
| 399 | SVGLYVFKV | 16 |
| 444 | ELTLPLTSA | 16 |
| 460 | TDDTEIVSY | 16 |
| 462 | DTEIVSYHW | 16 |
| 481 | KTSVDSPVL | 16 |
| 495 | DPGNYSFRL | 16 |
| 574 | HVVMQGVQT | 16 |
| 661 | EHVRGPSAV | 16 |
| 676 | KAIATVTGL | 16 |

TABLE XXVI-V1-continued

HLA-A26-9 mers-254P1D6B
Each peptide is a portion of SEQ ID NO: 3; each start position is specified, the length of peptide is 9 amino acids, and the end position for each peptide is the start position plus eight.

| Pos | 123456789 | score |
|---|---|---|
| 679 | ATVTGLQVG | 16 |
| 744 | TDDQRIVSY | 16 |
| 800 | DTDTATVEV | 16 |
| 819 | ELTLQVGVG | 16 |
| 842 | AVLLNVLDS | 16 |
| 865 | TVIVFYVQS | 16 |
| 896 | EKADFLLFK | 16 |
| 954 | WSIFYVTVL | 16 |
| 3 | PPTGVLSSL | 15 |
| 74 | EGRCYLVSC | 15 |
| 91 | KKMGPIRSY | 15 |
| 108 | QRPAQLLDY | 15 |
| 132 | DSPEDIRKD | 15 |
| 231 | ERSVLLPLP | 15 |
| 251 | EKASQLQEQ | 15 |
| 288 | EKSPVLTVT | 15 |
| 293 | LTVTPGSTE | 15 |
| 331 | TVKELTVSA | 15 |
| 339 | AGDNLIITL | 15 |
| 373 | NLISHPTDY | 15 |
| 384 | EIKQGHKQT | 15 |
| 395 | LSQLSVGLY | is |
| 403 | YVFKVTVSS | 15 |
| 472 | EINGPFIEE | 15 |
| 479 | EEKTSVDSP | 15 |
| 504 | TVTDSDGAT | 15 |
| 514 | STTAALIVN | 15 |
| 554 | SDDHQIVLY | 15 |
| 555 | DDHQIVLYE | 15 |
| 571 | EGKHVVMQG | 15 |
| 575 | VVMGVQTP | 15 |
| 614 | TVIVQPENN | 15 |
| 650 | SDDHGIVFY | 15 |
| 821 | TLQVGVGQL | 15 |
| 861 | SDLSTVIVF | 15 |
| 867 | IVFYVQSRP | 15 |

TABLE XXVI-V1-continued

HLA-A26-9 mers-254P1D6B
Each peptide is a portion of SEQ ID NO: 3; each start position is specified, the length of peptide is 9 amino acids, and the end position for each peptide is the start position plus eight.

| Pos | 123456789 | score |
|---|---|---|
| 936 | WMENLIQRY | 15 |
| 965 | TLIVLTGGF | 15 |
| 1021 | EHNSSLMVS | 15 |
| 1057 | GSIRNGASF | 15 |
| 5 | TGVLSSLLL | 14 |
| 71 | WWFEGRCYL | 14 |
| 94 | GPIRSYLTF | 14 |
| 102 | FVLRPVQRP | 14 |
| 181 | EYTDWGLLP | 14 |
| 230 | PERSVLLPL | 14 |
| 299 | STEHSIPTP | 14 |
| 316 | SPTSELPIS | 14 |
| 353 | ELKAFVAPA | 14 |
| 419 | FVNVTVKPA | 14 |
| 471 | EEINGPFIE | 14 |
| 515 | TTAALIVNN | 14 |
| 520 | IVNNAVDYP | 14 |
| 595 | YTFQLKVTD | 14 |
| 651 | DDHGIVFYH | 14 |
| 655 | IVFYHWEHV | 14 |
| 783 | EGVYTFHLR | 14 |
| 786 | YTFHLRVTD | 14 |
| 791 | RVTDSQGAS | 14 |
| 804 | ATVEVQPDP | 14 |
| 817 | LVELTLQVG | 14 |
| 833 | RDKTLVRQL | 14 |
| 849 | DSDIKVQKI | 14 |
| 906 | LRVDTAGCL | 14 |
| 950 | SNCEWSIFY | 14 |
| 956 | IFYVTVLAF | 14 |

TABLE XXVI-V2

A26-9 mers-254P1D6B
Each peptide is a portion of SEQ ID NO: 5; each start position is specified, the length of peptide is 9 amino acids, and the end position for each peptide is the start position plus eight.

| Pos | 123456789 | score |
|---|---|---|
| 4 | EMSEYADDY | 22 |
| 7 | EYADDYREL | 19 |
| 3 | EEMSEYADD | 11 |

TABLE XXVI-V3

A26-9 mers-254P1D6B
Each peptide is a portion of SEQ ID NO: 7; each start position is specified, the length of peptide is 9 amino acids, and the end position for each peptide is the start position plus eight.

| Pos | 123456789 | score |
|---|---|---|
| 1 | MTRLGWPSP | 9 |

TABLE XXVI-V5

A26-9 mers-254P1D6B
Each peptide is a portion of SEQ ID NO: 11; each start position is specified, the length of peptide is 9 amino acids, and the end position for each peptide is the start position plus eight.

| Pos | 1 2 3 4 5 6 7 8 9 | score |
|---|---|---|
| 2 | EDIRKDLTF | 25 |
| 3 | DIRKDLTFL | 24 |
| 8 | LTFLGKDWG | 12 |

TABLE XXVII-V1

HLA-B0702-9 mers-254P1D6B
Each peptide is a portion of SEQ ID NO: 3; each start position is specified, the length of peptide is 9 amino acids, and the end position for each peptide is the start position plus eight.

| Pos | 123456789 | score |
|---|---|---|
| 359 | APAPPVETT | 24 |
| 304 | IPTPPTSAA | 23 |
| 3 | PPTGVLSSL | 22 |
| 105 | RPVQRPAQL | 22 |
| 439 | SPQLQELTL | 22 |
| 809 | QPDPRKSGL | 22 |
| 133 | SPEDIRKDL | 21 |
| 175 | EPRGSAEYT | 21 |
| 226 | APKLPERSV | 21 |

TABLE XXVII-V1-continued

HLA-B0702-9 mers-254P1D6B
Each peptide is a portion of SEQ ID NO: 3; each start position is specified, the length of peptide is 9 amino acids, and the end position for each peptide is the start position plus eight.

| Pos | 123456789 | score |
|---|---|---|
| 495 | DPGNYSFRL | 21 |
| 270 | MPSHSLPPA | 20 |
| 328 | APRTVKELT | 20 |
| 486 | SPVLRLSNL | 20 |
| 874 | RPPFKVLKA | 20 |
| 618 | QPENNRPPV | 19 |
| 37 | SPNLETTRI | 18 |
| 52 | FPVVDCTAA | 18 |
| 94 | GPIRSYLTF | 18 |
| 567 | GPGSEGKHV | 18 |
| 627 | AVAGPDKEL | 18 |
| 872 | QSRPPFKVL | 18 |
| 875 | PPFKVLKAA | 18 |
| 296 | TPGSTEHSI | 17 |
| 483 | SVDSPVLRL | 17 |
| 582 | TPYLHLSAM | 17 |
| 721 | ARAGGRHVL | 17 |
| 723 | AGGRHVLVL | 17 |
| 811 | DPRKSGLVE | 17 |
| 221 | SASTPAPKL | 16 |
| 272 | SHSLPPASL | 16 |
| 312 | APSESTPSE | 16 |
| 321 | LPISPTTAP | 16 |
| 324 | SPTTAPRTV | 16 |
| 377 | HPTDYQGEI | 16 |
| 2 | APPTGVLSS | 15 |
| 96 | IRSYLTFVL | 15 |
| 136 | DIRKDLPFL | 15 |
| 169 | QPSGKQEPR | 15 |
| 230 | PERSVLLPL | 15 |
| 301 | EHSIPTPPT | 15 |
| 481 | KTSVDSPVL | 15 |
| 511 | ATNSTTAAL | 15 |
| 579 | GVQTPYLHL | 15 |
| 621 | NNRPPVAVA | 15 |

TABLE XXVII-V1-continued

HLA-B0702-9 mers-254P1D6B
Each peptide is a portion of SEQ ID NO: 3; each start position is specified, the length of peptide is 9 amino acids, and the end position for each peptide is the start position plus eight.

| Pos | 123456789 | score |
|---|---|---|
| 768 | DGSDHSVAL | 15 |
| 89 | EPKKMGPIR | 14 |
| 92 | KMGPIRSYL | 14 |
| 125 | SPSGIWGDS | 14 |
| 188 | LPGSEGAFN | 14 |
| 202 | SPAVPAETQ | 14 |
| 241 | TPSSGEVLE | 14 |
| 267 | EVLMPSHSL | 14 |
| 356 | AFVAPAPPV | 14 |
| 361 | APPVETTYN | 14 |
| 387 | QGHKQTLNL | 14 |
| 394 | NLSQLSVGL | 14 |
| 424 | VKPARRVNL | 14 |
| 441 | QLQELTLPL | 14 |
| 531 | ANAGPNHTI | 14 |
| 676 | KAIATVTGL | 14 |
| 715 | NNSPPRARA | 14 |
| 760 | SPAAGDVID | 14 |
| 814 | KSGLVELTL | 14 |
| 837 | LVRQLAVLL | 14 |
| 898 | ADFLLFKVL | 14 |
| 968 | VLTGGFTWL | 14 |
| 34 | AVISPNLET | 13 |
| 106 | PVQRPAQLL | 13 |
| 155 | EYSDDYREL | 13 |
| 199 | VGDSPAVPA | 13 |
| 207 | AETQQDPEL | 13 |
| 224 | TPAPKLPER | 13 |
| 227 | PKLPERSVL | 13 |
| 228 | KLPERSVLL | 13 |
| 229 | LPERSVLLP | 13 |
| 236 | LPLPTTPSS | 13 |
| 238 | LPTTPSSGE | 13 |
| 261 | SNSSGKEVL | 13 |
| 274 | SLPPASLEL | 13 |
| 276 | PPASLELSS | 13 |

TABLE XXVII-V1-continued

HLA-B0702-9 mers-254P1D6B
Each peptide is a portion of SEQ ID NO: 3; each start position is specified, the length of peptide is 9 amino acids, and the end position for each peptide is the start position plus eight.

| Pos | 123456789 | score |
|---|---|---|
| 290 | SPVLTVTPG | 13 |
| 339 | AGDNLIITL | 13 |
| 385 | IKQGHKQTL | 13 |
| 425 | KPARRVNLP | 13 |
| 429 | RVNLPPVAV | 13 |
| 430 | VNLPPVAVV | 13 |
| 432 | LPPVAVVSP | 13 |
| 433 | PPVAVVSPQ | 13 |
| 437 | VVSPQLQEL | 13 |
| 445 | LTLPLTSAL | 13 |
| 533 | AGPNHTITL | 13 |
| 577 | MQGVQTPYL | 13 |
| 620 | ENNRPPVAV | 13 |
| 623 | RPPVAVAGP | 13 |
| 630 | GPDKELIFP | 13 |
| 665 | GPSAVEMEN | 13 |
| 718 | PPRARAGGR | 13 |
| 833 | RKDTLVRQL | 13 |
| 907 | RVDTAGCLL | 13 |
| 918 | SGHGHCDPL | 13 |
| 954 | WSIFYVTVL | 13 |
| 1047 | ERGNPKVSM | 13 |
| 5 | TGVLSSLLL | 12 |
| 6 | GVLSSLLLL | 12 |
| 32 | SNAVISPNL | 12 |
| 47 | RVSHTFPVV | 12 |
| 109 | RPAQLLDYG | 12 |
| 142 | PFLGKDWGL | 12 |
| 159 | DYRELEKDL | 12 |
| 180 | AEYTDWGLL | 12 |
| 210 | QQDPELHYL | 12 |
| 212 | DPELHYLNE | 12 |
| 240 | TTPSSGEVL | 12 |
| 262 | NSSGKEVLM | 12 |
| 285 | VTVEKSPVL | 12 |

TABLE XXVII-V1-continued

HLA-B0702-9 mers-254P1D6B
Each peptide is a portion of SEQ ID NO: 3; each start position is specified, the length of peptide is 9 amino acids, and the end position for each peptide is the start position plus eight.

| Pos | 123456789 | score |
|---|---|---|
| 287 | VEKSPVLTV | 12 |
| 288 | EKSPVLTVT | 12 |
| 306 | TPPTSAAPS | 12 |
| 317 | TPSELPISP | 12 |
| 346 | TLPDNEVEL | 12 |
| 347 | LPDNEVELK | 12 |
| 358 | VAPAPPVET | 12 |
| 414 | AFGEGFVNV | 12 |
| 427 | ARRVNLPPV | 12 |
| 434 | PVAVVSPQL | 12 |
| 447 | LPLTSALID | 12 |
| 525 | VDYPPVANA | 12 |
| 528 | PPVANAGPN | 12 |
| 553 | SSDDHQIVL | 12 |
| 591 | QEGDYTFQL | 12 |
| 624 | PPVAVAGPD | 12 |
| 636 | IFPVESATL | 12 |
| 703 | STSTLTVAV | 12 |
| 717 | SPPRARAGG | 12 |
| 722 | RAGGRHVLV | 12 |
| 755 | IRDGQSPAA | 12 |
| 770 | SDHSVALQL | 12 |
| 773 | SVALQLTNL | 12 |
| 782 | VEGVYTFHL | 12 |
| 812 | PRKSGLVEL | 12 |
| 813 | RKSGLVELT | 12 |
| 836 | TLVRQLAVL | 12 |
| 840 | QLAVLLNVL | 12 |
| 859 | AHSDLSTVI | 12 |
| 881 | KAAEVARNL | 12 |
| 885 | VARNLHMRL | 12 |
| 927 | TKRCICSHL | 12 |
| 961 | VLAFTLIVL | 12 |
| 990 | RKKTKYTIL | 12 |
| 4 | PTGVLSSLL | 11 |
| 8 | LSSLLLLVT | 11 |
| 56 | DCTAACCDL | 11 |
| 61 | CCDLSSCDL | 11 |
| 71 | WWFEGRCYL | 11 |
| 82 | CPHKENCEP | 11 |
| 113 | LLDYGDMML | 11 |
| 205 | VPAETQQDP | 11 |
| 275 | LPPASLELS | 11 |
| 307 | PPTSAAPSE | 11 |
| 309 | TSAAPSEST | 11 |
| 315 | ESTPSELPI | 11 |
| 327 | TAPRTVKEL | 11 |
| 335 | LTVSAGDNL | 11 |
| 337 | VSAGDNLII | 11 |
| 353 | ELKAFVAPA | 11 |
| 362 | PPVETTYNY | 11 |
| 390 | KQTLNLSQL | 11 |
| 444 | ELTLPLTSA | 11 |
| 527 | YPPVANAGP | 11 |
| 534 | GPNHTITLP | 11 |
| 541 | LPQNSITLN | 11 |
| 569 | GSEGKHVVM | 11 |
| 607 | QQSTAVVTV | 11 |
| 634 | ELIFPVESA | 11 |
| 637 | FPVESATLD | 11 |
| 685 | QVGTYHFRL | 11 |
| 693 | LTVKDQQGL | 11 |
| 699 | QGLSSTSTL | 11 |
| 701 | LSSTSTLTV | 11 |
| 720 | RARAGGRHV | 11 |
| 731 | LPNNSITLD | 11 |
| 745 | DDQRIVSYL | 11 |
| 798 | ASDTDTATV | 11 |
| 821 | TLQVGVGQL | 11 |
| 871 | VQSRPPFKV | 11 |
| 883 | AEVARNLHM | 11 |

TABLE XXVII-V1-continued

HLA-B0702-9 mers-254P1D6B
Each peptide is a portion of SEQ ID NO: 3; each start position is specified, the length of peptide is 9 amino acids, and the end position for each peptide is the start position plus eight.

| Pos | 123456789 | score |
|---|---|---|
| 892 | RLSKEKADF | 11 |
| 893 | LSKEKADFL | 11 |
| 894 | SKEKADFLL | 11 |
| 895 | KEKADFLLF | 11 |
| 924 | DPLTKRCIC | 11 |
| 953 | EWSIFYVTV | 11 |
| 956 | IFYVTVLAF | 11 |
| 988 | KIRKKTKYT | 11 |
| 1001 | MDEQERMEL | 11 |
| 1010 | RPKYGIKHR | 11 |
| 1018 | RSTEHNSSL | 11 |

TABLE XXVII-V2

HLA-B0702-9 mers-254P1D6B
Each peptide is a portion of SEQ ID NO: 5; each start position is specified, the length of peptide is 9 amino acids, and the end position for each peptide is the start position plus eight.

| Pos | 123456789 | score |
|---|---|---|
| 7 | EYADDYREL | 12 |
| 1 | GLEEMSEYA | 6 |
| 9 | ADDYRELEK | 5 |

TABLE XXVII-V3

HLA-B0702-9 mers-254P1D6B
Each peptide is a portion of SEQ ID NO: 7; each start position is specified, the length of peptide is 9 amino acids, and the end position for each peptide is the start position plus eight.

| Pos | 123456789 | score |
|---|---|---|
| 6 | WPSPCCARK | 14 |
| 8 | SPCCARKQC | 11 |
| 4 | LGWPSPCCA | 7 |
| 3 | RLGWPSPCC | 6 |

TABLE XXVII-V5

HLA-B0702-9 mers-254P1D6B
Each peptide is a portion of SEQ ID NO: 11; each start position is specified, the length of peptide is 9 amino acids, and the end position for each peptide is the start position plus eight.

| Pos | 123456789 | score |
|---|---|---|
| 3 | DIRKDLTFL | 15 |
| 9 | TFLGKDWGL | 12 |
| 2 | EDIRKDLTF | 9 |
| 1 | PEDIRKDLT | 7 |

TABLE XXVIII-V1

HLA-B08-9 mers-254P1D6B
Each peptide is a portion of SEQ ID NO: 3; each start position is specified, the length of peptide is 9 amino acids, and the end position for each peptide is the start position plus eight.

| Pos | 123456789 | score |
|---|---|---|
| 248 | LEKEKASQL | 32 |
| 893 | LSKEKADFL | 32 |
| 990 | RKKTKYTIL | 30 |
| 228 | KLPERSVLL | 27 |
| 486 | SPVLRLSNL | 27 |
| 105 | RPVQRPAQL | 24 |
| 809 | QPDPRKSGL | 24 |
| 1008 | ELRPKYGIK | 24 |
| 1014 | GIKHRSTEH | 24 |
| 285 | VTVEKSPVL | 23 |
| 812 | PRKSGLVEL | 22 |
| 981 | CKRQKRTKI | 22 |
| 885 | VARNLHMRL | 21 |
| 988 | KIRKKTKYT | 21 |
| 136 | DIRKDLPFL | 20 |
| 142 | PFLGKDWGL | 20 |
| 424 | VKPARRVNL | 20 |
| 718 | PPRARAGGR | 20 |
| 133 | SPEDIRKDL | 19 |
| 159 | DYRELEKDL | 19 |
| 274 | SLPPASLEL | 19 |
| 353 | ELKAFVAPA | 19 |

TABLE XXVIII-V1-continued

HLA-B08-9 mers-254P1D6B
Each peptide is a portion of SEQ ID NO: 3; each start position is specified, the length of peptide is 9 amino acids, and the end position for each peptide is the start position plus eight.

| Pos | 123456789 | score |
|---|---|---|
| 439 | SPQLQELTL | 19 |
| 854 | VQKIRAHSD | 19 |
| 879 | VLKAAEVAR | 19 |
| 986 | RTKIRKKTK | 19 |
| 1010 | RPKYGIKHR | 19 |
| 1041 | FSREKMERG | 19 |
| 89 | EPKKMGPIR | 18 |
| 135 | EDIRKDLPF | 18 |
| 346 | TLPDNEVEL | 18 |
| 441 | QLQELTLPL | 18 |
| 821 | TLQVGVGQL | 18 |
| 829 | LTEQRKDTL | 18 |
| 900 | FLLFKVLRV | 18 |
| 113 | LLDYGDMML | 17 |
| 179 | SAEYTDWGL | 17 |
| 224 | TPAPKLPER | 17 |
| 226 | APKLPERSV | 17 |
| 327 | TAPRTVKEL | 17 |
| 384 | EIKQGHKQT | 17 |
| 394 | NLSQLSVGL | 17 |
| 477 | FIEEKTSVD | 17 |
| 598 | QLKVTDSSR | 17 |
| 692 | RLTVKDQQG | 17 |
| 730 | VLPNNSITL | 17 |
| 837 | LVRQLAVLL | 17 |
| 840 | QLAVLLNVL | 17 |
| 849 | DSDIKVQKI | 17 |
| 872 | QSRPPFKVL | 17 |
| 874 | RPPFKVLKA | 17 |
| 961 | VLAFTLIVL | 17 |
| 968 | VLTGGFTWL | 17 |
| 984 | QKRTKIRKK | 17 |

TABLE XXVIII-V1-continued

HLA-B08-9 mers-254P1D6B
Each peptide is a portion of SEQ ID NO: 3; each start position is specified, the length of peptide is 9 amino acids, and the end position for each peptide is the start position plus eight.

| Pos | 123456789 | score |
|---|---|---|
| 989 | IRKKTKYTI | 17 |
| 1050 | NPKVSMNGS | 17 |
| 3 | PPTGVLSSL | 16 |
| 88 | CEPKKMGPI | 16 |
| 169 | QPSGKQEPR | 16 |
| 221 | SASTPAPKL | 16 |
| 230 | PERSVLLPL | 16 |
| 246 | EVLEKEKAS | 16 |
| 495 | DPGNYSFRL | 16 |
| 540 | TLPQNSITL | 16 |
| 629 | AGPDKELIP | 16 |
| 836 | TLVRQLAVL | 16 |
| 881 | KAAEVARNL | 16 |
| 895 | KEKADFLLF | 16 |
| 914 | LLKCSGHGH | 16 |
| 924 | DPLTKRCIC | 16 |
| 927 | TKRCICSHL | 16 |
| 1025 | SLMVSESEF | 16 |
| 37 | SPNLETTRI | 15 |
| 425 | KPARRVNLP | 15 |
| 488 | VLRLSNLDP | 15 |
| 558 | QIVLYEWSL | 15 |
| 676 | KAIATVTGL | 15 |
| 709 | VAVKKENNS | 15 |
| 728 | VLVLPNNSI | 15 |
| 780 | NLVEGVYTF | 15 |
| 851 | DIKVQKIRA | 15 |

TABLE XXVIII-V2

HLA-B08-9 mers-254P1D6B
Each peptide is a portion of SEQ ID NO: 5; each start position is specified, the length of peptide is 9 amino acids, and the end position for each peptide is the start position plus eight.

| Pos | 123456789 | score |
|---|---|---|
| 7 | EYADDYREL | 13 |
| 9 | ADDYRELEK | 10 |
| 1 | GLEEMSEYA | 9 |

TABLE XXVIII-V3

HLA-B08-9 mers-254P1D6B
Each peptide is a portion of SEQ ID NO: 7; each start position is specified, the length of peptide is 9 amino acids, and the end position for each peptide is the start position plus eight.

| Pos | 123456789 | score |
|---|---|---|
| 10 | CCARKQCSE | 10 |
| 8 | SPCCARKQC | 9 |
| 9 | PCCARKQCS | 8 |
| 1 | MTRLGWPSP | 7 |
| 3 | RLGWPSPCC | 6 |
| 6 | WPSPCCARK | 6 |

TABLE XXVIII-V5

HLA-B08-9 mers-254P1D6B
Each peptide is a portion of SEQ ID NO: 11; each start position is specified, the length of peptide is 9 amino acids, and the end position for each peptide is the start position plus eight.

| Pos | 123456789 | score |
|---|---|---|
| 3 | DIRKDLTFL | 20 |
| 9 | TFLGKDWGL | 20 |
| 2 | EDIRKDLTF | 18 |
| 4 | IRKDLTFLG | 11 |

TABLE XXIX-V1

HLA-B1510-9 mers-254P1D6B
Each peptide is a portion of SEQ ID NO: 3; each start position is specified, the length of peptide is 9 amino acids, and the end position for each peptide is the start position plus eight.

| Pos | 123456789 | score |
|---|---|---|
| 272 | SHSLPPASL | 23 |
| 155 | EYSDDYREL | 16 |
| 346 | TLPDNEVEL | 16 |
| 721 | ARAGGRHVL | 16 |
| 96 | IRSYLTFVL | 15 |
| 227 | PKLPERSVL | 15 |
| 261 | SNSSGKEVL | 15 |
| 385 | IKQGHKQTK | 15 |
| 481 | KTSVDSPVL | 15 |
| 658 | YHWEHVRGP | 15 |
| 768 | DGSDHSVAL | 15 |
| 872 | QSRPPFKVL | 15 |
| 49 | SHTFPVVDC | 14 |
| 285 | VTVEKSPVL | 14 |
| 301 | EHSIPTPPT | 14 |
| 394 | NLSQLSVGL | 14 |
| 437 | VVSPQLQEL | 14 |
| 483 | SVDSPVLRL | 14 |
| 540 | TLPQNSITL | 14 |
| 627 | AVAGPDKEL | 14 |
| 636 | IFPVESATL | 14 |
| 661 | EHVRGPSAV | 14 |
| 812 | PRKSGLVEL | 14 |
| 821 | TLQVGVGQL | 14 |
| 829 | LTEQRKDTL | 14 |
| 840 | QLAVLLNVL | 14 |
| 859 | AHSDLSTVI | 14 |
| 881 | KAAEVARNL | 14 |
| 1001 | MDEQERMEL | 14 |
| 32 | SNAVISPNL | 13 |
| 71 | WWFEGRCYL | 13 |
| 92 | KMGPIRSYL | 13 |
| 133 | SPEDIRKDL | 13 |
| 160 | YRELEKDLL | 13 |
| 207 | AETQQDPEL | 13 |

TABLE XXIX-V1-continued

HLA-B1510-9 mers-254P1D6B
Each peptide is a portion of SEQ ID NO: 3; each start position is specified, the length of peptide is 9 amino acids, and the end position for each peptide is the start position plus eight.

| Pos | 123456789 | score |
|---|---|---|
| 221 | SASTPAPKL | 13 |
| 228 | KLPERSVLL | 13 |
| 240 | TTPSSGEVL | 13 |
| 274 | SLPPASLEL | 13 |
| 313 | PSESTPSEL | 13 |
| 327 | TAPRTVKEL | 13 |
| 424 | VKPARRVNL | 13 |
| 434 | PVAVVSPQL | 13 |
| 445 | LTLPLTSAL | 13 |
| 468 | YHWEEINGP | 13 |
| 553 | SSDDHQIVL | 13 |
| 569 | GSEGKHVVM | 13 |
| 573 | KHVVMQGVQ | 13 |
| 689 | YHFRLTVKD | 13 |
| 723 | AGGRHVLVL | 13 |
| 809 | QPDPRKSGL | 13 |
| 833 | RKDTLVRQL | 13 |
| 836 | TLVRQLAVL | 13 |
| 837 | LVRQLAVLL | 13 |
| 921 | GHCDPLTKR | 13 |
| 954 | WSIFYVTVL | 13 |
| 958 | YVTVLAFTL | 13 |
| 961 | VLAFTLIVL | 13 |
| 1021 | EHNSSLMVS | 13 |
| 83 | PHKENCEPK | 12 |
| 105 | RPVQRPAQL | 12 |
| 136 | DIRKDLPFL | 12 |
| 210 | QQDPELHYL | 12 |
| 215 | LHYLNESAS | 12 |
| 267 | EVLMPSHSL | 12 |
| 339 | AGDNLIITL | 12 |
| 388 | GHKQTLNLS | 12 |
| 495 | DPGNYSFRL | 12 |
| 577 | MQGVQTPYL | 12 |

TABLE XXIX-V1-continued

HLA-B1510-9 mers-254P1D6B
Each peptide is a portion of SEQ ID NO: 3; each start position is specified, the length of peptide is 9 amino acids, and the end position for each peptide is the start position plus eight.

| Pos | 123456789 | score |
|---|---|---|
| 579 | GVQTPYLHL | 12 |
| 585 | LHLSAMQEG | 12 |
| 685 | QVGTYHFRL | 12 |
| 730 | VLPNNSITL | 12 |
| 771 | DHSVALQLT | 12 |
| 885 | VARNLHMRL | 12 |
| 894 | SKEKADFLL | 12 |
| 898 | ADFLLFKVL | 12 |
| 919 | GHGHCDPLT | 12 |
| 968 | VLTGGFTWL | 12 |
| 3 | PPTGVLSSL | 11 |
| 4 | PTGVLSSLL | 11 |
| 5 | TGVLSSLLL | 11 |
| 6 | GVLSSLLLL | 11 |
| 106 | PVQRPAQLL | 11 |
| 113 | LLDYGDMML | 11 |
| 142 | PFLGKDWGL | 11 |
| 159 | DYRELEKDL | 11 |
| 179 | SAEYTDWGL | 11 |
| 248 | LEKEKASQL | 11 |
| 366 | TTYNYEWNL | 11 |
| 387 | QGHKQTLNL | 11 |
| 390 | KQTLNLSQL | 11 |
| 397 | QLSVGLYVF | 11 |
| 439 | SPQLQELTL | 11 |
| 441 | QLQELTLPL | 11 |
| 511 | ATNSTTAAL | 11 |
| 533 | AGPNHTITL | 11 |
| 536 | NHTITLPQN | 11 |
| 556 | DHQIVLYEW | 11 |
| 591 | QEGDYTFQL | 11 |
| 663 | VRGPSAVEM | 11 |
| 676 | KAIATVTGL | 11 |
| 693 | LTVKDQQGL | 11 |
| 699 | QGLSSTSTL | 11 |

TABLE XXIX-V1-continued

HLA-B1510-9 mers-254P1D6B
Each peptide is a portion of SEQ ID NO: 3; each start position is specified, the length of peptide is 9 amino acids, and the end position for each peptide is the start position plus eight.

| Pos | 123456789 | score |
|---|---|---|
| 726 | RHVLVLPNN | 11 |
| 745 | DDQRIVSYL | 11 |
| 773 | SVALQLTNL | 11 |
| 782 | VEGVYTFHL | 11 |
| 814 | KSGLVELTL | 11 |
| 889 | LHMRLSKEK | 11 |
| 893 | LSKEKADFL | 11 |
| 906 | LRVDTAGCL | 11 |
| 918 | SGHGHCDPL | 11 |
| 927 | TKRCICSHL | 11 |
| 932 | CSHLWMENL | 11 |
| 956 | IFYVTVLAF | 11 |
| 1018 | RSTEHNSSL | 11 |
| 1047 | ERGNPKVSM | 11 |

TABLE XXIX-V2

HLA-B1510-9 mers-254P1D6B
Each peptide is a portion of SEQ ID NO: 5; each start position is specified, the length of peptide is 9 amino acids, and the end position for each peptide is the start position plus eight.

| Pos | 123456789 | score |
|---|---|---|
| 7 | EYADDYREL | 16 |

TABLE XXIX-V3

HLA-B1510-9 mers-254P1D6B
Each peptide is a portion of SEQ ID NO: 7; each start position is specified, the length of peptide is 9 amino acids, and the end position for each peptide is the start position plus eight.

| Pos | 123456789 | score |
|---|---|---|
| 6 | WPSPCCARK | 5 |
| 2 | TRLGWPSPC | 3 |
| 4 | LGWPSPCCA | 3 |

TABLE XXIX-V3-continued

HLA-B1510-9 mers-254P1D6B
Each peptide is a portion of SEQ ID NO: 7; each start position is specified, the length of peptide is 9 amino acids, and the end position for each peptide is the start position plus eight.

| Pos | 123456789 | score |
|---|---|---|
| 5 | GWPSPCCAR | 3 |
| 1 | MTRLGWPSP | 2 |
| 3 | RLGWPSPCC | 2 |
| 7 | PSPCCARKQ | 2 |

TABLE XXIX-V5

HLA-B1510-9 mers-254P1D6B
Each peptide is a portion of SEQ ID NO: 11; each start position is specified, the length of peptide is 9 amino acids, and the end position for each peptide is the start position plus eight.

| Pos | 123456789 | score |
|---|---|---|
| 9 | TFLGKDWGL | 12 |
| 3 | DIRKDLTFL | 11 |
| 2 | EDIRKDLTF | 8 |

TABLE XXX-V1

HLA-B2705-9 mers-254P1D6B

No Results Found.

TABLE XXX-V2

B2705-9 mers-254P1D6B
Each peptide is a portion of SEQ ID NO: 5; each start position is specified, the length of peptide is 9 amino acids, and the end position for each peptide is the start position plus eight.

| Pos | 123456789 | score |
|---|---|---|
| 9 | ADDYRELEK | 13 |
| 5 | MSEYADDYR | 11 |
| 7 | EYADDYREL | 11 |
| 4 | EMSEYADDY | 10 |
| 6 | SEYADDYRE | 6 |

TABLE XXX-V3

B2705-9 mers-254P1D6B
Each peptide is a portion of SEQ ID NO: 7; each start position is specified, the length of peptide is 9 amino acids, and the end position for each peptide is the start position plus eight.

| Pos | 123456789 | score |
|---|---|---|
| 2 | TRLGWPSPC | 15 |
| 5 | GWPSPCCAR | 14 |
| 6 | WPSPCCARK | 14 |
| 3 | RLGWPSPCC | 7 |

TABLE XXX-V5

B2705-9 mers-254P1D6B
Each peptide is a portion of SEQ ID NO: 11; each start position is specified, the length of peptide is 9 amino acids, and the end position for each peptide is the start position plus eight.

| Pos | 123456789 | score |
|---|---|---|
| 9 | TFLGKDWGL | 17 |
| 2 | EDIRKDLTF | 16 |
| 5 | RKDLTFLGK | 16 |
| 3 | DIRKDLTFL | 15 |
| 4 | IRKDLTFLG | 12 |

TABLE XXXI-V1

HLA-B2709-9mers-254P1D6B

NoResultsFound.

TABLE XXXI-V2

HLA-B2709-9mers-254P1D6B

NoResultsFound.

TABLE XXXI-V3

VHLA-B2709-9mers-254P1D6B

NoResultsFound.

TABLE XXXI-V5

HLA-B2709-9mers-254P1D6B

NoResultsFound.

TABLE XXXII-V1

HLA-B2709-9mers-254P1D6B
Each peptide is a portion of SEQ ID NO: 3; each start position is specified, the length of peptide is 9 amino acids, and the endposition for each peptide is the start position plus eight.

| Pos | 123456789 | score |
|---|---|---|
| 28 | GRTYSNAVI | 22 |
| 812 | PRKSGLVEL | 22 |
| 906 | LRVDTAGCL | 22 |
| 96 | IRSYLTFVL | 21 |
| 663 | VRGPSAVEM | 21 |
| 721 | ARAGGRHVL | 21 |
| 46 | MRVSHTFPV | 20 |
| 160 | YRELEKDLL | 20 |
| 329 | PRTVKELTV | 20 |
| 427 | ARRVNLPPV | 20 |
| 741 | SRSTDDQRI | 20 |
| 747 | QRIVSYLWI | 20 |
| 989 | IRKKTKYTI | 20 |
| 1047 | ERGNPKVSM | 19 |
| 605 | SRQQSTAVV | 18 |
| 6 | GVLSSLLLL | 17 |
| 105 | RPVQRPAQL | 16 |
| 428 | RRVNLPPVA | 16 |
| 833 | RKDTLVRQL | 16 |
| 839 | RQLAVLLNV | 16 |
| 497 | GNYSFRLTV | 15 |
| 725 | GRHVLVLPN | 15 |
| 784 | GVYTFHLRV | 15 |
| 1018 | RSTEHNSSL | 15 |
| 75 | GRCYLVSCP | 14 |
| 92 | KMGPIRSYL | 14 |
| 180 | AEYTDWGLL | 14 |
| 390 | KQTLNLSQL | 14 |
| 401 | GLYVFKVTV | 14 |
| 481 | KTSVDSPVL | 14 |

TABLE XXXII-V1-continued

HLA-B2709-9mers-254P1D6B
Each peptide is a portion of SEQ ID NO: 3; each start position is specified, the length of peptide is 9 amino acids, and the endposition for each peptide is the start position plus eight.

| Pos | 123456789 | score |
|---|---|---|
| 483 | SVDSPVLRL | 14 |
| 579 | GVQTPYLHL | 14 |
| 593 | GDYTFQLKV | 14 |
| 676 | KAIATVTGL | 14 |
| 687 | GTYHFRLTV | 14 |
| 742 | RSTDDQRIV | 14 |
| 770 | SDHSVALQL | 14 |
| 816 | GLVELTLQV | 14 |
| 858 | RAHSDLSTV | 14 |
| 881 | KAAEVARNL | 14 |
| 907 | RVDTAGCLL | 14 |
| 929 | RCICSHLWM | 14 |
| 985 | KRTKIRKKT | 14 |
| 990 | RKKTKYTIL | 14 |
| 32 | SNAVISPNL | 13 |
| 47 | RVSHTFPVV | 13 |
| 94 | GPIRSYLTF | 13 |
| 207 | AETQQDPEL | 13 |
| 227 | PKLPERSVL | 13 |
| 228 | KLPERSVLL | 13 |
| 335 | LTVSAGDNL | 13 |
| 366 | TTYNYEWNL | 13 |
| 429 | RVNLPPVAV | 13 |
| 445 | LTLPLTSAL | 13 |
| 489 | LRLSNLDPG | 13 |
| 622 | NRPPVAVAG | 13 |
| 691 | FRLTVKDQQ | 13 |
| 699 | QGLSSTSTL | 13 |
| 722 | RAGGRHVLV | 13 |
| 723 | AGGRHVLVL | 13 |
| 758 | GQSPAAGDV | 13 |
| 814 | KSGLVELTL | 13 |
| 891 | MRLSKEKAD | 13 |
| 898 | ADFLLFKVL | 13 |

TABLE XXXII-V1-continued

HLA-B2709-9mers-254P1D6B
Each peptide is a portion of SEQ ID NO: 3; each start position is specified, the length of peptide is 9 amino acids, and the endposition for each peptide is the start position plus eight.

| Pos | 123456789 | score |
|---|---|---|
| 900 | FLLFKVLRV | 13 |
| 956 | IFYVTVLAF | 13 |
| 5 | TGVLSSLLL | 12 |
| 43 | TRIMRVSHT | 12 |
| 44 | RIMRVSHTF | 12 |
| 71 | WWFEGRCYL | 12 |
| 111 | AQLLDYGDM | 12 |
| 136 | DIRKDLPFL | 12 |
| 142 | PFLGKDWGL | 12 |
| 176 | PRGSAEYTD | 12 |
| 221 | SASTPAPKL | 12 |
| 230 | PERSVLLPL | 12 |
| 248 | LEKEKASQL | 12 |
| 267 | EVLMPSHSL | 12 |
| 274 | SLPPASLEL | 12 |
| 285 | VTVEKSPVL | 12 |
| 356 | AFVAPAPPV | 12 |
| 387 | QGHKQTLNL | 12 |
| 396 | SQLSVGLYV | 12 |
| 416 | GEGFVNVTV | 12 |
| 424 | VKPARRVNL | 12 |
| 430 | VNLPPVAVV | 12 |
| 434 | PVAVVSPQL | 12 |
| 486 | SPVLRLSNL | 12 |
| 501 | FRLTVTDSD | 12 |
| 511 | ATNSTTAAL | 12 |
| 567 | GPGSEGKHV | 12 |
| 569 | GSEGKHVVM | 12 |
| 678 | IATVTGLQV | 12 |
| 683 | GLQVGTYHF | 12 |
| 693 | LTVKDQQGL | 12 |
| 720 | RARAGGRHV | 12 |
| 745 | DDQRIVSYL | 12 |
| 755 | IRDGQSPAA | 12 |
| 790 | LRVTDSQGA | 12 |

TABLE XXXII-V1-continued

HLA-B2709-9mers-254P1D6B
Each peptide is a portion of SEQ ID NO: 3; each start position is specified, the length of peptide is 9 amino acids, and the endposition for each peptide is the start position plus eight.

| Pos | 123456789 | score |
|---|---|---|
| 821 | TLQVGVGQL | 12 |
| 832 | QRKDTLVRQ | 12 |
| 837 | LVRQLAVLL | 12 |
| 838 | VRQLAVLLN | 12 |
| 857 | IRAHSDLST | 12 |
| 861 | SDLSTVIVF | 12 |
| 873 | SRPPFKVLK | 12 |
| 892 | RLSKEKADF | 12 |
| 895 | KEKADFLLF | 12 |
| 928 | KRCICSHLW | 12 |
| 942 | QRYIWDGES | 12 |
| 954 | WSIFYVTVL | 12 |
| 958 | YVTVLAFTL | 12 |
| 982 | KRQKRTKIR | 12 |
| 993 | TKYTILDNM | 12 |
| 1057 | GSIRNGASF | 12 |
| 3 | PPTGVLSSL | 11 |
| 9 | SSLLLLVTI | 11 |
| 21 | ARKQCSEGR | 11 |
| 56 | DCTAACCDL | 11 |
| 104 | LRPVQRPAQ | 11 |
| 106 | PVQRPAQLL | 11 |
| 108 | QRPAQLLDY | 11 |
| 122 | NRGSPSGIW | 11 |
| 133 | SPEDIRKDL | 11 |
| 137 | IRKDLPFLG | 11 |
| 145 | GKDWGLEEM | 11 |
| 155 | EYSDDYREL | 11 |
| 197 | SSVGDSPAV | 11 |
| 210 | QQDPELHYL | 11 |
| 231 | ERSVLLPLP | 11 |
| 240 | TTPSSGEVL | 11 |
| 261 | SNSSGKEVL | 11 |
| 287 | VEKSPVLTV | 11 |

TABLE XXXII-V1-continued

HLA-B2709-9mers-254P1D6B
Each peptide is a portion of SEQ ID NO: 3; each start position is specified, the length of peptide is 9 amino acids, and the endposition for each peptide is the start position plus eight.

| Pos | 123456789 | score |
|---|---|---|
| 313 | PSESTPSEL | 11 |
| 315 | ESTPSELPI | 11 |
| 327 | TAPRTVKEL | 11 |
| 339 | AGDNLIITL | 11 |
| 346 | TLPDNEVEL | 11 |
| 385 | IKQGHKQTL | 11 |
| 394 | NLSQLSVGL | 11 |
| 414 | AFGEGFVNV | 11 |
| 422 | VTVKPARRV | 11 |
| 437 | VVSPQLQEL | 11 |
| 439 | SPQLQELTL | 11 |
| 441 | QLQELTLPL | 11 |
| 495 | DPGNYSFRL | 11 |
| 513 | NSTTAALIV | 11 |
| 517 | AALIVNNAV | 11 |
| 533 | AGPNHTITL | 11 |
| 551 | NQSSDDHQI | 11 |
| 558 | QIVLYEWSL | 11 |
| 572 | GKHVVMQGV | 11 |
| 577 | MQGVQTPYL | 11 |
| 591 | QEGDYTFQL | 11 |
| 627 | AVAGPDKEL | 11 |
| 636 | IFPVESATL | 11 |
| 655 | IVFYHWEHV | 11 |
| 685 | QVGTYHFRL | 11 |
| 719 | PRARAGGRH | 11 |
| 768 | DGSDHSVAL | 11 |
| 773 | SVALQLTNL | 11 |
| 780 | NLVEGVYTF | 11 |
| 809 | QPDPRKSGL | 11 |
| 818 | VELTLQVGV | 11 |
| 835 | DTLVRQLAV | 11 |
| 836 | TLVRQLAVL | 11 |
| 855 | QKIRAHSDL | 11 |
| 863 | LSTVIVFYV | 11 |

TABLE XXXII-V1-continued

HLA-B2709-9mers-254P1D6B
Each peptide is a portion of
SEQ ID NO: 3; each start
position is specified, the
length of peptide is 9 amino
acids, and the endposition
for each peptide is the start
position plus eight.

| Pos | 123456789 | score |
|---|---|---|
| 872 | QSRPPFKVL | 11 |
| 883 | AEVARNLHM | 11 |
| 885 | VARNLHMRL | 11 |
| 886 | ARNLHMRLS | 11 |
| 893 | LSKEKADFL | 11 |
| 927 | TKRCICSHL | 11 |
| 932 | CSHLWMENL | 11 |
| 948 | GESNCEWSI | 11 |
| 960 | TVLAFTLIV | 11 |
| 968 | VLTGGFTWL | 11 |
| 1005 | ERMELRPKY | 11 |
| 1007 | MELRPKYGI | 11 |
| 1045 | KMERGNPKV | 11 |
| 1059 | IRNGASFSY | 11 |
| 4 | IPTGVLSSLL | 10 |
| 7 | VLSSLLLLV | 10 |
| 38 | PNLETTRIM | 10 |
| 40 | LETTRIMRV | 10 |
| 61 | CCDLSSCDL | 10 |
| 85 | KENCEPKKM | 10 |
| 112 | QLLDYGDMM | 10 |
| 113 | LLDYGDMML | 10 |
| 135 | EDIRKDLPF | 10 |
| 159 | DYRELEKDL | 10 |
| 179 | SAEYTDWGL | 10 |
| 239 | PTTPSSGEV | 10 |
| 272 | SHSLPPASL | 10 |
| 337 | VSAGDNLII | 10 |
| 344 | IITLPDNEV | 10 |
| 407 | VTVSSENAF | 10 |
| 458 | QSTDDTEIV | 10 |
| 480 | EKTSVDSPV | 10 |
| 493 | NLDPGNYSF | 10 |
| 522 | NNAVDYPPV | 10 |
| 540 | TLPQNSITL | 10 |
| 553 | SSDDHQIVL | 10 |
| 582 | TPYLHLSAM | 10 |
| 589 | AMQEGDYTF | 10 |
| 607 | QQSTAVVTV | 10 |
| 608 | QSTAVVTVI | 10 |
| 628 | VAGPDKELI | 10 |
| 629 | AGPDKELIF | 10 |
| 647 | SSSSDDHGI | 10 |
| 730 | VLPNNSITL | 10 |
| 774 | VALQLTNLV | 10 |
| 777 | QLTNLVEGV | 10 |
| 782 | VEGVYTFHL | 10 |
| 798 | ASDTDTATV | 10 |
| 829 | LTEQRKDTL | 10 |
| 840 | QLAVLLNVL | 10 |
| 846 | NVLDSDIKV | 10 |
| 869 | FYVQSRPPF | 10 |
| 877 | FKVLKAAEV | 10 |
| 894 | SKEKADFLL | 10 |
| 897 | KADFLLFKV | 10 |
| 918 | SGHGHCDPL | 10 |
| 933 | SHLWMENLI | 10 |
| 961 | VLAFTLIVL | 10 |
| 1001 | MDEQERMEL | 10 |
| 1009 | LRPKYGIKH | 10 |
| 1017 | HRSTEHNSS | 10 |
| 1032 | EFDSDQDTI | 10 |
| 1042 | SREKMERGN | 10 |
| 1051 | PKVSMNGSI | 10 |

TABLE XXXI-V2

HLA-B2709-9mers-254P1D6B
Each peptide is a portion of SEQ ID NO: 5; each start position is specified, the length of peptide is 9 amino acids, and the end position for each peptide is the start position plus eight.

| Pos | 123456789 | score |
|---|---|---|
| 7 | EYADDYREL | 11 |
| 6 | SEYADDYRE | 5 |

TABLE XXXI-V3

HLA-B2709-9mers-254P1D6B
Each peptide is a portion of SEQ ID NO: 7; each start position is specified, the length of peptide is 9 amino acids, and the end position for each peptide is the start position plus eight.

| Pos | 123456789 | score |
|---|---|---|
| 2 | TRLGWPSPC | 12 |
| 3 | RLGWPSPCC | 5 |

TABLE XXXI-V5

HLA-B2709-9mers-254P1D6B
Each peptide is a portion of SEQ ID NO: 11; each start position is specified, the length of peptide is 9 amino acids, and the end position for each peptide is the start position plus eight.

| Pos | 123456789 | score |
|---|---|---|
| 9 | TFLGKDWGL | 12 |
| 3 | DIRKDLTFL | 11 |
| 4 | IRKDLTFLG | 11 |
| 2 | EDIRKDLTF | 10 |
| 5 | RKDLTFLGK | 5 |

TABLE XXXII-V1

HLA-B4402-9mers-254P1D6B
Each peptide is a portion of SEQ ID NO:3; each start position is specified, the length of peptide is 9 amino acids, and the end position for each peptide is the start position plus eight.

| Pos | 123456789 | score |
|---|---|---|
| 180 | AEYTDWGLL | 25 |
| 895 | KEKADFLLF | 24 |

TABLE XXXII-V1-continued

HLA-B4402-9mers-254P1D6B
Each peptide is a portion of SEQ ID NO:3; each start position is specified, the length of peptide is 9 amino acids, and the end position for each peptide is the start position plus eight.

| Pos | 123456789 | score |
|---|---|---|
| 207 | AETQQDPEL | 23 |
| 591 | QEGDYTFQL | 23 |
| 174 | QEPRGSAEY | 22 |
| 230 | PERSVLLPL | 22 |
| 248 | LEKEKASQL | 22 |
| 364 | VETTYNYEW | 21 |
| 411 | SENAFGEGF | 21 |
| 782 | VEGVYTFHL | 21 |
| 937 | MENLIQRYI | 21 |
| 339 | AGDNLIITL | 20 |
| 898 | ADFLLFKVL | 20 |
| 948 | GESNCEWSI | 20 |
| 1007 | MELRPKYGI | 20 |
| 88 | CEPKKMGPI | 19 |
| 470 | WEEINGPFI | 19 |
| 533 | AGPNHTITL | 18 |
| 91 | KKMGPIRSY | 17 |
| 135 | EDIRKDLPF | 17 |
| 319 | SELPISPTT | 17 |
| 445 | LTLPLTSAL | 17 |
| 471 | EEINGPFIE | 11 |
| 554 | SDDHQIVLY | 17 |
| 721 | ARAGGRHVL | 17 |
| 723 | AGGRHVLVL | 17 |
| 872 | QSRPPFKVL | 17 |
| 92 | KMGPIRSYL | 16 |
| 94 | GPIRSYLTF | 16 |
| 133 | SPEDIRKDL | 16 |
| 210 | QQDPELHYL | 16 |
| 227 | PKLPERSVL | 16 |
| 274 | SLPPASLEL | 16 |
| 460 | TDDTEIVSY | 16 |
| 511 | ATNSTTAAL | 16 |
| 627 | AVAGPDKEL | 16 |

TABLE XXXII-V1-continued

HLA-B4402-9mers-254P1D6B
Each peptide is a portion of
SEQ ID NO:3; each start
position is specified, the
length of peptide is 9 amino
acids, and the end position
for each peptide is the start
position plus eight.

| Pos | 123456789 | score |
|---|---|---|
| 629 | AGPDKELIF | 16 |
| 650 | SDDHGIVFY | 16 |
| 669 | VEMENIDKA | 16 |
| 670 | EMENIDKAI | 16 |
| 744 | TDDQRIVSY | 16 |
| 862 | DLSTVIVFY | 16 |
| 1046 | MERGNPKVS | 16 |
| 40 | LETTRIMRV | 15 |
| 85 | KENCEPKKM | 15 |
| 155 | EYSDDYREL | 15 |
| 219 | NESASTPAP | 15 |
| 221 | SASTPAPKL | 15 |
| 228 | KLPERSVLL | 15 |
| 327 | TAPRTVKEL | 15 |
| 349 | DNEVELKAF | 15 |
| 352 | VELKAFVAP | 15 |
| 360 | PAPPVETTY | 15 |
| 373 | NLISHPTDY | 15 |
| 383 | GEIKQGHKQ | 15 |
| 390 | KQTLNLSQL | 15 |
| 437 | VVSPQLQEL | 15 |
| 443 | QELTLPLTS | 15 |
| 493 | NLDPGNYSF | 15 |
| 553 | SSDDHQIVL | 15 |
| 649 | SSDDHGIVF | 15 |
| 676 | KAIATVTGL | 15 |
| 730 | VLPNNSITL | 15 |
| 768 | DGSDHSVAL | 15 |
| 809 | QPDPRKSGL | 15 |
| 833 | RKDTLVRQL | 15 |
| 861 | SDLSTVIVF | 15 |
| 883 | AEVARNLHM | 15 |
| 954 | WSIFYVTVL | 15 |
| 987 | TKIRKKTKY | 15 |
| 1005 | ERMELRPKY | 15 |

TABLE XXXII-V1-continued

HLA-B4402-9mers-254P1D6B
Each peptide is a portion of
SEQ ID NO:3; each start
position is specified, the
length of peptide is 9 amino
acids, and the end position
for each peptide is the start
position plus eight.

| Pos | 123456789 | score |
|---|---|---|
| 1057 | GSIRNGASF | 15 |
| 6 | GVLSSLLLL | 14 |
| 9 | SSLLLLVTI | 14 |
| 44 | RIMRVSHTF | 14 |
| 63 | DLSSCDLAW | 14 |
| 70 | AWWFEGRCY | 14 |
| 187 | LLPGSEGAF | 14 |
| 267 | EVLMPSHSL | 14 |
| 272 | SHSLPPASL | 14 |
| 314 | SESTPSELP | 14 |
| 315 | ESTPSELPI | 14 |
| 346 | TLPDNEVEL | 14 |
| 370 | YEWNLISHP | 14 |
| 424 | VKPARRVNL | 14 |
| 439 | SPQLQELTL | 14 |
| 463 | TEIVSYHWE | 14 |
| 479 | EEKTSVDSP | 14 |
| 483 | SVDSPVLRL | 14 |
| 486 | SPVLRLSNL | 14 |
| 519 | LIVNNAVDY | 14 |
| 531 | ANAGPNHTI | 14 |
| 540 | TLPQNSITL | 14 |
| 589 | AMQEGDYTF | 14 |
| 619 | PENNRPPVA | 14 |
| 633 | KELIFPVES | 14 |
| 770 | SDHSVALQL | 14 |
| 814 | KSGLVELTL | 14 |
| 855 | QKIRAHSDL | 14 |
| 859 | AHSDLSTVI | 14 |
| 936 | WMENLIQRY | 14 |
| 938 | ENLIQRYIW | 14 |
| 956 | IFYVTVLAF | 14 |
| 965 | TLIVLTGGF | 14 |
| 1031 | SEFDSDQDT | 14 |

TABLE XXXII-V1-continued

HLA-B4402-9mers-254P1D6B
Each peptide is a portion of SEQ ID NO:3; each start position is specified, the length of peptide is 9 amino acids, and the end position for each peptide is the start position plus eight.

| Pos | 123456789 | score |
|---|---|---|
| 5 | TGVLSSLLL | 13 |
| 23 | KQCSEGRTY | 13 |
| 65 | SSCDLAWWF | 13 |
| 71 | WWFEGRCYL | 13 |
| 73 | FEGRCYLVS | 13 |
| 96 | IRSYLTFVL | 13 |
| 105 | RPVQRPAQL | 13 |
| 106 | PVQRPAQLL | 13 |
| 108 | QRPAQLLDY | 13 |
| 134 | PEDIRKDLP | 13 |
| 140 | DLPFLGKDW | 13 |
| 151 | EEMSEYSDD | 13 |
| 152 | EMSEYSDDY | 13 |
| 161 | RELEKDLLQ | 13 |
| 213 | PELHYLNES | 13 |
| 250 | KEKASQLQE | 13 |
| 261 | SNSSGKEVL | 13 |
| 266 | KEVLMPSHS | 13 |
| 280 | LELSSVTVE | 13 |
| 287 | VEKSPVLTV | 13 |
| 333 | KELTVSAGD | 13 |
| 394 | NLSQLSVGL | 13 |
| 395 | LSQLSVGLY | 13 |
| 397 | QLSVGLYVF | 13 |
| 407 | VTVSSENAF | 13 |
| 481 | KTSVDSPVL | 13 |
| 570 | SEGKHVVMQ | 13 |
| 681 | VTGLQVGTY | 13 |
| 699 | QGLSSTSTL | 13 |
| 713 | KENNSPPRA | 13 |
| 745 | DDQRIVSYL | 13 |
| 773 | SVALQLTNL | 13 |
| 780 | NLVEGVYTF | 13 |
| 818 | VELTLQVGV | 13 |
| 836 | TLVRQLAVL | 13 |
| 837 | LVRQLAVLL | 13 |
| 840 | QLAVLLNVL | 13 |
| 881 | KAAEVARNL | 13 |
| 907 | RVDTAGCLL | 13 |
| 928 | KRCICSHLW | 13 |
| 952 | CEWSIFYVT | 13 |
| 961 | VLAFTLIVL | 13 |
| 967 | IVLTGGFTW | 13 |
| 3 | PPTGVLSSL | 12 |
| 26 | SEGRTYSNA | 12 |
| 32 | SNAVISPNL | 12 |
| 61 | CCDLSSCDL | 12 |
| 64 | LSSCDLAWW | 12 |
| 142 | PFLGKDWGL | 12 |
| 159 | DYRELEKDL | 12 |
| 160 | YRELEKDLL | 12 |
| 163 | LEKDLLQPS | 12 |
| 209 | TQQDPELHY | 12 |
| 240 | TTPSSGEVL | 12 |
| 245 | GEVLEKEKA | 12 |
| 300 | TEHSIPTPP | 12 |
| 385 | IKQGHKQTL | 12 |
| 387 | QGHKQTLNL | 12 |
| 416 | GEGFVNVTV | 12 |
| 441 | QLQELTLPL | 12 |
| 491 | LSNLDPGNY | 12 |
| 512 | TNSTTAALI | 12 |
| 551 | NQSSDDHQI | 12 |
| 579 | GVQTPYLHL | 12 |
| 628 | VAGPDKELI | 12 |
| 636 | IFPVESATL | 12 |
| 639 | VESATLDGS | 12 |
| 747 | QRIVSYLWI | 12 |
| 778 | LTNLVEGVY | 12 |

TABLE XXXII-V1-continued

HLA-B4402-9mers-254P1D6B
Each peptide is a portion of
SEQ ID NO:3; each start
position is specified, the
length of peptide is 9 amino
acids, and the end position
for each peptide is the start
position plus eight.

| Pos | 123456789 | score |
|---|---|---|
| 812 | PRKSGLVEL | 12 |
| 821 | TLQVGVGQL | 12 |
| 829 | LTEQRKDTL | 12 |
| 830 | TEQRKDTLV | 12 |
| 894 | SKEKADFLL | 12 |
| 906 | LRVDTAGCL | 12 |
| 918 | SGHGHCDPL | 12 |
| 933 | SHLWMENIL | 12 |
| 949 | ESNCEWSIF | 12 |
| 950 | SNCEWSIFY | 12 |
| 958 | YVTVLAFTL | 12 |
| 968 | VLTGGFTWL | 12 |
| 1002 | DEQERMELR | 12 |
| 1004 | QERMELRPK | 12 |
| 1020 | TEHNSSLMV | 12 |
| 1025 | SLMVSESEF | 12 |
| 1029 | SESEFDSDQ | 12 |
| 1032 | EFDSDQDTI | 12 |
| 1033 | FDSDQDTIF | 12 |

TABLE XXXII-V2

HLA-B4402-9mers-254P1D6B
Each peptide is a portion
of SEQ ID NO: 5; each
start position is specified,
the length of peptide is 9
amino acids, and the end
position for each peptide
is the start position plus
eight.

| Pos | 123456789 | score |
|---|---|---|
| 4 | EMSEYADDY | 14 |
| 7 | EYADDYREL | 14 |
| 3 | EEMSEYADD | 13 |
| 2 | LEEMSEYAD | 12 |
| 6 | SEYADDYRE | 11 |
| 9 | ADDYRELEK | 6 |

TABLE XXXII-V3

HLA-B4402-9mers-254P1D6B
Each peptide is a portion
of SEQ ID NO: 7; each
start position is specified,
the length of peptide is 9
amino acids, and the end
position for each peptide
is the start position plus
eight.

| Pos | 123456789 | score |
|---|---|---|
| 8 | SPCCARKQC | 5 |
| 4 | LGWPSPCCA | 4 |
| 6 | WPSPCCARK | 4 |
| 7 | PSPCCARKQ | 4 |
| 2 | TRLGWPSPC | 3 |
| 5 | GWPSPCCAR | 3 |

TABLE XXXII-V5

HLA-B4402-9mers-254P1D6B
Each peptide is a portion
of SEQ ID NO: 11; each
start position is specified,
the length of peptide is 9
amino acids, and the end
position for each peptide is
the start position plus
eight.

| Pos | 123456789 | score |
|---|---|---|
| 2 | EDIRKDLTF | 18 |
| 1 | PEDIRKDLT | 13 |
| 7 | DLTFLGKDW | 12 |
| 9 | TFLGKDWGL | 12 |
| 3 | DIRKDLTFL | 11 |

TABLE XXXIIII-V1

HLA-B5101-9mers-254P1D6B
Each peptide is a portion of
SEQ ID NO: 3; each start
position is specified, the
length of peptide is 9 amino
acids, and the end position
for each peptide is the start
position plus eight.

| Pos | 123456789 | score |
|---|---|---|
| 517 | AALIVNNAV | 24 |
| 324 | SPTTAPRTV | 23 |
| 37 | SPNLETTRI | 22 |
| 296 | TPGSTEHSI | 22 |
| 327 | TAPRTVKEL | 22 |
| 377 | HPTDYQGEI | 22 |
| 495 | DPGNYSFRL | 22 |

TABLE XXXIIII-V1-continued

HLA-B5101-9mers-254P1D6B
Each peptide is a portion of SEQ ID NO: 3; each start position is specified, the length of peptide is 9 amino acids, and the end position for each peptide is the start position plus eight.

| Pos | 123456789 | score |
|---|---|---|
| 678 | IATVTGLQV | 22 |
| 774 | VALQLTNLV | 22 |
| 881 | KAAEVARNL | 22 |
| 628 | VAGPDKELI | 21 |
| 676 | KAIATVTGL | 21 |
| 720 | RARAGGRHV | 21 |
| 858 | RAHSDLSTV | 21 |
| 897 | KADFLLFKV | 21 |
| 3 | PPTGVLSSL | 20 |
| 221 | SASTPAPKL | 20 |
| 567 | GPGSEGKHV | 20 |
| 722 | RAGGRHVLV | 20 |
| 811 | DPRKSGLVE | 20 |
| 226 | APKLPERSV | 19 |
| 277 | PASLELSSV | 19 |
| 439 | SPQLQELTL | 19 |
| 568 | PGSEGKHVV | 19 |
| 608 | QSTAVVTVI | 19 |
| 849 | DSDIKVQKI | 19 |
| 970 | TGGFTWLCI | 19 |
| 133 | SPEDIRKDL | 18 |
| 447 | LPLTSALID | 18 |
| 610 | TAVVTVIVQ | 18 |
| 618 | QPENNRPPV | 18 |
| 723 | AGGRHVLVL | 18 |
| 768 | DGSDHSVAL | 18 |
| 885 | VARNLHMRL | 18 |
| 924 | DPLTKRCIC | 18 |
| 27 | EGRTYSNAV | 17 |
| 105 | RPVQRPAQL | 17 |
| 179 | SAEYTDWGL | 17 |
| 486 | SPVLRLSNL | 17 |
| 523 | NAVDYPPVA | 17 |
| 699 | QGLSSTSTL | 17 |
| 874 | RPPFKVLKA | 17 |

TABLE XXXIIII-V1-continued

HLA-B5101-9mers-254P1D6B
Each peptide is a portion of SEQ ID NO: 3; each start position is specified, the length of peptide is 9 amino acids, and the end position for each peptide is the start position plus eight.

| Pos | 123456789 | score |
|---|---|---|
| 9 | SSLLLLVTI | 16 |
| 229 | LPERSVLLP | 16 |
| 275 | LPPASLELS | 16 |
| 339 | AGDNLIITL | 16 |
| 360 | PAPPVETTY | 16 |
| 400 | VGLYVFKVT | 16 |
| 413 | NAFGEGFVN | 16 |
| 430 | VNLPPVAVV | 16 |
| 432 | LPPVAVVSP | 16 |
| 533 | AGPNHTITL | 16 |
| 582 | TPYLHLSAM | 16 |
| 593 | GDYTFQLKV | 16 |
| 637 | FPVESATLD | 16 |
| 809 | QPDPRKSGL | 16 |
| 846 | NVLDSDIKV | 16 |
| 875 | PPFKVLKAA | 16 |
| 900 | FLLFKVLRV | 16 |
| 962 | LAFTLIVLT | 16 |
| 989 | IRKKTKYTI | 16 |
| 2 | APPTGVLSS | 15 |
| 5 | TGVLSSLLL | 15 |
| 28 | GRTYSNAVI | 15 |
| 121 | LNRGSPSGI | 15 |
| 129 | IWGDSPEDI | 15 |
| 212 | DPELHYLNE | 15 |
| 236 | LPLPTTPSS | 15 |
| 306 | TPPTSAAPS | 15 |
| 317 | TPSELPISP | 15 |
| 358 | VAPAPPVET | 15 |
| 401 | GLYVFKVTV | 15 |
| 433 | PPVAVVSPQ | 15 |
| 497 | GNYSFRLTV | 15 |
| 530 | VANAGPNHT | 15 |
| 541 | LPQNSITLN | 15 |

TABLE XXXIIII-V1-continued

HLA-B5101-9mers-254P1D6B
Each peptide is a portion of SEQ ID NO: 3; each start position is specified, the length of peptide is 9 amino acids, and the end position for each peptide is the start position plus eight.

| Pos | 123456789 | score |
|---|---|---|
| 626 | VAVAGPDKE | 15 |
| 687 | GTYHFRLTV | 15 |
| 701 | LSSTSTLTV | 15 |
| 731 | LPNNSITLD | 15 |
| 759 | QSPAAGDVI | 15 |
| 784 | GVYTFHLRV | 15 |
| 835 | DTLVRQLAV | 15 |
| 839 | RQLAVLLNV | 15 |
| 859 | AHSDLSTVI | 15 |
| 1 | MAPPTGVLS | 14 |
| 33 | NAVISPNLE | 14 |
| 69 | LAWWFEGRC | 14 |
| 94 | GPIRSYLTF | 14 |
| 99 | YLTFVLRPV | 14 |
| 205 | VPAETQQDP | 14 |
| 225 | PAPKLPERS | 14 |
| 287 | VEKSPVLTV | 14 |
| 290 | SPVLTVTPG | 14 |
| 337 | VSAGDNLII | 14 |
| 347 | LPDNEVELK | 14 |
| 359 | APAPPVETT | 14 |
| 387 | QGHKQTLNL | 14 |
| 415 | FGEGFVNVT | 14 |
| 416 | GEGFVNVTV | 14 |
| 426 | PARRVNLPP | 14 |
| 475 | GPFIEEKTS | 14 |
| 509 | DGATNSTTA | 14 |
| 512 | TNSTTAALI | 14 |
| 516 | TAALIVNNA | 14 |
| 527 | YPPVANAGP | 14 |
| 531 | ANAGPNHTI | 14 |
| 607 | QQSTAVVTV | 14 |
| 624 | PPVAVAGPD | 14 |
| 667 | SAVEMENID | 14 |
| 709 | VAVKKENNS | 14 |

TABLE XXXIIII-V1-continued

HLA-B5101-9mers-254P1D6B
Each peptide is a portion of SEQ ID NO: 3; each start position is specified, the length of peptide is 9 amino acids, and the end position for each peptide is the start position plus eight.

| Pos | 123456789 | score |
|---|---|---|
| 761 | PAAGDVIDG | 14 |
| 762 | AAGDVIDGS | 14 |
| 800 | DTDTATVEV | 14 |
| 841 | LAVLLNVLD | 14 |
| 933 | SHLWMENLI | 14 |
| 981 | CKRQKRTKI | 14 |
| 17 | IAGCARKQC | 13 |
| 40 | LETTRIMRV | 13 |
| 47 | RVSHTFPVV | 13 |
| 88 | CEPKKMGPI | 13 |
| 141 | LPFLGKDWG | 13 |
| 159 | DYRELEKDL | 13 |
| 175 | EPRGSAEYT | 13 |
| 193 | GAFNSSVGD | 13 |
| 202 | SPAVPAETQ | 13 |
| 224 | TPAPKLPER | 13 |
| 238 | LPTTPSSGE | 13 |
| 270 | MPSHSLPPA | 13 |
| 285 | VTVEKSPVL | 13 |
| 310 | SAAPSESTP | 13 |
| 312 | APSESTPSE | 13 |
| 321 | LPISPTTAP | 13 |
| 328 | APRTVKELT | 13 |
| 336 | TVSAGDNLI | 13 |
| 338 | SAGDNLIIT | 13 |
| 362 | PPVETTYNY | 13 |
| 396 | SQLSVGLYV | 13 |
| 399 | SVGLYVFKV | 13 |
| 417 | EGFVNVTVK | 13 |
| 422 | VTVKPARRV | 13 |
| 425 | KPARRVNLP | 13 |
| 435 | VAVVSPQLQ | 13 |
| 446 | TLPLTSALI | 13 |
| 534 | GPNHTITLP | 13 |

TABLE XXXIIII-V1-continued

HLA-B5101-9mers-254P1D6B
Each peptide is a portion of SEQ ID NO: 3; each start position is specified, the length of peptide is 9 amino acids, and the end position for each peptide is the start position plus eight.

| Pos | 123456789 | score |
|---|---|---|
| 566 | LGPGSEGKH | 13 |
| 623 | RPPVAVAGP | 13 |
| 630 | GPDKELIFP | 13 |
| 665 | GPSAVEMEN | 13 |
| 673 | NIDKAIATV | 13 |
| 728 | VLVLPNNSI | 13 |
| 797 | GASDTDTAT | 13 |
| 803 | TATVEVQPD | 13 |
| 818 | VELTLQVGV | 13 |
| 910 | TAGCLLKCS | 13 |
| 918 | SGHGHCDPL | 13 |
| 923 | CDPLTKRCI | 13 |
| 954 | WSIFYVTVL | 13 |
| 959 | VTVLAFTLI | 13 |
| 960 | TVLAFTLIV | 13 |
| 961 | VLAFTLIVL | 13 |
| 1007 | MELRPKYGI | 13 |
| 1010 | RPKYGIKHR | 13 |
| 1050 | NPKVSMNGS | 13 |
| 52 | FPVVDCTAA | 12 |
| 58 | TAACCDLSS | 12 |
| 82 | CPHKENCEP | 12 |
| 89 | EPKKMGPIR | 12 |
| 116 | YGDMMLNRG | 12 |
| 136 | DIRKDLPFL | 12 |
| 169 | QPSGKQEPR | 12 |
| 188 | LPGSEGAFN | 12 |
| 240 | TTPSSGEVL | 12 |
| 241 | TPSSGEVLE | 12 |
| 248 | LEKEKASQL | 12 |
| 279 | SLELSSVTV | 12 |
| 304 | IPTPPTSAA | 12 |
| 311 | AAPSESTPS | 12 |
| 315 | ESTPSELPI | 12 |
| 329 | PRTVKELTV | 12 |

TABLE XXXIIII-V1-continued

HLA-B5101-9mers-254P1D6B
Each peptide is a portion of SEQ ID NO: 3; each start position is specified, the length of peptide is 9 amino acids, and the end position for each peptide is the start position plus eight.

| Pos | 123456789 | score |
|---|---|---|
| 355 | KAFVAPAPP | 12 |
| 361 | APPVETTYN | 12 |
| 366 | TTYNYEWNL | 12 |
| 367 | TYNYEWNLI | 12 |
| 414 | AFGEGFVNV | 12 |
| 451 | SALIDGSQS | 12 |
| 457 | SQSTDDTEI | 12 |
| 465 | IVSYHWEEI | 12 |
| 510 | GATNSTTAA | 12 |
| 513 | NSTTAALIV | 12 |
| 528 | PPVANAGPN | 12 |
| 532 | NAGPNHTIT | 12 |
| 538 | TITLPQNSI | 12 |
| 605 | SRQQSTAVV | 12 |
| 655 | IVFYHWEHV | 12 |
| 682 | TGLQVGTYH | 12 |
| 718 | PPRARAGGR | 12 |
| 741 | SRSTDDQRI | 12 |
| 745 | DDQRIVSYL | 12 |
| 747 | QRIVSYLWI | 12 |
| 760 | SPAAGDVID | 12 |
| 844 | LLNVLDSDI | 12 |
| 863 | LSTVIVFYV | 12 |
| 871 | VQSRPPFKV | 12 |
| 893 | LSKEKADFL | 12 |
| 898 | ADFLLFKVL | 12 |
| 937 | MENLIQRYI | 12 |
| 1032 | EFDSDQDTI | 12 |
| 1051 | PKVSMNGSI | 12 |
| 6 | GVLSSLLLL | 11 |
| 7 | VLSSLLLLV | 11 |
| 20 | CARKQCSEG | 11 |
| 56 | DCTAACCDL | 11 |
| 59 | AACCDLSSC | 11 |

TABLE XXXIIII-V1-continued

HLA-B5101-9mers-254P1D6B
Each peptide is a portion of
SEQ ID NO: 3; each start
position is specified, the
length of peptide is 9 amino
acids, and the end position
for each peptide is the start
position plus eight.

| Pos | 123456789 | score |
|-----|-----------|-------|
| 95  | PIRSYLTFV | 11    |
| 96  | IRSYLTFVL | 11    |
| 109 | RPAQLLDYG | 11    |
| 125 | SPSGIWGDS | 11    |
| 132 | DSPEDIRKD | 11    |
| 158 | DDYRELEKD | 11    |
| 180 | AEYTDWGLL | 11    |
| 203 | PAVPAETQQ | 11    |
| 206 | PAETQQDPE | 11    |
| 227 | PKLPERSVL | 11    |
| 264 | SGKEVLMPS | 11    |
| 276 | PPASLELSS | 11    |
| 280 | LELSSVTVE | 11    |
| 307 | PPTSAAPSE | 11    |
| 344 | IITLPDNEV | 11    |
| 350 | NEVELKAFV | 11    |
| 385 | IKQGHKQTL | 11    |
| 392 | TLNLSQLSV | 11    |
| 455 | DGSQSTDDT | 11    |
| 476 | PFIEEKTSV | 11    |
| 540 | TLPQNSITL | 11    |
| 551 | NQSSDDHQI | 11    |
| 553 | SSDDHQIVL | 11    |
| 609 | STAVVTVIV | 11    |
| 631 | PDKELIFPV | 11    |
| 636 | IFPVESATL | 11    |
| 645 | DGSSSSDDH | 11    |
| 670 | EMENIDKAI | 11    |
| 717 | SPPRARAGG | 11    |
| 730 | VLPNNSITL | 11    |
| 739 | DGSRSTDDQ | 11    |
| 757 | DGQSPAAGD | 11    |
| 766 | VIDGSDHSV | 11    |
| 798 | ASDTDTATV | 11    |

TABLE XXXIIII-V1-continued

HLA-B5101-9mers-254P1D6B
Each peptide is a portion of
SEQ ID NO: 3; each start
position is specified, the
length of peptide is 9 amino
acids, and the end position
for each peptide is the start
position plus eight.

| Pos  | 123456789 | score |
|------|-----------|-------|
| 814  | KSGLVELTL | 11    |
| 816  | GLVELTLQV | 11    |
| 830  | TEQRKDTLV | 11    |
| 836  | TLVRQLAVL | 11    |
| 840  | QLAVLLNVL | 11    |
| 872  | QSRPPFKVL | 11    |
| 877  | FKVLKAAEV | 11    |
| 882  | AAEVARNLH | 11    |
| 901  | LLFKVLRVD | 11    |
| 906  | LRVDTAGCL | 11    |
| 951  | NCEWSIFYV | 11    |
| 953  | EWSIFYVTV | 11    |
| 958  | YVTVLAFTL | 11    |
| 1013 | YGIKHRSTE | 11    |
| 1020 | TEHNSSLMV | 11    |
| 1045 | KMERGNPKV | 11    |
| 1062 | GASFSYCSK | 11    |

TABLE XXXIIII-V2

HLA-B5101-9mers-254P1D6B
Each peptide is a portion
of SEQ ID NO: 5; each
start position is specified,
the length of peptide is 9
amino acids, and the end
position for each peptide
is the start position plus
eight.

| Pos | 123456789 | score |
|-----|-----------|-------|
| 8   | YADDYRELE | 14    |
| 7   | EYADDYREL | 8     |
| 6   | SEYADDYRE | 6     |

TABLE XXXIIII-V3

HLA-B5101-9mers-254P1D6B
Each peptide is a portion of
SEQ ID NO:7; each start
position is specified, the
length of peptide is 9 amino
acids, and the end position
for each peptide is the start
position plus eight.

| Pos | 123456789 | score |
|---|---|---|
| 4 | LGWPSPCCA | 11 |
| 6 | WPSPCCARK | 11 |
| 8 | SPCCARKQC | 11 |
| 11 | CARKQCSEG | 11 |
| 2 | TRLGWPSPC | 5 |
| 7 | PSPCCARKQ | 5 |

TABLE XXXIIII-V5

HLA-B5101-9 mers-254P1D6B
Each peptide is a portion of
SEQ ID NO: 11; each start
position is specified, the
length of peptide is 9 amino
acids, and the end position
for each peptide is the start
position plus eight.

| Pos | 123456789 | score |
|---|---|---|
| 3 | DIRKDLTFL | 13 |
| 9 | TFLGKDWGL | 11 |
| 6 | KDLTFLGKD | 6 |

TABLE XXXIV-V1

HLA-A1 10 mers-254P1D6B
Each peptide is a portion of
SEQ ID NO: 3; each start
position is specified, the
length of peptide is 10
amino acids, and the end
position for each peptide is
the start position plus nine.

| Pos | 1234567890 | score |
|---|---|---|
| 459 | STDDTEIVSY | 33 |
| 553 | SSDDHQIVLY | 33 |
| 743 | STDDQRIVSY | 33 |
| 649 | SSDDHGIVFY | 31 |
| 173 | KQEPRGSAEY | 29 |
| 208 | ETQQDPELHY | 27 |
| 107 | VQRPAQLLDY | 26 |
| 1019 | STEHNSSLMV | 25 |
| 894 | SKEKADFLLF | 23 |
| 949 | ESNCEWSIFY | 23 |
| 986 | RTKIRKKTKY | 23 |
| 156 | YSDDYRELEK | 22 |
| 378 | PTDYQGEIKQ | 22 |
| 160 | YRELEKDLLQ | 20 |
| 359 | APAPPVETTY | 20 |
| 769 | GSDHSVALQL | 20 |
| 860 | HSDLSTVIVF | 20 |
| 394 | NLSQLSVGLY | 19 |
| 554 | SDDHQIVLYE | 19 |
| 72 | WFEGRCYLVS | 18 |
| 182 | YTDWGLLPGS | 18 |
| 299 | STEHSIPTPP | 18 |
| 347 | LPDNEVELKA | 18 |
| 592 | EGDYTFQLKV | 18 |
| 800 | DTDTATVEVQ | 18 |
| 829 | LTEQRKDTLV | 18 |
| 882 | AAEVARNLHM | 18 |
| 907 | RVDTAGCLLK | 18 |
| 1004 | QERMELRPKY | 18 |
| 286 | TVEKSPVLTV | 17 |
| 410 | SSENAFGEGF | 17 |
| 505 | VTDSDGATNS | 17 |
| 518 | ALIVNNAVDY | 17 |
| 569 | GSEGKHVVMQ | 17 |
| 601 | VTDSSRQQST | 17 |
| 680 | TVTGLQVGTY | 17 |
| 777 | QLTNLVEGVY | 17 |
| 792 | VTDSQGASDT | 17 |
| 861 | SDLSTVIVFY | 17 |
| 1058 | SIRNGASFSY | 17 |
| 22 | RKQCSEGRTY | 16 |
| 69 | LAWWFEGRCY | 16 |
| 134 | PEDIRKDLPF | 16 |
| 190 | GSEGAFNSSV | 16 |
| 210 | QQDPELHYLN | 16 |

TABLE XXXIV-V1-continued

HLA-A1 10 mers-254P1D6B
Each peptide is a portion of SEQ ID NO: 3; each start position is specified, the length of peptide is 10 amino acids, and the end position for each peptide is the start position plus nine.

| Pos | 1234567890 | score |
|---|---|---|
| 229 | LPERSVLLPL | 16 |
| 249 | EKEKASQLQE | 16 |
| 313 | PSESTPSELP | 16 |
| 361 | APPVETTYNY | 16 |
| 442 | LQELTLPLTS | 16 |
| 462 | DTEIVSYHWE | 16 |
| 490 | RLSNLDPGNY | 16 |
| 507 | DSDGATNSTT | 16 |
| 575 | VVMQGVQTPY | 16 |
| 586 | HLSAMQEGDY | 16 |
| 798 | ASDTDTATVE | 16 |
| 809 | QPDPRKSGLV | 16 |

TABLE XXXIV-V2

HLA-A1 10 mers-254P1D6B
Each peptide is a portion of SEQ ID NO: 5; each start position is specified, the length of peptide is 10 amino acids, and the end position for each peptide is the start position plus nine.

| Pos | 1234567890 | score |
|---|---|---|
| 9 | YADDYRELEK | 18 |
| 4 | EEMSEYADDY | 15 |
| 6 | MSEYADDYRE | 14 |
| 10 | ADDYRELEKD | 13 |
| 2 | GLEEMSEYAD | 11 |
| 3 | LEEMSEYADD | 10 |

TABLE XXXIV-V3

HLA-A1 10 mers-254P1D6B
Each peptide is a portion of SEQ ID NO: 7; each start position is specified, the length of peptide is 10 amino acids, and the end position for each peptide is the start position plus nine.

| Pos | 1234567890 | score |
|---|---|---|
| 1 | MTRLGWPSPC | 6 |
| 6 | WPSPCCARKQ | 6 |

TABLE XXXIV-V3-continued

HLA-A1-10 mers-254P1D6B
Each peptide is a portion of SEQ ID NO: 7; each start position is specified, the length of peptide is 10 amino acids, and the end position for each peptide is the start position plus nine.

| Pos | 1234567890 | score |
|---|---|---|
| 7 | PSPCCARKQC | 5 |
| 4 | LGWPSPCCAR | 4 |
| 8 | SPCCARKQCS | 2 |

TABLE XXXIV-V5

HLA-A1-10mers-254P1D6B
Each peptide is a portion of SEQ ID NO: 11; each start position is specified, the length of peptide is 10 amino acids, and the end position for each peptide is the start position plus nine.

| Pos | 1234567890 | score |
|---|---|---|
| 2 | PEDIRKDLTF | 16 |
| 1 | SPEDIRKDLT | 14 |
| 6 | RKDLTFLGKD | 12 |
| 5 | IRKDLTFLGK | 9 |

TABLE XXXV-V1

A0201-10mers-254P1D6B1
Each peptide is a portion of SEQ ID NO: 3; each start position is specified, the length of peptide is 10 amino acids, and the end position for each peptide is the start position plus nine.

| Pos | 1234567890 | score |
|---|---|---|
| 635 | LIFPVESATL | 27 |
| 343 | LIITLPDNEV | 25 |
| 345 | ITLPDNEVEL | 24 |
| 700 | GLSSTSTLTV | 24 |
| 39 | NLETTRIMRV | 23 |
| 112 | QLLDYGDMML | 23 |
| 326 | TTAPRTVKEL | 23 |
| 338 | SAGDNLIITL | 23 |
| 677 | AIATVTGLQV | 23 |
| 828 | QLTEQRKDTL | 23 |
| 862 | DLSTVIVFYV | 23 |
| 6 | GVLSSLLLLV | 22 |
| 436 | AVVSPQLQEL | 22 |

TABLE XXXV-V1-continued

A0201-10mers-254P1D6B1
Each peptide is a portion of SEQ ID NO: 3; each start position is specified, the length of peptide is 10 amino acids, and the end position for each peptide is the start position plus nine.

| Pos | 1234567890 | score |
|---|---|---|
| 539 | ITLPQNSITL | 22 |
| 576 | VMQGVQTPYL | 22 |
| 729 | LVLPNNSITL | 22 |
| 820 | LTLQVGVGQL | 22 |
| 836 | TLVRQLAVLL | 22 |
| 961 | VLAFTLIVLT | 22 |
| 1000 | NMDEQERMEL | 22 |
| 11 | LLLLVTIAGC | 21 |
| 429 | RVNLPPVAVV | 21 |
| 441 | QLQELTLPLT | 21 |
| 722 | RAGGRHVLVL | 21 |
| 835 | DTLVRQLAVL | 21 |
| 843 | VLLNVLDSDI | 21 |
| 905 | VLRVDTAGCL | 21 |
| 7 | VLSSLLLLVT | 20 |
| 45 | IMRVSHTFPV | 20 |
| 120 | MLNRGSPSGI | 20 |
| 128 | GIWGDSPEDI | 20 |
| 247 | VLEKEKASQL | 20 |
| 278 | ASLELSSVTV | 20 |
| 286 | TVEKSPVLTV | 20 |
| 398 | LSVGLYVFKV | 20 |
| 431 | NLPPVAVVSP | 20 |
| 445 | LTLPLTSALI | 20 |
| 692 | RLTVKDQQGL | 20 |
| 775 | ALQLTNLVEG | 20 |
| 797 | GASDTDTATV | 20 |
| 857 | IRAHSDLSTV | 20 |
| 892 | RLSKEKADFL | 20 |
| 960 | TVLAFTLIVL | 20 |
| 988 | KIRKKTKYTI | 20 |
| 217 | YLNESASTPA | 19 |
| 269 | LMPSHSLPPA | 19 |
| 391 | QTLNLSQLSV | 19 |
| 413 | NAFGEGFVNV | 19 |
| 765 | DVIDGSDHSV | 19 |
| 773 | SVALQLTNLV | 19 |
| 776 | LQLTNLVEGV | 19 |
| 901 | LLFKVLRVDT | 19 |
| 1054 | SMNGSIRNGA | 19 |
| 2 | APPTGVLSSL | 18 |
| 8 | LSSLLLLVTI | 18 |
| 12 | LLLVTIAGCA | 18 |
| 34 | AVISPNLETT | 18 |
| 98 | SYLTFVLRPV | 18 |
| 228 | KLPERSVLLP | 18 |
| 274 | SLPPASLELS | 18 |
| 295 | VTPGSTEHSI | 18 |
| 516 | TAALIVNNAV | 18 |
| 532 | NAGPNHTITL | 18 |
| 560 | VLYEWSLGPG | 18 |
| 606 | RQQSTAVVTV | 18 |
| 627 | AVAGPDKELI | 18 |
| 654 | GIVFYHWEHV | 18 |
| 672 | ENIDKAIATV | 18 |
| 721 | ARAGGRHVLV | 18 |
| 817 | LVELTLQVGV | 18 |
| 870 | YVQSRPPFKV | 18 |
| 950 | SNCEWSIFYV | 18 |
| 967 | IVLTGGFTWL | 18 |
| 94 | GPIRSYLTFV | 17 |
| 273 | HSLPPASLEL | 17 |
| 355 | KAFVAPAPPV | 17 |
| 357 | FVAPAPPVET | 17 |
| 393 | LNLSQLSVGL | 17 |
| 423 | TVKPARRVNL | 17 |
| 444 | ELTLPLTSAL | 17 |
| 452 | ALIDGSQSTD | 17 |
| 510 | GATNSTTAAL | 17 |
| 511 | ATNSTTAALI | 17 |
| 530 | VANAGPNHTI | 17 |

TABLE XXXV-V1-continued

A0201-10mers-254P1D6B1
Each peptide is a portion of SEQ ID NO: 3; each
start position is specified, the length of
peptide is 10 amino acids, and the end position
for each peptide is the start position plus
nine.

| Pos | 1234567890 | score |
|---|---|---|
| 537 | HTITLPQNSI | 17 |
| 727 | HVLVLPNNSI | 17 |
| 781 | LVEGVYTFHL | 17 |
| 811 | DPRKSGLVEL | 17 |
| 816 | GLVELTLQVG | 17 |
| 839 | RQLAVLLNVL | 17 |
| 848 | LDSDIKVQKI | 17 |
| 969 | LTGGFTWLCI | 17 |
| 1006 | RMELRPKYGI | 17 |
| 92 | KMGPIRSYLT | 16 |
| 167 | LLQPSGKQEP | 16 |
| 178 | GSAEYTDWGL | 16 |
| 186 | GLLPGSEGAF | 16 |
| 187 | LLPGSEGAFN | 16 |
| 209 | TQQDPELHYL | 16 |
| 229 | LPERSVLLPL | 16 |
| 284 | SVTVEKSPVL | 16 |
| 312 | APSESTPSEL | 16 |
| 334 | ELTVSAGDNL | 16 |
| 384 | EIKQGHKQTL | 16 |
| 400 | VGLYVFKVTV | 16 |
| 401 | GLYVFKVTVS | 16 |
| 415 | FGEGFVNVTV | 16 |
| 426 | PARRVNLPPV | 16 |
| 482 | TSVDSPVLRL | 16 |
| 518 | ALIVNNAVDY | 16 |
| 565 | SLGPGSEGKH | 16 |
| 626 | VAVAGPDKEL | 16 |
| 675 | DKAIATVTGL | 16 |
| 799 | SDTDTATVEV | 16 |
| 838 | VRQLAVLLNV | 16 |
| 856 | KIRAHSDLST | 16 |
| 879 | VLKAAEVARN | 16 |
| 896 | EKADFLLFKV | 16 |
| 899 | DFLLFKVLRV | 16 |

TABLE XXXV-V1-continued

A0201-10mers-254P1D6B1
Each peptide is a portion of SEQ ID NO: 3; each
start position is specified, the length of
peptide is 10 amino acids, and the end position
for each peptide is the start position plus
nine.

| Pos | 1234567890 | score |
|---|---|---|
| 900 | FLLFKVLRVD | 16 |
| 939 | NLIQRYIWDG | 16 |
| 955 | SIFYVTVLAF | 16 |
| 959 | VTVLAFTLIV | 16 |
| 965 | TLIVLTGGFT | 16 |
| 1019 | STEHNSSLMV | 16 |
| 5 | TGVLSSLLLL | 15 |
| 10 | SLLLLVTIAG | 15 |
| 63 | DLSSCDLAWW | 15 |
| 95 | PIRSYLTFVL | 15 |
| 103 | VLRPVQRPAQ | 15 |
| 149 | GLEEMSEYSD | 15 |
| 154 | SEYSDDYREL | 15 |
| 234 | VLLPLPTTPS | 15 |
| 235 | LLPLPTTPSS | 15 |
| 255 | QLQEQSSNSS | 15 |
| 268 | VLMPSHSLPP | 15 |
| 276 | PPASLELSSV | 15 |
| 279 | SLELSSVTVE | 15 |
| 303 | SIPTPPTSAA | 15 |
| 328 | APRTVKELTV | 15 |
| 335 | LTVSAGDNLI | 15 |
| 346 | TLPDNEVELK | 15 |
| 358 | VAPAPPVETT | 15 |
| 392 | TLNLSQLSVG | 15 |
| 459 | STDDTEIVSY | 15 |
| 464 | EIVSYHWEEI | 15 |
| 488 | VLRLSNLDPG | 15 |
| 515 | TTAALIVNNA | 15 |
| 524 | AVDYPPVANA | 15 |
| 630 | GPDKELIFPV | 15 |
| 668 | AVEMENIDKA | 15 |
| 720 | RARAGGRHVL | 15 |
| 728 | VLVLPNNSIT | 15 |
| 730 | VLPNNSITLD | 15 |
| 735 | SITLDGSRST | 15 |

TABLE XXXV-V1-continued

A0201-10mers-254P1D6B1
Each peptide is a portion of SEQ ID NO: 3; each start position is specified, the length of peptide is 10 amino acids, and the end position for each peptide is the start position plus nine.

| Pos | 1234567890 | score |
|---|---|---|
| 743 | STDDQRIVSY | 15 |
| 752 | YLWIRDGQSP | 15 |
| 754 | WIRDGQSPAA | 15 |
| 766 | VIDGSDHSVA | 15 |
| 767 | IDGSDHSVAL | 15 |
| 789 | HLRVTDSQGA | 15 |
| 813 | RKSGLVELTL | 15 |
| 815 | SGLVELTLQV | 15 |
| 829 | LTEQRKDTLV | 15 |
| 859 | AHSDLSTVIV | 15 |
| 873 | SRPPFKVLKA | 15 |
| 926 | LTKRCICSHL | 15 |
| 934 | HLWMENLIQR | 15 |
| 936 | WMENLIQRYI | 15 |
| 952 | CEWSIFYVTV | 15 |
| 26 | SEGRTYSNAV | 14 |
| 31 | YSNAVISPNL | 14 |
| 71 | WWFEGRCYLV | 14 |
| 91 | KKMGPIRSYL | 14 |
| 104 | LRPVQRPAQL | 14 |
| 135 | EDIRKDLPFL | 14 |
| 141 | LPFLGKDWGL | 14 |
| 143 | FLGKDWGLEE | 14 |
| 179 | SAEYTDWGLL | 14 |
| 190 | GSEGAFNSSV | 14 |
| 266 | KEVLMPSHSL | 14 |
| 323 | ISPTTAPRTV | 14 |
| 366 | TTYNYEWNLI | 14 |
| 389 | HKQTLNLSQL | 14 |
| 394 | NLSQLSVGLY | 14 |
| 438 | VSPQLQELTL | 14 |
| 451 | SALIDGSQST | 14 |
| 472 | EINGPFIEEK | 14 |
| 475 | GPFIEEKTSV | 14 |
| 494 | LDPGNYSFRL | 14 |

TABLE XXXV-V1-continued

A0201-10mers-254P1D6B1
Each peptide is a portion of SEQ ID NO: 3; each start position is specified, the length of peptide is 10 amino acids, and the end position for each peptide is the start position plus nine.

| Pos | 1234567890 | score |
|---|---|---|
| 502 | RLTVTDSDGA | 14 |
| 519 | LIVNNAVDYP | 14 |
| 540 | TLPQNSITLN | 14 |
| 557 | HQIVLYEWSL | 14 |
| 584 | YLHLSAMQEG | 14 |
| 604 | SSRQQSTAVV | 14 |
| 617 | VQPENNRPPV | 14 |
| 662 | HVRGPSAVEM | 14 |
| 684 | LQVGTYHFRL | 14 |
| 702 | SSTSTLTVAV | 14 |
| 744 | TDDQRIVSYL | 14 |
| 772 | HSVALQLTNL | 14 |
| 784 | GVYTFHLRVT | 14 |
| 821 | TLQVGVGQLT | 14 |
| 832 | QRKDTLVRQL | 14 |
| 840 | QLAVLLNVLD | 14 |
| 842 | AVLLNVLDSD | 14 |
| 845 | LNVLDSDIKV | 14 |
| 880 | LKAAEVARNL | 14 |
| 913 | CLLKCSGHGH | 14 |
| 962 | LAFTLIVLTG | 14 |
| 997 | ILDNMDEQER | 14 |
| 1103 | SEFDSDQDTI | 14 |
| 1 | MAPPTGVLSS | 13 |
| 13 | LLVTIAGCAR | 13 |
| 35 | VISPNLETTR | 13 |
| 50 | HTFPVVDCTA | 13 |
| 60 | ACCDLSSCDL | 13 |
| 78 | YLVSCPHKEN | 13 |
| 119 | MMLNRGSPSG | 13 |
| 198 | SVGDSPAVPA | 13 |
| 206 | PAETQQDPEL | 13 |
| 223 | STPAPKLPER | 13 |
| 225 | PAPKLPERSV | 13 |
| 227 | PKLPERSVLL | 13 |
| 238 | LPTTPSSGEV | 13 |

TABLE XXXV-V1-continued

A0201-10mers-254P1D6B1
Each peptide is a portion of SEQ ID NO: 3; each start position is specified, the length of peptide is 10 amino acids, and the end position for each peptide is the start position plus nine.

| Pos | 1234567890 | score |
|---|---|---|
| 260 | SSNSSGKEVL | 13 |
| 281 | ELSSVTVEKS | 13 |
| 285 | VTVEKSPVLT | 13 |
| 336 | TVSAGDNLII | 13 |
| 337 | VSAGDNLIIT | 13 |
| 352 | VELKAFVAPA | 13 |
| 395 | LSQLSVGLYV | 13 |
| 403 | YVFKVTVSSE | 13 |
| 411 | SENAFGEGFV | 13 |
| 414 | AFGEGFVNVT | 13 |
| 421 | NVTVKPARRV | 13 |
| 428 | RRVNLPPVAV | 13 |
| 485 | DSPVLRLSNL | 13 |
| 521 | VNNAVDYPPV | 13 |
| 547 | TLNGNQSSDD | 13 |
| 566 | LGPGSEGKHV | 13 |
| 633 | KELIFPVESA | 13 |
| 634 | ELIFPVESAT | 13 |
| 679 | ATVTGLQVGT | 13 |
| 705 | STLTVAVKKE | 13 |
| 778 | LTNLVEGVYT | 13 |
| 808 | VQPDPRKSGL | 13 |
| 844 | LLNVLDSDIK | 13 |
| 847 | VLDSDIKVQK | 13 |
| 884 | EVARNLHMRL | 13 |
| 893 | LSKEKADFLL | 13 |
| 897 | KADFLLFKVL | 13 |
| 906 | LRVDTAGCLL | 13 |
| 944 | YIWDGESNCE | 13 |
| 956 | IFYVTVLAFT | 13 |
| 957 | FYVTVLAFTL | 13 |
| 958 | YVTVLAFTLI | 13 |
| 1025 | SLMVSESEFD | 13 |
| 1044 | EKMERGNPKV | 13 |

TABLE XXXV-V2

HLA-A0201-10mers-254P16B
Each peptide is a portion of SEQ ID NO: 5; each start position is specified, the length of peptide is 10 amino acids, and the end position for each peptide is the start position plus nine.

| Pos | 1234567890 | score |
|---|---|---|
| 7 | SEYADDYREL | 15 |
| 2 | GLEEMSEYAD | 14 |
| 9 | YADDYRELEK | 10 |
| 1 | WGLEEMSEYA | 8 |
| 5 | EMSEYADDYR | 7 |
| 10 | ADDYRELEKD | 7 |

TABLE XXXV-V3

HLA-A0201-10mers-254P16B
Each peptide is a portion of SEQ ID NO: 7; each start position is specified, the length of peptide is 10 amino acids, and the end position for each peptide is the start position plus nine.

| Pos | 1234567890 | score |
|---|---|---|
| 3 | RLGWPSPCCA | 14 |
| 4 | LGWPSPCCAR | 6 |

TABLE XXXV-V5

HLA-A0201-10mers-254P16B
Each peptide is a portion of SEQ ID NO: 11; each start position is specified, the length of peptide is 10 amino acids, and the end position for each peptide is the start position plus nine.

| Pos | 1234567890 | score |
|---|---|---|
| 9 | LTFLGKDWGL | 18 |
| 3 | EDIRKDLTFL | 13 |

TABLE XXXVI-V1

HLA-A0203-10mers-254P1D6B
Each peptide is a portion of SEQ ID NO: 3; each start position is specified, the length of peptide is 10 amino acids, and the end position for each peptide is the start position plus nine.

| Pos | 1234567890 | score |
|---|---|---|
| 51 | TFPVVDCTAA | 19 |
| 303 | SIPTPPTSAA | 19 |
| 509 | DGATNSTTAA | 19 |
| 754 | WIRDGQSPAA | 19 |
| 874 | RPPFKVLKAA | 19 |
| 352 | VELKAFVAPA | 18 |

TABLE XXXVI-V1-continued

HLA-A0203-10mers-254P1D6B
Each peptide is a portion of SEQ ID NO: 3; each start position is specified, the length of peptide is 10 amino acids, and the end position for each peptide is the start position plus nine.

| Pos | 1234567890 | score |
|---|---|---|
| 524 | AVDYPPVANA | 18 |
| 620 | ENNRPPVAVA | 18 |
| 670 | EMENIDKAIA | 18 |
| 714 | ENNSPPRARA | 18 |
| 52 | FPVVDCTAAC | 17 |
| 304 | IPTPPTSAAP | 17 |
| 510 | GATNSTTAAL | 17 |
| 755 | IRDGQSPAAG | 17 |
| 875 | PPFKVLKAAE | 17 |
| 9 | SSLLLLVTIA | 10 |
| 12 | LLLVTIAGCA | 10 |
| 25 | CSEGRTYSNA | 10 |
| 50 | HTFPVVDCTA | 10 |
| 61 | CCDLSSCDLA | 10 |
| 102 | FVLRPVQRPA | 10 |
| 171 | SGKQEPRGSA | 10 |
| 185 | WGLLPGSEGA | 10 |
| 195 | FNSSVGDSPA | 10 |
| 198 | SVGDSPAVPA | 10 |
| 213 | PELHYLNESA | 10 |
| 217 | YLNESASTPA | 10 |
| 244 | SGEVLEKEKA | 10 |
| 269 | LMPSHSLPPA | 10 |
| 302 | HSIPTPPTSA | 10 |
| 319 | SELPISPTTA | 10 |
| 330 | RTVKELTVSA | 10 |
| 347 | LPDNEVELKA | 10 |
| 350 | NEVELKAFVA | 10 |
| 405 | FKVTVSSENA | 10 |
| 418 | GFVNVTVKPA | 10 |
| 427 | ARRVNLPPVA | 10 |
| 443 | QELTLPLTSA | 10 |
| 502 | RLTVTDSDGA | 10 |
| 508 | SDGATNSTTA | 10 |
| 515 | TTAALIVNNA | 10 |

TABLE XXXVI-V1-continued

HLA-A0203-10mers-254P1D6B
Each peptide is a portion of SEQ ID NO: 3; each start position is specified, the length of peptide is 10 amino acids, and the end position for each peptide is the start position plus nine.

| Pos | 1234567890 | score |
|---|---|---|
| 522 | NNAVDYPPVA | 10 |
| 580 | VQTPYLHLSA | 10 |
| 602 | TDSSRQQSTA | 10 |
| 618 | QPENNRPPVA | 10 |
| 633 | KELIFPVESA | 10 |
| 659 | HWEHVRGPSA | 10 |
| 668 | AVEMENIDKA | 10 |
| 701 | LSSTSTLTVA | 10 |
| 712 | KKENNSPPRA | 10 |
| 753 | LWIRDGQSPA | 10 |
| 766 | VIDGSDHSVA | 10 |
| 789 | HLRVTDSQGA | 10 |
| 795 | SQGASDTDTA | 10 |
| 833 | RKDTLVRQLA | 10 |
| 850 | SDIKVQKIRA | 10 |
| 873 | SRPPFKVLKA | 10 |
| 877 | FKVLKAAEVA | 10 |
| 889 | LHMRLSKEKA | 10 |
| 902 | LFKVLRVDTA | 10 |
| 954 | WSIFYVTVLA | 10 |
| 1054 | SMNGSIRNGA | 10 |
| 10 | SLLLLVTIAG | 9 |
| 13 | LLVTIAGCAR | 9 |
| 26 | SEGRTYSNAV | 9 |
| 62 | CDLSSCDLAW | 9 |
| 103 | VLRPVQRPAQ | 9 |
| 172 | GKQEPRGSAE | 9 |
| 186 | GLLPGSEGAF | 9 |
| 196 | NSSVGDSPAV | 9 |
| 199 | VGDSPAVPAE | 9 |
| 214 | ELHYLNESAS | 9 |
| 218 | LNESASTPAP | 9 |
| 245 | GEVLEKEKAS | 9 |
| 270 | MPSHSLPPAS | 9 |
| 320 | ELPISPTTAP | 9 |
| 331 | TVKELTVSAG | 9 |

TABLE XXXVI-V1-continued

HLA-A0203-10mers-254P1D6B
Each peptide is a portion of SEQ ID NO: 3; each start position is specified, the length of peptide is 10 amino acids, and the end position for each peptide is the start position plus nine.

| Pos | 1234567890 | score |
|---|---|---|
| 348 | PDNEVELKAF | 9 |
| 351 | EVELKAFVAP | 9 |
| 353 | ELKAFVAPAP | 9 |
| 406 | KVTVSSENAF | 9 |
| 419 | FVNVTVKPAR | 9 |
| 428 | RRVNLPPVAV | 9 |
| 444 | ELTLPLTSAL | 9 |
| 503 | LTVTDSDGAT | 9 |
| 516 | TAALIVNNAV | 9 |
| 523 | NAVDYPPVAN | 9 |
| 525 | VDYPPVANAG | 9 |
| 581 | QTPYLHLSAM | 9 |
| 603 | DSSRQQSTAV | 9 |
| 619 | PENNRPPVAV | 9 |
| 621 | NNRPPVAVAG | 9 |
| 634 | ELIFPVESAT | 9 |
| 660 | WEHVRGPSAV | 9 |
| 669 | VEMENIDKAI | 9 |
| 671 | MENIDKAIAT | 9 |
| 702 | SSTSTLTVAV | 9 |
| 713 | KENNSPPRAR | 9 |
| 715 | NNSPPRARAG | 9 |
| 767 | IDGSDHSVAL | 9 |
| 790 | LRVTDSQGAS | 9 |
| 796 | QGASDTDTAT | 9 |
| 834 | KDTLVRQLAV | 9 |
| 851 | DIKVQKIRAH | 9 |
| 878 | KVLKAAEVAR | 9 |
| 890 | HMRLSKEKAD | 9 |
| 903 | FKVLRVDTAG | 9 |
| 955 | SIFYVTVLAF | 9 |
| 1055 | MNGSIRNGAS | 9 |

TABLE XXXVI-V2

HLA-A0203-10mers-254P1D6B
Each peptide is a portion of SEQ ID NO: 5; each start position is specified, the length of peptide is 10 amino acids, and the end position for each peptide is the start position plus nine.

| Pos | 1234567890 | score |
|---|---|---|
| 1 | WGLEEMSEYA | 10 |
| 2 | GLEEMSEYAD | 9 |
| 3 | LEEMSEYADD | 8 |

TABLE XXXVI-V3

HLA-A0203-10mers-254P1D6B
Each peptide is a portion of SEQ ID NO: 7; each start position is specified, the length of peptide is 10 amino acids, and the end position for each peptide is the start position plus nine.

| Pos | 1234567890 | score |
|---|---|---|
| 3 | RLGWPSPCCA | 10 |
| 4 | LGWPSPCCAR | 9 |
| 5 | GWPSPCCARK | 8 |

TABLE XXXVI-V5

HLA-A0203-10mers-254P1D6B

| Pos | 1234567890 | score |
|---|---|---|
| No Results Found. | | |

TABLE XXXVII-V1

HLA-A3-10mers-254P1D6B
Each peptide is a portion of SEQ ID NO: 3; each start position is specified, the length of peptide is 10 amino acids, and the end position for each peptide is the start position plus nine.

| Pos | 1234567890 | score |
|---|---|---|
| 518 | ALIVNNAVDY | 29 |
| 847 | VLDSDIKVQK | 27 |
| 907 | RVDTAGCLLK | 27 |
| 397 | QLSVGLYVFK | 26 |
| 14 | LVTIAGCARK | 24 |
| 452 | ALIDGSQSTD | 24 |
| 777 | QLTNLVEGVY | 24 |
| 878 | KVLKAAEVAR | 24 |
| 47 | RVSHTFPVVD | 23 |
| 490 | RLSNLDPGNY | 23 |
| 680 | TVTGLQYGTY | 23 |

TABLE XXXVII-V1-continued

HLA-A3-10mers-254P1D6B
Each peptide is a portion of SEQ ID NO: 3; each
start position is specified, the length of
peptide is 10 amino acids, and the end position
for each peptide is the start position plus
nine.

| Pos | 1234567890 | score |
|---|---|---|
| 791 | RVTDSQGASD | 23 |
| 1008 | ELRPKYGIKH | 23 |
| 429 | RVNLPPVAVV | 22 |
| 662 | HVRGPSAVEM | 22 |
| 872 | QSRPPFKVLK | 22 |
| 186 | GLLPGSEGAF | 21 |
| 346 | TLPDNEVELK | 21 |
| 504 | TVTDSDGATN | 21 |
| 677 | AIATVIGLQV | 21 |
| 856 | KIRAHSDLST | 21 |
| 904 | KVLRVDTAGC | 21 |
| 1058 | SIRNGASFSY | 21 |
| 34 | AVISPNLETT | 20 |
| 35 | VISPNLETTR | 20 |
| 233 | SVLLPLPTTP | 20 |
| 292 | VLTVTPGSTE | 20 |
| 472 | EINGPFIEEK | 20 |
| 493 | NLDPGNYSFR | 20 |
| 655 | IVFYHWEHVR | 20 |
| 694 | TVKDQQGLSS | 20 |
| 805 | TVEVQPDPRK | 20 |
| 825 | GVGQLTEQRK | 20 |
| 836 | TLVRQLAVLL | 20 |
| 844 | LLNVLDSDIK | 20 |
| 886 | ARNLHMRLSK | 20 |
| 888 | NLHMRLSKEK | 20 |
| 76 | RCYLVSCPHK | 19 |
| 198 | SVGDSPAVPA | 19 |
| 247 | VLEKEKASQL | 19 |
| 357 | FVAPAPPVET | 19 |
| 401 | GLYVFKVTVS | 19 |
| 423 | TVKPARRVNL | 19 |
| 431 | NLPPVAVVSP | 19 |
| 565 | SLGPGSEGKH | 19 |
| 586 | HLSAMQEGDY | 19 |
| 687 | GTYHFRLTVK | 19 |

TABLE XXXVII-V1-continued

HLA-A3-10mers-254P1D6B
Each peptide is a portion of SEQ ID NO: 3; each
start position is specified, the length of
peptide is 10 amino acids, and the end position
for each peptide is the start position plus
nine.

| Pos | 1234567890 | score |
|---|---|---|
| 729 | LVLPNNSITL | 19 |
| 865 | TVIVFYVQSR | 19 |
| 895 | KEKADFLLFK | 19 |
| 913 | CLLKCSGHGH | 19 |
| 13 | LLVTIAGCAR | 18 |
| 103 | VLRPVQRPAQ | 18 |
| 166 | DLLQPSGKQE | 18 |
| 187 | LLPGSEGAFN | 18 |
| 246 | EVLEKEKASQ | 18 |
| 359 | APAPPVETTY | 18 |
| 392 | TLNLSQLSVG | 18 |
| 406 | KVTVSSENAF | 18 |
| 487 | PVLRLSNLDP | 18 |
| 600 | KVTDSSRQQS | 18 |
| 635 | LIFPVESATL | 18 |
| 703 | STSTLTVAVK | 18 |
| 704 | TSTLTVAVKK | 18 |
| 775 | ALQLTNLVEG | 18 |
| 784 | GVYTFHLRVT | 18 |
| 819 | ELTLQVGVGQ | 18 |
| 842 | AVLLNVLDSD | 18 |
| 853 | KVQKIRAHSD | 18 |
| 919 | GHGHCDPLTK | 18 |
| 960 | TVLAFTLIVL | 18 |
| 983 | RQKRTKIRKK | 18 |
| 988 | KIRKKTKYTI | 18 |
| 1043 | REKMERGNPK | 18 |
| 7 | VLSSLLLLVT | 17 |
| 22 | RKQCSEGRTY | 17 |
| 53 | PVVDCTAACC | 17 |
| 112 | QLLDYGDMML | 17 |
| 120 | MLNRGSPSGI | 17 |
| 137 | IRKDLPFLGK | 17 |
| 228 | KLPERSVLLP | 17 |
| 279 | SLELSSVTVE | 17 |

TABLE XXXVII-V1-continued

HLA-A3-10mers-254P1D6B
Each peptide is a portion of SEQ ID NO: 3; each start position is specified, the length of peptide is 10 amino acids, and the end position for each peptide is the start position plus nine.

| Pos | 1234567890 | score |
|---|---|---|
| 286 | TVEKSPVLTV | 17 |
| 324 | SPTTAPRTVK | 17 |
| 353 | ELKAFVAPAP | 17 |
| 394 | NLSQLSVGLY | 17 |
| 446 | TLPLTSALID | 17 |
| 559 | IVLYEWSLGP | 17 |
| 575 | VVMQGYQTPY | 17 |
| 614 | TVIVQPENNR | 17 |
| 634 | ELIFPVESAT | 17 |
| 700 | GLSSTSTLTV | 17 |
| 710 | AVKKENNSPP | 17 |
| 766 | VIDGSDHSVA | 17 |
| 828 | QLTEQRKDTL | 17 |
| 840 | QLAVLLNVLD | 17 |
| 846 | NVLDSDIKVQ | 17 |
| 892 | RLSKEKADFL | 17 |
| 905 | VLRVDTAGCL | 17 |
| 934 | HLWMENLIQR | 17 |
| 955 | SIFYVTVLAF | 17 |
| 965 | TLIVLTGGFT | 17 |
| 985 | KRTKIRKKTK | 17 |
| 997 | ILDNMDEQER | 17 |
| 11 | LLLLVTIAGC | 16 |
| 12 | LLLVTIAGCA | 16 |
| 44 | RIMRVSHTFP | 16 |
| 106 | PVQRPAQLLD | 16 |
| 143 | FLGKDWGLEE | 16 |
| 219 | NESASTPAPK | 16 |
| 234 | VLLPLPTTPS | 16 |
| 268 | VLMPSHSLPP | 16 |
| 280 | LELSSVTVEK | 16 |
| 291 | PVLTVTPGST | 16 |
| 331 | TVKELTVSAG | 16 |
| 351 | EVELKAEVAP | 16 |
| 399 | SVGLYYFKVT | 16 |
| 430 | VNLPPVAVVS | 16 |
| 524 | AVDYPPYANA | 16 |
| 560 | VLYEWSLGPG | 16 |
| 598 | QLKVTDSSRQ | 16 |
| 627 | AVAGPDKELI | 16 |
| 673 | NIDKAIATVT | 16 |
| 752 | YLWIRDGQSP | 16 |
| 765 | DVIDGSDHSV | 16 |
| 780 | NLVEGVYTFH | 16 |
| 807 | EVQPDPRKSG | 16 |
| 837 | LVRQLAVLLN | 16 |
| 843 | VLLNVLDSDI | 16 |
| 879 | VLKAAEVARN | 16 |
| 900 | FLLFKVLRVD | 16 |
| 925 | PLTKRCICSH | 16 |
| 966 | LIVLTGGFTW | 16 |
| 967 | IVLTGGFTWL | 16 |
| 976 | LCICCCKRQK | 16 |
| 1007 | MELRPKYGIK | 16 |
| 6 | GVLSSLLLLV | 15 |
| 10 | SLLLLYIIAG | 15 |
| 16 | TIAGCARKQC | 15 |
| 95 | PIRSYLIFVL | 15 |
| 99 | YLTFVLRPVQ | 15 |
| 102 | FVLRPYQRPA | 15 |
| 107 | VQRPAQLLDY | 15 |
| 164 | EKDLLQPSGK | 15 |
| 173 | KQEPRGSAEY | 15 |
| 204 | AVPAETQQDP | 15 |
| 255 | QLQEQSSNSS | 15 |
| 257 | QEQSSNSSGK | 15 |
| 267 | EVLMPSHSLP | 15 |
| 284 | SVTVEKSPVL | 15 |
| 336 | TVSAGDNLII | 15 |
| 342 | NLIITLPDNE | 15 |
| 344 | IITLPDNEVE | 15 |

TABLE XXXVII-V1-continued

HLA-A3-10mers-254P1D6B
Each peptide is a portion of SEQ ID NO: 3; each start position is specified, the length of peptide is 10 amino acids, and the end position for each peptide is the start position plus nine.

| Pos | 1234567890 | score |
|---|---|---|
| 403 | YVFKVTVSSE | 15 |
| 416 | GEGFVNVTVK | 15 |
| 419 | FVNVTVKPAR | 15 |
| 444 | ELTLPLTSAL | 15 |
| 547 | TLNGNQSSDD | 15 |
| 616 | IVQPENNRPP | 15 |
| 624 | PPVAVAGPDK | 15 |
| 643 | TLDGSSSSDD | 15 |
| 816 | GLVELTLQVG | 15 |
| 817 | LVELTLQVGV | 15 |
| 884 | EVARNLHMRL | 15 |
| 901 | LLFKVLRVDT | 15 |
| 961 | VLAFTLIVLT | 15 |
| 41 | ETTRIMRVSH | 14 |
| 63 | DLSSCDLAWW | 14 |
| 156 | YSDDYRELEK | 14 |
| 214 | ELHYLNESAS | 14 |
| 274 | SLPPASLELS | 14 |
| 278 | ASLELSSVTV | 14 |
| 322 | PISPTTAPRT | 14 |
| 377 | HPTDYQGEIK | 14 |
| 459 | STDDTEIVSY | 14 |
| 488 | VLRLSNLDPG | 14 |
| 502 | RLTVTDSDGA | 14 |
| 558 | QIVLYEWSLG | 14 |
| 564 | WSLGPGSEGK | 14 |
| 574 | HVVMQGVQTP | 14 |
| 621 | NNRPPVAVAG | 14 |
| 683 | GLQVGTYHFR | 14 |
| 692 | RLTVKPQQGL | 14 |
| 720 | RARAGGRHVL | 14 |
| 727 | HVLVLPNNSI | 14 |
| 728 | VLVLPNNSIT | 14 |
| 743 | STDDQRIVSY | 14 |
| 830 | TEQRKDTLVR | 14 |
| 851 | DIKVQKIRAH | 14 |

TABLE XXXVII-V1-continued

HLA-A3-10mers-254P1D6B
Each peptide is a portion of SEQ ID NO: 3; each start position is specified, the length of peptide is 10 amino acids, and the end position for each peptide is the start position plus nine.

| Pos | 1234567890 | score |
|---|---|---|
| 979 | CCCKRQKRTK | 14 |
| 996 | TILDNMDEQE | 14 |

TABLE XXXVII-V2

HLA-A3-10mers-254P1D6B
Each peptide is a portion of SEQ ID NO: 5; each start position is specified, the length of peptide is 10 amino acids, and the end position for each peptide is the start position plus nine.

| Pos | 1234567890 | score |
|---|---|---|
| 9 | YADDYRELEK | 14 |
| 2 | GLEEMSEYAD | 12 |
| 4 | EEMSEYADDY | 9 |
| 7 | SEYADDYREL | 7 |

TABLE XXXVII-V3

HLA-A3-10mers-254P1D6B
Each peptide is a portion of SEQ ID NO: 7; each start position is specified, the length of peptide is 10 amino acids, and the end position for each peptide is the start position plus nine.

| Pos | 1234567890 | score |
|---|---|---|
| 3 | RLGWPSPCCA | 15 |
| 5 | GWPSPCCARK | 13 |
| 1 | MTRLGWPSPC | 8 |
| 4 | LGWPSPCCAR | 8 |
| 10 | CCARKQCSEG | 7 |

TABLE XXXVII-V5

HLA-A3-10mers-254P1D6B
Each peptide is a portion of SEQ ID NO: 11; each start position is specified, the length of peptide is 10 amino acids, and the end position for each peptide is the start position plus nine.

| Pos | 1234567890 | score |
|---|---|---|
| 5 | IRKDLTFLGK | 17 |
| 2 | PEDIRKDLTF | 12 |
| 4 | DIRKDLTFLG | 11 |
| 8 | DLTFLGKDWG | 11 |

TABLE XXXVII-V5-continued

HLA-A3-10mers-254P1D6B
Each peptide is a portion of SEQ ID NO: 11;
each start position is specified, the length of
peptide is 10 amino acids, and the end position
for each peptide is the start position plus nine.

| Pos | 1234567890 | score |
|---|---|---|
| 7 | KDLTFLGKDW | 8 |

TABLE XXXVIII-V1

HLA-A26-10mers-254P1D6B
Each peptide is a portion of SEQ ID NO: 3; each
start position is specified, the length of
peptide is 10 amino acids, and the end position
for each peptide is the start position plus nine.

| Pos | 1234567890 | score |
|---|---|---|
| 208 | ETQQDPELHY | 29 |
| 680 | TVTGLQVGTY | 28 |
| 835 | DTLVRQLAVL | 28 |
| 884 | EVARNLHMRL | 28 |
| 365 | ETTYNYEWNL | 27 |
| 436 | AVVSPQLQEL | 27 |
| 135 | EDIRKDLPFL | 26 |
| 459 | STDDTEIVSY | 25 |
| 743 | STDDQRIVSY | 25 |
| 765 | DVIDGSDHSV | 24 |
| 960 | TVLAFTLIVL | 24 |
| 246 | EVLEKEKASQ | 23 |
| 384 | EIKQGHKQTL | 23 |
| 955 | SIFYVTVLAF | 23 |
| 326 | TTAPRTVKEL | 22 |
| 807 | EVQPDPRKSG | 22 |
| 820 | LTLQVGVGQL | 22 |
| 953 | EWSIFYVTVL | 22 |
| 151 | EEMSEYSDDY | 21 |
| 267 | EVLMPSHSLP | 21 |
| 351 | EVELKAFVAP | 21 |
| 444 | ELTLPLTSAL | 21 |
| 485 | DSPVLRLSNL | 21 |
| 729 | LVLPNNSITL | 21 |
| 949 | ESNCEWSIFY | 21 |
| 1038 | DTIFSREKME | 21 |
| 34 | AVISPNLETT | 20 |
| 41 | ETTRIMRVSH | 20 |

TABLE XXXVIII-V1-continued

HLA-A26-10mers-254P1D6B
Each peptide is a portion of SEQ ID NO: 3; each
start position is specified, the length of
peptide is 10 amino acids, and the end position
for each peptide is the start position plus nine.

| Pos | 1234567890 | score |
|---|---|---|
| 220 | ESASTPAPKL | 20 |
| 284 | SVTVEKSPVL | 20 |
| 334 | ELTVSAGDNL | 20 |
| 403 | YVFKVTVSSE | 20 |
| 406 | KVTVSSENAF | 20 |
| 423 | TVKPARRVNL | 20 |
| 480 | EKTSVDSPVL | 20 |
| 575 | VVMQGVQTPY | 20 |
| 672 | ENIDKAIATV | 20 |
| 675 | DKAIATVTGL | 20 |
| 800 | DTDTATVEVQ | 20 |
| 802 | DTATVEVQPD | 20 |
| 811 | DPRKSGLVEL | 20 |
| 865 | TVIVFYVQSR | 20 |
| 909 | DTAGCLLKCS | 20 |
| 147 | DWGLEEMSEY | 19 |
| 239 | PTTPSSGEVL | 19 |
| 331 | TVKELTVSAG | 19 |
| 464 | EIVSYHWEEI | 19 |
| 482 | TSVDSPVLRL | 19 |
| 539 | ITLPQNSITL | 19 |
| 574 | HVVMQGVQTP | 19 |
| 986 | RTKIRKKTKY | 19 |
| 1032 | EFDSDQDTIF | 19 |
| 5 | TGVLSSLLLL | 18 |
| 132 | DSPEDIRKDL | 18 |
| 159 | DYRELEKDLL | 18 |
| 472 | EINGPFIEEK | 18 |
| 611 | AVVTVIVQPE | 18 |
| 635 | LIFPVESATL | 18 |
| 781 | LVEGVYTFHL | 18 |
| 967 | IVLTGGFTWL | 18 |
| 4 | PTGVLSSLLL | 17 |
| 181 | EYTDWGLLPG | 17 |
| 286 | TVEKSPVLTV | 17 |

TABLE XXXVIII-V1-continued

HLA-A26-10mers-254P1D6B
Each peptide is a portion of SEQ ID NO: 3; each start position is specified, the length of peptide is 10 amino acids, and the end position for each peptide is the start position plus nine.

| Pos | 1234567890 | score |
|---|---|---|
| 345 | ITLPDNEVEL | 17 |
| 851 | DIKVQKIRAH | 17 |
| 926 | LTKRCICSHL | 17 |
| 964 | FTLIVLTGGF | 17 |
| 6 | GVLSSLLLLV | 16 |
| 107 | VQRPAQLLDY | 16 |
| 158 | DDYRELEKDL | 16 |
| 281 | ELSSVTVEKS | 16 |
| 315 | ESTPSELPIS | 16 |
| 338 | SAGDNLIITL | 16 |
| 462 | DTEIVSYHWE | 16 |
| 483 | SVDSPVLRLS | 16 |
| 553 | SSDDHQIVLY | 16 |
| 595 | YTFQLKVTDS | 16 |
| 634 | ELIFPVESAT | 16 |
| 649 | SSDDHGIVFY | 16 |
| 772 | HSVALQLTNL | 16 |
| 786 | YTFHLRVTDS | 16 |
| 861 | SDLSTVIVFY | 16 |
| 896 | EKADFLLFKV | 16 |
| 935 | LWMENLIQRY | 16 |
| 1047 | ERGNPKVSMN | 16 |
| 1058 | SIRNGASFSY | 16 |
| 29 | RTYSNAVISP | 15 |
| 53 | PVVDCTAACC | 15 |
| 74 | EGRCYLVSCP | 15 |
| 90 | PKKMGPIRSY | 15 |
| 348 | PDNEVELKAF | 15 |
| 394 | NLSQLSVGLY | 15 |
| 417 | EGFVNVTVKP | 15 |
| 471 | EEINGPFIEE | 15 |
| 504 | TVTDSDGATN | 15 |
| 614 | TVIVQPENNR | 15 |
| 638 | PVESATLDGS | 15 |
| 668 | AVEMENIDKA | 15 |
| 694 | TVKDQQGLSS | 15 |
| 783 | EGVYTFHLRV | 15 |
| 837 | LVRQLAVLLN | 15 |
| 842 | AVLLNVLDSD | 15 |
| 846 | NVLDSDIKVQ | 15 |
| 2 | APPTGVLSSL | 14 |
| 42 | TTRIMRVSHT | 14 |
| 43 | TRIMRVSHTF | 14 |
| 50 | HTFPVVDCTA | 14 |
| 162 | ELEKDLLQPS | 14 |
| 209 | TQQDPELHYL | 14 |
| 285 | VTVEKSPVLT | 14 |
| 389 | HKQTLNLSQL | 14 |
| 396 | SQLSVGLYVF | 14 |
| 429 | RVNLPPVAVV | 14 |
| 503 | LTVTDSDGAT | 14 |
| 514 | STTAALIVNN | 14 |
| 518 | ALIVNNAVDY | 14 |
| 524 | AVDYPPVANA | 14 |
| 579 | GVQTPYLHLS | 14 |
| 581 | QTPYLHLSAM | 14 |
| 609 | STAVVTVIVQ | 14 |
| 620 | ENNRPPVAVA | 14 |
| 655 | IVFYHWEHVR | 14 |
| 661 | EHVRGPSAVE | 14 |
| 705 | STLTVAVKKE | 14 |
| 744 | TDDQRIVSYL | 14 |
| 749 | IVSYLWIRDG | 14 |
| 779 | TNLVEGVYTF | 14 |
| 784 | GVYTFHLRVT | 14 |
| 791 | RVTDSQGASD | 14 |
| 804 | ATVEVQPDPR | 14 |
| 823 | QVGVGQLTEQ | 14 |
| 831 | EQRKDTLVRQ | 14 |
| 832 | QRKDTLVRQL | 14 |
| 864 | STVIVFYVQS | 14 |

TABLE XXXVIII-V1-continued

HLA-A26-10mers-254P1D6B
Each peptide is a portion of SEQ ID NO: 3; each start position is specified, the length of peptide is 10 amino acids, and the end position for each peptide is the start position plus nine.

| Pos | 1234567890 | score |
|---|---|---|
| 867 | IVFYVQSRPP | 14 |
| 906 | LRVDTAGCLL | 14 |
| 1003 | EQERMEKRPK | 14 |
| 1008 | ELRPKYGIKH | 14 |

TABLE XXXVIII-V2

HLA-A26-10mers-254P1D6B
Each peptide is a portion of SEQ ID NO: 5; each start position is specified, the length of peptide is 10 amino acids, and the end position for each peptide is the start position plus nine.

| Pos | 1234567890 | score |
|---|---|---|
| 4 | EEMSEYADDY | 21 |
| 5 | EMSEYADDYR | 12 |
| 8 | EYADDYRELE | 11 |

TABLE XXXVIII-V3

HLA-A26-10mers-254P1D6B
Each peptide is a portion of SEQ ID NO: 7; each start position is specified, the length of peptide is 10 amino acids, and the end position for each peptide is the start position plus nine.

| Pos | 1234567890 | score |
|---|---|---|
| 1 | MTRLGWPSPC | 9 |

TABLE XXXVIII-V5

HLA-A26-10mers-254P1D6B
Each peptide is a portion of SEQ ID NO: 11; each start position is specified, the length of peptide is 10 amino acids, and the end position for each peptide is the start position plus nine.

| Pos | 1234567890 | score |
|---|---|---|
| 3 | EDIRKDLTFL | 26 |
| 9 | LTFLGKDWGL | 20 |
| 4 | DIRKDLTFLG | 12 |

TABLE XXXIX-V1

HLA-B0702-10mers-254P1D6B
Each peptide is a portion of SEQ ID NO: 3; each start position is specified, the length of peptide is 10 amino acids, and the end position for each peptide is the start position plus nine.

| Pos | 1234567890 | score |
|---|---|---|
| 811 | DPRKSGLVEL | 25 |
| 226 | APKLPERSVL | 24 |
| 312 | APSESTPSEL | 24 |
| 229 | LPERSVLLPL | 23 |
| 2 | APPTGVLSSL | 22 |
| 3 | PPTGVLSSLL | 22 |
| 328 | APRTVKELTV | 22 |
| 433 | PPVAVVSPQL | 22 |
| 105 | RPVQRPAQLL | 21 |
| 141 | LPFLGKDWGL | 20 |
| 317 | TPSELPISPT | 19 |
| 347 | LPDNEVELKA | 19 |
| 630 | GPDKELIFPV | 19 |
| 665 | GPSAVEMENI | 19 |
| 94 | GPIRSYLTFV | 18 |
| 495 | DPGNYSFRLT | 18 |
| 567 | GPGSEGKHVV | 18 |
| 618 | QPENNRPPVA | 18 |
| 722 | RAGGRHVLVL | 18 |
| 809 | QPDPRKSGLV | 18 |
| 874 | RPPFKVLKAA | 18 |
| 37 | SPNLETTRIM | 17 |
| 276 | PPASLELSSV | 17 |
| 475 | GPFIEEKTSV | 17 |
| 813 | RKSGLVELTL | 17 |
| 238 | LPTTPSSGEV | 16 |
| 720 | RARAGGRHVL | 16 |
| 953 | EWSIFYVTVL | 16 |
| 1050 | NPKVSMNGSI | 16 |
| 91 | KKMGPIRSYL | 15 |
| 169 | QPSGKQEPRG | 15 |
| 175 | EPRGSAEYTD | 15 |
| 241 | TPSSGEVLEK | 15 |
| 359 | APAPPVETTY | 15 |
| 386 | KQGHKQTLNL | 15 |
| 425 | KPARRVNLPP | 15 |

TABLE XXXIX-V1-continued

HLA-B0702-10mers-254P1D6B
Each peptide is a portion of SEQ ID NO: 3; each start position is specified, the length of peptide is 10 amino acids, and the end position for each peptide is the start position plus nine.

| Pos | 1234567890 | score |
|---|---|---|
| 767 | IDGSDHSVAL | 15 |
| 892 | RLSKEKADFL | 15 |
| 95 | PIRSYLTFVL | 14 |
| 125 | SPSGIWGDSP | 14 |
| 270 | MPSHSLPPAS | 14 |
| 304 | IPTPPTSAAP | 14 |
| 345 | ITLPDNEVEL | 14 |
| 423 | TVKPARRVNL | 14 |
| 440 | PQLQELTLPL | 14 |
| 534 | GPNHTITLPQ | 14 |
| 576 | VMQGVQTPYL | 14 |
| 871 | VQSRPPFKVL | 14 |
| 897 | KADFLLFKVL | 14 |
| 4 | PTGVLSSLLL | 13 |
| 52 | FPVVDCTAAC | 13 |
| 70 | AWWFEGRCYL | 13 |
| 135 | EDIRKDLPFL | 13 |
| 220 | ESASTPAPKL | 13 |
| 227 | PKLPERSVLL | 13 |
| 273 | HSLPPASLEL | 13 |
| 275 | LPPASLELSS | 13 |
| 321 | LPISPTTAPR | 13 |
| 324 | SPTTAPRTVK | 13 |
| 326 | TTAPRTVKEL | 13 |
| 361 | APPVETTYNY | 13 |
| 444 | ELTLPLTSAL | 13 |
| 480 | EKTSVDSPVL | 13 |
| 482 | TSVDSPVLRL | 13 |
| 510 | GATNSTTAAL | 13 |
| 532 | NAGPNHTITL | 13 |
| 541 | LPQNSITLNG | 13 |
| 552 | QSSDDHQIVL | 13 |
| 590 | MQEGDYTFQL | 13 |
| 637 | FPVESATLDG | 13 |
| 675 | DKAIATVTGL | 13 |

TABLE XXXIX-V1-continued

HLA-B0702-10mers-254P1D6B
Each peptide is a portion of SEQ ID NO: 3; each start position is specified, the length of peptide is 10 amino acids, and the end position for each peptide is the start position plus nine.

| Pos | 1234567890 | score |
|---|---|---|
| 718 | PPRARAGGRH | 13 |
| 721 | ARAGGRHVLV | 13 |
| 731 | LPNNSITLDG | 13 |
| 760 | SPAAGDVIDG | 13 |
| 769 | GSDHSVALQL | 13 |
| 781 | LVEGVYTFHL | 13 |
| 839 | RQLAVLLNVL | 13 |
| 859 | AHSDLSTVIV | 13 |
| 875 | PPFKVLKAAE | 13 |
| 931 | ICSHLWMENL | 13 |
| 967 | IVLTGGFTWL | 13 |
| 989 | IRKKTKYTIL | 13 |
| 5 | TGVLSSLLLL | 12 |
| 31 | YSNAVISPNL | 12 |
| 60 | ACCDLSSCDL | 12 |
| 82 | CPHKENCEPK | 12 |
| 89 | EPKKMGPIRS | 12 |
| 109 | RPAQLLDYGD | 12 |
| 159 | DYRELEKDLL | 12 |
| 202 | SPAVPAETQQ | 12 |
| 205 | VPAETQQDPE | 12 |
| 224 | TPAPKLPERS | 12 |
| 231 | ERSVLLPLPT | 12 |
| 239 | PTTPSSGEVL | 12 |
| 284 | SVTVEKSPVL | 12 |
| 290 | SPVLTVTPGS | 12 |
| 393 | LNLSQLSVGL | 12 |
| 427 | ARRVNLPPVA | 12 |
| 432 | LPPVAVVSPQ | 12 |
| 436 | AVVSPQLQEL | 12 |
| 438 | VSPQLQELTL | 12 |
| 494 | LDPGNYSFRL | 12 |
| 528 | PPVANAGPNH | 12 |

TABLE XXXIX-V1-continued

HLA-B0702-10mers-254P1D6B
Each peptide is a portion of SEQ ID NO: 3; each start position is specified, the length of peptide is 10 amino acids, and the end position for each peptide is the start position plus nine.

| Pos | 1234567890 | score |
|---|---|---|
| 531 | ANAGPNHTIT | 12 |
| 539 | ITLPQNSITL | 12 |
| 578 | QGVQTPYLHL | 12 |
| 623 | RPPVAVAGPD | 12 |
| 624 | PPVAVAGPDK | 12 |
| 635 | LIFPVESATL | 12 |
| 662 | HVRGPSAVEM | 12 |
| 684 | LQVGTYHFRL | 12 |
| 698 | QQGLSSTSTL | 12 |
| 744 | TDDQRIVSYL | 12 |
| 772 | HSVALQLTNL | 12 |
| 835 | DTLVRQLAVL | 12 |
| 836 | TLVRQLAVLL | 12 |
| 856 | KIRAHSDLST | 12 |
| 880 | LKAAEVARNL | 12 |
| 884 | EVARNLHMRL | 12 |
| 905 | VLRVDTAGCL | 12 |
| 917 | CSGHGHCDPL | 12 |
| 960 | TVLAFTLIVL | 12 |
| 1000 | NMDEQERMEL | 12 |
| 1017 | HRSTEHNSSL | 12 |
| 1046 | MERGNPKVSM | 12 |

TABLE XXXIX-V2

HLA-B0702-10mers-254P1D6B
Each peptide is a portion of SEQ ID NO: 5; each start position is specified, the length of peptide is 10 amino acids, and the end position for each peptide is the start position plus nine.

| Pos | 1234567890 | score |
|---|---|---|
| 7 | SEYADDYREL | 11 |
| 1 | WGLEEMSEYA | 6 |

TABLE XXXIX-V3

HLA-B0702-10mers-254P1D6B
Each peptide is a portion of SEQ ID NO: 7; each start position is specified, the length of peptide is 10 amino acids, and the end position for each peptide is the start position plus nine.

| Pos | 1234567890 | score |
|---|---|---|
| 6 | WPSPCCARKQ | 13 |
| 8 | SPCCARKQCS | 10 |
| 3 | RLGWPSPCCA | 8 |

TABLE XXXIX-V5

HLA-B0702-10mers-254P1D6B
Each peptide is a portion of SEQ ID NO: 11; each start position is specified, the length of peptide is 10 amino acids, and the end position for each peptide is the start position plus nine.

| Pos | 1234567890 | score |
|---|---|---|
| 1 | SPEDIRKDLT | 16 |
| 3 | EDIRKDLTFL | 13 |
| 9 | LTFLGKDWGL | 10 |
| 2 | PEDIRKDLTF | 9 |

TABLE XL-V1

HLA-B08-10mers-254P1D6B

| Pos | 1234567890 | score |
|---|---|---|
| NoResultsFound. | | |

TABLE XL-V2

HLA-B08-10mers-254P1D6B

| Pos | 1234567890 | score |
|---|---|---|
| NoResultsFound. | | |

TABLE XL-V3

HLA-B08-10mers-254P1D6B

| Pos | 1234567890 | score |
|---|---|---|
| NoResultsFound. | | |

TABLE XL-V5

HLA-B08-10mers-254P1D6B

| Pos | 1234567890 | score |
|---|---|---|
| NoResultsFound. | | |

TABLE XLI-V1

HLA-B1510-10mers-254P1D6B

| Pos | 1234567890 | score |
|---|---|---|
| NoResultsFound. | | |

TABLE XLI-V2

HLA-B1510-10mers-254P1D6B

| Pos | 1234567890 | score |
|---|---|---|
| NoResultsFound. | | |

TABLE XLI-V3

HLA-B1510-10mers-254P1D6B

| Pos | 1234567890 | score |
|---|---|---|
| NoResultsFound. | | |

TABLE XLI-V5

HLA-B1510-10mers-254P1D6B

| Pos | 1234567890 | score |
|---|---|---|
| NoResultsFound. | | |

TABLE XLII-V1

HLA-B2705-10mers-254P1D6B

| Pos | 1234567890 | score |
|---|---|---|
| NoResultsFound. | | |

TABLE XLII-V2

HLA-B2705-10mers-254P1D6B

| Pos | 1234567890 | score |
|---|---|---|
| NoResultsFound. | | |

TABLE XLII-V3

HLA-B2705-10mers-254P1D6B

| Pos | 1234567890 | score |
|---|---|---|
| NoResultsFound. | | |

TABLE XLII-V5

HLA-B2705-10mers-254P1D6B

| Pos | 1234567890 | score |
|---|---|---|
| NoResultsFound. | | |

TABLE XLIII-V1

HLA-B2709-10mers-254P1D6B

| Pos | 1234567890 | score |
|---|---|---|
| NoResultsFound. | | |

TABLE XLIII-V2

HLA-B2709-10mers-254P1D6B

| Pos | 1234567890 | score |
|---|---|---|
| NoResultsFound. | | |

TABLE XLIII-V3

HLA-B2709-10mers-254P1D6B

| Pos | 1234567890 | score |
|---|---|---|
| NoResultsFound. | | |

TABLE XLIII-V5

HLA-B2709-10mers-254P1D6B

| Pos | 1234567890 | score |
|---|---|---|
| NoResultsFound. | | |

TABLE XLIV-V2

HLA-B4402-10mers-254P1D6B
Each peptide is a portion of SEQ ID NO: 5; each start position is specified, the length of peptide is 10 amino acids, and the end position for each peptide is the start position plus nine.

| Pos | 1234567890 | score |
|---|---|---|
| 4 | EEMSEYADDY | 24 |
| 7 | SEYADDYREL | 22 |

TABLE XLIV-V3

HLA-B4402-10mers-254P1D6B
Each peptide is a portion of SEQ ID NO: 7; each start position is specified, the length of peptide is 10 amino acids, and the end position for each peptide is the start position plus nine.

| Pos | 1234567890 | score |
|---|---|---|
| 6 | WPSPCCARKQ | 7 |
| 4 | LGWPSPCCAR | 5 |
| 7 | PSPCCARKQC | 5 |

TABLE XLIV-V5

HLA-B4402-10mers-254P1D6B
Each peptide is a portion of SEQ ID NO: 11; each start position is specified, the length of peptide is 10 amino acids, and the end position for each peptide is the start position plus nine.

| Pos | 1234567890 | score |
|---|---|---|
| 2 | PEDIRKDLTF | 23 |
| 3 | EDIRKDLTFL | 17 |
| 7 | KDLTFLGKDW | 15 |
| 9 | LTFLGKDWGL | 13 |

TABLE XLV-V1

HLA-B5101-10mers-254P1D6B

| Pos | 1234567890 | score |
|---|---|---|
| NoResultsFound. | | |

TABLE XLV-V2

HLA-B5101-10mers-254P1D6B

| Pos | 1234567890 | score |
|---|---|---|
| NoResultsFound. | | |

TABLE XLV-V3

HLA-B5101-10mers-254P1D6B

| Pos | 1234567890 | score |
|---|---|---|
| NoResultsFound. | | |

TABLE XLV-V5

HLA-B5101-10mers-254P1D6B

| Pos | 1234567890 | score |
|---|---|---|
| NoResultsFound. | | |

TABLE XLVI-v1

HLA-B5101-15mers-254P1D6B

| Pos | 123456789012345 | score |
|---|---|---|
| NoResultsFound. | | |

TABLE XLVI-V2

HLA-DRB1-0101-15mers-254P1D6B
Each peptide is a portion of SEQ ID NO: 5; each start position is specified, the length of peptide is 15 amino acids, and the end position for each peptide is the start position plus fourteen.

| Pos | 123456789012345 | score |
|---|---|---|
| 15 | ADDYRELEKDLLQPS | 29 |
| 4 | KDWGLEEMSEYADDY | 14 |
| 5 | DWGLEEMSEYADDYR | 14 |

TABLE XLVI-V3

HLA-DRB1-0101-15mers-254P1D6B
Each peptide is a portion of SEQ ID NO: 7; each start position is specified, the length of peptide is 15 amino acids, and the end position for each peptide is the start position plus fourteen.

| Pos | 123456789012345 | score |
|---|---|---|
| 1 | MTRLGWPSPCCARKQ | 22 |
| 9 | PCCARKQCSEGRTYS | 18 |
| 3 | RLGWPSPCCARKQCS | 10 |
| 4 | LGWPSPCCARKQCSE | 10 |

TABLE XLVI-V5

HLA-DRB1-0101-15mers-254P1D6B
Each peptide is a portion of SEQ ID NO: 11; each start position is specified, the length of peptide is 15 amino acids, and the end position for each peptide is the start position plus fourteen.

| Pos | 123456789012345 | score |
|---|---|---|
| 11 | RKDLTFLGKDWGLEE | 19 |
| 7 | PEDIRKDLTFLGKDW | 18 |
| 14 | LTFLGKDWGLEEMSE | 18 |
| 5 | DSPEDIRKDLTFLGK | 11 |
| 8 | EDIRKDLTFLGKDWG | 11 |
| 12 | KDLTFLGKDWGLEEM | 11 |
| 13 | DLTFLGKDWGLEEMS | 10 |
| 15 | TFLGKDWGLEEMSEY | 10 |
| 3 | WGDSPEDIRKDLTFL | 9 |
| 6 | SPEDIRKDLTFLGKD | 9 |
| 10 | IRKDLTFLGKDWGLE | 9 |

TABLE XLVII-V1

HLA-DRB1-0301-15MERS-254P1D6B
Each peptide is a portion of SEQ ID NO: 3;
each start position is specified, the length of
peptide is 15 amino acids, and the end
position for each peptide is the start position
plus fourteen.

| Pos | 123456789012345 | score |
|---|---|---|
| 184 | DWGLLPGSEGAFNSS | 29 |
| 903 | FKVLRVDTAGCLLKC | 29 |
| 343 | LIITLPDNEVELKAF | 28 |
| 404 | VFKVTVSSENAFGEG | 28 |
| 421 | NVTVKPARRVNLPPV | 28 |
| 805 | TVEVQPDPRKSGLVE | 28 |
| 845 | LNVLDSDIKVQKIRA | 28 |
| 626 | VAVAGPDKELIFPVE | 27 |
| 1030 | ESEFDSDQDTIFSRE | 27 |
| 206 | PAETQQDPELHYLNE | 26 |
| 382 | QGEIKQGHKQTLNLS | 26 |
| 690 | HFRLTVKDQQGLSST | 26 |
| 826 | VGQLTEQRKDTLVRQ | 26 |
| 998 | LDNMDEQERMELRPK | 26 |
| 130 | WGDSPEDIRKDLPFL | 25 |
| 775 | ALQLTNLVEGVYTFH | 25 |
| 550 | GNQSSDDHQIVLYEW | 24 |
| 573 | KHVVMQGVQTPYLHL | 24 |
| 584 | YLHLSAMQEGDYTFQ | 24 |
| 134 | PEDIRKDLPFLGKDW | 23 |
| 733 | NNSITLDGSRSTDDQ | 23 |
| 866 | VIVFYVQSRPPFKVL | 23 |
| 160 | YRELEKDLLQPSGKQ | 22 |
| 442 | LQELTLPLTSALIDG | 22 |
| 834 | KDTLVRQLAVLLNVL | 22 |
| 93 | MGPIRSYLTFVLRPV | 21 |
| 110 | PAQLLDYGDMMLNRG | 21 |
| 126 | PSGIWGDSPEDIRKD | 21 |
| 141 | LPFLGKDWGLEEMSE | 21 |
| 244 | SGEVLEKEKASQLQE | 21 |
| 434 | PVAVVSPQLQELTLP | 21 |
| 633 | KELIFPVESATLDGS | 21 |
| 727 | HVLVLPNNSITLDGS | 21 |
| 765 | DVIDGSDHSVALQLT | 21 |
| 965 | TLIVLTGGFTWLCIC | 21 |
| 282 | LSSVTVEKSPVLTVT | 20 |
| 332 | VKELTVSAGDNLIIT | 20 |
| 392 | TLNLSQLSVGLYVFK | 20 |
| 485 | DSPVLRLSNLDPGNY | 20 |
| 516 | TAALIVNNAVDYPPV | 20 |
| 543 | QNSITLNGNQSSDDH | 20 |
| 612 | VVTVIVQPENNRPPV | 20 |
| 725 | GRHVLVLPNNSITLD | 20 |
| 876 | PFKVLKAAEVARNLH | 20 |
| 888 | NLHMRLSKEKADFLL | 20 |
| 953 | EWSIFYVTVLAFTLI | 20 |
| 958 | YVTVLAFTLIVLTGG | 20 |
| 62 | CDLSSCDLAWWFEGR | 19 |
| 101 | TFVLRPVQRPAQLLD | 19 |
| 152 | EMSEYSDDYRELEKD | 19 |
| 165 | KDLLQPSGKQEPRGS | 19 |
| 245 | GEVLEKEKASQLQEQ | 19 |
| 435 | VAVVSPQLQELTLPL | 19 |
| 488 | VLRLSNLDPGNYSFR | 19 |
| 563 | EWSLGPGSEGKHVVM | 19 |
| 598 | QLKVTDSSRQQSTAV | 19 |
| 613 | VTVIVQPENNRPPVA | 19 |
| 678 | IATVTGLQVGTYHFR | 19 |
| 706 | TLTVAVKKENNSPPR | 19 |
| 788 | FHLRVTDSQGASDTD | 19 |
| 815 | SGLVELTQVGVGQL | 19 |
| 838 | VRQLAVLLNVLDSDI | 19 |
| 882 | AAEVARNLHMRLSKE | 19 |
| 889 | LHMRLSKEKADFLLF | 19 |
| 890 | HMRLSKEKADFLLFK | 19 |
| 941 | IQRYIWDGESNCEWS | 19 |
| 975 | WLCICCCKRQKRTKI | 19 |
| 1024 | SSLMVSESEFDSDQD | 19 |
| 1056 | NGSIRNGASFSYCSK | 19 |
| 33 | NAVISPNLETTRIMR | 18 |
| 97 | RSYLTFVLRPVQRPA | 18 |

TABLE XLVII-V1-continued

HLA-DRB1-0301-15MERS-254P1D6B
Each peptide is a portion of SEQ ID NO: 3;
each start position is specified, the length of
peptide is 15 amino acids, and the end
position for each peptide is the start position
plus fourteen.

| Pos | 123456789012345 | score |
|---|---|---|
| 100 | LTFVLRPVQRPAQLL | 18 |
| 104 | LRPVQRPAQLLDYGD | 18 |
| 147 | DWGLEEMSEYSDDYR | 18 |
| 157 | SDDYRELEKDLLQPS | 18 |
| 342 | NLIITLPDNEVELKA | 18 |
| 450 | TSALIDGSQSTDDTE | 18 |
| 536 | NHTITLPQNSITLNG | 18 |
| 574 | HVVMQGVQTPYLHLS | 18 |
| 588 | SAMQEGDYTFQLKVT | 18 |
| 632 | DKELIFPVESATLDG | 18 |
| 646 | GSSSSDDHGIVFYHW | 18 |
| 691 | FRLTVKDQQGLSSTS | 18 |
| 726 | RHVLVLPNNSITLDG | 18 |
| 751 | SYLWIRDGQSPAAGD | 18 |
| 779 | TNLVEGVYTFHLRVT | 18 |
| 899 | DFLLFKVLRVDTAGC | 18 |
| 996 | TILDNMDEQERMELR | 18 |
| 1002 | DEQERMELRPKYGIK | 18 |
| 1004 | QERMELRPKYGIKHR | 18 |
| 1022 | HNSSLMVSESEFDSD | 18 |
| 1037 | QDTIFSREKMERGNP | 18 |
| 77 | CYLVSCPHKENCEPK | 17 |
| 138 | RKDLPFLGKDWGLEE | 17 |
| 153 | MSEYSDDYRELEKDL | 17 |
| 202 | SPAVPAETQQDPELH | 17 |
| 212 | DPELHYLNESASTPA | 17 |
| 224 | TPAPKLPERSVLLPL | 17 |
| 334 | ELTVSAGDNLIITLP | 17 |
| 417 | EGFVNVTVKPARRVN | 17 |
| 456 | GSQSTDDTEIVSYHW | 17 |
| 490 | RLSNLDPGNYSFRLT | 17 |
| 610 | TAVVTVIVQPENNRP | 17 |
| 614 | TVIVQPENNRPPVAV | 17 |
| 625 | PVAVGPDKELIFPV | 17 |
| 668 | AVEMENIDKAIATVT | 17 |
| 704 | TSTLTVAVKKENNSP | 17 |
| 708 | TVAVKKENNSPPRAR | 17 |
| 740 | GSRSTDDQRIVSYLW | 17 |
| 823 | QVGVGQLTEQRKDTL | 17 |
| 864 | STVIVFYVQSRPPFK | 17 |
| 984 | QKRTKIRKKTKYTIL | 17 |
| 986 | RTKIRKKTKYTILDN | 17 |
| 995 | YTILDNMDEQERMEL | 17 |
| 1052 | KVSMNGSIRNGASFS | 17 |
| 4 | PTGVLSSLLLLVTIA | 16 |
| 14 | LVTIAGCARKQCSEG | 16 |
| 66 | SCDLAWWFEGRCYLV | 16 |
| 258 | EQSSNSSGKEVLMPS | 16 |
| 361 | APPVETTYNYEWNLI | 16 |
| 363 | PVETTYNYEWNLISH | 16 |
| 374 | LISHPTDYQGEIKQG | 16 |
| 463 | TEIVSYHWEEINGPF | 16 |
| 653 | HGIVFYHWEHVRGPS | 16 |
| 688 | TYHFRLTVKDQQGLS | 16 |
| 718 | PPRARAGGRHVLVLP | 16 |
| 739 | DGSRSTDDQRIVSYL | 16 |
| 934 | HLWMENLIQRYIWDG | 16 |
| 68 | DLAWWFEGRCYLVSC | 15 |
| 156 | YSDDYRELEKDLLQP | 15 |
| 265 | GKEVLMPSHSLPPAS | 15 |
| 357 | FVAPAPPVETTYNYE | 15 |
| 436 | AVVSPQLQELTLPLT | 15 |
| 466 | VSYHWEEINGPFIEE | 15 |
| 555 | DDHQIVLYEWSLGPG | 15 |
| 811 | DPRKSGLVELTLQVG | 15 |
| 8 | LSSLLLLVTIAGCAR | 14 |
| 9 | SSLLLLVTIAGCARK | 14 |
| 89 | EPKKMGPIRSYLTFV | 14 |
| 226 | APKLPERSVLLPLPT | 14 |
| 231 | ERSVLLPLPTTPSSG | 14 |
| 232 | RSVLLPLPTTPSSGE | 14 |

TABLE XLVII-V1-continued

HLA-DRB1-0301-15MERS-254P1D6B
Each peptide is a portion of SEQ ID NO: 3;
each start position is specified, the length of
peptide is 15 amino acids, and the end
position for each peptide is the start position
plus fourteen.

| Pos | 123456789012345 | score |
|---|---|---|
| 449 | LTSALIDGSQSTDDT | 14 |
| 556 | DHQIVLYEWSLGPGS | 14 |
| 572 | GKHVVMQGVQTPYLH | 14 |
| 771 | DHSVALQLTNLVEGV | 14 |
| 806 | VEVQPDPRKSGLVEL | 14 |
| 843 | VLLNVLDSDIKVQKI | 14 |
| 1015 | IKHRSTEHNSSLMVS | 14 |

TABLE XLVII-V2

HLA-DRB1-0301-15mers-254P1D6B
Each peptide is a portion of SEQ ID NO: 5;
each start position is specified, the length of
peptide is 15 amino acids, and the end
position for each peptide is the start position
plus fourteen.

| Pos | 123456789012345 | score |
|---|---|---|
| 5 | DWGLEEMSEYADDYR | 19 |
| 10 | EMSEYADDYRELEKD | 18 |
| 15 | ADDYRELEKDLLQPS | 18 |
| 11 | MSEYADDYRELEKDL | 17 |
| 14 | YADDYRELEKDLLQP | 15 |
| 8 | LEEMSEYADDYRELE | 11 |
| 3 | GKDWGLEEMSEYADD | 10 |
| 7 | GLEEMSEYADDYREL | 9 |

TABLE XLVII-V3

HLA-DRB1-0301-15mers-254P1D6B
Each peptide is a portion of SEQ ID NO: 7; each
start position is specified, the length of pep-
tide is 15 amino acids, and the end position
for each peptide is the start position plus
fourteen.

| Pos | 123456789012345 | score |
|---|---|---|
| 1 | MTRLGWPSPCCARKQ | 11 |
| 10 | CCARKQCSEGRTYSN | 8 |
| 6 | WPSPCCARKQCSEGR | 7 |
| 7 | PSPCCARKQCSEGRT | 7 |
| 5 | GWPSPCCARKQCSEG | 6 |

TABLE XLVII-V5

HLA-DRB1-0301-15mers-254P1D6B
Each peptide is a portion of SEQ ID NO: 11;
each start position is specified, the length of
peptide is 15 amino acids, and the end position
for each peptide is the start position plus
fourteen.

| Pos | 123456789012345 | score |
|---|---|---|
| 3 | WGDSPEDIRKDLTFL | 25 |
| 7 | PEDIRKDLTFLGKDW | 23 |
| 14 | LTFLGKDWGLEEMSE | 21 |
| 11 | RKDLTFLGKDWGLEE | 18 |
| 13 | DLTFLGKDWGLEEMS | 11 |

TABLE XLVIII-V1

HLA-DR1-0401-15mers-254P1D6B
Each peptide is a portion of SEQ ID NO: 3;
each start position is specified, the length of
peptide is 15 amino acids, and the end position
for each peptide is the start position plus
fourteen.

| Pos | 123456789012345 | score |
|---|---|---|
| 68 | DLAWWFEGRCYLVSC | 28 |
| 365 | ETTYNYEWNLISHPT | 28 |
| 751 | SYLWIRDGQSPAAGD | 28 |
| 90 | PKKMGPIRSYLTFVL | 26 |
| 97 | RSYLTFVLRPVQRPA | 26 |
| 101 | TFVLRPVQRPAQLLD | 26 |
| 232 | RSVLLPLPTTPSSGE | 26 |
| 282 | LSSVTVEKSPVLTVT | 26 |
| 421 | NVTVKPARRVNLPPV | 26 |
| 574 | HVVMQGVQTPYLHLS | 26 |
| 610 | TAVVTVIVQPENNRP | 26 |
| 633 | KELIFPVESATLDGS | 26 |
| 725 | GRHVLVLPNNSITLD | 26 |
| 733 | NNSITLDGSRSTDDQ | 26 |
| 779 | TNLVEGVYTFHLRVT | 26 |
| 842 | AVLLNVLDSDIKVQK | 26 |
| 899 | DFLLFKVLRVDTAGC | 26 |
| 934 | HLWMENLIQRYIWDG | 26 |
| 28 | GRTYSNAVISPNLET | 22 |
| 49 | SHTFPVVDCTAACCD | 22 |
| 96 | IRSYLTFVLRPVQRP | 22 |
| 153 | MSEYSDDYRELEKDL | 22 |
| 157 | SDDYRELEKDLLQPS | 22 |
| 369 | NYEWNLISHPTDYQG | 22 |

TABLE XLVIII-V1-continued

HLA-DR1-0401-15mers-254P1D6B
Each peptide is a portion of SEQ ID NO: 3;
each start position is specified, the length of
peptide is 15 amino acids, and the end position
for each peptide is the start position plus
fourteen.

| Pos | 123456789012345 | score |
|---|---|---|
| 402 | LYVFKVTVSSENAFG | 22 |
| 416 | GEGFVNVTVKPARRV | 22 |
| 467 | SYHWEEINGPFIEEK | 22 |
| 474 | NGPFIEEKTSVDSPV | 22 |
| 524 | AVDYPPVANAGPNHT | 22 |
| 657 | FYHWEHVRGPSAVEM | 22 |
| 749 | IVSYLWIRDGQSPAA | 22 |
| 874 | RPPFKVLKAAEVARN | 22 |
| 897 | KADFLLFKVLRVDTA | 22 |
| 900 | FLLFKVLRVDTAGCL | 22 |
| 943 | RYIWDGESNCEWSIF | 22 |
| 951 | NCEWSIFYVTVLAFT | 22 |
| 955 | SIFYVTVLAFTLIVL | 22 |
| 992 | KTKYTILDNMDEQER | 22 |
| 5 | TGVLSSLLLLVTIAG | 20 |
| 8 | LSSLLLLVTIAGCAR | 20 |
| 12 | LLLVTIAGCARKQCS | 20 |
| 42 | TTRIMRVSHTFPVVD | 20 |
| 43 | TRIMRVSHTFPVVDC | 20 |
| 76 | RCYLVSCPHKENCEP | 20 |
| 93 | MGPIRSYLTFVLRPV | 20 |
| 100 | LTFVLRPVQRPAQLL | 20 |
| 126 | PSGIWGDSPEDIRKD | 20 |
| 160 | YRELEKDLLQPSGKQ | 20 |
| 202 | SPAVPAETQQDPELH | 20 |
| 212 | DPELHYLNESASTPA | 20 |
| 215 | LHYLNESASTPAPKL | 20 |
| 233 | SVLLPLPTTPSSGEV | 20 |
| 245 | GEVLEKEKASQLQEQ | 20 |
| 253 | ASQLQEQSSNSSGKE | 20 |
| 272 | SHSLPPASLELSSVT | 20 |
| 279 | SLELSSVTVEKSPVL | 20 |
| 289 | KSPVLTVTPGSTEHS | 20 |
| 292 | VLTVTPGSTEHSIPT | 20 |
| 301 | EHSIPTPPTSAAPSE | 20 |

TABLE XLVIII-V1-continued

HLA-DR1-0401-15mers-254P1D6B
Each peptide is a portion of SEQ ID NO: 3;
each start position is specified, the length of
peptide is 15 amino acids, and the end position
for each peptide is the start position plus
fourteen.

| Pos | 123456789012345 | score |
|---|---|---|
| 334 | ELTVSAGDNLIITLP | 20 |
| 341 | DNLIITLPDNEVELK | 20 |
| 355 | KAFVAPAPPVETTYN | 20 |
| 371 | EWNLISHPTDYQGEI | 20 |
| 399 | SVGLYVFKVTVSSEN | 20 |
| 432 | LPPVAVVSPQLQELT | 20 |
| 435 | VAVVSPQLQELTLPL | 20 |
| 439 | SPQLQELTLPLTSAL | 20 |
| 442 | LQELTLPLTSALIDG | 20 |
| 446 | TLPLTSALIDGSQST | 20 |
| 485 | DSPVLRLSNLDPGNY | 20 |
| 500 | SFRLTVTDSDGATNS | 20 |
| 527 | YPPVANAGPNHTITL | 20 |
| 536 | NHTITLPQNSITLNG | 20 |
| 543 | QNSITLNGNQSSDDH | 20 |
| 557 | HQIVLYEWSLGPGSE | 20 |
| 596 | TFQLKVTDSSRQQST | 20 |
| 598 | QLKVTDSSRQQSTAV | 20 |
| 614 | TVIVQPENNRPPVAV | 20 |
| 636 | IFPVESATLDGSSSS | 20 |
| 666 | PSAVEMENIDKAIAT | 20 |
| 668 | AVEMENIDKAIATVT | 20 |
| 671 | MENIDKAIATVTGLQ | 20 |
| 675 | DKAIATVTGLQVGTY | 20 |
| 698 | QQGLSSTSTLTVAVK | 20 |
| 704 | TSTLTVAVKKENNSP | 20 |
| 708 | TVAVKKENNSPPRAR | 20 |
| 726 | RHVLVLPNNSITLDG | 20 |
| 727 | HVLVLPNNSITLDGS | 20 |
| 752 | YLWIRDGQSPAAGDV | 20 |
| 764 | GDVIDGSDHSVALQL | 20 |
| 771 | DHSVALQLTNLVEGV | 20 |
| 782 | VEGVYTFHLRVTDSQ | 20 |
| 787 | TFHLRVTDSQGASDT | 20 |
| 805 | TVEVQPDPRKSGLVE | 20 |
| 815 | SGLVELTLQVGVGQL | 20 |

TABLE XLVIII-V1-continued

HLA-DR1-0401-15mers-254P1D6B
Each peptide is a portion of SEQ ID NO: 3;
each start position is specified, the length of
peptide is 15 amino acids, and the end position
for each peptide is the start position plus
fourteen.

| Pos | 123456789012345 | score |
|---|---|---|
| 823 | QVGVGQLTEQRKDTL | 20 |
| 835 | DTLVRQLAVLLNVLD | 20 |
| 838 | VRQLAVLLNVLDSDI | 20 |
| 841 | LAVLLNVLDSDIKVQ | 20 |
| 845 | LNVLDSDIKVQKIRA | 20 |
| 860 | HSDLSTVIVFYVQSR | 20 |
| 865 | TVIVFYVQSRPPFKV | 20 |
| 877 | FKVLKAAEVARNLHM | 20 |
| 882 | AAEVARNLHMRLSKE | 20 |
| 890 | HMRLSKEKADFLLFK | 20 |
| 902 | LFKVLRVDTAGCLLK | 20 |
| 903 | FKVLRVDTAGCLLKC | 20 |
| 905 | VLRVDTAGCLLKCSG | 20 |
| 956 | IFYVTVLAFTLIVLT | 20 |
| 958 | YVTVLAFTLIVLTGG | 20 |
| 963 | AFTLIVLTGGFTWLC | 20 |
| 998 | LDNMDEQERMELRPK | 20 |
| 1024 | SSLMVSESEFDSDQD | 20 |
| 1050 | NPKVSMNGSIRNGAS | 20 |
| 1052 | KVSMNGSIRNGASFS | 20 |
| 1 | MAPPTGVLSSLLLLV | 18 |
| 2 | APPTGVLSSLLLLVT | 18 |
| 21 | ARKQCSEGRTYSNAV | 18 |
| 29 | RTYSNAVISPNLETT | 18 |
| 34 | AVISPNLETTRIMRV | 18 |
| 35 | VISPNLETTRIMRVS | 18 |
| 58 | TAACCDLSSCDLAWW | 18 |
| 130 | WGDSPEDIRKDLPFL | 18 |
| 146 | KDWGLEEMSEYSDDY | 18 |
| 169 | QPSGKQEPRGSAEYT | 18 |
| 188 | LPGSEGAFNSSVGDS | 18 |
| 208 | ETQQDPELHYLNESA | 18 |
| 225 | PAPKLPERSVLLPLP | 18 |
| 252 | KASQLQEQSSNSSGK | 18 |
| 275 | LPPASLELSSVTVEK | 18 |

TABLE XLVIII-V1-continued

HLA-DR1-0401-15mers-254P1D6B
Each peptide is a portion of SEQ ID NO: 3;
each start position is specified, the length of
peptide is 15 amino acids, and the end position
for each peptide is the start position plus
fourteen.

| Pos | 123456789012345 | score |
|---|---|---|
| 276 | PPASLELSSVTVEKS | 18 |
| 295 | VTPGSTEHSIPTPPT | 18 |
| 298 | GSTEHSIPTPPTSAA | 18 |
| 306 | TPPTSAAPSESTPSE | 18 |
| 322 | PISPTTAPRTVKELT | 18 |
| 328 | APRTVKELTVSAGDN | 18 |
| 358 | VAPAPPVETTYNYEW | 18 |
| 368 | YNYEWNLISHPTDYQ | 18 |
| 374 | LISHPTDYQGEIKQG | 18 |
| 379 | TDYQGEIKQGHKQTL | 18 |
| 389 | HKQTLNLSQLSVGLY | 18 |
| 403 | YVFKVTVSSENAFGE | 18 |
| 413 | NAFGEGFVNVTVKPA | 18 |
| 431 | NLPPVAVVSPQLQEL | 18 |
| 438 | VSPQLQELTLPLTSA | 18 |
| 443 | QELTLPLTSALIDGS | 18 |
| 449 | LTSALIDGSQSTDDT | 18 |
| 455 | DGSQSTDDTEIVSYH | 18 |
| 478 | IEEKTSVDSPVLRLS | 18 |
| 482 | TSVDSPVLRLSNLDP | 18 |
| 505 | VTDSDGATNSTTAAL | 18 |
| 514 | STTAALIVNNAVDYP | 18 |
| 535 | PNHTITLPQNSITLN | 18 |
| 549 | NGNQSSDDHQIVLYE | 18 |
| 550 | GNQSSDDHQIVLYEW | 18 |
| 570 | SEGKHVVMQGVQTPY | 18 |
| 588 | SAMQEGDYTFQLKVT | 18 |
| 597 | FQLKVTDSSRQQSTA | 18 |
| 606 | RQQSTAVVTVIVQPE | 18 |
| 639 | VESATLDGSSSSDDH | 18 |
| 645 | DGSSSSDDHGIVFYH | 18 |
| 691 | FRLTVKDQQGLSSTS | 18 |
| 695 | VKDQQGLSSTSTLTV | 18 |
| 739 | DGSRSTDDQRIVSYL | 18 |
| 740 | GSRSTDDQRIVSYLW | 18 |
| 762 | AAGDVIDGSDHSVAL | 18 |

TABLE XLVIII-V1-continued

HLA-DR1-0401-15mers-254P1D6B
Each peptide is a portion of SEQ ID NO: 3;
each start position is specified, the length of
peptide is 15 amino acids, and the end position
for each peptide is the start position plus
fourteen.

| Pos | 123456789012345 | score |
|---|---|---|
| 765 | DVIDGSDHSVALQLT | 18 |
| 769 | GSDHSVALQLTNLVE | 18 |
| 788 | FHLRVTDSQGASDTD | 18 |
| 813 | RKSGLVELTLQVGVG | 18 |
| 825 | GVGQLTEQRKDTLVR | 18 |
| 831 | EQRKDTLVRQLAVLL | 18 |
| 832 | QRKDTLVRQLAVLLN | 18 |
| 853 | KVQKIRAHSDLSTVI | 18 |
| 856 | KIRAHSDLSTVIVFY | 18 |
| 857 | IRAHSDLSTVIVFYV | 18 |
| 880 | LKAAEVARNLHMRLS | 18 |
| 957 | FYVTVLAFTLIVLTG | 18 |
| 996 | TILDNMDEQERMELR | 18 |
| 1009 | LRPKYGIKHRSTEHN | 18 |
| 1015 | IKHRSTEHNSSLMVS | 18 |
| 1034 | DSDQDTIFSREKMER | 18 |
| 1035 | SDQDTIFSREKMERG | 18 |
| 1053 | VSMNGSIRNGASFSY | 18 |
| 400 | VGLYVFKVTVSSENA | 17 |
| 594 | DYTFQLKVTDSSRQQ | 17 |
| 785 | VYTFHLRVTDSQGAS | 17 |
| 69 | LAWWFEGRCYLVSCP | 16 |
| 145 | GKDWGLEEMSEYSDD | 16 |
| 182 | YTDWGLLPGSEGAFN | 16 |
| 214 | ELHYLNESASTPAPK | 16 |
| 378 | PTDYQGEIKQGHKQT | 16 |
| 412 | ENAFGEGFVNVTVKP | 16 |
| 465 | IVSYHWEEINGPFIE | 16 |
| 498 | NYSFRLTVTDSDGAT | 16 |
| 559 | IVLYEWSLGPGSEGK | 16 |
| 581 | QTPYLHLSAMQEGDY | 16 |
| 634 | ELIFPVESATLDGSS | 16 |
| 654 | GIVFYHWEHVRGPSA | 16 |
| 655 | IVFYHWEHVRGPSAV | 16 |
| 688 | TYHFRLTVKDQQGLS | 16 |

TABLE XLVIII-V1-continued

HLA-DR1-0401-15mers-254P1D6B
Each peptide is a portion of SEQ ID NO: 3;
each start position is specified, the length of
peptide is 15 amino acids, and the end position
for each peptide is the start position plus
fourteen.

| Pos | 123456789012345 | score |
|---|---|---|
| 783 | EGVYTFHLRVTDSQG | 16 |
| 866 | VIVFYVQSRPPFKVL | 16 |
| 867 | IVFYVQSRPPFKVLK | 16 |
| 941 | IQRYIWDGESNCEWS | 16 |
| 954 | WSIFYVTVLAFTLIV | 16 |
| 961 | VLAFTLIVLTGGFTW | 16 |
| 970 | TGGFTWLCICCCKRQ | 16 |
| 972 | GFTWLCICCCKRQKR | 16 |
| 1030 | ESEFDSDQDTIFSRE | 16 |
| 1038 | DTIFSREKMERGNPK | 16 |
| 475 | GPFIEEKTSVDSPVL | 15 |
| 690 | HFRLTVKDQQGLSST | 15 |
| 886 | ARNLHMRLSKEKADF | 15 |
| 1012 | KYGIKHRSTEHNSSL | 15 |
| 4 | PTGVLSSLLLLVTIA | 14 |
| 9 | SSLLLLVTIAGCARK | 14 |
| 10 | SLLLLVTIAGCARKQ | 14 |
| 11 | LLLLVTIAGCARKQC | 14 |
| 14 | LVTIAGCARKQCSEG | 14 |
| 32 | SNAVISPNLETTRIM | 14 |
| 37 | SPNLETTRIMRVSHT | 14 |
| 104 | LRPVQRPAQLLDYGD | 14 |
| 110 | PAQLLDYGDMMLNRG | 14 |
| 111 | AQLLDYGDMMLNRGS | 14 |
| 116 | YGDMMLNRGSPSGIW | 14 |
| 118 | DMMLNRGSPSGIWGD | 14 |
| 134 | PEDIRKDLPFLGKDW | 14 |
| 138 | RKDLPFLGKDWGLEE | 14 |
| 141 | LPFLGKDWGLEEMSE | 14 |
| 185 | WGLLPGSEGAFNSSV | 14 |
| 196 | NSSVGDSPAVPAETQ | 14 |
| 235 | LLPLPTTPSSGEVLE | 14 |
| 265 | GKEVLMPSHSLPPAS | 14 |
| 266 | KEVLMPSHSLPPASL | 14 |
| 267 | EVLMPSHSLPPASLE | 14 |
| 284 | SVTVEKSPVLTVTPG | 14 |

TABLE XLVIII-V1-continued

HLA-DR1-0401-15mers-254P1D6B
Each peptide is a portion of SEQ ID NO: 3;
each start position is specified, the length of
peptide is 15 amino acids, and the end position
for each peptide is the start position plus
fourteen.

| Pos | 123456789012345 | score |
|---|---|---|
| 318 | PSELPISPTTAPRTV | 14 |
| 320 | ELPISPTTAPRTVKE | 14 |
| 329 | PRTVKELTVSAGDNL | 14 |
| 332 | VKELTVSAGDNLIIT | 14 |
| 342 | NLIITLPDNEVELKA | 14 |
| 344 | IITLPDNEVELKAFV | 14 |
| 351 | EVELKAFVAPAPPVE | 14 |
| 361 | APPVETTYNYEWNLI | 14 |
| 382 | QGEIKQGHKQTLNLS | 14 |
| 392 | TLNLSQLSVGLYVFK | 14 |
| 395 | LSQLSVGLYVFKVTV | 14 |
| 397 | QLSVGLYVFKVTVSS | 14 |
| 401 | GLYVFKVTVSSENAF | 14 |
| 406 | KVTVSSENAFGEGFV | 14 |
| 427 | ARRVNLPPVAVVSPQ | 14 |
| 429 | RVNLPPVAVVSPQLQ | 14 |
| 434 | PVAVVSPQLQELTLP | 14 |
| 450 | TSALIDGSQSTDDTE | 14 |
| 451 | SALIDGSQSTDDTEI | 14 |
| 462 | DTEIVSYHWEEINGP | 14 |
| 463 | TEIVSYHWEEINGPF | 14 |
| 470 | WEEINGPFIEEKTSV | 14 |
| 481 | KTSVDSPVLRLSNLD | 14 |
| 488 | VLRLSNLDPGNYSFR | 14 |
| 502 | RLTVTDSDGATNSTT | 14 |
| 518 | ALIVNNAVDYPPVAN | 14 |
| 522 | NNAVDYPPVANAGPN | 14 |
| 538 | TITLPQNSITLNGNQ | 14 |
| 545 | SITLNGNQSSDDHQI | 14 |
| 573 | KHVVMQGVQTPYLHL | 14 |
| 577 | MQGVQTPYLHLSAMQ | 14 |
| 587 | LSAMQEGDYTFQLKV | 14 |
| 609 | STAVVTVIVQPENNR | 14 |
| 613 | VTVIVQPENNRPPVA | 14 |
| 623 | RPPVAVAGPDKELIF | 14 |
| 625 | PVAVAGPDKELIFPV | 14 |
| 632 | DKELIFPVESATLDG | 14 |
| 641 | SATLDGSSSSDDHGI | 14 |
| 652 | DHGIVFYHWEHVRGP | 14 |
| 660 | WEHVRGPSAVEMENI | 14 |
| 678 | IATVTGLQVGTYHFR | 14 |
| 683 | GLQVGTYHFRLTVKD | 14 |
| 692 | RLTVKDQQGLSSTST | 14 |
| 735 | SITLDGSRSTDDQRI | 14 |
| 747 | QRIVSYLWIRDGQSP | 14 |
| 763 | AGDVIDGSDHSVALQ | 14 |
| 775 | ALQLTNLVEGVYTFH | 14 |
| 803 | TATVEVQPDPRKSGL | 14 |
| 814 | KSGLVELTLQVGVGQ | 14 |
| 817 | LVELTLQVGVGQLTE | 14 |
| 819 | ELTLQVGVGQLTEQR | 14 |
| 821 | TLQVGVGQLTEQRKD | 14 |
| 826 | VGQLTEQRKDTLVRQ | 14 |
| 834 | KDTLVRQLAVLLNVL | 14 |
| 844 | LLNVLDSDIKVQKIR | 14 |
| 851 | DIKVQKIRAHSDLST | 14 |
| 854 | VQKIRAHSDLSTVIV | 14 |
| 863 | LSTVIVFYVQSRPPF | 14 |
| 864 | STVIVFYVQSRPPFK | 14 |
| 876 | PFKVLKAAEVARNLH | 14 |
| 912 | GCLLKCSGHGHCDPL | 14 |
| 928 | KRCICSHLWMENLIQ | 14 |
| 932 | CSHLWMENLIQRYIW | 14 |
| 942 | QRYIWDGESNCEWSI | 14 |
| 953 | EWSIFYVTVLAFTLI | 14 |
| 959 | VTVLAFTLIVLTGGF | 14 |
| 965 | TLIVLTGGFTWLCIC | 14 |
| 966 | LIVLTGGFTWLCICC | 14 |
| 973 | FTWLCICCCKRQKRT | 14 |
| 975 | WLCICCCKRQKRTKI | 14 |
| 1023 | NSSLMVSESEFDSDQ | 14 |

TABLE XLVIII-V1-continued

HLA-DR1-0401-15mers-254P1D6B
Each peptide is a portion of SEQ ID NO: 3;
each start position is specified, the length of
peptide is 15 amino acids, and the end position
for each peptide is the start position plus
fourteen.

| Pos | 123456789012345 | score |
|---|---|---|
| 1043 | REKMERGNPKVSMNG | 14 |
| 1056 | NGSIRNGASFSYCSK | 14 |

TABLE XLVIII-V2

HLA-DR1-0401-15mers-254P1D6B
Each peptide is a portion of SEQ ID NO: 5;
each start position is specified, the length of
peptide is 15 amino acids, and the end
position for each peptide is the start position
plus fourteen.

| Pos | 123456789012345 | score |
|---|---|---|
| 11 | MSEYADDYRELEKDL | 22 |
| 15 | ADDYRELEKDLLQPS | 22 |
| 4 | KDWGLEEMSEYADDY | 18 |
| 3 | GKDWGLEEMSEYADD | 16 |
| 10 | EMSEYADDYRELEKD | 12 |
| 14 | YADDYRELEKDLLQP | 12 |

TABLE XLVIII-V3

HLA-DR1-0401-15mers-254P1D6B
Each peptide is a portion of SEQ ID NO: 7;
each start position is specified, the length of
peptide is 15 amino acids, and the end
position for each peptide is the start position
plus fourteen.

| Pos | 123456789012345 | score |
|---|---|---|
| 3 | RLGWPSPCCARKQCS | 16 |
| 1 | MTRLGWPSPCCARKQ | 14 |
| 6 | WPSPCCARKQCSEGR | 12 |

TABLE XLVIII-V5

HLA-DR1-0401-15mers-254P1D6B
Each peptide is a portion of SEQ ID NO: 11;
each start position is specified, the length of
peptide is 15 amino acids, and the end position
for each peptide is the start position plus
fourteen.

| Pos | 123456789012345 | score |
|---|---|---|
| 7 | PEDIRKDLTFLGKDW | 20 |
| 3 | WGDSPEDIRKDLTFL | 18 |
| 11 | RKDLTFLGKDWGLEE | 14 |
| 14 | LTFLGKDWGLEEMSE | 14 |

TABLE XLVIII-V5-continued

HLA-DR1-0401-15mers-254P1D6B
Each peptide is a portion of SEQ ID NO: 11;
each start position is specified, the length of
peptide is 15 amino acids, and the end position
for each peptide is the start position plus
fourteen.

| Pos | 123456789012345 | score |
|---|---|---|
| 4 | GDSPEDIRKDLTFLG | 12 |
| 8 | EDIRKDLTFLGKDWG | 12 |

TABLE XLIX-V1

HLA-DRB1-1101-15mers-254P162B
Each peptide is a portion of
SEQ ID NO: 3; each start position is
specified, the length of peptide is 15
amino acids, and the end position for each
peptide is the start position plus fourteen.

| Pos | 123456789012345 | score |
|---|---|---|
| 668 | AVEMENIDKAIATVT | 27 |
| 42 | TTRIMRVSHTFPVVD | 26 |
| 138 | RKDLPFLGKDWGLEE | 26 |
| 654 | GIVFYHWEHVRGPSA | 26 |
| 961 | VLAFTLIVLTGGFTW | 26 |
| 157 | SDDYRELEKDLLQPS | 25 |
| 113 | LLDYGDMMLNRGSPS | 24 |
| 369 | NYEWNLISHPTDYQG | 24 |
| 49 | SHTFPVVDCTAACCD | 23 |
| 97 | RSYLTFVLRPVQRPA | 23 |
| 831 | EQRKDTLVRQLAVLL | 23 |
| 900 | FLLFKVLRVDTAGCL | 23 |
| 182 | YTDWGLLPGSEGAFN | 22 |
| 242 | PSSGEVLEKEKASQL | 22 |
| 416 | GEGFVNVTVKPARRV | 22 |
| 524 | AVDYPPVANAGPNHT | 22 |
| 598 | QLKVTDSSRQQSTAV | 22 |
| 657 | FYHWEHVRGPSAVEM | 22 |
| 749 | IVSYLWIRDGQSPAA | 22 |
| 848 | LDSDIKVQKIRAHSD | 22 |
| 131 | GDSPEDIRKDLPFLG | 21 |
| 265 | GKEVLMPSHSLPPAS | 21 |
| 764 | GDVIDGSDHSVALQL | 21 |
| 887 | RNLHMRLSKEKADFL | 21 |
| 899 | DFLLFKVLRVDTAGC | 21 |
| 8 | LSSLLLLVTIAGCAR | 20 |
| 101 | TFVLRPVQRPAQLLD | 20 |

TABLE XLIX-V1-continued

HLA-DRB1-1101-15mers-254P162B
Each peptide is a portion of
SEQ ID NO: 3; each start position is
specified, the length of peptide is 15
amino acids, and the end position for each
peptide is the start position plus fourteen.

| Pos | 123456789012345 | score |
|---|---|---|
| 115 | DYGDMMLNRGSPSGI | 20 |
| 165 | KDLLQPSGKQEPRGS | 20 |
| 592 | EGDYTFQLKVTDSSR | 20 |
| 688 | TYHFRLTVKDQQGLS | 20 |
| 783 | EGVYTFHLRVTDSQG | 20 |
| 805 | TVEVQPDPRKSGLVE | 20 |
| 865 | TVIVFYVQSRPPFKV | 20 |
| 908 | VDTAGCLLKCSGHGH | 20 |
| 1040 | IFSREKMERGNPKVS | 20 |
| 1052 | KVSMNGSIRNGASFS | 20 |
| 153 | MSEYSDDYRELEKDL | 19 |
| 279 | SLELSSVTVEKSPVL | 19 |
| 704 | TSTLTVAVKKENNSP | 19 |
| 747 | QRIVSYLWIRDGQSP | 19 |
| 814 | KSGLVELTLQVGVGQ | 19 |
| 866 | VIVFYVQSRPPFKVL | 19 |
| 68 | DLAWWFEGRCYLVSC | 18 |
| 99 | YLTFVLRPVQRPAQL | 18 |
| 179 | SAEYTDWGLLPGSEG | 18 |
| 192 | EGAFNSSVGDSPAVP | 18 |
| 212 | DPELHYLNESASTPA | 18 |
| 232 | RSVLLPLPTTPSSGE | 18 |
| 329 | PRTVKELTVSAGDNL | 18 |
| 378 | PTDYQGEIKQGHKQT | 18 |
| 400 | VGLYVFKVTVSSENA | 18 |
| 429 | RVNLPPVAVVSPQLQ | 18 |
| 485 | DSPVLRLSNLDPGNY | 18 |
| 594 | DYTFQLKVTDSSRQQ | 18 |
| 970 | TGGFTWLCICCCKRQ | 18 |
| 992 | KTKYTILDNMDEQER | 18 |
| 1010 | RPKYGIKHRSTEHNS | 18 |
| 1038 | DTIFSREKMERGNPK | 18 |
| 70 | AWWFEGRCYLVSCPH | 17 |
| 365 | ETTYNYEWNLISHPT | 17 |
| 417 | EGFVNVTVKPARRVN | 17 |

TABLE XLIX-V1-continued

HLA-DRB1-1101-15mers-254P162B
Each peptide is a portion of
SEQ ID NO: 3; each start position is
specified, the length of peptide is 15
amino acids, and the end position for each
peptide is the start position plus fourteen.

| Pos | 123456789012345 | score |
|---|---|---|
| 610 | TAVVTVIVQPENNRP | 17 |
| 655 | IVFYHWEHVRGPSAV | 17 |
| 740 | GSRSTDDQRIVSYLW | 17 |
| 775 | ALQLTNLVEGVYTFH | 17 |
| 874 | RPPFKVLKAAEVARN | 17 |
| 972 | GFTWLCICCCKRQKR | 17 |
| 39 | NLETTRIMRVSHTFP | 16 |
| 214 | ELHYLNESASTPAPK | 16 |
| 367 | TYNYEWNLISHPTDY | 16 |
| 465 | IVSYHWEEINGPFIE | 16 |
| 467 | SYHWEEINGPFIEEK | 16 |
| 481 | KTSVDSPVLRLSNLD | 16 |
| 559 | IVLYEWSLGPGSEGK | 16 |
| 561 | LYEWSLGPGSEGKHV | 16 |
| 578 | QGVQTPYLHLSAMQE | 16 |
| 581 | QTPYLHLSAMQEGDY | 16 |
| 656 | VFYHWEHVRGPSAVE | 16 |
| 712 | KKENNSPPRARAGGR | 16 |
| 751 | SYLWIRDGQSPAAGD | 16 |
| 826 | VGQLTEQRKDTLVRQ | 16 |
| 864 | STVIVFYVQSRPPFK | 16 |
| 882 | AAEVARNLHMRLSKE | 16 |
| 896 | EKADFLLFKVLRVDT | 16 |
| 955 | SIFYVTVLAFTLIVL | 16 |
| 956 | IFYVTVLAFTLIVLT | 16 |
| 983 | RQKRTKIRKKTKYTI | 16 |
| 1008 | ELRPKYGIKHRSTEH | 16 |
| 48 | VSHTFPVVDCTAACC | 15 |
| 100 | LTFVLRPVQRPAQLL | 15 |
| 294 | TVTPGSTEHSIPTPP | 15 |
| 500 | SFRLTVTDSDGATNS | 15 |
| 625 | PVAVAGPDKELIFPV | 15 |
| 873 | SRPPFKVLKAAEVAR | 15 |
| 879 | VLKAAEVARNLHMRL | 15 |
| 920 | HGHCDPLTKRCICSH | 15 |
| 935 | LWMENLIQRYIWDGE | 15 |

TABLE XLIX-V1-continued

HLA-DRB1-1101-15mers-254P162B
Each peptide is a portion of
SEQ ID NO: 3; each start position is
specified, the length of peptide is 15
amino acids, and the end position for each
peptide is the start position plus fourteen.

| Pos | 123456789012345 | score |
|---|---|---|
| 975 | WLCICCCKRQKRTKI | 15 |
| 1009 | LRPKYGIKHRSTEHN | 15 |
| 1037 | QDTIFSREKMERGNP | 15 |
| 14 | LVTIAGCARKQCSEG | 14 |
| 15 | VTIAGCARKQCSEGR | 14 |
| 21 | ARKQCSEGRTYSNAV | 14 |
| 76 | RCYLVSCPHKENCEP | 14 |
| 77 | CYLVSCPHKENCEPK | 14 |
| 83 | PHKENCEPKKMGPIR | 14 |
| 84 | HKENCEPKKMGPIRS | 14 |
| 87 | NCEPKKMGPIRSYLT | 14 |
| 169 | QPSGKQEPRGSAEYT | 14 |
| 244 | SGEVLEKEKASQLQE | 14 |
| 281 | ELSSVTVEKSPVLTV | 14 |
| 292 | VLTVTPGSTEHSIPT | 14 |
| 351 | EVELKAFVAPAPPVE | 14 |
| 382 | QGEIKQGHKQTLNLS | 14 |
| 398 | LSVGLYVFKVTVSSE | 14 |
| 399 | SVGLYVFKVTVSSEN | 14 |
| 421 | NVTVKPARRVNLPPV | 14 |
| 432 | LPPVAVVSPQLQELT | 14 |
| 446 | TLPLTSALIDGSQST | 14 |
| 482 | TSVDSPVLRLSNLDP | 14 |
| 518 | ALIVNNAVDYPPVAN | 14 |
| 543 | QNSITLNGNQSSDDH | 14 |
| 613 | VTVIVQPENNRPPVA | 14 |
| 678 | IATVTGLQVGTYHFR | 14 |
| 705 | STLTVAVKKENNSPP | 14 |
| 714 | ENNSPPRARAGGRHV | 14 |
| 732 | PNNSITLDGSRSTDD | 14 |
| 823 | QVGVGQLTEQRKDTL | 14 |
| 838 | VRQLAVLLNVLDSDI | 14 |
| 842 | AVLLNVLDSDIKVQK | 14 |
| 845 | LNVLDSDIKVQKIRA | 14 |
| 850 | SDIKVQKIRAHSDLS | 14 |
| 883 | AEVARNLHMRLSKEK | 14 |
| 912 | GCLLKCSGHGHCDPL | 14 |
| 914 | LLKCSGHGHCDPLTK | 14 |
| 986 | RTKIRKKTKYTILDN | 14 |
| 998 | LDNMDEQERMELRPK | 14 |
| 1004 | QERMELRPKYGIKHR | 14 |
| 1014 | GIKHRSTEHNSSLMV | 14 |
| 5 | TGVLSSLLLLVTIAG | 13 |
| 7 | VLSSLLLLVTIAGCA | 13 |
| 10 | SLLLLVTIAGCARKQ | 13 |
| 90 | PKKMGPIRSYLTFVL | 13 |
| 96 | IRSYLTFVLRPVQRP | 13 |
| 114 | LDYGDMMLNRGSPSG | 13 |
| 134 | PEDIRKDLPFLGKDW | 13 |
| 226 | APKLPERSVLLPLPT | 13 |
| 228 | KLPERSVLLPLPTTP | 13 |
| 263 | SSGKEVLMPSHSLPP | 13 |
| 272 | SHSLPPASLELSSVT | 13 |
| 287 | VEKSPVLTVTPGSTE | 13 |
| 337 | VSAGDNLIITLPDNE | 13 |
| 348 | PDNEVELKAFVAPAP | 13 |
| 390 | KQTLNLSQLSVGLYV | 13 |
| 392 | TLNLSQLSVGLYVFK | 13 |
| 401 | GLYVFKVTVSSENAF | 13 |
| 402 | LYVFKVTVSSENAFG | 13 |
| 439 | SPQLQELTLPLTSAL | 13 |
| 497 | GNYSFRLTVTDSDGA | 13 |
| 556 | DHQIVLYEWSLGPGS | 13 |
| 577 | MQGVQTPYLHLSAMQ | 13 |
| 593 | GDYTFQLKVTDSSRQ | 13 |
| 614 | TVIVQPENNRPPVAV | 13 |
| 633 | KELIFPVESATLDGS | 13 |
| 666 | PSAVEMENIDKAIAT | 13 |
| 706 | TLTVAVKKENNSPPR | 13 |
| 725 | GRHVLVLPNNSITLD | 13 |
| 784 | GVYTFHLRVTDSQGA | 13 |

TABLE XLIX-V1-continued

HLA-DRB1-1101-15mers-254P162B
Each peptide is a portion of
SEQ ID NO: 3; each start position is
specified, the length of peptide is 15
amino acids, and the end position for each
peptide is the start position plus fourteen.

| Pos | 123456789012345 | score |
|---|---|---|
| 787 | TFHLRVTDSQGASDT | 13 |
| 816 | GLVELTLQVGVGQLT | 13 |
| 835 | DTLVRQLAVLLNVLD | 13 |
| 934 | HLWMENLIQRYIWDG | 13 |
| 953 | EWSIFYVTVLAFTLI | 13 |
| 954 | WSIFYVTVLAFTLIV | 13 |
| 960 | TVLAFTLIVLTGGFT | 13 |
| 963 | AFTLIVLTGGFTWLC | 13 |
| 1043 | REKMERGNPKVSMNG | 13 |

TABLE XLIX-V2

HLA-DRB1-1101-15mers-254P162B
Each peptide is a portion of SEQ ID NO: 5;
each start position is specified, the length of
peptide is 15 amino acids, and the end
position for each peptide is the start position
plus fourteen.

| Pos | 123456789012345 | score |
|---|---|---|
| 15 | ADDYRELEKDLLQPS | 25 |
| 11 | MSEYADDYRELEKDL | 19 |
| 5 | DWGLEEMSEYADDYR | 12 |

TABLE XLIX-V3

HLA-DRB1-1101-15mers-254P162B
Each peptide is a portion of SEQ ID NO: 7;
each start position is specified, the length
of peptide is 15 amino acids, and the end
position for each peptide is the start
position plus fourteen.

| Pos | 123456789012345 | score |
|---|---|---|
| 6 | WPSPCCARKQCSEGR | 14 |
| 1 | MTRLGWPSPCCARKQ | 12 |
| 3 | RLGWPSPCCARKQCS | 12 |
| 5 | GWPSPCCARKQCSEG | 8 |
| 8 | SPCCARKQCSEGRTY | 6 |

TABLE XLIX-V5

HLA-DRB1-1101-15mers-254P162B
Each peptide is a portion of SEQ ID NO: 11;
each start position is specified, the length of
peptide is 15 amino acids, and the end
position for each peptide is the start position
plus fourteen.

| Pos | 123456789012345 | score |
|---|---|---|
| 11 | RKDLTFLGKDWGLEE | 28 |
| 4 | GDSPEDIRKDLTFLG | 15 |
| 7 | PEDIRKDLTFLGKDW | 13 |

TABLE L

| Protein Characteristics of 254P1D6B | | | |
|---|---|---|---|
| | Bioinformatic Program | World Wide Web address | Outcome |
| ORF | ORF finder | | 3216 bp |
| Protein length | | | 1072 aa |
| Transmembrane region | TM Pred | .ch.embnet.org/ | TM Helix AA 954-981 |
| | HMMTop | .enzim.hu/hmmtop/ | TM Helix AA 956-980 |
| | Sosui | .genome.ad.jp/SOSui/ | TM Helix AA 957-979 |
| | TMHMM | .cbs.dtu.dk/services/TMHMM | TM Helix AA 956-978 |
| Signal Peptide | Signal P | .cbs.dtu.dk/services/SignalP/ | Yes signal peptide |
| pI | pI/MW tool | .expasy.ch/tools/ | pI 5.34 |
| Molecular weight | pI/MW tool | .expasy.ch/tools/ | 1.17 |
| Localization | PSORT | psort.nibb.ac.jp/ | 46% Plasma Membrane 10% endoplasmic reticulum |
| | | | 33.3% Golgi 33.3% Endoplasmic reticulum 22.2% Plasma Membrane |
| | PSORT II | psort.nibb.ac.jp/ | 11.1% extracellular, including cell wall TYA transposon protein PKD |
| Motifs | Blocks | .blocks.fhcrc.org/ | Purothionin signature |
| | Repeats | dove.embl-heidelberg.de/ | No Repeats |

TABLE LI

Exon compositions of 254P1D6B

| Exon No. | Start position | End position | Length |
|---|---|---|---|
| 1 | 1 | 406 | 406 |
| 2 | 407 | 566 | 160 |
| 3 | 567 | 1312 | 746 |
| 4 | 1313 | 1505 | 193 |
| 5 | 1506 | 1604 | 99 |
| 6 | 1605 | 1702 | 98 |
| 7 | 1703 | 1790 | 88 |
| 8 | 1791 | 1883 | 93 |
| 9 | 1884 | 2016 | 133 |
| 10 | 2017 | 2245 | 229 |
| 11 | 2246 | 2369 | 124 |
| 12 | 2370 | 2502 | 133 |
| 13 | 2503 | 2651 | 149 |
| 14 | 2652 | 2803 | 152 |
| 15 | 2804 | 2942 | 139 |
| 16 | 2943 | 3102 | 160 |
| 17 | 3103 | 3245 | 143 |
| 18 | 3246 | 3368 | 123 |
| 19 | 3369 | 3459 | 91 |
| 20 | 3460 | 3551 | 92 |
| 21 | 3552 | 6791 | 3240 |

TABLE LII

Nucleotide sequence of transcript variant 254P1D6B v.3

```
gctgccgcgg gcggtgggcg gggatccccc gggggtgcaa ccttgctcca cctgtgctgc    60  (SEQ ID NO: 269)
cctcggcggg cctggctggc cccgcgcaga gcggcggcgg cgctcgctgt cactgccgga   120
ggtgagagcg cagcagtagc ttcagcctgt cttgggcttg gtccagattc gctcctctgg   180
ggctacgtcc cggggaagag gaagcgagga ttttgctggg gtggggctgt acctcttaac   240
agcaggtgcg cgcgcgaggg tgtgaacgtg tgtgtgtgtg tgtgtctgtg tgtgtgtgtg   300
taagacctgc gatgacgacg aggaggaaca agtgggacgg cgagtgatgc tcagggccag   360
cagcaacgca tggggcgagc ttcagtgtcg ccagcagtga ccacaggtac ggtatctact   420
tcccagagcg cctggccgag aaataggaaa gagggcagcc agtaggcagg ccaataccca   480
acaaaagtag aatcgagacg ccctgagttc agaagttctt gaggccaaat ctggctccta   540
aaaaacatca aaggaagctt gcaccaaact ctcttcaggg ccgcctcaga agcctgccat   600
cacccactgt gtggtgcaca atggcgcccc ccacaggtgt gctctcttca ttgctgctgc   660
tggtgacaat tgcagtttgc ttatggtgga tgcactcatg gcaaaaaaat cactggtgag   720
catcatttaa gaagacccat gactagactg ggctggccga gcccatgttg tgcccgtaag   780
cagtgcagcg aggggaggac atattccaat gcagtcattt cacctaactt ggaaaccacc   840
agaatcatgc gggtgtctca caccttccct gtcgtagact gcacggccgc ttgctgtgac   900
ctgtccagct gtgacctggc ctggtggttc gagggccgct gctacctggt gagctgcccc   960
cacaaagaga actgtgagcc caagaagatg ggccccatca ggtcttatct cacttttgtg  1020
ctccggcctg ttcagaggcc tgcacagctg ctggactatg gggacatgat gctgaacagg  1080
ggctcccccct cggggatctg gggggactca cctgaggata tcagaaagga cttgcccttt  1140
ctaggcaaag attggggcct agaggagatg tctgagtact cagatgacta ccgggagctg  1200
gagaaggacc tcttgcaacc cagtggcaag caggagccca gagggagtgc cgagtacacg  1260
gactggggcc tactgccggg cagcgagggg gccttcaact cctctgttgg agacagtcct  1320
gcggtgccag cggagacgca gcaggaccct gagctccatt acctgaatga gtcggcttca  1380
accccctgccc caaaactccc tgagagaagt gtgttgcttc ccttgccgac tactccatct  1440
tcaggagagg tgttggagaa agaaaaggct tctcagctcc aggaacaatc cagcaacagc  1500
tctggaaaag aggttctaat gccttcccat agtcttcctc cggcaagcct ggagctcagc  1560
tcagtcaccg tggagaaaag cccagtgctc acagtcaccc cggggagtac agagcacagc  1620
atcccaacac ctcccactag cgcagccccc tctgagtcca ccccatctga gctacccata  1680
tctcctacca ctgctcccag gacagtgaaa gaacttacgg tatcggctgg agataaccta  1740
```

TABLE LII-continued

Nucleotide sequence of transcript variant 254P1D6B v.3

```
attataactt tacccgacaa tgaagttgaa ctgaaggcct tgttgcgcc agcgccacct 1800
gtagaaacaa cctacaacta tgaatggaat ttaataagcc accccacaga ctaccaaggt 1860
gaaataaaac aaggacacaa gcaaactctt aacctctctc aattgtccgt cggactttat 1920
gtcttcaaag tcactgtttc tagtgaaaac gcctttggag aaggatttgt caatgtcact 1980
gttaagcctg ccagaagagt caacctgcca cctgtagcag ttgtttctcc ccaactgcaa 2040
gagctcactt tgcctttgac gtcagccctc attgatggca gccaaagtac agatgatact 2100
gaaatagtga gttatcattg gaagaaata acgggccct tcatagaaga gaagacttca 2160
gttgactctc ccgtcttacg cttgtctaac cttgatcctg gtaactatag tttcaggttg 2220
actgttacag actcggacgg agccactaac tctacaactg cagccctaat agtgaacaat 2280
gctgtggact acccaccagt tgctaatgca ggaccaaatc acaccataac tttgccccaa 2340
aactccatca ctttgaatgg aaaccagagc agtgacgatc accagattgt cctctatgag 2400
tggtccctgg gtcctgggag tgagggcaaa catgtggtca tgcagggagt acagacgcca 2460
taccttcatt tatctgcaat gcaggaagga gattatacat ttcagctgaa ggtgacagat 2520
tcttcaaggc aacagtctac tgctgtggtg actgtgattg tccagcctga aaacaataga 2580
cctccagtgg ctgtggccgg ccctgataaa gagctgatct tcccagtgga aagtgctacc 2640
ctggatggga gcagcagcag cgatgaccac ggcattgtct tctaccactg ggagcacgtc 2700
agaggcccca gtgcagtgga gatggaaaat attgacaaag caatagccac tgtgactggt 2760
ctccaggtgg ggacctacca cttccgtttg acagtgaaag accagcaggg actgagcagc 2820
acgtccaccc tcactgtggc tgtgaagaag gaaaataata gtcctcccag agcccgggct 2880
ggtggcagac atgttcttgt gcttcccaat aattccatta ctttggatgg ttcaaggtct 2940
actgatgacc aaagaattgt gtcctatctg tggatccggg atggccagag tccagcagct 3000
ggagatgtca tcgatggctc tgaccacagt gtggctctgc agcttacgaa tctggtggag 3060
ggggtgtaca ctttccactt gcgagtcacc gacagtcagg gggcctcgga cacagacact 3120
gccactgtgg aagtgcagcc agaccctagg aagagtggcc tggtggagct gacccctgcag 3180
gttggtgttg ggcagctgac agagcagcgg aaggacaccc ttgtgaggca gctggctgtg 3240
ctgctgaacg tgctggactc ggacattaag gtccagaaga ttcgggccca ctcggatctc 3300
agcaccgtga ttgtgtttta tgtacagagc aggccgcctt tcaaggttct caaagctgct 3360
gaagtggccc gaaatctgca catgcggctc tcaaaggaga aggctgactt cttgcttttc 3420
aaggtcttga gggttgatac agcaggttgc cttctgaagt gttctggcca tggtcactgc 3480
gacccccctca caaagcgctg catttgctct cacttatgga tggagaacct tatacagcgt 3540
tatatctggg atggagagag caactgtgag tggagtatat tctatgtgac agtgttggct 3600
tttactctta ttgtgctaac aggaggtttc acttggcttt gcatctgctg ctgcaaaaga 3660
caaaaaagga ctaaaatcag gaaaaaaaca aagtacacca tcctggataa catggatgaa 3720
caggaaagaa tggaactgag gcccaaatat ggtatcaagc accgaagcac agagcacaac 3780
tccagcctga tggtatccga gtctgagttt gacagtgacc aggacacaat cttcagccga 3840
gaaaagatgg agagagggaa tccaaaggtt tccatgaatg gttccatcag aaatggagct 3900
tccttcagtt attgctcaaa ggacagataa tggcgcagtt cattgtaaag tggaaggacc 3960
ccttgaatcc aagaccagtc agtgggagtt acagcacaaa acccactctt ttagaatagt 4020
tcattgacct tcttccccag tgggttagat gtgtatcccc acgtactaaa agaccggttt 4080
```

TABLE LII-continued

Nucleotide sequence of transcript variant 254P1D6B v.3

```
ttgaaggcac aaaacaaaaa ctttgctctt ttaactgaga tgcttgttaa tagaaataaa  4140
ggctgggtaa aactctaagg tatatactta aaagagtttt gagttttgt agctggcaca   4200 atctcatatt aaagatgaac aacgatttct atctgtagaa ccttagagaa ggtgaatgaa  4260
acaaggtttt aaaaagggat gatttctgtc ttagccgctg tgattgcctc taaggaacag  4320
cattctaaac acggtttctc ttgtaggacc tgcagtcaga tggctgtgta tgttaaaata  4380
gcttgtctaa gaggcacggg ccatctgtgg aggtacggag tcttgcatgt agcaagcttt  4440
ctgtgctgac ggcaacactc gcacagtgcc aagccctcct ggttttaat tctgtgctat   4500 gtcaatggca gttttcatct ctctcaagaa agcagctgtt ggccattcaa gagctaagga  4560
agaatcgtat tctaaggact gaggcaatag aaagggagg aggagcttaa tgccgtgcag   4620
gttgaaggta gcattgtaac attatctttt ctttctctaa gaaaaactac actgactcct  4680
ctcggtgttg tttagcagta tagttctcta atgtaaacgg atccccagtt tacattaaat  4740
gcaatagaag tgattaattc attaagcatt tattatgttc tgtaggctgt gcgtttggac  4800
tgccatagat agggataacg actcagcaat tgtgtatata ttccaaaact ctgaaataca  4860
gtcagtctta acttggatgg cgtggttatg atactctggt ccccgacagg tactttccaa  4920
aataacttga catagatgta ttcacttcat atgtttaaaa atacatttaa gttttctac   4980 cgaataaatc ttatttcaaa catgaaagac aattaaaaca ttcccaccca caaagcagta  5040
ctcccgagca attaactgga gttaattgta gcctgctacg ttgactggtt cagggtagtt  5100
ccccatccac ccttggtcct gaggctggtg gccttggtgg tgcccttggc attttttgtg  5160
ggaagattag aatgagagat agaaccagtg ttgtggtacc aagtgtgagc acacctaaac  5220
aatatcctgt tgcacaatgc ttttttaaca catgggaaaa ctaggaatgc attgctgatg  5280
aagaagcaag gtatttaaac accagggcag gagtgccaga gaaatgtttt ccccatgggt  5340
tcttaaaaaa aattcagctt ttaggtgctt ttgtcatctc ccggagtatt catcctcatg  5400
ggaccatctt attttactt attgtaattt actggggaaa ggcagaacta aaaagtgtgt   5460
cattttattt ttaaaataat tgctttgctt atgcctacac tttctgtata actagccaat  5520
tcaatactgt ctatagtgtt agaaggaaaa tgtgatttt tttttttaac cagtattgag   5580
cttcataagc ctagaatctg ccttatcagg tgaccaggt tatggttgtt tgcatgcaaa   5640
tgtgaatttc tggcatagg gacagcagcc caaatgtaaa gtcatcgggc gtaatgagga   5700
agaagggagt gaacatttac cgctttatgt acataacata tgcagtttac atactcattt  5760
gatccttata atcaaccttg aagaggagat actatcattc ttatgttgca gatagccctc  5820
tgaaggccca gagaggttaa gtaacttccc agaggtcatg ccaagaagt agtggctcca   5880 agaactgaat gcaaatttt taaactgtag agttctgctt tccactaaac aaagaactcc   5940
tgccttgatg gatggagggc aaattctggt ggaacttttg ggccacctga agttctatt   6000 cccaggacta agaggaattt cttttaatgg atccagagag ccaaggtcag agggagagat  6060
ggcctgcata gtctcctgtg gatcacaccc gggccacccc tccctctagg tttacagtgg  6120
acttcttctg cccctcctcc ttttctgtcc ttggccatct cagcctggcc tctctgatcc  6180
ttccatcaca gaaggatctt gaatctctgg gaaatcaaac atcacagtag tgatcagaaa  6240
gtgagtcctg tcttgtcacc ccatttctca tcagaacaaa gcacgagatg gaatgaccaa  6300
ccagcattct tcatggtgga ctgcttatca ttgaggatct ttgggagata aagcacgcta  6360
agagctctgg acagagaaaa acaggcccta gaatatggga gtgggtgttt gtagggctca  6420
```

TABLE LII-continued

Nucleotide sequence of transcript variant 254P1D6B v.3

```
taggctaaca agcactttag ttgctggttt acattcaatg aaggaggatt catacccatg  6480
gcattacaag gctaagcatg tgtatgacta aggaactatc tgaaaaacat gcagcaaggt  6540
aagaaaatgt accactcaac aagccagtga tgccaccttt tgtgcgcggg gaggagagtg  6600
actaccattg ttttttgtgt gacaaagcta tcatggacta ttttaatctt ggttttattg  6660
cttaaaatat attattttc cctatgtgtt gacaaggtat ttctaatatc acactattaa  6720
atatatgcac taatctaaat aaaggtgtct gtattttctg taatgcttat ttttaggggg  6780
aaatttgttt tctttatgct tcagggtaga gggattccct tgagtatagg tcagcaaact  6840
ctggcctgca gcctgtgtgt gcacgcccca tgagccgaaa agtgggtctt atgttttcaa  6900
atggttaaaa ataaataaaa aaatttgaaa catgtgaact atatgacatt cagatttgtg  6960
ttcataaata aagttttatt ggaacatatc c                                 6991
```

TABLE LIII

Nucleotide sequence alignment of 254P1D6B v.1 (SEQ ID NO: 270) and 254P1D6B v.3 (SEQ ID NO: 271)

Score = 781 bits (406), Expect = 0.0 Identities = 406/406 (100%) Strand = Plus/Plus

```
Query:    1  gctgccgcgggcggtgggcgggatccccgggggtgcaaccttgctccacctgtgctgc   60
             ||||||||||||||||||||||||||||||||||||||||||||||||||||||||||||
Sbjct:    1  gctgccgcgggcggtgggcgggatccccgggggtgcaaccttgctccacctgtgctgc   60

Query:   61  cctcggcgggcctggctggccccgcgcagagcggcggcggcgctcgctgtcactgccgga  120
             ||||||||||||||||||||||||||||||||||||||||||||||||||||||||||||
Sbjct:   61  cctcggcgggcctggctggccccgcgcagagcggcggcggcgctcgctgtcactgccgga  120

Query:  121  ggtgagagcgcagcagtagcttcagcctgtcttgggcttggtccagattcgctcctctgg  180
             ||||||||||||||||||||||||||||||||||||||||||||||||||||||||||||
Sbjct:  121  ggtgagagcgcagcagtagcttcagcctgtcttgggcttggtccagattcgctcctctgg  180

Query:  181  ggctacgtcccggggaagaggaagcgaggattttgctggggtggggctgtacctcttaac  240
             ||||||||||||||||||||||||||||||||||||||||||||||||||||||||||||
Sbjct:  181  ggctacgtcccggggaagaggaagcgaggattttgctggggtggggctgtacctcttaac  240

Query:  241  agcaggtgcgcgcgcgagggtgtgaacgtgtgtgtgtgtgtgtgtctgtgtgtgtgtgtg  300
             ||||||||||||||||||||||||||||||||||||||||||||||||||||||||||||
Sbjct:  241  agcaggtgcgcgcgcgagggtgtgaacgtgtgtgtgtgtgtgtgtctgtgtgtgtgtgtg  300

Query:  301  taagacctgcgatgacgacgaggaggaacaagtgggacggcgagtgatgctcagggccag  360
             ||||||||||||||||||||||||||||||||||||||||||||||||||||||||||||
Sbjct:  301  taagacctgcgatgacgacgaggaggaacaagtgggacggcgagtgatgctcagggccag  360

Query:  361  cagcaacgcatggggcgagcttcagtgtcgccagcagtgaccacag  406
             ||||||||||||||||||||||||||||||||||||||||||||||
Sbjct:  361  cagcaacgcatggggcgagcttcagtgtcgccagcagtgaccacag  406
```

Score = 314 bits (163), Expect = 2e − 81 Identities = 165/166 (99%) Strand = Plus/Plus

```
Query:  405  agttcttgaggccaaatctggctcctaaaaaacatcaaggaagcttgcaccaaactctc  464
             |||||||||||||||||||||||||||||||||||||||||||||||||||||||||||
Sbjct:  514  agttcttgaggccaaatctggctcctaaaaaacatcaaggaagcttgcaccaaactctc  573

Query:  465  ttcagggccgcctcagaagcctgccatcacccactgtgtggtgcacaatggcgccccca  524
             |||||||||||||||||||||||||||||||||||||||||||||||||||||||||||
Sbjct:  574  ttcagggccgcctcagaagcctgccatcacccactgtgtggtgcacaatggcgccccca  633

Query:  525  caggtgtgctctcttcattgctgctgctggtgacaattgcaggttg  570
             |||||||||||||||||||||||||||||||||||||||||||| 
Sbjct:  634  caggtgtgctctcttcattgctgctgctggtgacaattgcagtttg  679
```

Score = 1.197e + 04 bits (6225), Expect = 0.0 Identities = 6225/6225 (100%) Strand = Plus/Plus

```
Query:  567  gttgtgcccgtaagcagtgcagcgaggggaggacatattccaatgcagtcatttcaccta  626
             ||||||||||||||||||||||||||||||||||||||||||||||||||||||||||||
Sbjct:  767  gttgtgcccgtaagcagtgcagcgaggggaggacatattccaatgcagtcatttcaccta  826
```

TABLE LIII-continued

Nucleotide sequence alignment of 254P1D6B v.1 (SEQ ID NO: 270) and 254P1D6B v.3 (SEQ ID NO: 271)

```
Query:  627  acttggaaaccaccagaatcatgcgggtgtctcacaccttccctgtcgtagactgcacgg  686
             ||||||||||||||||||||||||||||||||||||||||||||||||||||||||||||
Sbjct:  827  acttggaaaccaccagaatcatgcgggtgtctcacaccttccctgtcgtagactgcacgg  886

Query:  687  ccgcttgctgtgacctgtccagctgtgacctggcctggtggttcgagggccgctgctacc  746
             ||||||||||||||||||||||||||||||||||||||||||||||||||||||||||||
Sbjct:  887  ccgcttgctgtgacctgtccagctgtgacctggcctggtggttcgagggccgctgctacc  946

Query:  747  tggtgagctgcccccacaaagagaactgtgagcccaagaagatgggccccatcaggtctt  806
             ||||||||||||||||||||||||||||||||||||||||||||||||||||||||||||
Sbjct:  947  tggtgagctgcccccacaaagagaactgtgagcccaagaagatgggccccatcaggtctt  1006

Query:  807  atctcacttttgtgctccggcctgttcagaggcctgcacagctgctggactatgggggaca  866
             ||||||||||||||||||||||||||||||||||||||||||||||||||||||||||||
Sbjct: 1007  atctcacttttgtgctccggcctgttcagaggcctgcacagctgctggactatgggggaca  1066

Query:  867  tgatgctgaacaggggctcccctcggggatctgggggggactcacctgaggatatcagaa  926
             ||||||||||||||||||||||||||||||||||||||||||||||||||||||||||||
Sbjct: 1067  tgatgctgaacaggggctcccctcggggatctgggggggactcacctgaggatatcagaa  1126

Query:  927  aggacttgccctttctaggcaaagattggggcctagaggagatgtctgagtactcagatg  986
             ||||||||||||||||||||||||||||||||||||||||||||||||||||||||||||
Sbjct: 1127  aggacttgccctttctaggcaaagattggggcctagaggagatgtctgagtactcagatg  1186

Query:  987  actaccgggagctggagaaggacctcttgcaacccagtggcaagcaggagcccagaggga  1046
             ||||||||||||||||||||||||||||||||||||||||||||||||||||||||||||
Sbjct: 1187  actaccgggagctggagaaggacctcttgcaacccagtggcaagcaggagcccagaggga  1246

Query: 1047  gtgccgagtacacggactggggcctactgccgggcagcgagggggccttcaactcctctg  1106
             ||||||||||||||||||||||||||||||||||||||||||||||||||||||||||||
Sbjct: 1247  gtgccgagtacacggactggggcctactgccgggcagcgagggggccttcaactcctctg  1306

Query: 1107  ttggagacagtcctgcggtgccagcggagacgcagcaggaccctgagctccattacctga  1166
             ||||||||||||||||||||||||||||||||||||||||||||||||||||||||||||
Sbjct: 1307  ttggagacagtcctgcggtgccagcggagacgcagcaggaccctgagctccattacctga  1366

Query: 1167  atgagtcggcttcaacccctgccccaaaactccctgagagaagtgtgttgcttcccttgc  1226
             ||||||||||||||||||||||||||||||||||||||||||||||||||||||||||||
Sbjct: 1367  atgagtcggcttcaacccctgccccaaaactccctgagagaagtgtgttgcttcccttgc  1426

Query: 1227  cgactactccatcttcaggagaggtgttggagaaagaaaaggcttctcagctccaggaac  1286
             ||||||||||||||||||||||||||||||||||||||||||||||||||||||||||||
Sbjct: 1427  cgactactccatcttcaggagaggtgttggagaaagaaaaggcttctcagctccaggaac  1486

Query: 1287  aatccagcaacagctctggaaaagaggttctaatgccttcccatagtcttcctccggcaa  1346
             ||||||||||||||||||||||||||||||||||||||||||||||||||||||||||||
Sbjct: 1487  aatccagcaacagctctggaaaagaggttctaatgccttcccatagtcttcctccggcaa  1546

Query: 1347  gcctggagctcagctcagtcaccgtggagaaaagcccagtgctcacagtcaccccgggga  1406
             ||||||||||||||||||||||||||||||||||||||||||||||||||||||||||||
Sbjct: 1547  gcctggagctcagctcagtcaccgtggagaaaagcccagtgctcacagtcaccccgggga  1606

Query: 1407  gtacagagcacagcatcccaacacctcccactagcgcagcccctctgagtccacccccat  1466
             ||||||||||||||||||||||||||||||||||||||||||||||||||||||||||||
Sbjct: 1607  gtacagagcacagcatcccaacacctcccactagcgcagcccctctgagtccacccccat  1666

Query: 1467  ctgagctacccatatctcctaccactgctcccaggacagtgaaagaacttacggtatcgg  1526
             ||||||||||||||||||||||||||||||||||||||||||||||||||||||||||||
Sbjct: 1667  ctgagctacccatatctcctaccactgctcccaggacagtgaaagaacttacggtatcgg  1726

Query: 1527  ctggagataacctaattataactttacccgacaatgaagttgaactgaaggcctttgttg  1586
             ||||||||||||||||||||||||||||||||||||||||||||||||||||||||||||
Sbjct: 1727  ctggagataacctaattataactttacccgacaatgaagttgaactgaaggcctttgttg  1786

Query: 1587  cgccagcgccacctgtagaaacaacctacaactatgaatggaatttaataagccacccca  1646
             ||||||||||||||||||||||||||||||||||||||||||||||||||||||||||||
Sbjct: 1787  cgccagcgccacctgtagaaacaacctacaactatgaatggaatttaataagccacccca  1846

Query: 1647  cagactaccaaggtgaaataaaacaaggacacaagcaaactcttaacctctctcaattgt  1706
             ||||||||||||||||||||||||||||||||||||||||||||||||||||||||||||
Sbjct: 1847  cagactaccaaggtgaaataaaacaaggacacaagcaaactcttaacctctctcaattgt  1906

Query: 1707  ccgtcggactttatgtcttcaaagtcactgtttctagtgaaaacgcctttggagaaggat  1766
             ||||||||||||||||||||||||||||||||||||||||||||||||||||||||||||
Sbjct: 1907  ccgtcggactttatgtcttcaaagtcactgtttctagtgaaaacgcctttggagaaggat  1966
```

TABLE LIII-continued

Nucleotide sequence alignment of 254P1D6B v.1 (SEQ ID NO: 270) and 254P1D6B v.3 (SEQ ID NO: 271)

```
Query: 1767 ttgtcaatgtcactgttaagcctgccagaagagtcaacctgccacctgtagcagttgttt 1826
            ||||||||||||||||||||||||||||||||||||||||||||||||||||||||||||
Sbjct: 1967 ttgtcaatgtcactgttaagcctgccagaagagtcaacctgccacctgtagcagttgttt 2026

Query: 1827 ctccccaactgcaagagctcactttgcctttgacgtcagccctcattgatggcagccaaa 1886
            ||||||||||||||||||||||||||||||||||||||||||||||||||||||||||||
Sbjct: 2027 ctccccaactgcaagagctcactttgcctttgacgtcagccctcattgatggcagccaaa 2086

Query: 1887 gtacagatgatactgaaatagtgagttatcattgggaagaaataaacgggcccttcatag 1946
            ||||||||||||||||||||||||||||||||||||||||||||||||||||||||||||
Sbjct: 2087 gtacagatgatactgaaatagtgagttatcattgggaagaaataaacgggcccttcatag 2146

Query: 1947 aagagaagacttcagttgactctcccgtcttacgcttgtctaaccttgatcctggtaact 2006
            ||||||||||||||||||||||||||||||||||||||||||||||||||||||||||||
Sbjct: 2147 aagagaagacttcagttgactctcccgtcttacgcttgtctaaccttgatcctggtaact 2206

Query: 2007 atagtttcaggttgactgttacagactcggacggagccactaactctacaactgcagccc 2066
            ||||||||||||||||||||||||||||||||||||||||||||||||||||||||||||
Sbjct: 2207 atagtttcaggttgactgttacagactcggacggagccactaactctacaactgcagccc 2266

Query: 2067 taatagtgaacaatgctgtggactacccaccagttgctaatgcaggaccaaatcacacca 2126
            ||||||||||||||||||||||||||||||||||||||||||||||||||||||||||||
Sbjct: 2267 taatagtgaacaatgctgtggactacccaccagttgctaatgcaggaccaaatcacacca 2326

Query: 2127 taactttgccccaaaactccatcactttgaatggaaaccagagcagtgacgatcaccaga 2186
            ||||||||||||||||||||||||||||||||||||||||||||||||||||||||||||
Sbjct: 2327 taactttgccccaaaactccatcactttgaatggaaaccagagcagtgacgatcaccaga 2386

Query: 2187 ttgtcctctatgagtggtccctgggtcctgggagtgagggcaaacatgtggtcatgcagg 2246
            ||||||||||||||||||||||||||||||||||||||||||||||||||||||||||||
Sbjct: 2387 ttgtcctctatgagtggtccctgggtcctgggagtgagggcaaacatgtggtcatgcagg 2446

Query: 2247 gagtacagacgccataccttcatttatctgcaatgcaggaaggagattatacatttcagc 2306
            ||||||||||||||||||||||||||||||||||||||||||||||||||||||||||||
Sbjct: 2447 gagtacagacgccataccttcatttatctgcaatgcaggaaggagattatacatttcagc 2506

Query: 2307 tgaaggtgacagattcttcaaggcaacagtctactgctgtggtgactgtgattgtccagc 2366
            ||||||||||||||||||||||||||||||||||||||||||||||||||||||||||||
Sbjct: 2507 tgaaggtgacagattcttcaaggcaacagtctactgctgtggtgactgtgattgtccagc 2566

Query: 2367 ctgaaaacaatagacctccagtggctgtggccggccctgataaagagctgatcttcccag 2426
            ||||||||||||||||||||||||||||||||||||||||||||||||||||||||||||
Sbjct: 2567 ctgaaaacaatagacctccagtggctgtggccggccctgataaagagctgatcttcccag 2626

Query: 2427 tggaaagtgctaccctggatgggagcagcagcagcgatgaccacggcattgtcttctacc 2486
            ||||||||||||||||||||||||||||||||||||||||||||||||||||||||||||
Sbjct: 2627 tggaaagtgctaccctggatgggagcagcagcagcgatgaccacggcattgtcttctacc 2686

Query: 2487 actgggagcacgtcagaggccccagtgcagtggagatggaaaatattgacaaagcaatag 2546
            ||||||||||||||||||||||||||||||||||||||||||||||||||||||||||||
Sbjct: 2687 actgggagcacgtcagaggccccagtgcagtggagatggaaaatattgacaaagcaatag 2746

Query: 2547 ccactgtgactggtctccaggtggggacctaccacttccgtttgacagtgaaagaccagc 2606
            ||||||||||||||||||||||||||||||||||||||||||||||||||||||||||||
Sbjct: 2747 ccactgtgactggtctccaggtggggacctaccacttccgtttgacagtgaaagaccagc 2806

Query: 2607 agggactgagcagcacgtccaccctcactgtggctgtgaagaaggaaaataatagtcctc 2666
            ||||||||||||||||||||||||||||||||||||||||||||||||||||||||||||
Sbjct: 2807 agggactgagcagcacgtccaccctcactgtggctgtgaagaaggaaaataatagtcctc 2866

Query: 2667 ccagagcccgggctggtggcagacatgttcttgtgcttcccaataattccattactttgg 2726
            ||||||||||||||||||||||||||||||||||||||||||||||||||||||||||||
Sbjct: 2867 ccagagcccgggctggtggcagacatgttcttgtgcttcccaataattccattactttgg 2926

Query: 2727 atggttcaaggtctactgatgaccaaagaattgtgtcctatctgtggatccgggatggcc 2786
            ||||||||||||||||||||||||||||||||||||||||||||||||||||||||||||
Sbjct: 2927 atggttcaaggtctactgatgaccaaagaattgtgtcctatctgtggatccgggatggcc 2986

Query: 2787 agagtccagcagctggagatgtcatcgatggctctgaccacagtgtggctctgcagctta 2846
            ||||||||||||||||||||||||||||||||||||||||||||||||||||||||||||
Sbjct: 2987 agagtccagcagctggagatgtcatcgatggctctgaccacagtgtggctctgcagctta 3046

Query: 2847 cgaatctggtggaggggtgtacactttccacttgcgagtcaccgacagtcagggggcct 2906
            |||||||||||||||||||||||||||||||||||||||||||||||||||||||||||
Sbjct: 3047 cgaatctggtggaggggtgtacactttccacttgcgagtcaccgacagtcagggggcct 3106
```

TABLE LIII-continued

Nucleotide sequence alignment of 254P1D6B v.1 (SEQ ID NO: 270) and 254P1D6B v.3 (SEQ ID NO: 271)

```
Query: 2907 cggacacagacactgccactgtggaagtgcagccagaccctaggaagagtggcctggtgg 2966
            ||||||||||||||||||||||||||||||||||||||||||||||||||||||||||||
Sbjct: 3107 cggacacagacactgccactgtggaagtgcagccagaccctaggaagagtggcctggtgg 3166

Query: 2967 agctgaccctgcaggttggtgttgggcagctgacagagcagcggaaggacacccttgtga 3026
            ||||||||||||||||||||||||||||||||||||||||||||||||||||||||||||
Sbjct: 3167 agctgaccctgcaggttggtgttgggcagctgacagagcagcggaaggacacccttgtga 3226

Query: 3027 ggcagctggctgtgctgctgaacgtgctggactcggacattaaggtccagaagattcggg 3086
            ||||||||||||||||||||||||||||||||||||||||||||||||||||||||||||
Sbjct: 3227 ggcagctggctgtgctgctgaacgtgctggactcggacattaaggtccagaagattcggg 3286

Query: 3087 cccactcggatctcagcaccgtgattgtgttttatgtacagagcaggccgcctttcaagg 3146
            ||||||||||||||||||||||||||||||||||||||||||||||||||||||||||||
Sbjct: 3287 cccactcggatctcagcaccgtgattgtgttttatgtacagagcaggccgcctttcaagg 3346

Query: 3147 ttctcaaagctgctgaagtggcccgaaatctgcacatgcggctctcaaaggagaaggctg 3206
            ||||||||||||||||||||||||||||||||||||||||||||||||||||||||||||
Sbjct: 3347 ttctcaaagctgctgaagtggcccgaaatctgcacatgcggctctcaaaggagaaggctg 3406

Query: 3207 acttcttgcttttcaaggtcttgagggttgatacagcaggttgccttctgaagtgttctg 3266
            ||||||||||||||||||||||||||||||||||||||||||||||||||||||||||||
Sbjct: 3407 acttcttgcttttcaaggtcttgagggttgatacagcaggttgccttctgaagtgttctg 3466

Query: 3267 gccatggtcactgcgaccccctcacaaagcgctgcatttgctctcacttatggatggaga 3326
            ||||||||||||||||||||||||||||||||||||||||||||||||||||||||||||
Sbjct: 3467 gccatggtcactgcgaccccctcacaaagcgctgcatttgctctcacttatggatggaga 3526

Query: 3327 accttatacagcgttatatctgggatggagagagcaactgtgagtggagtatattctatg 3386
            ||||||||||||||||||||||||||||||||||||||||||||||||||||||||||||
Sbjct: 3527 accttatacagcgttatatctgggatggagagagcaactgtgagtggagtatattctatg 3586

Query: 3387 tgacagtgttggcttttactcttattgtgctaacaggagggtttcacttggctttgcatct 3446
            ||||||||||||||||||||||||||||||||||||||||||||||||||||||||||||
Sbjct: 3587 tgacagtgttggcttttactcttattgtgctaacaggagggtttcacttggctttgcatct 3646

Query: 3447 gctgctgcaaaagacaaaaaaggactaaaatcaggaaaaaaacaaagtacaccatcctgg 3506
            ||||||||||||||||||||||||||||||||||||||||||||||||||||||||||||
Sbjct: 3647 gctgctgcaaaagacaaaaaaggactaaaatcaggaaaaaaacaaagtacaccatcctgg 3706

Query: 3507 ataacatggatgaacaggaaagaatggaactgaggcccaaatatggtatcaagcaccgaa 3566
            ||||||||||||||||||||||||||||||||||||||||||||||||||||||||||||
Sbjct: 3707 ataacatggatgaacaggaaagaatggaactgaggcccaaatatggtatcaagcaccgaa 3766

Query: 3567 gcacagagcacaactccagcctgatggtatccgagtctgagtttgacagtgaccaggaca 3626
            ||||||||||||||||||||||||||||||||||||||||||||||||||||||||||||
Sbjct: 3767 gcacagagcacaactccagcctgatggtatccgagtctgagtttgacagtgaccaggaca 3826

Query: 3627 caatcttcagccgagaaaagatggagagagggaatccaaaggtttccatgaatggttcca 3686
            ||||||||||||||||||||||||||||||||||||||||||||||||||||||||||||
Sbjct: 3827 caatcttcagccgagaaaagatggagagagggaatccaaaggtttccatgaatggttcca 3886

Query: 3687 tcagaaatggagcttccttcagttattgctcaaaggacagataatggcgcagttcattgt 3746
            ||||||||||||||||||||||||||||||||||||||||||||||||||||||||||||
Sbjct: 3887 tcagaaatggagcttccttcagttattgctcaaaggacagataatggcgcagttcattgt 3946

Query: 3747 aaagtggaaggacccccttgaatccaagaccagtcagtgggagttacagcacaaaacccac 3806
            ||||||||||||||||||||||||||||||||||||||||||||||||||||||||||||
Sbjct: 3947 aaagtggaaggacccccttgaatccaagaccagtcagtgggagttacagcacaaaacccac 4006

Query: 3807 tcttttagaatagttcattgaccttcttccccagtgggttagatgtgtatccccacgtac 3866
            ||||||||||||||||||||||||||||||||||||||||||||||||||||||||||||
Sbjct: 4007 tcttttagaatagttcattgaccttcttccccagtgggttagatgtgtatccccacgtac 4066

Query: 3867 taaaagaccggttttttgaaggcacaaaacaaaaactttgctcttttaactgagatgcttg 3926
            ||||||||||||||||||||||||||||||||||||||||||||||||||||||||||||
Sbjct: 4067 taaaagaccggttttttgaaggcacaaaacaaaaactttgctcttttaactgagatgcttg 4126

Query: 3927 ttaatagaaataaaggctgggtaaaactctaaggtatatacttaaaagagttttgagttt 3986
            ||||||||||||||||||||||||||||||||||||||||||||||||||||||||||||
Sbjct: 4127 ttaatagaaataaaggctgggtaaaactctaaggtatatacttaaaagagttttgagttt 4186

Query: 3987 ttgtagctggcacaatctcatattaaagatgaacaacgatttctatctgtagaaccttag 4046
            ||||||||||||||||||||||||||||||||||||||||||||||||||||||||||||
Sbjct: 4187 ttgtagctggcacaatctcatattaaagatgaacaacgatttctatctgtagaaccttag 4246
```

TABLE LIII-continued

Nucleotide sequence alignment of 254P1D6B v.1 (SEQ ID NO: 270) and 254P1D6B v.3 (SEQ ID NO: 271)

```
Query:  4047  agaaggtgaatgaaacaaggttttaaaaagggatgatttctgtcttagccgctgtgattg  4106
              ||||||||||||||||||||||||||||||||||||||||||||||||||||||||||||
Sbjct:  4247  agaaggtgaatgaaacaaggttttaaaaagggatgatttctgtcttagccgctgtgattg  4306

Query:  4107  cctctaaggaacagcattctaaacacggtttctcttgtaggacctgcagtcagatggctg  4166
              ||||||||||||||||||||||||||||||||||||||||||||||||||||||||||||
Sbjct:  4307  cctctaaggaacagcattctaaacacggtttctcttgtaggacctgcagtcagatggctg  4366

Query:  4167  tgtatgttaaaatagcttgtctaagaggcacgggccatctgtggaggtacggagtcttgc  4226
              ||||||||||||||||||||||||||||||||||||||||||||||||||||||||||||
Sbjct:  4367  tgtatgttaaaatagcttgtctaagaggcacgggccatctgtggaggtacggagtcttgc  4426

Query:  4227  atgtagcaagctttctgtgctgacggcaacactcgcacagtgccaagccctcctggtttt  4286
              ||||||||||||||||||||||||||||||||||||||||||||||||||||||||||||
Sbjct:  4427  atgtagcaagctttctgtgctgacggcaacactcgcacagtgccaagccctcctggtttt  4486

Query:  4287  taattctgtgctatgtcaatggcagttttcatctctctcaagaaagcagctgttggccat  4346
              ||||||||||||||||||||||||||||||||||||||||||||||||||||||||||||
Sbjct:  4487  taattctgtgctatgtcaatggcagttttcatctctctcaagaaagcagctgttggccat  4546

Query:  4347  tcaagagctaaggaagaatcgtattctaaggactgaggcaatagaaagggaggaggagc  4406
              ||||||||||||||||||||||||||||||||||||||||||||||||||||||||||||
Sbjct:  4547  tcaagagctaaggaagaatcgtattctaaggactgaggcaatagaaagggaggaggagc  4606

Query:  4407  ttaatgccgtgcaggttgaaggtagcattgtaacattatcttttctttctctaagaaaaa  4466
              ||||||||||||||||||||||||||||||||||||||||||||||||||||||||||||
Sbjct:  4607  ttaatgccgtgcaggttgaaggtagcattgtaacattatcttttctttctctaagaaaaa  4666

Query:  4467  ctacactgactcctctcggtgttgtttagcagtatagttctctaatgtaaacggatcccc  4526
              ||||||||||||||||||||||||||||||||||||||||||||||||||||||||||||
Sbjct:  4667  ctacactgactcctctcggtgttgtttagcagtatagttctctaatgtaaacggatcccc  4726

Query:  4527  agtttacattaaatgcaatagaagtgattaattcattaagcatttattatgttctgtagg  4586
              ||||||||||||||||||||||||||||||||||||||||||||||||||||||||||||
Sbjct:  4727  agtttacattaaatgcaatagaagtgattaattcattaagcatttattatgttctgtagg  4786

Query:  4587  ctgtgcgtttggactgccatagatagggataacgactcagcaattgtgtatatattccaa  4646
              ||||||||||||||||||||||||||||||||||||||||||||||||||||||||||||
Sbjct:  4787  ctgtgcgtttggactgccatagatagggataacgactcagcaattgtgtatatattccaa  4846

Query:  4647  aactctgaaatacagtcagtcttaacttggatggcgtggttatgatactctggtccccga  4706
              ||||||||||||||||||||||||||||||||||||||||||||||||||||||||||||
Sbjct:  4847  aactctgaaatacagtcagtcttaacttggatggcgtggttatgatactctggtccccga  4906

Query:  4707  caggtactttccaaaataacttgacatagatgtattcacttcatatgtttaaaaatacat  4766
              ||||||||||||||||||||||||||||||||||||||||||||||||||||||||||||
Sbjct:  4907  caggtactttccaaaataacttgacatagatgtattcacttcatatgtttaaaaatacat  4966

Query:  4767  ttaagttttctaccgaataaatcttatttcaaacatgaaagacaattaaaacattccca  4826
              ||||||||||||||||||||||||||||||||||||||||||||||||||||||||||||
Sbjct:  4967  ttaagttttctaccgaataaatcttatttcaaacatgaaagacaattaaaacattccca  5026

Query:  4827  cccacaaagcagtactcccgagcaattaactggagttaattgtagcctgctacgttgact  4886
              ||||||||||||||||||||||||||||||||||||||||||||||||||||||||||||
Sbjct:  5027  cccacaaagcagtactcccgagcaattaactggagttaattgtagcctgctacgttgact  5086

Query:  4887  ggttcagggtagttccccatccacccttggtcctgaggctggtggccttggtggtgccct  4946
              ||||||||||||||||||||||||||||||||||||||||||||||||||||||||||||
Sbjct:  5087  ggttcagggtagttccccatccacccttggtcctgaggctggtggccttggtggtgccct  5146

Query:  4947  tggcatttttgtgggaagattagaatgagagatagaaccagtgttgtggtaccaagtgt  5006
              ||||||||||||||||||||||||||||||||||||||||||||||||||||||||||||
Sbjct:  5147  tggcatttttgtgggaagattagaatgagagatagaaccagtgttgtggtaccaagtgt  5206

Query:  5007  gagcacacctaaacaatatcctgttgcacaatgctttttaacacatgggaaaactagga  5066
              ||||||||||||||||||||||||||||||||||||||||||||||||||||||||||||
Sbjct:  5207  gagcacacctaaacaatatcctgttgcacaatgctttttaacacatgggaaaactagga  5266

Query:  5067  atgcattgctgatgaagaagcaaggtatttaaacaccagggcaggagtgccagagaaaat  5126
              ||||||||||||||||||||||||||||||||||||||||||||||||||||||||||||
Sbjct:  5267  atgcattgctgatgaagaagcaaggtatttaaacaccagggcaggagtgccagagaaaat  5326

Query:  5127  gtttccccatgggttcttaaaaaaaattcagcttttaggtgcttttgtcatctcccggag  5186
              ||||||||||||||||||||||||||||||||||||||||||||||||||||||||||||
Sbjct:  5327  gtttccccatgggttcttaaaaaaaattcagcttttaggtgcttttgtcatctcccggag  5386
```

TABLE LIII-continued

Nucleotide sequence alignment of 254P1D6B v.1 (SEQ ID NO: 270) and 254P1D6B v.3 (SEQ ID NO: 271)

```
Query:  5187 tattcatcctcatgggaccatcttattttacttattgtaatttactggggaaaggcaga 5246
             ||||||||||||||||||||||||||||||||||||||||||||||||||||||||||||
Sbjct:  5387 tattcatcctcatgggaccatcttattttacttattgtaatttactggggaaaggcaga 5446

Query:  5247 actaaaaagtgtgtcattttattttaaaataattgctttgcttatgcctacactttctg 5306
             ||||||||||||||||||||||||||||||||||||||||||||||||||||||||||||
Sbjct:  5447 actaaaaagtgtgtcattttattttaaaataattgctttgcttatgcctacactttctg 5506

Query:  5307 tataactagccaattcaatactgtctatagtgttagaaggaaaatgtgatttttttttt 5366
             ||||||||||||||||||||||||||||||||||||||||||||||||||||||||||||
Sbjct:  5507 tataactagccaattcaatactgtctatagtgttagaaggaaaatgtgatttttttttt 5566

Query:  5367 taaccagtattgagcttcataagcctagaatctgccttatcaggtgaccagggttatggt 5426
             ||||||||||||||||||||||||||||||||||||||||||||||||||||||||||||
Sbjct:  5567 taaccagtattgagcttcataagcctagaatctgccttatcaggtgaccagggttatggt 5626

Query:  5427 tgtttgcatgcaaatgtgaatttctggcataggggacagcagcccaaatgtaaagtcatc 5486
             ||||||||||||||||||||||||||||||||||||||||||||||||||||||||||||
Sbjct:  5627 tgtttgcatgcaaatgtgaatttctggcataggggacagcagcccaaatgtaaagtcatc 5686

Query:  5487 gggcgtaatgaggaagaagggagtgaacatttaccgctttatgtacataacatatgcagt 5546
             ||||||||||||||||||||||||||||||||||||||||||||||||||||||||||||
Sbjct:  5687 gggcgtaatgaggaagaagggagtgaacatttaccgctttatgtacataacatatgcagt 5746

Query:  5547 ttacatactcatttgatccttataatcaaccttgaagaggagatactatcattcttatgt 5606
             ||||||||||||||||||||||||||||||||||||||||||||||||||||||||||||
Sbjct:  5747 ttacatactcatttgatccttataatcaaccttgaagaggagatactatcattcttatgt 5806

Query:  5607 tgcagatagccctctgaaggcccagagaggttaagtaacttcccagaggtcatggccaag 5666
             ||||||||||||||||||||||||||||||||||||||||||||||||||||||||||||
Sbjct:  5807 tgcagatagccctctgaaggcccagagaggttaagtaacttcccagaggtcatggccaag 5866

Query:  5667 aagtagtggctccaagaactgaatgcaaatttttaaactgtagagttctgctttccact 5726
             ||||||||||||||||||||||||||||||||||||||||||||||||||||||||||||
Sbjct:  5867 aagtagtggctccaagaactgaatgcaaatttttaaactgtagagttctgctttccact 5926

Query:  5727 aaacaaagaactcctgccttgatggatggagggcaaattctggtggaacttttgggccac 5786
             ||||||||||||||||||||||||||||||||||||||||||||||||||||||||||||
Sbjct:  5927 aaacaaagaactcctgccttgatggatggagggcaaattctggtggaacttttgggccac 5986

Query:  5787 ctgaaagttctattcccaggactaagaggaatttcttttaatggatccagagagccaagg 5846
             ||||||||||||||||||||||||||||||||||||||||||||||||||||||||||||
Sbjct:  5987 ctgaaagttctattcccaggactaagaggaatttcttttaatggatccagagagccaagg 6046

Query:  5847 tcagagggagagatggcctgcatagtctcctgtggatcacacccgggccacccctccctc 5906
             ||||||||||||||||||||||||||||||||||||||||||||||||||||||||||||
Sbjct:  6047 tcagagggagagatggcctgcatagtctcctgtggatcacacccgggccacccctccctc 6106

Query:  5907 taggtttacagtggacttcttctgcccctcctccttttctgtccttggccatctcagcct 5966
             ||||||||||||||||||||||||||||||||||||||||||||||||||||||||||||
Sbjct:  6107 taggtttacagtggacttcttctgcccctcctccttttctgtccttggccatctcagcct 6166

Query:  5967 ggcctctctgatccttccatcacagaaggatcttgaatctctgggaaatcaaacatcaca 6026
             ||||||||||||||||||||||||||||||||||||||||||||||||||||||||||||
Sbjct:  6167 ggcctctctgatccttccatcacagaaggatcttgaatctctgggaaatcaaacatcaca 6226

Query:  6027 gtagtgatcagaaagtgagtcctgtcttgtcaccccatttctcatcagaacaaagcacga 6086
             ||||||||||||||||||||||||||||||||||||||||||||||||||||||||||||
Sbjct:  6227 gtagtgatcagaaagtgagtcctgtcttgtcaccccatttctcatcagaacaaagcacga 6286

Query:  6087 gatggaatgaccaaccagcattcttcatggtggactgcttatcattgaggatctttggga 6146
             ||||||||||||||||||||||||||||||||||||||||||||||||||||||||||||
Sbjct:  6287 gatggaatgaccaaccagcattcttcatggtggactgcttatcattgaggatctttggga 6346

Query:  6147 gataaagcacgctaagagctctggacagagaaaaacaggccctagaatatgggagtgggt 6206
             ||||||||||||||||||||||||||||||||||||||||||||||||||||||||||||
Sbjct:  6347 gataaagcacgctaagagctctggacagagaaaaacaggccctagaatatgggagtgggt 6406

Query:  6207 gtttgtagggctcataggctaacaagcactttagttgctggtttacattcaatgaaggag 6266
             ||||||||||||||||||||||||||||||||||||||||||||||||||||||||||||
Sbjct:  6407 gtttgtagggctcataggctaacaagcactttagttgctggtttacattcaatgaaggag 6466

Query:  6267 gattcatacccatggcattacaaggctaagcatgtgtatgactaaggaactatctgaaaa 6326
             ||||||||||||||||||||||||||||||||||||||||||||||||||||||||||||
Sbjct:  6467 gattcatacccatggcattacaaggctaagcatgtgtatgactaaggaactatctgaaaa 6526
```

TABLE LIII-continued

Nucleotide sequence alignment of 254P1D6B v.1 (SEQ ID NO: 270) and 254P1D6B v.3 (SEQ ID NO: 271)

```
Query: 6327  acatgcagcaaggtaagaaaatgtaccactcaacaagccagtgatgccacctttgtgcg  6386
             ||||||||||||||||||||||||||||||||||||||||||||||||||||||||||
Sbjct: 6527  acatgcagcaaggtaagaaaatgtaccactcaacaagccagtgatgccacctttgtgcg  6586

Query: 6387  cggggaggagagtgactaccattgtttttgtgtgacaaagctatcatggactattttaa  6446
             ||||||||||||||||||||||||||||||||||||||||||||||||||||||||||
Sbjct: 6587  cggggaggagagtgactaccattgtttttgtgtgacaaagctatcatggactattttaa  6646

Query: 6447  tcttggttttattgcttaaaatatattattttcccctatgtgttgacaaggtatttctaa  6506
             ||||||||||||||||||||||||||||||||||||||||||||||||||||||||||
Sbjct: 6647  tcttggttttattgcttaaaatatattattttcccctatgtgttgacaaggtatttctaa  6706

Query: 6507  tatcacactattaaatatatgcactaatctaaataaaggtgtctgtattttctgtaatgc  6566
             ||||||||||||||||||||||||||||||||||||||||||||||||||||||||||
Sbjct: 6707  tatcacactattaaatatatgcactaatctaaataaaggtgtctgtattttctgtaatgc  6766

Query: 6567  ttattttaggggggaaatttgttttctttatgcttcagggtagagggattcccttgagta  6626
             ||||||||||||||||||||||||||||||||||||||||||||||||||||||||||
Sbjct: 6767  ttattttaggggggaaatttgttttctttatgcttcagggtagagggattcccttgagta  6826

Query: 6627  taggtcagcaaactctggcctgcagcctgtgtgtgcacgcccatgagccgaaaagtggg  6686
             ||||||||||||||||||||||||||||||||||||||||||||||||||||||||||
Sbjct: 6827  taggtcagcaaactctggcctgcagcctgtgtgtgcacgcccatgagccgaaaagtggg  6886

Query: 6687  tcttatgttttcaaatggttaaaaataaataaaaaaatttgaaacatgtgaactatatga  6746
             ||||||||||||||||||||||||||||||||||||||||||||||||||||||||||
Sbjct: 6887  tcttatgttttcaaatggttaaaaataaataaaaaaatttgaaacatgtgaactatatga  6946

Query: 6747  cattcagatttgtgttcataaataaagttttattggaacatatcc  6791
             |||||||||||||||||||||||||||||||||||||||||||||
Sbjct: 6947  cattcagatttgtgttcataaataaagttttattggaacatatcc  6991
```

TABLE LIV

Peptide sequences of protein coded by 254P1D6B v.3

| | | | | | | |
|---|---|---|---|---|---|---|
| MTRLGWPSPC | CARKQCSEGR | TYSNAVISPN | LETTRIMRVS | HTFPVVDCTA | ACCDLSSCDL | 60 (SEQ ID NO: 272) |
| AWWFEGRCYL | VSCPHKENCE | PKKMGPIRSY | LTFVLRPVQR | PAQLLDYGDM | MLNRGSPSGI | 120 |
| WGDSPEDIRK | DLPFLGKDWG | LEEMSEYSDD | YRELEKDLLQ | PSGKQEPRGS | AEYTDWGLLP | 180 |
| GSEGAFNSSV | GDSPAVPAET | QQDPELHYLN | ESASTPAPKL | PERSVLLPLP | TTPSSGEVLE | 240 |
| KEKASQLQEQ | SSNSSGKEVL | MPSHSLPPAS | LELSSVTVEK | SPVLTVTPGS | TEHSIPTPPT | 300 |
| SAAPSESTPS | ELPISPTTAP | RTVKELTVSA | GDNLIITLPD | NEVELKAFVA | PAPPVETTYN | 360 |
| YEWNLISHPT | DYQGEIKQGH | KQTLNLSQLS | VGLYVFKVTV | SSENAFGEGF | VNVTVKPARR | 420 |
| VNLPPVAVVS | PQLQELTLPL | TSALIDGSQS | TDDTEIVSYH | WEEINGPFIE | EKTSVDSPVL | 480 |
| RLSNDLPGNY | SFRLTVTDSD | GATNSTTAAL | IVNNAVDYPP | VANAGPNHTI | TLPQNSITLN | 540 |
| GNQSSDDHQI | VLYEWSLGPG | SEGKHVVMQG | VQTPYLHLSA | MQEGDYTFQL | KVTDSSRQQS | 600 |
| TAVVTVIVQP | ENNRPPVAVA | GPDKELIFPV | ESATLDGSSS | SDDHGIVFYH | WEHVRGPSAV | 660 |
| EMENIDKAIA | TVTGLQVGTY | HFRLTVKDQQ | GLSSTSTLTV | AVKKENNSPP | RARAGGRHVL | 720 |
| VLPNNSITLD | GSRSTDDQRI | VSYLWIRDGQ | SPAAGDVIDG | SDHSVALQLT | NLVEGVYTFH | 780 |
| LRVTDSQGAS | DTDTATVEVQ | PDPRKSGLVE | LTLQVGVGQL | TEQRKDTLVR | QLAVLLNVLD | 840 |
| SDIKVQKIRA | HSDLSTVIVF | YVQSRPPFKV | LKAAEVARNL | HMRLSEKEAD | FLLFKVLRVD | 900 |
| TAGCLLKCSG | HGHCDPLTKR | CICSHLWMEN | LIQRYIWDGE | SNCEWSIFYV | TVLAFTLIVL | 960 |
| TGGFTWLCIC | CCKRQKRTKI | RKKTKYTILD | NMDEQERMEL | RPKYGIKHRS | TEHNSSLMVS | 1020 |
| ESEFDSDQDT | IFSREKMERG | NPKVSMNGSI | RNGASFSYCS | KDR | | 1063 |

TABLE LV

Amino acid sequence alignment of 254P1D6B v.1 (SEQ ID NO: 273)
and 254P1D6B v.3 (SEQ ID NO: 274)
Score = 2124 bits (5503), Expect = 0.0 Identities = 1053/1053 (100%),
Positives = 1053/1053 (100%)

```
V.1:   20  CARKQCSEGRTYSNAVISPNLETTRIMRVSHTFPVVDCTAACCDLSSCDLAWWFEGRCYL   79
           CARKQCSEGRTYSNAVISPNLETTRIMRVSHTFPVVDCTAACCDLSSCDLAWWFEGRCYL
V.3:   11  CARKQCSEGRTYSNAVISPNLETTRIMRVSHTFPVVDCTAACCDLSSCDLAWWFEGRCYL   70

V.1:   80  VSCPHKENCEPKKMGPIRSYLTFVLRPVQRPAQLLDYGDMMLNRGSPSGIWGDSPEDIRK  139
           VSCPHKENCEPKKMGPIRSYLTFVLRPVQRPAQLLDYGDMMLNRGSPSGIWGDSPEDTRK
V.3:   71  VSCPHKENCEPKKMGPIRSYLTFVLRPVQRPAQLLDYGDMMLNRGSPSGIWGDSPEDTRK  130

V.1:  140  DLPFLGKDWGLEEMSEYSDDYRELEKDLLQPSGKQEPRGSAEYTDWGLLPGSEGAFNSSV  199
           DLPFLGKDWGLEEMSEYSDDYRELEKDLLQPSGKQEPRGSAEYTDWGLLPGSEGAFNSSV
V.3:  131  DLPFLGKDWGLEEMSEYSDDYRELEKDLLQPSGKQEPRGSAEYTDWGLLPGSEGAFNSSV  190

V.1:  200  GDSPAVPAETQQDPELHYLNESASTPAPKLPERSVLLPLTTPSSGEVLEKEKASQLQEQ  259
           GDSPAVPAETQQDPELHYLNESASTPAPKLPERSVLLPLTTPSSGEVLEKEKASQLQEQ
V.3:  191  GDSPAVPAETQQDPELHYLNESASTPAPKLPERSVLLPLTTPSSGEVLEKEKASQLQEQ  250

V.1:  260  SSNSSGKEVLMPSHSLPPASLELSSVTVEKSPVLTVTPGSTEHSIPTPPTSAAPSESTPS  319
           SSNSSGKEVLMPSHSLPPASLELSSVTVEKSPVLTVTPGSTEHSIPTPPTSAAPSESTPS
V.3:  251  SSNSSGKEVLMPSHSLPPASLELSSVTVEKSPVLTVTPGSTEHSIPTPPTSAAPSESTPS  310

V.1:  320  ELPISPTTAPRTVKELTVSAGDNLIITLPDNEVELKAFVAPAPPVETTYNYEWNLISHPT  379
           ELPISPTTAPRTVKELTVSAGDNLIITLPDNEVELKAFVAPAPPVETTYNYEWNLISHPT
V.3:  311  ELPISPTTAPRTVKELTVSAGDNLIITLPDNEVELKAFVAPAPPVETTYNYEWNLISHPT  370

V.1:  380  DYQGEIKQGHKQTLNLSQLSVGLYVFKVTVSSENAFGEGFVNVTVKPARRVNLPPVAVVS  439
           DYQGEIKQGHKQTLNLSQLSVGLYVFKVTVSSENAFGEGFVNVTVKPARRVNLPPVAVVS
V.3:  371  DYQGEIKQGHKQTLNLSQLSVGLYVFKVTVSSENAFGEGFVNVTVKPARRVNLPPVAVVS  430

V.1:  440  PQLQELTLPLTSALIDGSQSTDDTEIVSYHWEEINGPFIEEKTSVDSPVLRLSNLDPGNY  499
           PQLQELTLPLTSALIDGSQSTDDTEIVSYHWEEINGPFIEEKTSVDSPVLRLSNLDPGNY
V.3:  431  PQLQELTLPLTSALIDGSQSTDDTEIVSYHWEEINGPFIEEKTSVDSPVLRLSNLDPGNY  490

V.1:  500  SFRLTVTDSDGATNSTTAALIVNNAVDYPPVANAGPNHTITLPQNSITLNGNQSSDDHQI  559
           SFRLTVTDSDGATNSTTAALIVNNAVDYPPVANAGPNHTITLPQNSITLNGNQSSDDHQI
V.3:  491  SFRLTVTDSDGATNSTTAALIVNNAVDYPPVANAGPNHTITLPQNSITLNGNQSSDDHQI  550

V.1:  560  VLYEWSLGPGSEGKHVVMQGVQTPYLHLSAMQEGDYTFQLKVTDSSRQQSTAVVTVIVQP  619
           VLYEWSLGPGSEGKHVVMQGVQTPYLHLSAMQEGDYTFQLKVTDSSRQQSTAVVTVIVQP
V.3:  551  VLYEWSLGPGSEGKHVVMQGVQTPYLHLSAMQEGDYTFQLKVTDSSRQQSTAVVTVIVQP  610

V.1:  620  ENNRPPVAVAGPDKELIFPVESATLDGSSSSDDHGIVFYHWEHVRGPSAVEMENIDKAIA  679
           ENNRPPVAVAGPDKELIFPVESATLDGSSSSDDHGIVFYHWEHVRGPSAVEMENIDKAIA
V.3:  611  ENNRPPVAVAGPDKELIFPVESATLDGSSSSDDHGIVFYHWEHVRGPSAVEMENIDKAIA  670

V.1:  680  TVTGLQVGTYHFRLTVKDQQGLSSTSTLTVAVKKENNSPPRARAGGRHVLVLPNNSITLD  739
           TVTGLQVGTYHFRLTVKDQQGLSSTSTLTVAVKKENNSPPRARAGGRHVLVLPNNSITLD
V.3:  671  TVTGLQVGTYHFRLTVKDQQGLSSTSTLTVAVKKENNSPPRARAGGRHVLVLPNNSITLD  730

V.1:  740  GSRSTDDQRIVSYLWIRDGQSPAAGDVIDGSDHSVALQLTNLVEGVYTFHLRVTDSQGAS  799
           GSRSTDDQRIVSYLWIRDGQSPAAGDVIDGSDHSVALQLTNLVEGVYTFHLRVTDSQGAS
V.3:  731  GSRSTDDQRIVSYLWIRDGQSPAAGDVIDGSDHSVALQLTNLVEGVYTFHLRVTDSQGAS  790

V.1:  800  DTDTATVEVQPDPRKSGLVELTLQVGVGQLTEQRKDTLVRQLAVLLNVLDSDIKVQKIRA  859
           DTDTATVEVQPDPRKSGLVELTLQVGVGQLTEQRKDTLVRQLAVLLNVLDSDIKVQKIRA
V.3:  791  DTDTATVEVQPDPRKSGLVELTLQVGVGQLTEQRKDTLVRQLAVLLNVLDSDIKVQKIRA  850

V.1:  860  HSDLSTVIVFYVQSRPPFKVLKAAEVARNLHMRLSKEKADFLLFKVLRVDTAGCLLKCSG  919
           HSDLSTVIVFYVQSRPPFKVLKAAEVARNLHMRLSKEKADFLLFKVLRVDTAGCLLKCSG
V.3:  851  HSDLSTVIVFYVQSRPPFKVLKAAEVARNLHMRLSKEKADFLLFKVLRVDTAGCLLKCSG  910

V.1:  920  HGHCDPLTKRCICSHLWMENLIQRYIWDGESNCEWSIFYVTVLAFTLIVLTGGFTWLCIC  979
           HGHCDPLTKRCICSHLWMENLIQRYIWDGESNCEWSIFYVTVLAFTLIVLTGGFTWLCIC
V.3:  911  HGHCDPLTKRCICSHLWMENLIQRYIWDGESNCEWSIFYVTVLAFTLIVLTGGFTWLCIC  970

V.1:  980  CCKRQKRTKIRKKTKYTTLDNMDEQERMELRPKYGIKHRSTEHNSSLMVSESEFDSDQDT 1039
           CCKRQKRTKIRKKTKYTILDNMDEQERMELRPKYGIKHRSTEHNSSLMVSESEFDSDQDT
V.3:  971  CCKRQKRTKIRKKTKYTILDNMDEQERMELRPKYGIKHRSTEHNSSLMVSESEFDSDQDT 1030

V.1: 1040  IFSREKMERGNPKVSMNGSIRNGASFSYCSKDR                            1072
           IFSREKMERGNPKVSMNGSIRNGASFSYCSKDR
V.3: 1031  IFSREKMERGNPKVSMNGSIRNGASFSYCSKDR                            1063
```

The invention claimed is:

1. A method for detecting the presence of a protein comprising SEQ ID NO:3 or SEQ ID NO:5 in a sample comprising:
   contacting a sample with an antibody or fragment thereof that specifically binds to SEQ ID NO:3 or SEQ ID NO:5;
   determining the presence of the protein in the sample by detecting a complex between the antibody or fragment thereof and the protein;
   wherein the sample is selected from the group consisting of lung, ovary, prostate, pancreas and breast tissue.

2. The method of claim 1, wherein the sample is from a patient who has or who is suspected of having cancer.

* * * * *

SEQUENCE LISTING

<160> NUMBER OF SEQ ID NOS: 277

<210> SEQ ID NO 1
<211> LENGTH: 284
<212> TYPE: DNA
<213> ORGANISM: Homo sapiens

<400> SEQUENCE: 1

```
gatccacaga taggacacaa ttctttggtc atcagtagac cttgaaccat ccaaagtaat    60
ggaattattg ggaagcacaa gaacatgtct gccaccagcc cgggctctgg gaggactatt   120
attttccttc ttcacagcca cagtgagggt ggacgtgctg ctcagtccct gctggtcttt   180
tactgtcaaa cggaagtggt aggtccccac ctggagacca gtcacagtgg ctattgcttt   240
gtcaatattt tccatctcca ctgcactggg gcctctgacg tgct                    284
```

<210> SEQ ID NO 2
<211> LENGTH: 6791
<212> TYPE: DNA
<213> ORGANISM: Homo sapiens
<220> FEATURE:
<221> NAME/KEY: CDS
<222> LOCATION: (512)...(3730)
<221> NAME/KEY: misc_feature
<222> LOCATION: 286
<223> OTHER INFORMATION: s = g or c
<221> NAME/KEY: misc_feature
<222> LOCATION: 935
<223> OTHER INFORMATION: m = c or a
<221> NAME/KEY: misc_feature
<222> LOCATION: 980
<223> OTHER INFORMATION: k = t or g
<221> NAME/KEY: misc_feature
<222> LOCATION: 2347
<223> OTHER INFORMATION: r = g or a
<221> NAME/KEY: misc_feature
<222> LOCATION: 3762
<223> OTHER INFORMATION: y = c or t
<221> NAME/KEY: misc_feature
<222> LOCATION: (0)...(0)
<223> OTHER INFORMATION: Pos: 3772; r = a or g
<221> NAME/KEY: misc_feature
<222> LOCATION: (0)...(0)
<223> OTHER INFORMATION: Pos: 3955; y = c or t
<221> NAME/KEY: misc_feature
<222> LOCATION: (0)...(0)
<223> OTHER INFORMATION: Pos: 4096; y = c or t
<221> NAME/KEY: misc_feature
<222> LOCATION: (0)...(0)
<223> OTHER INFORMATION: Pos: 4415; r = g or a
<221> NAME/KEY: misc_feature
<222> LOCATION: (0)...(0)
<223> OTHER INFORMATION: Pos: 4519; r = g or a
<221> NAME/KEY: misc_feature
<222> LOCATION: (0)...(0)
<223> OTHER INFORMATION: Pos: 4539; r = a or g
<221> NAME/KEY: misc_feature
<222> LOCATION: (0)...(0)
<223> OTHER INFORMATION: Pos: 4614; k = t or g
<221> NAME/KEY: misc_feature
<222> LOCATION: (0)...(0)
<223> OTHER INFORMATION: Pos: 5184; s = g or c
<221> NAME/KEY: misc_feature
<222> LOCATION: (0)...(0)
<223> OTHER INFORMATION: Pos: 5528; k = t or g
<221> NAME/KEY: misc_feature
<222> LOCATION: (0)...(0)
<223> OTHER INFORMATION: Pos: 5641; r = g or a
<221> NAME/KEY: misc_feature
<222> LOCATION: (0)...(0)
<223> OTHER INFORMATION: Pos: 6221; y = t or c
<221> NAME/KEY: misc_feature
<222> LOCATION: (0)...(0)

<223> OTHER INFORMATION: Pos: 6223; r = g or a

<400> SEQUENCE: 2

```
gctgccgcgg gcggtgggcg gggatccccc gggggtgcaa ccttgctcca cctgtgctgc      60
cctcggcggg cctggctggc cccgcgcaga gcggcggcgg cgctcgctgt cactgccgga     120
ggtgagagcg cagcagtagc ttcagcctgt cttgggcttg gtccagattc gctcctctgg     180
ggctacgtcc cggggaagag gaagcgagga ttttgctggg gtggggctgt acctcttaac     240
agcaggtgcg cgcgcgaggg tgtgaacgtg tgtgtgtgtg tgtgtstgtg tgtgtgtgtg     300
taagacctgc gatgacgacg aggaggaaca agtgggacgg cgagtgatgc tcagggccag     360
cagcaacgca tggggcgagc ttcagtgtcg ccagcagtga ccacagttct tgaggccaaa     420
tctggctcct aaaaaacatc aaaggaagct tgcaccaaac tctcttcagg gccgcctcag     480
aagcctgcca tcacccactg tgtggtgcac a atg gcg ccc ccc aca ggt gtg        532
                                   Met Ala Pro Pro Thr Gly Val
                                   1               5
```

| | | | | | | | | | | | | | | |
|---|---|---|---|---|---|---|---|---|---|---|---|---|---|---|
| ctc | tct | tca | ttg | ctg | ctg | ctg | gtg | aca | att | gca | ggt | tgt | gcc | cgt aag | 580 |
| Leu | Ser | Ser | Leu | Leu | Leu | Leu | Val | Thr | Ile | Ala | Gly | Cys | Ala | Arg Lys | |
| | | 10 | | | | 15 | | | | 20 | | | | | |

```
cag tgc agc gag ggg agg aca tat tcc aat gca gtc att tca cct aac      628
Gln Cys Ser Glu Gly Arg Thr Tyr Ser Asn Ala Val Ile Ser Pro Asn
    25                  30                  35 ttg gaa acc acc aga atc atg cgg gtg tct cac acc ttc cct gtc gta      676
Leu Glu Thr Thr Arg Ile Met Arg Val Ser His Thr Phe Pro Val Val
 40                  45                  50                  55 gac tgc acg gcc gct tgc tgt gac ctg tcc agc tgt gac ctg gcc tgg      724
Asp Cys Thr Ala Ala Cys Cys Asp Leu Ser Ser Cys Asp Leu Ala Trp
                 60                  65                  70 tgg ttc gag ggc cgc tgc tac ctg gtg agc tgc ccc cac aaa gag aac      772
Trp Phe Glu Gly Arg Cys Tyr Leu Val Ser Cys Pro His Lys Glu Asn
             75                  80                  85 tgt gag ccc aag aag atg ggc ccc atc agg tct tat ctc act ttt gtg      820
Cys Glu Pro Lys Lys Met Gly Pro Ile Arg Ser Tyr Leu Thr Phe Val
         90                  95                 100 ctc cgg cct gtt cag agg cct gca cag ctg ctg gac tat ggg gac atg      868
Leu Arg Pro Val Gln Arg Pro Ala Gln Leu Leu Asp Tyr Gly Asp Met
105                 110                 115 atg ctg aac agg ggc tcc ccc tcg ggg atc tgg ggg gac tca cct gag      916
Met Leu Asn Arg Gly Ser Pro Ser Gly Ile Trp Gly Asp Ser Pro Glu
120                 125                 130                 135 gat atc aga aag gac ttg mcc ttt cta ggc aaa gat tgg ggc cta gag      964
Asp Ile Arg Lys Asp Leu Xaa Phe Leu Gly Lys Asp Trp Gly Leu Glu
                140                 145                 150 gag atg tct gag tac kca gat gac tac cgg gag ctg gag aag gac ctc     1012
Glu Met Ser Glu Tyr Xaa Asp Asp Tyr Arg Glu Leu Glu Lys Asp Leu
            155                 160                 165 ttg caa ccc agt ggc aag cag gag ccc aga ggg agt gcc gag tac acg     1060
Leu Gln Pro Ser Gly Lys Gln Glu Pro Arg Gly Ser Ala Glu Tyr Thr
        170                 175                 180 gac tgg ggc cta ctg ccg ggc agc gag ggg gcc ttc aac tcc tct gtt     1108
Asp Trp Gly Leu Leu Pro Gly Ser Glu Gly Ala Phe Asn Ser Ser Val
185                 190                 195 gga gac agt cct gcg gtg cca gcg gag acg cag cag gac cct gag ctc     1156
Gly Asp Ser Pro Ala Val Pro Ala Glu Thr Gln Gln Asp Pro Glu Leu
200                 205                 210                 215 cat tac ctg aat gag tcg gct tca acc cct gcc cca aaa ctc cct gag     1204
His Tyr Leu Asn Glu Ser Ala Ser Thr Pro Ala Pro Lys Leu Pro Glu
                220                 225                 230
```

```
aga agt gtg ttg ctt ccc ttg ccg act act cca tct tca gga gag gtg      1252
Arg Ser Val Leu Leu Pro Leu Pro Thr Thr Pro Ser Ser Gly Glu Val
            235                 240                 245 ttg gag aaa gaa aag gct tct cag ctc cag gaa caa tcc agc aac agc      1300
Leu Glu Lys Glu Lys Ala Ser Gln Leu Gln Glu Gln Ser Ser Asn Ser
        250                 255                 260 tct gga aaa gag gtt cta atg cct tcc cat agt ctt cct ccg gca agc      1348
Ser Gly Lys Glu Val Leu Met Pro Ser His Ser Leu Pro Pro Ala Ser
    265                 270                 275 ctg gag ctc agc tca gtc acc gtg gag aaa agc cca gtg ctc aca gtc      1396
Leu Glu Leu Ser Ser Val Thr Val Glu Lys Ser Pro Val Leu Thr Val
280                 285                 290                 295 acc ccg ggg agt aca gag cac agc atc cca aca cct ccc act agc gca      1444
Thr Pro Gly Ser Thr Glu His Ser Ile Pro Thr Pro Pro Thr Ser Ala
                300                 305                 310 gcc ccc tct gag tcc acc cca tct gag cta ccc ata tct cct acc act      1492
Ala Pro Ser Glu Ser Thr Pro Ser Glu Leu Pro Ile Ser Pro Thr Thr
            315                 320                 325 gct ccc agg aca gtg aaa gaa ctt acg gta tcg gct gga gat aac cta      1540
Ala Pro Arg Thr Val Lys Glu Leu Thr Val Ser Ala Gly Asp Asn Leu
        330                 335                 340 att ata act tta ccc gac aat gaa gtt gaa ctg aag gcc ttt gtt gcg      1588
Ile Ile Thr Leu Pro Asp Asn Glu Val Glu Leu Lys Ala Phe Val Ala
    345                 350                 355 cca gcg cca cct gta gaa aca acc tac aac tat gaa tgg aat tta ata      1636
Pro Ala Pro Pro Val Glu Thr Thr Tyr Asn Tyr Glu Trp Asn Leu Ile
360                 365                 370                 375 agc cac ccc aca gac tac caa ggt gaa ata aaa caa gga cac aag caa      1684
Ser His Pro Thr Asp Tyr Gln Gly Glu Ile Lys Gln Gly His Lys Gln
                380                 385                 390 act ctt aac ctc tct caa ttg tcc gtc gga ctt tat gtc ttc aaa gtc      1732
Thr Leu Asn Leu Ser Gln Leu Ser Val Gly Leu Tyr Val Phe Lys Val
            395                 400                 405 act gtt tct agt gaa aac gcc ttt gga gaa gga ttt gtc aat gtc act      1780
Thr Val Ser Ser Glu Asn Ala Phe Gly Glu Gly Phe Val Asn Val Thr
        410                 415                 420 gtt aag cct gcc aga aga gtc aac ctg cca cct gta gca gtt gtt tct      1828
Val Lys Pro Ala Arg Arg Val Asn Leu Pro Pro Val Ala Val Val Ser
    425                 430                 435 ccc caa ctg caa gag ctc act ttg cct ttg acg tca gcc ctc att gat      1876
Pro Gln Leu Gln Glu Leu Thr Leu Pro Leu Thr Ser Ala Leu Ile Asp
440                 445                 450                 455 ggc agc caa agt aca gat gat act gaa ata gtg agt tat cat tgg gaa      1924
Gly Ser Gln Ser Thr Asp Asp Thr Glu Ile Val Ser Tyr His Trp Glu
                460                 465                 470 gaa ata aac ggg ccc ttc ata gaa gag aag act tca gtt gac tct ccc      1972
Glu Ile Asn Gly Pro Phe Ile Glu Glu Lys Thr Ser Val Asp Ser Pro
            475                 480                 485 gtc tta cgc ttg tct aac ctt gat cct ggt aac tat agt ttc agg ttg      2020
Val Leu Arg Leu Ser Asn Leu Asp Pro Gly Asn Tyr Ser Phe Arg Leu
        490                 495                 500 act gtt aca gac tcg gac gga gcc act aac tct aca act gca gcc cta      2068
Thr Val Thr Asp Ser Asp Gly Ala Thr Asn Ser Thr Thr Ala Ala Leu
    505                 510                 515 ata gtg aac aat gct gtg gac tac cca cca gtt gct aat gca gga cca      2116
Ile Val Asn Asn Ala Val Asp Tyr Pro Pro Val Ala Asn Ala Gly Pro
520                 525                 530                 535 aat cac acc ata act ttg ccc caa aac tcc atc act ttg aat gga aac      2164
Asn His Thr Ile Thr Leu Pro Gln Asn Ser Ile Thr Leu Asn Gly Asn
                540                 545                 550
```

```
cag agc agt gac gat cac cag att gtc ctc tat gag tgg tcc ctg ggt     2212
Gln Ser Ser Asp Asp His Gln Ile Val Leu Tyr Glu Trp Ser Leu Gly
        555                 560                 565 cct ggg agt gag ggc aaa cat gtg gtc atg cag gga gta cag acg cca     2260
Pro Gly Ser Glu Gly Lys His Val Val Met Gln Gly Val Gln Thr Pro
570                 575                 580 tac ctt cat tta tct gca atg cag gaa gga gat tat aca ttt cag ctg     2308
Tyr Leu His Leu Ser Ala Met Gln Glu Gly Asp Tyr Thr Phe Gln Leu
585                 590                 595 aag gtg aca gat tct tca agg caa cag tct act gct gtr gtg act gtg     2356
Lys Val Thr Asp Ser Ser Arg Gln Gln Ser Thr Ala Xaa Val Thr Val
600                 605                 610                 615 att gtc cag cct gaa aac aat aga cct cca gtg gct gtg gcc ggc cct     2404
Ile Val Gln Pro Glu Asn Asn Arg Pro Pro Val Ala Val Ala Gly Pro
                620                 625                 630 gat aaa gag ctg atc ttc cca gtg gaa agt gct acc ctg gat ggg agc     2452
Asp Lys Glu Leu Ile Phe Pro Val Glu Ser Ala Thr Leu Asp Gly Ser
        635                 640                 645 agc agc agc gat gac cac ggc att gtc ttc tac cac tgg gag cac gtc     2500
Ser Ser Ser Asp Asp His Gly Ile Val Phe Tyr His Trp Glu His Val
650                 655                 660 aga ggc ccc agt gca gtg gag atg gaa aat att gac aaa gca ata gcc     2548
Arg Gly Pro Ser Ala Val Glu Met Glu Asn Ile Asp Lys Ala Ile Ala
665                 670                 675 act gtg act ggt ctc cag gtg ggg acc tac cac ttc cgt ttg aca gtg     2596
Thr Val Thr Gly Leu Gln Val Gly Thr Tyr His Phe Arg Leu Thr Val
680                 685                 690                 695 aaa gac cag cag gga ctg agc agc acg tcc acc ctc act gtg gct gtg     2644
Lys Asp Gln Gln Gly Leu Ser Ser Thr Ser Thr Leu Thr Val Ala Val
                700                 705                 710 aag aag gaa aat aat agt cct ccc aga gcc cgg gct ggt ggc aga cat     2692
Lys Lys Glu Asn Asn Ser Pro Pro Arg Ala Arg Ala Gly Gly Arg His
        715                 720                 725 gtt ctt gtg ctt ccc aat aat tcc att act ttg gat ggt tca agg tct     2740
Val Leu Val Leu Pro Asn Asn Ser Ile Thr Leu Asp Gly Ser Arg Ser
730                 735                 740 act gat gac caa aga att gtg tcc tat ctg tgg atc cgg gat ggc cag     2788
Thr Asp Asp Gln Arg Ile Val Ser Tyr Leu Trp Ile Arg Asp Gly Gln
745                 750                 755 agt cca gca gct gga gat gtc atc gat ggc tct gac cac agt gtg gct     2836
Ser Pro Ala Ala Gly Asp Val Ile Asp Gly Ser Asp His Ser Val Ala
760                 765                 770                 775 ctg cag ctt acg aat ctg gtg gag ggg gtg tac act ttc cac ttg cga     2884
Leu Gln Leu Thr Asn Leu Val Glu Gly Val Tyr Thr Phe His Leu Arg
                780                 785                 790 gtc acc gac agt cag ggg gcc tcg gac aca gac act gcc act gtg gaa     2932
Val Thr Asp Ser Gln Gly Ala Ser Asp Thr Asp Thr Ala Thr Val Glu
        795                 800                 805 gtg cag cca gac cct agg aag agt ggc ctg gtg gag ctg acc ctg cag     2980
Val Gln Pro Asp Pro Arg Lys Ser Gly Leu Val Glu Leu Thr Leu Gln
810                 815                 820 gtt ggt gtt ggg cag ctg aca gag cag cgg aag gac acc ctt gtg agg     3028
Val Gly Val Gly Gln Leu Thr Glu Gln Arg Lys Asp Thr Leu Val Arg
825                 830                 835 cag ctg gct gtg ctg ctg aac gtg ctg gac tcg gac att aag gtc cag     3076
Gln Leu Ala Val Leu Leu Asn Val Leu Asp Ser Asp Ile Lys Val Gln
840                 845                 850                 855 aag att cgg gcc cac tcg gat ctc agc acc gtg att gtg ttt tat gta     3124
Lys Ile Arg Ala His Ser Asp Leu Ser Thr Val Ile Val Phe Tyr Val
                860                 865                 870
```

```
cag agc agg ccg cct ttc aag gtt ctc aaa gct gct gaa gtg gcc cga    3172
Gln Ser Arg Pro Pro Phe Lys Val Leu Lys Ala Ala Glu Val Ala Arg
            875                 880                 885 aat ctg cac atg cgg ctc tca aag gag aag gct gac ttg ctt ttc        3220
Asn Leu His Met Arg Leu Ser Lys Glu Lys Ala Asp Phe Leu Leu Phe
            890                 895                 900 aag gtc ttg agg gtt gat aca gca ggt tgc ctt ctg aag tgt tct ggc    3268
Lys Val Leu Arg Val Asp Thr Ala Gly Cys Leu Leu Lys Cys Ser Gly
        905                 910                 915 cat ggt cac tgc gac ccc ctc aca aag cgc tgc att tgc tct cac tta    3316
His Gly His Cys Asp Pro Leu Thr Lys Arg Cys Ile Cys Ser His Leu
920             925                 930                 935 tgg atg gag aac ctt ata cag cgt tat atc tgg gat gga gag agc aac    3364
Trp Met Glu Asn Leu Ile Gln Arg Tyr Ile Trp Asp Gly Glu Ser Asn
                940                 945                 950 tgt gag tgg agt ata ttc tat gtg aca gtg ttg gct ttt act ctt att    3412
Cys Glu Trp Ser Ile Phe Tyr Val Thr Val Leu Ala Phe Thr Leu Ile
                955                 960                 965 gtg cta aca gga ggt ttc act tgg ctt tgc atc tgc tgc aaa aga        3460
Val Leu Thr Gly Gly Phe Thr Trp Leu Cys Ile Cys Cys Lys Arg
        970                 975                 980 caa aaa agg act aaa atc agg aaa aaa aca aag tac acc atc ctg gat    3508
Gln Lys Arg Thr Lys Ile Arg Lys Lys Thr Lys Tyr Thr Ile Leu Asp
985                 990                 995 aac atg gat gaa cag gaa aga atg gaa ctg agg ccc aaa tat ggt atc    3556
Asn Met Asp Glu Gln Glu Arg Met Glu Leu Arg Pro Lys Tyr Gly Ile
1000                1005                1010                1015 aag cac cga agc aca gag cac aac tcc agc ctg atg gta tcc gag tct    3604
Lys His Arg Ser Thr Glu His Asn Ser Ser Leu Met Val Ser Glu Ser
                1020                1025                1030 gag ttt gac agt gac cag gac aca atc ttc agc cga gaa aag atg gag    3652
Glu Phe Asp Ser Asp Gln Asp Thr Ile Phe Ser Arg Glu Lys Met Glu
1035                1040                1045 aga ggg aat cca aag gtt tcc atg aat ggt tcc atc aga aat gga gct    3700
Arg Gly Asn Pro Lys Val Ser Met Asn Gly Ser Ile Arg Asn Gly Ala
        1050                1055                1060 tcc ttc agt tat tgc tca aag gac aga taa tggcgcagtt cattgtaaag     3750
Ser Phe Ser Tyr Cys Ser Lys Asp Arg  *
        1065                1070 tggaaggacc cyttgaatcc argaccagtc agtgggagtt acagcacaaa acccactctt  3810
ttagaatagt tcattgacct tcttccccag tgggttagat gtgtatcccc acgtactaaa  3870
agaccggttt ttgaaggcac aaaacaaaaa ctttgctctt ttaactgaga tgcttgttaa  3930
tagaaataaa ggctgggtaa aactytaagg tatatactta aaagagtttt gagttttttgt 3990 agctggcaca atctcatatt aaagatgaac aacgatttct atctgtagaa ccttagagaa  4050
ggtgaatgaa acaaggtttt aaaaagggat gatttctgtc ttagcygctg tgattgcctc  4110
taaggaacag cattctaaac acggtttctc ttgtaggacc tgcagtcaga tggctgtgta  4170
tgttaaaata gcttgtctaa gaggcacggg ccatctgtgg aggtacggag tcttgcatgt  4230
agcaagcttt ctgtgctgac ggcaacactc gcacagtgcc aagccctcct ggtttttaat  4290
tctgtgctat gtcaatggca gttttcatct ctctcaagaa agcagctgtt ggccattcaa  4350
gagctaagga agaatcgtat tctaaggact gaggcaatag aaaggggagg aggagcttaa  4410
tgccrtgcag gttgaaggta gcattgtaac attatctttt ctttctctaa gaaaaactac  4470
actgactcct ctcggtgttg tttagcagta tagttctcta atgtaaacrg atccccagtt  4530
tacattaart gcaatagaag tgattaattc attaagcatt tattatgttc tgtaggctgt  4590
```

-continued

| | |
|---|---|
| gcgtttggac tgccatagat aggkataacg actcagcaat tgtgtatata ttccaaaact | 4650 |
| ctgaaataca gtcagtctta acttggatgg cgtggttatg atactctggt ccccgacagg | 4710 |
| tactttccaa ataacttga catagatgta ttcacttcat atgttaaaa atacatttaa | 4770 |
| gttttttctac cgaataaatc ttatttcaaa catgaaagac aattaaaaca ttcccaccca | 4830 |
| caaagcagta ctcccgagca attaactgga gttaattgta gcctgctacg ttgactggtt | 4890 |
| cagggtagtt ccccatccac ccttggtcct gaggctggtg gccttggtgg tgcccttggc | 4950 |
| attttttgtg ggaagattag aatgagagat agaaccagtg ttgtggtacc aagtgtgagc | 5010 |
| acacctaaac aatatcctgt tgcacaatgc ttttttaaca catgggaaaa ctaggaatgc | 5070 |
| attgctgatg aagaagcaag gtatttaaac accagggcag gagtgccaga gaaaatgttt | 5130 |
| ccccatgggt tcttaaaaaa aattcagctt ttaggtgctt ttgtcatctc ccgsagtatt | 5190 |
| catcctcatg ggaccatctt attttactt attgtaattt actggggaaa ggcagaacta | 5250 |
| aaaagtgtgt cattttattt ttaaaataat tgctttgctt atgcctacac tttctgtata | 5310 |
| actagccaat tcaatactgt ctatagtgtt agaaggaaaa tgtgattttt ttttttaac | 5370 |
| cagtattgag cttcataagc ctagaatctg ccttatcagg tgaccagggt tatggttgtt | 5430 |
| tgcatgcaaa tgtgaatttc tggcataggg gacagcagcc caaatgtaaa gtcatcgggc | 5490 |
| gtaatgagga agaagggagt gaacatttac cgctttakgt acataacata tgcagtttac | 5550 |
| atactcattt gatccttata atcaaccttg aagaggagat actatcattc ttatgttgca | 5610 |
| gatagccctc tgaaggccca gagaggttaa rtaacttccc agaggtcatg ccaagaagt | 5670 |
| agtggctcca agaactgaat gcaaattttt taaactgtag agttctgctt tccactaaac | 5730 |
| aaagaactcc tgccttgatg gatggagggc aaattctggt ggaactttg ggccacctga | 5790 |
| aagttctatt cccaggacta agaggaattt cttttaatgg atccagagag ccaaggtcag | 5850 |
| agggagagat ggcctgcata gtctcctgtg gatcacaccc gggccacccc tccctctagg | 5910 |
| tttacagtgg acttcttctg cccctcctcc ttttctgtcc ttggccatct cagcctggcc | 5970 |
| tctctgatcc ttccatcaca gaaggatctt gaatctctgg gaaatcaaac atcacagtag | 6030 |
| tgatcagaaa gtgagtcctg tcttgtcacc ccatttctca tcagaacaaa gcacgagatg | 6090 |
| gaatgaccaa ccagcattct tcatggtgga ctgcttatca ttgaggatct ttgggagata | 6150 |
| aagcacgcta agagctctgg acagagaaaa acaggcccta gaatatggga gtgggtgttt | 6210 |
| gtagggctca yargctaaca agcactttag ttgctggttt acattcaatg aaggaggatt | 6270 |
| catacccatg gcattacaag gctaagcatg tgtatgacta aggaactatc tgaaaaacat | 6330 |
| gcagcaaggt aagaaaatgt accactcaac aagccagtga tgccaccttt tgtgcgcggg | 6390 |
| gaggagagtg actaccattg ttttttgtgt gacaaagcta tcatggacta ttttaatctt | 6450 |
| ggttttattg cttaaaatat attattttc cctatgtgtt gacaaggtat ttctaatatc | 6510 |
| acactattaa atatatgcac taatctaaat aaaggtgtct gtattttctg taatgcttat | 6570 |
| ttttaggggg aaatttgttt tctttatgct tcagggtaga gggattccct tgagtatagg | 6630 |
| tcagcaaact ctggcctgca gcctgtgtgt gcacgcccca tgagccgaaa agtgggtctt | 6690 |
| atgttttcaa atggttaaaa ataaataaaa aaatttgaaa catgtgaact atatgacatt | 6750 |
| cagatttgtg ttcataaata aagtttatt ggaacatatc c | 6791 |

<210> SEQ ID NO 3
<211> LENGTH: 1072
<212> TYPE: PRT
<213> ORGANISM: Homo sapiens
<220> FEATURE:

-continued

```
<221> NAME/KEY: VARIANT
<222> LOCATION: 142
<223> OTHER INFORMATION: Xaa = any amino acid
<221> NAME/KEY: VARIANT
<222> LOCATION: 157
<223> OTHER INFORMATION: Xaa = any amino acid
<221> NAME/KEY: VARIANT
<222> LOCATION: 612
<223> OTHER INFORMATION: Xaa = any amino acid

<400> SEQUENCE: 3

Met Ala Pro Pro Thr Gly Val Leu Ser Ser Leu Leu Leu Leu Val Thr
 1               5                  10                  15

Ile Ala Gly Cys Ala Arg Lys Gln Cys Ser Glu Gly Arg Thr Tyr Ser
            20                  25                  30

Asn Ala Val Ile Ser Pro Asn Leu Glu Thr Thr Arg Ile Met Arg Val
        35                  40                  45

Ser His Thr Phe Pro Val Val Asp Cys Thr Ala Ala Cys Cys Asp Leu
    50                  55                  60

Ser Ser Cys Asp Leu Ala Trp Trp Phe Glu Gly Arg Cys Tyr Leu Val
65                  70                  75                  80

Ser Cys Pro His Lys Glu Asn Cys Glu Pro Lys Lys Met Gly Pro Ile
                85                  90                  95

Arg Ser Tyr Leu Thr Phe Val Leu Arg Pro Val Gln Arg Pro Ala Gln
            100                 105                 110

Leu Leu Asp Tyr Gly Asp Met Met Leu Asn Arg Gly Ser Pro Ser Gly
        115                 120                 125

Ile Trp Gly Asp Ser Pro Glu Asp Ile Arg Lys Asp Leu Xaa Phe Leu
130                 135                 140

Gly Lys Asp Trp Gly Leu Glu Glu Met Ser Glu Tyr Xaa Asp Asp Tyr
145                 150                 155                 160

Arg Glu Leu Glu Lys Asp Leu Leu Gln Pro Ser Gly Lys Gln Glu Pro
                165                 170                 175

Arg Gly Ser Ala Glu Tyr Thr Asp Trp Gly Leu Leu Pro Gly Ser Glu
            180                 185                 190

Gly Ala Phe Asn Ser Ser Val Gly Asp Ser Pro Ala Val Pro Ala Glu
        195                 200                 205

Thr Gln Gln Asp Pro Glu Leu His Tyr Leu Asn Glu Ser Ala Ser Thr
    210                 215                 220

Pro Ala Pro Lys Leu Pro Glu Arg Ser Val Leu Leu Pro Leu Pro Thr
225                 230                 235                 240

Thr Pro Ser Ser Gly Glu Val Leu Glu Lys Glu Lys Ala Ser Gln Leu
                245                 250                 255

Gln Glu Gln Ser Ser Asn Ser Gly Lys Glu Val Leu Met Pro Ser
            260                 265                 270

His Ser Leu Pro Pro Ala Ser Leu Glu Leu Ser Ser Val Thr Val Glu
        275                 280                 285

Lys Ser Pro Val Leu Thr Val Thr Pro Gly Ser Thr Glu His Ser Ile
    290                 295                 300

Pro Thr Pro Pro Thr Ser Ala Ala Pro Ser Glu Ser Thr Pro Ser Glu
305                 310                 315                 320

Leu Pro Ile Ser Pro Thr Thr Ala Pro Arg Thr Val Lys Glu Leu Thr
                325                 330                 335

Val Ser Ala Gly Asp Asn Leu Ile Ile Thr Leu Pro Asp Asn Glu Val
            340                 345                 350

Glu Leu Lys Ala Phe Val Ala Pro Ala Pro Val Glu Thr Thr Tyr
        355                 360                 365
```

```
Asn Tyr Glu Trp Asn Leu Ile Ser His Pro Thr Asp Tyr Gln Gly Glu
    370                 375                 380

Ile Lys Gln Gly His Lys Gln Thr Leu Asn Leu Ser Gln Leu Ser Val
385                 390                 395                 400

Gly Leu Tyr Val Phe Lys Val Thr Val Ser Ser Glu Asn Ala Phe Gly
                405                 410                 415

Glu Gly Phe Val Asn Val Thr Val Lys Pro Ala Arg Arg Val Asn Leu
            420                 425                 430

Pro Pro Val Ala Val Ser Pro Gln Leu Gln Glu Leu Thr Leu Pro
        435                 440                 445

Leu Thr Ser Ala Leu Ile Asp Gly Ser Gln Ser Thr Asp Thr Glu
    450                 455                 460

Ile Val Ser Tyr His Trp Glu Glu Ile Asn Gly Pro Phe Ile Glu Glu
465                 470                 475                 480

Lys Thr Ser Val Asp Ser Pro Val Leu Arg Leu Ser Asn Leu Asp Pro
                485                 490                 495

Gly Asn Tyr Ser Phe Arg Leu Thr Val Thr Asp Ser Asp Gly Ala Thr
            500                 505                 510

Asn Ser Thr Thr Ala Ala Leu Ile Val Asn Asn Ala Val Asp Tyr Pro
        515                 520                 525

Pro Val Ala Asn Ala Gly Pro Asn His Thr Ile Thr Leu Pro Gln Asn
530                 535                 540

Ser Ile Thr Leu Asn Gly Asn Gln Ser Ser Asp Asp His Gln Ile Val
545                 550                 555                 560

Leu Tyr Glu Trp Ser Leu Gly Pro Gly Ser Glu Gly Lys His Val Val
                565                 570                 575

Met Gln Gly Val Gln Thr Pro Tyr Leu His Leu Ser Ala Met Gln Glu
            580                 585                 590

Gly Asp Tyr Thr Phe Gln Leu Lys Val Thr Asp Ser Ser Arg Gln Gln
        595                 600                 605

Ser Thr Ala Xaa Val Thr Val Ile Val Gln Pro Glu Asn Asn Arg Pro
610                 615                 620

Pro Val Ala Val Ala Gly Pro Asp Lys Glu Leu Ile Phe Pro Val Glu
625                 630                 635                 640

Ser Ala Thr Leu Asp Gly Ser Ser Ser Asp Asp His Gly Ile Val
                645                 650                 655

Phe Tyr His Trp Glu His Val Arg Gly Pro Ser Ala Val Glu Met Glu
            660                 665                 670

Asn Ile Asp Lys Ala Ile Ala Thr Val Thr Gly Leu Gln Val Gly Thr
        675                 680                 685

Tyr His Phe Arg Leu Thr Val Lys Asp Gln Gln Gly Leu Ser Ser Thr
    690                 695                 700

Ser Thr Leu Thr Val Ala Val Lys Lys Glu Asn Asn Ser Pro Pro Arg
705                 710                 715                 720

Ala Arg Ala Gly Gly Arg His Val Leu Val Leu Pro Asn Asn Ser Ile
                725                 730                 735

Thr Leu Asp Gly Ser Arg Ser Thr Asp Asp Gln Arg Ile Val Ser Tyr
            740                 745                 750

Leu Trp Ile Arg Asp Gly Gln Ser Pro Ala Ala Gly Asp Val Ile Asp
        755                 760                 765

Gly Ser Asp His Ser Val Ala Leu Gln Leu Thr Asn Leu Val Glu Gly
    770                 775                 780

Val Tyr Thr Phe His Leu Arg Val Thr Asp Ser Gln Gly Ala Ser Asp
```

```
                        785                 790                 795                 800
Thr Asp Thr Ala Thr Val Glu Val Gln Pro Asp Pro Arg Lys Ser Gly
                805                 810                 815
Leu Val Glu Leu Thr Leu Gln Val Gly Val Gly Gln Leu Thr Glu Gln
                820                 825                 830
Arg Lys Asp Thr Leu Val Arg Gln Leu Ala Val Leu Leu Asn Val Leu
                835                 840                 845
Asp Ser Asp Ile Lys Val Gln Lys Ile Arg Ala His Ser Asp Leu Ser
            850                 855                 860
Thr Val Ile Val Phe Tyr Val Gln Ser Arg Pro Pro Phe Lys Val Leu
865                 870                 875                 880
Lys Ala Ala Glu Val Ala Arg Asn Leu His Met Arg Leu Ser Lys Glu
                885                 890                 895
Lys Ala Asp Phe Leu Leu Phe Lys Val Leu Arg Val Asp Thr Ala Gly
                900                 905                 910
Cys Leu Leu Lys Cys Ser Gly His Gly His Cys Asp Pro Leu Thr Lys
                915                 920                 925
Arg Cys Ile Cys Ser His Leu Trp Met Glu Asn Leu Ile Gln Arg Tyr
                930                 935                 940
Ile Trp Asp Gly Glu Ser Asn Cys Glu Trp Ser Ile Phe Tyr Val Thr
945                 950                 955                 960
Val Leu Ala Phe Thr Leu Ile Val Leu Thr Gly Gly Phe Thr Trp Leu
                965                 970                 975
Cys Ile Cys Cys Lys Arg Gln Lys Arg Thr Lys Ile Arg Lys Lys
                980                 985                 990
Thr Lys Tyr Thr Ile Leu Asp Asn Met Asp Glu Gln Glu Arg Met Glu
                995                 1000                1005
Leu Arg Pro Lys Tyr Gly Ile Lys His Arg Ser Thr Glu His Asn Ser
            1010                1015                1020
Ser Leu Met Val Ser Glu Ser Glu Phe Asp Ser Asp Gln Asp Thr Ile
1025                1030                1035                1040
Phe Ser Arg Glu Lys Met Glu Arg Gly Asn Pro Lys Val Ser Met Asn
                1045                1050                1055
Gly Ser Ile Arg Asn Gly Ala Ser Phe Ser Tyr Cys Ser Lys Asp Arg
            1060                1065                1070

<210> SEQ ID NO 4
<211> LENGTH: 6791
<212> TYPE: DNA
<213> ORGANISM: Homo sapiens
<220> FEATURE:
<221> NAME/KEY: CDS
<222> LOCATION: (512)...(3730)

<400> SEQUENCE: 4
gctgccgcgg gcggtgggcg gggatccccc gggggtgcaa ccttgctcca cctgtgctgc      60
cctcggcggg cctggctggc cccgcgcaga gcggcggcgg cgctcgctgt cactgccgga     120
ggtgagagcg cagcagtagc ttcagcctgt cttgggcttg gtccagattc gctcctctgg     180
ggctacgtcc cggggaagag gaagcgagga ttttgctggg gtgggctgt  acctcttaac     240 agcaggtgcg cgcgcgaggg tgtgaacgtg tgtgtgtgtg tgtgtctgtg tgtgtgtgtg     300
taagacctgc gatgacgacg aggaggaaca agtgggacgc gagtgatgc  tcagggccag     360 cagcaacgca tggggcgagc ttcagtgtcg ccagcagtga ccacagttct tgaggccaaa     420
tctggctcct aaaaaacatc aaaggaagct tgcaccaaac tctcttcagg gccgcctcag     480
```

-continued

| | |
|---|---|
| aagcctgcca tcacccactg tgtggtgcac a atg gcg ccc cca aca ggt gtg<br>                                                          Met Ala Pro Pro Thr Gly Val<br>                                                           1               5 | 532 |
| ctc tct tca ttg ctg ctg ctg gtg aca att gca ggt tgt gcc cgt aag<br>Leu Ser Ser Leu Leu Leu Leu Val Thr Ile Ala Gly Cys Ala Arg Lys<br>         10                         15                        20 | 580 |
| cag tgc agc gag ggg agg aca tat tcc aat gca gtc att tca cct aac<br>Gln Cys Ser Glu Gly Arg Thr Tyr Ser Asn Ala Val Ile Ser Pro Asn<br>     25                      30                        35 | 628 |
| ttg gaa acc acc aga atc atg cgg gtg tct cac acc ttc cct gtc gta<br>Leu Glu Thr Thr Arg Ile Met Arg Val Ser His Thr Phe Pro Val Val<br> 40                        45                       50                       55 | 676 |
| gac tgc acg gcc gct tgc tgt gac ctg tcc agc tgt gac ctg gcc tgg<br>Asp Cys Thr Ala Ala Cys Cys Asp Leu Ser Ser Cys Asp Leu Ala Trp<br>                 60                        65                       70 | 724 |
| tgg ttc gag ggc cgc tgc tac ctg gtg agc tgc ccc cac aaa gag aac<br>Trp Phe Glu Gly Arg Cys Tyr Leu Val Ser Cys Pro His Lys Glu Asn<br>               75                      80                     85 | 772 |
| tgt gag ccc aag aag atg ggc ccc atc agg tct tat ctc act ttt gtg<br>Cys Glu Pro Lys Lys Met Gly Pro Ile Arg Ser Tyr Leu Thr Phe Val<br>         90                         95                      100 | 820 |
| ctc cgg cct gtt cag agg cct gca cag ctg ctg gac tat ggg gac atg<br>Leu Arg Pro Val Gln Arg Pro Ala Gln Leu Leu Asp Tyr Gly Asp Met<br>     105                     110                     115 | 868 |
| atg ctg aac agg ggc tcc ccc tcg ggg atc tgg ggg gac tca cct gag<br>Met Leu Asn Arg Gly Ser Pro Ser Gly Ile Trp Gly Asp Ser Pro Glu<br>120                        125                     130                 135 | 916 |
| gat atc aga aag gac ttg ccc ttt cta ggc aaa gat tgg ggc cta gag<br>Asp Ile Arg Lys Asp Leu Pro Phe Leu Gly Lys Asp Trp Gly Leu Glu<br>               140                     145                     150 | 964 |
| gag atg tct gag tac gca gat gac tac cgg gag ctg gag aag gac ctc<br>Glu Met Ser Glu Tyr Ala Asp Asp Tyr Arg Glu Leu Glu Lys Asp Leu<br>         155                     160                     165 | 1012 |
| ttg caa ccc agt ggc aag cag gag ccc aga ggg agt gcc gag tac acg<br>Leu Gln Pro Ser Gly Lys Gln Glu Pro Arg Gly Ser Ala Glu Tyr Thr<br>               170                     175                     180 | 1060 |
| gac tgg ggc cta ctg ccg ggc agc gag ggg gcc ttc aac tcc tct gtt<br>Asp Trp Gly Leu Leu Pro Gly Ser Glu Gly Ala Phe Asn Ser Ser Val<br>185                        190                     195 | 1108 |
| gga gac agt cct gcg gtg cca gcg gag acg cag cag gac cct gag ctc<br>Gly Asp Ser Pro Ala Val Pro Ala Glu Thr Gln Gln Asp Pro Glu Leu<br>200                        205                     210                 215 | 1156 |
| cat tac ctg aat gag tcg gct tca acc cct gcc cca aaa ctc cct gag<br>His Tyr Leu Asn Glu Ser Ala Ser Thr Pro Ala Pro Lys Leu Pro Glu<br>               220                     225                     230 | 1204 |
| aga agt gtg ttg ctt ccc ttg ccg act act cca tct tca gga gag gtg<br>Arg Ser Val Leu Leu Pro Leu Pro Thr Thr Pro Ser Ser Gly Glu Val<br>         235                     240                     245 | 1252 |
| ttg gag aaa gaa aag gct tct cag ctc cag gaa caa tcc agc aac agc<br>Leu Glu Lys Glu Lys Ala Ser Gln Leu Gln Glu Gln Ser Ser Asn Ser<br>               250                     255                     260 | 1300 |
| tct gga aaa gag gtt cta atg cct tcc cat agt ctt cct ccg gca agc<br>Ser Gly Lys Glu Val Leu Met Pro Ser His Ser Leu Pro Pro Ala Ser<br>265                        270                     275 | 1348 |
| ctg gag ctc agc tca gtc acc gtg gag aaa agc cca gtg ctc aca gtc<br>Leu Glu Leu Ser Ser Val Thr Val Glu Lys Ser Pro Val Leu Thr Val<br>280                        285                     290                 295 | 1396 |
| acc ccg ggg agt aca gag cac agc atc cca aca cct ccc act agc gca<br>Thr Pro Gly Ser Thr Glu His Ser Ile Pro Thr Pro Pro Thr Ser Ala<br>               300                     305                     310 | 1444 |

```
gcc ccc tct gag tcc acc cca tct gag cta ccc ata tct cct acc act    1492
Ala Pro Ser Glu Ser Thr Pro Ser Glu Leu Pro Ile Ser Pro Thr Thr
            315                 320                 325 gct ccc agg aca gtg aaa gaa ctt acg gta tcg gct gga gat aac cta    1540
Ala Pro Arg Thr Val Lys Glu Leu Thr Val Ser Ala Gly Asp Asn Leu
330                 335                 340 att ata act tta ccc gac aat gaa gtt gaa ctg aag gcc ttt gtt gcg    1588
Ile Ile Thr Leu Pro Asp Asn Glu Val Glu Leu Lys Ala Phe Val Ala
        345                 350                 355 cca gcg cca cct gta gaa aca acc tac aac tat gaa tgg aat tta ata    1636
Pro Ala Pro Pro Val Glu Thr Thr Tyr Asn Tyr Glu Trp Asn Leu Ile
360                 365                 370                 375 agc cac ccc aca gac tac caa ggt gaa ata aaa caa gga cac aag caa    1684
Ser His Pro Thr Asp Tyr Gln Gly Glu Ile Lys Gln Gly His Lys Gln
                380                 385                 390 act ctt aac ctc tct caa ttg tcc gtc gga ctt tat gtc ttc aaa gtc    1732
Thr Leu Asn Leu Ser Gln Leu Ser Val Gly Leu Tyr Val Phe Lys Val
            395                 400                 405 act gtt tct agt gaa aac gcc ttt gga gaa gga ttt gtc aat gtc act    1780
Thr Val Ser Ser Glu Asn Ala Phe Gly Glu Gly Phe Val Asn Val Thr
        410                 415                 420 gtt aag cct gcc aga aga gtc aac ctg cca cct gta gca gtt gtt tct    1828
Val Lys Pro Ala Arg Arg Val Asn Leu Pro Pro Val Ala Val Val Ser
425                 430                 435 ccc caa ctg caa gag ctc act ttg cct ttg acg tca gcc ctc att gat    1876
Pro Gln Leu Gln Glu Leu Thr Leu Pro Leu Thr Ser Ala Leu Ile Asp
440                 445                 450                 455 ggc agc caa agt aca gat gat act gaa ata gtg agt tat cat tgg gaa    1924
Gly Ser Gln Ser Thr Asp Asp Thr Glu Ile Val Ser Tyr His Trp Glu
                460                 465                 470 gaa ata aac ggg ccc ttc ata gaa gag aag act tca gtt gac tct ccc    1972
Glu Ile Asn Gly Pro Phe Ile Glu Glu Lys Thr Ser Val Asp Ser Pro
            475                 480                 485 gtc tta cgc ttg tct aac ctt gat cct ggt aac tat agt ttc agg ttg    2020
Val Leu Arg Leu Ser Asn Leu Asp Pro Gly Asn Tyr Ser Phe Arg Leu
        490                 495                 500 act gtt aca gac tcg gac gga gcc act aac tct aca act gca gcc cta    2068
Thr Val Thr Asp Ser Asp Gly Ala Thr Asn Ser Thr Thr Ala Ala Leu
505                 510                 515 ata gtg aac aat gct gtg gac tac cca cca gtt gct aat gca gga cca    2116
Ile Val Asn Asn Ala Val Asp Tyr Pro Pro Val Ala Asn Ala Gly Pro
520                 525                 530                 535 aat cac acc ata act ttg ccc caa aac tcc atc act ttg aat gga aac    2164
Asn His Thr Ile Thr Leu Pro Gln Asn Ser Ile Thr Leu Asn Gly Asn
                540                 545                 550 cag agc agt gac gat cac cag att gtc ctc tat gag tgg tcc ctg ggt    2212
Gln Ser Ser Asp Asp His Gln Ile Val Leu Tyr Glu Trp Ser Leu Gly
            555                 560                 565 cct ggg agt gag ggc aaa cat gtg gtc atg cag gga gta cag acg cca    2260
Pro Gly Ser Glu Gly Lys His Val Val Met Gln Gly Val Gln Thr Pro
        570                 575                 580 tac ctt cat tta tct gca atg cag gaa gga gat tat aca ttt cag ctg    2308
Tyr Leu His Leu Ser Ala Met Gln Glu Gly Asp Tyr Thr Phe Gln Leu
585                 590                 595 aag gtg aca gat tct tca agg caa cag tct act gct gta gtg act gtg    2356
Lys Val Thr Asp Ser Ser Arg Gln Gln Ser Thr Ala Val Val Thr Val
600                 605                 610                 615 att gtc cag cct gaa aac aat aga cct cca gtg gct gtg gcc ggc cct    2404
Ile Val Gln Pro Glu Asn Asn Arg Pro Pro Val Ala Val Ala Gly Pro
                620                 625                 630
```

```
gat aaa gag ctg atc ttc cca gtg gaa agt gct acc ctg gat ggg agc    2452
Asp Lys Glu Leu Ile Phe Pro Val Glu Ser Ala Thr Leu Asp Gly Ser
        635                 640                 645 agc agc agc gat gac cac ggc att gtc ttc tac cac tgg gag cac gtc    2500
Ser Ser Ser Asp Asp His Gly Ile Val Phe Tyr His Trp Glu His Val
            650                 655                 660 aga ggc ccc agt gca gtg gag atg gaa aat att gac aaa gca ata gcc    2548
Arg Gly Pro Ser Ala Val Glu Met Glu Asn Ile Asp Lys Ala Ile Ala
        665                 670                 675 act gtg act ggt ctc cag gtg ggg acc tac cac ttc cgt ttg aca gtg    2596
Thr Val Thr Gly Leu Gln Val Gly Thr Tyr His Phe Arg Leu Thr Val
680                 685                 690                 695 aaa gac cag cag gga ctg agc agc acg tcc acc ctc act gtg gct gtg    2644
Lys Asp Gln Gln Gly Leu Ser Ser Thr Ser Thr Leu Thr Val Ala Val
                700                 705                 710 aag aag gaa aat aat agt cct ccc aga gcc cgg gct ggt ggc aga cat    2692
Lys Lys Glu Asn Asn Ser Pro Pro Arg Ala Arg Ala Gly Gly Arg His
            715                 720                 725 gtt ctt gtg ctt ccc aat aat tcc att act ttg gat ggt tca agg tct    2740
Val Leu Val Leu Pro Asn Asn Ser Ile Thr Leu Asp Gly Ser Arg Ser
        730                 735                 740 act gat gac caa aga att gtg tcc tat ctg tgg atc cgg gat ggc cag    2788
Thr Asp Asp Gln Arg Ile Val Ser Tyr Leu Trp Ile Arg Asp Gly Gln
745                 750                 755 agt cca gca gct gga gat gtc atc gat ggc tct gac cac agt gtg gct    2836
Ser Pro Ala Ala Gly Asp Val Ile Asp Gly Ser Asp His Ser Val Ala
760                 765                 770                 775 ctg cag ctt acg aat ctg gtg gag ggg gtg tac act ttc cac ttg cga    2884
Leu Gln Leu Thr Asn Leu Val Glu Gly Val Tyr Thr Phe His Leu Arg
                780                 785                 790 gtc acc gac agt cag ggg gcc tcg gac aca gac act gcc act gtg gaa    2932
Val Thr Asp Ser Gln Gly Ala Ser Asp Thr Asp Thr Ala Thr Val Glu
            795                 800                 805 gtg cag cca gac cct agg aag agt ggc ctg gtg gag ctg acc ctg cag    2980
Val Gln Pro Asp Pro Arg Lys Ser Gly Leu Val Glu Leu Thr Leu Gln
        810                 815                 820 gtt ggt gtt ggg cag ctg aca gag cag cgg aag gac acc ctt gtg agg    3028
Val Gly Val Gly Gln Leu Thr Glu Gln Arg Lys Asp Thr Leu Val Arg
825                 830                 835 cag ctg gct gtg ctg ctg aac gtg ctg gac tcg gac att aag gtc cag    3076
Gln Leu Ala Val Leu Leu Asn Val Leu Asp Ser Asp Ile Lys Val Gln
840                 845                 850                 855 aag att cgg gcc cac tcg gat ctc agc acc gtg att gtg ttt tat gta    3124
Lys Ile Arg Ala His Ser Asp Leu Ser Thr Val Ile Val Phe Tyr Val
                860                 865                 870 cag agc agg ccg cct ttc aag gtt ctc aaa gct gct gaa gtg gcc cga    3172
Gln Ser Arg Pro Pro Phe Lys Val Leu Lys Ala Ala Glu Val Ala Arg
            875                 880                 885 aat ctg cac atg cgg ctc tca aag gag aag gct gac ttc ttg ctt ttc    3220
Asn Leu His Met Arg Leu Ser Lys Glu Lys Ala Asp Phe Leu Leu Phe
        890                 895                 900 aag gtc ttg agg gtt gat aca gca ggt tgc ctt ctg aag tgt tct ggc    3268
Lys Val Leu Arg Val Asp Thr Ala Gly Cys Leu Leu Lys Cys Ser Gly
905                 910                 915 cat ggt cac tgc gac ccc ctc aca aag cgc tgc att tgc tct cac tta    3316
His Gly His Cys Asp Pro Leu Thr Lys Arg Cys Ile Cys Ser His Leu
920                 925                 930                 935 tgg atg gag aac ctt ata cag cgt tat atc tgg gat gga gag agc aac    3364
Trp Met Glu Asn Leu Ile Gln Arg Tyr Ile Trp Asp Gly Glu Ser Asn
                940                 945                 950
```

```
tgt gag tgg agt ata ttc tat gtg aca gtg ttg gct ttt act ctt att      3412
Cys Glu Trp Ser Ile Phe Tyr Val Thr Val Leu Ala Phe Thr Leu Ile
            955                 960                 965 gtg cta aca gga ggt ttc act tgg ctt tgc atc tgc tgc tgc aaa aga      3460
Val Leu Thr Gly Gly Phe Thr Trp Leu Cys Ile Cys Cys Cys Lys Arg
            970                 975                 980 caa aaa agg act aaa atc agg aaa aaa aca aag tac acc atc ctg gat      3508
Gln Lys Arg Thr Lys Ile Arg Lys Lys Thr Lys Tyr Thr Ile Leu Asp
            985                 990                 995 aac atg gat gaa cag gaa aga atg gaa ctg agg ccc aaa tat ggt atc      3556
Asn Met Asp Glu Gln Glu Arg Met Glu Leu Arg Pro Lys Tyr Gly Ile
1000                1005                1010                1015 aag cac cga agc aca gag cac aac tcc agc ctg atg gta tcc gag tct      3604
Lys His Arg Ser Thr Glu His Asn Ser Ser Leu Met Val Ser Glu Ser
                    1020                1025                1030 gag ttt gac agt gac cag gac aca atc ttc agc cga gaa aag atg gag      3652
Glu Phe Asp Ser Asp Gln Asp Thr Ile Phe Ser Arg Glu Lys Met Glu
                    1035                1040                1045 aga ggg aat cca aag gtt tcc atg aat ggt tcc atc aga aat gga gct      3700
Arg Gly Asn Pro Lys Val Ser Met Asn Gly Ser Ile Arg Asn Gly Ala
                    1050                1055                1060 tcc ttc agt tat tgc tca aag gac aga taa tggcgcagtt cattgtaaag        3750
Ser Phe Ser Tyr Cys Ser Lys Asp Arg *
                    1065                1070 tggaaggacc ccttgaatcc aagaccagtc agtgggagtt acagcacaaa acccactctt    3810
ttagaatagt tcattgacct tcttccccag tgggttagat gtgtatcccc acgtactaaa    3870
agaccggttt ttgaaggcac aaaacaaaaa ctttgctctt ttaactgaga tgcttgttaa    3930
tagaaataaa ggctgggtaa aactctaagg tatatactta aaagagtttt gagttttgt     3990 agctggcaca atctcatatt aaagatgaac aacgatttct atctgtagaa ccttagagaa    4050
ggtgaatgaa acaaggtttt aaaaagggat gatttctgtc ttagccgctg tgattgcctc    4110
taaggaacag cattctaaac acggtttctc ttgtaggacc tgcagtcaga tggctgtgta    4170
tgttaaaata gcttgtctaa gaggcacggg ccatctgtgg aggtacggag tcttgcatgt    4230
agcaagcttt ctgtgctgac ggcaacactc gcacagtgcc aagccctcct ggttttttaat  4290 tctgtgctat gtcaatggca gttttcatct ctctcaagaa agcagctgtt ggccattcaa    4350
gagctaagga agaatcgtat tctaaggact gaggcaatag aaaggggagg aggagcttaa    4410
tgccgtgcag gttgaaggta gcattgtaac attatctttt ctttctctaa gaaaaactac    4470
actgactcct ctcggtgttg tttagcagta tagttctcta atgtaaacgg atccccagtt    4530
tacattaaat gcaatagaag tgattaattc attaagcatt tattatgttc tgtaggctgt    4590
gcgtttggac tgccatagat agggataacg actcagcaat tgtgtatata ttccaaaact    4650
ctgaaataca gtcagtctta acttggatgg cgtggttatg atactctggt ccccgacagg    4710
tactttccaa ataacttgac atagatgta ttcacttcat atgttaaaa atacatttaa      4770 gttttttctac cgaataaatc ttatttcaaa catgaaagac aattaaaaca ttcccaccca   4830
caaagcagta ctcccgagca attaactgga gttaattgta gcctgctacg ttgactggtt   4890
cagggtagtt ccccatccac ccttggtcct gaggctggtg gccttggtgg tgcccttggc   4950
attttttgtg ggaagattag aatgagagat agaaccagtg ttgtggtacc aagtgtgagc   5010
acacctaaac aatatcctgt tgcacaatgc ttttttaaca catgggaaaa ctaggaatgc   5070
attgctgatg aagaagcaag gtatttaaac accagggcag gagtgccaga gaaaatgttt   5130
ccccatgggt tcttaaaaaa aattcagctt ttaggtgctt ttgtcatctc ccggagtatt   5190
```

-continued

```
catcctcatg ggaccatctt atttttactt attgtaattt actggggaaa ggcagaacta      5250
aaaagtgtgt catttatttt ttaaaataat tgctttgctt atgcctacac tttctgtata      5310
actagccaat tcaatactgt ctatagtgtt agaaggaaaa tgtgattttt ttttttttaac     5370 cagtattgag cttcataagc ctagaatctg ccttatcagg tgaccagggt tatggttgtt      5430
tgcatgcaaa tgtgaatttc tggcataggg gacagcagcc caaatgtaaa gtcatcgggc      5490
gtaatgagga gaagggagt gaacatttac cgctttatgt acataacata tgcagtttac       5550
atactcattt gatccttata atcaaccttg aagaggagat actatcattc ttatgttgca      5610
gatagccctc tgaaggccca gagaggttaa gtaacttccc agaggtcatg gccaagaagt      5670
agtggctcca agaactgaat gcaaattttt taaactgtag agttctgctt tccactaaac      5730
aaagaactcc tgccttgatg gatggagggc aaattctggt ggaacttttg ggccacctga      5790
aagttctatt cccaggacta agaggaattt ctttaatgg atccagagag ccaaggtcag       5850
agggagagat ggcctgcata gtctcctgtg gatcacaccc gggccacccc tccctctagg      5910
tttacagtgg acttcttctg cccctcctcc ttttctgtcc ttggccatct cagcctggcc      5970
tctctgatcc ttccatcaca gaaggatctt gaatctctgg gaaatcaaac atcacagtag      6030
tgatcagaaa gtgagtcctg tcttgtcacc ccatttctca tcagaacaaa gcacgagatg      6090
gaatgaccaa ccagcattct tcatggtgga ctgcttatca ttgaggatct ttgggagata      6150
aagcacgcta agagctctgg acagagaaaa acaggcccta gaatatggga gtgggtgttt      6210
gtagggctca taggctaaca agcactttag ttgctggttt acattcaatg aaggaggatt      6270
catacccatg gcattacaag gctaagcatg tgtatgacta aggaactatc tgaaaaacat      6330
gcagcaaggt aagaaaatgt accactcaac aagccagtga tgccaccttt tgtgcgcggg      6390
gaggagagtg actaccattg ttttttgtgt gacaaagcta tcatggacta ttttaatctt      6450
ggttttattg cttaaaatat attattttc cctatgtgtt gacaaggtat ttctaatatc       6510
acactattaa atatatgcac taatctaaat aaaggtgtct gtattttctg taatgcttat      6570 tttaggggg aaatttgttt tctttatgct tcagggtaga gggattccct tgagtatagg       6630
tcagcaaact ctggcctgca gcctgtgtgt gcacgcccca tgagccgaaa agtgggtctt      6690
atgttttcaa atggttaaaa ataaataaaa aaatttgaaa catgtgaact atatgacatt      6750
cagatttgtg ttcataaata aagttttatt ggaacatatc c                         6791
```

<210> SEQ ID NO 5
<211> LENGTH: 1072
<212> TYPE: PRT
<213> ORGANISM: Homo sapiens

<400> SEQUENCE: 5

Met Ala Pro Pro Thr Gly Val Leu Ser Ser Leu Leu Leu Leu Val Thr
1               5                   10                  15

Ile Ala Gly Cys Ala Arg Lys Gln Cys Ser Glu Gly Arg Thr Tyr Ser
            20                  25                  30

Asn Ala Val Ile Ser Pro Asn Leu Glu Thr Thr Arg Ile Met Arg Val
        35                  40                  45

Ser His Thr Phe Pro Val Val Asp Cys Thr Ala Ala Cys Cys Asp Leu
    50                  55                  60

Ser Ser Cys Asp Leu Ala Trp Trp Phe Glu Gly Arg Cys Tyr Leu Val
65                  70                  75                  80

Ser Cys Pro His Lys Glu Asn Cys Glu Pro Lys Lys Met Gly Pro Ile
                85                  90                  95

-continued

```
Arg Ser Tyr Leu Thr Phe Val Leu Arg Pro Val Gln Arg Pro Ala Gln
            100                 105                 110

Leu Leu Asp Tyr Gly Asp Met Met Leu Asn Arg Gly Ser Pro Ser Gly
            115                 120                 125

Ile Trp Gly Asp Ser Pro Glu Asp Ile Arg Lys Asp Leu Pro Phe Leu
130                 135                 140

Gly Lys Asp Trp Gly Leu Glu Glu Met Ser Glu Tyr Ala Asp Asp Tyr
145                 150                 155                 160

Arg Glu Leu Glu Lys Asp Leu Leu Gln Pro Ser Gly Lys Gln Glu Pro
                165                 170                 175

Arg Gly Ser Ala Glu Tyr Thr Asp Trp Gly Leu Leu Pro Gly Ser Glu
            180                 185                 190

Gly Ala Phe Asn Ser Ser Val Gly Asp Ser Pro Ala Val Pro Ala Glu
            195                 200                 205

Thr Gln Gln Asp Pro Glu Leu His Tyr Leu Asn Glu Ser Ala Ser Thr
210                 215                 220

Pro Ala Pro Lys Leu Pro Glu Arg Ser Val Leu Leu Pro Leu Pro Thr
225                 230                 235                 240

Thr Pro Ser Ser Gly Glu Val Leu Glu Lys Glu Lys Ala Ser Gln Leu
                245                 250                 255

Gln Glu Gln Ser Ser Asn Ser Ser Gly Lys Glu Val Leu Met Pro Ser
            260                 265                 270

His Ser Leu Pro Pro Ala Ser Leu Glu Leu Ser Ser Val Thr Val Glu
            275                 280                 285

Lys Ser Pro Val Leu Thr Val Thr Pro Gly Ser Thr Glu His Ser Ile
290                 295                 300

Pro Thr Pro Pro Thr Ser Ala Ala Pro Ser Glu Ser Thr Pro Ser Glu
305                 310                 315                 320

Leu Pro Ile Ser Pro Thr Thr Ala Pro Arg Thr Val Lys Glu Leu Thr
                325                 330                 335

Val Ser Ala Gly Asp Asn Leu Ile Ile Thr Leu Pro Asp Asn Glu Val
            340                 345                 350

Glu Leu Lys Ala Phe Val Ala Pro Ala Pro Val Glu Thr Thr Tyr
            355                 360                 365

Asn Tyr Glu Trp Asn Leu Ile Ser His Pro Thr Asp Tyr Gln Gly Glu
370                 375                 380

Ile Lys Gln Gly His Lys Gln Thr Leu Asn Leu Ser Gln Leu Ser Val
385                 390                 395                 400

Gly Leu Tyr Val Phe Lys Val Thr Val Ser Ser Glu Asn Ala Phe Gly
                405                 410                 415

Glu Gly Phe Val Asn Val Thr Lys Pro Ala Arg Arg Val Asn Leu
            420                 425                 430

Pro Pro Val Ala Val Val Ser Pro Gln Leu Gln Glu Leu Thr Leu Pro
            435                 440                 445

Leu Thr Ser Ala Leu Ile Asp Gly Ser Gln Ser Thr Asp Asp Thr Glu
            450                 455                 460

Ile Val Ser Tyr His Trp Glu Glu Ile Asn Gly Pro Phe Ile Glu Glu
465                 470                 475                 480

Lys Thr Ser Val Asp Ser Pro Val Leu Arg Leu Ser Asn Leu Asp Pro
                485                 490                 495

Gly Asn Tyr Ser Phe Arg Leu Thr Val Thr Asp Ser Asp Gly Ala Thr
            500                 505                 510

Asn Ser Thr Thr Ala Ala Leu Ile Val Asn Asn Ala Val Asp Tyr Pro
            515                 520                 525
```

```
Pro Val Ala Asn Ala Gly Pro Asn His Thr Ile Thr Leu Pro Gln Asn
    530                 535                 540

Ser Ile Thr Leu Asn Gly Asn Gln Ser Ser Asp Asp His Gln Ile Val
545                 550                 555                 560

Leu Tyr Glu Trp Ser Leu Gly Pro Gly Ser Glu Gly Lys His Val Val
                565                 570                 575

Met Gln Gly Val Gln Thr Pro Tyr Leu His Leu Ser Ala Met Gln Glu
            580                 585                 590

Gly Asp Tyr Thr Phe Gln Leu Lys Val Thr Asp Ser Ser Arg Gln Gln
        595                 600                 605

Ser Thr Ala Val Val Thr Val Ile Val Gln Pro Glu Asn Asn Arg Pro
    610                 615                 620

Pro Val Ala Val Ala Gly Pro Asp Lys Glu Leu Ile Phe Pro Val Glu
625                 630                 635                 640

Ser Ala Thr Leu Asp Gly Ser Ser Ser Asp Asp His Gly Ile Val
                645                 650                 655

Phe Tyr His Trp Glu His Val Arg Gly Pro Ser Ala Val Glu Met Glu
                660                 665                 670

Asn Ile Asp Lys Ala Ile Ala Thr Val Thr Gly Leu Gln Val Gly Thr
            675                 680                 685

Tyr His Phe Arg Leu Thr Val Lys Asp Gln Gln Gly Leu Ser Ser Thr
    690                 695                 700

Ser Thr Leu Thr Val Ala Val Lys Lys Glu Asn Asn Ser Pro Pro Arg
705                 710                 715                 720

Ala Arg Ala Gly Gly Arg His Val Leu Val Leu Pro Asn Asn Ser Ile
                725                 730                 735

Thr Leu Asp Gly Ser Arg Ser Thr Asp Asp Gln Arg Ile Val Ser Tyr
            740                 745                 750

Leu Trp Ile Arg Asp Gly Gln Ser Pro Ala Ala Gly Asp Val Ile Asp
    755                 760                 765

Gly Ser Asp His Ser Val Ala Leu Gln Leu Thr Asn Leu Val Glu Gly
770                 775                 780

Val Tyr Thr Phe His Leu Arg Val Thr Asp Ser Gln Gly Ala Ser Asp
785                 790                 795                 800

Thr Asp Thr Ala Thr Val Glu Val Gln Pro Asp Pro Arg Lys Ser Gly
                805                 810                 815

Leu Val Glu Leu Thr Leu Gln Val Gly Val Gly Gln Leu Thr Glu Gln
            820                 825                 830

Arg Lys Asp Thr Leu Val Arg Gln Leu Ala Val Leu Leu Asn Val Leu
    835                 840                 845

Asp Ser Asp Ile Lys Val Gln Lys Ile Arg Ala His Ser Asp Leu Ser
    850                 855                 860

Thr Val Ile Val Phe Tyr Val Gln Ser Arg Pro Pro Phe Lys Val Leu
865                 870                 875                 880

Lys Ala Ala Glu Val Ala Arg Asn Leu His Met Arg Leu Ser Lys Glu
                885                 890                 895

Lys Ala Asp Phe Leu Leu Phe Lys Val Leu Arg Val Asp Thr Ala Gly
            900                 905                 910

Cys Leu Leu Lys Cys Ser Gly His Gly His Cys Asp Pro Leu Thr Lys
    915                 920                 925

Arg Cys Ile Cys Ser His Leu Trp Met Glu Asn Leu Ile Gln Arg Tyr
    930                 935                 940

Ile Trp Asp Gly Glu Ser Asn Cys Glu Trp Ser Ile Phe Tyr Val Thr
```

```
                                  945                 950                 955                 960
                             Val Leu Ala Phe Thr Leu Ile Val Leu Thr Gly Gly Phe Thr Trp Leu
                                             965                 970                 975

Cys Ile Cys Cys Cys Lys Arg Gln Lys Arg Thr Lys Ile Arg Lys Lys
                                             980                 985                 990

Thr Lys Tyr Thr Ile Leu Asp Asn Met Asp Glu Gln Glu Arg Met Glu
                                             995                1000                1005

Leu Arg Pro Lys Tyr Gly Ile Lys His Arg Ser Thr Glu His Asn Ser
                                        1010                1015                1020

Ser Leu Met Val Ser Glu Ser Glu Phe Asp Ser Asp Gln Asp Thr Ile
                             1025                1030                1035                1040

Phe Ser Arg Glu Lys Met Glu Arg Gly Asn Pro Lys Val Ser Met Asn
                                             1045                1050                1055

Gly Ser Ile Arg Asn Gly Ala Ser Phe Ser Tyr Cys Ser Lys Asp Arg
                                        1060                1065                1070

<210> SEQ ID NO 6
<211> LENGTH: 6991
<212> TYPE: DNA
<213> ORGANISM: Homo sapiens
<220> FEATURE:
<221> NAME/KEY: CDS
<222> LOCATION: (739)...(3930)

<400> SEQUENCE: 6
gctgccgcgg gcggtgggcg gggatccccc gggggtgcaa ccttgctcca cctgtgctgc        60
cctcggcggg cctggctggc cccgcgcaga gcggcggcgg cgctcgctgt cactgccgga       120
ggtgagagcg cagcagtagc ttcagcctgt cttgggcttg gtccagattc gctcctctgg       180
ggctacgtcc cggggaagag gaagcgagga ttttgctggg gtggggctgt acctcttaac       240
agcaggtgcg cgcgcgaggg tgtgaacgtg tgtgtgtgtg tgtgtctgtg tgtgtgtgtg       300
taagacctgc gatgacgacg aggaggaaca agtgggacgg cgagtgatgc tcagggccag       360
cagcaacgca tggggcgagc ttcagtgtcg ccagcagtga ccacaggtac ggtatctact       420
tcccagagcg cctggccgag aaataggaaa gagggcagcc agtaggcagg ccaatacccc       480
acaaaagtag aatcgagacg ccctgagttc agaagttctt gaggccaaat ctggctccta       540
aaaaacatca aaggaagctt gcaccaaact ctcttcaggg ccgcctcaga agcctgccat       600
cacccactgt gtggtgcaca atggcgcccc ccacaggtgt gctctcttca ttgctgctgc       660
tggtgacaat tgcagtttgc ttatggtgga tgcactcatg gcaaaaaaat cactggtgag       720
catcatttaa gaagaccc atg act aga ctg ggc tgg ccg agc cca tgt tgt        771
                    Met Thr Arg Leu Gly Trp Pro Ser Pro Cys Cys
                     1               5                  10 gcc cgt aag cag tgc agc gag ggg agg aca tat tcc aat gca gtc att        819
Ala Arg Lys Gln Cys Ser Glu Gly Arg Thr Tyr Ser Asn Ala Val Ile
             15                  20                  25 tca cct aac ttg gaa acc acc aga atc atg cgg gtg tct cac acc ttc        867
Ser Pro Asn Leu Glu Thr Thr Arg Ile Met Arg Val Ser His Thr Phe
         30                  35                  40 cct gtc gta gac tgc acg gcc gct tgc tgt gac ctg tcc agc tgt gac        915
Pro Val Val Asp Cys Thr Ala Ala Cys Cys Asp Leu Ser Ser Cys Asp
     45                  50                  55 ctg gcc tgg tgg ttc gag ggc cgc tgc tac ctg gtg agc tgc ccc cac        963
Leu Ala Trp Trp Phe Glu Gly Arg Cys Tyr Leu Val Ser Cys Pro His
 60                  65                  70                  75 aaa gag aac tgt gag ccc aag aag atg ggc ccc atc agg tct tat ctc       1011
Lys Glu Asn Cys Glu Pro Lys Lys Met Gly Pro Ile Arg Ser Tyr Leu
```

```
                 80                  85                  90
act ttt gtg ctc cgg cct gtt cag agg cct gca cag ctg ctg gac tat    1059
Thr Phe Val Leu Arg Pro Val Gln Arg Pro Ala Gln Leu Leu Asp Tyr
             95                 100                 105 ggg gac atg atg ctg aac agg ggc tcc ccc tcg ggg atc tgg ggg gac    1107
Gly Asp Met Met Leu Asn Arg Gly Ser Pro Ser Gly Ile Trp Gly Asp
        110                 115                 120 tca cct gag gat atc aga aag gac ttg ccc ttt cta ggc aaa gat tgg    1155
Ser Pro Glu Asp Ile Arg Lys Asp Leu Pro Phe Leu Gly Lys Asp Trp
    125                 130                 135 ggc cta gag gag atg tct gag tac tca gat gac tac cgg gag ctg gag    1203
Gly Leu Glu Glu Met Ser Glu Tyr Ser Asp Asp Tyr Arg Glu Leu Glu
140                 145                 150                 155 aag gac ctc ttg caa ccc agt ggc aag cag gag ccc aga ggg agt gcc    1251
Lys Asp Leu Leu Gln Pro Ser Gly Lys Gln Glu Pro Arg Gly Ser Ala
                160                 165                 170 gag tac acg gac tgg ggc cta ctg ccg ggc agc gag ggg gcc ttc aac    1299
Glu Tyr Thr Asp Trp Gly Leu Leu Pro Gly Ser Glu Gly Ala Phe Asn
            175                 180                 185 tcc tct gtt gga gac agt cct gcg gtg cca gcg gag acg cag cag gac    1347
Ser Ser Val Gly Asp Ser Pro Ala Val Pro Ala Glu Thr Gln Gln Asp
        190                 195                 200 cct gag ctc cat tac ctg aat gag tcg gct tca acc cct gcc cca aaa    1395
Pro Glu Leu His Tyr Leu Asn Glu Ser Ala Ser Thr Pro Ala Pro Lys
    205                 210                 215 ctc cct gag aga agt gtg ttg ctt ccc ttg ccg act act cca tct tca    1443
Leu Pro Glu Arg Ser Val Leu Leu Pro Leu Pro Thr Thr Pro Ser Ser
220                 225                 230                 235 gga gag gtg ttg gag aaa gaa aag gct tct cag ctc cag gaa caa tcc    1491
Gly Glu Val Leu Glu Lys Glu Lys Ala Ser Gln Leu Gln Glu Gln Ser
                240                 245                 250 agc aac agc tct gga aaa gag gtt cta atg cct tcc cat agt ctt cct    1539
Ser Asn Ser Ser Gly Lys Glu Val Leu Met Pro Ser His Ser Leu Pro
            255                 260                 265 ccg gca agc ctg gag ctc agc tca gtc acc gtg gag aaa agc cca gtg    1587
Pro Ala Ser Leu Glu Leu Ser Ser Val Thr Val Glu Lys Ser Pro Val
        270                 275                 280 ctc aca gtc acc ccg ggg agt aca gag cac agc atc cca aca cct ccc    1635
Leu Thr Val Thr Pro Gly Ser Thr Glu His Ser Ile Pro Thr Pro Pro
    285                 290                 295 act agc gca gcc ccc tct gag tcc acc cca tct gag cta ccc ata tct    1683
Thr Ser Ala Ala Pro Ser Glu Ser Thr Pro Ser Glu Leu Pro Ile Ser
300                 305                 310                 315 cct acc act gct ccc agg aca gtg aaa gaa ctt acg gta tcg gct gga    1731
Pro Thr Thr Ala Pro Arg Thr Val Lys Glu Leu Thr Val Ser Ala Gly
                320                 325                 330 gat aac cta att ata act tta ccc gac aat gaa gtt gaa ctg aag gcc    1779
Asp Asn Leu Ile Ile Thr Leu Pro Asp Asn Glu Val Glu Leu Lys Ala
            335                 340                 345 ttt gtt gcg cca gcg cca cct gta gaa aca acc tac aac tat gaa tgg    1827
Phe Val Ala Pro Ala Pro Pro Val Glu Thr Thr Tyr Asn Tyr Glu Trp
        350                 355                 360 aat tta ata agc cac ccc aca gac tac caa ggt gaa ata aaa caa gga    1875
Asn Leu Ile Ser His Pro Thr Asp Tyr Gln Gly Glu Ile Lys Gln Gly
    365                 370                 375 cac aag caa act ctt aac ctc tct caa ttg tcc gtc gga ctt tat gtc    1923
His Lys Gln Thr Leu Asn Leu Ser Gln Leu Ser Val Gly Leu Tyr Val
380                 385                 390                 395 ttc aaa gtc act gtt tct agt gaa aac gcc ttt gga gaa gga ttt gtc    1971
Phe Lys Val Thr Val Ser Ser Glu Asn Ala Phe Gly Glu Gly Phe Val
```

-continued

```
                  400                 405                 410
aat gtc act gtt aag cct gcc aga aga gtc aac ctg cca cct gta gca    2019
Asn Val Thr Val Lys Pro Ala Arg Arg Val Asn Leu Pro Pro Val Ala
            415                 420                 425 gtt gtt tct ccc caa ctg caa gag ctc act ttg cct ttg acg tca gcc    2067
Val Val Ser Pro Gln Leu Gln Glu Leu Thr Leu Pro Leu Thr Ser Ala
                430                 435                 440 ctc att gat ggc agc caa agt aca gat gat act gaa ata gtg agt tat    2115
Leu Ile Asp Gly Ser Gln Ser Thr Asp Asp Thr Glu Ile Val Ser Tyr
445                 450                 455 cat tgg gaa gaa ata aac ggg ccc ttc ata gaa gag aag act tca gtt    2163
His Trp Glu Glu Ile Asn Gly Pro Phe Ile Glu Glu Lys Thr Ser Val
460                 465                 470                 475 gac tct ccc gtc tta cgc ttg tct aac ctt gat cct ggt aac tat agt    2211
Asp Ser Pro Val Leu Arg Leu Ser Asn Leu Asp Pro Gly Asn Tyr Ser
                480                 485                 490 ttc agg ttg act gtt aca gac tcg gac gga gcc act aac tct aca act    2259
Phe Arg Leu Thr Val Thr Asp Ser Asp Gly Ala Thr Asn Ser Thr Thr
            495                 500                 505 gca gcc cta ata gtg aac aat gct gtg gac tac cca cca gtt gct aat    2307
Ala Ala Leu Ile Val Asn Asn Ala Val Asp Tyr Pro Pro Val Ala Asn
        510                 515                 520 gca gga cca aat cac acc ata act ttg ccc caa aac tcc atc act ttg    2355
Ala Gly Pro Asn His Thr Ile Thr Leu Pro Gln Asn Ser Ile Thr Leu
525                 530                 535 aat gga aac cag agc agt gac gat cac cag att gtc ctc tat gag tgg    2403
Asn Gly Asn Gln Ser Ser Asp Asp His Gln Ile Val Leu Tyr Glu Trp
540                 545                 550                 555 tcc ctg ggt cct ggg agt gag ggc aaa cat gtg gtc atg cag gga gta    2451
Ser Leu Gly Pro Gly Ser Glu Gly Lys His Val Val Met Gln Gly Val
                560                 565                 570 cag acg cca tac ctt cat tta tct gca atg cag gaa gga gat tat aca    2499
Gln Thr Pro Tyr Leu His Leu Ser Ala Met Gln Glu Gly Asp Tyr Thr
            575                 580                 585 ttt cag ctg aag gtg aca gat tct tca agg caa cag tct act gct gtg    2547
Phe Gln Leu Lys Val Thr Asp Ser Ser Arg Gln Gln Ser Thr Ala Val
        590                 595                 600 gtg act gtg att gtc cag cct gaa aac aat aga cct cca gtg gct gtg    2595
Val Thr Val Ile Val Gln Pro Glu Asn Asn Arg Pro Pro Val Ala Val
605                 610                 615 gcc ggc cct gat aaa gag ctg atc ttc cca gtg gaa agt gct acc ctg    2643
Ala Gly Pro Asp Lys Glu Leu Ile Phe Pro Val Glu Ser Ala Thr Leu
620                 625                 630                 635 gat ggg agc agc agc agc gat gac cac ggc att gtc ttc tac cac tgg    2691
Asp Gly Ser Ser Ser Ser Asp Asp His Gly Ile Val Phe Tyr His Trp
                640                 645                 650 gag cac gtc aga ggc ccc agt gca gtg gag atg gaa aat att gac aaa    2739
Glu His Val Arg Gly Pro Ser Ala Val Glu Met Glu Asn Ile Asp Lys
            655                 660                 665 gca ata gcc act gtg act ggt ctc cag gtg ggg acc tac cac ttc cgt    2787
Ala Ile Ala Thr Val Thr Gly Leu Gln Val Gly Thr Tyr His Phe Arg
        670                 675                 680 ttg aca gtg aaa gac cag cag gga ctg agc agc acg tcc acc ctc act    2835
Leu Thr Val Lys Asp Gln Gln Gly Leu Ser Ser Thr Ser Thr Leu Thr
685                 690                 695 gtg gct gtg aag aag gaa aat aat agt cct ccc aga gcc cgg gct ggt    2883
Val Ala Val Lys Lys Glu Asn Asn Ser Pro Pro Arg Ala Arg Ala Gly
700                 705                 710                 715 ggc aga cat gtt ctt gtg ctt ccc aat aat tcc att act ttg gat ggt    2931
Gly Arg His Val Leu Val Leu Pro Asn Asn Ser Ile Thr Leu Asp Gly
```

```
                720                 725                 730
tca agg tct act gat gac caa aga att gtg tcc tat ctg tgg atc cgg          2979
Ser Arg Ser Thr Asp Asp Gln Arg Ile Val Ser Tyr Leu Trp Ile Arg
                735                 740                 745
gat ggc cag agt cca gca gct gga gat gtc atc gat ggc tct gac cac          3027
Asp Gly Gln Ser Pro Ala Ala Gly Asp Val Ile Asp Gly Ser Asp His
                750                 755                 760
agt gtg gct ctg cag ctt acg aat ctg gtg gag ggg gtg tac act ttc          3075
Ser Val Ala Leu Gln Leu Thr Asn Leu Val Glu Gly Val Tyr Thr Phe
                765                 770                 775
cac ttg cga gtc acc gac agt cag ggg gcc tcg gac aca gac act gcc          3123
His Leu Arg Val Thr Asp Ser Gln Gly Ala Ser Asp Thr Asp Thr Ala
780                 785                 790                 795
act gtg gaa gtg cag cca gac cct agg aag agt ggc ctg gtg gag ctg          3171
Thr Val Glu Val Gln Pro Asp Pro Arg Lys Ser Gly Leu Val Glu Leu
                800                 805                 810
acc ctg cag gtt ggt gtt ggg cag ctg aca gag cag cgg aag gac acc          3219
Thr Leu Gln Val Gly Val Gly Gln Leu Thr Glu Gln Arg Lys Asp Thr
                815                 820                 825
ctt gtg agg cag ctg gct gtg ctg ctg aac gtg ctg gac tcg gac att          3267
Leu Val Arg Gln Leu Ala Val Leu Leu Asn Val Leu Asp Ser Asp Ile
                830                 835                 840
aag gtc cag aag att cgg gcc cac tcg gat ctc agc acc gtg att gtg          3315
Lys Val Gln Lys Ile Arg Ala His Ser Asp Leu Ser Thr Val Ile Val
                845                 850                 855
ttt tat gta cag agc agg ccg cct ttc aag gtt ctc aaa gct gct gaa          3363
Phe Tyr Val Gln Ser Arg Pro Pro Phe Lys Val Leu Lys Ala Ala Glu
860                 865                 870                 875
gtg gcc cga aat ctg cac atg cgg ctc tca aag gag aag gct gac ttc          3411
Val Ala Arg Asn Leu His Met Arg Leu Ser Lys Glu Lys Ala Asp Phe
                880                 885                 890
ttg ctt ttc aag gtc ttg agg gtt gat aca gca ggt tgc ctt ctg aag          3459
Leu Leu Phe Lys Val Leu Arg Val Asp Thr Ala Gly Cys Leu Leu Lys
                895                 900                 905
tgt tct ggc cat ggt cac tgc gac ccc ctc aca aag cgc tgc att tgc          3507
Cys Ser Gly His Gly His Cys Asp Pro Leu Thr Lys Arg Cys Ile Cys
                910                 915                 920
tct cac tta tgg atg gag aac ctt ata cag cgt tat atc tgg gat gga          3555
Ser His Leu Trp Met Glu Asn Leu Ile Gln Arg Tyr Ile Trp Asp Gly
                925                 930                 935
gag agc aac tgt gag tgg agt ata ttc tat gtg aca gtg ttg gct ttt          3603
Glu Ser Asn Cys Glu Trp Ser Ile Phe Tyr Val Thr Val Leu Ala Phe
940                 945                 950                 955
act ctt att gtg cta aca gga ggt ttc act tgg ctt tgc atc tgc tgc          3651
Thr Leu Ile Val Leu Thr Gly Gly Phe Thr Trp Leu Cys Ile Cys Cys
                960                 965                 970
tgc aaa aga caa aaa agg act aaa atc agg aaa aaa aca aag tac acc          3699
Cys Lys Arg Gln Lys Arg Thr Lys Ile Arg Lys Lys Thr Lys Tyr Thr
                975                 980                 985
atc ctg gat aac atg gat gaa cag gaa aga atg gaa ctg agg ccc aaa          3747
Ile Leu Asp Asn Met Asp Glu Gln Glu Arg Met Glu Leu Arg Pro Lys
                990                 995                 1000
tat ggt atc aag cac cga agc aca gag cac aac tcc agc ctg atg gta          3795
Tyr Gly Ile Lys His Arg Ser Thr Glu His Asn Ser Ser Leu Met Val
                1005                1010                1015
tcc gag tct gag ttt gac agt gac cag gac aca atc ttc agc cga gaa          3843
Ser Glu Ser Glu Phe Asp Ser Asp Gln Asp Thr Ile Phe Ser Arg Glu
1020                1025                1030                1035
aag atg gag aga ggg aat cca aag gtt tcc atg aat ggt tcc atc aga          3891
Lys Met Glu Arg Gly Asn Pro Lys Val Ser Met Asn Gly Ser Ile Arg
```

```
                 1040              1045              1050
aat gga gct tcc ttc agt tat tgc tca aag gac aga taa tggcgcagtt    3940
Asn Gly Ala Ser Phe Ser Tyr Cys Ser Lys Asp Arg *
             1055              1060 cattgtaaag tggaaggacc ccttgaatcc aagaccagtc agtgggagtt acagcacaaa  4000
acccactctt ttagaatagt tcattgacct tcttccccag tgggttagat gtgtatcccc  4060
acgtactaaa agaccggttt tgaaggcac aaaacaaaaa ctttgctctt ttaactgaga   4120
tgcttgttaa tagaaataaa ggctgggtaa aactctaagg tatatactta aaagagtttt  4180
gagttttttgt agctggcaca atctcatatt aaagatgaac aacgattttct atctgtagaa 4240
ccttagagaa ggtgaatgaa acaaggtttt aaaaagggat gatttctgtc ttagccgctg  4300
tgattgcctc taaggaacag cattctaaac acggtttctc ttgtaggacc tgcagtcaga  4360
tggctgtgta tgttaaaata gcttgtctaa gaggcacggg ccatctgtgg aggtacggag  4420
tcttgcatgt agcaagcttt ctgtgctgac ggcaacactc gcacagtgcc aagccctcct  4480
ggtttttaat tctgtgctat gtcaatggca gttttcatct ctctcaagaa agcagctgtt  4540
ggccattcaa gagctaagga agaatcgtat tctaaggact gaggcaatag aaaggggagg  4600
aggagcttaa tgccgtgcag gttgaaggta gcattgtaac attatctttt ctttctctaa  4660
gaaaaactac actgactcct ctcggtgttg tttagcagta tagttctcta atgtaaacgg  4720
atccccagtt tacattaaat gcaatagaag tgattaattc attaagcatt tattatgttc  4780
tgtaggctgt gcgtttggac tgccatagat agggataacg actcagcaat tgtgtatata  4840
ttccaaaact ctgaaataca gtcagtctta acttggatgg cgtggttatg atactctggt  4900
ccccgacagg tactttccaa ataacttga catagatgta ttcacttcat atgtttaaaa   4960
atacatttaa gtttttctac cgaataaatc ttatttcaaa catgaaagac aattaaaaca  5020
ttcccaccca caaagcagta ctcccgagca attaactgga gttaattgta gcctgctacg  5080
ttgactggtt cagggtagtt ccccatccac ccttggtcct gaggctggtg gccttggtgg  5140
tgcccttggc attttttgtg ggaagattag aatgagagat agaaccagtg ttgtggtacc  5200
aagtgtgagc acacctaaac aatatcctgt tgcacaatgc tttttaaca catgggaaaa   5260
ctaggaatgc attgctgatg aagaagcaag gtatttaaac accagggcag gagtgccaga  5320
gaaaatgttt ccccatgggt tcttaaaaaa aattcagctt ttaggtgctt ttgtcatctc   5380
ccggagtatt catcctcatg ggaccatctt atttttactt attgtaattt actggggaaa  5440
ggcagaacta aaaagtgtgt cattttattt taaaataat tgctttgctt atgcctacac    5500
tttctgtata actagccaat tcaatactgt ctatagtgtt agaaggaaaa tgtgattttt   5560
ttttttttaac cagtattgag cttcataagc ctagaatctg ccttatcagg tgaccagggt  5620
tatggttgtt tgcatgcaaa tgtgaatttc tggcatagggg acagcagcc caaatgtaaa   5680
gtcatcgggc gtaatgagga agaagggagt gaacatttac cgctttatgt acataacata  5740
tgcagtttac atactcattt gatccttata atcaaccttg aagaggagat actatcattc  5800
ttatgttgca gatagccctc tgaaggccca gagaggttaa gtaacttccc agaggtcatg   5860
gccaagaagt agtggctcca agaactgaat gcaaattttt taaactgtag agttctgctt  5920
tccactaaac aaagaactcc tgccttgatg gatgagggc aaattctggt ggaacttttg   5980
ggccacctga aagttctatt cccaggacta agaggaattt cttttaatgg atccagagag   6040
ccaaggtcag agggagagat ggcctgcata gtcctgtg gatcacaccc gggccacccc    6100
tccctctagg tttacagtgg acttcttctg ccctcctcc ttttctgtcc ttggccatct     6160
```

-continued

```
cagcctggcc tctctgatcc ttccatcaca gaaggatctt gaatctctgg gaaatcaaac    6220
atcacagtag tgatcagaaa gtgagtcctg tcttgtcacc ccatttctca tcagaacaaa    6280
gcacgagatg gaatgaccaa ccagcattct tcatggtgga ctgcttatca ttgaggatct    6340
ttgggagata aagcacgcta agagctctgg acagagaaaa acaggcccta gaatatggga    6400
gtgggtgttt gtagggctca taggctaaca agcactttag ttgctggttt acattcaatg    6460
aaggaggatt catacccatg gcattacaag gctaagcatg tgtatgacta aggaactatc    6520 tgaaaacat gcagcaaggt aagaaaatgt accactcaac aagccagtga tgccaccttt    6580
tgtgcgcggg gaggagagtg actaccattg ttttttgtgt gacaaagcta tcatggacta    6640
ttttaatctt ggttttattg cttaaaatat attattttc cctatgtgtt gacaaggtat    6700
ttctaatatc acactattaa atatatgcac taatctaaat aaaggtgtct gtattttctg    6760
taatgcttat ttttagggggg aaatttgttt tctttatgct tcagggtaga gggattccct    6820
tgagtatagg tcagcaaact ctggcctgca gcctgtgtgt gcacgcccca tgagccgaaa    6880
agtgggtctt atgttttcaa atggttaaaa ataataaaaa aaatttgaaa catgtgaact    6940
atatgacatt cagatttgtg ttcataaata aagtttttatt ggaacatatc c            6991
```

<210> SEQ ID NO 7
<211> LENGTH: 1063
<212> TYPE: PRT
<213> ORGANISM: Homo sapiens

<400> SEQUENCE: 7

```
Met Thr Arg Leu Gly Trp Pro Ser Pro Cys Cys Ala Arg Lys Gln Cys
  1               5                  10                  15

Ser Glu Gly Arg Thr Tyr Ser Asn Ala Val Ile Ser Pro Asn Leu Glu
             20                  25                  30

Thr Thr Arg Ile Met Arg Val Ser His Thr Phe Pro Val Val Asp Cys
         35                  40                  45

Thr Ala Ala Cys Cys Asp Leu Ser Ser Cys Asp Leu Ala Trp Trp Phe
     50                  55                  60

Glu Gly Arg Cys Tyr Leu Val Ser Cys Pro His Lys Glu Asn Cys Glu
 65                  70                  75                  80

Pro Lys Lys Met Gly Pro Ile Arg Ser Tyr Leu Thr Phe Val Leu Arg
                 85                  90                  95

Pro Val Gln Arg Pro Ala Gln Leu Leu Asp Tyr Gly Asp Met Met Leu
            100                 105                 110

Asn Arg Gly Ser Pro Ser Gly Ile Trp Gly Asp Ser Pro Glu Asp Ile
        115                 120                 125

Arg Lys Asp Leu Pro Phe Leu Gly Lys Asp Trp Gly Leu Glu Glu Met
    130                 135                 140

Ser Glu Tyr Ser Asp Asp Tyr Arg Glu Leu Glu Lys Asp Leu Leu Gln
145                 150                 155                 160

Pro Ser Gly Lys Gln Glu Pro Arg Gly Ser Ala Glu Tyr Thr Asp Trp
                165                 170                 175

Gly Leu Leu Pro Gly Ser Glu Gly Ala Phe Asn Ser Ser Val Gly Asp
            180                 185                 190

Ser Pro Ala Val Pro Ala Glu Thr Gln Gln Asp Pro Glu Leu His Tyr
        195                 200                 205

Leu Asn Glu Ser Ala Ser Thr Pro Ala Pro Lys Leu Pro Glu Arg Ser
    210                 215                 220

Val Leu Leu Pro Leu Pro Thr Thr Pro Ser Ser Gly Glu Val Leu Glu
225                 230                 235                 240
```

```
Lys Glu Lys Ala Ser Gln Leu Gln Gln Ser Ser Asn Ser Ser Gly
            245                 250                 255

Lys Glu Val Leu Met Pro Ser His Ser Leu Pro Pro Ala Ser Leu Glu
            260                 265                 270

Leu Ser Ser Val Thr Val Glu Lys Ser Pro Val Leu Thr Val Thr Pro
            275                 280                 285

Gly Ser Thr Glu His Ser Ile Pro Thr Pro Pro Thr Ser Ala Ala Pro
            290                 295                 300

Ser Glu Ser Thr Pro Ser Glu Leu Pro Ile Ser Pro Thr Thr Ala Pro
305                 310                 315                 320

Arg Thr Val Lys Glu Leu Thr Val Ser Ala Gly Asp Asn Leu Ile Ile
                325                 330                 335

Thr Leu Pro Asp Asn Glu Val Glu Leu Lys Ala Phe Val Ala Pro Ala
                340                 345                 350

Pro Pro Val Glu Thr Thr Tyr Asn Tyr Glu Trp Asn Leu Ile Ser His
                355                 360                 365

Pro Thr Asp Tyr Gln Gly Glu Ile Lys Gln Gly His Lys Gln Thr Leu
            370                 375                 380

Asn Leu Ser Gln Leu Ser Val Gly Leu Tyr Val Phe Lys Val Thr Val
385                 390                 395                 400

Ser Ser Glu Asn Ala Phe Gly Glu Gly Phe Val Asn Val Thr Val Lys
                405                 410                 415

Pro Ala Arg Arg Val Asn Leu Pro Pro Val Ala Val Ser Pro Gln
                420                 425                 430

Leu Gln Glu Leu Thr Leu Pro Leu Thr Ser Ala Leu Ile Asp Gly Ser
            435                 440                 445

Gln Ser Thr Asp Asp Thr Glu Ile Val Ser Tyr His Trp Glu Glu Ile
    450                 455                 460

Asn Gly Pro Phe Ile Glu Glu Lys Thr Ser Val Asp Ser Pro Val Leu
465                 470                 475                 480

Arg Leu Ser Asn Leu Asp Pro Gly Asn Tyr Ser Phe Arg Leu Thr Val
                485                 490                 495

Thr Asp Ser Asp Gly Ala Thr Asn Ser Thr Thr Ala Ala Leu Ile Val
            500                 505                 510

Asn Asn Ala Val Asp Tyr Pro Pro Val Ala Asn Ala Gly Pro Asn His
            515                 520                 525

Thr Ile Thr Leu Pro Gln Asn Ser Ile Thr Leu Asn Gly Asn Gln Ser
    530                 535                 540

Ser Asp Asp His Gln Ile Val Leu Tyr Glu Trp Ser Leu Gly Pro Gly
545                 550                 555                 560

Ser Glu Gly Lys His Val Val Met Gln Gly Val Gln Thr Pro Tyr Leu
                565                 570                 575

His Leu Ser Ala Met Gln Glu Gly Asp Tyr Thr Phe Gln Leu Lys Val
            580                 585                 590

Thr Asp Ser Ser Arg Gln Gln Ser Thr Ala Val Val Thr Val Ile Val
            595                 600                 605

Gln Pro Glu Asn Asn Arg Pro Pro Val Ala Val Ala Gly Pro Asp Lys
            610                 615                 620

Glu Leu Ile Phe Pro Val Glu Ser Ala Thr Leu Asp Gly Ser Ser Ser
625                 630                 635                 640

Ser Asp Asp His Gly Ile Val Phe Tyr His Trp Glu His Val Arg Gly
                645                 650                 655

Pro Ser Ala Val Glu Met Glu Asn Ile Asp Lys Ala Ile Ala Thr Val
```

660                 665                 670
Thr Gly Leu Gln Val Gly Thr Tyr His Phe Arg Leu Thr Val Lys Asp
                675                 680                 685

Gln Gln Gly Leu Ser Ser Thr Ser Thr Leu Thr Val Ala Val Lys Lys
        690                 695                 700

Glu Asn Asn Ser Pro Pro Arg Ala Arg Ala Gly Arg His Val Leu
705                 710                 715                 720

Val Leu Pro Asn Asn Ser Ile Thr Leu Asp Gly Ser Arg Ser Thr Asp
                725                 730                 735

Asp Gln Arg Ile Val Ser Tyr Leu Trp Ile Arg Asp Gly Gln Ser Pro
            740                 745                 750

Ala Ala Gly Asp Val Ile Asp Gly Ser Asp His Ser Val Ala Leu Gln
            755                 760                 765

Leu Thr Asn Leu Val Glu Gly Val Tyr Thr Phe His Leu Arg Val Thr
            770                 775                 780

Asp Ser Gln Gly Ala Ser Asp Thr Asp Thr Ala Thr Val Glu Val Gln
785                 790                 795                 800

Pro Asp Pro Arg Lys Ser Gly Leu Val Glu Leu Thr Leu Gln Val Gly
                805                 810                 815

Val Gly Gln Leu Thr Glu Gln Arg Lys Asp Thr Leu Val Arg Gln Leu
            820                 825                 830

Ala Val Leu Leu Asn Val Leu Asp Ser Asp Ile Lys Val Gln Lys Ile
            835                 840                 845

Arg Ala His Ser Asp Leu Ser Thr Val Ile Val Phe Tyr Val Gln Ser
850                 855                 860

Arg Pro Pro Phe Lys Val Leu Lys Ala Ala Glu Val Ala Arg Asn Leu
865                 870                 875                 880

His Met Arg Leu Ser Lys Glu Lys Ala Asp Phe Leu Leu Phe Lys Val
                885                 890                 895

Leu Arg Val Asp Thr Ala Gly Cys Leu Leu Lys Cys Ser Gly His Gly
            900                 905                 910

His Cys Asp Pro Leu Thr Lys Arg Cys Ile Cys Ser His Leu Trp Met
            915                 920                 925

Glu Asn Leu Ile Gln Arg Tyr Ile Trp Asp Gly Glu Ser Asn Cys Glu
        930                 935                 940

Trp Ser Ile Phe Tyr Val Thr Val Leu Ala Phe Thr Leu Ile Val Leu
945                 950                 955                 960

Thr Gly Gly Phe Thr Trp Leu Cys Ile Cys Cys Cys Lys Arg Gln Lys
                965                 970                 975

Arg Thr Lys Ile Arg Lys Lys Thr Lys Tyr Thr Ile Leu Asp Asn Met
            980                 985                 990

Asp Glu Gln Glu Arg Met Glu Leu Arg Pro Lys Tyr Gly Ile Lys His
        995                 1000                1005

Arg Ser Thr Glu His Asn Ser Ser Leu Met Val Ser Glu Ser Glu Phe
        1010                1015                1020

Asp Ser Asp Gln Asp Thr Ile Phe Ser Arg Glu Lys Met Glu Arg Gly
1025                1030                1035                1040

Asn Pro Lys Val Ser Met Asn Gly Ser Ile Arg Asn Gly Ala Ser Phe
                1045                1050                1055

Ser Tyr Cys Ser Lys Asp Arg
            1060

<210> SEQ ID NO 8
<211> LENGTH: 1072

-continued

```
<212> TYPE: PRT
<213> ORGANISM: Homo sapiens

<400> SEQUENCE: 8

Met Ala Pro Pro Thr Gly Val Leu Ser Ser Leu Leu Leu Val Thr
1               5                   10                  15

Ile Ala Gly Cys Ala Arg Lys Gln Cys Ser Glu Gly Arg Thr Tyr Ser
                20                  25                  30

Asn Ala Val Ile Ser Pro Asn Leu Glu Thr Thr Arg Ile Met Arg Val
            35                  40                  45

Ser His Thr Phe Pro Val Val Asp Cys Thr Ala Ala Cys Cys Asp Leu
        50                  55                  60

Ser Ser Cys Asp Leu Ala Trp Trp Phe Glu Gly Arg Cys Tyr Leu Val
65              70                  75                  80

Ser Cys Pro His Lys Glu Asn Cys Glu Pro Lys Lys Met Gly Pro Ile
                85                  90                  95

Arg Ser Tyr Leu Thr Phe Val Leu Arg Pro Val Gln Arg Pro Ala Gln
            100                 105                 110

Leu Leu Asp Tyr Gly Asp Met Met Leu Asn Arg Gly Ser Pro Ser Gly
        115                 120                 125

Ile Trp Gly Asp Ser Pro Glu Asp Ile Arg Lys Asp Leu Pro Phe Leu
130             135                 140

Gly Lys Asp Trp Gly Leu Glu Glu Met Ser Glu Tyr Ser Asp Asp Tyr
145                 150                 155                 160

Arg Glu Leu Glu Lys Asp Leu Leu Gln Pro Ser Gly Lys Gln Glu Pro
                165                 170                 175

Arg Gly Ser Ala Glu Tyr Thr Asp Trp Gly Leu Leu Pro Gly Ser Glu
            180                 185                 190

Gly Ala Phe Asn Ser Ser Val Gly Asp Ser Pro Ala Val Pro Ala Glu
        195                 200                 205

Thr Gln Gln Asp Pro Glu Leu His Tyr Leu Asn Glu Ser Ala Ser Thr
210                 215                 220

Pro Ala Pro Lys Leu Pro Glu Arg Ser Val Leu Leu Pro Leu Pro Thr
225                 230                 235                 240

Thr Pro Ser Ser Gly Glu Val Leu Glu Lys Glu Lys Ala Ser Gln Leu
                245                 250                 255

Gln Glu Gln Ser Ser Asn Ser Ser Gly Lys Glu Val Leu Met Pro Ser
            260                 265                 270

His Ser Leu Pro Pro Ala Ser Leu Glu Leu Ser Ser Val Thr Val Glu
        275                 280                 285

Lys Ser Pro Val Leu Thr Val Thr Pro Gly Ser Thr Glu His Ser Ile
    290                 295                 300

Pro Thr Pro Pro Thr Ser Ala Ala Pro Ser Glu Ser Thr Pro Ser Glu
305                 310                 315                 320

Leu Pro Ile Ser Pro Thr Thr Ala Pro Arg Thr Val Lys Glu Leu Thr
                325                 330                 335

Val Ser Ala Gly Asp Asn Leu Ile Ile Thr Leu Pro Asp Asn Glu Val
            340                 345                 350

Glu Leu Lys Ala Phe Val Ala Pro Ala Pro Val Glu Thr Thr Tyr
        355                 360                 365

Asn Tyr Glu Trp Asn Leu Ile Ser His Pro Thr Asp Tyr Gln Gly Glu
    370                 375                 380

Ile Lys Gln Gly His Lys Gln Thr Leu Asn Leu Ser Gln Leu Ser Val
385                 390                 395                 400
```

-continued

```
Gly Leu Tyr Val Phe Lys Val Thr Val Ser Ser Glu Asn Ala Phe Gly
                405                 410                 415

Glu Gly Phe Val Asn Val Thr Val Lys Pro Ala Arg Arg Val Asn Leu
            420                 425                 430

Pro Pro Val Ala Val Ser Pro Gln Leu Gln Glu Leu Thr Leu Pro
        435                 440                 445

Leu Thr Ser Ala Leu Ile Asp Gly Ser Gln Ser Thr Asp Asp Thr Glu
450                 455                 460

Ile Val Ser Tyr His Trp Glu Glu Ile Asn Gly Pro Phe Ile Glu Glu
465                 470                 475                 480

Lys Thr Ser Val Asp Ser Pro Val Leu Arg Leu Ser Asn Leu Asp Pro
                485                 490                 495

Gly Asn Tyr Ser Phe Arg Leu Thr Val Thr Asp Ser Asp Gly Ala Thr
            500                 505                 510

Asn Ser Thr Thr Ala Ala Leu Ile Val Asn Asn Ala Val Asp Tyr Pro
        515                 520                 525

Pro Val Ala Asn Ala Gly Pro Asn His Thr Ile Thr Leu Pro Gln Asn
530                 535                 540

Ser Ile Thr Leu Asn Gly Asn Gln Ser Ser Asp Asp His Gln Ile Val
545                 550                 555                 560

Leu Tyr Glu Trp Ser Leu Gly Pro Gly Ser Glu Gly Lys His Val Val
                565                 570                 575

Met Gln Gly Val Gln Thr Pro Tyr Leu His Leu Ser Ala Met Gln Glu
            580                 585                 590

Gly Asp Tyr Thr Phe Gln Leu Lys Val Thr Asp Ser Ser Arg Gln Gln
        595                 600                 605

Ser Thr Ala Val Val Thr Val Ile Val Gln Pro Glu Asn Asn Arg Pro
610                 615                 620

Pro Val Ala Val Ala Gly Pro Asp Lys Glu Leu Ile Phe Pro Val Glu
625                 630                 635                 640

Ser Ala Thr Leu Asp Gly Ser Ser Ser Asp Asp His Gly Ile Val
                645                 650                 655

Phe Tyr His Trp Glu His Val Arg Gly Pro Ser Ala Val Glu Met Glu
            660                 665                 670

Asn Ile Asp Lys Ala Ile Ala Thr Val Thr Gly Leu Gln Val Gly Thr
        675                 680                 685

Tyr His Phe Arg Leu Thr Val Lys Asp Gln Gln Gly Leu Ser Ser Thr
690                 695                 700

Ser Thr Leu Thr Val Ala Val Lys Lys Glu Asn Asn Ser Pro Pro Arg
705                 710                 715                 720

Ala Arg Ala Gly Gly Arg His Val Leu Val Leu Pro Asn Asn Ser Ile
                725                 730                 735

Thr Leu Asp Gly Ser Arg Ser Thr Asp Asp Gln Arg Ile Val Ser Tyr
            740                 745                 750

Leu Trp Ile Arg Asp Gly Gln Ser Pro Ala Ala Gly Asp Val Ile Asp
        755                 760                 765

Gly Ser Asp His Ser Val Ala Leu Gln Leu Thr Asn Leu Val Glu Gly
770                 775                 780

Val Tyr Thr Phe His Leu Arg Val Thr Asp Ser Gln Gly Ala Ser Asp
785                 790                 795                 800

Thr Asp Thr Ala Thr Val Glu Val Gln Pro Asp Pro Arg Lys Ser Gly
                805                 810                 815

Leu Val Glu Leu Thr Leu Gln Val Gly Val Gly Gln Leu Thr Glu Gln
            820                 825                 830
```

Arg Lys Asp Thr Leu Val Arg Gln Leu Ala Val Leu Leu Asn Val Leu
            835                 840                 845

Asp Ser Asp Ile Lys Val Gln Lys Ile Arg Ala His Ser Asp Leu Ser
        850                 855                 860

Thr Val Ile Val Phe Tyr Val Gln Ser Arg Pro Pro Phe Lys Val Leu
865                 870                 875                 880

Lys Ala Ala Glu Val Ala Arg Asn Leu His Met Arg Leu Ser Lys Glu
                885                 890                 895

Lys Ala Asp Phe Leu Leu Phe Lys Val Leu Arg Val Asp Thr Ala Gly
                900                 905                 910

Cys Leu Leu Lys Cys Ser Gly His Gly His Cys Asp Pro Leu Thr Lys
            915                 920                 925

Arg Cys Ile Cys Ser His Leu Trp Met Glu Asn Leu Ile Gln Arg Tyr
        930                 935                 940

Ile Trp Asp Gly Glu Ser Asn Cys Glu Trp Ser Ile Phe Tyr Val Thr
945                 950                 955                 960

Val Leu Ala Phe Thr Leu Ile Val Leu Thr Gly Gly Phe Thr Trp Leu
                965                 970                 975

Cys Ile Cys Cys Cys Lys Arg Gln Lys Arg Thr Lys Ile Arg Lys Lys
                980                 985                 990

Thr Lys Tyr Thr Ile Leu Asp Asn Met Asp Glu Gln Glu Arg Met Glu
            995                 1000                1005

Leu Arg Pro Lys Tyr Gly Ile Lys His Arg Ser Thr Glu His Asn Ser
        1010                1015                1020

Ser Leu Met Val Ser Glu Ser Glu Phe Asp Ser Asp Gln Asp Thr Ile
1025                1030                1035                1040

Phe Ser Arg Glu Lys Met Glu Arg Gly Asn Pro Lys Val Ser Met Asn
                1045                1050                1055

Gly Ser Ile Arg Asn Gly Ala Ser Phe Ser Tyr Cys Ser Lys Asp Arg
                1060                1065                1070

<210> SEQ ID NO 9
<211> LENGTH: 1072
<212> TYPE: PRT
<213> ORGANISM: Homo sapiens

<400> SEQUENCE: 9

Met Ala Pro Pro Thr Gly Val Leu Ser Ser Leu Leu Leu Leu Val Thr
1               5                   10                  15

Ile Ala Gly Cys Ala Arg Lys Gln Cys Ser Glu Gly Arg Thr Tyr Ser
                20                  25                  30

Asn Ala Val Ile Ser Pro Asn Leu Glu Thr Thr Arg Ile Met Arg Val
            35                  40                  45

Ser His Thr Phe Pro Val Val Asp Cys Thr Ala Ala Cys Cys Asp Leu
        50                  55                  60

Ser Ser Cys Asp Leu Ala Trp Trp Phe Glu Gly Arg Cys Tyr Leu Val
65                  70                  75                  80

Ser Cys Pro His Lys Glu Asn Cys Glu Pro Lys Lys Met Gly Pro Ile
                85                  90                  95

Arg Ser Tyr Leu Thr Phe Val Leu Arg Pro Val Gln Arg Pro Ala Gln
                100                 105                 110

Leu Leu Asp Tyr Gly Asp Met Met Leu Asn Arg Gly Ser Pro Ser Gly
            115                 120                 125

Ile Trp Gly Asp Ser Pro Glu Asp Ile Arg Lys Asp Leu Pro Phe Leu
            130                 135                 140

-continued

```
Gly Lys Asp Trp Gly Leu Glu Glu Met Ser Glu Tyr Ala Asp Asp Tyr
145                 150                 155                 160

Arg Glu Leu Glu Lys Asp Leu Leu Gln Pro Ser Gly Lys Gln Glu Pro
            165                 170                 175

Arg Gly Ser Ala Glu Tyr Thr Asp Trp Gly Leu Leu Pro Gly Ser Glu
            180                 185                 190

Gly Ala Phe Asn Ser Ser Val Gly Asp Ser Pro Ala Val Pro Ala Glu
            195                 200                 205

Thr Gln Gln Asp Pro Glu Leu His Tyr Leu Asn Glu Ser Ala Ser Thr
210                 215                 220

Pro Ala Pro Lys Leu Pro Glu Arg Ser Val Leu Leu Pro Leu Pro Thr
225                 230                 235                 240

Thr Pro Ser Ser Gly Glu Val Leu Glu Lys Glu Lys Ala Ser Gln Leu
            245                 250                 255

Gln Glu Gln Ser Ser Asn Ser Ser Gly Lys Glu Val Leu Met Pro Ser
            260                 265                 270

His Ser Leu Pro Pro Ala Ser Leu Glu Leu Ser Ser Val Thr Val Glu
            275                 280                 285

Lys Ser Pro Val Leu Thr Val Thr Pro Gly Ser Thr Glu His Ser Ile
290                 295                 300

Pro Thr Pro Pro Thr Ser Ala Ala Pro Ser Glu Ser Thr Pro Ser Glu
305                 310                 315                 320

Leu Pro Ile Ser Pro Thr Thr Ala Pro Arg Thr Val Lys Glu Leu Thr
            325                 330                 335

Val Ser Ala Gly Asp Asn Leu Ile Ile Thr Leu Pro Asp Asn Glu Val
            340                 345                 350

Glu Leu Lys Ala Phe Val Ala Pro Ala Pro Val Glu Thr Thr Tyr
            355                 360                 365

Asn Tyr Glu Trp Asn Leu Ile Ser His Pro Thr Asp Tyr Gln Gly Glu
370                 375                 380

Ile Lys Gln Gly His Lys Gln Thr Leu Asn Leu Ser Gln Leu Ser Val
385                 390                 395                 400

Gly Leu Tyr Val Phe Lys Val Thr Val Ser Ser Glu Asn Ala Phe Gly
            405                 410                 415

Glu Gly Phe Val Asn Val Thr Val Lys Pro Ala Arg Arg Val Asn Leu
            420                 425                 430

Pro Pro Val Ala Val Val Ser Pro Gln Leu Gln Glu Leu Thr Leu Pro
            435                 440                 445

Leu Thr Ser Ala Leu Ile Asp Gly Ser Gln Ser Thr Asp Asp Thr Glu
450                 455                 460

Ile Val Ser Tyr His Trp Glu Glu Ile Asn Gly Pro Phe Ile Glu Glu
465                 470                 475                 480

Lys Thr Ser Val Asp Ser Pro Val Leu Arg Leu Ser Asn Leu Asp Pro
            485                 490                 495

Gly Asn Tyr Ser Phe Arg Leu Thr Val Thr Asp Ser Asp Gly Ala Thr
            500                 505                 510

Asn Ser Thr Thr Ala Ala Leu Ile Val Asn Asn Ala Val Asp Tyr Pro
            515                 520                 525

Pro Val Ala Asn Ala Gly Pro Asn His Thr Ile Thr Leu Pro Gln Asn
            530                 535                 540

Ser Ile Thr Leu Asn Gly Asn Gln Ser Asp Asp His Gln Ile Val
545                 550                 555                 560

Leu Tyr Glu Trp Ser Leu Gly Pro Gly Ser Glu Gly Lys His Val Val
```

```
                    565                 570                 575
        Met Gln Gly Val Gln Thr Pro Tyr Leu His Leu Ser Ala Met Gln Glu
                    580                 585                 590

Gly Asp Tyr Thr Phe Gln Leu Lys Val Thr Asp Ser Ser Arg Gln Gln
                    595                 600                 605

Ser Thr Ala Val Val Thr Val Ile Val Gln Pro Glu Asn Asn Arg Pro
                    610                 615                 620

Pro Val Ala Val Ala Gly Pro Asp Lys Glu Leu Ile Phe Pro Val Glu
        625                 630                 635                 640

Ser Ala Thr Leu Asp Gly Ser Ser Ser Asp Asp His Gly Ile Val
                            645                 650                 655

Phe Tyr His Trp Glu His Val Arg Gly Pro Ser Ala Val Glu Met Glu
                            660                 665                 670

Asn Ile Asp Lys Ala Ile Ala Thr Val Thr Gly Leu Gln Val Gly Thr
                            675                 680                 685

Tyr His Phe Arg Leu Thr Val Lys Asp Gln Gln Gly Leu Ser Ser Thr
                    690                 695                 700

Ser Thr Leu Thr Val Ala Val Lys Lys Glu Asn Asn Ser Pro Pro Arg
        705                 710                 715                 720

Ala Arg Ala Gly Gly Arg His Val Leu Val Leu Pro Asn Asn Ser Ile
                            725                 730                 735

Thr Leu Asp Gly Ser Arg Ser Thr Asp Asp Gln Arg Ile Val Ser Tyr
                            740                 745                 750

Leu Trp Ile Arg Asp Gly Gln Ser Pro Ala Ala Gly Asp Val Ile Asp
                    755                 760                 765

Gly Ser Asp His Ser Val Ala Leu Gln Leu Thr Asn Leu Val Glu Gly
                    770                 775                 780

Val Tyr Thr Phe His Leu Arg Val Thr Asp Ser Gln Gly Ala Ser Asp
        785                 790                 795                 800

Thr Asp Thr Ala Thr Val Glu Val Gln Pro Asp Pro Arg Lys Ser Gly
                            805                 810                 815

Leu Val Glu Leu Thr Leu Gln Val Gly Val Gly Gln Leu Thr Glu Gln
                            820                 825                 830

Arg Lys Asp Thr Leu Val Arg Gln Leu Ala Val Leu Leu Asn Val Leu
                    835                 840                 845

Asp Ser Asp Ile Lys Val Gln Lys Ile Arg Ala His Ser Asp Leu Ser
                    850                 855                 860

Thr Val Ile Val Phe Tyr Val Gln Ser Arg Pro Pro Phe Lys Val Leu
        865                 870                 875                 880

Lys Ala Ala Glu Val Ala Arg Asn Leu His Met Arg Leu Ser Lys Glu
                            885                 890                 895

Lys Ala Asp Phe Leu Leu Phe Lys Val Leu Arg Val Asp Thr Ala Gly
                    900                 905                 910

Cys Leu Leu Lys Cys Ser Gly His Gly His Cys Asp Pro Leu Thr Lys
                    915                 920                 925

Arg Cys Ile Cys Ser His Leu Trp Met Glu Asn Leu Ile Gln Arg Tyr
                    930                 935                 940

Ile Trp Asp Gly Glu Ser Asn Cys Glu Trp Ser Ile Phe Tyr Val Thr
        945                 950                 955                 960

Val Leu Ala Phe Thr Leu Ile Val Leu Thr Gly Gly Phe Thr Trp Leu
                            965                 970                 975

Cys Ile Cys Cys Cys Lys Arg Gln Lys Arg Thr Lys Ile Arg Lys Lys
                    980                 985                 990
```

-continued

```
Thr Lys Tyr Thr Ile Leu Asp Asn Met Asp Glu Gln Glu Arg Met Glu
    995                 1000                1005

Leu Arg Pro Lys Tyr Gly Ile Lys His Arg Ser Thr Glu His Asn Ser
1010                1015                1020

Ser Leu Met Val Ser Glu Ser Glu Phe Asp Ser Asp Gln Asp Thr Ile
1025                1030                1035                1040

Phe Ser Arg Glu Lys Met Glu Arg Gly Asn Pro Lys Val Ser Met Asn
            1045                1050                1055

Gly Ser Ile Arg Asn Gly Ala Ser Phe Ser Tyr Cys Ser Lys Asp Arg
            1060                1065                1070

<210> SEQ ID NO 10
<211> LENGTH: 1063
<212> TYPE: PRT
<213> ORGANISM: Homo sapiens

<400> SEQUENCE: 10

Met Thr Arg Leu Gly Trp Pro Ser Pro Cys Cys Ala Arg Lys Gln Cys
 1               5                   10                  15

Ser Glu Gly Arg Thr Tyr Ser Asn Ala Val Ile Ser Pro Asn Leu Glu
            20                  25                  30

Thr Thr Arg Ile Met Arg Val Ser His Thr Phe Pro Val Val Asp Cys
        35                  40                  45

Thr Ala Ala Cys Cys Asp Leu Ser Ser Cys Asp Leu Ala Trp Trp Phe
 50                  55                  60

Glu Gly Arg Cys Tyr Leu Val Ser Cys Pro His Lys Glu Asn Cys Glu
 65                  70                  75                  80

Pro Lys Lys Met Gly Pro Ile Arg Ser Tyr Leu Thr Phe Val Leu Arg
                85                  90                  95

Pro Val Gln Arg Pro Ala Gln Leu Leu Asp Tyr Gly Asp Met Met Leu
            100                 105                 110

Asn Arg Gly Ser Pro Ser Gly Ile Trp Gly Asp Ser Pro Glu Asp Ile
        115                 120                 125

Arg Lys Asp Leu Pro Phe Leu Gly Lys Asp Trp Gly Leu Glu Glu Met
130                 135                 140

Ser Glu Tyr Ser Asp Asp Tyr Arg Glu Leu Glu Lys Asp Leu Leu Gln
145                 150                 155                 160

Pro Ser Gly Lys Gln Glu Pro Arg Gly Ser Ala Glu Tyr Thr Asp Trp
                165                 170                 175

Gly Leu Leu Pro Gly Ser Glu Gly Ala Phe Asn Ser Ser Val Gly Asp
            180                 185                 190

Ser Pro Ala Val Pro Ala Glu Thr Gln Gln Asp Pro Glu Leu His Tyr
        195                 200                 205

Leu Asn Glu Ser Ala Ser Thr Pro Ala Pro Lys Leu Pro Glu Arg Ser
210                 215                 220

Val Leu Leu Pro Leu Pro Thr Thr Pro Ser Ser Gly Glu Val Leu Glu
225                 230                 235                 240

Lys Glu Lys Ala Ser Gln Leu Gln Glu Gln Ser Ser Asn Ser Ser Gly
                245                 250                 255

Lys Glu Val Leu Met Pro Ser His Ser Leu Pro Pro Ala Ser Leu Glu
            260                 265                 270

Leu Ser Ser Val Thr Val Glu Lys Ser Pro Val Leu Thr Val Thr Pro
        275                 280                 285

Gly Ser Thr Glu His Ser Ile Pro Thr Pro Pro Thr Ser Ala Ala Pro
290                 295                 300
```

-continued

```
Ser Glu Ser Thr Pro Ser Glu Leu Pro Ile Ser Pro Thr Thr Ala Pro
305                 310                 315                 320

Arg Thr Val Lys Glu Leu Thr Val Ser Ala Gly Asp Asn Leu Ile Ile
                325                 330                 335

Thr Leu Pro Asp Asn Glu Val Glu Leu Lys Ala Phe Val Ala Pro Ala
            340                 345                 350

Pro Pro Val Glu Thr Thr Tyr Asn Tyr Glu Trp Asn Leu Ile Ser His
        355                 360                 365

Pro Thr Asp Tyr Gln Gly Glu Ile Lys Gln Gly His Lys Gln Thr Leu
    370                 375                 380

Asn Leu Ser Gln Leu Ser Val Gly Leu Tyr Val Phe Lys Val Thr Val
385                 390                 395                 400

Ser Ser Glu Asn Ala Phe Gly Glu Gly Phe Val Asn Val Thr Val Lys
                405                 410                 415

Pro Ala Arg Arg Val Asn Leu Pro Pro Val Ala Val Ser Pro Gln
            420                 425                 430

Leu Gln Glu Leu Thr Leu Pro Leu Thr Ser Ala Leu Ile Asp Gly Ser
        435                 440                 445

Gln Ser Thr Asp Thr Glu Ile Val Ser Tyr His Trp Glu Glu Ile
    450                 455                 460

Asn Gly Pro Phe Ile Glu Glu Lys Thr Ser Val Asp Ser Pro Val Leu
465                 470                 475                 480

Arg Leu Ser Asn Leu Asp Pro Gly Asn Tyr Ser Phe Arg Leu Thr Val
                485                 490                 495

Thr Asp Ser Asp Gly Ala Thr Asn Ser Thr Thr Ala Ala Leu Ile Val
            500                 505                 510

Asn Asn Ala Val Asp Tyr Pro Pro Val Ala Asn Ala Gly Pro Asn His
        515                 520                 525

Thr Ile Thr Leu Pro Gln Asn Ser Ile Thr Leu Asn Gly Asn Gln Ser
    530                 535                 540

Ser Asp Asp His Gln Ile Val Leu Tyr Glu Trp Ser Leu Gly Pro Gly
545                 550                 555                 560

Ser Glu Gly Lys His Val Val Met Gln Gly Val Gln Thr Pro Tyr Leu
                565                 570                 575

His Leu Ser Ala Met Gln Glu Gly Asp Tyr Thr Phe Gln Leu Lys Val
            580                 585                 590

Thr Asp Ser Ser Arg Gln Gln Ser Thr Ala Val Val Thr Val Ile Val
        595                 600                 605

Gln Pro Glu Asn Asn Arg Pro Pro Val Ala Val Ala Gly Pro Asp Lys
    610                 615                 620

Glu Leu Ile Phe Pro Val Glu Ser Ala Thr Leu Asp Gly Ser Ser Ser
625                 630                 635                 640

Ser Asp Asp His Gly Ile Val Phe Tyr His Trp Glu His Val Arg Gly
                645                 650                 655

Pro Ser Ala Val Glu Met Glu Asn Ile Asp Lys Ala Ile Ala Thr Val
            660                 665                 670

Thr Gly Leu Gln Val Gly Thr Tyr His Phe Arg Leu Thr Val Lys Asp
        675                 680                 685

Gln Gln Gly Leu Ser Ser Thr Ser Thr Leu Thr Val Ala Val Lys Lys
    690                 695                 700

Glu Asn Asn Ser Pro Pro Arg Ala Arg Ala Gly Gly Arg His Val Leu
705                 710                 715                 720

Val Leu Pro Asn Asn Ser Ile Thr Leu Asp Gly Ser Arg Ser Thr Asp
                725                 730                 735
```

```
Asp Gln Arg Ile Val Ser Tyr Leu Trp Ile Arg Asp Gly Gln Ser Pro
            740                 745                 750

Ala Ala Gly Asp Val Ile Asp Gly Ser Asp His Ser Val Ala Leu Gln
            755                 760                 765

Leu Thr Asn Leu Val Glu Gly Val Tyr Thr Phe His Leu Arg Val Thr
        770                 775                 780

Asp Ser Gln Gly Ala Ser Asp Thr Asp Thr Ala Thr Val Glu Val Gln
785                 790                 795                 800

Pro Asp Pro Arg Lys Ser Gly Leu Val Glu Leu Thr Leu Gln Val Gly
                805                 810                 815

Val Gly Gln Leu Thr Glu Gln Arg Lys Asp Thr Leu Val Arg Gln Leu
            820                 825                 830

Ala Val Leu Leu Asn Val Leu Asp Ser Asp Ile Lys Val Gln Lys Ile
            835                 840                 845

Arg Ala His Ser Asp Leu Ser Thr Val Ile Val Phe Tyr Val Gln Ser
        850                 855                 860

Arg Pro Pro Phe Lys Val Leu Lys Ala Ala Glu Val Ala Arg Asn Leu
865                 870                 875                 880

His Met Arg Leu Ser Lys Glu Lys Ala Asp Phe Leu Leu Phe Lys Val
                885                 890                 895

Leu Arg Val Asp Thr Ala Gly Cys Leu Leu Lys Cys Ser Gly His Gly
            900                 905                 910

His Cys Asp Pro Leu Thr Lys Arg Cys Ile Cys Ser His Leu Trp Met
            915                 920                 925

Glu Asn Leu Ile Gln Arg Tyr Ile Trp Asp Gly Glu Ser Asn Cys Glu
        930                 935                 940

Trp Ser Ile Phe Tyr Val Thr Val Leu Ala Phe Thr Leu Ile Val Leu
945                 950                 955                 960

Thr Gly Gly Phe Thr Trp Leu Cys Ile Cys Cys Cys Lys Arg Gln Lys
                965                 970                 975

Arg Thr Lys Ile Arg Lys Lys Thr Lys Tyr Thr Ile Leu Asp Asn Met
            980                 985                 990

Asp Glu Gln Glu Arg Met Glu Leu Arg Pro Lys Tyr Gly Ile Lys His
        995                 1000                1005

Arg Ser Thr Glu His Asn Ser Ser Leu Met Val Ser Glu Ser Glu Phe
    1010                1015                1020

Asp Ser Asp Gln Asp Thr Ile Phe Ser Arg Glu Lys Met Glu Arg Gly
1025                1030                1035                1040

Asn Pro Lys Val Ser Met Asn Gly Ser Ile Arg Asn Gly Ala Ser Phe
                1045                1050                1055

Ser Tyr Cys Ser Lys Asp Arg
            1060

<210> SEQ ID NO 11
<211> LENGTH: 1072
<212> TYPE: PRT
<213> ORGANISM: Homo sapiens

<400> SEQUENCE: 11

Met Ala Pro Pro Thr Gly Val Leu Ser Ser Leu Leu Leu Val Thr
1               5                   10                  15

Ile Ala Gly Cys Ala Arg Lys Gln Cys Ser Glu Gly Arg Thr Tyr Ser
            20                  25                  30

Asn Ala Val Ile Ser Pro Asn Leu Glu Thr Thr Arg Ile Met Arg Val
        35                  40                  45
```

Ser His Thr Phe Pro Val Val Asp Cys Thr Ala Ala Cys Cys Asp Leu
50                      55                      60

Ser Ser Cys Asp Leu Ala Trp Trp Phe Glu Gly Arg Cys Tyr Leu Val
65                      70                      75                      80

Ser Cys Pro His Lys Glu Asn Cys Glu Pro Lys Lys Met Gly Pro Ile
                    85                      90                      95

Arg Ser Tyr Leu Thr Phe Val Leu Arg Pro Val Gln Arg Pro Ala Gln
                100                     105                     110

Leu Leu Asp Tyr Gly Asp Met Met Leu Asn Arg Gly Ser Pro Ser Gly
            115                     120                     125

Ile Trp Gly Asp Ser Pro Glu Asp Ile Arg Lys Asp Leu Thr Phe Leu
        130                     135                     140

Gly Lys Asp Trp Gly Leu Glu Glu Met Ser Glu Tyr Ser Asp Asp Tyr
145                     150                     155                     160

Arg Glu Leu Glu Lys Asp Leu Leu Gln Pro Ser Gly Lys Gln Glu Pro
                165                     170                     175

Arg Gly Ser Ala Glu Tyr Thr Asp Trp Gly Leu Leu Pro Gly Ser Glu
                180                     185                     190

Gly Ala Phe Asn Ser Ser Val Gly Asp Ser Pro Ala Val Pro Ala Glu
            195                     200                     205

Thr Gln Gln Asp Pro Glu Leu His Tyr Leu Asn Glu Ser Ala Ser Thr
        210                     215                     220

Pro Ala Pro Lys Leu Pro Glu Arg Ser Val Leu Leu Pro Leu Pro Thr
225                     230                     235                     240

Thr Pro Ser Ser Gly Glu Val Leu Glu Lys Glu Lys Ala Ser Gln Leu
                245                     250                     255

Gln Glu Gln Ser Ser Asn Ser Ser Gly Lys Glu Val Leu Met Pro Ser
                260                     265                     270

His Ser Leu Pro Pro Ala Ser Leu Glu Leu Ser Ser Val Thr Val Glu
            275                     280                     285

Lys Ser Pro Val Leu Thr Val Thr Pro Gly Ser Thr Glu His Ser Ile
        290                     295                     300

Pro Thr Pro Pro Thr Ser Ala Ala Pro Ser Glu Ser Thr Pro Ser Glu
305                     310                     315                     320

Leu Pro Ile Ser Pro Thr Thr Ala Pro Arg Thr Val Lys Glu Leu Thr
                325                     330                     335

Val Ser Ala Gly Asp Asn Leu Ile Ile Thr Leu Pro Asp Asn Glu Val
                340                     345                     350

Glu Leu Lys Ala Phe Val Ala Pro Ala Pro Val Glu Thr Thr Tyr
            355                     360                     365

Asn Tyr Glu Trp Asn Leu Ile Ser His Pro Thr Asp Tyr Gln Gly Glu
        370                     375                     380

Ile Lys Gln Gly His Lys Gln Thr Leu Asn Leu Ser Gln Leu Ser Val
385                     390                     395                     400

Gly Leu Tyr Val Phe Lys Val Thr Val Ser Ser Glu Asn Ala Phe Gly
                405                     410                     415

Glu Gly Phe Val Asn Val Thr Val Lys Pro Ala Arg Arg Val Asn Leu
                420                     425                     430

Pro Pro Val Ala Val Ser Pro Gln Leu Gln Glu Leu Thr Leu Pro
            435                     440                     445

Leu Thr Ser Ala Leu Ile Asp Gly Ser Gln Ser Thr Asp Asp Thr Glu
450                     455                     460

Ile Val Ser Tyr His Trp Glu Glu Ile Asn Gly Pro Phe Ile Glu Glu

```
                465                 470                 475                 480
Lys Thr Ser Val Asp Ser Pro Val Leu Arg Leu Ser Asn Leu Asp Pro
                    485                 490                 495

Gly Asn Tyr Ser Phe Arg Leu Thr Val Thr Asp Ser Asp Gly Ala Thr
                    500                 505                 510

Asn Ser Thr Thr Ala Ala Leu Ile Val Asn Asn Ala Val Asp Tyr Pro
                    515                 520                 525

Pro Val Ala Asn Ala Gly Pro Asn His Thr Ile Thr Leu Pro Gln Asn
                    530                 535                 540

Ser Ile Thr Leu Asn Gly Asn Gln Ser Ser Asp Asp His Gln Ile Val
545                 550                 555                 560

Leu Tyr Glu Trp Ser Leu Gly Pro Gly Ser Glu Gly Lys His Val Val
                    565                 570                 575

Met Gln Gly Val Gln Thr Pro Tyr Leu His Leu Ser Ala Met Gln Glu
                    580                 585                 590

Gly Asp Tyr Thr Phe Gln Leu Lys Val Thr Asp Ser Ser Arg Gln Gln
                    595                 600                 605

Ser Thr Ala Val Val Thr Val Ile Val Gln Pro Glu Asn Asn Arg Pro
610                 615                 620

Pro Val Ala Val Ala Gly Pro Asp Lys Glu Leu Ile Phe Pro Val Glu
625                 630                 635                 640

Ser Ala Thr Leu Asp Gly Ser Ser Ser Asp Asp His Gly Ile Val
                    645                 650                 655

Phe Tyr His Trp Glu His Val Arg Gly Pro Ser Ala Val Glu Met Glu
                    660                 665                 670

Asn Ile Asp Lys Ala Ile Ala Thr Val Thr Gly Leu Gln Val Gly Thr
                    675                 680                 685

Tyr His Phe Arg Leu Thr Val Lys Asp Gln Gln Gly Leu Ser Ser Thr
                    690                 695                 700

Ser Thr Leu Thr Val Ala Val Lys Lys Glu Asn Asn Ser Pro Pro Arg
705                 710                 715                 720

Ala Arg Ala Gly Gly Arg His Val Leu Val Leu Pro Asn Asn Ser Ile
                    725                 730                 735

Thr Leu Asp Gly Ser Arg Ser Thr Asp Asp Gln Arg Ile Val Ser Tyr
                    740                 745                 750

Leu Trp Ile Arg Asp Gly Gln Ser Pro Ala Ala Gly Asp Val Ile Asp
                    755                 760                 765

Gly Ser Asp His Ser Val Ala Leu Gln Leu Thr Asn Leu Val Glu Gly
770                 775                 780

Val Tyr Thr Phe His Leu Arg Val Thr Asp Ser Gln Gly Ala Ser Asp
785                 790                 795                 800

Thr Asp Thr Ala Thr Val Glu Val Gln Pro Asp Pro Arg Lys Ser Gly
                    805                 810                 815

Leu Val Glu Leu Thr Leu Gln Val Gly Val Gln Leu Thr Glu Gln
                    820                 825                 830

Arg Lys Asp Thr Leu Val Arg Gln Leu Ala Val Leu Leu Asn Val Leu
                    835                 840                 845

Asp Ser Asp Ile Lys Val Gln Lys Ile Arg Ala His Ser Asp Leu Ser
850                 855                 860

Thr Val Ile Val Phe Tyr Val Gln Ser Arg Pro Pro Phe Lys Val Leu
865                 870                 875                 880

Lys Ala Ala Glu Val Ala Arg Asn Leu His Met Arg Leu Ser Lys Glu
                    885                 890                 895
```

```
Lys Ala Asp Phe Leu Leu Phe Lys Val Leu Arg Val Asp Thr Ala Gly
        900                 905                 910

Cys Leu Leu Lys Cys Ser Gly His Gly His Cys Asp Pro Leu Thr Lys
        915                 920                 925

Arg Cys Ile Cys Ser His Leu Trp Met Glu Asn Leu Ile Gln Arg Tyr
        930                 935                 940

Ile Trp Asp Gly Glu Ser Asn Cys Glu Trp Ser Ile Phe Tyr Val Thr
945                 950                 955                 960

Val Leu Ala Phe Thr Leu Ile Val Leu Thr Gly Phe Thr Trp Leu
                965                 970                 975

Cys Ile Cys Cys Lys Arg Gln Lys Arg Thr Lys Ile Arg Lys Lys
        980                 985                 990

Thr Lys Tyr Thr Ile Leu Asp Asn Met Asp Glu Gln Glu Arg Met Glu
        995                 1000                1005

Leu Arg Pro Lys Tyr Gly Ile Lys His Arg Ser Thr Glu His Asn Ser
        1010                1015                1020

Ser Leu Met Val Ser Glu Ser Glu Phe Asp Ser Asp Gln Asp Thr Ile
1025                1030                1035                1040

Phe Ser Arg Glu Lys Met Glu Arg Gly Asn Pro Lys Val Ser Met Asn
                1045                1050                1055

Gly Ser Ile Arg Asn Gly Ala Ser Phe Ser Tyr Cys Ser Lys Asp Arg
        1060                1065                1070

<210> SEQ ID NO 12
<211> LENGTH: 1072
<212> TYPE: PRT
<213> ORGANISM: Homo sapiens

<400> SEQUENCE: 12

Met Ala Pro Pro Thr Gly Val Leu Ser Ser Leu Leu Leu Leu Val Thr
1               5                   10                  15

Ile Ala Gly Cys Ala Arg Lys Gln Cys Ser Glu Gly Arg Thr Tyr Ser
            20                  25                  30

Asn Ala Val Ile Ser Pro Asn Leu Glu Thr Thr Arg Ile Met Arg Val
        35                  40                  45

Ser His Thr Phe Pro Val Val Asp Cys Thr Ala Ala Cys Cys Asp Leu
    50                  55                  60

Ser Ser Cys Asp Leu Ala Trp Trp Phe Glu Gly Arg Cys Tyr Leu Val
65                  70                  75                  80

Ser Cys Pro His Lys Glu Asn Cys Glu Pro Lys Lys Met Gly Pro Ile
                85                  90                  95

Arg Ser Tyr Leu Thr Phe Val Leu Arg Pro Val Gln Arg Pro Ala Gln
            100                 105                 110

Leu Leu Asp Tyr Gly Asp Met Met Leu Asn Arg Gly Ser Pro Ser Gly
        115                 120                 125

Ile Trp Gly Asp Ser Pro Glu Asp Ile Arg Lys Asp Leu Pro Phe Leu
    130                 135                 140

Gly Lys Asp Trp Gly Leu Glu Glu Met Ser Glu Tyr Ala Asp Asp Tyr
145                 150                 155                 160

Arg Glu Leu Glu Lys Asp Leu Leu Gln Pro Ser Gly Lys Gln Glu Pro
                165                 170                 175

Arg Gly Ser Ala Glu Tyr Thr Asp Trp Gly Leu Leu Pro Gly Ser Glu
            180                 185                 190

Gly Ala Phe Asn Ser Ser Val Gly Asp Ser Pro Ala Val Pro Ala Glu
        195                 200                 205
```

```
Thr Gln Gln Asp Pro Glu Leu His Tyr Leu Asn Glu Ser Ala Ser Thr
    210                 215                 220

Pro Ala Pro Lys Leu Pro Glu Arg Ser Val Leu Leu Pro Leu Pro Thr
225                 230                 235                 240

Thr Pro Ser Ser Gly Glu Val Leu Glu Lys Glu Lys Ala Ser Gln Leu
                245                 250                 255

Gln Glu Gln Ser Ser Asn Ser Ser Gly Lys Glu Val Leu Met Pro Ser
            260                 265                 270

His Ser Leu Pro Pro Ala Ser Leu Glu Leu Ser Ser Val Thr Val Glu
        275                 280                 285

Lys Ser Pro Val Leu Thr Val Thr Pro Gly Ser Thr Glu His Ser Ile
290                 295                 300

Pro Thr Pro Pro Thr Ser Ala Ala Pro Ser Glu Ser Thr Pro Ser Glu
305                 310                 315                 320

Leu Pro Ile Ser Pro Thr Thr Ala Pro Arg Thr Val Lys Glu Leu Thr
                325                 330                 335

Val Ser Ala Gly Asp Asn Leu Ile Ile Thr Leu Pro Asp Asn Glu Val
            340                 345                 350

Glu Leu Lys Ala Phe Val Ala Pro Ala Pro Val Glu Thr Thr Tyr
        355                 360                 365

Asn Tyr Glu Trp Asn Leu Ile Ser His Pro Thr Asp Tyr Gln Gly Glu
    370                 375                 380

Ile Lys Gln Gly His Lys Gln Thr Leu Asn Leu Ser Gln Leu Ser Val
385                 390                 395                 400

Gly Leu Tyr Val Phe Lys Val Thr Val Ser Ser Glu Asn Ala Phe Gly
                405                 410                 415

Glu Gly Phe Val Asn Val Thr Val Lys Pro Ala Arg Arg Val Asn Leu
            420                 425                 430

Pro Pro Val Ala Val Val Ser Pro Gln Leu Gln Glu Leu Thr Leu Pro
        435                 440                 445

Leu Thr Ser Ala Leu Ile Asp Gly Ser Gln Ser Thr Asp Asp Thr Glu
    450                 455                 460

Ile Val Ser Tyr His Trp Glu Glu Ile Asn Gly Pro Phe Ile Glu Glu
465                 470                 475                 480

Lys Thr Ser Val Asp Ser Pro Val Leu Arg Leu Ser Asn Leu Asp Pro
                485                 490                 495

Gly Asn Tyr Ser Phe Arg Leu Thr Val Thr Asp Ser Asp Gly Ala Thr
            500                 505                 510

Asn Ser Thr Thr Ala Ala Leu Ile Val Asn Asn Ala Val Asp Tyr Pro
        515                 520                 525

Pro Val Ala Asn Ala Gly Pro Asn His Thr Ile Thr Leu Pro Gln Asn
    530                 535                 540

Ser Ile Thr Leu Asn Gly Asn Gln Ser Ser Asp Asp His Gln Ile Val
545                 550                 555                 560

Leu Tyr Glu Trp Ser Leu Gly Pro Gly Ser Glu Gly Lys His Val Val
                565                 570                 575

Met Gln Gly Val Gln Thr Pro Tyr Leu His Leu Ser Ala Met Gln Glu
            580                 585                 590

Gly Asp Tyr Thr Phe Gln Leu Lys Val Thr Asp Ser Ser Arg Gln Gln
        595                 600                 605

Ser Thr Ala Val Val Thr Val Ile Val Gln Pro Glu Asn Asn Arg Pro
    610                 615                 620

Pro Val Ala Val Ala Gly Pro Asp Lys Glu Leu Ile Phe Pro Val Glu
625                 630                 635                 640
```

```
Ser Ala Thr Leu Asp Gly Ser Ser Ser Asp His Gly Ile Val
            645             650             655

Phe Tyr His Trp Glu His Val Arg Gly Pro Ser Ala Val Glu Met Glu
            660             665             670

Asn Ile Asp Lys Ala Ile Ala Thr Val Thr Gly Leu Gln Val Gly Thr
            675             680             685

Tyr His Phe Arg Leu Thr Val Lys Asp Gln Gln Gly Leu Ser Ser Thr
            690             695             700

Ser Thr Leu Thr Val Ala Val Lys Lys Glu Asn Asn Ser Pro Pro Arg
705             710             715             720

Ala Arg Ala Gly Gly Arg His Val Leu Val Leu Pro Asn Asn Ser Ile
                725             730             735

Thr Leu Asp Gly Ser Arg Ser Thr Asp Asp Gln Arg Ile Val Ser Tyr
            740             745             750

Leu Trp Ile Arg Asp Gly Gln Ser Pro Ala Ala Gly Asp Val Ile Asp
            755             760             765

Gly Ser Asp His Ser Val Ala Leu Gln Leu Thr Asn Leu Val Glu Gly
    770             775             780

Val Tyr Thr Phe His Leu Arg Val Thr Asp Ser Gln Gly Ala Ser Asp
785             790             795             800

Thr Asp Thr Ala Thr Val Glu Val Gln Pro Asp Pro Arg Lys Ser Gly
            805             810             815

Leu Val Glu Leu Thr Leu Gln Val Gly Val Gly Gln Leu Thr Glu Gln
            820             825             830

Arg Lys Asp Thr Leu Val Arg Gln Leu Ala Val Leu Leu Asn Val Leu
    835             840             845

Asp Ser Asp Ile Lys Val Gln Lys Ile Arg Ala His Ser Asp Leu Ser
    850             855             860

Thr Val Ile Val Phe Tyr Val Gln Ser Arg Pro Pro Phe Lys Val Leu
865             870             875             880

Lys Ala Ala Glu Val Ala Arg Asn Leu His Met Arg Leu Ser Lys Glu
            885             890             895

Lys Ala Asp Phe Leu Leu Phe Lys Val Leu Arg Val Asp Thr Ala Gly
            900             905             910

Cys Leu Leu Lys Cys Ser Gly His Gly His Cys Asp Pro Leu Thr Lys
            915             920             925

Arg Cys Ile Cys Ser His Leu Trp Met Glu Asn Leu Ile Gln Arg Tyr
    930             935             940

Ile Trp Asp Gly Glu Ser Asn Cys Glu Trp Ser Ile Phe Tyr Val Thr
945             950             955             960

Val Leu Ala Phe Thr Leu Ile Val Leu Thr Gly Gly Phe Thr Trp Leu
            965             970             975

Cys Ile Cys Cys Cys Lys Arg Gln Lys Arg Thr Lys Ile Arg Lys Lys
            980             985             990

Thr Lys Tyr Thr Ile Leu Asp Asn Met Asp Glu Gln Glu Arg Met Glu
            995             1000            1005

Leu Arg Pro Lys Tyr Gly Ile Lys His Arg Ser Thr Glu His Asn Ser
    1010            1015            1020

Ser Leu Met Val Ser Glu Ser Glu Phe Asp Ser Asp Gln Asp Thr Ile
1025            1030            1035            1040

Phe Ser Arg Glu Lys Met Glu Arg Gly Asn Pro Lys Val Ser Met Asn
            1045            1050            1055

Gly Ser Ile Arg Asn Gly Ala Ser Phe Ser Tyr Cys Ser Lys Asp Arg
```

-continued

<210> SEQ ID NO 13
<211> LENGTH: 14
<212> TYPE: PRT
<213> ORGANISM: tetanus toxoid

<400> SEQUENCE: 13

Gln Tyr Ile Lys Ala Asn Ser Lys Phe Ile Gly Ile Thr Glu
1               5                   10

<210> SEQ ID NO 14
<211> LENGTH: 21
<212> TYPE: PRT
<213> ORGANISM: Plasmodium falciparum

<400> SEQUENCE: 14

Asp Ile Glu Lys Lys Ile Ala Lys Met Glu Lys Ala Ser Ser Val Phe
1               5                   10                  15

Asn Val Val Asn Ser
            20

<210> SEQ ID NO 15
<211> LENGTH: 16
<212> TYPE: PRT
<213> ORGANISM: Streptococcus

<400> SEQUENCE: 15

Gly Ala Val Asp Ser Ile Leu Gly Gly Val Ala Thr Tyr Gly Ala Ala
1               5                   10                  15

<210> SEQ ID NO 16
<211> LENGTH: 13
<212> TYPE: PRT
<213> ORGANISM: Artificial Sequence
<220> FEATURE:
<223> OTHER INFORMATION: pan-DR-binding epitope
<221> NAME/KEY: VARIANT
<222> LOCATION: 1, 13
<223> OTHER INFORMATION: Xaa = D-alanine or L-alanine
<221> NAME/KEY: VARIANT
<222> LOCATION: 3
<223> OTHER INFORMATION: Xaa = cyclohexylalanine, phenylalanine, or
      tyrosine

<400> SEQUENCE: 16

Xaa Lys Xaa Val Ala Ala Trp Thr Leu Lys Ala Ala Xaa
1               5                   10

<210> SEQ ID NO 17
<211> LENGTH: 14
<212> TYPE: DNA
<213> ORGANISM: Artificial Sequence
<220> FEATURE:
<223> OTHER INFORMATION: cDNA synthesis primer

<400> SEQUENCE: 17
ttttgatcaa gctt                                                        14

<210> SEQ ID NO 18
<211> LENGTH: 42
<212> TYPE: DNA
<213> ORGANISM: Artificial Sequence
<220> FEATURE:
<223> OTHER INFORMATION: Primer

<400> SEQUENCE: 18

-continued

```
ctaatacgac tcactatagg gctcgagcgg ccgcccgggc ag            42

<210> SEQ ID NO 19
<211> LENGTH: 12
<212> TYPE: DNA
<213> ORGANISM: Artificial Sequence
<220> FEATURE:
<223> OTHER INFORMATION: Primer

<400> SEQUENCE: 19
gatcctgccc gg                                             12

<210> SEQ ID NO 20
<211> LENGTH: 40
<212> TYPE: DNA
<213> ORGANISM: Artificial Sequence
<220> FEATURE:
<223> OTHER INFORMATION: Primer

<400> SEQUENCE: 20
gtaatacgac tcactatagg gcagcgtggt cgcggccgag               40

<210> SEQ ID NO 21
<211> LENGTH: 10
<212> TYPE: DNA
<213> ORGANISM: Artificial Sequence
<220> FEATURE:
<223> OTHER INFORMATION: Primer

<400> SEQUENCE: 21
gatcctcggc                                                10

<210> SEQ ID NO 22
<211> LENGTH: 22
<212> TYPE: DNA
<213> ORGANISM: Artificial Sequence
<220> FEATURE:
<223> OTHER INFORMATION: Primer

<400> SEQUENCE: 22
ctaatacgac tcactatagg gc                                  22

<210> SEQ ID NO 23
<211> LENGTH: 22
<212> TYPE: DNA
<213> ORGANISM: Artificial Sequence
<220> FEATURE:
<223> OTHER INFORMATION: Primer

<400> SEQUENCE: 23
tcgagcggcc gcccgggcag ga                                  22

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
agcgtggtcg cggccgagga                                     20

<210> SEQ ID NO 25
<211> LENGTH: 25
<212> TYPE: DNA
<213> ORGANISM: Artificial Sequence
<220> FEATURE:
```

<223> OTHER INFORMATION: Primer

<400> SEQUENCE: 25
atatcgccgc gctcgtcgtc gacaa                                          25

<210> SEQ ID NO 26
<211> LENGTH: 26
<212> TYPE: DNA
<213> ORGANISM: Artificial Sequence
<220> FEATURE:
<223> OTHER INFORMATION: Primer

<400> SEQUENCE: 26
agccacacgc agctcattgt agaagg                                         26

<210> SEQ ID NO 27
<211> LENGTH: 24
<212> TYPE: DNA
<213> ORGANISM: Artificial Sequence
<220> FEATURE:
<223> OTHER INFORMATION: Flag Tag

<400> SEQUENCE: 27
gattacaagg atgacgacga taag                                           24

<210> SEQ ID NO 28
<211> LENGTH: 4
<212> TYPE: PRT
<213> ORGANISM: Homo sapiens

<400> SEQUENCE: 28

Asn Ser Ser Val
 1

<210> SEQ ID NO 29
<211> LENGTH: 4
<212> TYPE: PRT
<213> ORGANISM: Homo sapiens

<400> SEQUENCE: 29

Asn Glu Ser Ala
 1

<210> SEQ ID NO 30
<211> LENGTH: 4
<212> TYPE: PRT
<213> ORGANISM: Homo sapiens

<400> SEQUENCE: 30

Asn Ser Ser Gly
 1

<210> SEQ ID NO 31
<211> LENGTH: 4
<212> TYPE: PRT
<213> ORGANISM: Homo sapiens

<400> SEQUENCE: 31

Asn Leu Ser Gln
 1

<210> SEQ ID NO 32
<211> LENGTH: 4
<212> TYPE: PRT
<213> ORGANISM: Homo sapiens

```
<400> SEQUENCE: 32

Asn Val Thr Val
1

<210> SEQ ID NO 33
<211> LENGTH: 4
<212> TYPE: PRT
<213> ORGANISM: Homo sapiens

<400> SEQUENCE: 33

Asn Tyr Ser Phe
1

<210> SEQ ID NO 34
<211> LENGTH: 4
<212> TYPE: PRT
<213> ORGANISM: Homo sapiens

<400> SEQUENCE: 34

Asn Ser Thr Thr
1

<210> SEQ ID NO 35
<211> LENGTH: 4
<212> TYPE: PRT
<213> ORGANISM: Homo sapiens

<400> SEQUENCE: 35

Asn His Thr Ile
1

<210> SEQ ID NO 36
<211> LENGTH: 4
<212> TYPE: PRT
<213> ORGANISM: Homo sapiens

<400> SEQUENCE: 36

Asn Gln Ser Ser
1

<210> SEQ ID NO 37
<211> LENGTH: 4
<212> TYPE: PRT
<213> ORGANISM: Homo sapiens

<400> SEQUENCE: 37

Asn Asn Ser Pro
1

<210> SEQ ID NO 38
<211> LENGTH: 4
<212> TYPE: PRT
<213> ORGANISM: Homo sapiens

<400> SEQUENCE: 38

Asn Asn Ser Ile
1

<210> SEQ ID NO 39
<211> LENGTH: 4
<212> TYPE: PRT
<213> ORGANISM: Homo sapiens

<400> SEQUENCE: 39

Asn Ser Ser Leu
```

```
<210> SEQ ID NO 40
<211> LENGTH: 4
<212> TYPE: PRT
<213> ORGANISM: Homo sapiens

<400> SEQUENCE: 40

Asn Gly Ser Ile
1

<210> SEQ ID NO 41
<211> LENGTH: 12
<212> TYPE: PRT
<213> ORGANISM: Homo sapiens

<400> SEQUENCE: 41

Glu Glu Met Ser Glu Tyr Ser Asp Asp Tyr Arg Glu
1               5                   10

<210> SEQ ID NO 42
<211> LENGTH: 11
<212> TYPE: PRT
<213> ORGANISM: Homo sapiens

<400> SEQUENCE: 42

Glu Tyr Ser Asp Asp Tyr Arg Glu Leu Glu Lys
1               5                   10

<210> SEQ ID NO 43
<211> LENGTH: 16
<212> TYPE: PRT
<213> ORGANISM: Homo sapiens

<400> SEQUENCE: 43

Asn Asn Ala Val Asp Tyr Pro Pro Val Ala Asn Ala Gly Pro Asn His
1               5                   10                  15

<210> SEQ ID NO 44
<211> LENGTH: 9
<212> TYPE: PRT
<213> ORGANISM: Homo sapiens

<400> SEQUENCE: 44

Thr Gly Val Leu Ser Ser Leu Leu Leu
1               5

<210> SEQ ID NO 45
<211> LENGTH: 9
<212> TYPE: PRT
<213> ORGANISM: Homo sapiens

<400> SEQUENCE: 45

Gly Val Leu Ser Ser Leu Leu Leu Leu
1               5

<210> SEQ ID NO 46
<211> LENGTH: 9
<212> TYPE: PRT
<213> ORGANISM: Homo sapiens

<400> SEQUENCE: 46

Arg Lys Gln Cys Ser Glu Gly Arg Thr
1               5
```

<210> SEQ ID NO 47
<211> LENGTH: 9
<212> TYPE: PRT
<213> ORGANISM: Homo sapiens

<400> SEQUENCE: 47

Gly Arg Thr Tyr Ser Asn Ala Val Ile
1               5

<210> SEQ ID NO 48
<211> LENGTH: 9
<212> TYPE: PRT
<213> ORGANISM: Homo sapiens

<400> SEQUENCE: 48

Asn Ala Val Ile Ser Pro Asn Leu Glu
1               5

<210> SEQ ID NO 49
<211> LENGTH: 9
<212> TYPE: PRT
<213> ORGANISM: Homo sapiens

<400> SEQUENCE: 49

Ile Met Arg Val Ser His Thr Phe Pro
1               5

<210> SEQ ID NO 50
<211> LENGTH: 9
<212> TYPE: PRT
<213> ORGANISM: Homo sapiens

<400> SEQUENCE: 50

Cys Cys Asp Leu Ser Ser Cys Asp Leu
1               5

<210> SEQ ID NO 51
<211> LENGTH: 9
<212> TYPE: PRT
<213> ORGANISM: Homo sapiens

<400> SEQUENCE: 51

Cys Asp Leu Ser Ser Cys Asp Leu Ala
1               5

<210> SEQ ID NO 52
<211> LENGTH: 9
<212> TYPE: PRT
<213> ORGANISM: Homo sapiens

<400> SEQUENCE: 52

Cys Tyr Leu Val Ser Cys Pro His Lys
1               5

<210> SEQ ID NO 53
<211> LENGTH: 9
<212> TYPE: PRT
<213> ORGANISM: Homo sapiens

<400> SEQUENCE: 53

Gly Pro Ile Arg Ser Tyr Leu Thr Phe
1               5

<210> SEQ ID NO 54
<211> LENGTH: 9
<212> TYPE: PRT

<213> ORGANISM: Homo sapiens

<400> SEQUENCE: 54

Leu Asn Arg Gly Ser Pro Ser Gly Ile
 1               5

<210> SEQ ID NO 55
<211> LENGTH: 9
<212> TYPE: PRT
<213> ORGANISM: Homo sapiens

<400> SEQUENCE: 55

Arg Gly Ser Pro Ser Gly Ile Trp Gly
 1               5

<210> SEQ ID NO 56
<211> LENGTH: 9
<212> TYPE: PRT
<213> ORGANISM: Homo sapiens

<400> SEQUENCE: 56

Ile Trp Gly Asp Ser Pro Glu Asp Ile
 1               5

<210> SEQ ID NO 57
<211> LENGTH: 9
<212> TYPE: PRT
<213> ORGANISM: Homo sapiens

<400> SEQUENCE: 57

Leu Glu Glu Met Ser Glu Tyr Ser Asp
 1               5

<210> SEQ ID NO 58
<211> LENGTH: 9
<212> TYPE: PRT
<213> ORGANISM: Homo sapiens

<400> SEQUENCE: 58

Met Ser Glu Tyr Ser Asp Asp Tyr Arg
 1               5

<210> SEQ ID NO 59
<211> LENGTH: 9
<212> TYPE: PRT
<213> ORGANISM: Homo sapiens

<400> SEQUENCE: 59

Leu Leu Gln Pro Ser Gly Lys Gln Glu
 1               5

<210> SEQ ID NO 60
<211> LENGTH: 9
<212> TYPE: PRT
<213> ORGANISM: Homo sapiens

<400> SEQUENCE: 60

Glu Pro Arg Gly Ser Ala Glu Tyr Thr
 1               5

<210> SEQ ID NO 61
<211> LENGTH: 9
<212> TYPE: PRT
<213> ORGANISM: Homo sapiens

<400> SEQUENCE: 61

```
Leu Leu Pro Gly Ser Glu Gly Ala Phe
1               5
```

<210> SEQ ID NO 62
<211> LENGTH: 9
<212> TYPE: PRT
<213> ORGANISM: Homo sapiens

<400> SEQUENCE: 62

```
Gly Ala Phe Asn Ser Ser Val Gly Asp
1               5
```

<210> SEQ ID NO 63
<211> LENGTH: 9
<212> TYPE: PRT
<213> ORGANISM: Homo sapiens

<400> SEQUENCE: 63

```
Ala Phe Asn Ser Ser Val Gly Asp Ser
1               5
```

<210> SEQ ID NO 64
<211> LENGTH: 9
<212> TYPE: PRT
<213> ORGANISM: Homo sapiens

<400> SEQUENCE: 64

```
Ser Val Gly Asp Ser Pro Ala Val Pro
1               5
```

<210> SEQ ID NO 65
<211> LENGTH: 9
<212> TYPE: PRT
<213> ORGANISM: Homo sapiens

<400> SEQUENCE: 65

```
Tyr Leu Asn Glu Ser Ala Ser Thr Pro
1               5
```

<210> SEQ ID NO 66
<211> LENGTH: 9
<212> TYPE: PRT
<213> ORGANISM: Homo sapiens

<400> SEQUENCE: 66

```
Asn Glu Ser Ala Ser Thr Pro Ala Pro
1               5
```

<210> SEQ ID NO 67
<211> LENGTH: 9
<212> TYPE: PRT
<213> ORGANISM: Homo sapiens

<400> SEQUENCE: 67

```
Leu Pro Glu Arg Ser Val Leu Leu Pro
1               5
```

<210> SEQ ID NO 68
<211> LENGTH: 9
<212> TYPE: PRT
<213> ORGANISM: Homo sapiens

<400> SEQUENCE: 68

```
Pro Thr Thr Pro Ser Ser Gly Glu Val
1               5
```

<210> SEQ ID NO 69
<211> LENGTH: 9
<212> TYPE: PRT
<213> ORGANISM: Homo sapiens

<400> SEQUENCE: 69

Thr Thr Pro Ser Ser Gly Glu Val Leu
 1               5

<210> SEQ ID NO 70
<211> LENGTH: 9
<212> TYPE: PRT
<213> ORGANISM: Homo sapiens

<400> SEQUENCE: 70

Lys Glu Lys Ala Ser Gln Leu Gln Glu
 1               5

<210> SEQ ID NO 71
<211> LENGTH: 9
<212> TYPE: PRT
<213> ORGANISM: Homo sapiens

<400> SEQUENCE: 71

Ser Ser Asn Ser Ser Gly Lys Glu Val
 1               5

<210> SEQ ID NO 72
<211> LENGTH: 9
<212> TYPE: PRT
<213> ORGANISM: Homo sapiens

<400> SEQUENCE: 72

Val Leu Met Pro Ser His Ser Leu Pro
 1               5

<210> SEQ ID NO 73
<211> LENGTH: 9
<212> TYPE: PRT
<213> ORGANISM: Homo sapiens

<400> SEQUENCE: 73

Met Pro Ser His Ser Leu Pro Pro Ala
 1               5

<210> SEQ ID NO 74
<211> LENGTH: 9
<212> TYPE: PRT
<213> ORGANISM: Homo sapiens

<400> SEQUENCE: 74

Leu Pro Pro Ala Ser Leu Glu Leu Ser
 1               5

<210> SEQ ID NO 75
<211> LENGTH: 9
<212> TYPE: PRT
<213> ORGANISM: Homo sapiens

<400> SEQUENCE: 75

Ser Leu Glu Leu Ser Ser Val Thr Val
 1               5

<210> SEQ ID NO 76

<211> LENGTH: 9
<212> TYPE: PRT
<213> ORGANISM: Homo sapiens

<400> SEQUENCE: 76

Leu Glu Leu Ser Ser Val Thr Val Glu
1               5

<210> SEQ ID NO 77
<211> LENGTH: 9
<212> TYPE: PRT
<213> ORGANISM: Homo sapiens

<400> SEQUENCE: 77

Thr Val Glu Lys Ser Pro Val Leu Thr
1               5

<210> SEQ ID NO 78
<211> LENGTH: 9
<212> TYPE: PRT
<213> ORGANISM: Homo sapiens

<400> SEQUENCE: 78

Val Thr Pro Gly Ser Thr Glu His Ser
1               5

<210> SEQ ID NO 79
<211> LENGTH: 9
<212> TYPE: PRT
<213> ORGANISM: Homo sapiens

<400> SEQUENCE: 79

Ser Thr Glu His Ser Ile Pro Thr Pro
1               5

<210> SEQ ID NO 80
<211> LENGTH: 9
<212> TYPE: PRT
<213> ORGANISM: Homo sapiens

<400> SEQUENCE: 80

Thr Pro Pro Thr Ser Ala Ala Pro Ser
1               5

<210> SEQ ID NO 81
<211> LENGTH: 9
<212> TYPE: PRT
<213> ORGANISM: Homo sapiens

<400> SEQUENCE: 81

Ser Ala Ala Pro Ser Glu Ser Thr Pro
1               5

<210> SEQ ID NO 82
<211> LENGTH: 9
<212> TYPE: PRT
<213> ORGANISM: Homo sapiens

<400> SEQUENCE: 82

Ala Pro Ser Glu Ser Thr Pro Ser Glu
1               5

<210> SEQ ID NO 83
<211> LENGTH: 9
<212> TYPE: PRT
<213> ORGANISM: Homo sapiens

-continued

<400> SEQUENCE: 83

Glu Ser Thr Pro Ser Glu Leu Pro Ile
1               5

<210> SEQ ID NO 84
<211> LENGTH: 9
<212> TYPE: PRT
<213> ORGANISM: Homo sapiens

<400> SEQUENCE: 84

Glu Leu Pro Ile Ser Pro Thr Thr Ala
1               5

<210> SEQ ID NO 85
<211> LENGTH: 9
<212> TYPE: PRT
<213> ORGANISM: Homo sapiens

<400> SEQUENCE: 85

Glu Leu Thr Val Ser Ala Gly Asp Asn
1               5

<210> SEQ ID NO 86
<211> LENGTH: 9
<212> TYPE: PRT
<213> ORGANISM: Homo sapiens

<400> SEQUENCE: 86

Trp Asn Leu Ile Ser His Pro Thr Asp
1               5

<210> SEQ ID NO 87
<211> LENGTH: 9
<212> TYPE: PRT
<213> ORGANISM: Homo sapiens

<400> SEQUENCE: 87

Thr Leu Asn Leu Ser Gln Leu Ser Val
1               5

<210> SEQ ID NO 88
<211> LENGTH: 9
<212> TYPE: PRT
<213> ORGANISM: Homo sapiens

<400> SEQUENCE: 88

Leu Ser Gln Leu Ser Val Gly Leu Tyr
1               5

<210> SEQ ID NO 89
<211> LENGTH: 9
<212> TYPE: PRT
<213> ORGANISM: Homo sapiens

<400> SEQUENCE: 89

Lys Val Thr Val Ser Ser Glu Asn Ala
1               5

<210> SEQ ID NO 90
<211> LENGTH: 9
<212> TYPE: PRT
<213> ORGANISM: Homo sapiens

<400> SEQUENCE: 90

```
Val Thr Val Ser Ser Glu Asn Ala Phe
1               5

<210> SEQ ID NO 91
<211> LENGTH: 9
<212> TYPE: PRT
<213> ORGANISM: Homo sapiens

<400> SEQUENCE: 91

Val Ala Val Val Ser Pro Gln Leu Gln
1               5

<210> SEQ ID NO 92
<211> LENGTH: 9
<212> TYPE: PRT
<213> ORGANISM: Homo sapiens

<400> SEQUENCE: 92

Leu Pro Leu Thr Ser Ala Leu Ile Asp
1               5

<210> SEQ ID NO 93
<211> LENGTH: 9
<212> TYPE: PRT
<213> ORGANISM: Homo sapiens

<400> SEQUENCE: 93

Leu Ile Asp Gly Ser Gln Ser Thr Asp
1               5

<210> SEQ ID NO 94
<211> LENGTH: 9
<212> TYPE: PRT
<213> ORGANISM: Homo sapiens

<400> SEQUENCE: 94

Asp Gly Ser Gln Ser Thr Asp Asp Thr
1               5

<210> SEQ ID NO 95
<211> LENGTH: 9
<212> TYPE: PRT
<213> ORGANISM: Homo sapiens

<400> SEQUENCE: 95

Thr Glu Ile Val Ser Tyr His Trp Glu
1               5

<210> SEQ ID NO 96
<211> LENGTH: 9
<212> TYPE: PRT
<213> ORGANISM: Homo sapiens

<400> SEQUENCE: 96

Glu Glu Lys Thr Ser Val Asp Ser Pro
1               5

<210> SEQ ID NO 97
<211> LENGTH: 9
<212> TYPE: PRT
<213> ORGANISM: Homo sapiens

<400> SEQUENCE: 97

Thr Ser Val Asp Ser Pro Val Leu Arg
1               5
```

```
<210> SEQ ID NO 98
<211> LENGTH: 9
<212> TYPE: PRT
<213> ORGANISM: Homo sapiens

<400> SEQUENCE: 98

Val Leu Arg Leu Ser Asn Leu Asp Pro
1               5

<210> SEQ ID NO 99
<211> LENGTH: 9
<212> TYPE: PRT
<213> ORGANISM: Homo sapiens

<400> SEQUENCE: 99

Pro Gly Asn Tyr Ser Phe Arg Leu Thr
1               5

<210> SEQ ID NO 100
<211> LENGTH: 9
<212> TYPE: PRT
<213> ORGANISM: Homo sapiens

<400> SEQUENCE: 100

Thr Val Thr Asp Ser Asp Gly Ala Thr
1               5

<210> SEQ ID NO 101
<211> LENGTH: 9
<212> TYPE: PRT
<213> ORGANISM: Homo sapiens

<400> SEQUENCE: 101

Gly Ala Thr Asn Ser Thr Thr Ala Ala
1               5

<210> SEQ ID NO 102
<211> LENGTH: 9
<212> TYPE: PRT
<213> ORGANISM: Homo sapiens

<400> SEQUENCE: 102

Leu Pro Gln Asn Ser Ile Thr Leu Asn
1               5

<210> SEQ ID NO 103
<211> LENGTH: 9
<212> TYPE: PRT
<213> ORGANISM: Homo sapiens

<400> SEQUENCE: 103

Asn Gly Asn Gln Ser Ser Asp Asp His
1               5

<210> SEQ ID NO 104
<211> LENGTH: 9
<212> TYPE: PRT
<213> ORGANISM: Homo sapiens

<400> SEQUENCE: 104

Gly Asn Gln Ser Ser Asp Asp His Gln
1               5

<210> SEQ ID NO 105
<211> LENGTH: 9
```

```
<212> TYPE: PRT
<213> ORGANISM: Homo sapiens

<400> SEQUENCE: 105

Leu Tyr Glu Trp Ser Leu Gly Pro Gly
 1               5

<210> SEQ ID NO 106
<211> LENGTH: 9
<212> TYPE: PRT
<213> ORGANISM: Homo sapiens

<400> SEQUENCE: 106

Leu Gly Pro Gly Ser Glu Gly Lys His
 1               5

<210> SEQ ID NO 107
<211> LENGTH: 9
<212> TYPE: PRT
<213> ORGANISM: Homo sapiens

<400> SEQUENCE: 107

Tyr Leu His Leu Ser Ala Met Gln Glu
 1               5

<210> SEQ ID NO 108
<211> LENGTH: 9
<212> TYPE: PRT
<213> ORGANISM: Homo sapiens

<400> SEQUENCE: 108

Lys Val Thr Asp Ser Ser Arg Gln Gln
 1               5

<210> SEQ ID NO 109
<211> LENGTH: 9
<212> TYPE: PRT
<213> ORGANISM: Homo sapiens

<400> SEQUENCE: 109

Val Thr Asp Ser Ser Arg Gln Gln Ser
 1               5

<210> SEQ ID NO 110
<211> LENGTH: 9
<212> TYPE: PRT
<213> ORGANISM: Homo sapiens

<400> SEQUENCE: 110

Ser Arg Gln Gln Ser Thr Ala Val Val
 1               5

<210> SEQ ID NO 111
<211> LENGTH: 9
<212> TYPE: PRT
<213> ORGANISM: Homo sapiens

<400> SEQUENCE: 111

Phe Pro Val Glu Ser Ala Thr Leu Asp
 1               5

<210> SEQ ID NO 112
<211> LENGTH: 9
<212> TYPE: PRT
<213> ORGANISM: Homo sapiens
```

```
<400> SEQUENCE: 112

Thr Leu Asp Gly Ser Ser Ser Ser Asp
1               5

<210> SEQ ID NO 113
<211> LENGTH: 9
<212> TYPE: PRT
<213> ORGANISM: Homo sapiens

<400> SEQUENCE: 113

Leu Asp Gly Ser Ser Ser Ser Asp Asp
1               5

<210> SEQ ID NO 114
<211> LENGTH: 9
<212> TYPE: PRT
<213> ORGANISM: Homo sapiens

<400> SEQUENCE: 114

Asp Gly Ser Ser Ser Ser Asp Asp His
1               5

<210> SEQ ID NO 115
<211> LENGTH: 9
<212> TYPE: PRT
<213> ORGANISM: Homo sapiens

<400> SEQUENCE: 115

Gly Ser Ser Ser Ser Asp Asp His Gly
1               5

<210> SEQ ID NO 116
<211> LENGTH: 9
<212> TYPE: PRT
<213> ORGANISM: Homo sapiens

<400> SEQUENCE: 116

Val Arg Gly Pro Ser Ala Val Glu Met
1               5

<210> SEQ ID NO 117
<211> LENGTH: 9
<212> TYPE: PRT
<213> ORGANISM: Homo sapiens

<400> SEQUENCE: 117

Gln Gln Gly Leu Ser Ser Thr Ser Thr
1               5

<210> SEQ ID NO 118
<211> LENGTH: 9
<212> TYPE: PRT
<213> ORGANISM: Homo sapiens

<400> SEQUENCE: 118

Gln Gly Leu Ser Ser Thr Ser Thr Leu
1               5

<210> SEQ ID NO 119
<211> LENGTH: 9
<212> TYPE: PRT
<213> ORGANISM: Homo sapiens

<400> SEQUENCE: 119

Leu Ser Ser Thr Ser Thr Leu Thr Val
```

<210> SEQ ID NO 120
<211> LENGTH: 9
<212> TYPE: PRT
<213> ORGANISM: Homo sapiens

<400> SEQUENCE: 120

Lys Glu Asn Asn Ser Pro Pro Arg Ala
1               5

<210> SEQ ID NO 121
<211> LENGTH: 9
<212> TYPE: PRT
<213> ORGANISM: Homo sapiens

<400> SEQUENCE: 121

Leu Pro Asn Asn Ser Ile Thr Leu Asp
1               5

<210> SEQ ID NO 122
<211> LENGTH: 9
<212> TYPE: PRT
<213> ORGANISM: Homo sapiens

<400> SEQUENCE: 122

Thr Leu Asp Gly Ser Arg Ser Thr Asp
1               5

<210> SEQ ID NO 123
<211> LENGTH: 9
<212> TYPE: PRT
<213> ORGANISM: Homo sapiens

<400> SEQUENCE: 123

Asp Gly Ser Arg Ser Thr Asp Asp Gln
1               5

<210> SEQ ID NO 124
<211> LENGTH: 9
<212> TYPE: PRT
<213> ORGANISM: Homo sapiens

<400> SEQUENCE: 124

Gln Arg Ile Val Ser Tyr Leu Trp Ile
1               5

<210> SEQ ID NO 125
<211> LENGTH: 9
<212> TYPE: PRT
<213> ORGANISM: Homo sapiens

<400> SEQUENCE: 125

Arg Asp Gly Gln Ser Pro Ala Ala Gly
1               5

<210> SEQ ID NO 126
<211> LENGTH: 9
<212> TYPE: PRT
<213> ORGANISM: Homo sapiens

<400> SEQUENCE: 126

Val Ile Asp Gly Ser Asp His Ser Val
1               5

```
<210> SEQ ID NO 127
<211> LENGTH: 9
<212> TYPE: PRT
<213> ORGANISM: Homo sapiens

<400> SEQUENCE: 127

Gly Ser Asp His Ser Val Ala Leu Gln
1               5

<210> SEQ ID NO 128
<211> LENGTH: 9
<212> TYPE: PRT
<213> ORGANISM: Homo sapiens

<400> SEQUENCE: 128

Arg Val Thr Asp Ser Gln Gly Ala Ser
1               5

<210> SEQ ID NO 129
<211> LENGTH: 9
<212> TYPE: PRT
<213> ORGANISM: Homo sapiens

<400> SEQUENCE: 129

Ser Gln Gly Ala Ser Asp Thr Asp Thr
1               5

<210> SEQ ID NO 130
<211> LENGTH: 9
<212> TYPE: PRT
<213> ORGANISM: Homo sapiens

<400> SEQUENCE: 130

Asp Pro Arg Lys Ser Gly Leu Val Glu
1               5

<210> SEQ ID NO 131
<211> LENGTH: 9
<212> TYPE: PRT
<213> ORGANISM: Homo sapiens

<400> SEQUENCE: 131

Asn Val Leu Asp Ser Asp Ile Lys Val
1               5

<210> SEQ ID NO 132
<211> LENGTH: 9
<212> TYPE: PRT
<213> ORGANISM: Homo sapiens

<400> SEQUENCE: 132

Ile Arg Ala His Ser Asp Leu Ser Thr
1               5

<210> SEQ ID NO 133
<211> LENGTH: 9
<212> TYPE: PRT
<213> ORGANISM: Homo sapiens

<400> SEQUENCE: 133

His Ser Asp Leu Ser Thr Val Ile Val
1               5

<210> SEQ ID NO 134
<211> LENGTH: 9
<212> TYPE: PRT
```

```
<213> ORGANISM: Homo sapiens

<400> SEQUENCE: 134

Phe Tyr Val Gln Ser Arg Pro Pro Phe
1               5

<210> SEQ ID NO 135
<211> LENGTH: 9
<212> TYPE: PRT
<213> ORGANISM: Homo sapiens

<400> SEQUENCE: 135

His Met Arg Leu Ser Lys Glu Lys Ala
1               5

<210> SEQ ID NO 136
<211> LENGTH: 9
<212> TYPE: PRT
<213> ORGANISM: Homo sapiens

<400> SEQUENCE: 136

Leu Leu Lys Cys Ser Gly His Gly His
1               5

<210> SEQ ID NO 137
<211> LENGTH: 9
<212> TYPE: PRT
<213> ORGANISM: Homo sapiens

<400> SEQUENCE: 137

Arg Cys Ile Cys Ser His Leu Trp Met
1               5

<210> SEQ ID NO 138
<211> LENGTH: 9
<212> TYPE: PRT
<213> ORGANISM: Homo sapiens

<400> SEQUENCE: 138

Trp Asp Gly Glu Ser Asn Cys Glu Trp
1               5

<210> SEQ ID NO 139
<211> LENGTH: 9
<212> TYPE: PRT
<213> ORGANISM: Homo sapiens

<400> SEQUENCE: 139

Asn Cys Glu Trp Ser Ile Phe Tyr Val
1               5

<210> SEQ ID NO 140
<211> LENGTH: 9
<212> TYPE: PRT
<213> ORGANISM: Homo sapiens

<400> SEQUENCE: 140

Ile Lys His Arg Ser Thr Glu His Asn
1               5

<210> SEQ ID NO 141
<211> LENGTH: 9
<212> TYPE: PRT
<213> ORGANISM: Homo sapiens

<400> SEQUENCE: 141
```

Thr Glu His Asn Ser Ser Leu Met Val
1               5

<210> SEQ ID NO 142
<211> LENGTH: 9
<212> TYPE: PRT
<213> ORGANISM: Homo sapiens

<400> SEQUENCE: 142

Glu His Asn Ser Ser Leu Met Val Ser
1               5

<210> SEQ ID NO 143
<211> LENGTH: 9
<212> TYPE: PRT
<213> ORGANISM: Homo sapiens

<400> SEQUENCE: 143

Ser Leu Met Val Ser Glu Ser Glu Phe
1               5

<210> SEQ ID NO 144
<211> LENGTH: 9
<212> TYPE: PRT
<213> ORGANISM: Homo sapiens

<400> SEQUENCE: 144

Met Val Ser Glu Ser Glu Phe Asp Ser
1               5

<210> SEQ ID NO 145
<211> LENGTH: 9
<212> TYPE: PRT
<213> ORGANISM: Homo sapiens

<400> SEQUENCE: 145

Ser Glu Phe Asp Ser Asp Gln Asp Thr
1               5

<210> SEQ ID NO 146
<211> LENGTH: 9
<212> TYPE: PRT
<213> ORGANISM: Homo sapiens

<400> SEQUENCE: 146

Asp Thr Ile Phe Ser Arg Glu Lys Met
1               5

<210> SEQ ID NO 147
<211> LENGTH: 9
<212> TYPE: PRT
<213> ORGANISM: Homo sapiens

<400> SEQUENCE: 147

Asn Pro Lys Val Ser Met Asn Gly Ser
1               5

<210> SEQ ID NO 148
<211> LENGTH: 9
<212> TYPE: PRT
<213> ORGANISM: Homo sapiens

<400> SEQUENCE: 148

Ser Met Asn Gly Ser Ile Arg Asn Gly
1               5

<210> SEQ ID NO 149
<211> LENGTH: 9
<212> TYPE: PRT
<213> ORGANISM: Homo sapiens

<400> SEQUENCE: 149

Arg Asn Gly Ala Ser Phe Ser Tyr Cys
1               5

<210> SEQ ID NO 150
<211> LENGTH: 9
<212> TYPE: PRT
<213> ORGANISM: Homo sapiens

<400> SEQUENCE: 150

Gly Ala Ser Phe Ser Tyr Cys Ser Lys
1               5

<210> SEQ ID NO 151
<211> LENGTH: 8
<212> TYPE: PRT
<213> ORGANISM: Homo sapiens

<400> SEQUENCE: 151

Phe Ser Tyr Cys Ser Lys Asp Arg
1               5

<210> SEQ ID NO 152
<211> LENGTH: 9
<212> TYPE: PRT
<213> ORGANISM: Homo sapiens

<400> SEQUENCE: 152

Met Ala Pro Pro Thr Gly Val Leu Ser
1               5

<210> SEQ ID NO 153
<211> LENGTH: 9
<212> TYPE: PRT
<213> ORGANISM: Homo sapiens

<400> SEQUENCE: 153

Leu Leu Leu Val Thr Ile Ala Gly Cys
1               5

<210> SEQ ID NO 154
<211> LENGTH: 9
<212> TYPE: PRT
<213> ORGANISM: Homo sapiens

<400> SEQUENCE: 154

Ser Glu Gly Arg Thr Tyr Ser Asn Ala
1               5

<210> SEQ ID NO 155
<211> LENGTH: 9
<212> TYPE: PRT
<213> ORGANISM: Homo sapiens

<400> SEQUENCE: 155

Pro Asn Leu Glu Thr Thr Arg Ile Met
1               5

<210> SEQ ID NO 156

```
<211> LENGTH: 9
<212> TYPE: PRT
<213> ORGANISM: Homo sapiens

<400> SEQUENCE: 156

Asn Leu Glu Thr Thr Arg Ile Met Arg
1               5

<210> SEQ ID NO 157
<211> LENGTH: 9
<212> TYPE: PRT
<213> ORGANISM: Homo sapiens

<400> SEQUENCE: 157

Arg Val Ser His Thr Phe Pro Val Val
1               5

<210> SEQ ID NO 158
<211> LENGTH: 9
<212> TYPE: PRT
<213> ORGANISM: Homo sapiens

<400> SEQUENCE: 158

Val Val Asp Cys Thr Ala Ala Cys Cys
1               5

<210> SEQ ID NO 159
<211> LENGTH: 9
<212> TYPE: PRT
<213> ORGANISM: Homo sapiens

<400> SEQUENCE: 159

Arg Ser Tyr Leu Thr Phe Val Leu Arg
1               5

<210> SEQ ID NO 160
<211> LENGTH: 9
<212> TYPE: PRT
<213> ORGANISM: Homo sapiens

<400> SEQUENCE: 160

Ser Ala Glu Tyr Thr Asp Trp Gly Leu
1               5

<210> SEQ ID NO 161
<211> LENGTH: 9
<212> TYPE: PRT
<213> ORGANISM: Homo sapiens

<400> SEQUENCE: 161

Val Pro Ala Glu Thr Gln Gln Asp Pro
1               5

<210> SEQ ID NO 162
<211> LENGTH: 9
<212> TYPE: PRT
<213> ORGANISM: Homo sapiens

<400> SEQUENCE: 162

Glu Ser Ala Ser Thr Pro Ala Pro Lys
1               5

<210> SEQ ID NO 163
<211> LENGTH: 9
<212> TYPE: PRT
<213> ORGANISM: Homo sapiens
```

<400> SEQUENCE: 163

Leu Pro Leu Pro Thr Thr Pro Ser Ser
1               5

<210> SEQ ID NO 164
<211> LENGTH: 9
<212> TYPE: PRT
<213> ORGANISM: Homo sapiens

<400> SEQUENCE: 164

Pro Leu Pro Thr Thr Pro Ser Ser Gly
1               5

<210> SEQ ID NO 165
<211> LENGTH: 9
<212> TYPE: PRT
<213> ORGANISM: Homo sapiens

<400> SEQUENCE: 165

Leu Ser Ser Val Thr Val Glu Lys Ser
1               5

<210> SEQ ID NO 166
<211> LENGTH: 9
<212> TYPE: PRT
<213> ORGANISM: Homo sapiens

<400> SEQUENCE: 166

Ser Pro Val Leu Thr Val Thr Pro Gly
1               5

<210> SEQ ID NO 167
<211> LENGTH: 9
<212> TYPE: PRT
<213> ORGANISM: Homo sapiens

<400> SEQUENCE: 167

Val Leu Thr Val Thr Pro Gly Ser Thr
1               5

<210> SEQ ID NO 168
<211> LENGTH: 9
<212> TYPE: PRT
<213> ORGANISM: Homo sapiens

<400> SEQUENCE: 168

Thr Pro Gly Ser Thr Glu His Ser Ile
1               5

<210> SEQ ID NO 169
<211> LENGTH: 9
<212> TYPE: PRT
<213> ORGANISM: Homo sapiens

<400> SEQUENCE: 169

His Ser Ile Pro Thr Pro Pro Thr Ser
1               5

<210> SEQ ID NO 170
<211> LENGTH: 9
<212> TYPE: PRT
<213> ORGANISM: Homo sapiens

<400> SEQUENCE: 170

-continued

Pro Thr Pro Pro Thr Ser Ala Ala Pro
1               5

<210> SEQ ID NO 171
<211> LENGTH: 9
<212> TYPE: PRT
<213> ORGANISM: Homo sapiens

<400> SEQUENCE: 171

Pro Ser Glu Ser Thr Pro Ser Glu Leu
1               5

<210> SEQ ID NO 172
<211> LENGTH: 9
<212> TYPE: PRT
<213> ORGANISM: Homo sapiens

<400> SEQUENCE: 172

Pro Ile Ser Pro Thr Thr Ala Pro Arg
1               5

<210> SEQ ID NO 173
<211> LENGTH: 9
<212> TYPE: PRT
<213> ORGANISM: Homo sapiens

<400> SEQUENCE: 173

Ile Ser Pro Thr Thr Ala Pro Arg Thr
1               5

<210> SEQ ID NO 174
<211> LENGTH: 9
<212> TYPE: PRT
<213> ORGANISM: Homo sapiens

<400> SEQUENCE: 174

Thr Ala Pro Arg Thr Val Lys Glu Leu
1               5

<210> SEQ ID NO 175
<211> LENGTH: 9
<212> TYPE: PRT
<213> ORGANISM: Homo sapiens

<400> SEQUENCE: 175

Val Lys Glu Leu Thr Val Ser Ala Gly
1               5

<210> SEQ ID NO 176
<211> LENGTH: 9
<212> TYPE: PRT
<213> ORGANISM: Homo sapiens

<400> SEQUENCE: 176

Asn Leu Ile Ile Thr Leu Pro Asp Asn
1               5

<210> SEQ ID NO 177
<211> LENGTH: 9
<212> TYPE: PRT
<213> ORGANISM: Homo sapiens

<400> SEQUENCE: 177

Pro Pro Val Glu Thr Thr Tyr Asn Tyr
1               5

```
<210> SEQ ID NO 178
<211> LENGTH: 9
<212> TYPE: PRT
<213> ORGANISM: Homo sapiens

<400> SEQUENCE: 178

Pro Val Glu Thr Thr Tyr Asn Tyr Glu
1               5

<210> SEQ ID NO 179
<211> LENGTH: 9
<212> TYPE: PRT
<213> ORGANISM: Homo sapiens

<400> SEQUENCE: 179

Ile Ser His Pro Thr Asp Tyr Gln Gly
1               5

<210> SEQ ID NO 180
<211> LENGTH: 9
<212> TYPE: PRT
<213> ORGANISM: Homo sapiens

<400> SEQUENCE: 180

Gly His Lys Gln Thr Leu Asn Leu Ser
1               5

<210> SEQ ID NO 181
<211> LENGTH: 9
<212> TYPE: PRT
<213> ORGANISM: Homo sapiens

<400> SEQUENCE: 181

Val Phe Lys Val Thr Val Ser Ser Glu
1               5

<210> SEQ ID NO 182
<211> LENGTH: 9
<212> TYPE: PRT
<213> ORGANISM: Homo sapiens

<400> SEQUENCE: 182

Phe Val Asn Val Thr Val Lys Pro Ala
1               5

<210> SEQ ID NO 183
<211> LENGTH: 9
<212> TYPE: PRT
<213> ORGANISM: Homo sapiens

<400> SEQUENCE: 183

Leu Gln Glu Leu Thr Leu Pro Leu Thr
1               5

<210> SEQ ID NO 184
<211> LENGTH: 9
<212> TYPE: PRT
<213> ORGANISM: Homo sapiens

<400> SEQUENCE: 184

Thr Leu Pro Leu Thr Ser Ala Leu Ile
1               5

<210> SEQ ID NO 185
<211> LENGTH: 9
```

```
<212> TYPE: PRT
<213> ORGANISM: Homo sapiens

<400> SEQUENCE: 185

Gly Ser Gln Ser Thr Asp Asp Thr Glu
1               5

<210> SEQ ID NO 186
<211> LENGTH: 9
<212> TYPE: PRT
<213> ORGANISM: Homo sapiens

<400> SEQUENCE: 186

Ser Thr Asp Asp Thr Glu Ile Val Ser
1               5

<210> SEQ ID NO 187
<211> LENGTH: 9
<212> TYPE: PRT
<213> ORGANISM: Homo sapiens

<400> SEQUENCE: 187

Ile Glu Glu Lys Thr Ser Val Asp Ser
1               5

<210> SEQ ID NO 188
<211> LENGTH: 9
<212> TYPE: PRT
<213> ORGANISM: Homo sapiens

<400> SEQUENCE: 188

Arg Leu Thr Val Thr Asp Ser Asp Gly
1               5

<210> SEQ ID NO 189
<211> LENGTH: 9
<212> TYPE: PRT
<213> ORGANISM: Homo sapiens

<400> SEQUENCE: 189

Ser Asp Gly Ala Thr Asn Ser Thr Thr
1               5

<210> SEQ ID NO 190
<211> LENGTH: 9
<212> TYPE: PRT
<213> ORGANISM: Homo sapiens

<400> SEQUENCE: 190

Ala Thr Asn Ser Thr Thr Ala Ala Leu
1               5

<210> SEQ ID NO 191
<211> LENGTH: 9
<212> TYPE: PRT
<213> ORGANISM: Homo sapiens

<400> SEQUENCE: 191

Thr Asn Ser Thr Thr Ala Ala Leu Ile
1               5

<210> SEQ ID NO 192
<211> LENGTH: 9
<212> TYPE: PRT
<213> ORGANISM: Homo sapiens
```

```
<400> SEQUENCE: 192

Gly Pro Asn His Thr Ile Thr Leu Pro
1               5

<210> SEQ ID NO 193
<211> LENGTH: 9
<212> TYPE: PRT
<213> ORGANISM: Homo sapiens

<400> SEQUENCE: 193

Asn His Thr Ile Thr Leu Pro Gln Asn
1               5

<210> SEQ ID NO 194
<211> LENGTH: 9
<212> TYPE: PRT
<213> ORGANISM: Homo sapiens

<400> SEQUENCE: 194

Gln Asn Ser Ile Thr Leu Asn Gly Asn
1               5

<210> SEQ ID NO 195
<211> LENGTH: 9
<212> TYPE: PRT
<213> ORGANISM: Homo sapien

<400> SEQUENCE: 195

Gln Gly Val Gln Thr Pro Tyr Leu His
1               5

<210> SEQ ID NO 196
<211> LENGTH: 9
<212> TYPE: PRT
<213> ORGANISM: Homo sapiens

<400> SEQUENCE: 196

Glu Gly Asp Tyr Thr Phe Gln Leu Lys
1               5

<210> SEQ ID NO 197
<211> LENGTH: 9
<212> TYPE: PRT
<213> ORGANISM: Homo sapiens

<400> SEQUENCE: 197

Gln Leu Lys Val Thr Asp Ser Ser Arg
1               5

<210> SEQ ID NO 198
<211> LENGTH: 9
<212> TYPE: PRT
<213> ORGANISM: Homo sapiens

<400> SEQUENCE: 198

Arg Gln Gln Ser Thr Ala Val Val Thr
1               5

<210> SEQ ID NO 199
<211> LENGTH: 9
<212> TYPE: PRT
<213> ORGANISM: Homo sapiens

<400> SEQUENCE: 199

Thr Ala Val Val Thr Val Ile Val Gln
```

<210> SEQ ID NO 200
<211> LENGTH: 9
<212> TYPE: PRT
<213> ORGANISM: Homo sapiens

<400> SEQUENCE: 200

Val Glu Ser Ala Thr Leu Asp Gly Ser
1               5

<210> SEQ ID NO 201
<211> LENGTH: 9
<212> TYPE: PRT
<213> ORGANISM: Homo sapiens

<400> SEQUENCE: 201

Lys Ala Ile Ala Thr Val Thr Gly Leu
1               5

<210> SEQ ID NO 202
<211> LENGTH: 9
<212> TYPE: PRT
<213> ORGANISM: Homo sapiens

<400> SEQUENCE: 202

Ile Ala Thr Val Thr Gly Leu Gln Val
1               5

<210> SEQ ID NO 203
<211> LENGTH: 9
<212> TYPE: PRT
<213> ORGANISM: Homo sapiens

<400> SEQUENCE: 203

Leu Gln Val Gly Thr Tyr His Phe Arg
1               5

<210> SEQ ID NO 204
<211> LENGTH: 9
<212> TYPE: PRT
<213> ORGANISM: Homo sapiens

<400> SEQUENCE: 204

His Phe Arg Leu Thr Val Lys Asp Gln
1               5

<210> SEQ ID NO 205
<211> LENGTH: 9
<212> TYPE: PRT
<213> ORGANISM: Homo sapiens

<400> SEQUENCE: 205

Gly Leu Ser Ser Thr Ser Thr Leu Thr
1               5

<210> SEQ ID NO 206
<211> LENGTH: 9
<212> TYPE: PRT
<213> ORGANISM: Homo sapiens

<400> SEQUENCE: 206

Ser Ser Thr Ser Thr Leu Thr Val Ala
1               5

```
<210> SEQ ID NO 207
<211> LENGTH: 9
<212> TYPE: PRT
<213> ORGANISM: Homo sapiens

<400> SEQUENCE: 207

Thr Ser Thr Leu Thr Val Ala Val Lys
 1               5

<210> SEQ ID NO 208
<211> LENGTH: 9
<212> TYPE: PRT
<213> ORGANISM: Homo sapiens

<400> SEQUENCE: 208

Asn Asn Ser Ile Thr Leu Asp Gly Ser
 1               5

<210> SEQ ID NO 209
<211> LENGTH: 9
<212> TYPE: PRT
<213> ORGANISM: Homo sapiens

<400> SEQUENCE: 209

Gly Ser Arg Ser Thr Asp Asp Gln Arg
 1               5

<210> SEQ ID NO 210
<211> LENGTH: 9
<212> TYPE: PRT
<213> ORGANISM: Homo sapiens

<400> SEQUENCE: 210

Ala Leu Gln Leu Thr Asn Leu Val Glu
 1               5

<210> SEQ ID NO 211
<211> LENGTH: 9
<212> TYPE: PRT
<213> ORGANISM: Homo sapiens

<400> SEQUENCE: 211

Glu Gly Val Tyr Thr Phe His Leu Arg
 1               5

<210> SEQ ID NO 212
<211> LENGTH: 9
<212> TYPE: PRT
<213> ORGANISM: Homo sapiens

<400> SEQUENCE: 212

His Leu Arg Val Thr Asp Ser Gln Gly
 1               5

<210> SEQ ID NO 213
<211> LENGTH: 9
<212> TYPE: PRT
<213> ORGANISM: Homo sapiens

<400> SEQUENCE: 213

Gly Ala Ser Asp Thr Asp Thr Ala Thr
 1               5

<210> SEQ ID NO 214
<211> LENGTH: 9
<212> TYPE: PRT
```

```
<213> ORGANISM: Homo sapiens

<400> SEQUENCE: 214

Ser Asp Thr Asp Thr Ala Thr Val Glu
1               5

<210> SEQ ID NO 215
<211> LENGTH: 9
<212> TYPE: PRT
<213> ORGANISM: Homo sapiens

<400> SEQUENCE: 215

Thr Asp Thr Ala Thr Val Glu Val Gln
1               5

<210> SEQ ID NO 216
<211> LENGTH: 9
<212> TYPE: PRT
<213> ORGANISM: Homo sapiens

<400> SEQUENCE: 216

Leu Val Glu Leu Thr Leu Gln Val Gly
1               5

<210> SEQ ID NO 217
<211> LENGTH: 9
<212> TYPE: PRT
<213> ORGANISM: Homo sapiens

<400> SEQUENCE: 217

Val Gly Gln Leu Thr Glu Gln Arg Lys
1               5

<210> SEQ ID NO 218
<211> LENGTH: 9
<212> TYPE: PRT
<213> ORGANISM: Homo sapiens

<400> SEQUENCE: 218

Gln Arg Lys Asp Thr Leu Val Arg Gln
1               5

<210> SEQ ID NO 219
<211> LENGTH: 9
<212> TYPE: PRT
<213> ORGANISM: Homo sapiens

<400> SEQUENCE: 219

Ser Asp Leu Ser Thr Val Ile Val Phe
1               5

<210> SEQ ID NO 220
<211> LENGTH: 9
<212> TYPE: PRT
<213> ORGANISM: Homo sapiens

<400> SEQUENCE: 220

Leu Arg Val Asp Thr Ala Gly Cys Leu
1               5

<210> SEQ ID NO 221
<211> LENGTH: 9
<212> TYPE: PRT
<213> ORGANISM: Homo sapiens

<400> SEQUENCE: 221
```

Cys Asp Pro Leu Thr Lys Arg Cys Ile
1               5

<210> SEQ ID NO 222
<211> LENGTH: 9
<212> TYPE: PRT
<213> ORGANISM: Homo sapiens

<400> SEQUENCE: 222

Ile Phe Tyr Val Thr Val Leu Ala Phe
1               5

<210> SEQ ID NO 223
<211> LENGTH: 9
<212> TYPE: PRT
<213> ORGANISM: Homo sapiens

<400> SEQUENCE: 223

Val Leu Ala Phe Thr Leu Ile Val Leu
1               5

<210> SEQ ID NO 224
<211> LENGTH: 9
<212> TYPE: PRT
<213> ORGANISM: Homo sapiens

<400> SEQUENCE: 224

Leu Ile Val Leu Thr Gly Gly Phe Thr
1               5

<210> SEQ ID NO 225
<211> LENGTH: 9
<212> TYPE: PRT
<213> ORGANISM: Homo sapiens

<400> SEQUENCE: 225

Thr Gly Gly Phe Thr Trp Leu Cys Ile
1               5

<210> SEQ ID NO 226
<211> LENGTH: 9
<212> TYPE: PRT
<213> ORGANISM: Homo sapiens

<400> SEQUENCE: 226

Arg Gln Lys Arg Thr Lys Ile Arg Lys
1               5

<210> SEQ ID NO 227
<211> LENGTH: 9
<212> TYPE: PRT
<213> ORGANISM: Homo sapiens

<400> SEQUENCE: 227

Ile Arg Lys Lys Thr Lys Tyr Thr Ile
1               5

<210> SEQ ID NO 228
<211> LENGTH: 9
<212> TYPE: PRT
<213> ORGANISM: Homo sapiens

<400> SEQUENCE: 228

Lys Thr Lys Tyr Thr Ile Leu Asp Asn
1               5

<210> SEQ ID NO 229
<211> LENGTH: 9
<212> TYPE: PRT
<213> ORGANISM: Homo sapiens

<400> SEQUENCE: 229

Lys His Arg Ser Thr Glu His Asn Ser
1               5

<210> SEQ ID NO 230
<211> LENGTH: 9
<212> TYPE: PRT
<213> ORGANISM: Homo sapiens

<400> SEQUENCE: 230

Ser Asp Gln Asp Thr Ile Phe Ser Arg
1               5

<210> SEQ ID NO 231
<211> LENGTH: 9
<212> TYPE: PRT
<213> ORGANISM: Homo sapiens

<400> SEQUENCE: 231

Glu Gly Arg Thr Tyr Ser Asn Ala Val
1               5

<210> SEQ ID NO 232
<211> LENGTH: 9
<212> TYPE: PRT
<213> ORGANISM: Homo sapiens

<400> SEQUENCE: 232

Glu Gly Arg Cys Tyr Leu Val Ser Cys
1               5

<210> SEQ ID NO 233
<211> LENGTH: 9
<212> TYPE: PRT
<213> ORGANISM: Homo sapiens

<400> SEQUENCE: 233

Pro Ile Arg Ser Tyr Leu Thr Phe Val
1               5

<210> SEQ ID NO 234
<211> LENGTH: 9
<212> TYPE: PRT
<213> ORGANISM: Homo sapiens

<400> SEQUENCE: 234

Gln Leu Leu Asp Tyr Gly Asp Met Met
1               5

<210> SEQ ID NO 235
<211> LENGTH: 9
<212> TYPE: PRT
<213> ORGANISM: Homo sapiens

<400> SEQUENCE: 235

Glu Met Ser Glu Tyr Ser Asp Asp Tyr
1               5

<210> SEQ ID NO 236

```
<211> LENGTH: 9
<212> TYPE: PRT
<213> ORGANISM: Homo sapiens

<400> SEQUENCE: 236

Tyr Ser Asp Asp Tyr Arg Glu Leu Glu
1               5

<210> SEQ ID NO 237
<211> LENGTH: 9
<212> TYPE: PRT
<213> ORGANISM: Homo sapiens

<400> SEQUENCE: 237

Gly Ser Ala Glu Tyr Thr Asp Trp Gly
1               5

<210> SEQ ID NO 238
<211> LENGTH: 9
<212> TYPE: PRT
<213> ORGANISM: Homo sapiens

<400> SEQUENCE: 238

Pro Glu Leu His Tyr Leu Asn Glu Ser
1               5

<210> SEQ ID NO 239
<211> LENGTH: 9
<212> TYPE: PRT
<213> ORGANISM: Homo sapiens

<400> SEQUENCE: 239

Val Glu Thr Thr Tyr Asn Tyr Glu Trp
1               5

<210> SEQ ID NO 240
<211> LENGTH: 9
<212> TYPE: PRT
<213> ORGANISM: Homo sapiens

<400> SEQUENCE: 240

Thr Thr Tyr Asn Tyr Glu Trp Asn Leu
1               5

<210> SEQ ID NO 241
<211> LENGTH: 9
<212> TYPE: PRT
<213> ORGANISM: Homo sapiens

<400> SEQUENCE: 241

His Pro Thr Asp Tyr Gln Gly Glu Ile
1               5

<210> SEQ ID NO 242
<211> LENGTH: 9
<212> TYPE: PRT
<213> ORGANISM: Homo sapiens

<400> SEQUENCE: 242

Ser Val Gly Leu Tyr Val Phe Lys Val
1               5

<210> SEQ ID NO 243
<211> LENGTH: 9
<212> TYPE: PRT
<213> ORGANISM: Homo sapiens
```

<400> SEQUENCE: 243

Glu Ile Val Ser Tyr His Trp Glu Glu
1               5

<210> SEQ ID NO 244
<211> LENGTH: 9
<212> TYPE: PRT
<213> ORGANISM: Homo sapiens

<400> SEQUENCE: 244

Asp Pro Gly Asn Tyr Ser Phe Arg Leu
1               5

<210> SEQ ID NO 245
<211> LENGTH: 9
<212> TYPE: PRT
<213> ORGANISM: Homo sapiens

<400> SEQUENCE: 245

Asn Ala Val Asp Tyr Pro Pro Val Ala
1               5

<210> SEQ ID NO 246
<211> LENGTH: 9
<212> TYPE: PRT
<213> ORGANISM: Homo sapiens

<400> SEQUENCE: 246

Gln Ile Val Leu Tyr Glu Trp Ser Leu
1               5

<210> SEQ ID NO 247
<211> LENGTH: 9
<212> TYPE: PRT
<213> ORGANISM: Homo sapiens

<400> SEQUENCE: 247

Val Gln Thr Pro Tyr Leu His Leu Ser
1               5

<210> SEQ ID NO 248
<211> LENGTH: 9
<212> TYPE: PRT
<213> ORGANISM: Homo sapiens

<400> SEQUENCE: 248

Gln Glu Gly Asp Tyr Thr Phe Gln Leu
1               5

<210> SEQ ID NO 249
<211> LENGTH: 9
<212> TYPE: PRT
<213> ORGANISM: Homo sapiens

<400> SEQUENCE: 249

Gly Ile Val Phe Tyr His Trp Glu His
1               5

<210> SEQ ID NO 250
<211> LENGTH: 9
<212> TYPE: PRT
<213> ORGANISM: Homo sapiens

<400> SEQUENCE: 250

Gln Val Gly Thr Tyr His Phe Arg Leu
1               5

<210> SEQ ID NO 251
<211> LENGTH: 9
<212> TYPE: PRT
<213> ORGANISM: Homo sapiens

<400> SEQUENCE: 251

Arg Ile Val Ser Tyr Leu Trp Ile Arg
1               5

<210> SEQ ID NO 252
<211> LENGTH: 9
<212> TYPE: PRT
<213> ORGANISM: Homo sapiens

<400> SEQUENCE: 252

Val Glu Gly Val Tyr Thr Phe His Leu
1               5

<210> SEQ ID NO 253
<211> LENGTH: 9
<212> TYPE: PRT
<213> ORGANISM: Homo sapiens

<400> SEQUENCE: 253

Val Ile Val Phe Tyr Val Gln Ser Arg
1               5

<210> SEQ ID NO 254
<211> LENGTH: 9
<212> TYPE: PRT
<213> ORGANISM: Homo sapiens

<400> SEQUENCE: 254

Leu Ile Gln Arg Tyr Ile Trp Asp Gly
1               5

<210> SEQ ID NO 255
<211> LENGTH: 9
<212> TYPE: PRT
<213> ORGANISM: Homo sapiens

<400> SEQUENCE: 255

Trp Ser Ile Phe Tyr Val Thr Val Leu
1               5

<210> SEQ ID NO 256
<211> LENGTH: 9
<212> TYPE: PRT
<213> ORGANISM: Homo sapiens

<400> SEQUENCE: 256

Lys Lys Thr Lys Tyr Thr Ile Leu Asp
1               5

<210> SEQ ID NO 257
<211> LENGTH: 9
<212> TYPE: PRT
<213> ORGANISM: Homo sapiens

<400> SEQUENCE: 257

Leu Arg Pro Lys Tyr Gly Ile Lys His
1               5

```
<210> SEQ ID NO 258
<211> LENGTH: 9
<212> TYPE: PRT
<213> ORGANISM: Homo sapiens

<400> SEQUENCE: 258

Ala Ser Phe Ser Tyr Cys Ser Lys Asp
1               5

<210> SEQ ID NO 259
<211> LENGTH: 1072
<212> TYPE: PRT
<213> ORGANISM: Homo sapiens

<400> SEQUENCE: 259

Met Ala Pro Pro Thr Gly Val Leu Ser Ser Leu Leu Leu Val Thr
1               5                   10                  15

Ile Ala Gly Cys Ala Arg Lys Gln Cys Ser Glu Gly Arg Thr Tyr Ser
                20                  25                  30

Asn Ala Val Ile Ser Pro Asn Leu Glu Thr Thr Arg Ile Met Arg Val
            35                  40                  45

Ser His Thr Phe Pro Val Val Asp Cys Thr Ala Ala Cys Cys Asp Leu
50                  55                  60

Ser Ser Cys Asp Leu Ala Trp Trp Phe Glu Gly Arg Cys Tyr Leu Val
65                  70                  75                  80

Ser Cys Pro His Lys Glu Asn Cys Glu Pro Lys Lys Met Gly Pro Ile
                85                  90                  95

Arg Ser Tyr Leu Thr Phe Val Leu Arg Pro Val Gln Arg Pro Ala Gln
                100                 105                 110

Leu Leu Asp Tyr Gly Asp Met Met Leu Asn Arg Gly Pro Ser Gly
                115                 120                 125

Ile Trp Gly Asp Ser Pro Glu Asp Ile Arg Lys Asp Leu Pro Phe Leu
            130                 135                 140

Gly Lys Asp Trp Gly Leu Glu Glu Met Ser Glu Tyr Ser Asp Asp Tyr
145                 150                 155                 160

Arg Glu Leu Glu Lys Asp Leu Leu Gln Pro Ser Gly Lys Gln Glu Pro
                165                 170                 175

Arg Gly Ser Ala Glu Tyr Thr Asp Trp Gly Leu Leu Pro Gly Ser Glu
                180                 185                 190

Gly Ala Phe Asn Ser Ser Val Gly Asp Ser Pro Ala Val Pro Ala Glu
                195                 200                 205

Thr Gln Gln Asp Pro Glu Leu His Tyr Leu Asn Glu Ser Ala Ser Thr
210                 215                 220

Pro Ala Pro Lys Leu Pro Glu Arg Ser Val Leu Leu Pro Leu Pro Thr
225                 230                 235                 240

Thr Pro Ser Ser Gly Glu Val Leu Glu Lys Glu Lys Ala Ser Gln Leu
                245                 250                 255

Gln Glu Gln Ser Ser Asn Ser Ser Gly Lys Glu Val Leu Met Pro Ser
                260                 265                 270

His Ser Leu Pro Pro Ala Ser Leu Glu Leu Ser Ser Val Thr Val Glu
                275                 280                 285

Lys Ser Pro Val Leu Thr Val Thr Pro Gly Ser Thr Glu His Ser Ile
                290                 295                 300

Pro Thr Pro Pro Thr Ser Ala Ala Pro Ser Glu Ser Thr Pro Ser Glu
305                 310                 315                 320

Leu Pro Ile Ser Pro Thr Thr Ala Pro Arg Thr Val Lys Glu Leu Thr
```

```
                   325                 330                 335
Val Ser Ala Gly Asp Asn Leu Ile Ile Thr Leu Pro Asp Asn Glu Val
                340                 345                 350

Glu Leu Lys Ala Phe Val Ala Pro Ala Pro Val Glu Thr Thr Tyr
            355                 360                 365

Asn Tyr Glu Trp Asn Leu Ile Ser His Pro Thr Asp Tyr Gln Gly Glu
            370                 375                 380

Ile Lys Gln Gly His Lys Gln Thr Leu Asn Leu Ser Gln Leu Ser Val
385                 390                 395                 400

Gly Leu Tyr Val Phe Lys Val Thr Val Ser Ser Glu Asn Ala Phe Gly
                405                 410                 415

Glu Gly Phe Val Asn Val Thr Val Lys Pro Ala Arg Arg Val Asn Leu
                420                 425                 430

Pro Pro Val Ala Val Ser Pro Gln Leu Gln Glu Leu Thr Leu Pro
            435                 440                 445

Leu Thr Ser Ala Leu Ile Asp Gly Ser Gln Ser Thr Asp Asp Thr Glu
    450                 455                 460

Ile Val Ser Tyr His Trp Glu Glu Ile Asn Gly Pro Phe Ile Glu Glu
465                 470                 475                 480

Lys Thr Ser Val Asp Ser Pro Val Leu Arg Leu Ser Asn Leu Asp Pro
            485                 490                 495

Gly Asn Tyr Ser Phe Arg Leu Thr Val Thr Asp Ser Asp Gly Ala Thr
                500                 505                 510

Asn Ser Thr Thr Ala Ala Leu Ile Val Asn Asn Ala Val Asp Tyr Pro
    515                 520                 525

Pro Val Ala Asn Ala Gly Pro Asn His Thr Ile Thr Leu Pro Gln Asn
            530                 535                 540

Ser Ile Thr Leu Asn Gly Asn Gln Ser Ser Asp Asp His Gln Ile Val
545                 550                 555                 560

Leu Tyr Glu Trp Ser Leu Gly Pro Gly Ser Glu Gly Lys His Val Val
                565                 570                 575

Met Gln Gly Val Gln Thr Pro Tyr Leu His Leu Ser Ala Met Gln Glu
            580                 585                 590

Gly Asp Tyr Thr Phe Gln Leu Lys Val Thr Asp Ser Ser Arg Gln Gln
            595                 600                 605

Ser Thr Ala Val Val Thr Val Ile Val Gln Pro Glu Asn Asn Arg Pro
    610                 615                 620

Pro Val Ala Val Ala Gly Pro Asp Lys Glu Leu Ile Phe Pro Val Glu
625                 630                 635                 640

Ser Ala Thr Leu Asp Gly Ser Ser Ser Asp Asp His Gly Ile Val
            645                 650                 655

Phe Tyr His Trp Glu His Val Arg Gly Pro Ser Ala Val Glu Met Glu
            660                 665                 670

Asn Ile Asp Lys Ala Ile Ala Thr Val Thr Gly Leu Gln Val Gly Thr
            675                 680                 685

Tyr His Phe Arg Leu Thr Val Lys Asp Gln Gln Gly Leu Ser Ser Thr
    690                 695                 700

Ser Thr Leu Thr Val Ala Val Lys Lys Glu Asn Asn Ser Pro Pro Arg
705                 710                 715                 720

Ala Arg Ala Gly Gly Arg His Val Leu Val Leu Pro Asn Asn Ser Ile
                725                 730                 735

Thr Leu Asp Gly Ser Arg Ser Thr Asp Asp Gln Arg Ile Val Ser Tyr
            740                 745                 750
```

```
Leu Trp Ile Arg Asp Gly Gln Ser Pro Ala Ala Gly Asp Val Ile Asp
        755                 760                 765

Gly Ser Asp His Ser Val Ala Leu Gln Leu Thr Asn Leu Val Glu Gly
    770                 775                 780

Val Tyr Thr Phe His Leu Arg Val Thr Asp Ser Gln Gly Ala Ser Asp
785                 790                 795                 800

Thr Asp Thr Ala Thr Val Glu Val Gln Pro Asp Pro Arg Lys Ser Gly
                805                 810                 815

Leu Val Glu Leu Thr Leu Gln Val Gly Val Gly Leu Thr Glu Gln
            820                 825                 830

Arg Lys Asp Thr Leu Val Arg Gln Leu Ala Val Leu Leu Asn Val Leu
        835                 840                 845

Asp Ser Asp Ile Lys Val Gln Lys Ile Arg Ala His Ser Asp Leu Ser
    850                 855                 860

Thr Val Ile Val Phe Tyr Val Gln Ser Arg Pro Pro Phe Lys Val Leu
865                 870                 875                 880

Lys Ala Ala Glu Val Ala Arg Asn Leu His Met Arg Leu Ser Lys Glu
                885                 890                 895

Lys Ala Asp Phe Leu Leu Phe Lys Val Leu Arg Val Asp Thr Ala Gly
            900                 905                 910

Cys Leu Leu Lys Cys Ser Gly His Gly His Cys Asp Pro Leu Thr Lys
        915                 920                 925

Arg Cys Ile Cys Ser His Leu Trp Met Glu Asn Leu Ile Gln Arg Tyr
    930                 935                 940

Ile Trp Asp Gly Glu Ser Asn Cys Glu Trp Ser Ile Phe Tyr Val Thr
945                 950                 955                 960

Val Leu Ala Phe Thr Leu Ile Val Leu Thr Gly Gly Phe Thr Trp Leu
                965                 970                 975

Cys Ile Cys Cys Cys Lys Arg Gln Lys Arg Thr Lys Ile Arg Lys Lys
            980                 985                 990

Thr Lys Tyr Thr Ile Leu Asp Asn Met Asp Glu Gln Glu Arg Met Glu
        995                 1000                1005

Leu Arg Pro Lys Tyr Gly Ile Lys His Arg Ser Thr Glu His Asn Ser
    1010                1015                1020

Ser Leu Met Val Ser Glu Ser Glu Phe Asp Ser Asp Gln Asp Thr Ile
1025                1030                1035                1040

Phe Ser Arg Glu Lys Met Glu Arg Gly Asn Pro Lys Val Ser Met Asn
                1045                1050                1055

Gly Ser Ile Arg Asn Gly Ala Ser Phe Ser Tyr Cys Ser Lys Asp Arg
            1060                1065                1070

<210> SEQ ID NO 260
<211> LENGTH: 17
<212> TYPE: PRT
<213> ORGANISM: Homo sapiens

<400> SEQUENCE: 260

Gly Leu Glu Glu Met Ser Glu Tyr Ala Asp Asp Tyr Arg Glu Leu Glu
1               5                   10                  15

Lys

<210> SEQ ID NO 261
<211> LENGTH: 19
<212> TYPE: PRT
<213> ORGANISM: Homo sapiens

<400> SEQUENCE: 261
```

Trp Gly Leu Glu Glu Met Ser Glu Tyr Ala Asp Asp Tyr Arg Glu Leu
1               5                   10                  15

Glu Lys Asp

<210> SEQ ID NO 262
<211> LENGTH: 29
<212> TYPE: PRT
<213> ORGANISM: Homo sapiens

<400> SEQUENCE: 262

Phe Leu Gly Lys Asp Trp Gly Leu Glu Glu Met Ser Glu Tyr Ala Asp
1               5                   10                  15

Asp Tyr Arg Glu Leu Glu Lys Asp Leu Leu Gln Pro Ser
            20                  25

<210> SEQ ID NO 263
<211> LENGTH: 18
<212> TYPE: PRT
<213> ORGANISM: Homo sapiens

<400> SEQUENCE: 263

Met Thr Arg Leu Gly Trp Pro Ser Pro Cys Cys Ala Arg Lys Gln Cys
1               5                   10                  15

Ser Glu

<210> SEQ ID NO 264
<211> LENGTH: 19
<212> TYPE: PRT
<213> ORGANISM: Homo sapiens

<400> SEQUENCE: 264

Met Thr Arg Leu Gly Trp Pro Ser Pro Cys Cys Ala Arg Lys Gln Cys
1               5                   10                  15

Ser Glu Gly

<210> SEQ ID NO 265
<211> LENGTH: 24
<212> TYPE: PRT
<213> ORGANISM: Homo sapiens

<400> SEQUENCE: 265

Met Thr Arg Leu Gly Trp Pro Ser Pro Cys Cys Ala Arg Lys Gln Cys
1               5                   10                  15

Ser Glu Gly Arg Thr Tyr Ser Asn
            20

<210> SEQ ID NO 266
<211> LENGTH: 17
<212> TYPE: PRT
<213> ORGANISM: Homo sapiens

<400> SEQUENCE: 266

Pro Glu Asp Ile Arg Lys Asp Leu Thr Phe Leu Gly Lys Asp Trp Gly
1               5                   10                  15

Leu

<210> SEQ ID NO 267
<211> LENGTH: 19
<212> TYPE: PRT
<213> ORGANISM: Homo sapiens

<400> SEQUENCE: 267

Ser Pro Glu Asp Ile Arg Lys Asp Leu Thr Phe Leu Gly Lys Asp Trp
 1               5                   10                  15

Gly Leu Glu

<210> SEQ ID NO 268
<211> LENGTH: 29
<212> TYPE: PRT
<213> ORGANISM: Homo sapiens

<400> SEQUENCE: 268

Gly Ile Trp Gly Asp Ser Pro Glu Asp Ile Arg Lys Asp Leu Thr Phe
 1               5                   10                  15

Leu Gly Lys Asp Trp Gly Leu Glu Glu Met Ser Glu Tyr
             20                  25

<210> SEQ ID NO 269
<211> LENGTH: 6991
<212> TYPE: DNA
<213> ORGANISM: Homo sapiens

<400> SEQUENCE: 269

```
gctgccgcgg gcggtgggcg gggatccccc gggggtgcaa ccttgctcca cctgtgctgc      60
cctcggcggg cctggctggc cccgcgcaga gcggcggcgg cgctcgctgt cactgccgga     120
ggtgagagcg cagcagtagc ttcagcctgt cttgggcttg gtccagattc gctcctctgg     180
ggctacgtcc cggggaagag gaagcgagga ttttgctggg gtggggctgt acctcttaac     240
agcaggtgcg cgcgcgaggg tgtgaacgtg tgtgtgtgtg tgtgtctgtg tgtgtgtgtg     300
taagacctgc gatgacgacg aggaggaaca agtgggacgg cgagtgatgc tcagggccag     360
cagcaacgca tggggcgagc ttcagtgtcg ccagcagtga ccacaggtac ggtatctact     420
tcccagagcg cctggccgag aaataggaaa gagggcagcc agtaggcagg ccaatacccca    480
acaaaagtag aatcgagacg ccctgagttc agaagttctt gaggccaaat ctggctccta     540
aaaaacatca aggaagcttg caccaaaact ctcttcaggg ccgcctcaga agcctgccat     600
cacccactgt gtggtgcaca atggcgcccc ccacaggtgt gctctcttca ttgctgctgc     660
tggtgacaat tgcagtttgc ttatggtgga tgcactcatg gcaaaaaaat cactggtgag     720
catcatttaa gaagacccat gactagactg ggctggccga gcccatgttg tgcccgtaag     780
cagtgcagcg aggggaggac atattccaat gcagtcattt cacctaactt ggaaaccacc     840
agaatcatgc gggtgtctca cacctcccct gtcgtagact gcacggccgc ttgctgtgac     900
ctgtccagct gtgacctggc ctggtggttc gagggccgct gctacctggt gagctgcccc     960
cacaaagaga actgtgagcc caagaagatg ggccccatca ggtcttatct cacttttgtg    1020
ctccggcctg ttcagaggcc tgcacagctg ctggactatg ggacatgat gctgaacagg     1080
ggctcccccct cggggatctg gggggactca cctgaggata tcagaaagga cttgcccttt    1140
ctaggcaaag attggggcct agaggagatg tctgagtact cagatgacta ccgggagctg    1200
gagaaggacc tcttgcaacc cagtggcaag caggagccca gggagtgc cgagtacacg      1260
gactggggcc tactgccggg cagcgagggg gccttcaact cctctgttgg agacagtcct    1320
gcggtgccag cggagacgca gcaggaccct gagctccatt acctgaatga gtcggcttca    1380
accctgccc caaaactccc tgagagaagt gtgttgcttc ccttgccgac tactccatct    1440
tcaggagagg tgttggagaa agaaaaggct tctcagctcc aggaacaatc cagcaacagc    1500
tctggaaaag aggttctaat gccttcccat agtcttcctc cggcaagcct ggagctcagc    1560
```

```
tcagtcaccg tggagaaaag cccagtgctc acagtcaccc cggggagtac agagcacagc   1620
atcccaacac ctcccactag cgcagccccc tctgagtcca ccccatctga gctacccata   1680
tctcctacca ctgctcccag gacagtgaaa gaacttacgg tatcggctgg agataaccta   1740
attataactt tacccgacaa tgaagttgaa ctgaaggcct tgttgcgcc agcgccacct    1800
gtagaaacaa cctacaacta tgaatggaat ttaataagcc accccacaga ctaccaaggt   1860
gaaataaaac aaggacacaa gcaaactctt aacctctctc aattgtccgt cggactttat   1920
gtcttcaaag tcactgtttc tagtgaaaac gcctttggag aaggatttgt caatgtcact   1980
gttaagcctg ccagaagagt caacctgcca cctgtagcag ttgtttctcc ccaactgcaa   2040
gagctcactt tgcctttgac gtcagccctc attgatggca gccaaagtac agatgatact   2100
gaaatagtga gttatcattg gaagaaaata acgggccct tcatagaaga gaagacttca    2160
gttgactctc ccgtcttacg cttgtctaac cttgatcctg gtaactatag tttcaggttg   2220
actgttacag actcggacgg agccactaac tctacaactg cagccctaat agtgaacaat   2280
gctgtggact acccaccagt tgctaatgca ggaccaaatc acaccataac tttgccccaa   2340
aactccatca ctttgaatgg aaaccagagc agtgacgatc accagattgt cctctatgag   2400
tggtccctgg gtcctgggag tgagggcaaa catgtggtca tgcagggagt acagacgcca   2460
taccttcatt tatctgcaat gcaggaagga gattatacat ttcagctgaa ggtgacagat   2520
tcttcaaggc aacagtctac tgctgtggtg actgtgattg tccagcctga aaacaataga   2580
cctcagtgg ctgtggccgg ccctgataaa gagctgatct cccagtgga aagtgctacc     2640
ctggatggga gcagcagcag cgatgaccac ggcattgtct tctaccactg ggagcacgtc   2700
agaggcccca gtgcagtgga gatggaaaat attgacaaag caatagccac tgtgactggt   2760
ctccaggtgg ggacctacca cttccgtttg acagtgaaag accagcaggg actgagcagc   2820
acgtccaccc tcactgtggc tgtgaagaag gaaaataata gtcctcccag agcccgggct   2880
ggtggcagac atgttcttgt gcttcccaat aattccatta ctttggatgg ttcaaggtct   2940
actgatgacc aaagaattgt gtcctatctg tggatccggg atggccagag tccagcagct   3000
ggagatgtca tcgatggctc tgaccacagt gtggctctgc agcttacgaa tctggtggag   3060
ggggtgtaca cttttccactt gcgagtcacc gacagtcagg gggcctcgga cacagacact   3120
gccactgtga agtgcagcc agaccctagg aagagtggcc tggtggagct gaccctgcag    3180
gttggtgttg ggcagctgac agagcagcgg aaggacaccc ttgtgaggca gctggctgtg   3240
ctgctgaacg tgctggactc ggacattaag gtccagaaga ttcgggccca ctcggatctc   3300
agcaccgtga ttgtgtttta tgtacagagc aggccgcctt tcaaggttct caaagctgct   3360
gaagtggccc gaaatctgca catgcggctc tcaaaggaga aggctgactt cttgcttttc   3420
aaggtcttga gggttgatac agcaggttgc cttctgaagt gttctggcca tggtcactgc   3480
gacccctca caaagcgctg catttgctct cacttatgga tggagaacct tatacagcgt   3540
tatatctggg atggagagag caactgtgag tggagtatat tctatgtgac agtgttggct   3600
tttactctta ttgtgctaac aggaggtttc acttggcttt gcatctgctg ctgcaaaaga   3660
caaaaaagga ctaaaatcag gaaaaaaaca aagtacacca tcctggataa catggatgaa   3720
caggaaagaa tggaactgag gcccaaatat ggtatcaagc accgaagcac agagcacaac   3780
tccagcctga tggtatccga gtctgagttt gacagtgacc aggacacaat cttcagccga   3840
gaaaagatgg agagagggaa tccaaaggtt ccatgaatg gttccatcag aaatggagct    3900
tccttcagtt attgctcaaa ggacagataa tggcgcagtt cattgtaaag tggaaggacc   3960
```

```
ccttgaatcc aagaccagtc agtgggagtt acagcacaaa acccactctt ttagaatagt    4020
tcattgacct tcttccccag tgggttagat gtgtatcccc acgtactaaa agaccggttt    4080
ttgaaggcac aaaacaaaaa ctttgctctt ttaactgaga tgcttgttaa tagaaataaa    4140
ggctgggtaa aactctaagg tatatactta aaagagtttt gagttttttgt agctggcaca    4200 atctcatatt aaagatgaac aacgatttct atctgtagaa ccttagagaa ggtgaatgaa    4260
acaaggtttt aaaaagggat gatttctgtc ttagccgctg tgattgcctc taaggaacag    4320
cattctaaac acggtttctc ttgtaggacc tgcagtcaga tggctgtgta tgttaaaata    4380
gcttgtctaa gaggcacggg ccatctgtgg aggtacggag tcttgcatgt agcaagcttt    4440
ctgtgctgac ggcaacactc gcacagtgcc aagccctcct ggttttaat tctgtgctat     4500 gtcaatggca gttttcatct ctctcaagaa agcagctgtt ggccattcaa gagctaagga    4560
agaatcgtat tctaaggact gaggcaatag aaaggggagg aggagcttaa tgccgtgcag    4620
gttgaaggta gcattgtaac attatctttt cttctctaa gaaaaactac actgactcct      4680
ctcggtgttg tttagcagta tagttctcta atgtaaacgg atccccagtt tacattaaat    4740
gcaatagaag tgattaattc attaagcatt tattatgttc tgtaggctgt gcgtttggac    4800
tgccatagat agggataacg actcagcaat tgtgtatata ttccaaaact ctgaaataca    4860
gtcagtctta acttggatgg cgtggttatg atactctggt ccccgacagg tactttccaa    4920 ataacttga catagatgta ttcacttcat atgtttaaaa atacatttaa gtttttctac       4980
cgaataaatc ttatttcaaa catgaaagac aattaaaaca ttcccaccca caaagcagta    5040
ctcccgagca attaactgga gttaattgta gcctgctacg ttgactggtt cagggtagtt    5100
ccccatccac ccttggtcct gaggctggtg gccttggtgg tgcccttggc atttttttgtg   5160 ggaagattag aatgagagat agaaccagtg ttgtggtacc aagtgtgagc acacctaaac    5220
aatatcctgt tgcacaatgc ttttttaaca catgggaaaa ctaggaatgc attgctgatg    5280
aagaagcaag gtatttaaac accagggcag gagtgccaga gaaaatgttt ccccatgggt    5340
tcttaaaaaa aattcagctt ttaggtgctt ttgtcatctc ccggagtatt catcctcatg    5400
ggaccatctt attttacttt attgtaattt actggggaaa ggcagaacta aaaagtgtgt    5460 catttttattt ttaaaataat tgctttgctt atgcctacac tttctgtata actagccaat  5520
tcaatactgt ctatagtgtt agaaggaaaa tgtgattttt ttttttaac cagtattgag     5580 cttcataagc ctagaatctg ccttatcagg tgaccagggt tatggttgtt tgcatgcaaa    5640
tgtgaatttc tggcataggg gacagcagcc caaatgtaaa gtcatcgggc gtaatgagga    5700
agaagggagt gaacatttac cgctttatgt acataacata tgcagtttac atactcattt    5760
gatccttata atcaaccttg aagaggagat actatcattc ttatgttgca gatagccctc    5820
tgaaggccca gagaggttaa gtaacttccc agaggtcatg gccaagaagt agtggctcca    5880
agaactgaat gcaaattttt taaactgtag agttctgctt tccactaaac aaagaactcc    5940
tgccttgatg gatggagggc aaattctggt ggaacttttg ggccacctga agttctatt     6000 cccaggacta gaggaatttc ttttaatgg atccagagag ccaaggtcag agggagagat    6060
ggcctgcata gtctcctgtg gatcacaccc gggccacccc tccctctagg tttacagtgg    6120
acttcttctg cccctcctcc ttttctgtcc ttggccatct cagcctggcc tctctgatcc    6180
ttccatcaca gaaggatctt gaatctctgg gaaatcaaac atcacagtag tgatcagaaa    6240
gtgagtcctg tcttgtcacc ccatttctca tcagaacaaa gcacgagatg gaatgaccaa    6300
ccagcattct tcatggtgga ctgcttatca ttgaggatct ttgggagata aagcacgcta    6360
```

| | |
|---|---|
| agagctctgg acagagaaaa acaggccta gaatatggga gtgggtgttt gtagggctca | 6420 |
| taggctaaca agcactttag ttgctggttt acattcaatg aaggaggatt catacccatg | 6480 |
| gcattacaag gctaagcatg tgtatgacta aggaactatc tgaaaaacat gcagcaaggt | 6540 |
| aagaaaatgt accactcaac aagccagtga tgccacctt tgtgcgcggg gaggagagtg | 6600 |
| actaccattg ttttttgtgt gacaaagcta tcatggacta ttttaatctt ggttttattg | 6660 |
| cttaaaatat attattttc cctatgtgtt gacaaggtat ttctaatatc acactattaa | 6720 |
| atatatgcac taatctaaat aaaggtgtct gtattttctg taatgcttat ttttagggg | 6780 |
| aaatttgttt tctttatgct tcagggtaga gggattccct tgagtatagg tcagcaaact | 6840 |
| ctggcctgca gcctgtgtgt gcacgcccca tgagccgaaa agtgggtctt atgttttcaa | 6900 |
| atggttaaaa ataaataaaa aaatttgaaa catgtgaact atatgacatt cagatttgtg | 6960 |
| ttcataaata aagttttatt ggaacatatc c | 6991 |

<210> SEQ ID NO 270
<211> LENGTH: 6797
<212> TYPE: DNA
<213> ORGANISM: Homo sapiens

<400> SEQUENCE: 270

| | |
|---|---|
| gctgccgcgg gcggtgggcg ggatccccc gggggtgcaa ccttgctcca cctgtgctgc | 60 |
| cctcggcggg cctggctggc cccgcgcaga gcggcggcgg cgctcgctgt cactgccgga | 120 |
| ggtgagagcg cagcagtagc ttcagcctgt cttgggcttg gtccagattc gctcctctgg | 180 |
| ggctacgtcc cggggaagag gaagcgagga ttttgctggg gtgggctgt acctcttaac | 240 |
| agcaggtgcg cgcgcgaggg tgtgaacgtg tgtgtgtgtg tgtgtctgtg tgtgtgtgtg | 300 |
| taagacctgc gatgacgacg aggaggaaca agtgggacgg cgagtgatgc tcagggccag | 360 |
| cagcaacgca tggggcgagc ttcagtgtcg ccagcagtga ccacagagtt cttgaggcca | 420 |
| aatctggctc ctaaaaaaca tcaaaggaag cttgcaccaa actctcttca gggccgcctc | 480 |
| agaagcctgc catcacccac tgtgtggtgc acaatggcgc cccccacagg tgtgctctct | 540 |
| tcattgctgc tgctggtgac aattgcaggt tggttgtgcc cgtaagcagt gcagcgaggg | 600 |
| gaggacatat tccaatgcag tcatttcacc taacttggaa accaccagaa tcatgcgggt | 660 |
| gtctcacacc ttccctgtcg tagactgcac ggccgcttgc tgtgacctgt ccagctgtga | 720 |
| cctggcctgg tggttcgagg gccgctgcta cctggtgagc tgccccaca aagagaactg | 780 |
| tgagcccaag aagatgggcc ccatcaggtc ttatctcact tttgtgctcc ggcctgttca | 840 |
| gaggcctgca cagctgctgg actatgggga catgatgctg aacaggggct cccctcggg | 900 |
| gatctggggg gactcacctg aggatatcag aaaggacttg cccttctag gcaaagattg | 960 |
| gggcctagag gagatgtctg agtactcaga tgactaccgg gagctggaga aggacctctt | 1020 |
| gcaacccagt ggcaagcagg agcccagagg gagtgccgag tacacggact ggggcctact | 1080 |
| gccgggcagc gagggggcct tcaactcctc tgttggagac agtcctgcgg tgccagcgga | 1140 |
| gacgcagcag gaccctgagc tccattacct gaatgagtcg gcttcaaccc ctgccccaaa | 1200 |
| actccctgag agaagtgtgt tgcttccctt gccgactact ccatcttcag gagaggtgtt | 1260 |
| ggagaaagaa aaggcttctc agctccagga acaatccagc aacagctctg gaaaagaggt | 1320 |
| tctaatgcct tcccatagtc ttcctccggc aagcctggag ctcagctcag tcaccgtgga | 1380 |
| gaaaagccca gtgctcacag tcaccccggg gagtacagag cacagcatcc caacacctcc | 1440 |
| cactagcgca gccccctctg agtccacccc atctgagcta cccatatctc ctaccactgc | 1500 |

```
tcccaggaca gtgaaagaac ttacggtatc ggctggagat aacctaatta taactttacc    1560
cgacaatgaa gttgaactga aggcctttgt tgcgccagcg ccacctgtag aaacaaccta    1620
caactatgaa tggaatttaa taagccaccc cacagactac caaggtgaaa taaaacaagg    1680
acacaagcaa actcttaacc tctctcaatt gtccgtcgga ctttatgtct tcaaagtcac    1740
tgtttctagt gaaaacgcct ttggagaagg atttgtcaat gtcactgtta agcctgccag    1800
aagagtcaac ctgccacctg tagcagttgt ttctccccaa ctgcaagagc tcactttgcc    1860
tttgacgtca gccctcattg atggcagcca agtacagat gatactgaaa tagtgagtta     1920
tcattgggaa gaaataaacg ggcccttcat agaagagaag acttcagttg actctcccgt    1980
cttacgcttg tctaaccttg atcctggtaa ctatagtttc aggttgactg ttacagactc    2040
ggacggagcc actaactcta caactgcagc cctaatagtg aacaatgctg tggactaccc    2100
accagttgct aatgcaggac caaatcacac cataactttg ccccaaaact ccatcacttt    2160
gaatggaaac cagagcagtg acgatcacca gattgtcctc tatgagtggt ccctgggtcc    2220
tgggagtgag ggcaaacatg tggtcatgca gggagtacag acgccatacc ttcatttatc    2280
tgcaatgcag gaaggagatt atacatttca gctgaaggtg acagattctt caaggcaaca    2340
gtctactgct gtggtgactg tgattgtcca gcctgaaaac aatagacctc cagtggctgt    2400
ggccggccct gataaagagc tgatcttccc agtggaaagt gctaccctgg atgggagcag    2460
cagcagcgat gaccacggca ttgtcttcta ccactgggag cacgtcagag ccccagtgc    2520
agtggagatg gaaaatattg acaaagcaat agccactgtg actggtctcc aggtggggac    2580
ctaccacttc cgtttgacag tgaaagacca gcagggactg agcagcacgt ccaccctcac    2640
tgtggctgtg aagaaggaaa ataatagtcc tcccagagcc cggctggtg gcagacatgt     2700
tcttgtgctt cccaataatt ccattacttt ggatggttca aggtctactg atgaccaaag    2760
aattgtgtcc tatctgtgga tccgggatgg ccagagtcca gcagctggag atgtcatcga    2820
tggctctgac cacagtgtgg ctctgcagct tacgaatctg gtggagggg tgtacacttt      2880
ccacttgcga gtcaccgaca gtcaggggc ctcggacaca gacactgcca ctgtggaagt     2940
gcagccagac cctaggaaga gtggcctggt ggagctgacc ctgcaggttg gtgttgggca    3000
gctgacagag cagcggaagg acacccttgt gaggcagctg ctgtgctgc tgaacgtgct     3060
ggactcggac attaaggtcc agaagattcg ggcccactcg gatctcagca ccgtgattgt    3120
gttttatgta cagagcaggc cgcctttcaa ggttctcaaa gctgctgaag tggcccgaaa    3180
tctgcacatg cggctctcaa aggagaaggc tgacttcttg cttttcaagg tcttgagggt    3240
tgatacagca ggttgccttc tgaagtgttc tggccatggt cactgcgacc ccctcacaaa    3300
gcgctgcatt tgctctcact tatggatgga aaaccttata cagcgttata tctgggatgg    3360
agagagcaac tgtgagtgga gtatattcta tgtgacagtg ttggctttta ctcttattgt    3420
gctaacagga ggtttcactt ggctttgcat ctgctgctgc aaaagacaaa aaggactaa     3480
aatcaggaaa aaaacaaagt acaccatcct ggataacatg gatgaacagg aaagaatgga    3540
actgaggccc aaatatggta tcaagcaccg aagcacagag cacaactcca gcctgatggt    3600
atccgagtct gagtttgaca gtgaccagga cacaatcttc agccgagaaa agatggagag    3660
agggaatcca aaggtttcca tgaatggttc catcagaaat ggagcttcct tcagttattg    3720
ctcaaaggac agataatggc gcagttcatt gtaaagtgga aggacccctt gaatccaaga    3780
ccagtcagtg ggagttacag cacaaaaccc actcttttag aatagttcat tgaccttctt    3840
ccccagtggg ttagatgtgt atccccacgt actaaaagac cggttttga aggcacaaaa      3900
```

```
caaaaacttt gctcttttaa ctgagatgct tgttaataga aataaaggct gggtaaaact    3960
ctaaggtata tacttaaaag agttttgagt ttttgtagct ggcacaatct catattaaag    4020
atgaacaacg atttctatct gtagaacctt agagaaggtg aatgaaacaa ggttttaaaa    4080
agggatgatt tctgtcttag ccgctgtgat tgcctctaag aacagcatt ctaaacacgg     4140 tttctcttgt aggacctgca gtcagatggc tgtgtatgtt aaaatagctt gtctaagagg    4200
cacgggccat ctgtggaggt acggagtctt gcatgtagca agctttctgt gctgacggca    4260
acactcgcac agtgccaagc cctcctggtt tttaattctg tgctatgtca atggcagttt    4320
tcatctctct caagaaagca gctgttggcc attcaagagc taaggaagaa tcgtattcta    4380
aggactgagg caatagaaag ggaggagga gcttaatgcc gtgcaggttg aaggtagcat     4440
tgtaacatta tcttttcttt ctctaagaaa aactacactg actcctctcg gtgttgttta    4500
gcagtatagt tctctaatgt aaacggatcc ccagtttaca ttaaatgcaa tagaagtgat    4560
taattcatta agcatttatt atgttctgta ggctgtgcgt ttggactgcc atagataggg    4620
ataacgactc agcaattgtg tatatattcc aaaactctga atacagtca gtcttaactt     4680 ggatggcgtg gttatgatac tctggtcccc gacaggtact ttccaaaata acttgacata    4740
gatgtattca cttcatatgt ttaaaaatac atttaagttt ttctaccgaa taaatcttat    4800
ttcaaacatg aaagacaatt aaaacattcc cacccacaaa gcagtactcc cgagcaatta    4860
actggagtta attgtagcct gctacgttga ctggttcagg gtagttcccc atccacccct    4920
ggtcctgagg ctggtggcct tggtggtgcc cttggcattt tttgtgggaa gattagaatg    4980
agagatagaa ccagtgttgt ggtaccaagt gtgagcacac ctaaacaata tcctgttgca    5040
caatgctttt ttaacacatg ggaaaactag gaatgcattg ctgatgaaga agcaaggtat    5100
ttaaacacca gggcaggagt gccagagaaa atgtttcccc atgggttctt aaaaaaaatt    5160
cagcttttag gtgcttttgt catctcccgg agtattcatc ctcatgggac catcttattt    5220
ttacttattg taatttactg gggaaaggca gaactaaaaa gtgtgtcatt ttattttaa     5280 aataattgct ttgcttatgc ctacactttc tgtataacta gccaattcaa tactgtctat    5340
agtgttagaa ggaaaatgtg attttttttt tttaaccagt attgagcttc ataagcctag    5400
aatctgcctt atcaggtgac cagggttatg gttgtttgca tgcaaatgtg aatttctggc    5460
ataggggaca gcagcccaaa tgtaaagtca tcgggcgtaa tgaggaagaa gggagtgaac    5520
atttaccgct ttatgtacat aacatatgca gtttacatac tcatttgatc cttataatca    5580
accttgaaga ggagatacta tcattcttat gttgcagata gccctctgaa ggcccagaga    5640
ggttaagtaa cttcccagag gtcatggcca agaagtagtg gctccaagaa ctgaatgcaa    5700
attttttaaa ctgtagagtt ctgctttcca ctaaacaaag aactcctgcc ttgatggatg    5760
gagggcaaat tctggtggaa cttttgggcc acctgaaagt tctattccca ggactaagag    5820
gaatttcttt taatggatcc agagagccaa ggtcagaggg agatggcc tgcatagtct      5880 cctgtggatc acaccgggc caccctccc tctaggttta cagtggactt cttctgcccc      5940
tcctcctttt ctgtccttgg ccatctcagc ctggcctctc tgatccttcc atcacagaag    6000
gatcttgaat ctctgggaaa tcaaacatca cagtagtgat cagaaagtga gtcctgtctt    6060
gtcaccccat ttctcatcag aacaaagcac gagatggaat gaccaaccag cattcttcat    6120
ggtggactgc ttatcattga ggatctttgg gagataaagc acgctaagag ctctggacag    6180
agaaaaacag gccctagaat atgggagtgg gtgtttgtag ggctcatagg ctaacaagca    6240
ctttagttgc tggtttacat tcaatgaagg aggattcata cccatggcat tacaaggcta    6300
```

```
agcatgtgta tgactaagga actatctgaa aaacatgcag caaggtaaga aaatgtacca    6360
ctcaacaagc cagtgatgcc acctttttgtg cgcggggagg agagtgacta ccattgtttt    6420
ttgtgtgaca aagctatcat ggactatttt aatcttggtt ttattgctta aaatatatta    6480
tttttcccta tgtgttgaca aggtatttct aatatcacac tattaaatat atgcactaat    6540
ctaaataaag gtgtctgtat tttctgtaat gcttattttt aggggaaat ttgttttctt     6600 tatgcttcag ggtagaggga ttcccttgag tataggtcag caaactctgg cctgcagcct    6660
gtgtgtgcac gccccatgag ccgaaaagtg ggtcttatgt tttcaaatgg ttaaaaataa    6720
ataaaaaaat ttgaaacatg tgaactatat gacattcaga tttgtgttca taaataaagt    6780
tttattggaa catatcc                                                  6797

<210> SEQ ID NO 271
<211> LENGTH: 6797
<212> TYPE: DNA
<213> ORGANISM: Homo sapiens

<400> SEQUENCE: 271
gctgccgcgg gcggtgggcg gggatccccc gggggtgcaa ccttgctcca cctgtgctgc      60
cctcggcggg cctggctggc cccgcgcaga gcggcggcgg cgctcgctgt cactgccgga     120
ggtgagagcg cagcagtagc ttcagcctgt ctttgggcttg gtccagattc gctcctctgg    180
ggctacgtcc cggggaagag gaagcgagga ttttgctggg gtggggctgt acctcttaac    240
agcaggtgcg cgcgcgaggg tgtgaacgtg tgtgtgtgtg tgtgtctgtg tgtgtgtgtg    300
taagacctgc gatgacgacg aggaggaaca agtgggacgg cgagtgatgc tcagggccag    360
cagcaacgca tggggcgagc ttcagtgtcg ccagcagtga ccacagagtt cttgaggcca    420
aatctggctc ctaaaaaaca tcaaaggaag cttgcaccaa actctcttca gggccgcctc    480
agaagcctgc catcacccac tgtgtggtgc acaatggcgc cccccacagg tgtgctctct    540
tcattgctgc tgctggtgac aattgcagtt tggttgtgcc cgtaagcagt gcagcgaggg    600
gaggacatat tccaatgcag tcatttcacc taacttggaa accaccagaa tcatgcgggt    660
gtctcacacc ttccctgtcg tagactgcac ggccgcttgc tgtgacctgt ccagctgtga    720
cctggcctgg tggttcgagg gccgctgcta cctggtgagc tgcccccaca aagagaactg    780
tgagcccaag aagatgggcc ccatcaggtc ttatctcact tttgtgctcc ggcctgttca    840
gaggcctgca cagctgctgg actatgggga catgatgctg aacaggggct cccctcggg    900 gatctggggg gactccacctg aggatatcag aaaggacttg cccttttctag gcaaagattg    960 gggcctagag gagatgtctg agtactcaga tgactaccgg gagctggaga aggacctctt    1020
gcaacccagt ggcaagcagg agcccagagg gagtgccgag tacacggact ggggcctact    1080
gccgggcagc gagggggcct tcaactcctc tgttggagac agtcctgcgg tgccagcgga    1140
gacgcagcag gaccctgagc tccattacct gaatgagtcg gcttcaaccc ctgccccaaa    1200
actccctgag agaagtgtgt tgcttccctt gccgactact ccatcttcag gagaggtgtt    1260
ggagaaagaa aaggcttctc agctccagga acaatccagc aacagctctg gaaaagaggt    1320
tctaatgcct tcccatagtc ttcctccggc aagcctggag ctcagctcag tcaccgtgga    1380
gaaaagccca gtgctcacag tcaccccggg gagtacagag cacagcatcc caacacctcc    1440
cactagcgca gccccctctg agtccacccc atctgagcta cccatatctc ctaccactgc    1500
tcccaggaca gtgaaagaac ttacggtatc ggctggagat aacctaatta taactttacc    1560
cgacaatgaa gttgaactga aggcctttgt tgcgccagcg ccacctgtag aaacaaccta    1620
```

```
caactatgaa tggaatttaa taagccaccc cacagactac caaggtgaaa taaaacaagg    1680
acacaagcaa actcttaacc tctctcaatt gtccgtcgga ctttatgtct tcaaagtcac    1740
tgtttctagt gaaaacgcct ttggagaagg atttgtcaat gtcactgtta agcctgccag    1800
aagagtcaac ctgccacctg tagcagttgt ttctccccaa ctgcaagagc tcactttgcc    1860
tttgacgtca gccctcattg atggcagcca agtacagat gatactgaaa tagtgagtta    1920
tcattgggaa gaaataaacg ggcccttcat agaagagaag acttcagttg actctcccgt    1980
cttacgcttg tctaaccttg atcctggtaa ctatagtttc aggttgactg ttacagactc    2040
ggacggagcc actaactcta caactgcagc cctaatagtg aacaatgctg tggactaccc    2100
accagttgct aatgcaggac caaatcacac cataactttg ccccaaaact ccatcacttt    2160
gaatggaaac cagagcagtg acgatcacca gattgtcctc tatgagtggt ccctgggtcc    2220
tgggagtgag ggcaaacatg tggtcatgca gggagtacag acgccatacc ttcatttatc    2280
tgcaatgcag gaaggagatt atacatttca gctgaaggtg acagattctt caaggcaaca    2340
gtctactgct gtggtgactg tgattgtcca gcctgaaaac aatagacctc cagtggctgt    2400
ggccggccct gataaagagc tgatcttccc agtggaaagt gctaccctgg atgggagcag    2460
cagcagcgat gaccacggca ttgtcttcta ccactgggag cacgtcagag ccccagtgc    2520 agtggagatg gaaaatattg acaaagcaat agccactgtg actggtctcc aggtggggac    2580
ctaccacttc cgtttgacag tgaaagacca gcagggactg agcagcacgt ccaccctcac    2640
tgtggctgtg aagaaggaaa ataatagtcc tcccagagcc cgggctggtg gcagacatgt    2700
tcttgtgctt cccaataatt ccattacttt ggatggttca aggtctactg atgaccaaag    2760
aattgtgtcc tatctgtgga tccgggatgg ccagagtcca gcagctggag atgtcatcga    2820
tggctctgac cacagtgtgg ctctgcagct tacgaatctg gtggagggg tgtacacttt    2880 ccacttgcga gtcaccgaca gtcagggggc ctcggacaca gacactgcca ctgtggaagt    2940
gcagccagac cctaggaaga gtggcctggt ggagctgacc ctgcaggttg gtgttgggca    3000
gctgacagag cagcggaagg acacccttgt gaggcagctg gctgtgctgc tgaacgtgct    3060
ggactcggac attaaggtcc agaagattcg ggcccactcg gatctcagca ccgtgattgt    3120
gttttatgta cagagcaggc cgcctttcaa ggttctcaaa gctgctgaag tggcccgaaa    3180
tctgcacatg cggctctcaa aggagaaggc tgacttcttg cttttcaagg tcttgagggt    3240
tgatacagca ggttgccttc tgaagtgttc tggccatggt cactgcgacc cctcacaaa    3300 gcgctgcatt tgctctcact tatggatgga aaccttata cagcgttata tctgggatgg    3360
agagagcaac tgtgagtgga gtatattcta tgtgacagtg ttggctttta ctcttattgt    3420
gctaacagga ggtttcactt ggcttttgcat ctgctgctgc aaaagacaaa aaaggactaa    3480
aatcaggaaa aaaacaaagt acaccatcct ggataacatg gatgaacagg aaagaatgga    3540
actgaggccc aaatatggta tcaagcaccg aagcacagag cacaactcca gcctgatggt    3600
atccgagtct gagtttgaca gtgaccagga cacaatcttc agccgagaaa agatggagag    3660
agggaatcca aaggtttcca tgaatggttc catcagaaat ggagcttcct tcagttattg    3720
ctcaaaggac agataatggc gcagttcatt gtaaagtgga aggacccctt gaatccaaga    3780
ccagtcagtg ggagttacag cacaaaaccc actcttttag aatagttcat tgaccttctt    3840
ccccagtggg ttagatgtgt atcccacgt actaaaagac cggttttga aggcacaaaa    3900 caaaaacttt gctctttaa ctgagatgct tgttaataga aataaaggct gggtaaaact    3960
ctaaggtata tacttaaaag agttttgagt ttttgtagct ggcacaatct catattaaag    4020
```

```
atgaacaacg atttctatct gtagaacctt agagaaggtg aatgaaacaa ggttttaaaa    4080
agggatgatt tctgtcttag ccgctgtgat tgcctctaag gaacagcatt ctaaacacgg    4140
tttctcttgt aggacctgca gtcagatggc tgtgtatgtt aaaatagctt gtctaagagg    4200
cacgggccat ctgtggaggt acggagtctt gcatgtagca agctttctgt gctgacggca    4260
acactcgcac agtgccaagc cctcctggtt tttaattctg tgctatgtca atggcagttt    4320
tcatctctct caagaaagca gctgttggcc attcaagagc taaggaagaa tcgtattcta    4380
aggactgagg caatagaaag gggaggagga gcttaatgcc gtgcaggttg aaggtagcat    4440
tgtaacatta tcttttcttt ctctaagaaa aactacactg actcctctcg gtgttgttta    4500
gcagtatagt tctctaatgt aaacggatcc ccagtttaca ttaaatgcaa tagaagtgat    4560
taattcatta agcatttatt atgttctgta ggctgtgcgt ttggactgcc atagataggg    4620
ataacgactc agcaattgtg tatatattcc aaaactctga atacagtca  gtcttaactt    4680
ggatggcgtg ttatgatac  tctggtcccc gacaggtact ttccaaaata acttgacata    4740
gatgtattca cttcatatgt ttaaaaatac atttaagttt ttctaccgaa taaatcttat    4800
ttcaaacatg aaagacaatt aaaacattcc cacccacaaa gcagtactcc cgagcaatta    4860
actggagtta attgtagcct gctacgttga ctggttcagg gtagttcccc atccacccct    4920
ggtcctgagg ctggtggcct tggtggtgcc cttggcattt tttgtgggaa gattagaatg    4980
agagatagaa ccagtgttgt ggtaccaagt gtgagcacac ctaaacaata tcctgttgca    5040
caatgctttt ttaacacatg ggaaaactag gaatgcattg ctgatgaaga agcaaggtat    5100
ttaaacacca gggcaggagt gccagagaaa atgtttcccc atgggttctt aaaaaaaatt    5160
cagcttttag gtgcttttgt catctcccgg agtattcatc ctcatgggac catcttattt    5220
ttacttattg taatttactg gggaaaggca gaactaaaaa gtgtgtcatt ttattttaa    5280
aataattgct ttgcttatgc ctacactttc tgtataacta gccaattcaa tactgtctat    5340
agtgttagaa ggaaaatgtg attttttttt tttaaccagt attgagcttc ataagcctag    5400
aatctgcctt atcaggtgac cagggttatg gttgtttgca tgcaaatgtg aatttctggc    5460
atagggga    gcagcccaaa tgtaaagtca tcgggcgtaa tgaggaagaa gggagtgaac    5520
atttaccgct ttatgtacat aacatatgca gtttacatac tcatttgatc cttataatca    5580
accttgaaga ggagatacta tcattcttat gttgcagata gccctctgaa ggcccagaga    5640
ggttaagtaa cttcccagag gtcatggcca agaagtagtg gctccaagaa ctgaatgcaa    5700
atttttaaa ctgtagagtt ctgctttcca ctaaacaaag aactcctgcc ttgatggatg    5760
gagggcaaat tctggtggaa cttttgggcc acctgaaagt tctattccca ggactaagag    5820
gaatttcttt taatggatcc agagagccaa ggtcagaggg agagatggcc tgcatagtct    5880
cctgtggatc acacccgggc caccccctcc tctaggttta cagtggactt cttctgcccc    5940
tcctcctttt ctgtccttgg ccatctcagc ctggcctctc tgatccttcc atcacagaag    6000
gatcttgaat ctctgggaaa tcaaacatca cagtagtgat cagaaagtga gtcctgtctt    6060
gtcaccccat ttctcatcag aacaaagcac gagatggaat gaccaaccag cattcttcat    6120
ggtggactgc ttatcattga ggatctttgg gagataaagc acgctaagag ctctggacag    6180
agaaaaacag gccctagaat atgggagtgg gtgtttgtag ggctcatagg ctaacaagca    6240
ctttagttgc tggtttacat tcaatgaagg aggattcata cccatggcat tacaaggcta    6300
agcatgtgta tgactaagga actatctgaa aaacatgcag caaggtaaga aaatgtacca    6360
ctcaacaagc cagtgatgcc accttttgtg cgcggggagg agagtgacta ccattgtttt    6420
```

```
ttgtgtgaca aagctatcat ggactatttt aatcttggtt ttattgctta aaatatatta   6480
tttttcccta tgtgttgaca aggtatttct aatatcacac tattaaatat atgcactaat   6540
ctaaataaag gtgtctgtat tttctgtaat gcttattttt agggggaaat ttgttttctt   6600
tatgcttcag ggtagaggga ttcccttgag tataggtcag caaactctgg cctgcagcct   6660
gtgtgtgcac gccccatgag ccgaaaagtg ggtcttatgt tttcaaatgg ttaaaaataa   6720
ataaaaaaat ttgaaacatg tgaactatat gacattcaga tttgtgttca taaataaagt   6780
tttattggaa catatcc                                                  6797

<210> SEQ ID NO 272
<211> LENGTH: 1063
<212> TYPE: PRT
<213> ORGANISM: Homo sapiens

<400> SEQUENCE: 272

Met Thr Arg Leu Gly Trp Pro Ser Pro Cys Cys Ala Arg Lys Gln Cys
 1               5                  10                  15

Ser Glu Gly Arg Thr Tyr Ser Asn Ala Val Ile Ser Pro Asn Leu Glu
            20                  25                  30

Thr Thr Arg Ile Met Arg Val Ser His Thr Phe Pro Val Val Asp Cys
        35                  40                  45

Thr Ala Ala Cys Cys Asp Leu Ser Ser Cys Asp Leu Ala Trp Trp Phe
    50                  55                  60

Glu Gly Arg Cys Tyr Leu Val Ser Cys Pro His Lys Glu Asn Cys Glu
65                  70                  75                  80

Pro Lys Lys Met Gly Pro Ile Arg Ser Tyr Leu Thr Phe Val Leu Arg
                85                  90                  95

Pro Val Gln Arg Pro Ala Gln Leu Leu Asp Tyr Gly Asp Met Met Leu
            100                 105                 110

Asn Arg Gly Ser Pro Ser Gly Ile Trp Gly Asp Ser Pro Glu Asp Ile
        115                 120                 125

Arg Lys Asp Leu Pro Phe Leu Gly Lys Asp Trp Gly Leu Glu Glu Met
    130                 135                 140

Ser Glu Tyr Ser Asp Asp Tyr Arg Glu Leu Glu Lys Asp Leu Leu Gln
145                 150                 155                 160

Pro Ser Gly Lys Gln Glu Pro Arg Gly Ser Ala Glu Tyr Thr Asp Trp
                165                 170                 175

Gly Leu Leu Pro Gly Ser Glu Gly Ala Phe Asn Ser Ser Val Gly Asp
            180                 185                 190

Ser Pro Ala Val Pro Ala Glu Thr Gln Gln Asp Pro Glu Leu His Tyr
        195                 200                 205

Leu Asn Glu Ser Ala Ser Thr Pro Ala Pro Lys Leu Pro Glu Arg Ser
    210                 215                 220

Val Leu Leu Pro Leu Pro Thr Thr Pro Ser Ser Gly Glu Val Leu Glu
225                 230                 235                 240

Lys Glu Lys Ala Ser Gln Leu Gln Glu Gln Ser Ser Asn Ser Ser Gly
                245                 250                 255

Lys Glu Val Leu Met Pro Ser His Ser Leu Pro Pro Ala Ser Leu Glu
            260                 265                 270

Leu Ser Ser Val Thr Val Glu Lys Ser Pro Val Leu Thr Val Thr Pro
        275                 280                 285

Gly Ser Thr Glu His Ser Ile Pro Thr Pro Pro Thr Ser Ala Ala Pro
    290                 295                 300

Ser Glu Ser Thr Pro Ser Glu Leu Pro Ile Ser Pro Thr Thr Ala Pro
```

-continued

```
                305                 310                 315                 320
            Arg Thr Val Lys Glu Leu Thr Val Ser Ala Gly Asp Asn Leu Ile Ile
                            325                 330                 335

Thr Leu Pro Asp Asn Glu Val Glu Leu Lys Ala Phe Val Ala Pro Ala
                            340                 345                 350

Pro Pro Val Glu Thr Thr Tyr Asn Tyr Glu Trp Asn Leu Ile Ser His
                            355                 360                 365

Pro Thr Asp Tyr Gln Gly Glu Ile Lys Gln Gly His Lys Gln Thr Leu
                            370                 375                 380

Asn Leu Ser Gln Leu Ser Val Gly Leu Tyr Val Phe Lys Val Thr Val
            385                 390                 395                 400

Ser Ser Glu Asn Ala Phe Gly Glu Gly Phe Val Asn Val Thr Val Lys
                            405                 410                 415

Pro Ala Arg Arg Val Asn Leu Pro Pro Val Ala Val Val Ser Pro Gln
                            420                 425                 430

Leu Gln Glu Leu Thr Leu Pro Leu Thr Ser Ala Leu Ile Asp Gly Ser
                            435                 440                 445

Gln Ser Thr Asp Asp Thr Glu Ile Val Ser Tyr His Trp Glu Glu Ile
                            450                 455                 460

Asn Gly Pro Phe Ile Glu Glu Lys Thr Ser Val Asp Ser Pro Val Leu
            465                 470                 475                 480

Arg Leu Ser Asn Leu Asp Pro Gly Asn Tyr Ser Phe Arg Leu Thr Val
                            485                 490                 495

Thr Asp Ser Asp Gly Ala Thr Asn Ser Thr Thr Ala Ala Leu Ile Val
                            500                 505                 510

Asn Asn Ala Val Asp Tyr Pro Pro Val Ala Asn Ala Gly Pro Asn His
                            515                 520                 525

Thr Ile Thr Leu Pro Gln Asn Ser Ile Thr Leu Asn Gly Asn Gln Ser
                            530                 535                 540

Ser Asp Asp His Gln Ile Val Leu Tyr Glu Trp Ser Leu Gly Pro Gly
            545                 550                 555                 560

Ser Glu Gly Lys His Val Val Met Gln Gly Val Gln Thr Pro Tyr Leu
                            565                 570                 575

His Leu Ser Ala Met Gln Glu Gly Asp Tyr Thr Phe Gln Leu Lys Val
                            580                 585                 590

Thr Asp Ser Ser Arg Gln Gln Ser Thr Ala Val Val Thr Val Ile Val
                            595                 600                 605

Gln Pro Glu Asn Asn Arg Pro Pro Val Ala Val Ala Gly Pro Asp Lys
                            610                 615                 620

Glu Leu Ile Phe Pro Val Glu Ser Ala Thr Leu Asp Gly Ser Ser Ser
            625                 630                 635                 640

Ser Asp Asp His Gly Ile Val Phe Tyr His Trp Glu His Val Arg Gly
                            645                 650                 655

Pro Ser Ala Val Glu Met Glu Asn Ile Asp Lys Ala Ile Ala Thr Val
                            660                 665                 670

Thr Gly Leu Gln Val Gly Thr Tyr His Phe Arg Leu Thr Val Lys Asp
                            675                 680                 685

Gln Gln Gly Leu Ser Ser Thr Ser Thr Leu Thr Val Ala Val Lys Lys
                            690                 695                 700

Glu Asn Asn Ser Pro Pro Arg Ala Arg Ala Gly Gly Arg His Val Leu
            705                 710                 715                 720

Val Leu Pro Asn Asn Ser Ile Thr Leu Asp Gly Ser Arg Ser Thr Asp
                            725                 730                 735
```

```
Asp Gln Arg Ile Val Ser Tyr Leu Trp Ile Arg Asp Gly Gln Ser Pro
            740                 745                 750

Ala Ala Gly Asp Val Ile Asp Gly Ser Asp His Ser Val Ala Leu Gln
                755                 760                 765

Leu Thr Asn Leu Val Glu Gly Val Tyr Thr Phe His Leu Arg Val Thr
        770                 775                 780

Asp Ser Gln Gly Ala Ser Asp Thr Asp Thr Ala Thr Val Glu Val Gln
785                 790                 795                 800

Pro Asp Pro Arg Lys Ser Gly Leu Val Glu Leu Thr Leu Gln Val Gly
                805                 810                 815

Val Gly Gln Leu Thr Glu Gln Arg Lys Asp Thr Leu Val Arg Gln Leu
            820                 825                 830

Ala Val Leu Leu Asn Val Leu Asp Ser Asp Ile Lys Val Gln Lys Ile
                835                 840                 845

Arg Ala His Ser Asp Leu Ser Thr Val Ile Val Phe Tyr Val Gln Ser
            850                 855                 860

Arg Pro Pro Phe Lys Val Leu Lys Ala Ala Glu Val Ala Arg Asn Leu
865                 870                 875                 880

His Met Arg Leu Ser Lys Glu Lys Ala Asp Phe Leu Leu Phe Lys Val
                885                 890                 895

Leu Arg Val Asp Thr Ala Gly Cys Leu Leu Lys Cys Ser Gly His Gly
            900                 905                 910

His Cys Asp Pro Leu Thr Lys Arg Cys Ile Cys Ser His Leu Trp Met
            915                 920                 925

Glu Asn Leu Ile Gln Arg Tyr Ile Trp Asp Gly Glu Ser Asn Cys Glu
            930                 935                 940

Trp Ser Ile Phe Tyr Val Thr Val Leu Ala Phe Thr Leu Ile Val Leu
945                 950                 955                 960

Thr Gly Gly Phe Thr Trp Leu Cys Ile Cys Cys Cys Lys Arg Gln Lys
                965                 970                 975

Arg Thr Lys Ile Arg Lys Lys Thr Lys Tyr Thr Ile Leu Asp Asn Met
            980                 985                 990

Asp Glu Gln Glu Arg Met Glu Leu Arg Pro Lys Tyr Gly Ile Lys His
                995                 1000                1005

Arg Ser Thr Glu His Asn Ser Ser Leu Met Val Ser Glu Ser Glu Phe
        1010                1015                1020

Asp Ser Asp Gln Asp Thr Ile Phe Ser Arg Glu Lys Met Glu Arg Gly
1025                1030                1035                1040

Asn Pro Lys Val Ser Met Asn Gly Ser Ile Arg Asn Gly Ala Ser Phe
                1045                1050                1055

Ser Tyr Cys Ser Lys Asp Arg
            1060

<210> SEQ ID NO 273
<211> LENGTH: 1053
<212> TYPE: PRT
<213> ORGANISM: Homo sapiens

<400> SEQUENCE: 273

Cys Ala Arg Lys Gln Cys Ser Glu Gly Arg Thr Tyr Ser Asn Ala Val
1               5                   10                  15

Ile Ser Pro Asn Leu Glu Thr Thr Arg Ile Met Arg Val Ser His Thr
                20                  25                  30

Phe Pro Val Val Asp Cys Thr Ala Ala Cys Cys Asp Leu Ser Ser Cys
        35                  40                  45
```

-continued

```
Asp Leu Ala Trp Trp Phe Glu Gly Arg Cys Tyr Leu Val Ser Cys Pro
 50                  55                  60
His Lys Glu Asn Cys Glu Pro Lys Lys Met Gly Pro Ile Arg Ser Tyr
 65                  70                  75                  80
Leu Thr Phe Val Leu Arg Pro Val Gln Arg Pro Ala Gln Leu Leu Asp
                 85                  90                  95
Tyr Gly Asp Met Met Leu Asn Arg Gly Ser Pro Ser Gly Ile Trp Gly
            100                 105                 110
Asp Ser Pro Glu Asp Ile Arg Lys Asp Leu Pro Phe Leu Gly Lys Asp
        115                 120                 125
Trp Gly Leu Glu Glu Met Ser Glu Tyr Ser Asp Asp Tyr Arg Glu Leu
    130                 135                 140
Glu Lys Asp Leu Leu Gln Pro Ser Gly Lys Gln Glu Pro Arg Gly Ser
145                 150                 155                 160
Ala Glu Tyr Thr Asp Trp Gly Leu Leu Pro Gly Ser Glu Gly Ala Phe
                165                 170                 175
Asn Ser Ser Val Gly Asp Ser Pro Ala Val Pro Ala Glu Thr Gln Gln
            180                 185                 190
Asp Pro Glu Leu His Tyr Leu Asn Glu Ser Ala Ser Thr Pro Ala Pro
        195                 200                 205
Lys Leu Pro Glu Arg Ser Val Leu Leu Pro Leu Pro Thr Thr Pro Ser
    210                 215                 220
Ser Gly Glu Val Leu Glu Lys Glu Lys Ala Ser Gln Leu Gln Glu Gln
225                 230                 235                 240
Ser Ser Asn Ser Ser Gly Lys Glu Val Leu Met Pro Ser His Ser Leu
                245                 250                 255
Pro Pro Ala Ser Leu Glu Leu Ser Ser Val Thr Val Glu Lys Ser Pro
            260                 265                 270
Val Leu Thr Val Thr Pro Gly Ser Thr Glu His Ser Ile Pro Thr Pro
        275                 280                 285
Pro Thr Ser Ala Ala Pro Ser Glu Ser Thr Pro Ser Glu Leu Pro Ile
    290                 295                 300
Ser Pro Thr Thr Ala Pro Arg Thr Val Lys Glu Leu Thr Val Ser Ala
305                 310                 315                 320
Gly Asp Asn Leu Ile Ile Thr Leu Pro Asp Asn Glu Val Glu Leu Lys
                325                 330                 335
Ala Phe Val Ala Pro Ala Pro Val Glu Thr Thr Tyr Asn Tyr Glu
            340                 345                 350
Trp Asn Leu Ile Ser His Pro Thr Asp Tyr Gln Gly Glu Ile Lys Gln
        355                 360                 365
Gly His Lys Gln Thr Leu Asn Leu Ser Gln Leu Ser Val Gly Leu Tyr
    370                 375                 380
Val Phe Lys Val Thr Val Ser Ser Glu Asn Ala Phe Gly Glu Gly Phe
385                 390                 395                 400
Val Asn Val Thr Val Lys Pro Ala Arg Arg Val Asn Leu Pro Pro Val
                405                 410                 415
Ala Val Val Ser Pro Gln Leu Gln Glu Leu Thr Leu Pro Leu Thr Ser
            420                 425                 430
Ala Leu Ile Asp Gly Ser Gln Ser Thr Asp Asp Thr Glu Ile Val Ser
        435                 440                 445
Tyr His Trp Glu Glu Ile Asn Gly Pro Phe Ile Glu Glu Lys Thr Ser
    450                 455                 460
Val Asp Ser Pro Val Leu Arg Leu Ser Asn Leu Asp Pro Gly Asn Tyr
465                 470                 475                 480
```

Ser Phe Arg Leu Thr Val Thr Asp Ser Asp Gly Ala Thr Asn Ser Thr
                485                 490                 495

Thr Ala Ala Leu Ile Val Asn Asn Ala Val Asp Tyr Pro Pro Val Ala
            500                 505                 510

Asn Ala Gly Pro Asn His Thr Ile Thr Leu Pro Gln Asn Ser Ile Thr
            515                 520                 525

Leu Asn Gly Asn Gln Ser Ser Asp Asp His Gln Ile Val Leu Tyr Glu
        530                 535                 540

Trp Ser Leu Gly Pro Gly Ser Glu Gly Lys His Val Val Met Gln Gly
545                 550                 555                 560

Val Gln Thr Pro Tyr Leu His Leu Ser Ala Met Gln Glu Gly Asp Tyr
                565                 570                 575

Thr Phe Gln Leu Lys Val Thr Asp Ser Ser Arg Gln Gln Ser Thr Ala
            580                 585                 590

Val Val Thr Val Ile Val Gln Pro Glu Asn Asn Arg Pro Pro Val Ala
        595                 600                 605

Val Ala Gly Pro Asp Lys Glu Leu Ile Phe Pro Val Glu Ser Ala Thr
        610                 615                 620

Leu Asp Gly Ser Ser Ser Asp Asp His Gly Ile Val Phe Tyr His
625                 630                 635                 640

Trp Glu His Val Arg Gly Pro Ser Ala Val Glu Met Glu Asn Ile Asp
                645                 650                 655

Lys Ala Ile Ala Thr Val Thr Gly Leu Gln Val Gly Thr Tyr His Phe
            660                 665                 670

Arg Leu Thr Val Lys Asp Gln Gln Gly Leu Ser Ser Thr Ser Thr Leu
        675                 680                 685

Thr Val Ala Val Lys Lys Glu Asn Asn Ser Pro Arg Ala Arg Ala
        690                 695                 700

Gly Gly Arg His Val Leu Val Leu Pro Asn Asn Ser Ile Thr Leu Asp
705                 710                 715                 720

Gly Ser Arg Ser Thr Asp Asp Gln Arg Ile Val Ser Tyr Leu Trp Ile
                725                 730                 735

Arg Asp Gly Gln Ser Pro Ala Ala Gly Asp Val Ile Asp Gly Ser Asp
            740                 745                 750

His Ser Val Ala Leu Gln Leu Thr Asn Leu Val Glu Gly Val Tyr Thr
        755                 760                 765

Phe His Leu Arg Val Thr Asp Ser Gln Gly Ala Ser Asp Thr Asp Thr
    770                 775                 780

Ala Thr Val Glu Val Gln Pro Asp Pro Arg Lys Ser Gly Leu Val Glu
785                 790                 795                 800

Leu Thr Leu Gln Val Gly Val Gly Gln Leu Thr Glu Gln Arg Lys Asp
                805                 810                 815

Thr Leu Val Arg Gln Leu Ala Val Leu Leu Asn Val Leu Asp Ser Asp
            820                 825                 830

Ile Lys Val Gln Lys Ile Arg Ala His Ser Asp Leu Ser Thr Val Ile
        835                 840                 845

Val Phe Tyr Val Gln Ser Arg Pro Pro Phe Lys Val Leu Lys Ala Ala
    850                 855                 860

Glu Val Ala Arg Asn Leu His Met Arg Leu Ser Lys Glu Lys Ala Asp
865                 870                 875                 880

Phe Leu Leu Phe Lys Val Leu Arg Val Asp Thr Ala Gly Cys Leu Leu
                885                 890                 895

Lys Cys Ser Gly His Gly His Cys Asp Pro Leu Thr Lys Arg Cys Ile

```
                    900                 905                 910
Cys Ser His Leu Trp Met Glu Asn Leu Ile Gln Arg Tyr Ile Trp Asp
        915                 920                 925

Gly Glu Ser Asn Cys Glu Trp Ser Ile Phe Tyr Val Thr Val Leu Ala
930                 935                 940

Phe Thr Leu Ile Val Leu Thr Gly Gly Phe Thr Trp Leu Cys Ile Cys
945                 950                 955                 960

Cys Cys Lys Arg Gln Lys Arg Thr Lys Ile Arg Lys Lys Thr Lys Tyr
            965                 970                 975

Thr Ile Leu Asp Asn Met Asp Glu Gln Glu Arg Met Glu Leu Arg Pro
            980                 985                 990

Lys Tyr Gly Ile Lys His Arg Ser Thr Glu His Asn Ser Ser Leu Met
            995                 1000                1005

Val Ser Glu Ser Glu Phe Asp Ser Asp Gln Asp Thr Ile Phe Ser Arg
            1010                1015                1020

Glu Lys Met Glu Arg Gly Asn Pro Lys Val Ser Met Asn Gly Ser Ile
1025                1030                1035                1040

Arg Asn Gly Ala Ser Phe Ser Tyr Cys Ser Lys Asp Arg
                1045                1050

<210> SEQ ID NO 274
<211> LENGTH: 1053
<212> TYPE: PRT
<213> ORGANISM: Homo sapiens

<400> SEQUENCE: 274

Cys Ala Arg Lys Gln Cys Ser Glu Gly Arg Thr Tyr Ser Asn Ala Val
1               5                   10                  15

Ile Ser Pro Asn Leu Glu Thr Thr Arg Ile Met Arg Val Ser His Thr
            20                  25                  30

Phe Pro Val Val Asp Cys Thr Ala Ala Cys Cys Asp Leu Ser Ser Cys
        35                  40                  45

Asp Leu Ala Trp Trp Phe Glu Gly Arg Cys Tyr Leu Val Ser Cys Pro
    50                  55                  60

His Lys Glu Asn Cys Glu Pro Lys Lys Met Gly Pro Ile Arg Ser Tyr
65                  70                  75                  80

Leu Thr Phe Val Leu Arg Pro Val Gln Arg Pro Ala Gln Leu Leu Asp
                85                  90                  95

Tyr Gly Asp Met Met Leu Asn Arg Gly Ser Pro Ser Gly Ile Trp Gly
            100                 105                 110

Asp Ser Pro Glu Asp Ile Arg Lys Asp Leu Pro Phe Leu Gly Lys Asp
        115                 120                 125

Trp Gly Leu Glu Glu Met Ser Glu Tyr Ser Asp Asp Tyr Arg Glu Leu
    130                 135                 140

Glu Lys Asp Leu Leu Gln Pro Ser Gly Lys Gln Glu Pro Arg Gly Ser
145                 150                 155                 160

Ala Glu Tyr Thr Asp Trp Gly Leu Leu Pro Gly Ser Glu Gly Ala Phe
                165                 170                 175

Asn Ser Ser Val Gly Asp Ser Pro Ala Val Pro Ala Glu Thr Gln Gln
            180                 185                 190

Asp Pro Glu Leu His Tyr Leu Asn Glu Ser Ala Ser Thr Pro Ala Pro
        195                 200                 205

Lys Leu Pro Glu Arg Ser Val Leu Leu Pro Leu Pro Thr Thr Pro Ser
    210                 215                 220

Ser Gly Glu Val Leu Glu Lys Glu Lys Ala Ser Gln Leu Gln Glu Gln
```

```
              225                 230                 235                 240
    Ser Ser Asn Ser Ser Gly Lys Glu Val Leu Met Pro Ser His Ser Leu
                    245                 250                 255

Pro Pro Ala Ser Leu Glu Leu Ser Ser Val Thr Val Glu Lys Ser Pro
                    260                 265                 270

Val Leu Thr Val Thr Pro Gly Ser Thr Glu His Ser Ile Pro Thr Pro
                    275                 280                 285

Pro Thr Ser Ala Ala Pro Ser Glu Ser Thr Pro Ser Glu Leu Pro Ile
        290                 295                 300

Ser Pro Thr Thr Ala Pro Arg Thr Val Lys Glu Leu Thr Val Ser Ala
    305                 310                 315                 320

Gly Asp Asn Leu Ile Ile Thr Leu Pro Asp Asn Glu Val Glu Leu Lys
                    325                 330                 335

Ala Phe Val Ala Pro Ala Pro Val Glu Thr Thr Tyr Asn Tyr Glu
                    340                 345                 350

Trp Asn Leu Ile Ser His Pro Thr Asp Tyr Gln Gly Glu Ile Lys Gln
                    355                 360                 365

Gly His Lys Gln Thr Leu Asn Leu Ser Gln Leu Ser Val Gly Leu Tyr
        370                 375                 380

Val Phe Lys Val Thr Val Ser Ser Glu Asn Ala Phe Gly Glu Gly Phe
    385                 390                 395                 400

Val Asn Val Thr Val Lys Pro Ala Arg Arg Val Asn Leu Pro Pro Val
                    405                 410                 415

Ala Val Val Ser Pro Gln Leu Gln Glu Leu Thr Leu Pro Leu Thr Ser
                    420                 425                 430

Ala Leu Ile Asp Gly Ser Gln Ser Thr Asp Thr Glu Ile Val Ser
                    435                 440                 445

Tyr His Trp Glu Glu Ile Asn Gly Pro Phe Ile Glu Glu Lys Thr Ser
        450                 455                 460

Val Asp Ser Pro Val Leu Arg Leu Ser Asn Leu Asp Pro Gly Asn Tyr
    465                 470                 475                 480

Ser Phe Arg Leu Thr Val Thr Asp Ser Asp Gly Ala Thr Asn Ser Thr
                    485                 490                 495

Thr Ala Ala Leu Ile Val Asn Asn Ala Val Asp Tyr Pro Pro Val Ala
                    500                 505                 510

Asn Ala Gly Pro Asn His Thr Ile Thr Leu Pro Gln Asn Ser Ile Thr
                    515                 520                 525

Leu Asn Gly Asn Gln Ser Ser Asp Asp His Gln Ile Val Leu Tyr Glu
        530                 535                 540

Trp Ser Leu Gly Pro Gly Ser Glu Gly Lys His Val Val Met Gln Gly
    545                 550                 555                 560

Val Gln Thr Pro Tyr Leu His Leu Ser Ala Met Gln Glu Gly Asp Tyr
                    565                 570                 575

Thr Phe Gln Leu Lys Val Thr Asp Ser Ser Arg Gln Gln Ser Thr Ala
                    580                 585                 590

Val Val Thr Val Ile Val Gln Pro Glu Asn Asn Arg Pro Pro Val Ala
                    595                 600                 605

Val Ala Gly Pro Asp Lys Glu Leu Ile Phe Pro Val Glu Ser Ala Thr
        610                 615                 620

Leu Asp Gly Ser Ser Ser Ser Asp Asp His Gly Ile Val Phe Tyr His
    625                 630                 635                 640

Trp Glu His Val Arg Gly Pro Ser Ala Val Glu Met Glu Asn Ile Asp
                    645                 650                 655
```

-continued

Lys Ala Ile Ala Thr Val Thr Gly Leu Gln Val Gly Thr Tyr His Phe
            660                 665                 670

Arg Leu Thr Val Lys Asp Gln Gln Gly Leu Ser Ser Thr Ser Thr Leu
        675                 680                 685

Thr Val Ala Val Lys Lys Glu Asn Asn Ser Pro Pro Arg Ala Arg Ala
    690                 695                 700

Gly Gly Arg His Val Leu Val Leu Pro Asn Asn Ser Ile Thr Leu Asp
705                 710                 715                 720

Gly Ser Arg Ser Thr Asp Asp Gln Arg Ile Val Ser Tyr Leu Trp Ile
                725                 730                 735

Arg Asp Gly Gln Ser Pro Ala Ala Gly Asp Val Ile Asp Gly Ser Asp
            740                 745                 750

His Ser Val Ala Leu Gln Leu Thr Asn Leu Val Glu Gly Val Tyr Thr
        755                 760                 765

Phe His Leu Arg Val Thr Asp Ser Gln Gly Ala Ser Asp Thr Asp Thr
    770                 775                 780

Ala Thr Val Glu Val Gln Pro Asp Pro Arg Lys Ser Gly Leu Val Glu
785                 790                 795                 800

Leu Thr Leu Gln Val Gly Val Gly Gln Leu Thr Glu Gln Arg Lys Asp
                805                 810                 815

Thr Leu Val Arg Gln Leu Ala Val Leu Leu Asn Val Leu Asp Ser Asp
            820                 825                 830

Ile Lys Val Gln Lys Ile Arg Ala His Ser Asp Leu Ser Thr Val Ile
        835                 840                 845

Val Phe Tyr Val Gln Ser Arg Pro Pro Phe Lys Val Leu Lys Ala Ala
    850                 855                 860

Glu Val Ala Arg Asn Leu His Met Arg Leu Ser Lys Glu Lys Ala Asp
865                 870                 875                 880

Phe Leu Leu Phe Lys Val Leu Arg Val Asp Thr Ala Gly Cys Leu Leu
                885                 890                 895

Lys Cys Ser Gly His Gly His Cys Asp Pro Leu Thr Lys Arg Cys Ile
            900                 905                 910

Cys Ser His Leu Trp Met Glu Asn Leu Ile Gln Arg Tyr Ile Trp Asp
        915                 920                 925

Gly Glu Ser Asn Cys Glu Trp Ser Ile Phe Tyr Val Thr Val Leu Ala
    930                 935                 940

Phe Thr Leu Ile Val Leu Thr Gly Gly Phe Thr Trp Leu Cys Ile Cys
945                 950                 955                 960

Cys Cys Lys Arg Gln Lys Arg Thr Lys Ile Arg Lys Lys Thr Lys Tyr
                965                 970                 975

Thr Ile Leu Asp Asn Met Asp Glu Gln Glu Arg Met Glu Leu Arg Pro
            980                 985                 990

Lys Tyr Gly Ile Lys His Arg Ser Thr Glu His Asn Ser Ser Leu Met
        995                 1000                1005

Val Ser Glu Ser Glu Phe Asp Ser Asp Gln Asp Thr Ile Phe Ser Arg
    1010                1015                1020

Glu Lys Met Glu Arg Gly Asn Pro Lys Val Ser Met Asn Gly Ser Ile
1025                1030                1035                1040

Arg Asn Gly Ala Ser Phe Ser Tyr Cys Ser Lys Asp Arg
                1045                1050

<210> SEQ ID NO 275
<211> LENGTH: 23
<212> TYPE: DNA
<213> ORGANISM: Artificial Sequence

```
<220> FEATURE:
<223> OTHER INFORMATION: Primer

<400> SEQUENCE: 275
aattctccga acgtgtcacg ttt                                               23

<210> SEQ ID NO 276
<211> LENGTH: 24
<212> TYPE: DNA
<213> ORGANISM: Artificial Sequence
<220> FEATURE:
<223> OTHER INFORMATION: Primer

<400> SEQUENCE: 276
aagggacgaa gacgaacacu uctt                                              24

<210> SEQ ID NO 277
<211> LENGTH: 23
<212> TYPE: DNA
<213> ORGANISM: Artificial Sequence
<220> FEATURE:
<223> OTHER INFORMATION: Primer

<400> SEQUENCE: 277
aactgaagac ctgaagacaa taa                                               23
```